United States Patent
Bebbington et al.

(10) Patent No.: US 7,008,948 B2
(45) Date of Patent: Mar. 7, 2006

(54) FUSED PYRIMIDYL PYRAZOLE COMPOUNDS USEFUL AS PROTEIN KINASE INHIBITORS

(75) Inventors: David Bebbington, Newbury (GB); Hayley Binch, Harwell (GB); Ronald Knegtel, Abingdon (GB); Julian Golec, Swindon (GB); Sanjay Patel, Abingdon (GB); Jean-Damien Charrier, Wantage (GB); David Kay, Purton (GB); Robert Davies, Arlington, MA (US); Pan Li, Arlington, MA (US); Marion Wannamaker, Stow, MA (US); Cornelia Forster, Pelham, NH (US); Albert Pierce, Somerville, MA (US)

(73) Assignee: Vertex Pharmaceuticals, Incorporated, Cambridge, MA (US)

( * ) Notice: Subject to any disclaimer, the term of this patent is extended or adjusted under 35 U.S.C. 154(b) by 0 days.

(21) Appl. No.: 10/624,800

(22) Filed: Jul. 22, 2003

(65) Prior Publication Data

US 2004/0224944 A1 Nov. 11, 2004

Related U.S. Application Data

(62) Division of application No. 09/952,671, filed on Sep. 14, 2001, now Pat. No. 6,660,731.
(60) Provisional application No. 60/286,949, filed on Apr. 27, 2001, provisional application No. 60/257,887, filed on Dec. 21, 2000, and provisional application No. 60/232,795, filed on Sep. 15, 2000.

(51) Int. Cl.
| | |
|---|---|
| C07D 471/04 | (2006.01) |
| C07D 487/04 | (2006.01) |
| A61K 31/519 | (2006.01) |
| A61P 5/48 | (2006.01) |
| A61P 35/00 | (2006.01) |

(52) U.S. Cl. ............... 514/260.1; 514/263.22; 514/263.37; 514/264.11; 544/277; 544/278; 544/279

(58) Field of Classification Search ............. 514/260.1, 514/263.22, 263.37, 264.11; 544/277, 278, 544/279
See application file for complete search history.

(56) References Cited

FOREIGN PATENT DOCUMENTS

| WO | WO 95/15758 | 6/1995 |
|---|---|---|
| WO | WO 00/21955 | 4/2000 |
| WO | WO 00/39101 | 7/2000 |

OTHER PUBLICATIONS

Heutink P. Untangling tau–related dementia.Hum Mol Genet. Apr. 12, 2000;9(6):979–86.
Fisher A. Therapeutic strategies in Alzheimer's disease: M1 muscarinic agonists.Jpn J Pharmacol. Oct. 2000;84(2):101–12.
Eldar–Finkelman et al Expert Opinion on Investigational Drugs (Ashley Publications), 2003, vol. 12, No. 9, pp. 1511–1519.
Anonymous, Expert Opinion on Therapeutic Patents (Ashley Publications), 2004, vol. 14, No. 3, pp. 439–443.

*Primary Examiner*—Thomas C. McKenzie
(74) *Attorney, Agent, or Firm*—Lisa A. Dixon

(57) ABSTRACT

This invention describes novel pyrazole compounds of formula IV:

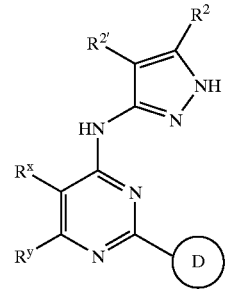

wherein Ring D is a 5–7 membered monocyclic ring or 8–10 membered bicyclic ring selected from aryl, heteroaryl, heterocyclyl or carbocyclyl; $R^x$ and $R^y$ are independently selected from T-$R^3$, or taken together with their intervening atoms to form a fused, unsaturated or partially unsaturated, 5–8 membered ring having 1–3 ring heteroatoms selected from oxygen, sulfur, or nitrogen; and $R^2$, $R^{2'}$, T, and $R^3$ are as described in the specification. The compounds are useful as protein kinase inhibitors, especially as inhibitors of aurora-2 and GSK-3, for treating diseases such as cancer, diabetes and Alzheimer's disease.

16 Claims, No Drawings

FUSED PYRIMIDYL PYRAZOLE COMPOUNDS USEFUL AS PROTEIN KINASE INHIBITORS

CROSS REFERENCE TO RELATED APPLICATIONS

This application is a divisional of U.S. patent application Ser. No. 09/952,671, filed Sep. 14, 2001 now U.S. Pat. No. 6,660,731, which claims priority to U.S. Provisional Application Ser. No. 60/232,795 filed Sep. 15, 2000, U.S. Provisional Application Ser. No. 60/357,887 filed Dec. 21, 2000, and U.S. Provisional Application Ser. No. 60/286,949 filed Apr. 27, 2001, the entirety of which is incorporated herein by reference.

FIELD OF THE INVENTION

The present invention is in the field of medicinal chemistry and relates to compounds that are protein kinase inhibitors, compositions containing such compounds and methods of use. More particularly, this invention relates to compounds that are inhibitors of GSK-3 and Aurora-2 protein kinases. The invention also relates to methods of treating diseases associated with these protein kinases, such as diabetes, cancer and Alzheimer's disease.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. Examples of such stimuli include environmental and chemical stress signals (e.g. osmotic shock, heat shock, ultraviolet radiation, bacterial endotoxin, $H_2O_2$), cytokines (e.g. interleukin-1 (IL-1) and tumor necrosis factor α (TNF-α)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Aurora-2 is a serine/threonine protein kinase that has been implicated in human cancer, such as colon, breast and other solid tumors. This kinase is believed to be involved in protein phosphorylation events that regulate the cell cycle. Specifically, Aurora-2 may play a role in controlling the accurate segregation of chromosomes during mitosis. Misregulation of the cell cycle can lead to cellular proliferation and other abnormalities. In human colon cancer tissue, the aurora-2 protein has been found to be overexpressed. See Bischoff et al., *EMBO J.*, 1998, 17, 3052–3065; Schumacher et al., *J. Cell Biol.*, 1998, 143, 1635–1646; Kimura et al., *J. Biol. Chem.*, 1997, 272, 13766–13771.

Glycogen synthase kinase-3 (GSK-3) is a serine/threonine protein kinase comprised of α and β isoforms that are each encoded by distinct genes [Coghlan et al., *Chemistry & Biology*, 7, 793–803 (2000); Kim and Kimmel, *Curr. Opinion Genetics Dev.*, 10, 508–514 (2000)]. GSK-3 has been implicated in various diseases including diabetes, Alzheimer's disease, CNS disorders such as manic depressive disorder and neurodegenerative diseases, and cardiomyocete hypertrophy [WO 99/65897; WO 00/38675; and Haq et al., *J. Cell Biol.* (2000) 151, 117]. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP. citrate lyase, axin, heat shock factor-1, c-Jun, c-Myc, c-Myb, CREB, and CEPBα. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS*, 93, 8455–9 (1996); Cross et al., *Biochem. J.*, 303, 21–26 (1994); Cohen, *Biochem. Soc. Trans.*, 21, 555–567 (1993); Massillon et al., *Biochem J.* 299, 123–128 (1994)]. However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [WO 00/38675]. Therapeutic inhibitors of GSK-3 are therefore potentially useful for treating diabetic patients suffering from an impaired response to insulin.

GSK-3 activity has also been associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells [Lovestone et al., *Current Biology* 4, 1077–86 (1994), Brownlees et al., *Neuroreport* 8, 3251–55 (1997)]. Therefore, it is believed that GSK-3 activity may promote generation of the neurofibrillary tangles and the progression of Alzheimer's disease.

Another substrate of GSK-3 is β-catenin which is degradated after phosphorylation by GSK-3. Reduced levels of β-catenin have been reported in schizophrenic patients and have also been associated with other diseases related to increase in neuronal cell death [Zhong et al., *Nature*, 395, 698–702 (1998); Takashima et al., *PNAS*, 90, 7789–93 (1993); Pei et al., *J. Neuropathol. Exp*, 56, 70–78 (1997)].

As a result of the biological importance of GSK-3, there is current interest in therapeutically effective GSK-3 inhbitors. Small molecules that inhibit GSK-3 have recently been reported [WO 99/65897 (Chiron) and WO 00/38675 (SmithKline Beecham)].

For many of the aforementioned diseases associated with abnormal GSK-3 activity, other protein kinases have also been targeted for treating the same diseases. However, the various protein kinases often act through different biological pathways. For example, certain quinazoline derivatives have been reported recently as inhibitors of p38 kinase (WO 00/12497 to Scios). The compounds are reported to be useful for treating conditions characterized by enhanced p38-α activity and/or enhanced TGF-β activity. While p38 activity has been implicated in a wide variety of diseases, including diabetes, p38 kinase is not reported to be a constituent of an insulin signaling pathway that regulates glycogen synthesis or glucose uptake. Therefore, unlike GSK-3, p38 inhibition would not be expected to enhance glycogen synthesis and/or glucose uptake.

There is a continued need to find new therapeutic agents to treat human diseases. The protein kinases aurora-2 and GSK-3 are especially attractive targets for the discovery of new therapeutics due to their important role in cancer, diabetes, Alzheimer's disease and other diseases.

DESCRIPTION OF THE INVENTION

It has now been found that compounds of this invention and pharmaceutical compositions thereof are effective as protein kinase inhibitors, particularly as inhibitors of aurora-2 and GSK-3. These compounds have the general formula I:

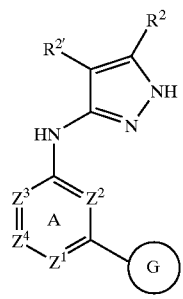

I or a pharmaceutically acceptable derivative or prodrug thereof, wherein:
$Z^1$ to $Z^4$ are as described below;
Ring A is selected from the group consisting of:

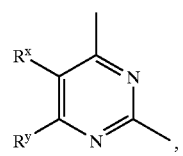

a

-continued

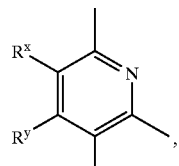

b

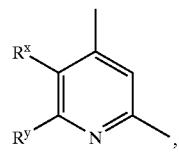

c

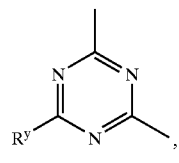

d

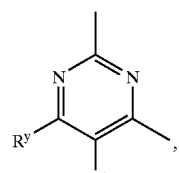

e

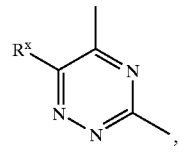

f

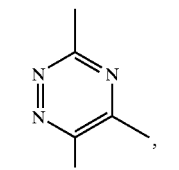

g

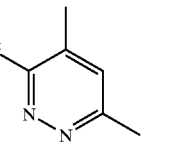

and h

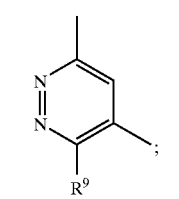

i

G is Ring C or Ring D;
Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —R$^8$;

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —R$^5$, and at any substitutable ring nitrogen by —R$^4$, provided that when Ring D is a six-membered aryl or heteroaryl ring, —R$^5$ is hydrogen at each ortho carbon position of Ring D;

R$^1$ is selected from -halo, —CN, —NO$_2$, T-V—R$^6$, phenyl, 5–6 membered heteroaryl ring, 5–6 membered heterocyclyl ring, or C$_{1-6}$ aliphatic group, said phenyl, heteroaryl, and heterocyclyl rings each optionally substituted by up to three groups independently selected from halo, oxo, or —R$^8$, said C$_{1-6}$ aliphatic group optionally substituted with halo, cyano, nitro, or oxygen, or R$^1$ and an adjacent substituent taken together with their intervening atoms form said ring fused to Ring C;

R$^x$ and R$^y$ are independently selected from T-R$^3$, or R$^x$ and R$^y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by R$^x$ and R$^y$ is substituted by oxo or T-R$^3$, and any substitutable nitrogen on said ring formed by R$^x$ and R$^y$ is substituted by R$^4$;

T is a valence bond or a C$_{1-4}$ alkylidene chain;

R$^2$ and R$^{2'}$ are independently selected from —R, -T-W—R$^6$, or R$^2$ and R$^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by R$^2$ and R$^{2'}$ is substituted by halo, oxo, —CN, —NO$_2$, —R$^7$, or —V—R$^6$, and any substitutable nitrogen on said ring formed by R$^2$ and R$^{2'}$ is substituted by R$^4$;

R$^3$ is selected from —R, -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$ (optionally substituted C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is independently selected from hydrogen or an optionally substituted group selected from C$_{1-6}$ aliphatic, C$_{6-10}$ aryl, a heteroaryl ring having 5–10 ring atoms, or a heterocyclyl ring having 5–10 ring atoms;

each R$^4$ is independently selected from —R$^7$, —COR$^7$, —CO$_2$(C$_{1-6}$ aliphatic), —CON(R$^7$)$_2$, or —SO$_2$R$^7$, or two R$^4$ on the same nitrogen are taken together to form a 5–8 membered heterocyclyl or heteroaryl ring;

each R$^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, or R$^5$ and an adjacent substituent taken together with their intervening atoms form said ring fused to Ring C;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each R$^6$ is independently selected from hydrogen or an optionally substituted C$_{1-4}$ aliphatic group, or two R$^6$ groups on the same nitrogen atom are taken together with the nitrogen atom to form a 5–6 membered heterocyclyl or heteroaryl ring;

each R$^7$ is independently selected from hydrogen or an optionally substituted C$_{1-6}$ aliphatic group, or two R$^7$ on the same nitrogen are taken together with the nitrogen to form a 5–8 membered heterocyclyl or heteroaryl ring;

each R$^8$ is independently selected from an optionally substituted C$_{1-4}$ aliphatic group, —OR$^6$, —SR$^6$, COR$^6$, —SO$_2$R$^6$, —N(R$^6$)$_2$, —N(R$^6$)N(R$^6$)$_2$, —CN, —NO$_2$, —CON(R$^6$)$_2$, or —CO$_2$R$^6$; and R$^9$ is selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$.

As used herein, the following definitions shall apply unless otherwise indicated. The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "aliphatic" as used herein means straight-chain, branched or cyclic C$_1$–C$_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms. The term "cycloalkyl" used alone or as part of a larger moiety shall include cyclic C$_3$–C$_{12}$ hydrocarbons which are completely saturated or which contain one or more units of unsaturation, but which are not aromatic.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, —(CH$_2$)$_y$NHC(O)CH(V—R°)(R°); wherein R° is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0–6; and V is a linker group. Examples of substituents on the aliphatic group or the phenyl ring of R° include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is hydrogen, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated C$_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of formula I or salts thereof may be formulated into compositions. In a preferred embodiment, the composition is a pharmaceutical composition. In one embodiment, the composition comprises an amount of the protein kinase inhibitor effective to inhibit a protein kinase, particularly GSK-3, in a biological sample or in a patient. In another embodiment, compounds of this invention and pharmaceutical compositions thereof, which comprise an amount of the protein kinase inhibitor effective to treat or prevent a GSK-3-mediated condition and a pharmaceutically acceptable carrier, adjuvant, or vehicle, may be formulated for administration to a patient.

The term "GSK-3-mediated condition" or "disease", as used herein, means any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

One aspect of this invention relates to a method of enhancing glycogen synthesis and/or lowering blood levels of glucose in a patient in need thereof, which method comprises administering to the patient a therapeutically effective amount of a compound of formula I or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

Another aspect of the invention relates to inhibiting GSK-3 activity in a biological sample, which method comprises contacting the biological sample with a GSK-3 inhibitor of formula I.

Another aspect of this invention relates to a method of inhibiting Aurora-2 activity in a patient, which method comprises administering to the patient a compound of formula I or a composition comprising said compound.

Another aspect of this invention relates to a method of treating or preventing an Aurora-2-mediated disease with an Aurora-2 inhibitor, which method comprises administering to a patient in need of such a treatment a therapeutically effective amount of a compound of formula I or a pharmaceutical composition thereof.

The term "Aurora-2-mediated condition" or "disease", as used herein, means any disease or other deleterious condition in which Aurora is known to play a role. The term "Aurora-2-mediated condition" or "disease" also means those diseases or conditions that are alleviated by treatment with an Aurora-2 inhibitor. Such conditions include, without limitation, cancer. The term "cancer" includes, but is not limited to the following cancers: colon and ovarian.

Another aspect of the invention relates to inhibiting Aurora-2 activity in a biological sample, which method comprises contacting the biological sample with the Aurora-2 inhibitor of formula I, or a composition thereof.

Another aspect of this invention relates to a method of treating or preventing a CDK-2-mediated diseases with a CDK-2 inhibitor, which method comprises administering to a patient in need of such a treatment a therapeutically effective amount of a compound of formula I or a pharmaceutical composition thereof.

The term "CDK-2-mediated condition" or "disease", as used herein, means any disease or other deleterious condition in which CDK-2 is known to play a role. The term "CDK-2-mediated condition" or "disease" also means those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P., *Current Medicinal Chemistry*, 7, 1213–1245 (2000); Mani, S., Wang, C., Wu, K., Francis, R. and Pestell, R., *Exp. Opin. Invest. Drugs*, 9, 1849 (2000); Fry, D. W. and Garrett, M. D., *Current Opinion in Oncologic, Endocrine & Metabolic Investigational Drugs*, 2, 40–59 (2000).

Another aspect of the invention relates to inhibiting CDK-2 activity in a biological sample or a patient, which method comprises administering to the patient a compound of formula I or a composition comprising said compound.

Another aspect of this invention relates to a method of treating or preventing an ERK-2-mediated diseases with an ERK-2 inhibitor, which method comprises administering to a patient in need of such a treatment a therapeutically effective amount of a compound of formula I or a pharmaceutical composition thereof.

The term "ERK-mediated condition", as used herein means any disease state or other deleterious condition in which ERK is known to play a role. The term "ERK-2-mediated condition" or "disease" also means those diseases or conditions that are alleviated by treatment with a ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. ERK-2 protein kinase and its implication in various diseases has been described [Bokemeyer et al. 1996, *Kidney Int.* 49, 1187; Anderson et al., 1990, *Nature* 343, 651; Crews et al., 1992, *Science* 258, 478; Bjorbaek et al., 1995, *J. Biol. Chem.* 270, 18848; Rouse et al., 1994, *Cell* 78, 1027; Raingeaud et al., 1996, *Mol. Cell Biol.* 16, 1247; Raingeaud et al. 1996; Chen et al., 1993 *Proc. Natl. Acad. Sci. USA* 90, 10952; Oliver et al., 1995, *Proc. Soc. Exp. Biol. Med.* 210, 162; Moodie et al., 1993, *Science* 260, 1658; Frey and Mulder, 1997, *Cancer Res.* 57, 628; Sivaraman et al., 1997, *J Clin. Invest.* 99, 1478; Whelchel et al., 1997, *Am. J. Respir. Cell Mol. Biol.* 16, 589].

Another aspect of the invention relates to inhibiting ERK-2 activity in a biological sample or a patient, which method comprises administering to the patient a compound of formula I or a composition comprising said compound.

Another aspect of this invention relates to a method of treating or preventing an AKT-mediated diseases with an AKT inhibitor, which method comprises administering to a patient in need of such a treatment a therapeutically effective amount of a compound of formula I or a pharmaceutical composition thereof.

The term "AKT-mediated condition", as used herein, means any disease state or other deleterious condition in which AKT is known to play a role. The term "AKT-mediated condition" or "disease" also means those diseases or conditions that are alleviated by treatment with a AKT inhibitor. AKT-mediated diseases or conditions include, but are not limited to, proliferative disorders, cancer, and neurodegenerative disorders. The association of AKT, also known as protein kinase B, with various diseases has been described [Khwaja, A., *Nature*, pp. 33–34, 1990; Zang, Q. Y., et al, *Oncogene*, 19 2000; Kazuhiko, N., et al, *The Journal of Neuroscience*, 20 2000].

Another aspect of the invention relates to inhibiting AKT activity in a biological sample or a patient, which method comprises administering to the patient a compound of formula I or a composition comprising said compound.

Another aspect of this invention relates to a method of treating or preventing a Src-mediated disease with a Src inhibitor, which method comprises administering to a patient in need of such a treatment a therapeutically effective amount of a compound of formula I or a pharmaceutical composition thereof.

The term "Src-mediated condition", as used herein means any disease state or other deleterious condition in which Src is known to play a role. The term "Src-mediated condition" or "disease" also means those diseases or conditions that are alleviated by treatment with a Src inhibitor. Such conditions include, without limitation, hypercalcemia, osteoporosis, osteoarthritis, cancer, symptomatic treatment of bone metastasis, and Paget's disease. Src protein kinase and its implication in various diseases has been described [Soriano, *Cell*, 69, 551 (1992); Soriano et al., *Cell*, 64, 693 (1991); Takayanagi, *J. Clin. Invest.*, 104, 137 (1999); Boschelli, *Drugs of the Future* 2000, 25(7), 717, (2000); Talamonti, *J. Clin. Invest.*, 91, 53 (1993); Lutz, *Biochem. Biophys. Res.* 243, 503 (1998); Rosen, *J. Biol. Chem.*, 261, 13754 (1986); Bolen, *Proc. Natl. Acad. Sci. USA*, 84, 2251 (1987); Masaki, *Hepatology*, 27, 1257 (1998); Biscardi, *Adv. Cancer Res.*, 76, 61 (1999); Lynch, *Leukemia*, 7, 1416 (1993); Wiener, *Clin. Cancer Res.*, 5, 2164 (1999); Staley, *Cell Growth Diff.*, 8, 269 (1997)].

Another aspect of the invention relates to inhibiting Src activity in a biological sample or a patient, which method comprises administering to the patient a compound of formula I or a composition comprising said compound.

The term "pharmaceutically acceptable carrier, adjuvant, or vehicle" refers to a non-toxic carrier, adjuvant, or vehicle that may be administered to a patient, together with a compound of this invention, and which does not destroy the pharmacological activity thereof.

The term "patient" includes human and veterinary subjects.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

The amount effective to inhibit protein kinase, for example, GSK-3 and Aurora-2, is one that measurably inhibits the kinase activity where compared to the activity of the enzyme in the absence of an inhibitor. Any method may be used to determine inhibition, such as, for example, the Biological Testing Examples described below.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In addition to the compounds of this invention, pharmaceutically acceptable derivatives or prodrugs of the compounds of this invention may also be employed in compositions to treat or prevent the above-identified diseases or disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The amount of the protein kinase inhibitor that may be combined with the carrier materials to produce a single dosage form will vary depending upon the patient treated and the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of the inhibitor will also depend upon the particular compound in the composition.

Depending upon the particular protein kinase-mediated condition to be treated or prevented, additional therapeutic agents, which are normally administered to treat or prevent that condition, may be administered together with the inhibitors of this invention. For example, in the treatment of diabetes other anti-diabetic agents may be combined with the GSK-3 inhibitors of this invention to treat diabetes. These agents include, without limitation, insulin or insulin analogues, in injectable or inhalation form, glitazones, alpha glucosidase inhibitors, biguanides, insulin sensitizers, and sulfonyl ureas.

Other examples of agents the inhibitors of this invention may also be combined with include, without limitation, chemotherapeutic agents or other anti-proliferative agents such as adriamycin, dexamethasone, vincristine, cyclophosphamide, fluorouracil, topotecan, taxol, interferons, and platinum derivatives; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Those additional agents may be administered separately from the protein kinase inhibitor-containing composition, as part of a multiple dosage regimen. Alternatively, those agents may be part of a single dosage form, mixed together with the protein kinase inhibitor of this invention in a single composition.

Compounds of this invention may exist in alternative tautomeric forms, as in tautomers 1 and 2 shown below. Unless otherwise indicated, the representation of either tautomer is meant to include the other.

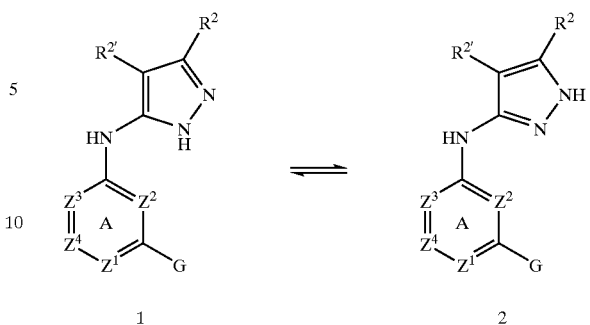

$R^x$ and $R^y$ (at positions $Z^3$ and $Z^4$, respectively) may be taken together to form a fused ring, providing a bicyclic ring system containing Ring A. Preferred $R^x/R^y$ rings include a 5-, 6-, 7-, or 8-membered unsaturated or partially unsaturated ring having 0–2 heteroatoms, wherein said $R^x/R^y$ ring is optionally substituted. Examples of Ring A systems are shown below by compounds I-A through I-DD, wherein $Z^1$ is nitrogen or $C(R^9)$ and $Z^2$ is nitrogen or $C(H)$.

I-A

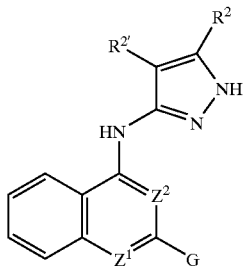

I-B

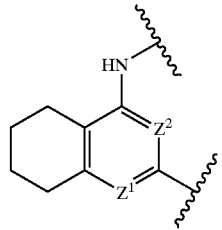

I-C

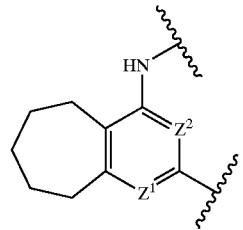

I-D

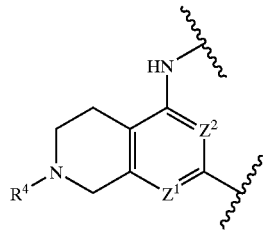

I-E
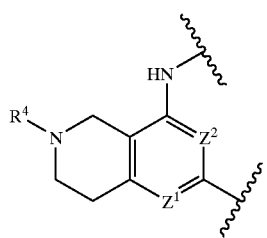
I-F
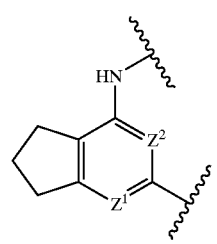
I-G
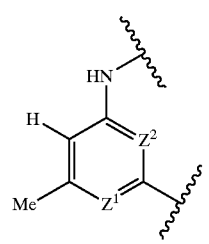
I-H
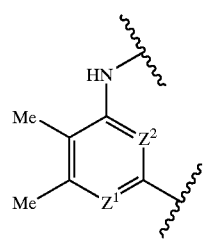
I-I
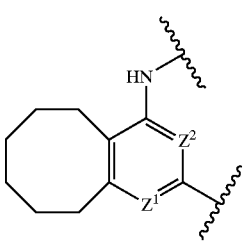
I-J
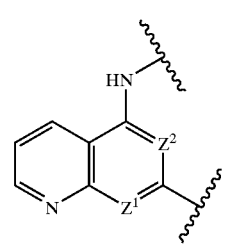
I-K
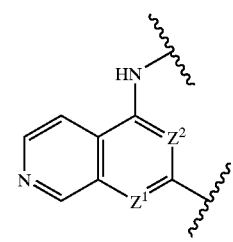
I-L
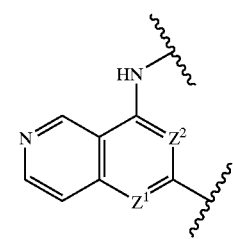
I-M
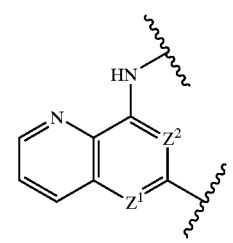
I-N
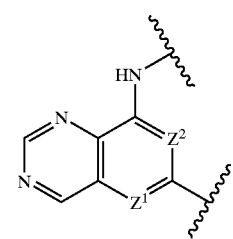
I-O
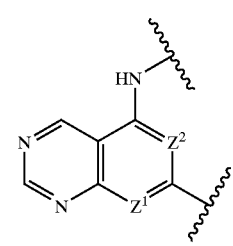
I-P
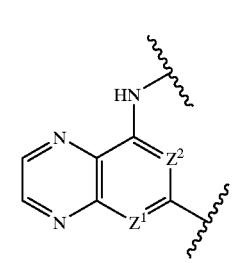

-continued
I-Q
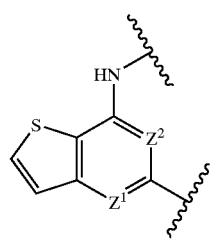
I-R
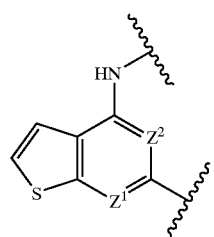
I-S
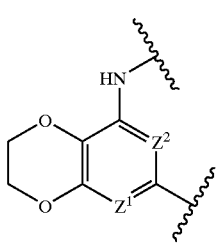
I-T
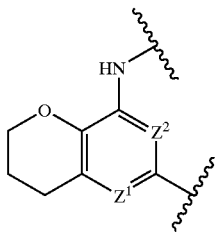
I-U
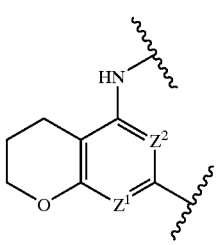
I-V
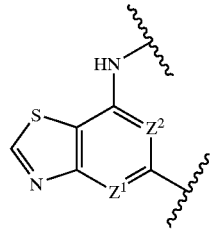
-continued
I-W
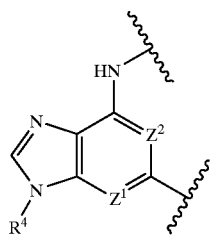
I-X
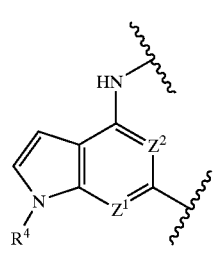
I-Y
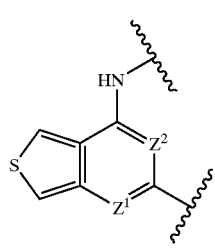
I-Z
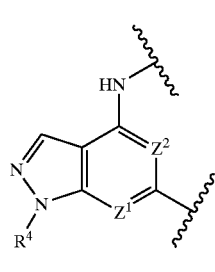
I-AA
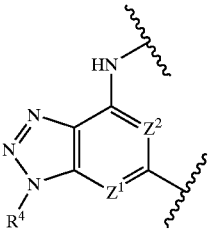
I-BB
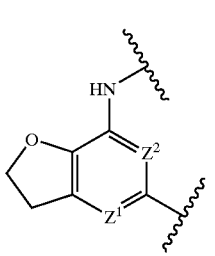

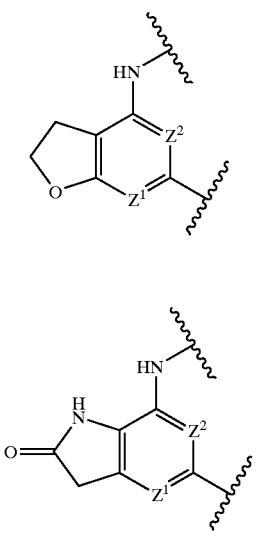

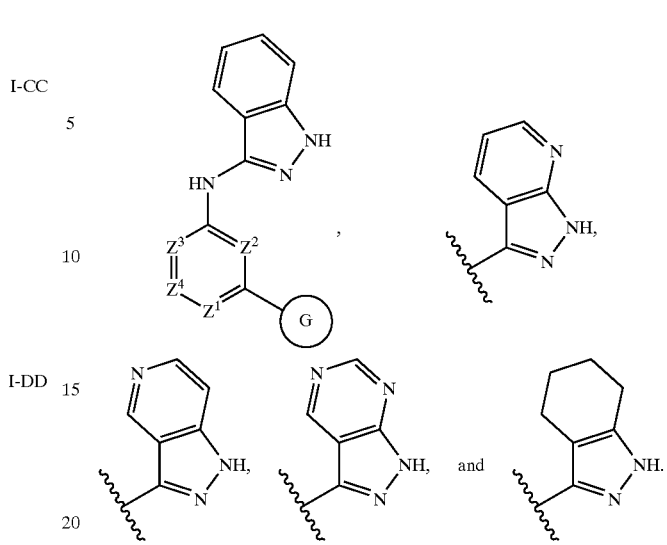

Preferred bicyclic Ring A systems include I-A, I-B, I-C, I-D, I-E, I-F, I-G, I-H, I-I, I-J, I-K, I-L, and I-M, more preferably I-A, I-B, I-C, I-F, and I-H, and most preferably I-A, I-B, and I-H.

In the monocyclic Ring A system, preferred $R^x$ groups, when present, include hydrogen, alkyl- or dialkylamino, acetamido, or a $C_{1-4}$ aliphatic group such as methyl, ethyl, cyclopropyl, isopropyl or t-butyl. Preferred $R^y$ groups, when present, include T-$R^3$ wherein T is a valence bond or a methylene, and $R^3$ is —R, —N($R^4$)$_2$, or —OR. Examples of preferred $R^y$ include 2-pyridyl, 4-pyridyl, piperidinyl, methyl, ethyl, cyclopropyl, isopropyl, t-butyl, alkyl- or dialkylamino, acetamido, optionally substituted phenyl such as phenyl or halo-substituted phenyl, and methoxymethyl.

In the bicyclic Ring A system, the ring formed when $R^x$ and $R^y$ are taken together may be substituted or unsubstituted. Suitable substituents include —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$, wherein R and $R^4$ are as defined above. Preferred $R^x$/$R^y$ ring substituents include -halo, —R, —OR, —COR, —CO$_2$R, —CON($R^4$)$_2$, —CN, or —N($R^4$)$_2$ wherein R is hydrogen or an optionally substituted $C_{1-6}$ aliphatic group.

$R^2$ and $R^{2'}$ may be taken together to form a fused ring, thus providing a bicyclic ring system containing a pyrazole ring. Preferred fused rings include benzo, pyrido, pyrimido, and a partially unsaturated 6-membered carbocyclo ring, wherein said fused ring is optionally substituted. These are exemplified in the following formula I compounds having a pyrazole-containing bicyclic ring system:

Preferred substituents on the $R^2$/$R^{2'}$ fused ring include one or more of the following: -halo, —N($R^4$)$_2$, —$C_{1-3}$ alkyl, —$C_{1-3}$ haloalkyl, —NO$_2$, —O($C_{1-3}$ alkyl), —CO$_2$($C_{1-3}$ alkyl), —CN, —SO$_2$($C_{1-3}$ alkyl), —SO$_2$NH$_2$, —OC(O)NH$_2$, —NH$_2$SO$_2$($C_{1-3}$ alkyl), —NHC(O)($C_{1-3}$ alkyl), —C(O)NH$_2$, and —CO($C_{1-3}$ alkyl), wherein the ($C_{1-3}$ alkyl) is most preferably methyl.

When the pyrazole ring system is monocyclic, preferred $R^2$ groups include hydrogen, $C_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred $R^2$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-$C_3H_7$), CON(Et)CH$_2$CH$_2$CH$_3$, CONHCH$_2$CH(CH$_3$)$_2$, CON(n-$C_3H_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl). A preferred $R^{2'}$ group is hydrogen.

An embodiment that is particularly useful for treating GSK3-mediated diseases relates to compounds of formula II:

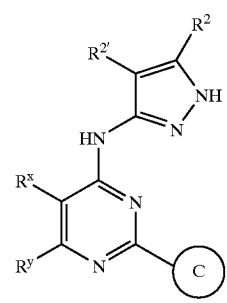

II or a pharmaceutically acceptable derivative or prodrug thereof, wherein;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —$R^8$;

$R^1$ is selected from -halo, —CN, —$NO_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

$R^x$ and $R^y$ are independently selected from T-$R^3$, or $R^x$ and $R^y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by $R^x$ and $R^y$ is substituted by oxo or T-$R^3$, and any substitutable nitrogen on said ring formed by $R^x$ and $R^y$ is substituted by $R^4$;

T is a valence bond or a $C_{1-4}$ alkylidene chain;

$R^2$ and $R^{2'}$ are independently selected from —R, -T-W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by $R^2$ and $R^{2'}$ is substituted by halo, oxo, —CN, —$NO_2$, —$R^7$, or —V—$R^6$, and any substitutable nitrogen on said ring formed by $R^2$ and $R^{2'}$ is substituted by $R^4$;

$R^3$ is selected from —R, -halo, —OR, —C(=O)R, —$CO_2$R, —COCOR, —$COCH_2$COR, —$NO_2$, —CN, —S(O)R, —S(O)$_2$R, —SR, —N($R^4$)$_2$, —CON($R^7$)$_2$, —$SO_2$N($R^7$)$_2$, —OC(=O)R, —N($R^7$)COR, —N($R^7$)$CO_2$ (optionally substituted $C_{1-6}$ aliphatic), —N($R^4$)N($R^4$)$_2$, —C=NN($R^4$)$_2$, —C=N—OR, —N($R^7$)CON($R^7$)$_2$, —N($R^7$)$SO_2$N($R^7$)$_2$, —N($R^4$)$SO_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$ (optionally substituted $C_{1-6}$ aliphatic), —CON($R^7$)$_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$, or $R^5$ and an adjacent substituent taken together with their intervening atoms form said ring fused to Ring C;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$ $SO_2$—, —C($R^6$)$_2$$SO_2$N($R^6$)—, —C($R^6$)$_2$N($R^6$)—, —CO—, —$CO_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, —C($R^6$)$_2$N($R^6$)CON($R^6$)—, or —CON($R^6$)—;

each $R^6$ is independently selected from hydrogen, an optionally substituted $C_{1-4}$ aliphatic group, or two $R^6$ groups on the same nitrogen atom are taken together with the nitrogen atom to form a 5–6-membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring; and each $R^8$ is independently selected from an optionally substituted $C_{1-4}$ aliphatic group, —$OR^6$, —$SR^6$, —$COR^6$, —$SO_2R^6$, —N($R^6$)$_2$, —N($R^6$)N($R^6$)$_2$, —CN, —$NO_2$, —CON($R^6$)$_2$, or —$CO_2R^6$.

When the $R^x$ and $R^y$ groups of formula II are taken together to form a fused ring, preferred $R^x/R^y$ rings include a 5-, 6-, 7-, or 8-membered unsaturated or partially unsaturated ring having 0–2 heteroatoms, wherein said $R^x/R^y$ ring is optionally substituted. This provides a bicyclic ring system containing a pyrimidine ring. Examples of preferred pyrimidine ring systems of formula II are the mono- and bicyclic systems shown below.

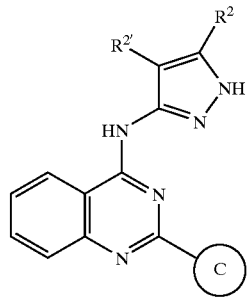

II-A

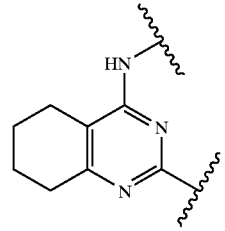

II-B

II-C 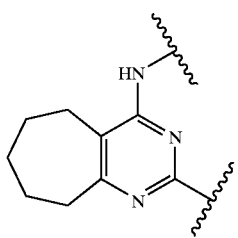
II-D 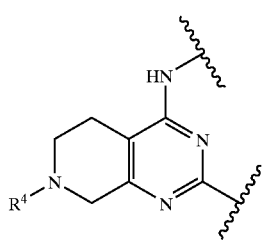
II-E 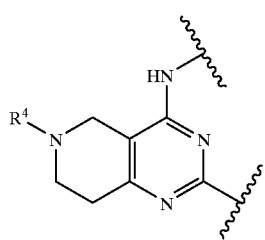
II-F 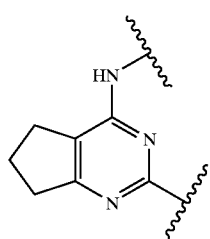
II-G 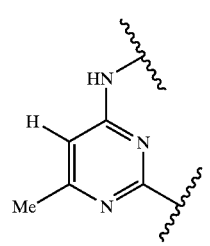
II-H 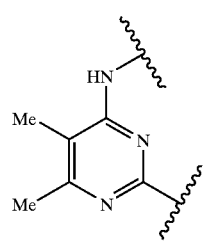
II-I 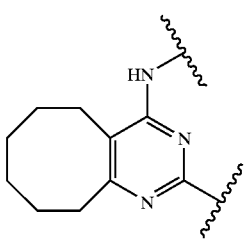
II-J 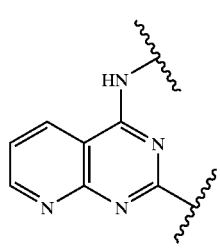
II-K 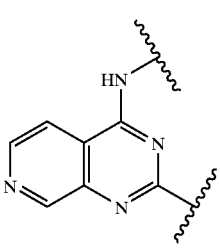
II-L 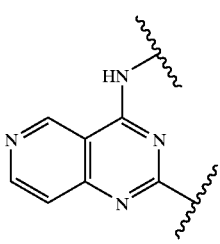
II-M 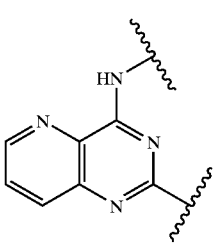
II-N 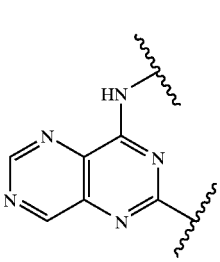

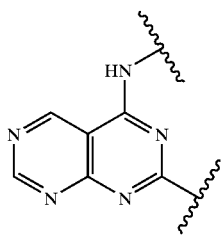

II-O

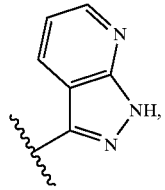

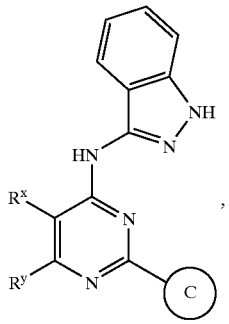

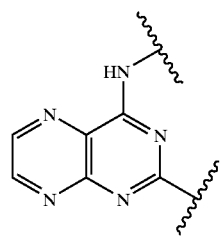

II-P

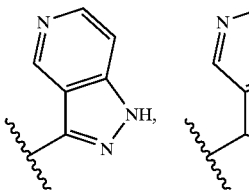 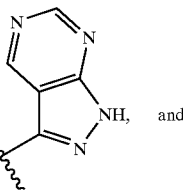

More preferred pyrimidine ring systems of formula II include II-A, II-B, II-C, II-F, and II-H, most preferably II-A, II-B, and II-H.

In the monocyclic pyrimidine ring system of formula II, preferred $R^x$ groups include hydrogen, alkyl- or dialkylamino, acetamido, or a $C_{1-4}$ aliphatic group such as methyl, ethyl, cyclopropyl, isopropyl or t-butyl. Preferred $R^y$ groups include T-$R^3$ wherein T is a valence bond or a methylene, and $R^3$ is —R, —N($R^4$)$_2$, or —OR. When $R^3$ is —R or —OR, a preferred R is an optionally substituted group selected from $C_{1-6}$ aliphatic, phenyl, or a 5–6 membered heteroaryl or heterocyclyl ring. Examples of preferred $R^y$ include 2-pyridyl, 4-pyridyl, piperidinyl, methyl, ethyl, cyclopropyl, isopropyl, t-butyl, alkyl- or dialkylamino, acetamido, optionally substituted phenyl such as phenyl or halo-substituted phenyl, and methoxymethyl.

In the bicyclic pyrimidine ring system of formula II, the ring formed when $R^x$ and $R^y$ are taken together may be substituted or unsubstituted. Suitable substituents include —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$, wherein R and $R^4$ are as defined above. Preferred $R^x$/$R^y$ ring substituents include -halo, —R, —OR, —COR, —CO$_2$R, —CON($R^4$)$_2$, —CN, or —N($R^4$)$_2$ wherein R is an optionally substituted $C_{1-6}$ aliphatic group.

The $R^2$ and $R^{2'}$ groups of formula II may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula II compounds having a pyrazole-containing bicyclic ring system:

Preferred substituents on the $R^2$/$R^{2'}$ fused ring of formula II include one or more of the following: -halo, —N($R^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl.

When the pyrazole ring system of formula II is monocyclic, preferred $R^2$ groups include hydrogen, a substituted or unsubstituted group selected from aryl, heteroaryl, or a $C_{1-6}$ aliphatic group. Examples of such preferred $R^2$ groups include methyl, t-butyl, —CH$_2$OCH$_3$, cyclopropyl, furanyl, thienyl, and phenyl. A preferred $R^{2'}$ group is hydrogen.

More preferred ring systems of formula II are the following, which may be substituted as described above, wherein $R^2$ and $R^{2'}$ are taken together with the pyrazole ring to form an indazole ring; and $R^x$ and $R^y$ are each methyl, or $R^x$ and $R^y$ are taken together with the pyrimidine ring to form a quinazoline or tetrahydroquinazoline ring:

II-Aa

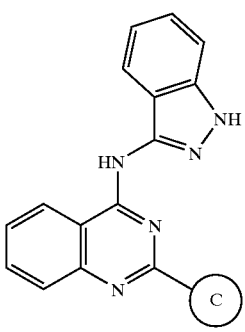

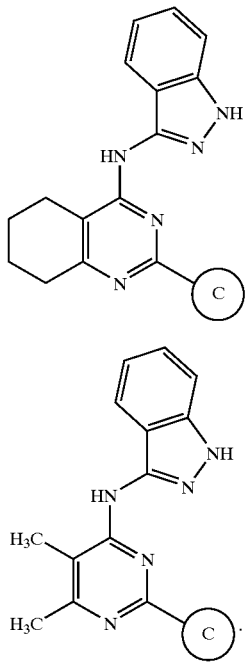

Particularly preferred are those compounds of formula II-Aa, II-Ba, or II-Ha wherein ring C is a phenyl ring and $R^1$ is halo, methyl, or trifluoromethyl.

Preferred formula II Ring C groups are phenyl and pyridinyl. When two adjacent substituents on Ring C are taken together to form a fused ring, Ring C is contained in a bicyclic ring system. Preferred fused rings include a benzo or pyrido ring. Such rings preferably are fused at ortho and meta positions of Ring C. Examples of preferred bicyclic Ring C systems include naphthyl, quinolinyl and isoquinolinyl.

An important feature of the formula II compounds is the $R^1$ ortho substituent on Ring C. An ortho position on Ring C or Ring D is defined relative to the position where Ring A is attached. Preferred $R^1$ groups include -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —OC(O)$NH_2$, or —$NHSO_2R^6$. When $R^1$ is an optionally substituted $C_{1-6}$ aliphatic group, the most preferred optional substituents are halogen. Examples of preferred $R^1$ groups include —$CF_3$, —Cl, —F, —CN, —$COCH_3$, —$OCH_3$, —OH, —$CH_2CH_3$, —$OCH_2CH_3$, —$CH_3$, —$CF_2CH_3$, cyclohexyl, t-butyl, isopropyl, cyclopropyl, —C≡CH, —C≡C—$CH_3$, —$SO_2CH_3$, —$SO_2NH_2$, —$N(CH_3)_2$, —$CO_2CH_3$, —$CONH_2$, —$NHCOCH_3$, —OC(O)$NH_2$, —$NHSO_2CH_3$, and —$OCF_3$.

On Ring C of formula II, preferred $R^5$ substituents, when present, include -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$SO_2N(R^4)_2$, and —$N(R^4)SO_2R$. More preferred $R^5$ substituents include —Cl, —F, —CN, —$CF_3$, —$NH_2$, —$NH(C_{1-4}$ aliphatic), —$N(C_{1-4}$ aliphatic)$_2$, —O($C_{1-4}$ aliphatic), $C_{1-4}$ aliphatic, and —$CO_2$($C_{1-4}$ aliphatic). Examples of such preferred $R^5$ substituents include —Cl, —F, —CN, —$CF_3$, —$NH_2$, —NHMe, —$NMe_2$, —OEt, methyl, ethyl, cyclopropyl, isopropyl, t-butyl, and —$CO_2Et$.

Preferred formula II compounds have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is selected from a naphthyl, quinolinyl or isoquinolinyl ring;

(b) $R^x$ is hydrogen or $C_{1-4}$ aliphatic and $R^y$ is T-$R^3$, or $R^x$ and $R^y$ are taken together with their intervening atoms to form an optionally substituted 5–7 membered unsaturated or partially unsaturated ring having 0–2 ring nitrogens;

(c) $R^1$ is -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —OC(O)$NH_2$, or —$NHSO_2R^6$; and (d) $R^2$ is hydrogen and $R^{2'}$ is hydrogen or a substituted or unsubstituted group selected from aryl, heteroaryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring.

More preferred compounds of formula II have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is a naphthyl ring;

(b) $R^x$ is hydrogen or methyl and $R^y$ is —R, $N(R^4)_2$, or —OR, or $R^x$ and $R^y$ are taken together with their intervening atoms to form a 5–7 membered unsaturated or partially unsaturated carbocyclo ring optionally substituted with —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=NN$(R^4)_2$, —C=N—OR, —$N(R^4)CON(R^4)_2$, —$N(R^4)SO_2N(R^4)_2$, —$N(R^4)SO_2R$, or —OC(=O)$N(R^4)_2$;

(c) $R^1$ is -halo, a $C_{1-6}$ haloaliphatic group, a $C_{1-6}$ aliphatic group, phenyl, or —CN;

(d) $R^2$ is hydrogen and $R^{2'}$ is hydrogen or a substituted or unsubstituted group selected from aryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring; and (e) each $R^5$ is independently selected from -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$SO_2N(R^4)_2$, or —$N(R^4)SO_2R$.

Even more preferred compounds of formula II have one or more, and more preferably all, of the features selected from the group consisting of:

(a) Ring C is a phenyl ring optionally substituted by —$R^5$;

(b) $R^x$ is hydrogen or methyl and $R^y$ is methyl, methoxymethyl, ethyl, cyclopropyl, isopropyl, t-butyl, alkyl- or an optionally substituted group selected from 2-pyridyl, 4-pyridyl, piperidinyl, or phenyl, or $R^x$ and $R^y$ are taken together with their intervening atoms to form an optionally substituted benzo ring or partially unsaturated 6-membered carbocyclo ring;

(c) $R^1$ is -halo, a $C_{1-4}$ aliphatic group optionally substituted with halogen, or —CN;

(d) $R^2$ and $R^{2'}$ are taken together with their intervening atoms to form a benzo, pyrido, pyrimido or partially unsaturated 6-membered carbocyclo ring optionally substituted with -halo, —$N(R^4)_2$, —$C_{1-4}$ alkyl, —$C_{1-4}$ haloalkyl, —$NO_2$, —O($C_{1-4}$ alkyl), —$CO_2$($C_{1-4}$ alkyl), —CN, —$SO_2$($C_{1-4}$ alkyl), —$SO_2NH_2$, —OC(O)$NH_2$, —$NH_2SO_2$($C_{1-4}$ alkyl), —NHC(O)(C$_{1-4}$ alkyl), —C(O)NH$_2$, or —CO(C$_{1-4}$ alkyl), wherein the (C$_{1-4}$ alkyl) is a straight, branched, or cyclic alkyl group; and (e) each R$^5$ is independently selected from —Cl, —F, —CN, —CF$_3$, —NH$_2$, —NH(C$_{1-4}$ aliphatic), —N(C$_{1-4}$ aliphatic)$_2$, —O(C$_{1-4}$ aliphatic), C$_{1-4}$ aliphatic, and —CO$_2$ (C$_{1-4}$ aliphatic).

Representative compounds of formula II are shown below in Table 1.

TABLE 1

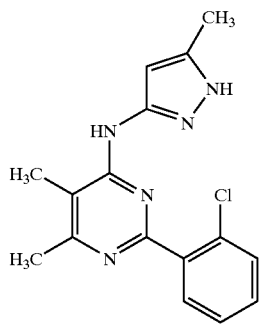

II-1

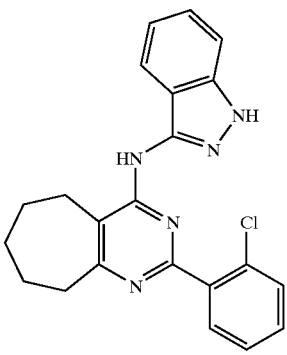

II-2

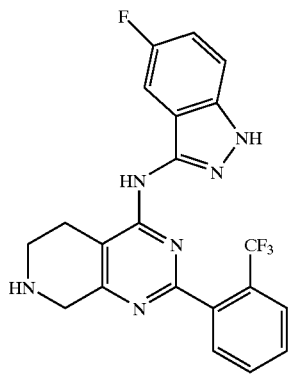

II-3

TABLE 1-continued

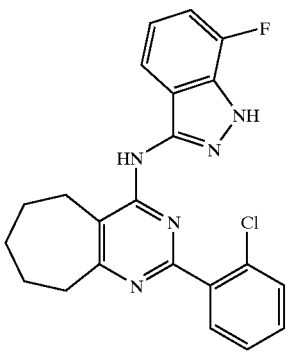

II-4

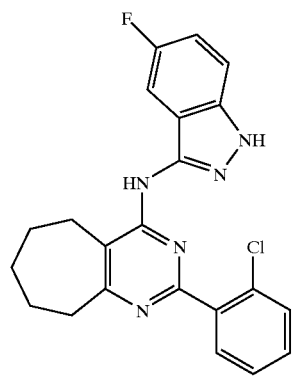

II-5

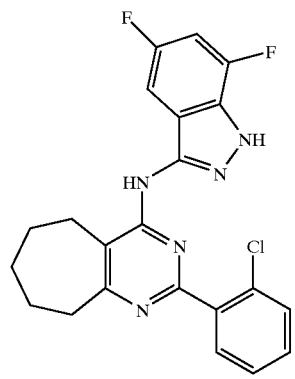

II-6

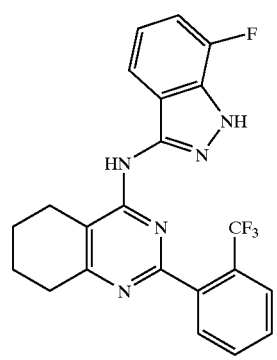

II-7

TABLE 1-continued
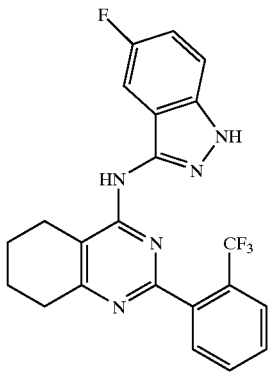
II-8
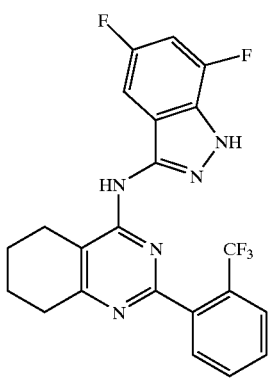
II-9
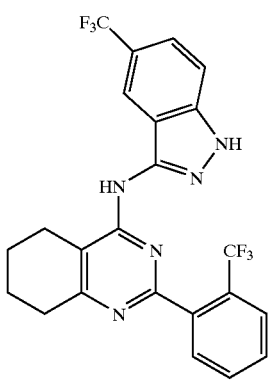
II-10
TABLE 1-continued
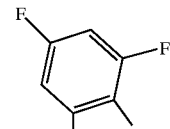
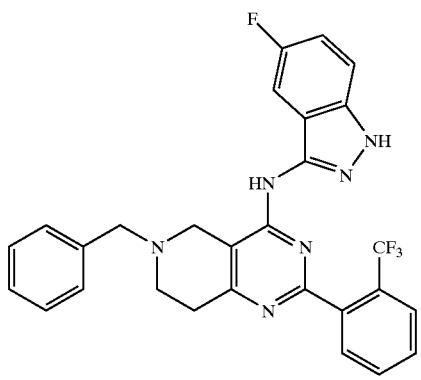
II-11
II-12
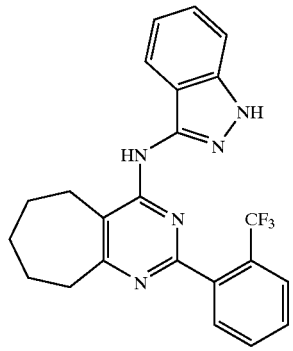
II-13
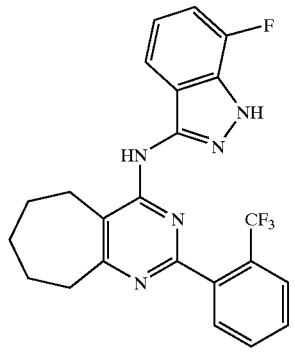
II-14

TABLE 1-continued
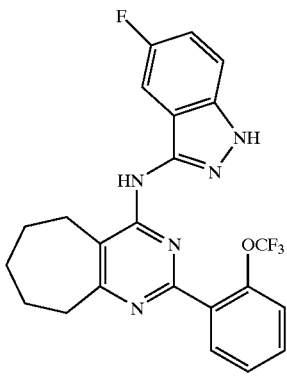
II-15
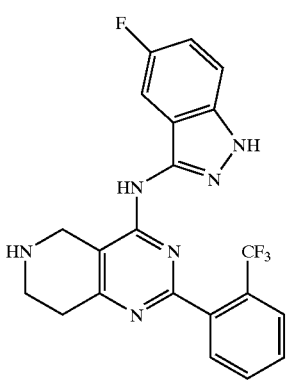
II-16
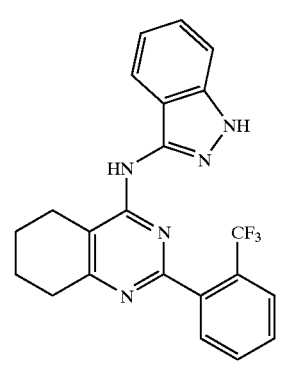
II-17
TABLE 1-continued
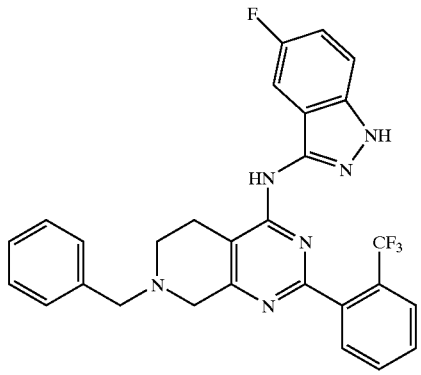
II-18
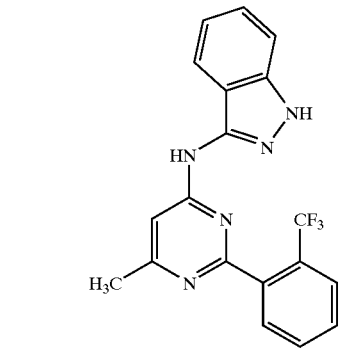
II-19
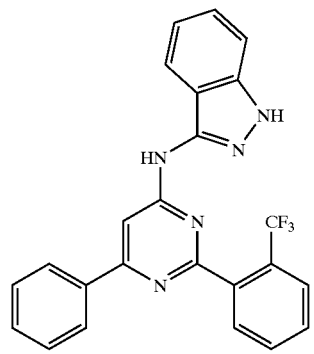
II-20
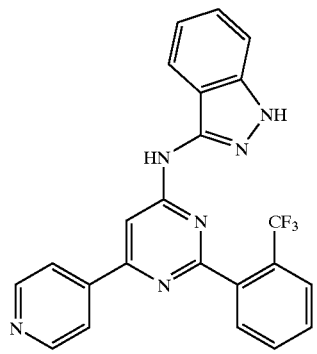
II-21

TABLE 1-continued
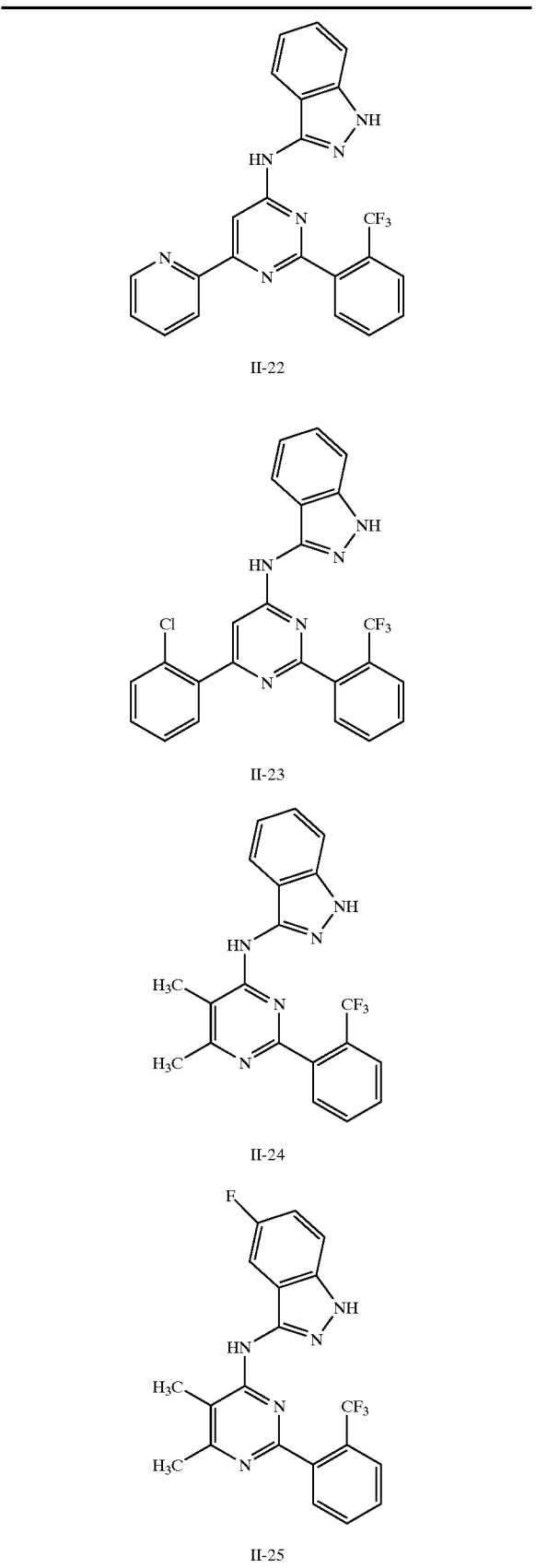
II-22
II-23
II-24
II-25
TABLE 1-continued
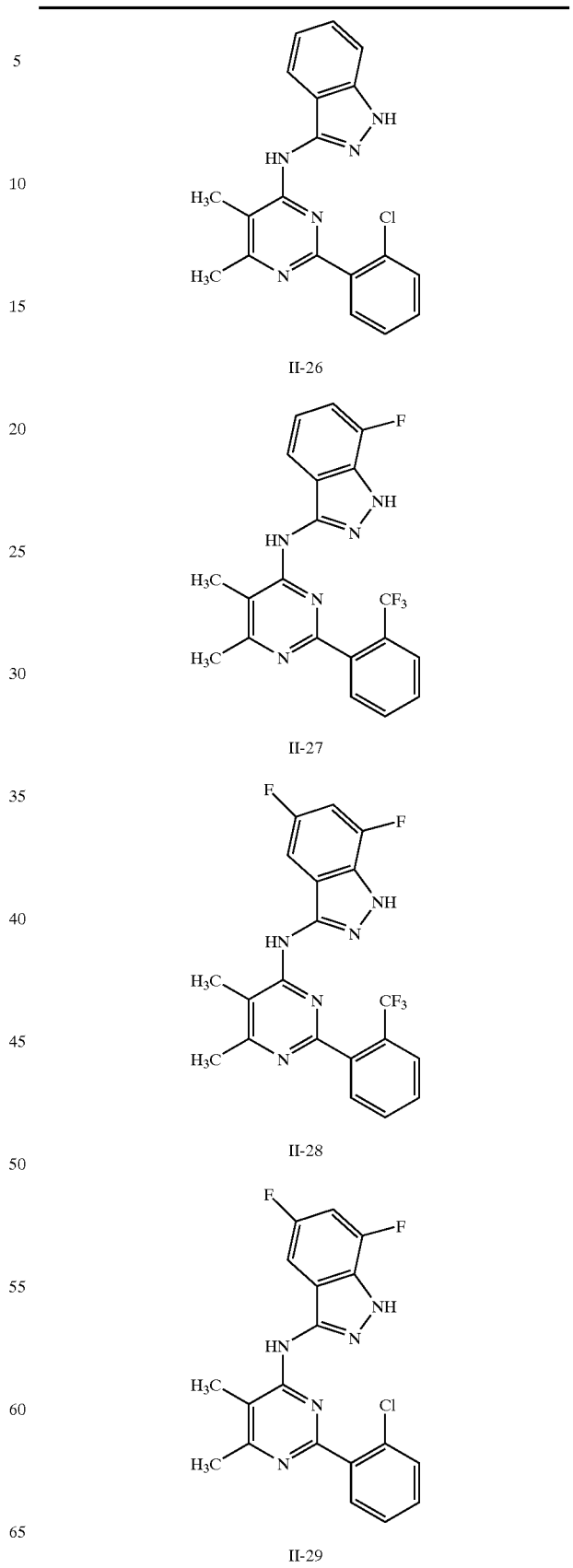
II-26
II-27
II-28
II-29

TABLE 1-continued
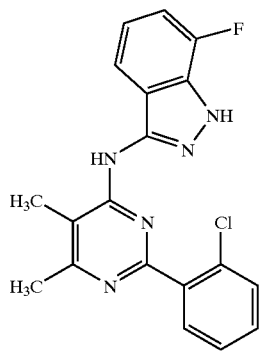
II-30
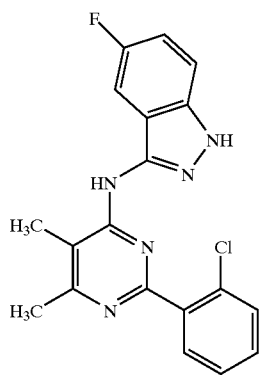
II-31
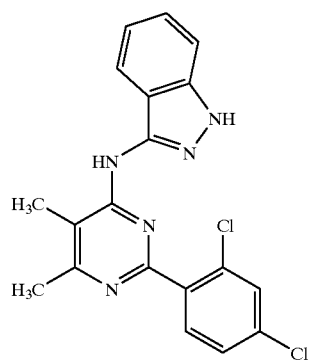
II-32
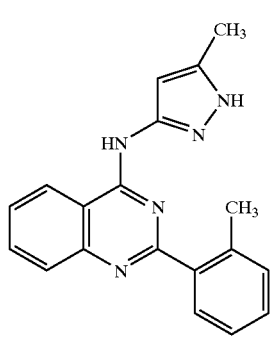
II-33
TABLE 1-continued
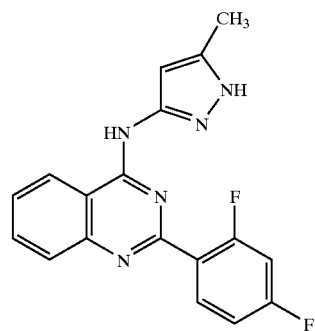
II-34
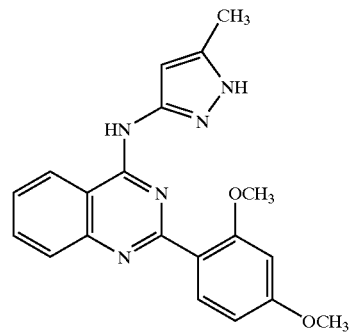
II-35
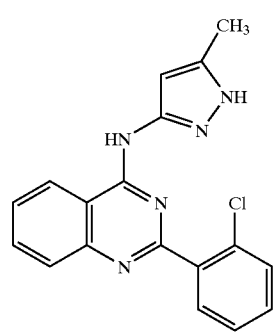
II-36
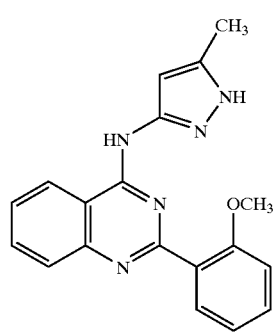
II-37

TABLE 1-continued
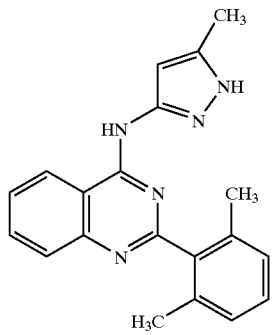
II-38
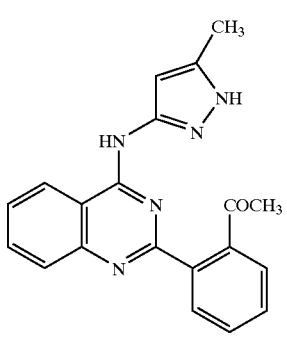
II-39
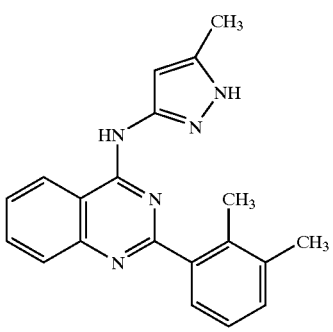
II-40
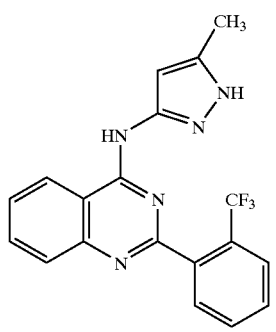
II-41
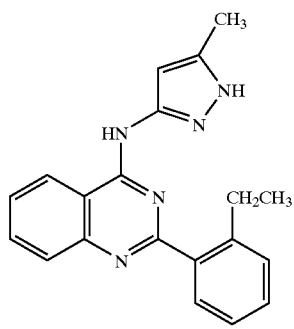
II-42
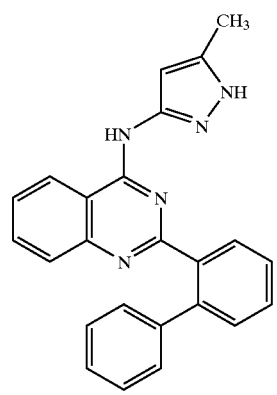
II-43
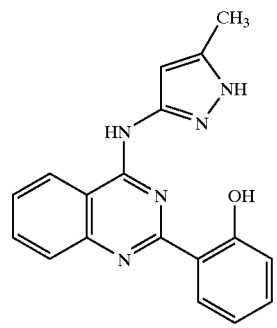
II-44
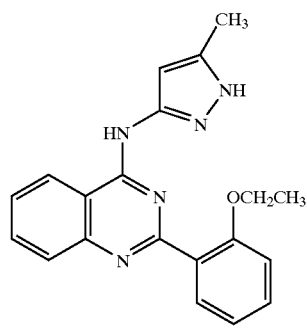
II-45

TABLE 1-continued
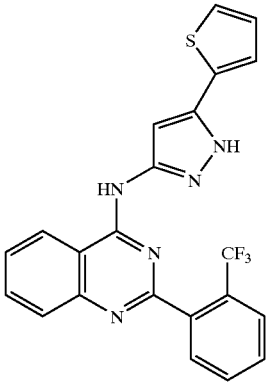
II-46
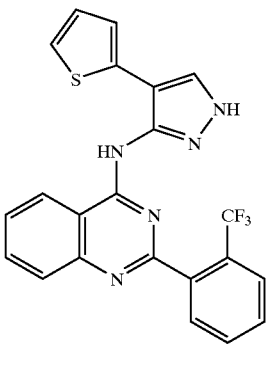
II-47
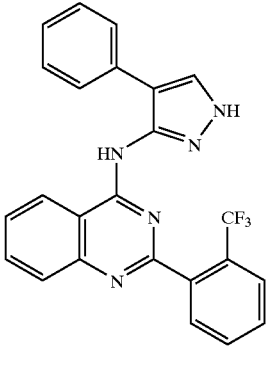
II-48
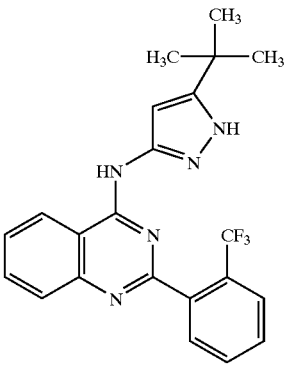
II-49
TABLE 1-continued
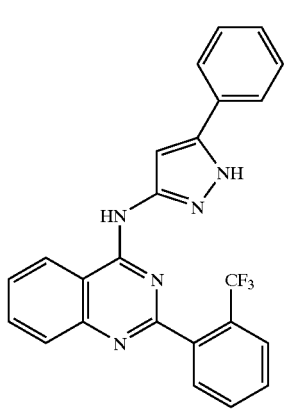
II-50
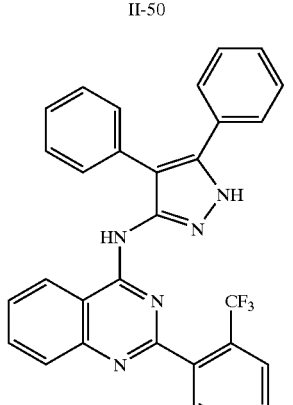
II-51
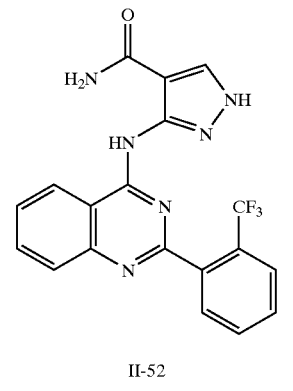
II-52
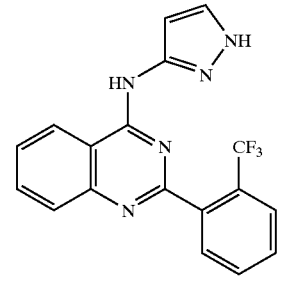
II-53

TABLE 1-continued
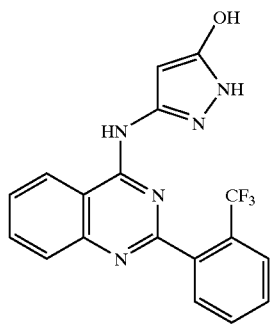
II-54
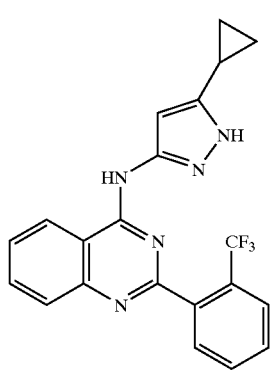
II-55
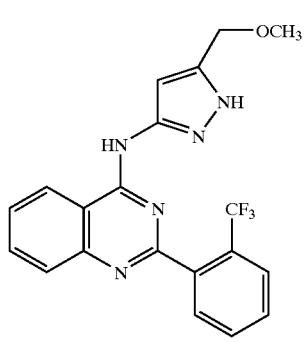
II-56
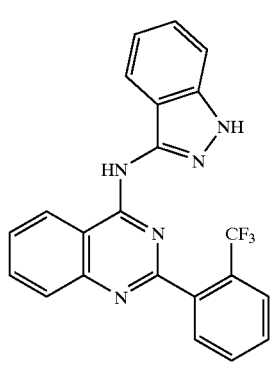
II-57
TABLE 1-continued
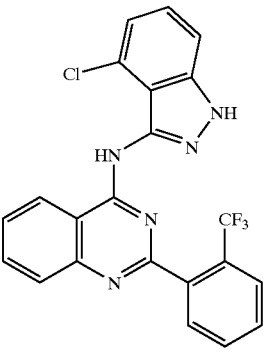
II-58
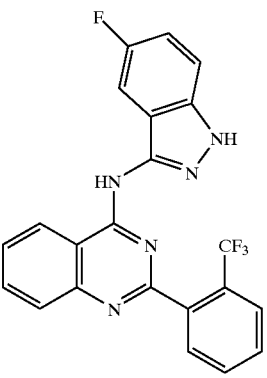
II-59
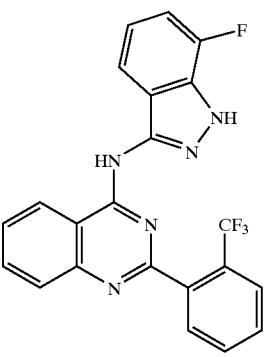
II-60
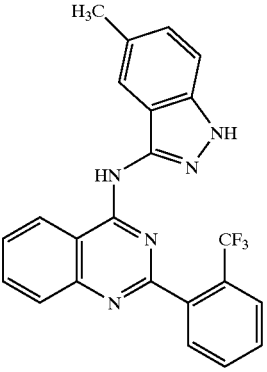
II-61

TABLE 1-continued
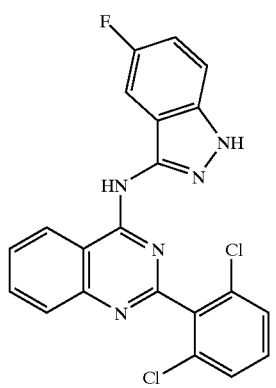
II-62
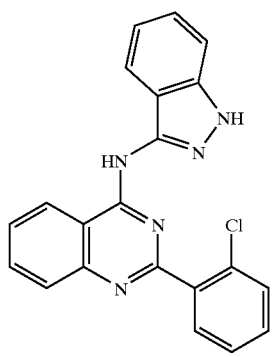
II-63
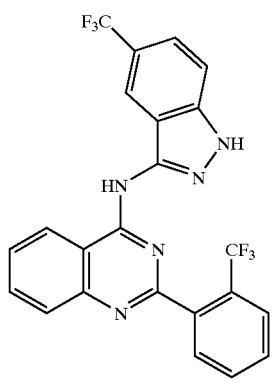
II-64
TABLE 1-continued
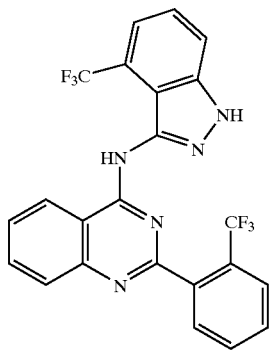
II-65
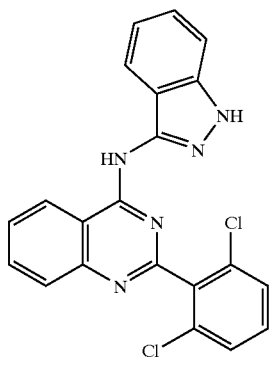
II-66
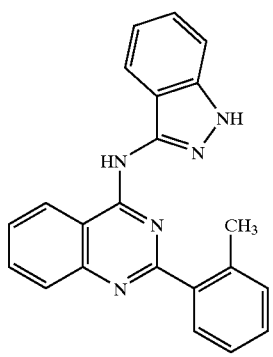
II-67
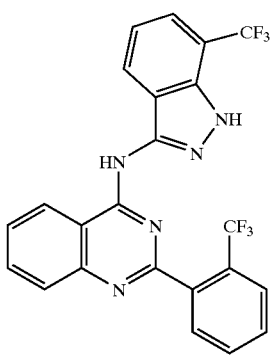
II-68

TABLE 1-continued
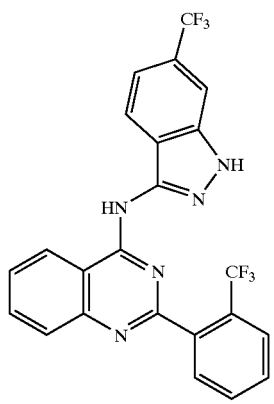
II-69
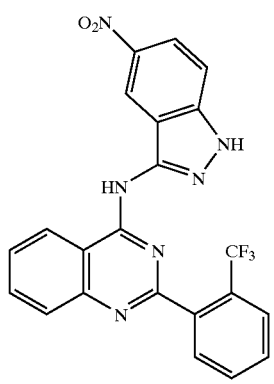
II-70
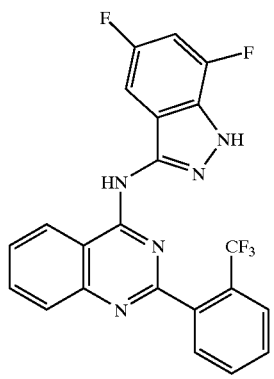
II-71
TABLE 1-continued
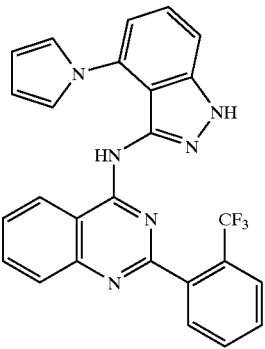
II-72
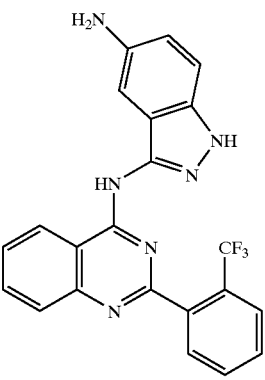
II-73
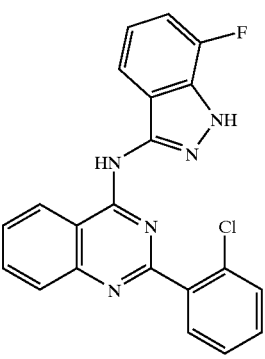
II-74
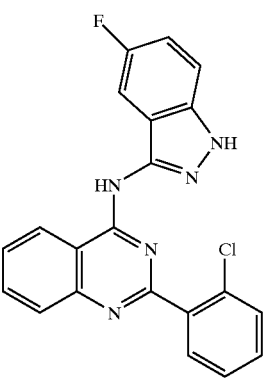
II-75

TABLE 1-continued
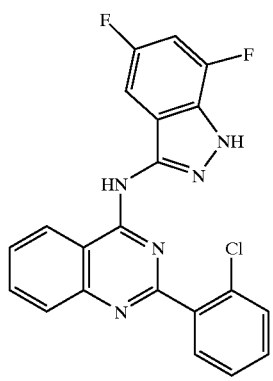
II-76
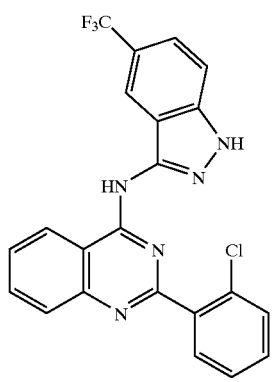
II-77
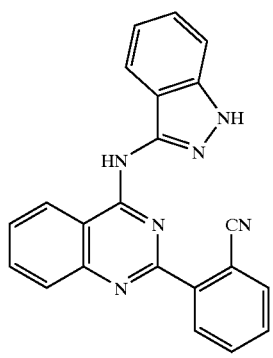
II-78
TABLE 1-continued
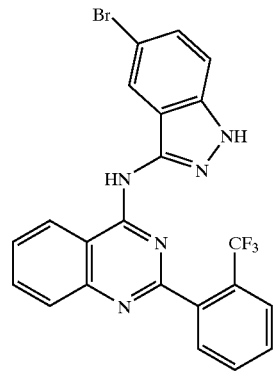
II-79
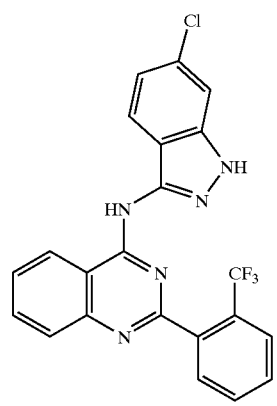
II-80
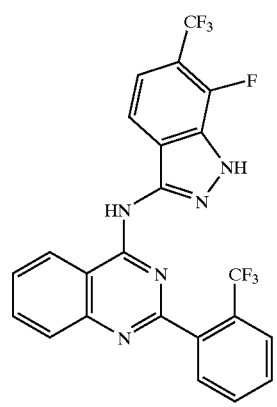
II-81

TABLE 1-continued
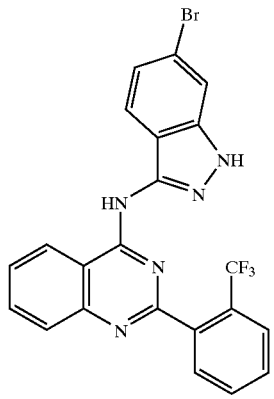
II-82
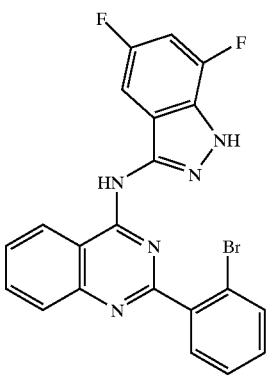
II-85
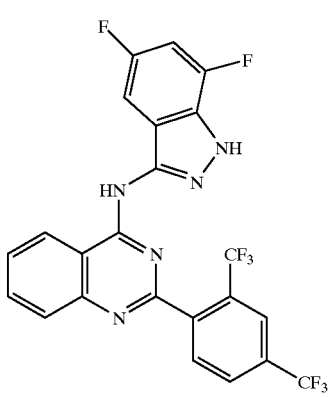
II-83
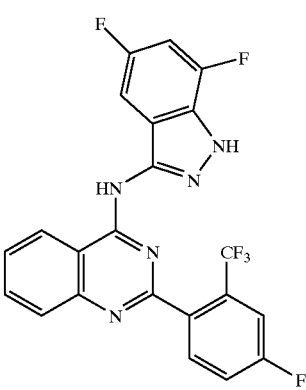
II-86
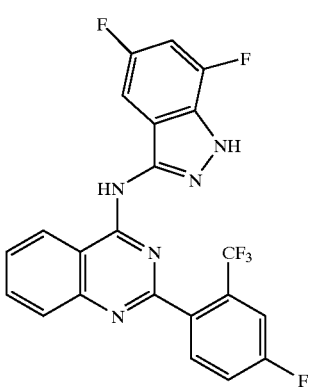
II-84
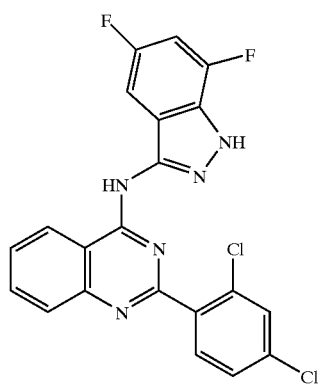
II-87

TABLE 1-continued
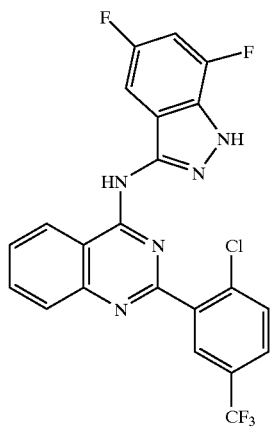
II-88
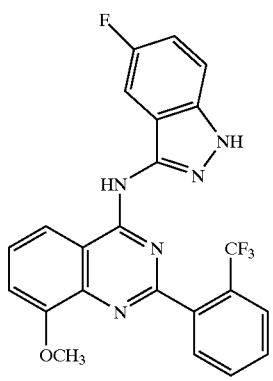
II-91
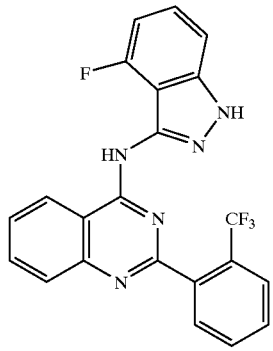
II-89
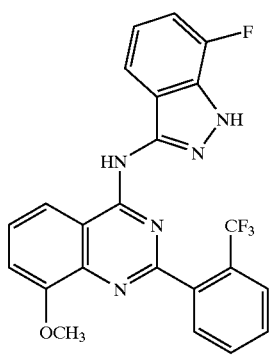
II-92
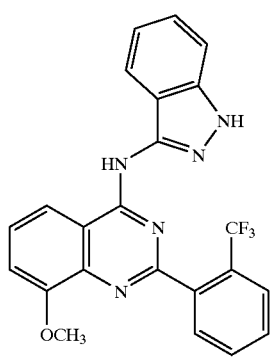
II-90
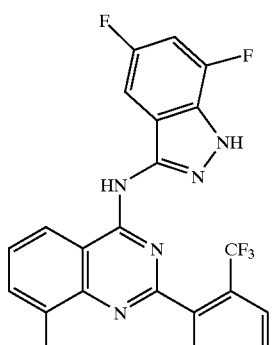
II-93

TABLE 1-continued
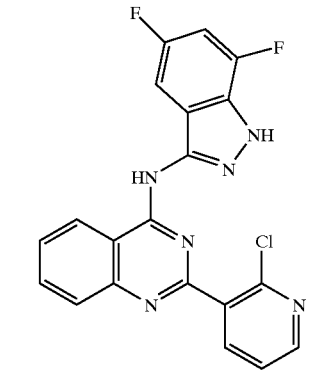
II-94
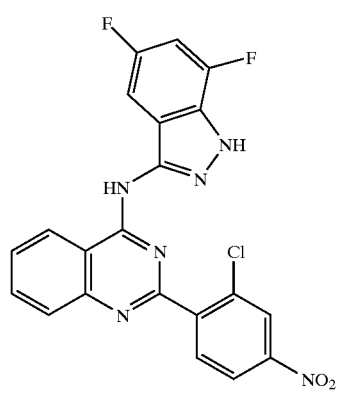
II-95
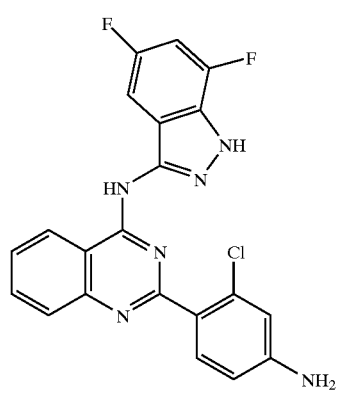
II-96
TABLE 1-continued
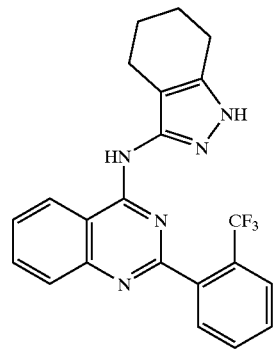
II-97
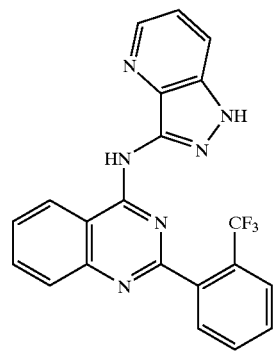
II-98
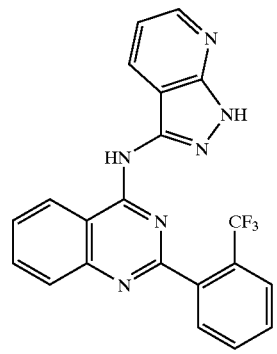
II-99
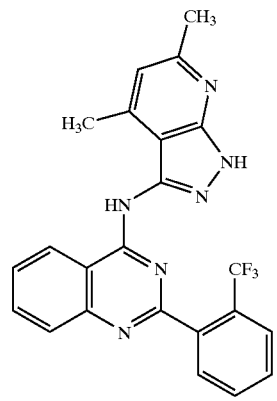
II-100

TABLE 1-continued
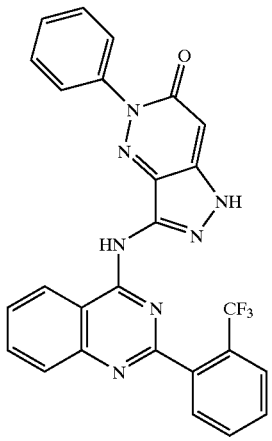
II-101
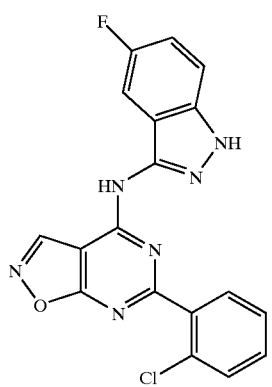
II-102
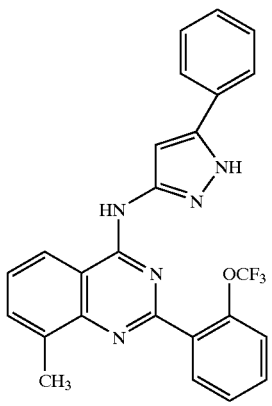
II-103
TABLE 1-continued
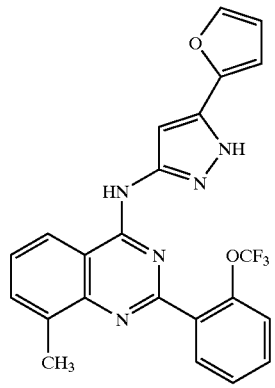
II-104
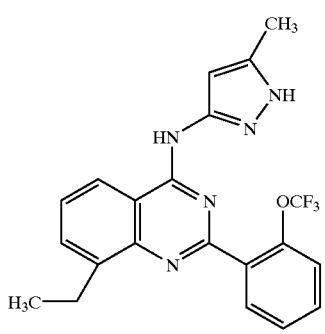
II-105
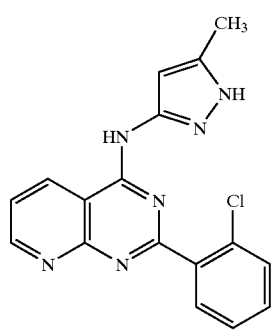
II-106
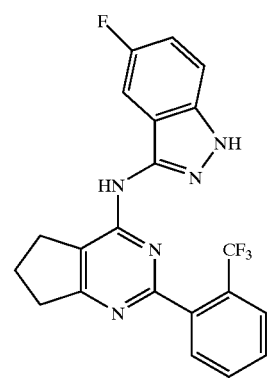
II-107

TABLE 1-continued
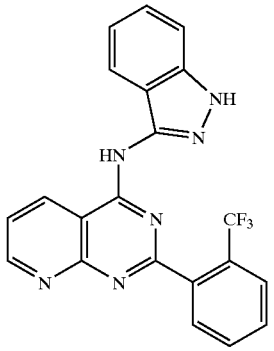
II-108
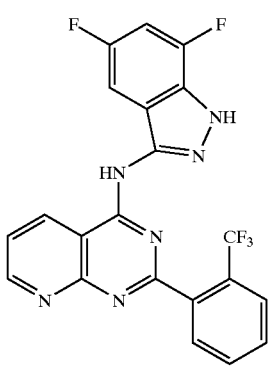
II-109
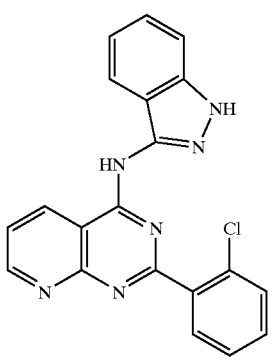
II-110
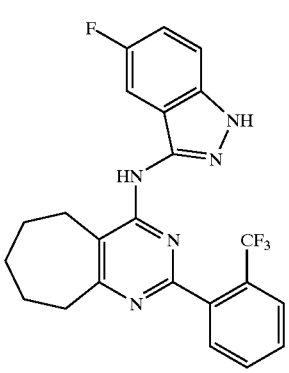
II-111
TABLE 1-continued
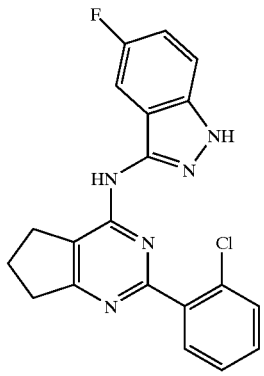
II-112
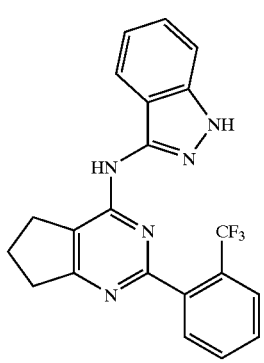
II-113
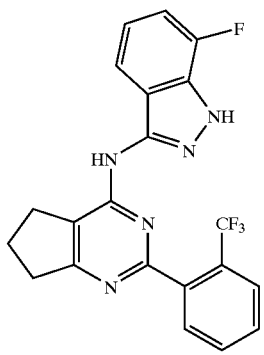
II-114
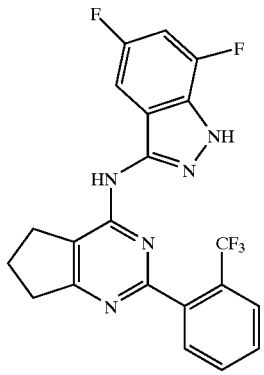
II-115

TABLE 1-continued
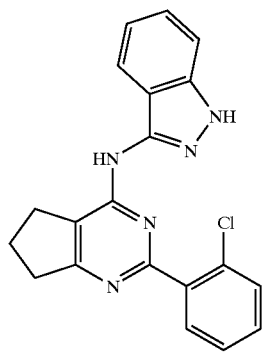
II-116
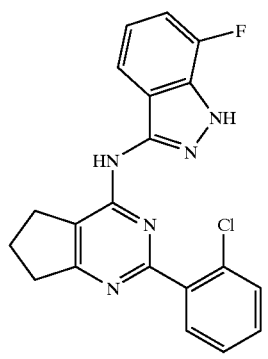
II-117
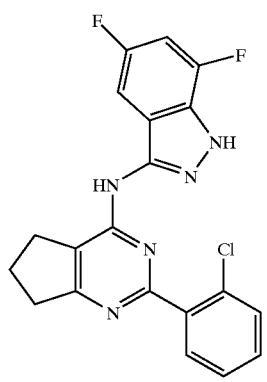
II-118
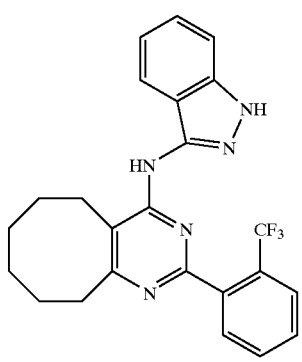
II-119
TABLE 1-continued
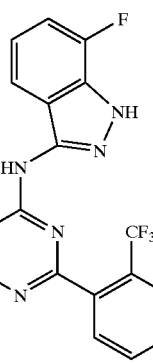
II-120
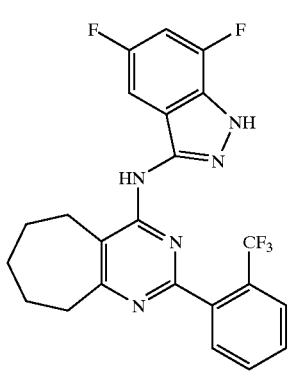
II-121
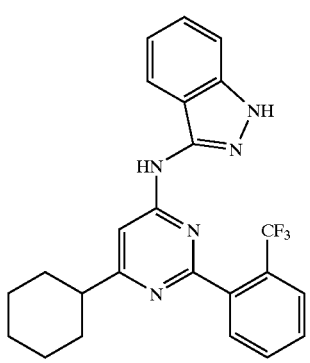
II-122
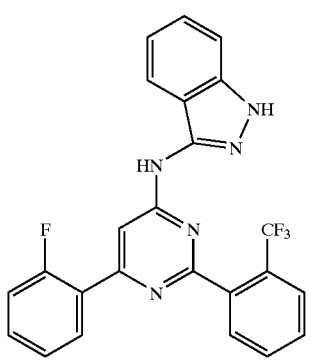
II-123

TABLE 1-continued
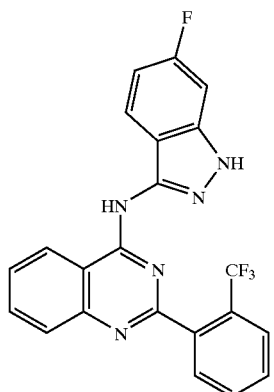
II-124
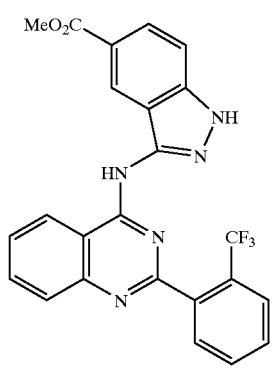
II-125
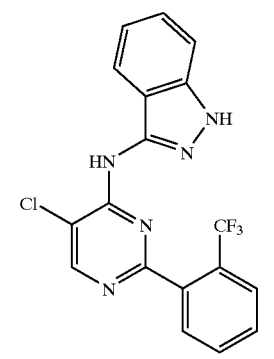
II-126
TABLE 1-continued
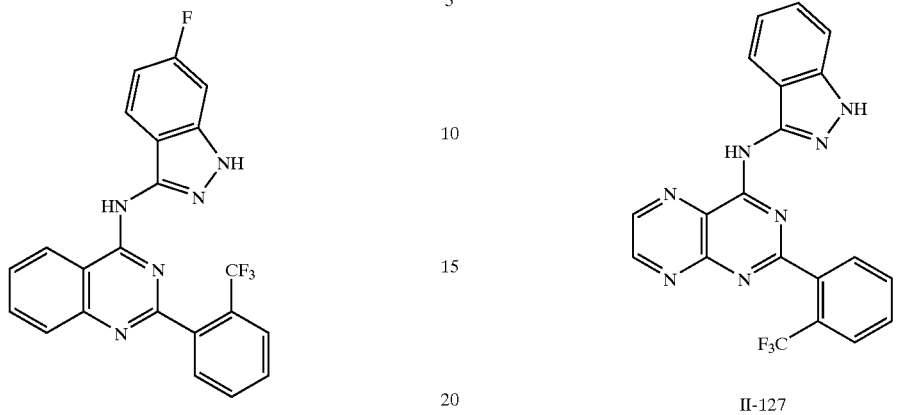
II-127
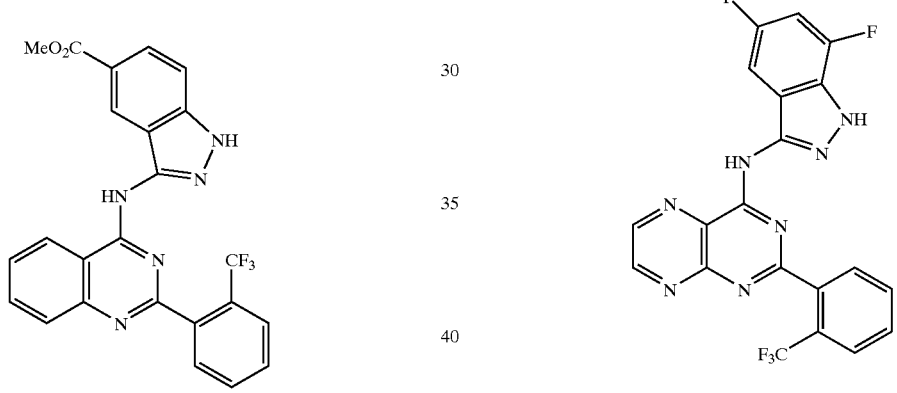
II-128
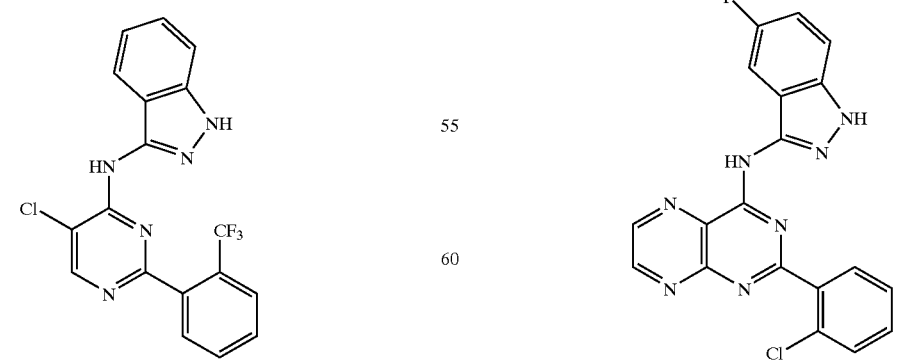
II-129

TABLE 1-continued
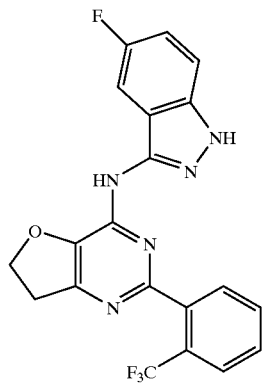
II-130
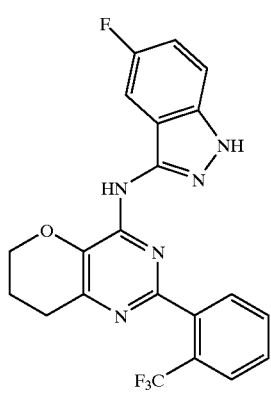
II-131
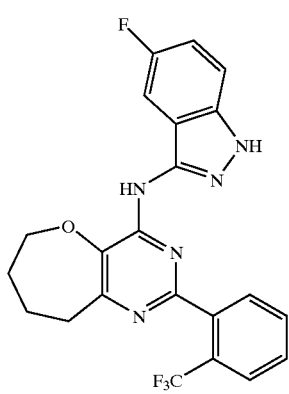
II-132
TABLE 1-continued
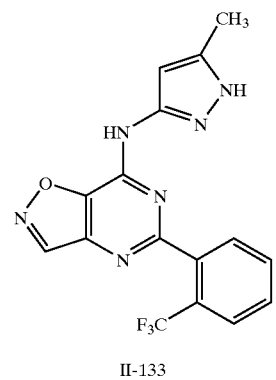
II-133
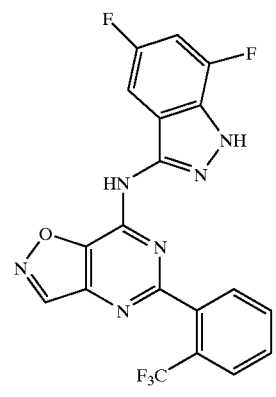
II-134
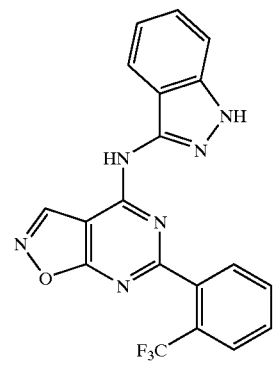
II-135
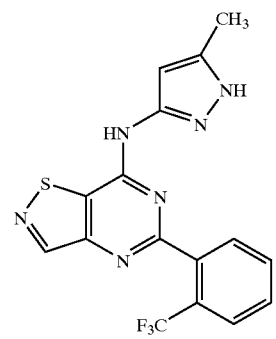
II-136

TABLE 1-continued
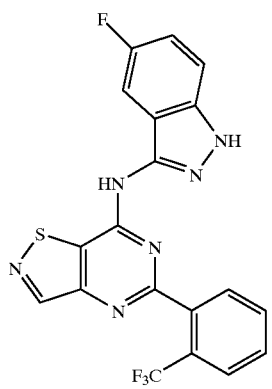
II-137
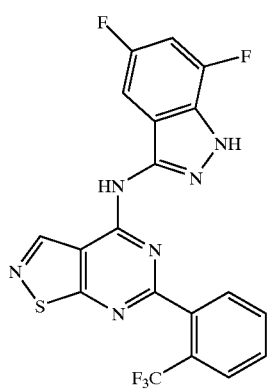
II-138
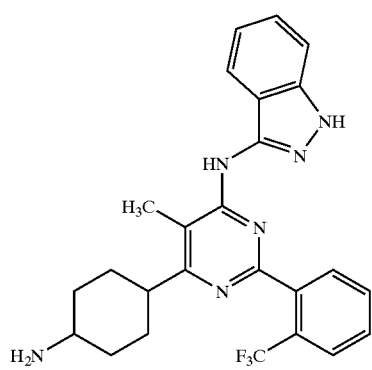
II-139
TABLE 1-continued
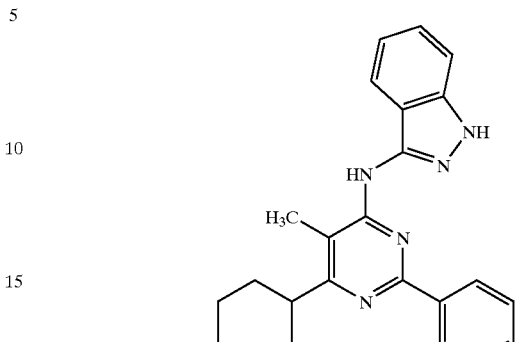
II-140
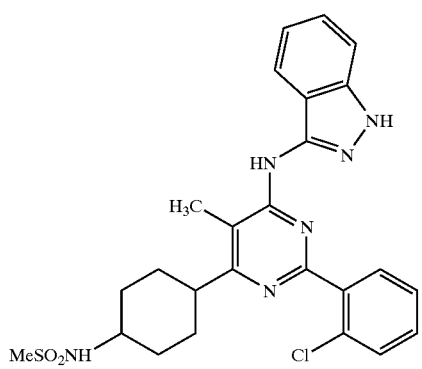
II-141
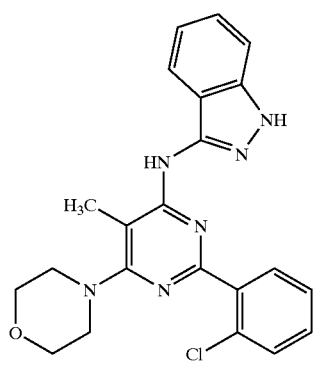
II-142

TABLE 1-continued
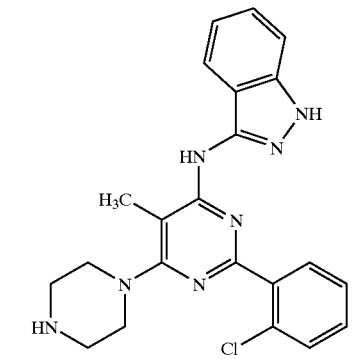
II-143
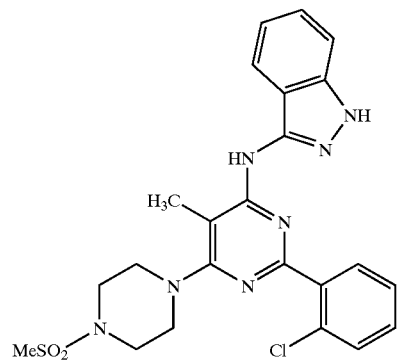
II-146
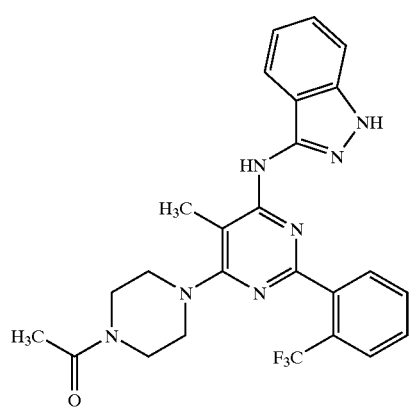
II-144
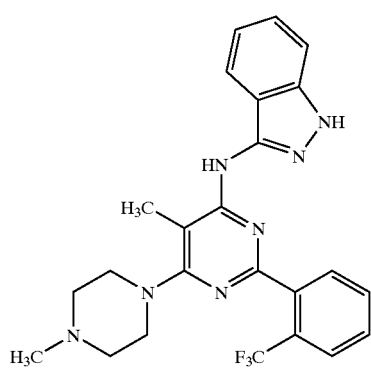
II-147
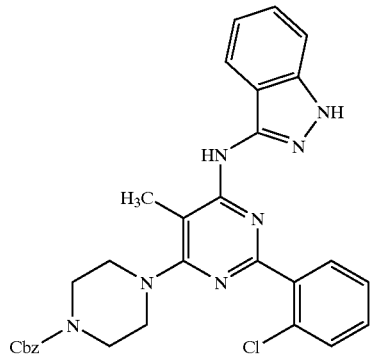
II-145
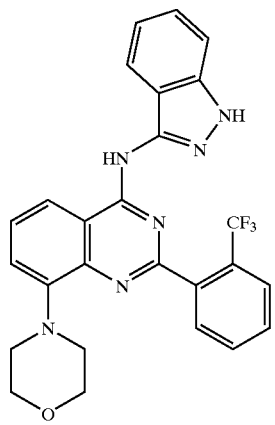
II-148

TABLE 1-continued
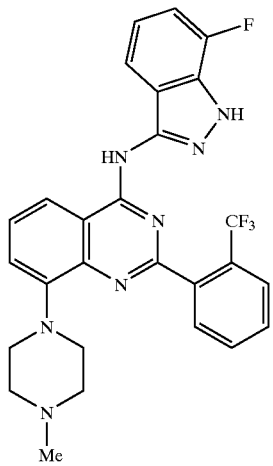
II-149
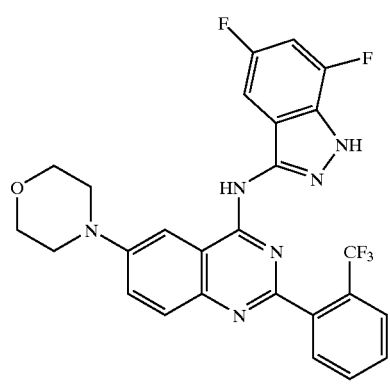
II-150
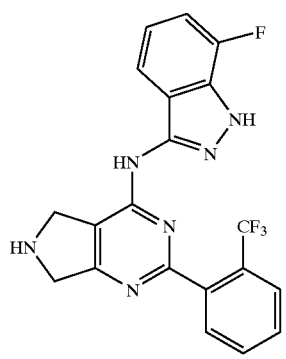
II-151
TABLE 1-continued
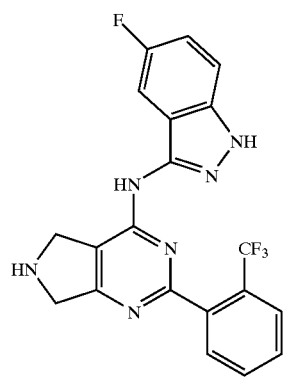
II-152
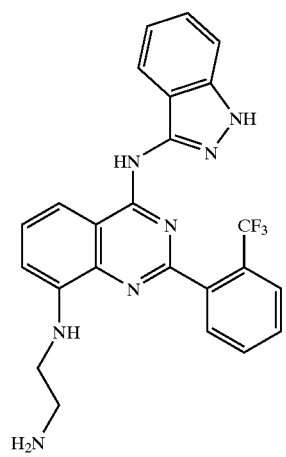
II-153
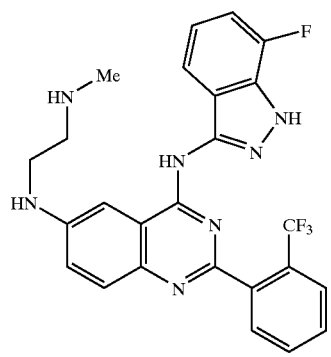
II-154

TABLE 1-continued
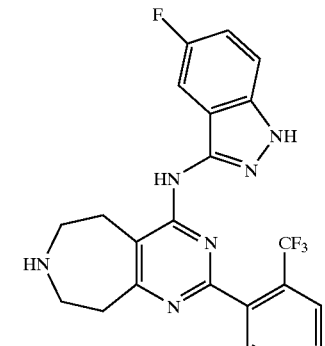
II-155
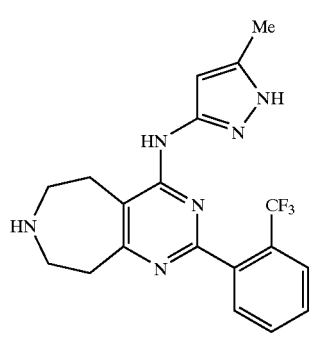
II-156
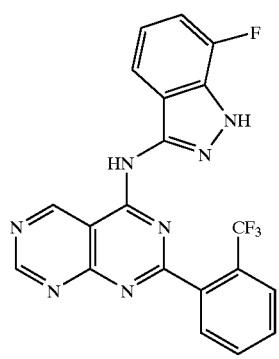
II-157
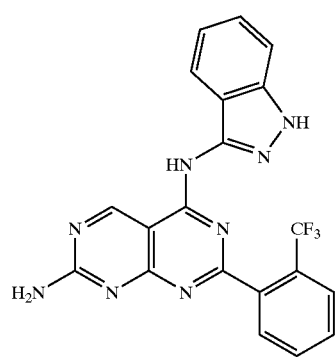
II-158
TABLE 1-continued
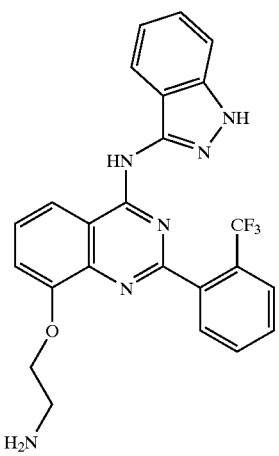
II-159
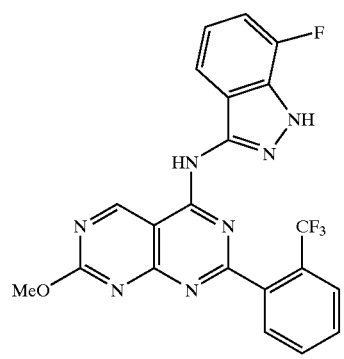
II-160
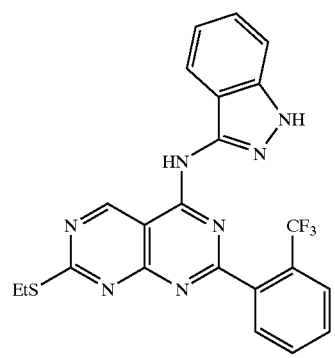
II-161

TABLE 1-continued
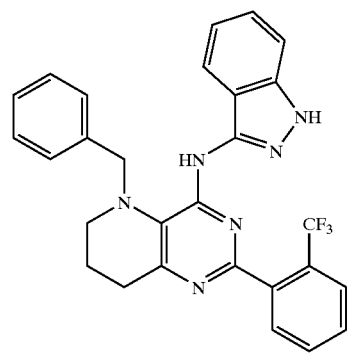
II-162
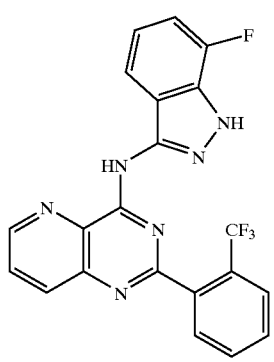
II-163
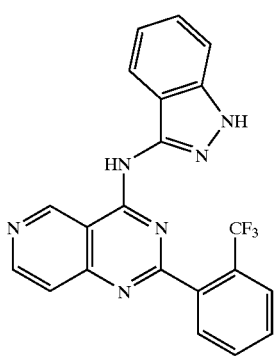
II-164
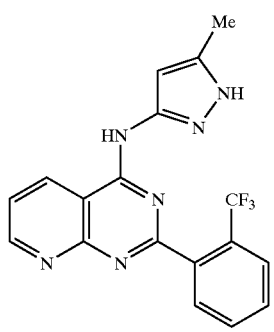
II-165
TABLE 1-continued
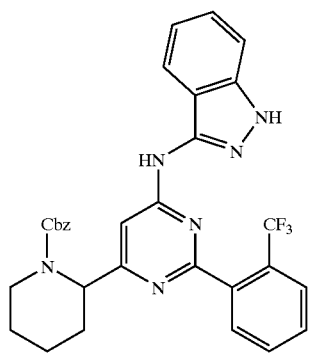
II-166
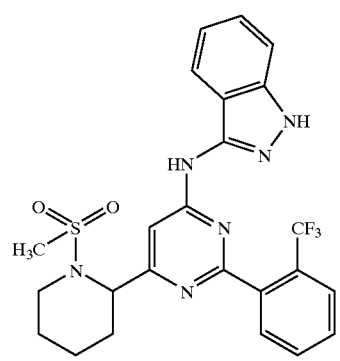
II-167
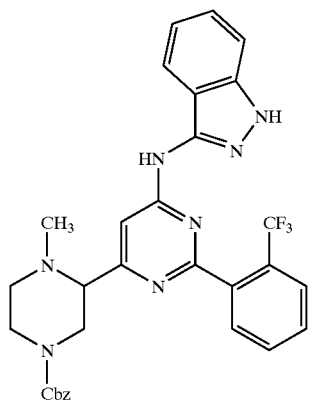
II-168

TABLE 1-continued
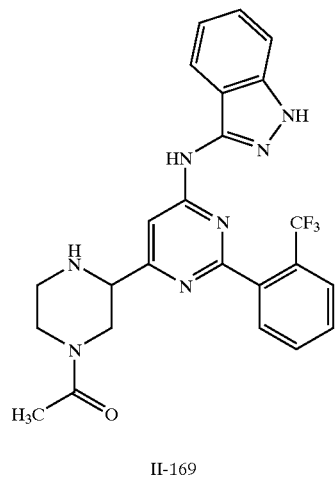
II-169
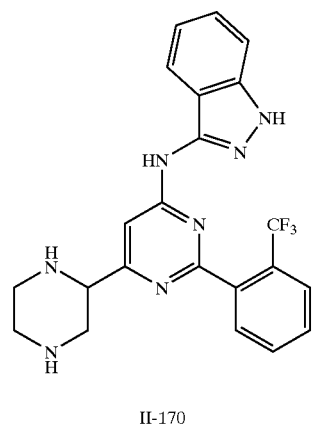
II-170
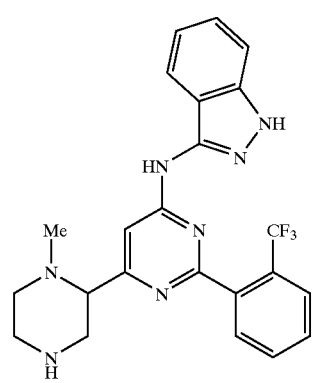
II-171
TABLE 1-continued
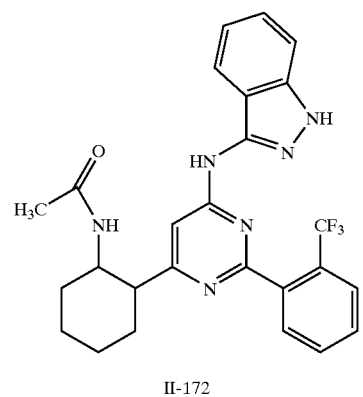
II-172
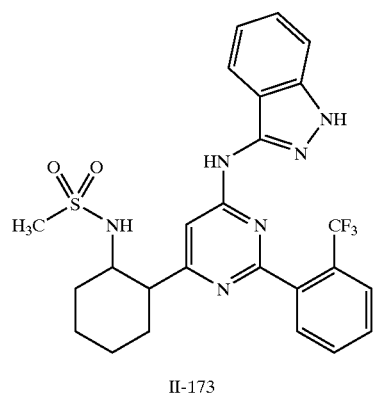
II-173
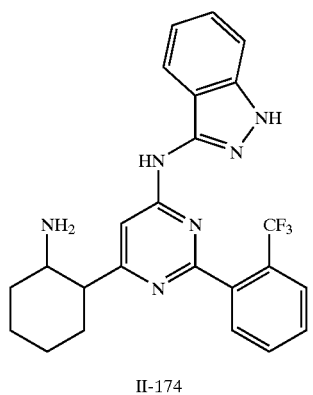
II-174
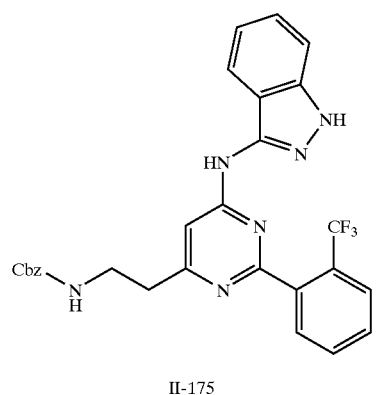
II-175

TABLE 1-continued
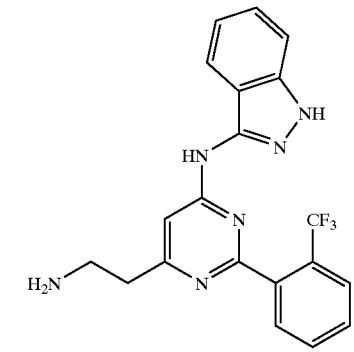
II-176
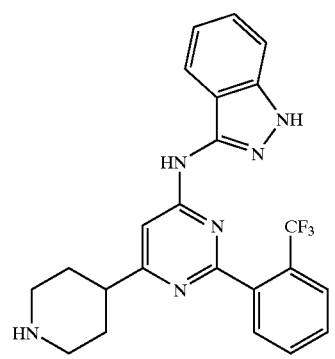
II-177
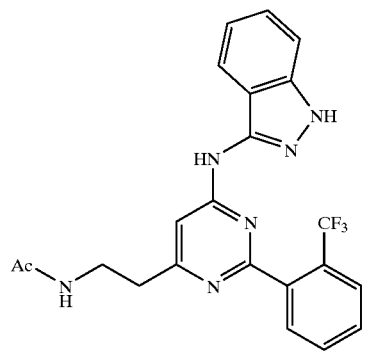
II-178
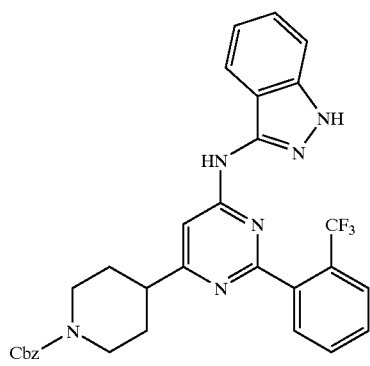
II-179
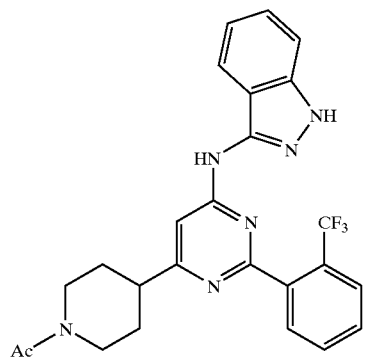
II-180
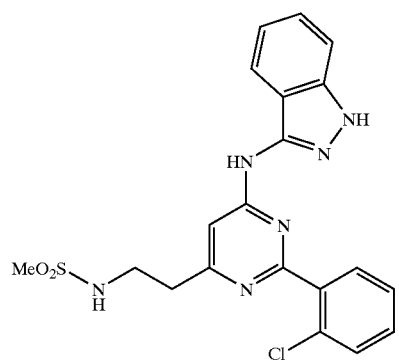
II-181
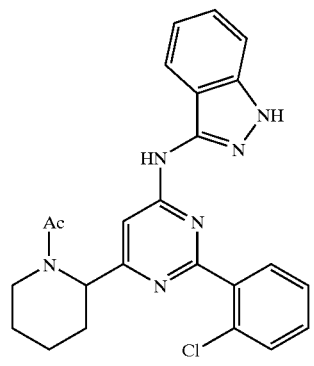
II-182
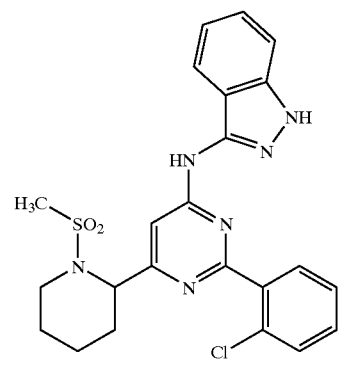
II-183

TABLE 1-continued
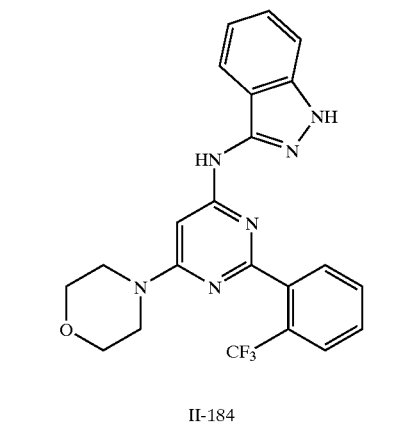
II-184
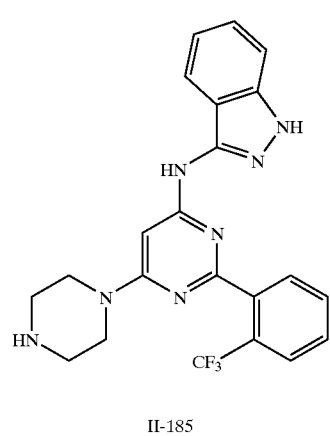
II-185
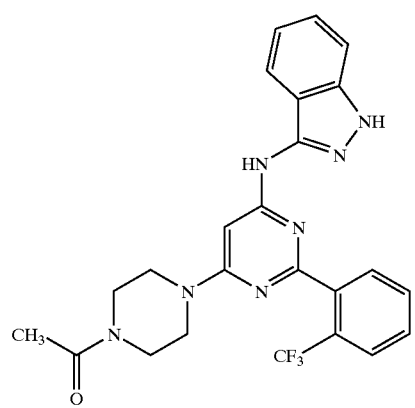
II-186
TABLE 1-continued
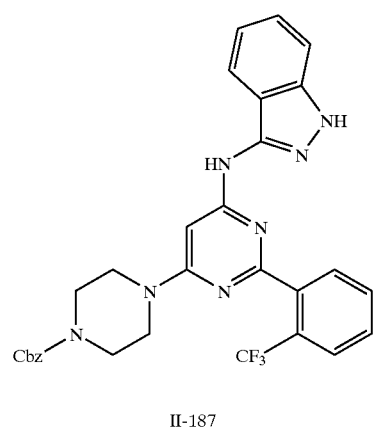
II-187
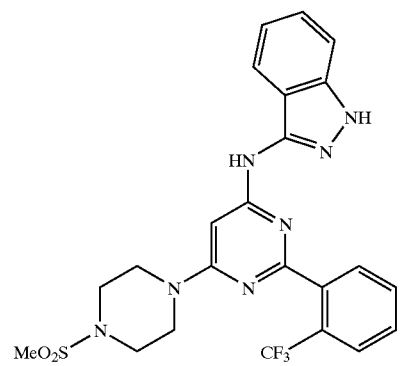
II-188
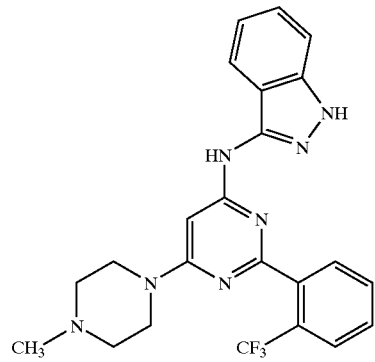
II-189

TABLE 1-continued
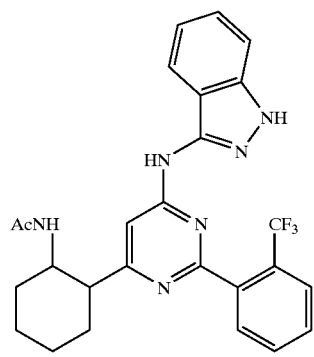
II-190
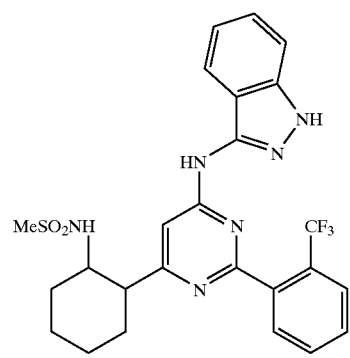
II-191
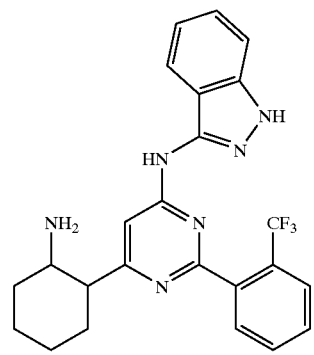
II-192
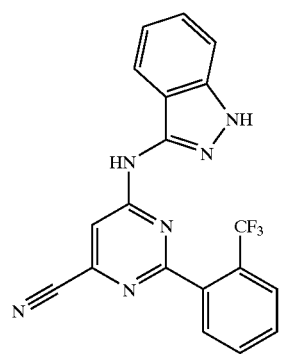
II-193
TABLE 1-continued
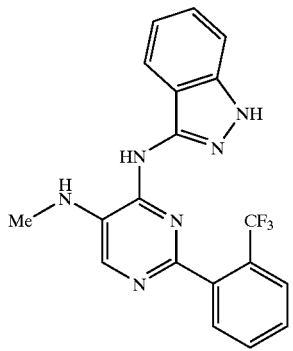
II-194
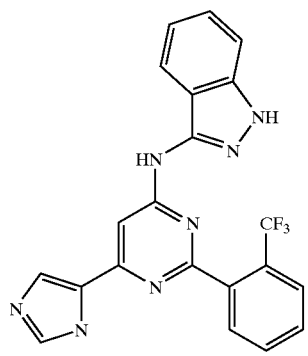
II-195
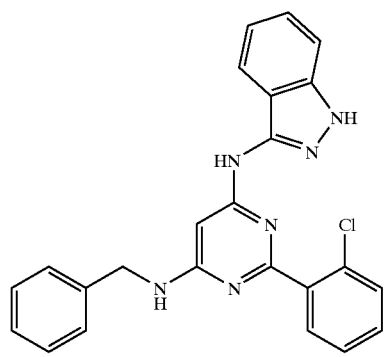
II-196
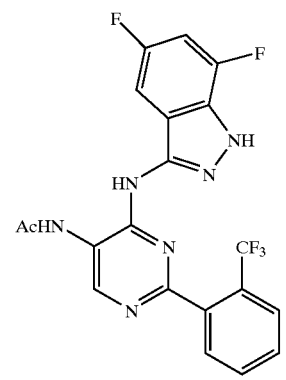
II-197

TABLE 1-continued
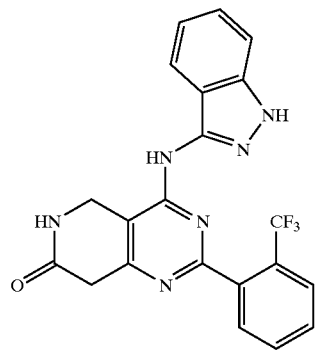
II-198
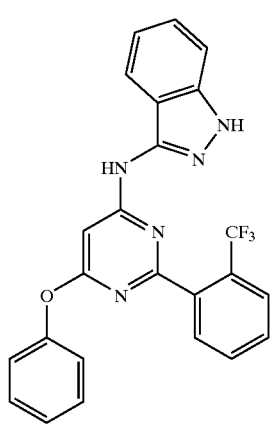
II-199
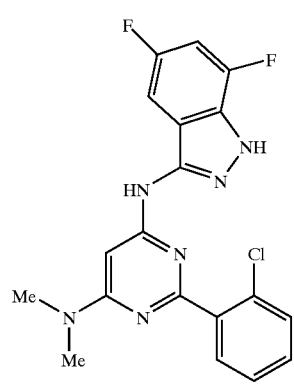
II-200
TABLE 1-continued
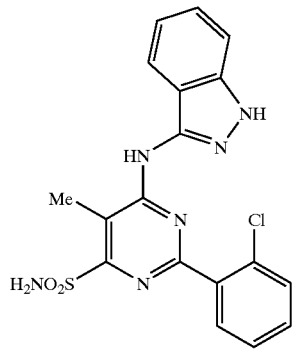
II-201
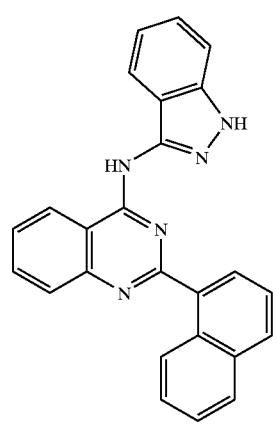
II-202
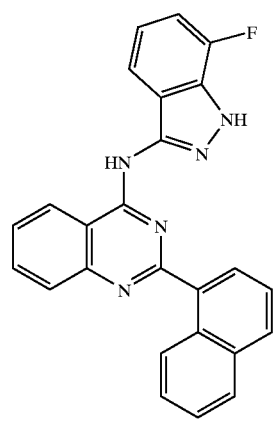
II-203

TABLE 1-continued
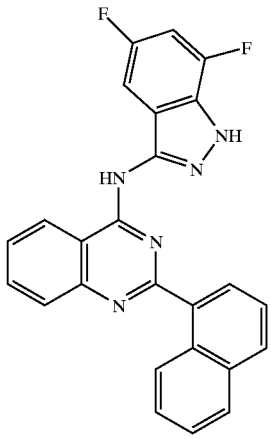
II-204
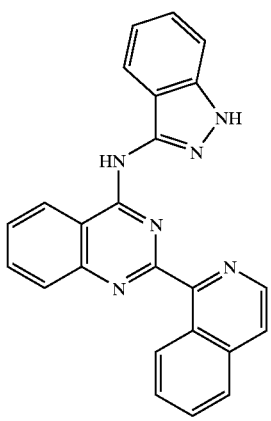
II-205

II-206
TABLE 1-continued
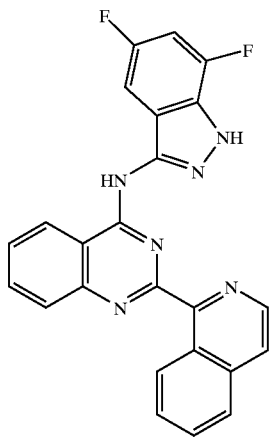
II-207
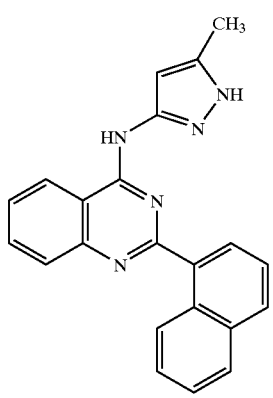
II-208
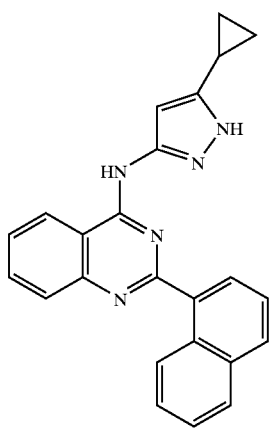
II-209

TABLE 1-continued
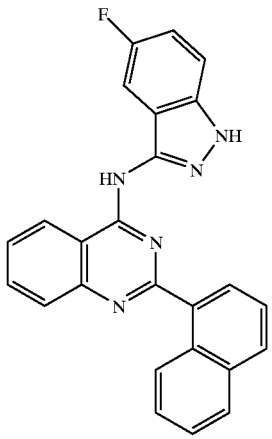
II-210
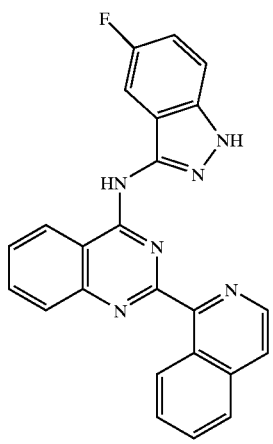
II-213
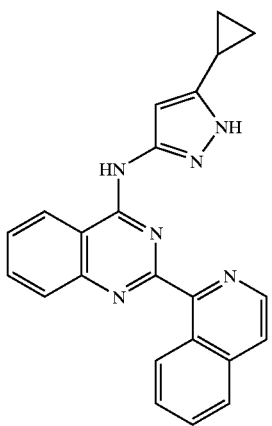
II-211
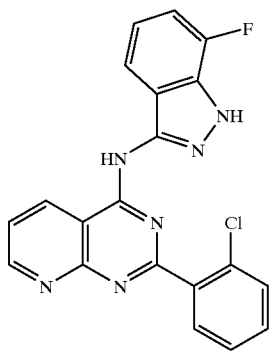
II-214
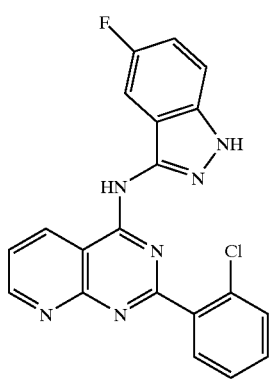
II-212
II-215

TABLE 1-continued
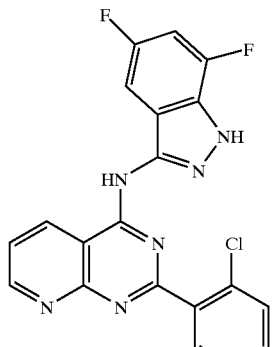
II-216
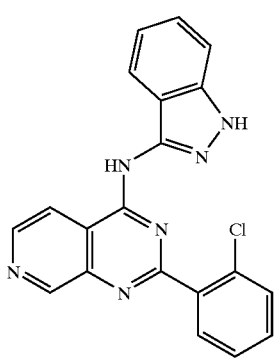
II-217
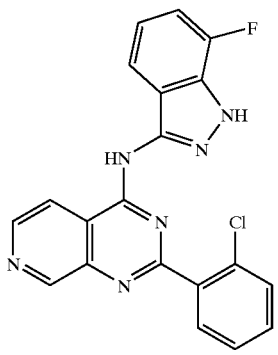
II-218
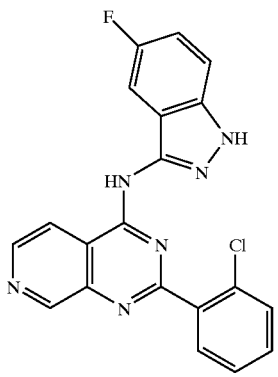
II-219
TABLE 1-continued
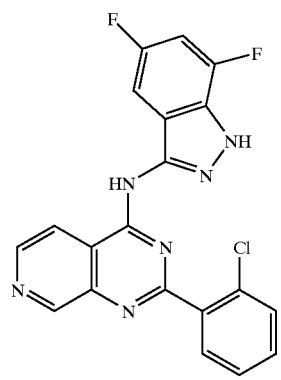
II-220
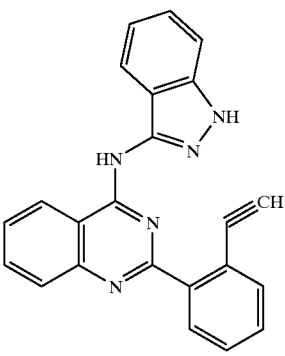
II-221
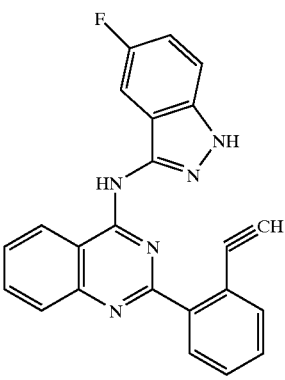
II-222

TABLE 1-continued
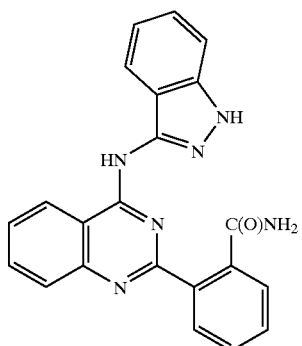
II-223
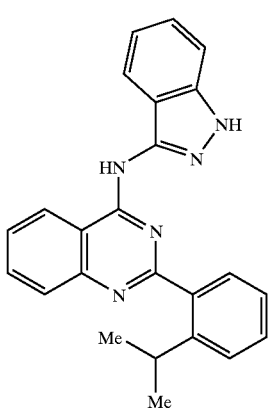
II-224
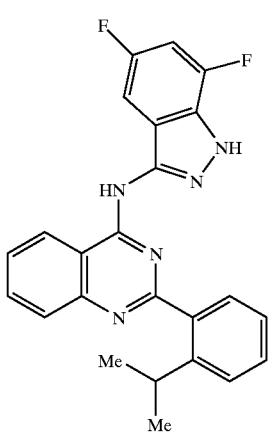
II-225
TABLE 1-continued
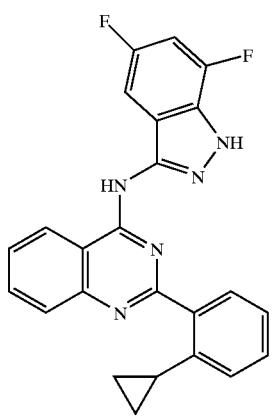
II-226
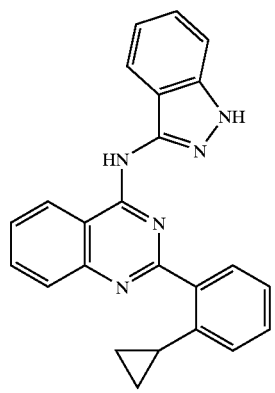
II-227
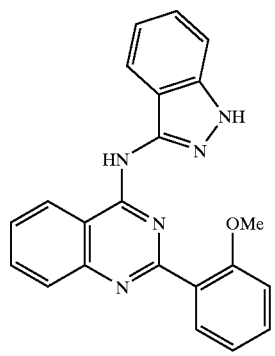
II-228

TABLE 1-continued
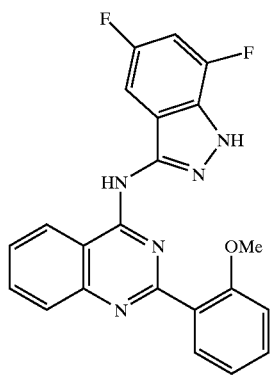
II-229
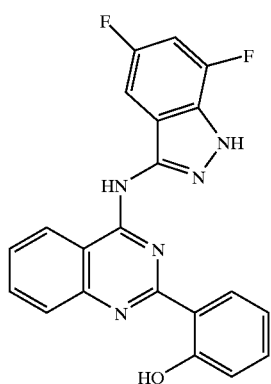
II-230
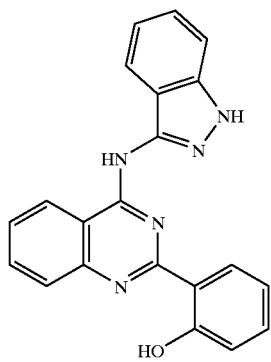
II-231
TABLE 1-continued
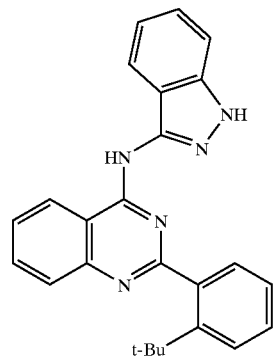
II-232
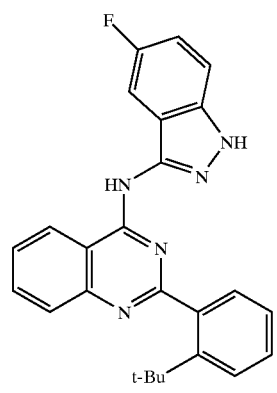
II-233
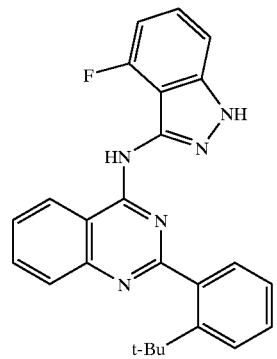
II-234

TABLE 1-continued
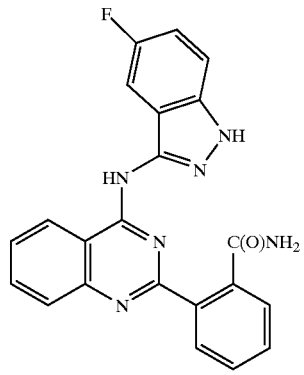
II-235
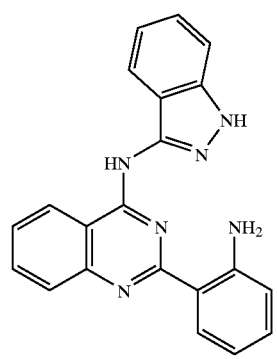
II-236
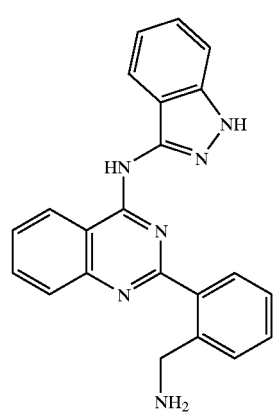
II-237
TABLE 1-continued
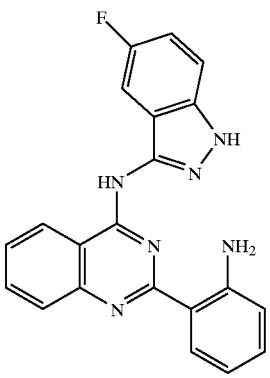
II-238
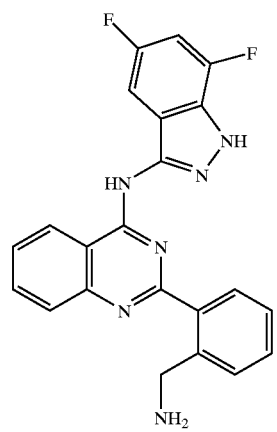
II-239
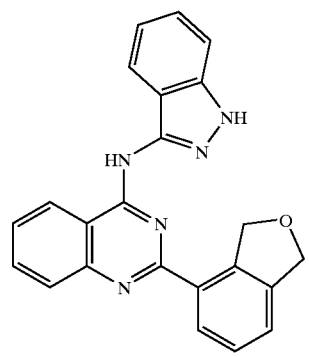
II-240

TABLE 1-continued
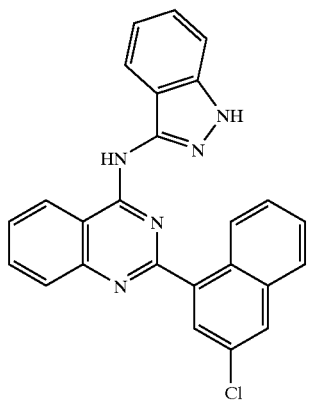
II-241
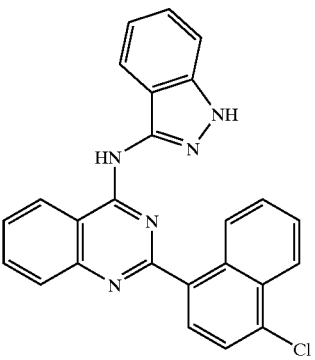
II-242
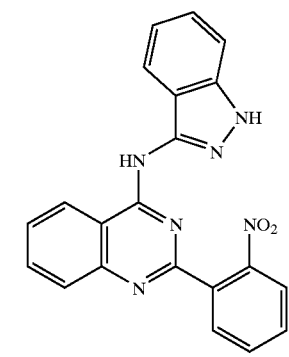
II-243
TABLE 1-continued
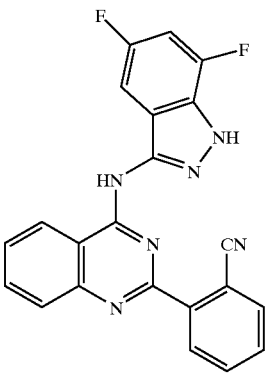
II-244
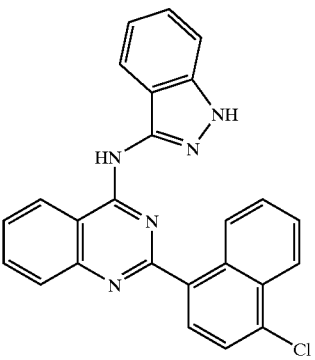
II-245
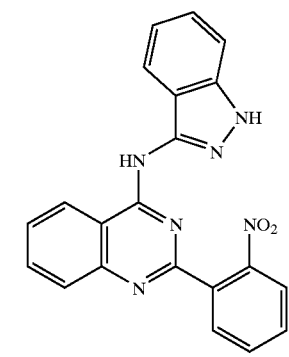
II-246

TABLE 1-continued

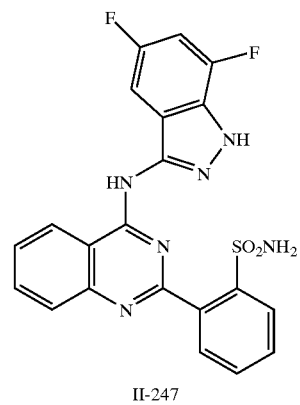

II-247

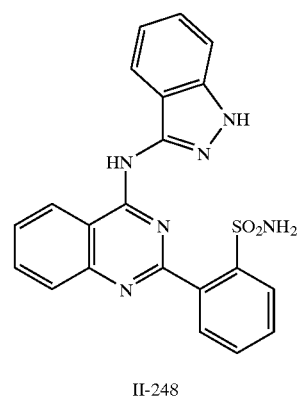

II-248

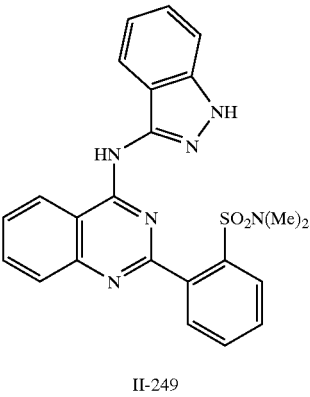

II-249

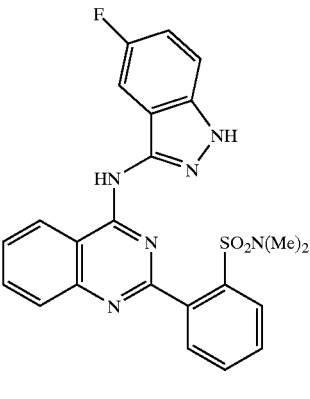

II-250

TABLE 1-continued

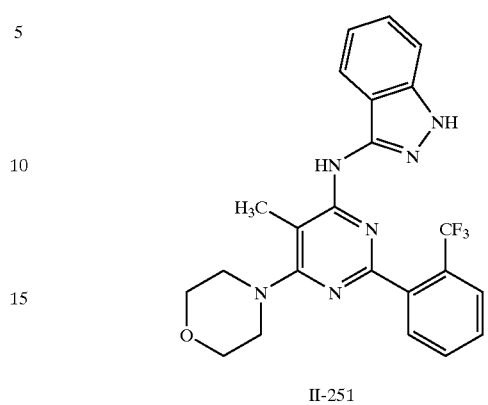

II-251

In another embodiment, this invention provides a composition comprising a compound of formula II and a pharmaceutically acceptable carrier.

One aspect of this invention relates to a method of inhibiting GSK-3 activity in a patient, comprising administering to the patient a therapeutically effective amount of a composition comprising a compound of formula II.

Another aspect relates to a method of treating a disease that is alleviated by treatment with a GSK-3 inhibitor, said method comprising the step of administering to a patient in need of such a treatment a therapeutically effective amount of a composition comprising a compound of formula II.

Another aspect relates to a method of enhancing glycogen synthesis and/or lowering blood levels of glucose in a patient in need thereof, comprising administering to said patient a therapeutically effective amount of a composition comprising a compound of formula II. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula II. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula II. This method is especially useful for treating schizophrenia.

One aspect of this invention relates to a method of inhibiting Aurora activity in a patient, comprising administering to the patient a therapeutically effective amount of a composition comprising a compound of formula II.

Another aspect relates to a method of treating a disease that is alleviated by treatment with an Aurora inhibitor, said method comprising the step of administering to a patient in need of such a treatment a therapeutically effective amount of a composition comprising a compound of formula II. This method is especially useful for treating cancer, such as colon, ovarian, and breast cancer.

One aspect of this invention relates to a method of inhibiting CDK-2 activity in a patient, comprising administering to the patient a therapeutically effective amount of a composition comprising a compound of formula II.

Another aspect relates to a method of treating a disease that is alleviated by treatment with a CDK-2 inhibitor, said method comprising the step of administering to a patient in need of such a treatment a therapeutically effective amount of a composition comprising a compound of formula II. This method is especially useful for treating cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

Another method relates to inhibiting GSK-3, Aurora, or CDK-2 activity in a biological sample, which method comprises contacting the biological sample with the GSK-3 or Aurora inhibitor of formula II, or a pharmaceutical composition thereof, in an amount effective to inhibit GSK-3, Aurora or CDK-2.

Each of the aforementioned methods directed to the inhibition of GSK-3, Aurora or CDK-2, or the treatment of a disease alleviated thereby, is preferably carried out with a preferred compound of formula II, as described above.

Another embodiment of this invention relates to compounds of formula III:

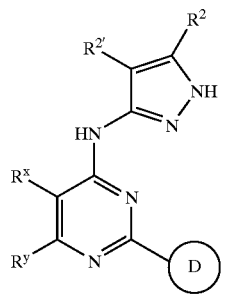

III or a pharmaceutically acceptable derivative or prodrug thereof, wherein:

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^x$ and $R^y$ are taken together with their intervening atoms to form a fused, benzo ring or a 5–8 membered carbocyclo ring, wherein any substitutable carbon on said fused ring formed by $R^x$ and $R^y$ is substituted by oxo or T-$R^3$;

T is a valence bond or a $C_{1-4}$ alkylidene chain;

$R^2$ and $R^{2'}$ are independently selected from —R, -T-W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by $R^2$ and $R^{2'}$ is substituted by halo, oxo, —CN, —$NO_2$, —$R^7$, or —V—$R^6$, and any substitutable nitrogen on said ring formed by $R^2$ and $R^{2'}$ is substituted by $R^4$;

$R^3$ is selected from —R, -halo, =O, —OR, —C(=O)R, —$CO_2$R, —COCOR, —$COCH_2$COR, —$NO_2$, —CN, —S(O)R, —$S(O)_2$R, —SR, —$N(R^4)_2$, —$CON(R^4)_2$, —$SO_2N(R^4)_2$, —OC(=O)R, —$N(R^4)$COR, —$N(R^4)CO_2$ (optionally substituted $C_{1-6}$ aliphatic), —$N(R^4)N(R^4)_2$, —C=$NN(R^4)_2$, —C=N—OR, —$N(R^4)$CON$(R^4)_2$, —$N(R^4)SO_2N(R^4)_2$, —$N(R^4)SO_2R$, or —OC(=O)N$(R^4)_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$ (optionally substituted $C_{1-6}$ aliphatic), —CON$(R^7)_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2$R, —COCOR, —$NO_2$, —CN, —S(O)R, —$SO_2$R, —SR, —$N(R^4)_2$, —$CON(R^4)_2$, —$SO_2N(R^4)_2$, —OC(=O)R, —$N(R^4)$COR, —$N(R^4)CO_2$ (optionally substituted $C_{1-6}$ aliphatic), —$N(R^4)N(R^4)_2$, —C=$NN(R^4)_2$, —C=N—OR, —$N(R^4)$CON$(R^4)_2$, —$N(R^4)SO_2N(R^4)_2$, —$N(R^4)SO_2R$, or —OC(=O)N$(R^4)_2$;

V is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)C(O)O$—, —$N(R^6)CON(R^6)$—, —$N(R^6)SO_2N(R^6)$—, —$N(R^6)N(R^6)$—, —C(O)N$(R^6)$—, —OC(O)N$(R^6)$—, —$C(R^6)_2$O—, —$C(R^6)_2$S—, —$C(R^6)_2$SO—, —$C(R^6)_2SO_2$—, —$C(R^6)_2SO_2N(R^6)$—, —$C(R^6)_2$ N$(R^6)$—, —$C(R^6)_2N(R^6)C(O)$—, —$C(R^6)_2N(R^6)C(O)O$—, —$C(R^6)$=NN$(R^6)$—, —$C(R^6)$=N—O—, —$C(R^6)_2$ N$(R^6)N(R^6)$—, —$C(R^6)_2N(R^6)SO_2N(R^6)$—, or —$C(R^6)_2N(R^6)CON(R^6)$—;

W is —$C(R^6)_2$O—, —$C(R^6)_2$S—, —$C(R^6)_2$SO—, —$C(R^6)_2$ $SO_2$—, —$C(R^6)_2SO_2N(R^6)$—, —$C(R^6)_2$N$(R^6)$—, —CO—, —$CO_2$—, —$C(R^6)$OC(O)—, —$C(R^6)$ OC(O)N$(R^6)$—, —$C(R^6)_2N(R^6)$CO—, —$C(R^6)_2N(R^6)$C(O)O—, —$C(R^6)$=NN$(R^6)$—, —$C(R^6)$=N—O—, —$C(R^6)_2N(R^6)N(R^6)$—, —$C(R^6)_2N(R^6)SO_2N(R^6)$—, —$C(R^6)_2N(R^6)CON(R^6)$—, or —CON$(R^6)$—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring; and each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring.

Preferred formula III Ring D monocyclic rings include substituted and unsubstituted phenyl, pyridinyl, piperidinyl, piperazinyl, pyrrolidinyl, thienyl, azepanyl, and morpholinyl rings. When two adjacent substituents on Ring D are taken together to form a fused ring, the Ring D system is bicyclic. Preferred formula III Ring D bicyclic rings include 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, and naphthyl. Examples of more preferred bicyclic Ring D systems include naphthyl and isoquinolinyl.

Preferred $R^5$ substituents on Ring D of formula III include halo, oxo, CN, —$NO_2$, —$N(R^4)_2$, —$CO_2$R, —CONH$(R^4)$, —$N(R^4)$COR, —$SO_2N(R^4)_2$, —$N(R^4)SO_2R$, —SR, —OR, —C(O)R, or substituted or unsubstituted group selected from 5–6 membered heterocyclyl, $C_{6-10}$ aryl, or $C_{1-6}$ aliphatic. More preferred $R^5$ substituents include -halo, —CN, -oxo, —SR, —OR, —$N(R^4)_2$, —C(O)R, or a substituted or unsubstituted group selected from 5–6 membered heterocyclyl, $C_{6-10}$ aryl, or $C_{1-6}$ aliphatic. Examples of Ring D substituents include —OH, phenyl, methyl, $CH_2$OH, $CH_2CH_2$OH, pyrrolidinyl, OPh, $CF_3$, C≡CH, Cl, Br, F, I, $NH_2$, C(O)$CH_3$, i-propyl, tert-butyl, SEt, OMe, N(Me)$_2$, methylene dioxy, and ethylene dioxy.

Preferred rings formed when the $R^x$ and $R^y$ groups of formula III are taken together to form a fused ring include a 5-, 6-, or 7-membered unsaturated or partially unsaturated carbocyclo ring, wherein any substitutable carbon on said fused ring is substituted by oxo or T-$R^3$. Examples of preferred bicyclic ring systems are shown below.

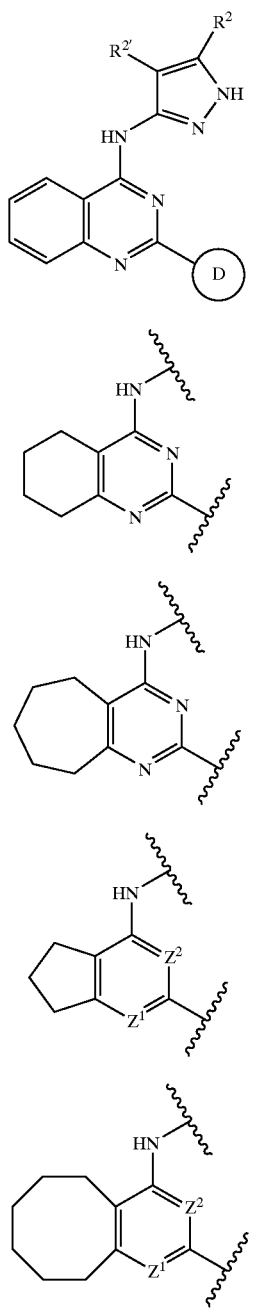

III-A

III-B

III-C

III-F

III-I

Preferred substituents on the $R^x$/$R^y$ fused ring of formula III include —R, oxo, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, wherein R and R$^4$ are as defined above. More preferred substituents on the $R^x$/$R^y$ fused ring include halo, CN, oxo, C$_{1-6}$ alkyl, C$_{1-6}$ alkoxy, (C$_{1-6}$ alkyl)carbonyl, (C$_{1-6}$ alkyl)sulfonyl, mono- or dialkylamino, mono- or dialkylaminocarbonyl, mono- or dialkylaminocarbonyloxy, or 5–6 membered heteroaryl. Examples of such preferred substituents include methoxy, methyl, isopropyl, methylsulfonyl, cyano, chloro, pyrrolyl, methoxy, ethoxy, ethylamino, acetyl, and acetamido.

Preferred R$^2$ substituents of formula III include hydrogen, C$_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred R$^2$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl).

When the R$^2$ and R$^{2'}$ groups of formula III are taken together to form a ring, preferred R$^2$/R$^{2'}$ ring systems containing the pyrazole ring include benzo, pyrido, pyrimido, 3-oxo-2H-pyridazino, and a partially unsaturated 6-membered carbocyclo ring. Examples of such preferred R$^2$/R$^{2'}$ ring systems containing the pyrazole ring include the following:

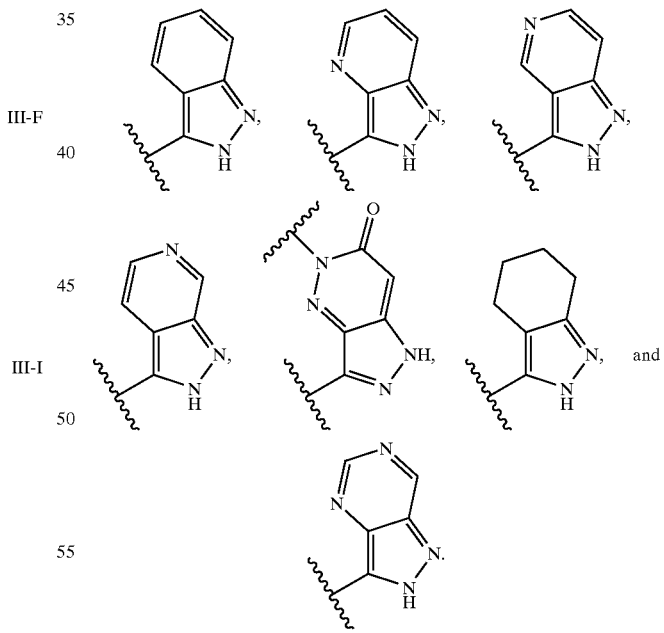

Preferred substituents on the R$^2$/R$^{2'}$ fused ring of formula III include one or more of the following: -halo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl.

Preferred formula III compounds have one or more, and more preferably all, of the features selected from the group consisting of:

(a) Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ and $R^y$ are taken together with their intervening atoms to form an optionally substituted benzo ring or a 5–7 membered carbocyclo ring; and (c) $R^{2'}$ is hydrogen or methyl and $R^2$ is T-W—$R^6$ or R, wherein W is —C($R^6$)$_2$O—, —C($R^6$)$_2$N($R^6$)—, —CO—, —CO$_2$—, —C($R^6$)OC(O)—, —C($R^6$)$_2$N($R^6$)CO—, —C($R^6$)$_2$N($R^6$)C(O)O—, or —CON($R^6$)—, and R is an optionally substituted group selected from $C_{1-6}$ aliphatic or phenyl, or $R^2$ and $R^{2'}$ are taken together with their intervening atoms to form a substituted or unsubstituted benzo, pyrido, pyrimido, or partially unsaturated 6-membered carbocyclo ring.

More preferred compounds of formula III have one or more, and more preferably all, of the features selected from the group consisting of:

(a) Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ and $R^y$ are taken together with their intervening atoms to form a benzo ring or a 5–7 membered carbocyclo ring optionally substituted with —R, oxo, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$; and (c) each $R^5$ is independently selected from halo, oxo, CN, NO$_2$, —N($R^4$)$_2$, —CO$_2$R, —CONH($R^4$), —N($R^4$)COR, —SO$_2$N($R^4$)$_2$, —N($R^4$)SO$_2$R, —SR, —OR, —C(O)R, or a substituted or unsubstituted group selected from 5–6 membered heterocyclyl, $C_{6-10}$ aryl, or $C_{1-6}$ aliphatic.

Even more preferred compounds of formula III have one or more, and more preferably all, of the features selected from the group consisting of:

(a) $R^x$ and $R^y$ are taken together with their intervening atoms to form a benzo or 6-membered partially unsaturated carbocyclo ring optionally substituted with halo, CN, oxo, $C_{1-6}$ alkyl, $C_{1-6}$ alkoxy, ($C_{1-6}$ alkyl)carbonyl, ($C_{1-6}$ alkyl) sulfonyl, mono- or dialkylamino, mono- or dialkylaminocarbonyl, mono- or dialkylaminocarbonyloxy, or 5–6 membered heteroaryl;

(b) each $R^5$ is independently selected from -halo, —CN, -oxo, —SR, —OR, —N($R^4$)$_2$, —C(O)R, or a substituted or unsubstituted group selected from 5–6 membered heterocyclyl, $C_{6-10}$ aryl, or $C_{1-6}$ aliphatic; and (c) $R^{2'}$ is hydrogen and $R^2$ is selected from $R^{2'}$ is hydrogen or methyl and $R^2$ is T-W—$R^6$ or R, wherein W is —C($R^6$)$_2$O—, —C($R^6$)$_2$N($R^6$)—, —CO—, —CO$_2$—, —C($R^6$)OC(O)—, —C($R^6$)$_2$N($R^6$)CO—, or —CON($R^6$)—, and R is an optionally substituted group selected from $C_{1-6}$ aliphatic or phenyl, or $R^2$ and $R^{2'}$ are taken together with their intervening atoms to form a benzo, pyrido, or partially unsaturated 6-membered carbocyclo ring optionally substituted with -halo, —N($R^4$)$_2$, —$C_{1-4}$ alkyl, —$C_{1-4}$ haloalkyl, —NO$_2$, —O($C_{1-4}$ alkyl), —CO$_2$($C_{1-4}$ alkyl), —CN, —SO$_2$($C_{1-4}$ alkyl), —SO$_2$NH$_2$, —OC(O)NH$_2$, —NH$_2$SO$_2$($C_{1-4}$ alkyl), —NHC(O)($C_{1-4}$ alkyl), —C(O)NH$_2$, or —CO($C_{1-4}$ alkyl), wherein the ($C_{1-4}$ alkyl) is a straight, branched, or cyclic alkyl group.

Representative compounds of formula III are set forth in Table 2 below.

TABLE 2

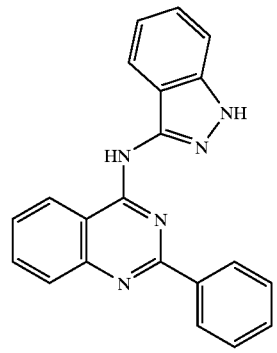

III-1

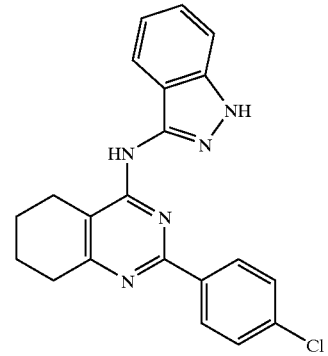

III-2

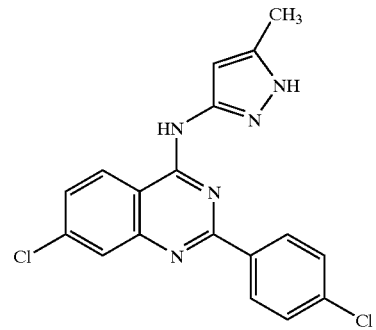

III-3

TABLE 2-continued
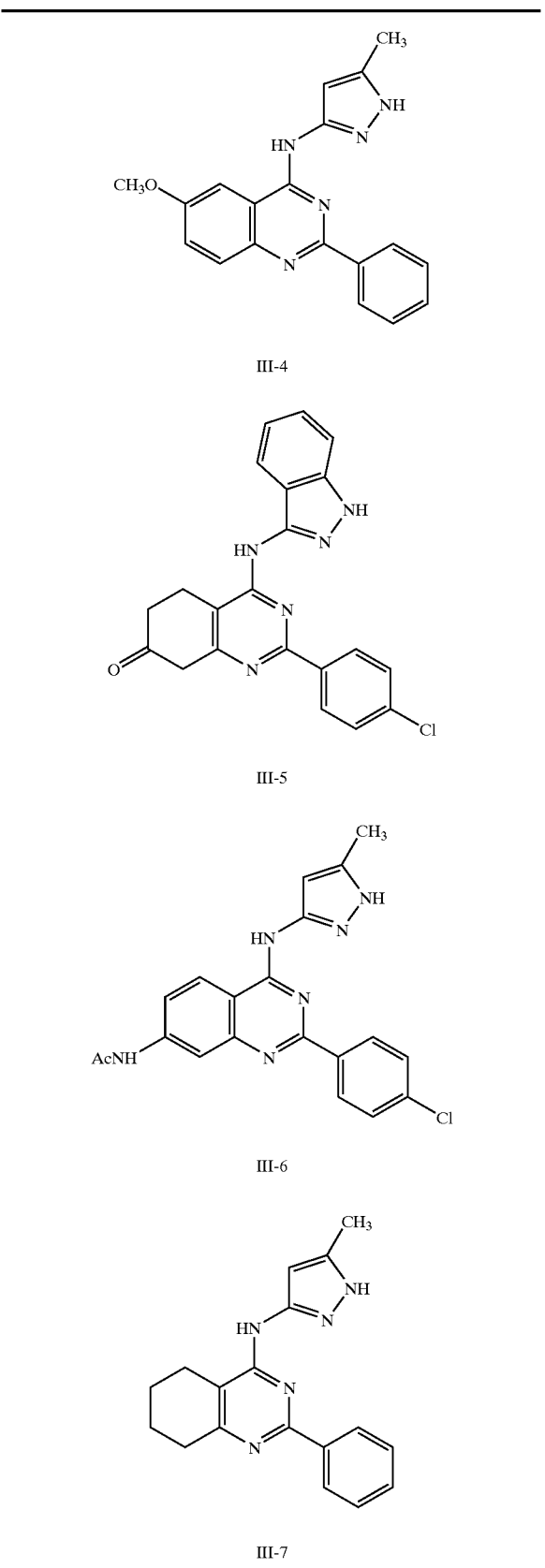
III-4
III-5
III-6
III-7
TABLE 2-continued
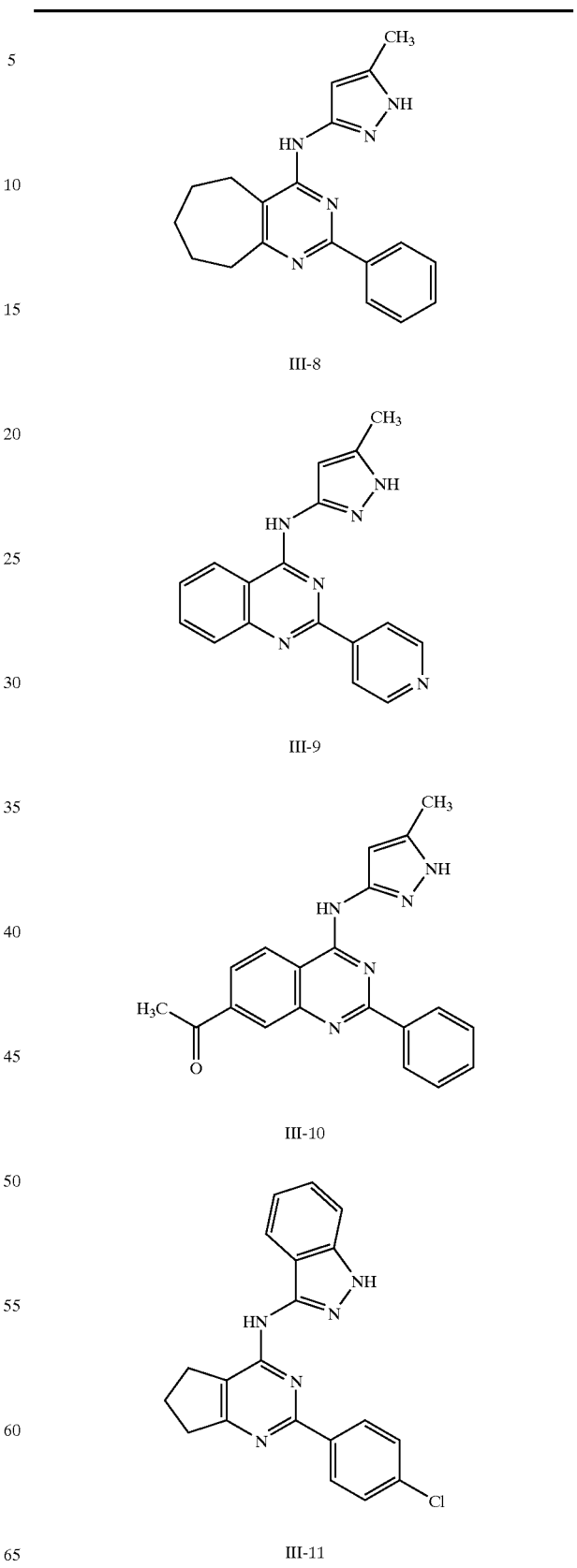
III-8
III-9
III-10
III-11

TABLE 2-continued
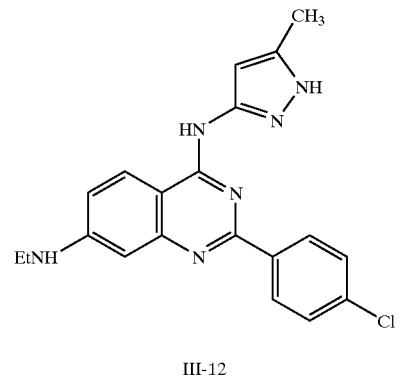
III-12
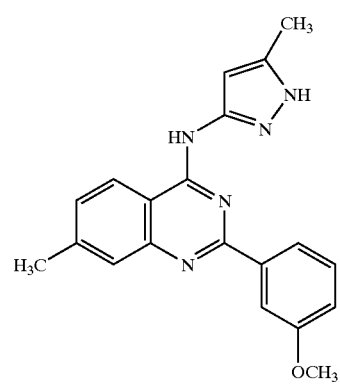
III-13
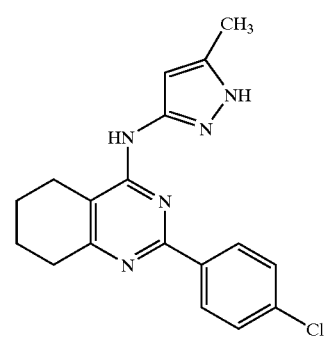
III-14
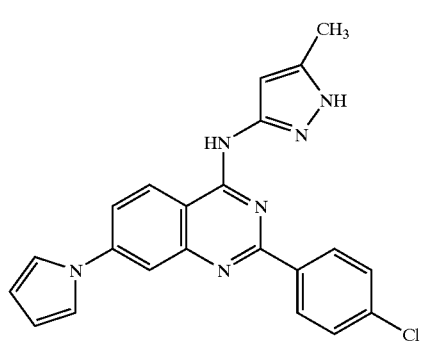
III-15
TABLE 2-continued
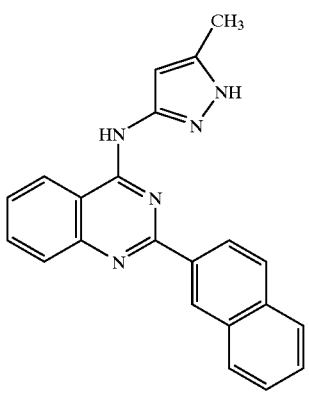
III-16
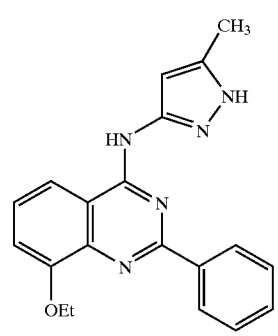
III-17
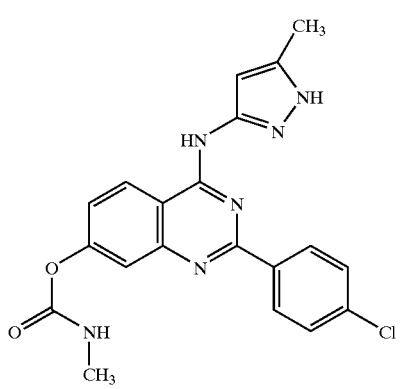
III-18

TABLE 2-continued
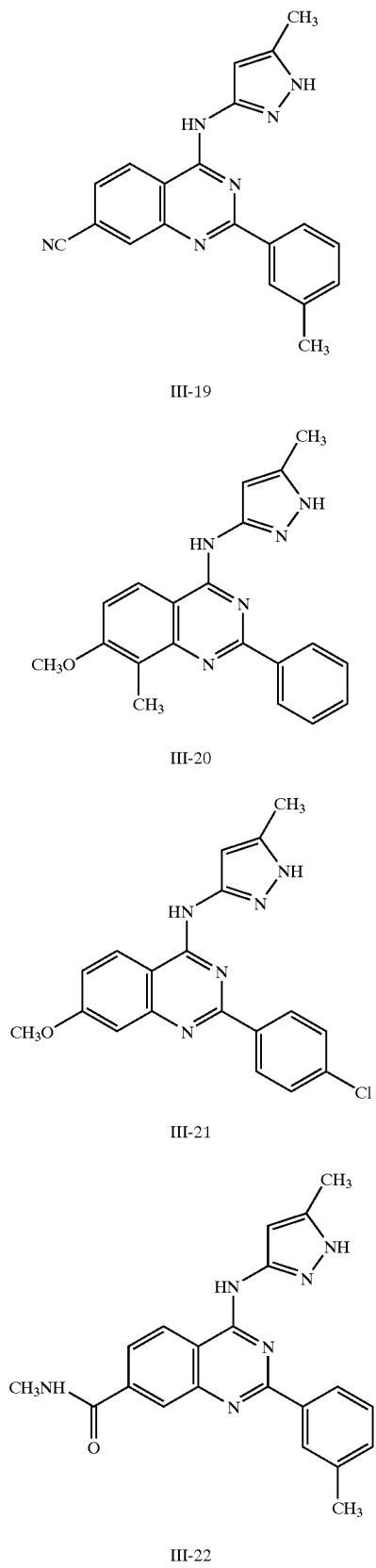
III-19
III-20
III-21
III-22
TABLE 2-continued
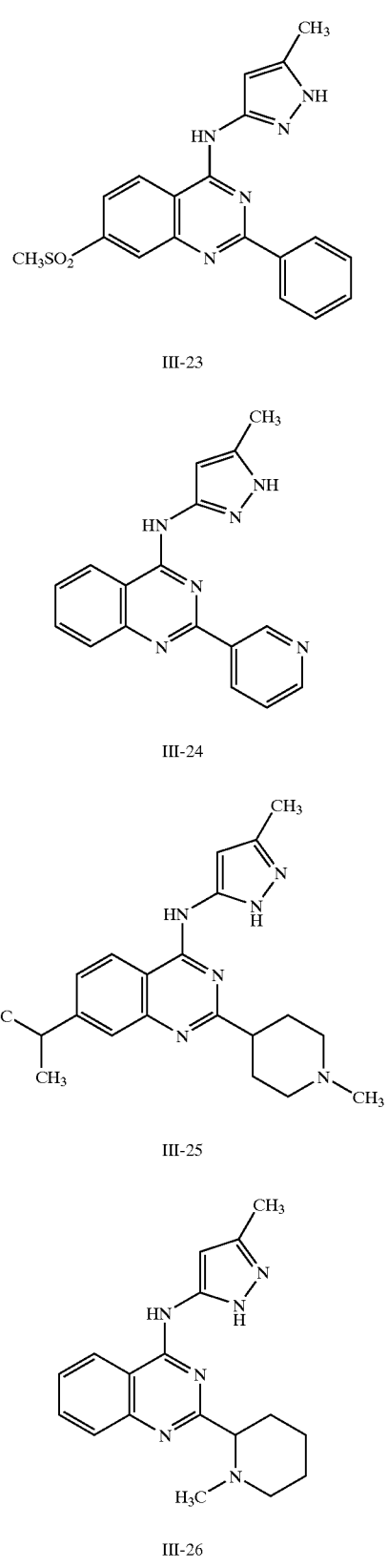
III-23
III-24
III-25
III-26

TABLE 2-continued
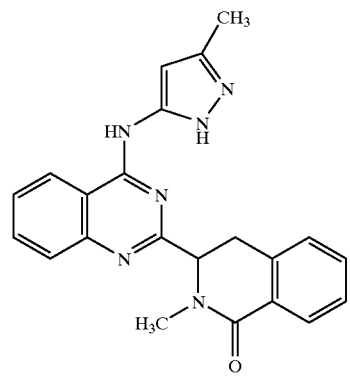
III-27
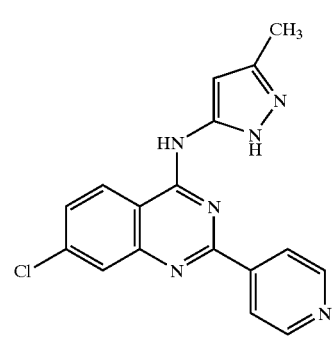
III-28
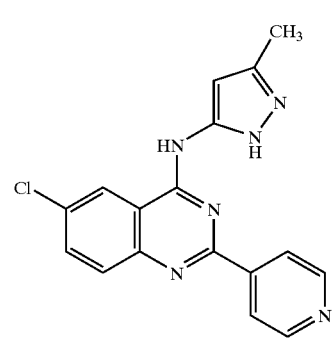
III-29
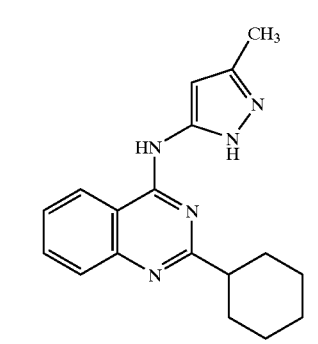
III-30
TABLE 2-continued
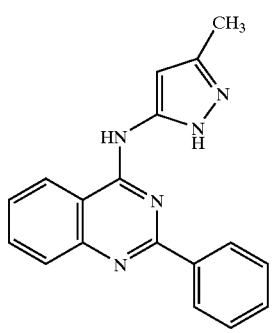
III-31
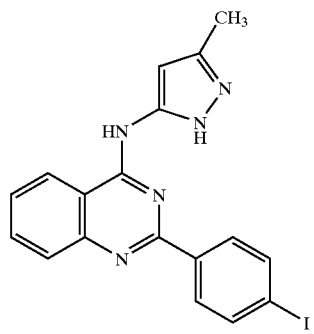
III-32
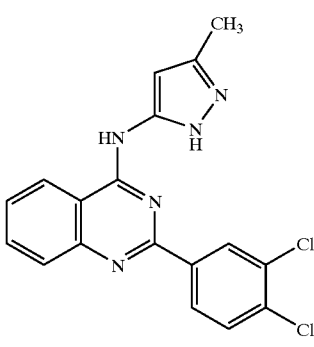
III-33
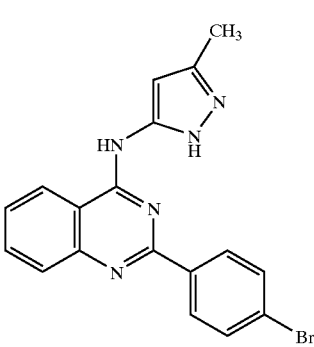
III-34

TABLE 2-continued
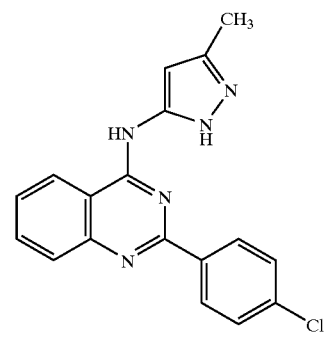
III-35
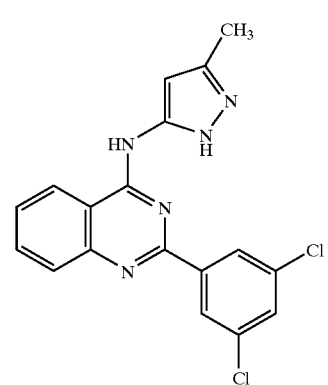
III-36
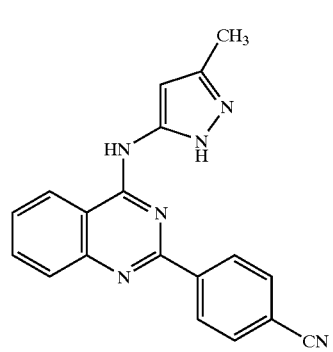
III-37
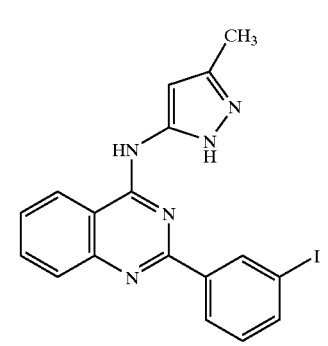
III-38
TABLE 2-continued
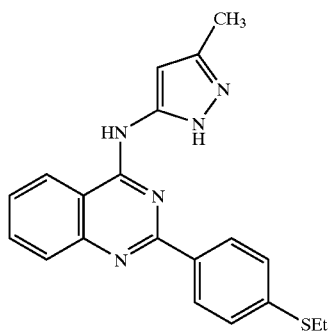
III-39
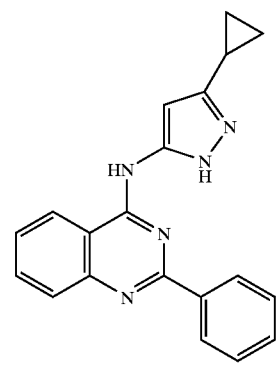
III-40
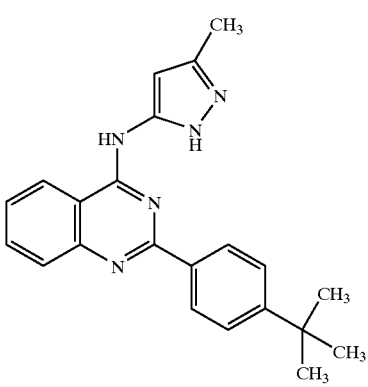
III-41
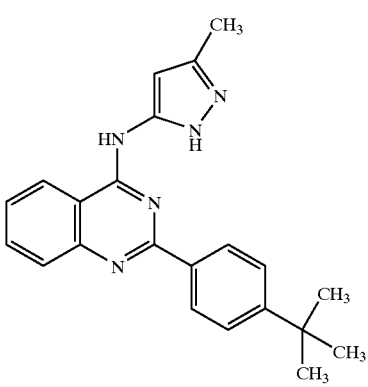
III-42

TABLE 2-continued
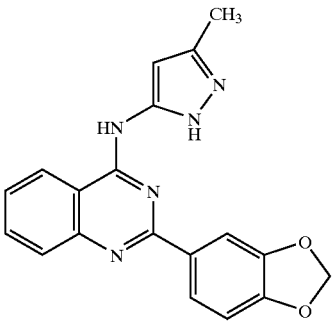
III-43
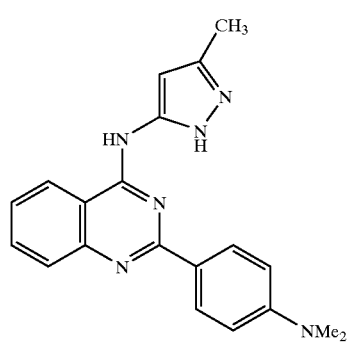
III-44
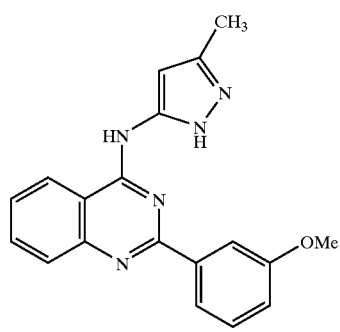
III-45
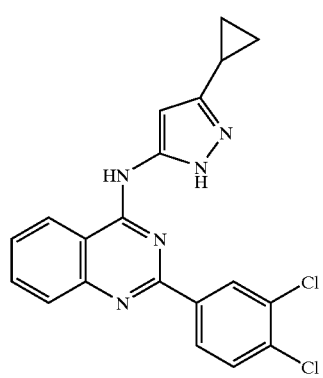
III-46
TABLE 2-continued
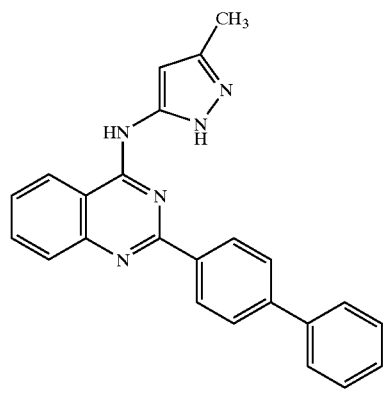
III-47
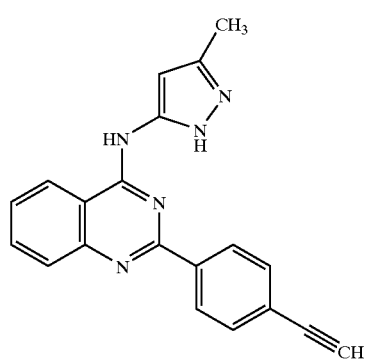
III-48
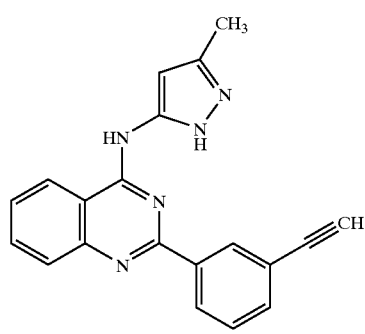
III-49
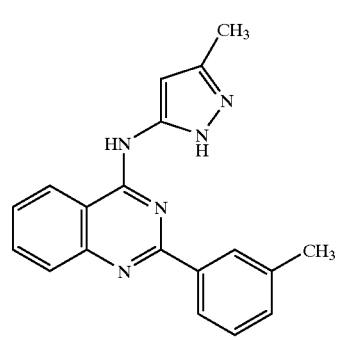
III-50

TABLE 2-continued
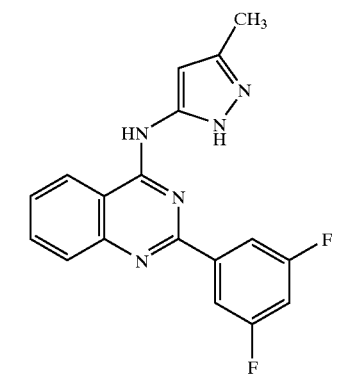
III-51
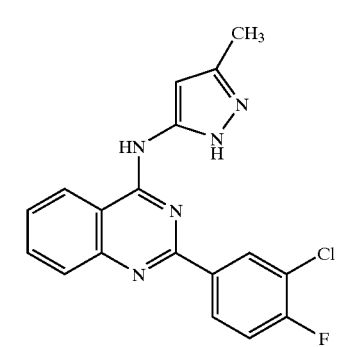
III-52
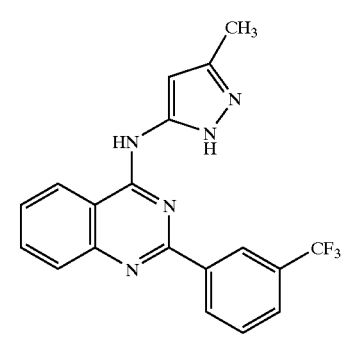
III-53
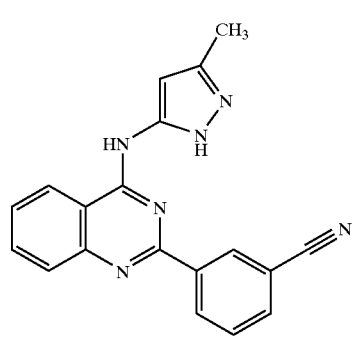
III-54
TABLE 2-continued
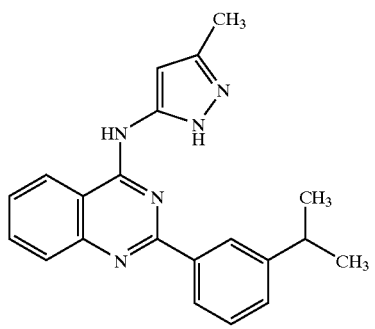
III-55
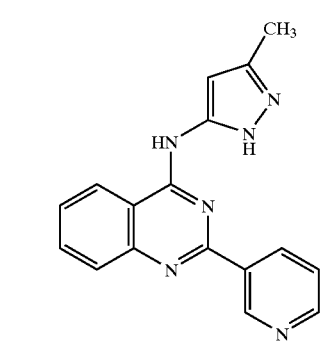
III-56
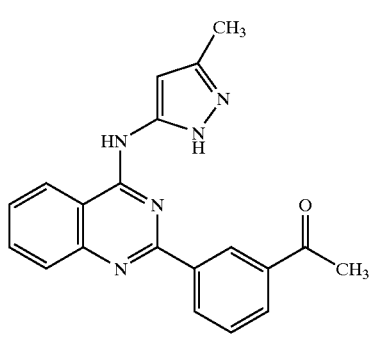
III-57
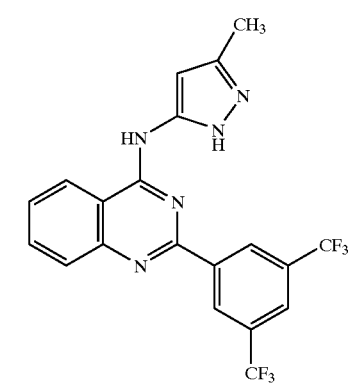
III-58

TABLE 2-continued
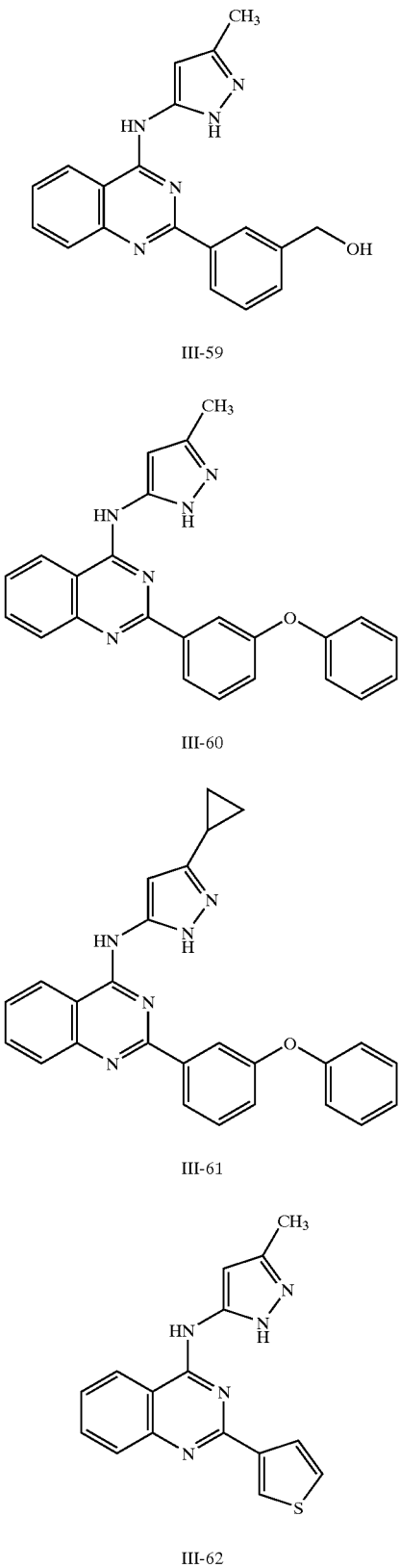
III-59
III-60
III-61
III-62
TABLE 2-continued
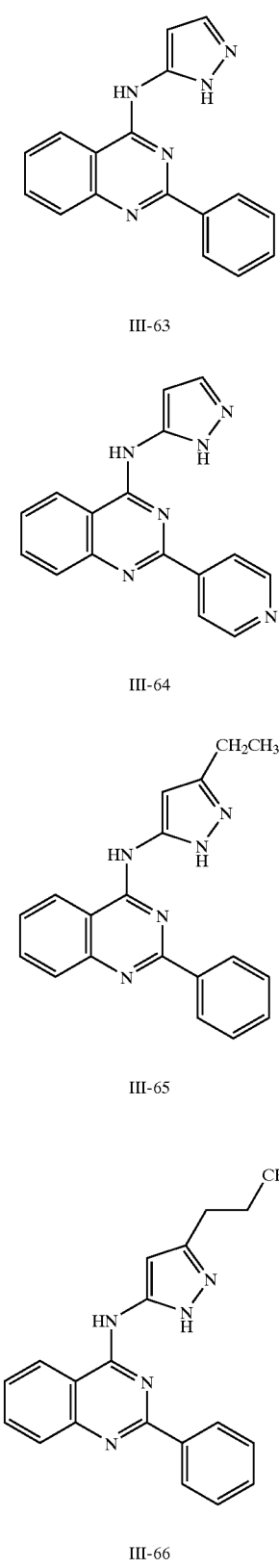
III-63
III-64
III-65
III-66

TABLE 2-continued
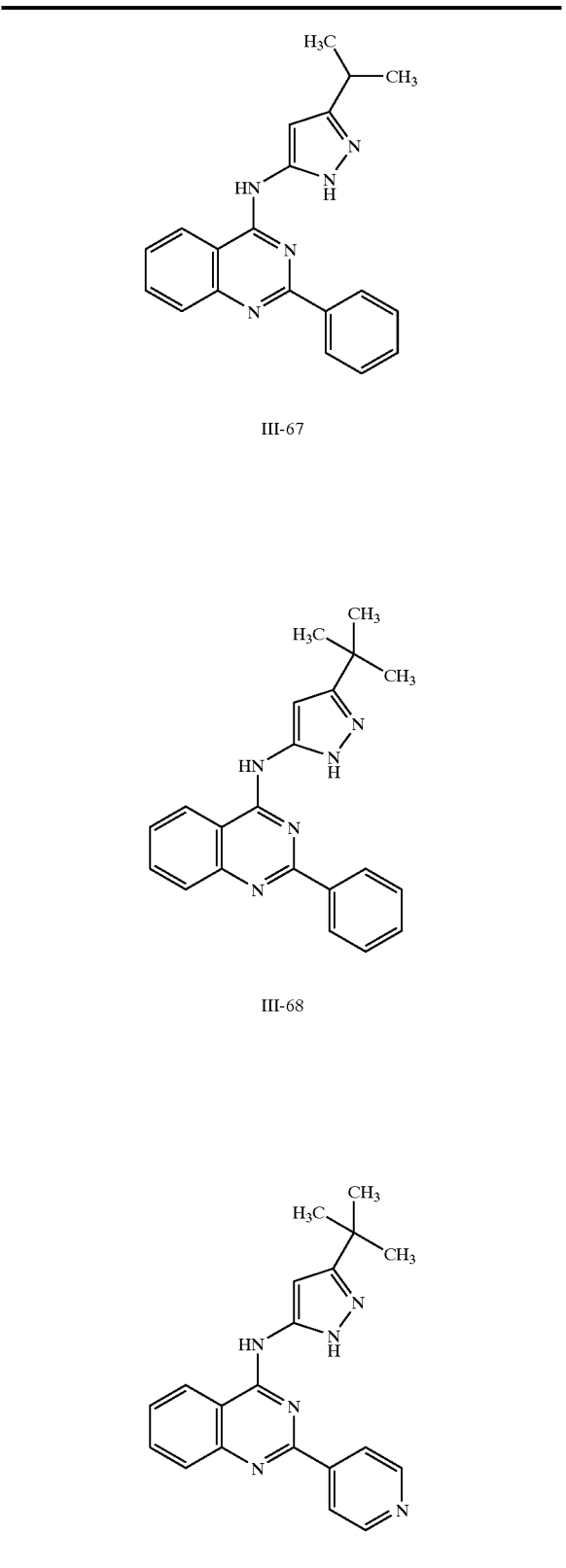
III-67
III-68
III-69
TABLE 2-continued
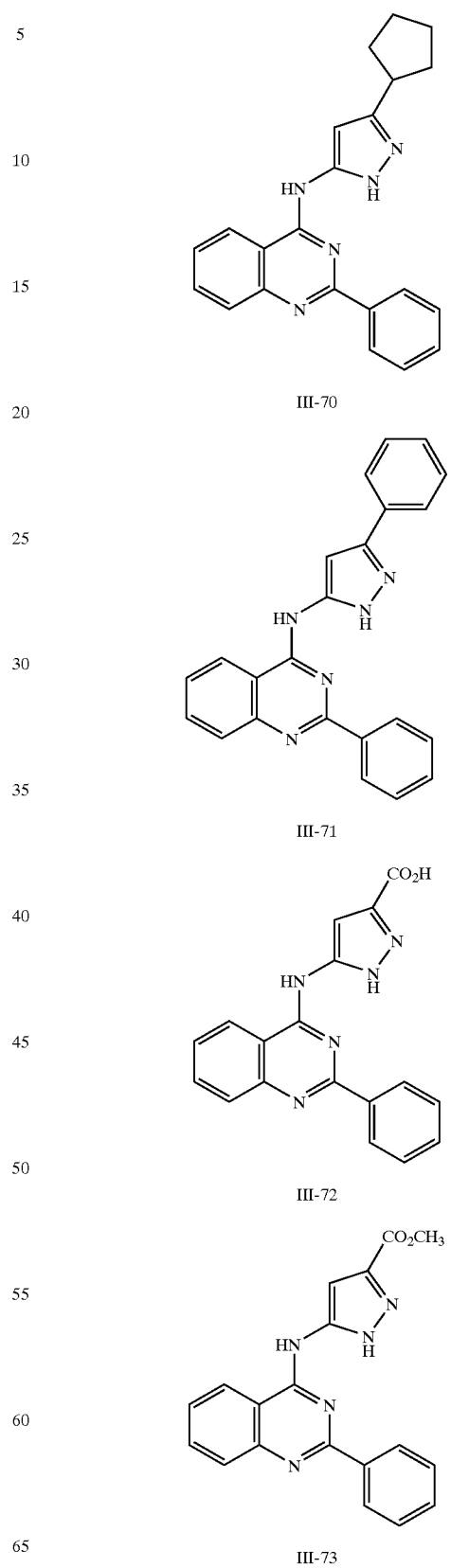
III-70
III-71
III-72
III-73

TABLE 2-continued
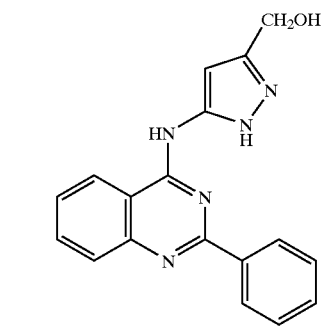
III-74
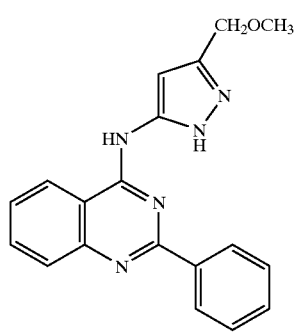
III-75
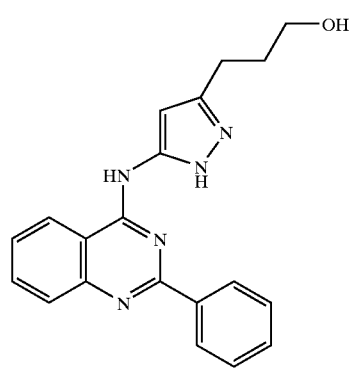
III-76
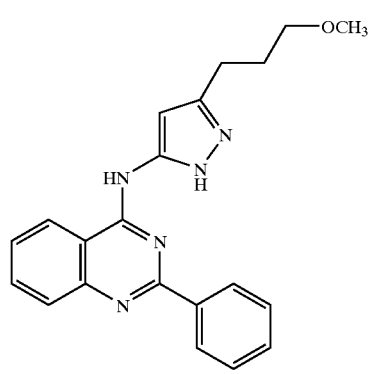
III-77
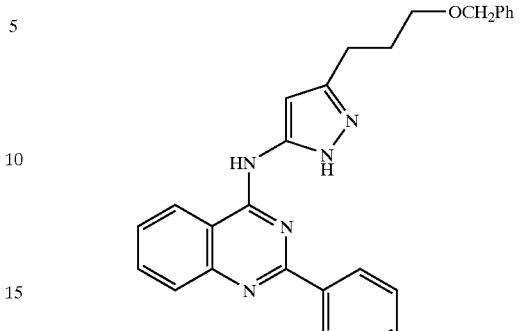
III-78
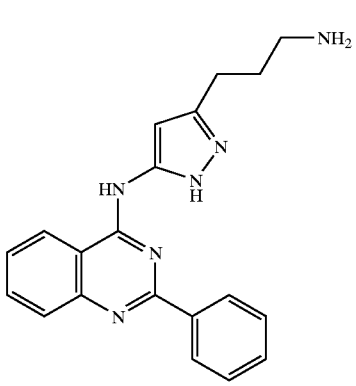
III-79
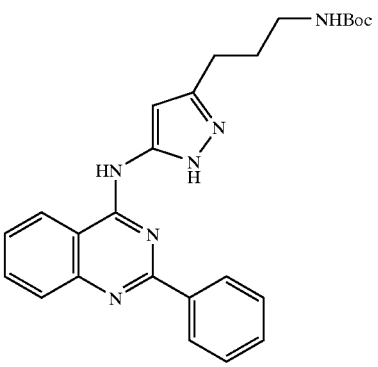
III-80

TABLE 2-continued
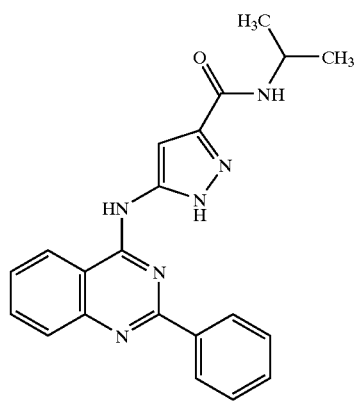
III-81
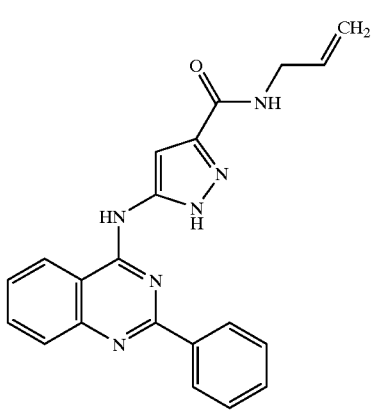
III-82
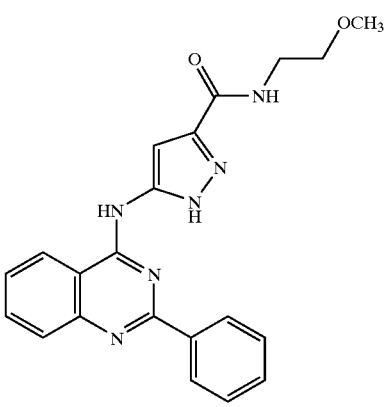
III-83
TABLE 2-continued
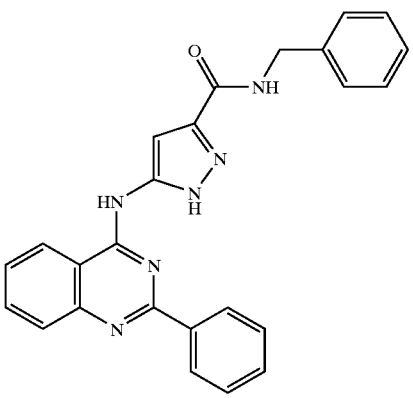
III-84
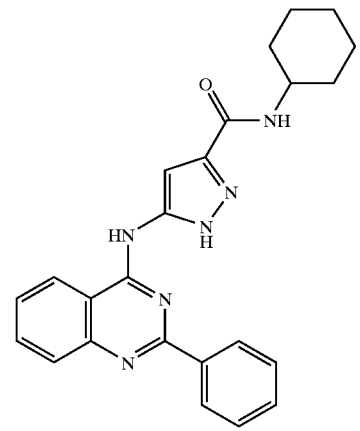
III-85
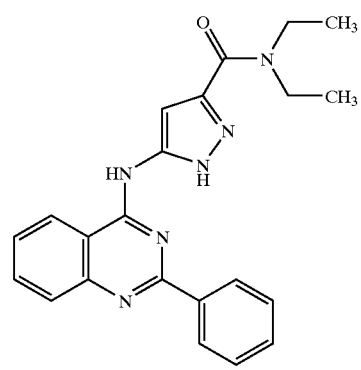
III-86

TABLE 2-continued
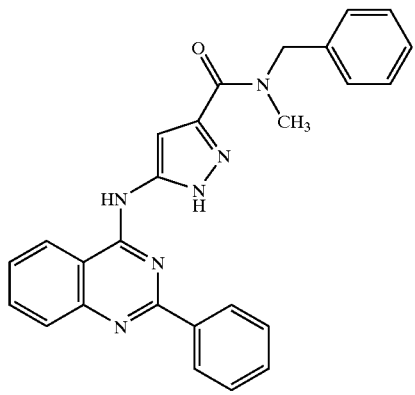
III-87
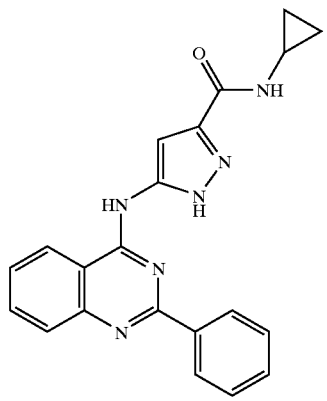
III-90
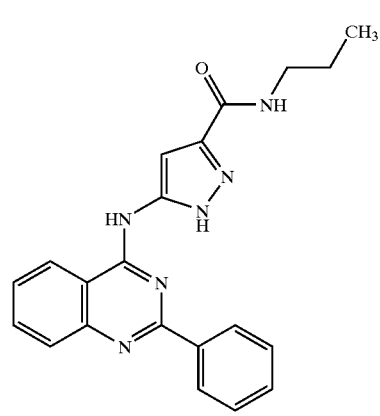
III-88
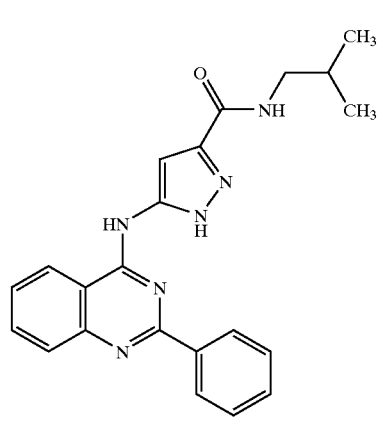
III-91
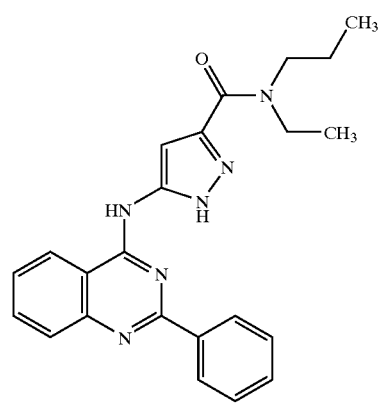
III-89
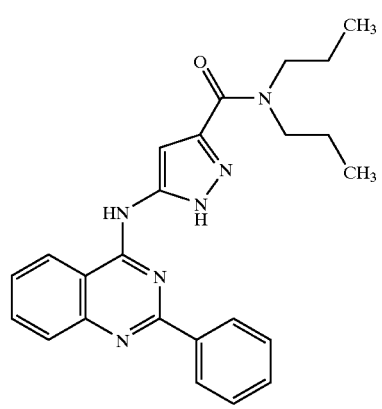
III-92

TABLE 2-continued
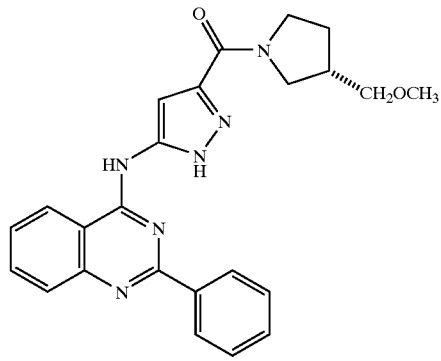
III-93
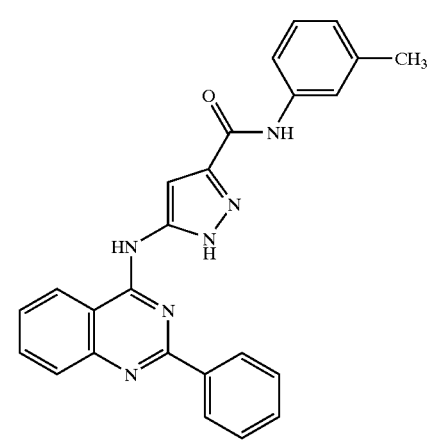
III-94
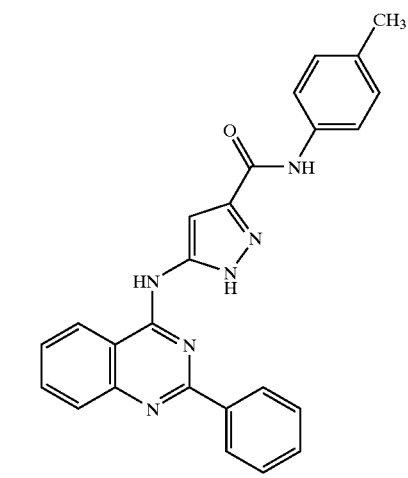
III-95
TABLE 2-continued
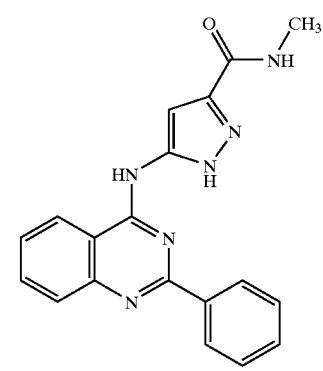
III-96
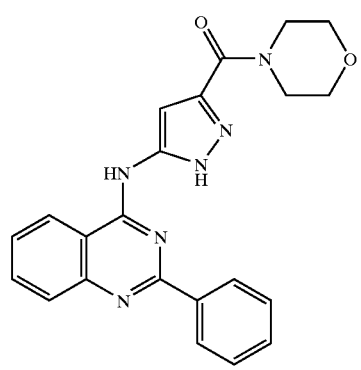
III-97
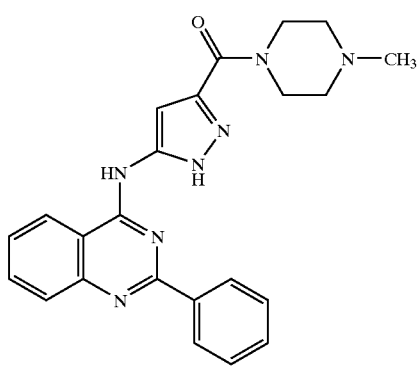
III-98

TABLE 2-continued
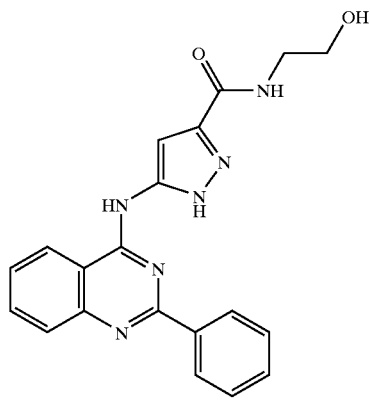
III-99
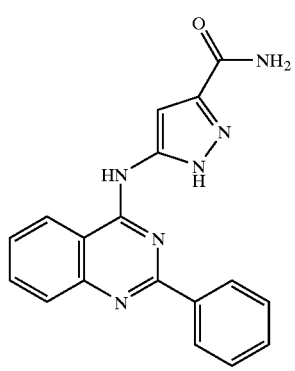
III-100
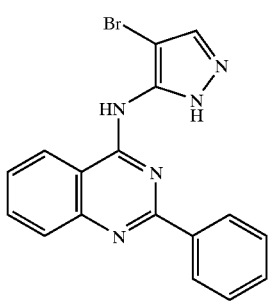
III-101
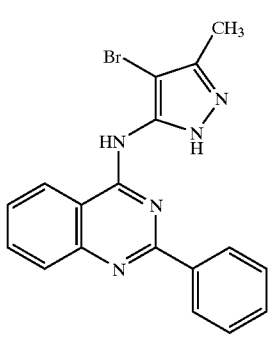
III-102
TABLE 2-continued
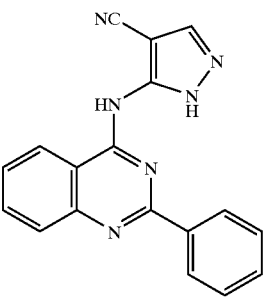
III-103
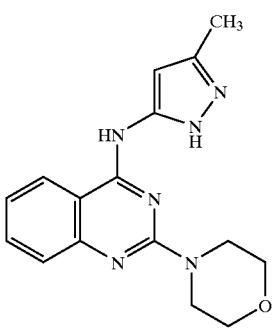
III-104
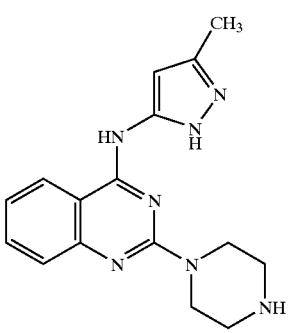
III-105
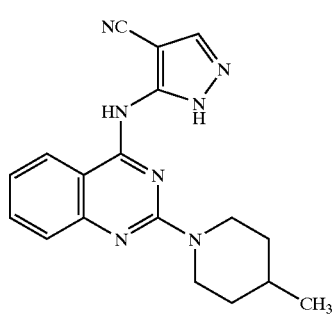
III-106

TABLE 2-continued
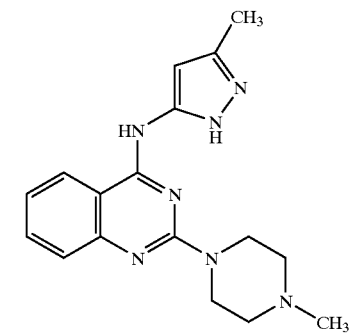
III-107
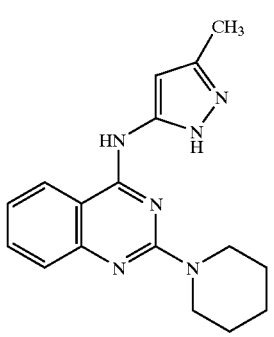
III-108
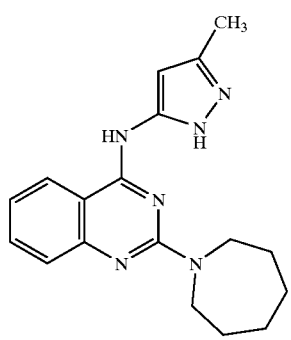
III-109
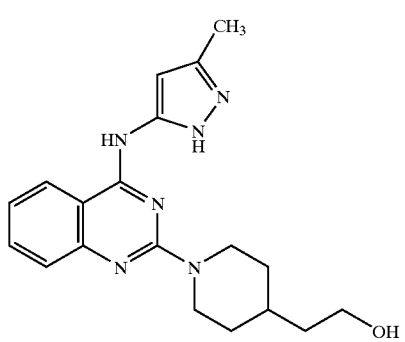
III-110
TABLE 2-continued
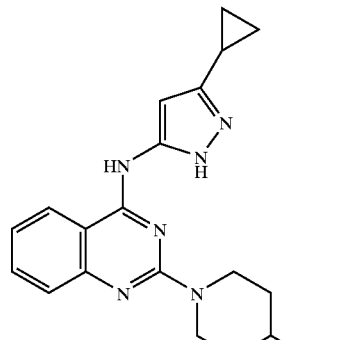
III-111
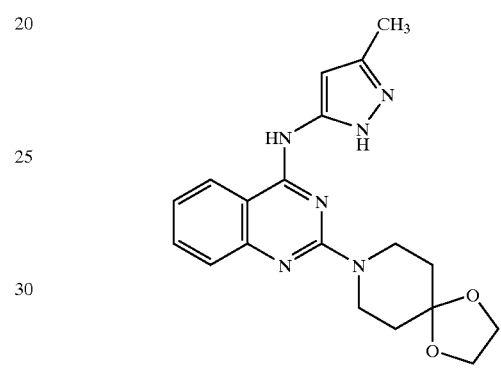
III-112
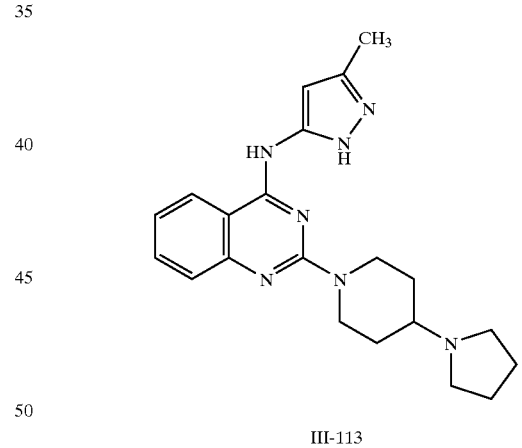
III-113
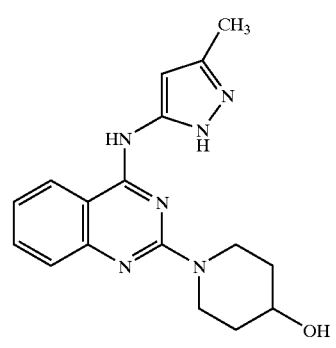
III-114

TABLE 2-continued
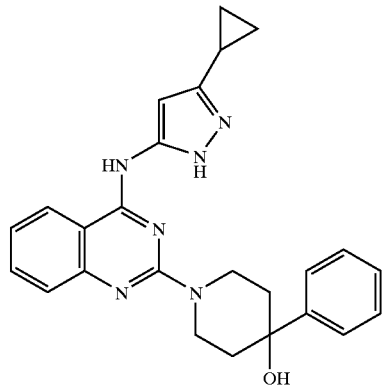
III-115
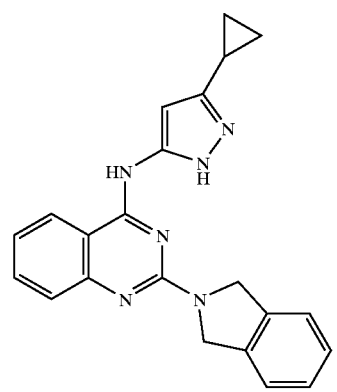
III-116
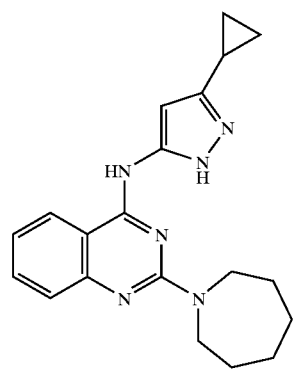
III-117
TABLE 2-continued
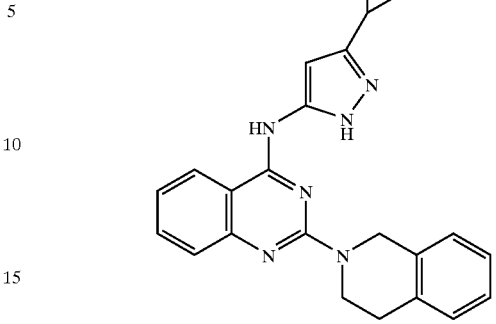
III-118
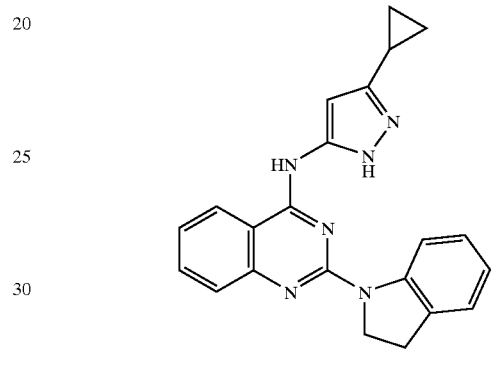
III-119
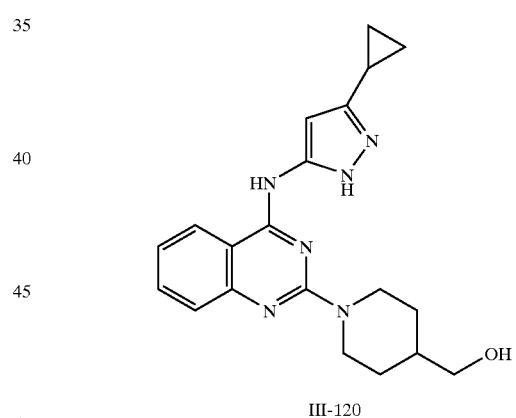
III-120
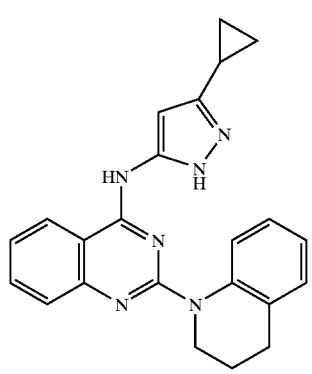
III-121

TABLE 2-continued
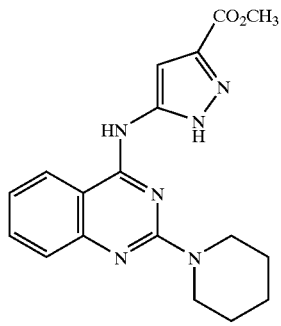
III-122
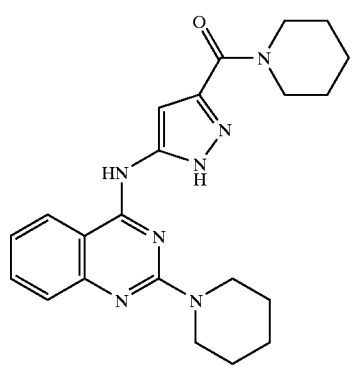
III-123
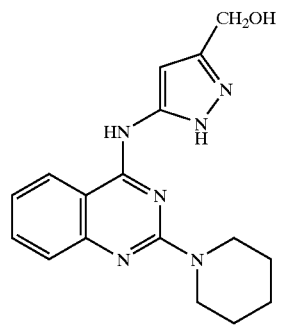
III-124
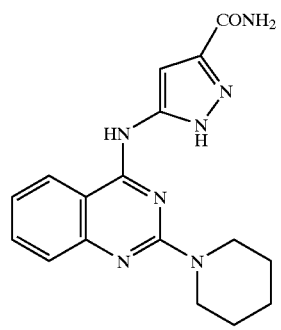
IIII-125
TABLE 2-continued
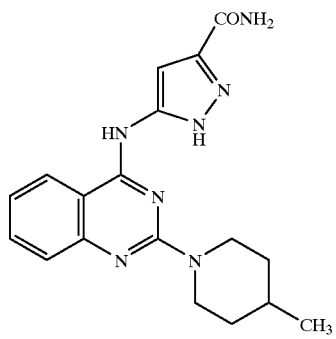
III-126
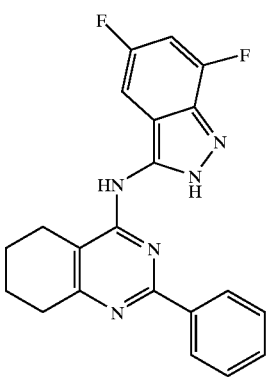
III-127
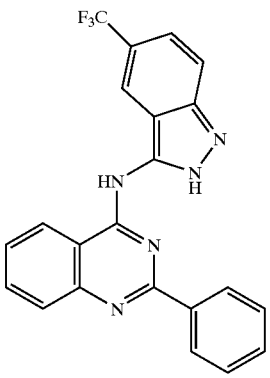
III-128
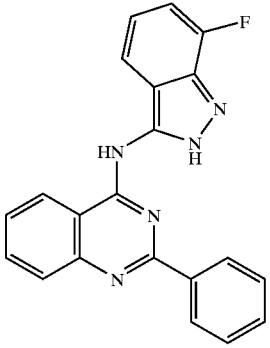
III-129

TABLE 2-continued
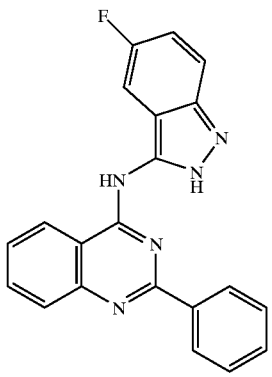
III-130
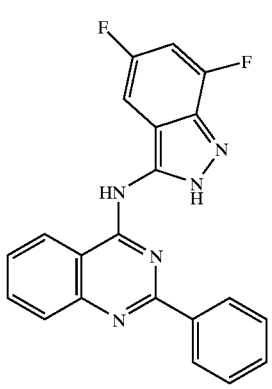
III-131
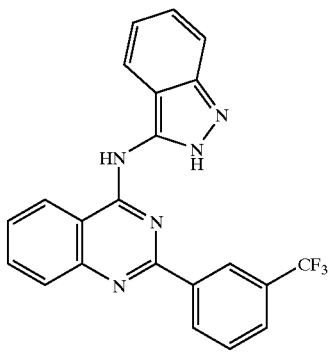
III-132
TABLE 2-continued
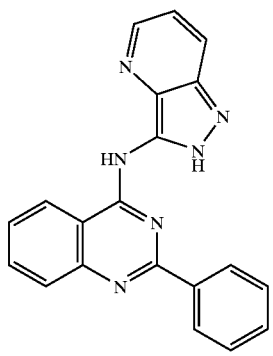
III-133
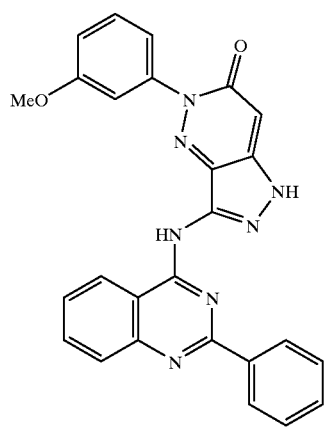
III-134
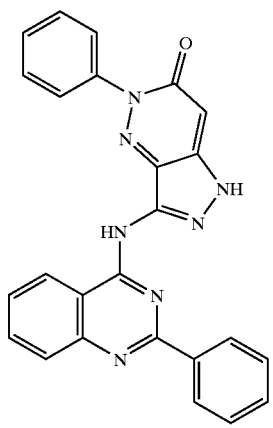
III-135

TABLE 2-continued
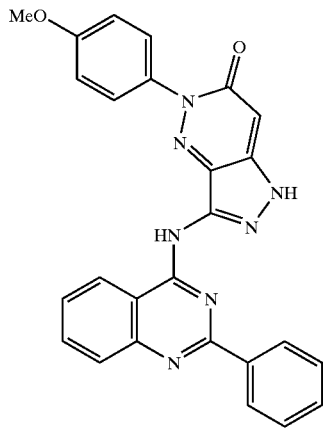
III-136
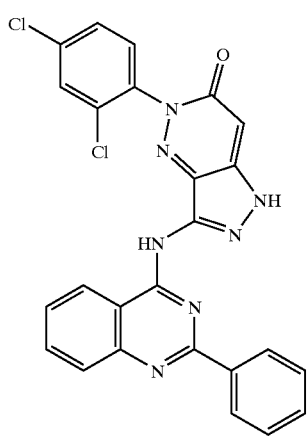
III-137
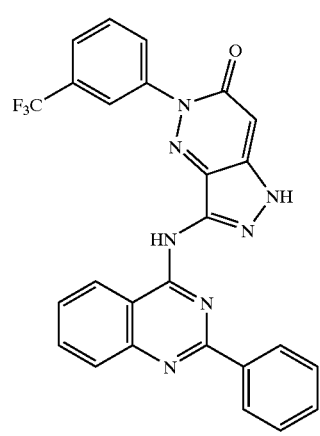
III-138
TABLE 2-continued
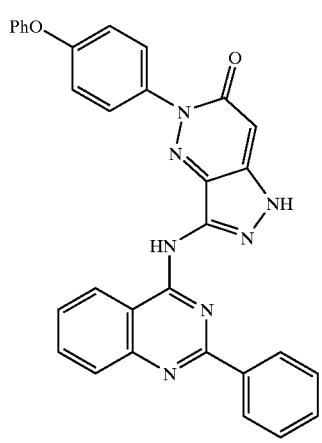
III-139
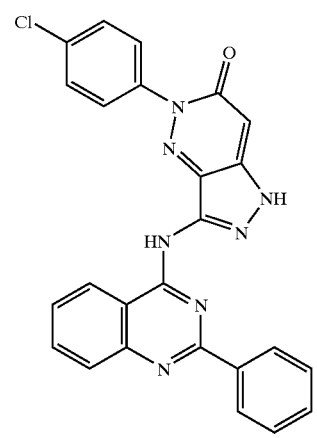
III-140
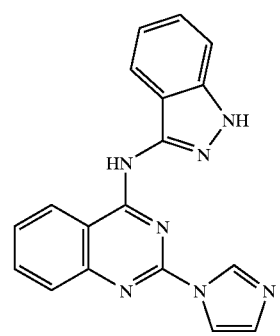
III-141

TABLE 2-continued

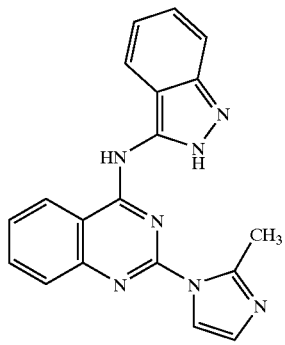

III-142

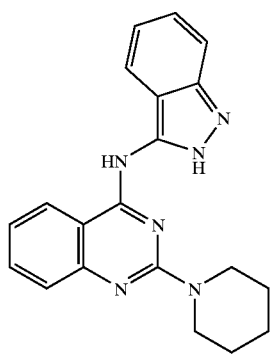

III-143

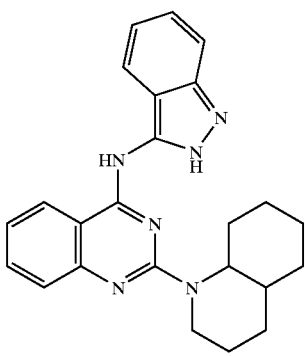

III-144

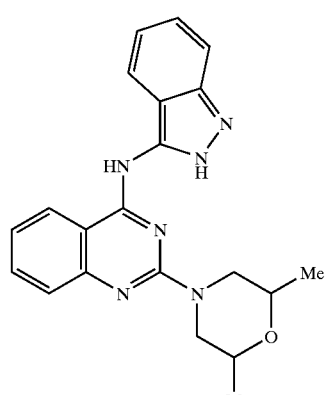

III-145

TABLE 2-continued

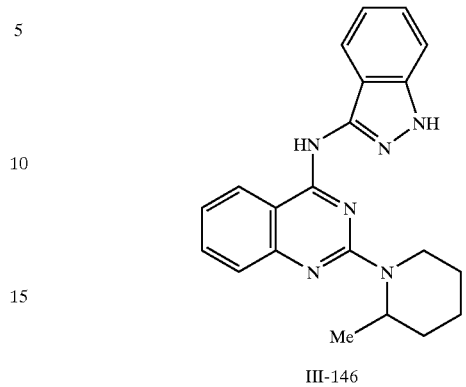

III-146

In another embodiment, this invention provides a composition comprising a compound of formula III and a pharmaceutically acceptable carrier.

One aspect of this invention relates to a method of inhibiting GSK-3 activity in a patient, comprising administering to the patient a therapeutically effective amount of a composition comprising a compound of formula III.

Another aspect relates to a method of treating a disease that is alleviated by treatment with a GSK-3 inhibitor, said method comprising the step of administering to a patient in need of such a treatment a therapeutically effective amount of a composition comprising a compound of formula III.

Another aspect relates to a method of enhancing glycogen synthesis and/or lowering blood levels of glucose in a patient in need thereof, comprising administering to said patient a therapeutically effective amount of a composition comprising a compound of formula III. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula III. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula III. This method is especially useful for treating schizophrenia.

One aspect of this invention relates to a method of inhibiting Aurora activity in a patient, comprising administering to the patient a therapeutically effective amount of a composition comprising a compound of formula III.

Another aspect relates to a method of treating a disease that is alleviated by treatment with an Aurora inhibitor, said method comprising the step of administering to a patient in need of such a treatment a therapeutically effective amount of a composition comprising a compound of formula III. This method is especially useful for treating cancer, such as colon, ovarian, and breast cancer.

One aspect of this invention relates to a method of inhibiting CDK-2 activity in a patient, comprising administering to the patient a therapeutically effective amount of a composition comprising a compound of formula III.

Another aspect relates to a method of treating a disease that is alleviated by treatment with a CDK-2 inhibitor, said method comprising the step of administering to a patient in need of such a treatment a therapeutically effective amount of a composition comprising a compound of formula III. This method is especially useful for treating cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

One aspect of this invention relates to a method of inhibiting Src activity in a patient, comprising administering to the patient a therapeutically effective amount of a composition comprising a compound of formula III.

Another aspect relates to a method of treating a disease that is alleviated by treatment with a Src inhibitor, said method comprising the step of administering to a patient in need of such a treatment a therapeutically effective amount of a composition comprising a compound of formula III. This method is especially useful for treating hypercalcemia, osteoporosis, osteoarthritis, cancer, symptomatic treatment of bone metastasis, and Paget's disease.

Another method relates to inhibiting GSK-3, Aurora, CDK-2, or Src activity in a biological sample, which method comprises contacting the biological sample with the GSK-3, Aurora, CDK-2, or Src inhibitor of formula III, or a pharmaceutical composition thereof, in an amount effective to inhibit GSK-3, Aurora, CDK-2, or Src.

Each of the aforementioned methods directed to the inhibition of GSK-3, Aurora, CDK-2, or Src, or the treatment of a disease alleviated thereby, is preferably carried out with a preferred compound of formula III, as described above.

Compounds of formula III, wherein $R^{2'}$ is hydrogen and $R^x$ and $R^y$ are taken together with the pyrimidine ring to form an optionally substituted quinazoline ring system, are also inhibitors of ERK-2 and AKT protein kinases.

Accordingly, another method of this invention relates to a method of inhibiting ERK-2 or AKT activity in a patient, comprising administering to the patient a therapeutically effective amount of a composition comprising a compound of formula III, wherein $R^{2'}$ is hydrogen and $R^x$ and $R^y$ are taken together with the pyrimidine ring to form an optionally substituted quinazoline ring system.

Another aspect relates to a method of treating a disease that is alleviated by treatment with a ERK-2 or AKT inhibitor, said method comprising the step of administering to a patient in need of such a treatment a therapeutically effective amount of a composition comprising a compound of formula III, wherein $R^{2'}$ is hydrogen and $R^x$ and $R^y$ are taken together with the pyrimidine ring to form an optionally substituted quinazoline ring system. This method is especially useful for treating cancer, stroke, hepatomegaly, cardiovascular disease, Alzheimer's disease, cystic fibrosis, viral disease, autoimmune diseases, restenosis, psoriasis, allergic disorders including asthma, inflammation, and neurological disorders.

Another embodiment of this invention relates to compounds of formula IV:

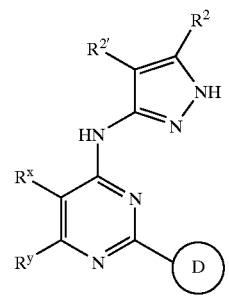

IV or a pharmaceutically acceptable derivative or prodrug thereof, wherein:

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^x$ and $R^y$ are independently selected from T-$R^3$, or $R^x$ and $R^y$ are taken together with their intervening atoms to form a fused, unsaturated or partially unsaturated, 5–8 membered ring having 1–3 ring heteroatoms selected from oxygen, sulfur, or nitrogen, wherein any substitutable carbon on said fused ring is optionally and independently substituted by T-$R^3$, and any substitutable nitrogen on said ring is substituted by $R^4$;

T is a valence bond or a $C_{1-4}$ alkylidene chain;

$R^2$ and $R^{2'}$ are independently selected from —R, -T-W—$R^6$, or $R^2$ and $R^{2'}$ are taken together with their intervening atoms to form a fused, 5–8 membered, unsaturated or partially unsaturated, ring containing 0–3 ring heteroatoms selected from nitrogen, oxygen, or sulfur, wherein said fused ring is optionally substituted by up to three groups independently selected from halo, oxo, —CN, —$NO_2$, —$R^7$, or —V—$R^6$;

$R^3$ is selected from —R, -halo, =O, —OR, —C(=O)R, —$CO_2$R, —COCOR, —$COCH_2$COR, —$NO_2$, —CN, —S(O)R, —$S(O)_2$R, —SR, —$N(R^4)_2$, —$CON(R^4)_2$, —$SO_2N(R^4)_2$, —OC(=O)R, —$N(R^4)$COR, —$N(R^4)$$CO_2$ (optionally substituted $C_{1-6}$ aliphatic), —$N(R^4)$N$(R^4)_2$, —C=NN$(R^4)_2$, —C=N—OR, —$N(R^4)$CON$(R^4)_2$, —$N(R^4)SO_2N(R^4)_2$, —$N(R^4)SO_2$R, or —OC(=O)N$(R^4)_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —$CO_2$ (optionally substituted $C_{1-6}$ aliphatic), —CON$(R^7)_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2$R, —COCOR, —$NO_2$, —CN, —S(O)R, —$SO_2$R, —SR, —$N(R^4)_2$, —$CON(R^4)_2$, —$SO_2N(R^4)_2$, —OC(=O)R, —$N(R^4)$COR, —$N(R^4)$$CO_2$ (optionally substituted $C_{1-6}$ aliphatic), —$N(R^4)$N$(R^4)_2$, —C=NN$(R^4)_2$, —C=N—OR, —$N(R^4)$CON$(R^4)_2$, —$N(R^4)SO_2N(R^4)_2$, —$N(R^4)SO_2$R, or —OC(=O)N$(R^4)_2$;

V is —O—, —S—, —SO—, —SO₂—, —N(R⁶)SO₂—, —SO₂N(R⁶)—, —N(R⁶)—, —CO—, —CO₂—, —N(R⁶) CO—, —N(R⁶)C(O)O—, —N(R⁶)CON(R⁶)—, —N(R⁶) SO₂N(R⁶)—, —N(R⁶)N(R⁶)—, —C(O)N(R⁶)—, —OC (O)N(R⁶)—, —C(R⁶)₂O—, —C(R⁶)₂S—, —C(R⁶)₂ SO—, —C(R⁶)₂SO₂—, —C(R⁶)₂SO₂N(R⁶)—, —C(R⁶)₂ N(R⁶)—, —C(R⁶)₂N(R⁶)C(O)—, —C(R⁶)₂N(R⁶)C(O) O—, —C(R⁶)=NN(R⁶)—, —C(R⁶)=N—O—, —C(R⁶)₂ N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂ SO₂—, —C(R⁶)₂SO₂N(R⁶)—, —C(R⁶)₂N (R⁶)—, —CO—, —CO₂—, —C(R⁶)OC(O)—, —C(R⁶) OC(O)N(R⁶)—, —C(R⁶)₂N(R⁶)CO—, —C(R⁶)₂N(R⁶)C (O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each R⁶ is independently selected from hydrogen or an optionally substituted $C_{1-4}$ aliphatic group, or two R⁶ groups on the same nitrogen atom are taken together with the nitrogen atom to form a 5–6 membered heterocyclyl or heteroaryl ring; and each R⁷ is independently selected from hydrogen or an optionally substituted $C_{1-6}$ aliphatic group, or two R⁷ on the same nitrogen are taken together with the nitrogen to form a 5–8 membered heterocyclyl ring or heteroaryl.

Preferred formula IV Ring D monocyclic rings include substituted and unsubstituted phenyl, pyridinyl, piperidinyl, piperazinyl, pyrrolidinyl, thienyl, azepanyl, and morpholinyl rings. Preferred formula IV Ring D bicyclic rings include 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, and naphthyl. Examples of more preferred Ring D bicyclic rings include naphthyl and isoquinolinyl.

Preferred substituents on Ring D of formula IV include halo, oxo, CN, —NO₂, —N(R⁴)₂, —CO₂R, —CONH(R⁴), —N(R⁴)COR, —SO₂N(R⁴)₂, —N(R⁴)SO₂R, —SR, —OR, —C(O)R, or substituted or unsubstituted group selected from 5–6 membered heterocyclyl, $C_{6-10}$ aryl, or $C_{1-6}$ aliphatic. More preferred R⁵ substituents include -halo, —CN, -oxo, —SR, —OR, —N(R⁴)₂, —C(O)R, or a substituted or unsubstituted group selected from 5–6 membered heterocyclyl, $C_{6-10}$ aryl, or $C_{1-6}$ aliphatic. Examples of Ring D substituents include —OH, phenyl, methyl, CH₂OH, CH₂CH₂OH, pyrrolidinyl, OPh, CF₃, C≡CH, Cl, Br, F, I, NH₂, C(O)CH₃, i-propyl, tert-butyl, SEt, OMe, N(Me)₂, methylene dioxy, and ethylene dioxy.

When the $R^x$ and $R^y$ groups of formula IV are taken together to form a fused ring, preferred $R^x/R^y$ rings include a 5-, 6-, 7-, or 8-membered unsaturated or partially unsaturated ring having 1–2 heteroatoms. This provides a bicyclic ring system containing the pyrimidine ring. Examples of preferred pyrimidine ring systems of formula IV are the mono- and bicyclic systems shown below.

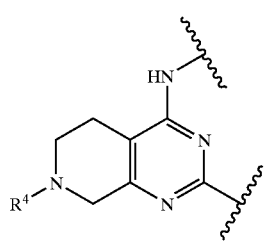

IV-D

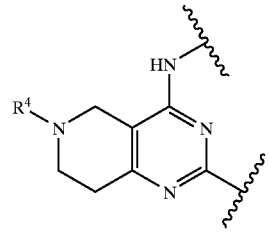

IV-E

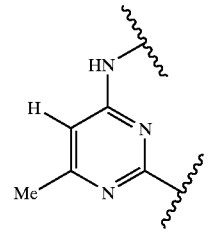

IV-G

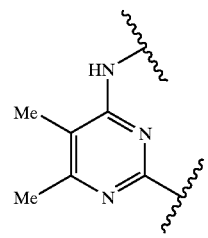

IV-H

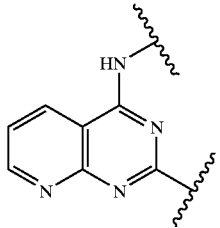

IV-J

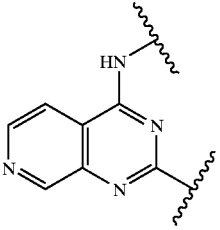

IV-K

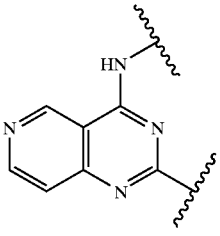

IV-L

-continued
IV-M
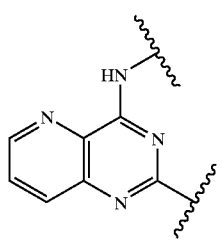
IV-N
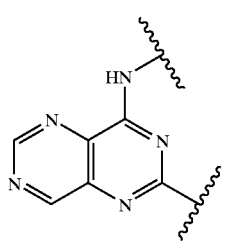
IV-O
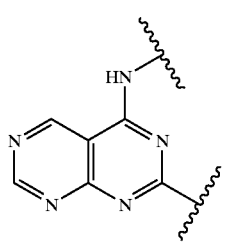
IV-P
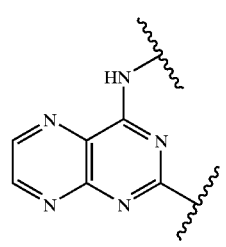
IV-Q
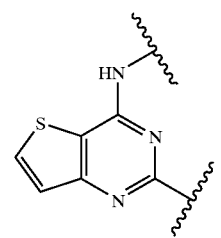
IV-R
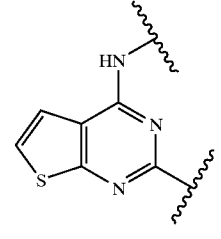
-continued
IV-S
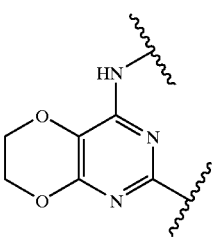
IV-T
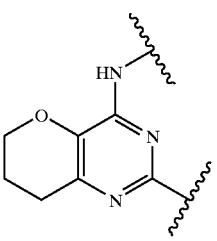
IV-U
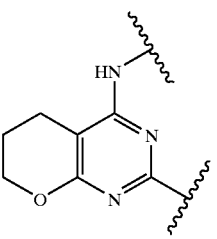
IV-V
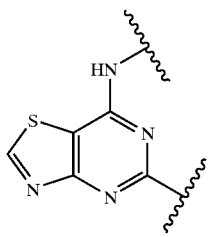
IV-W
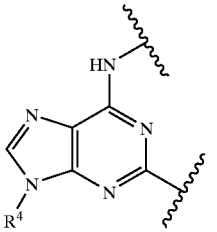
IV-X
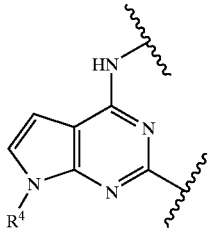

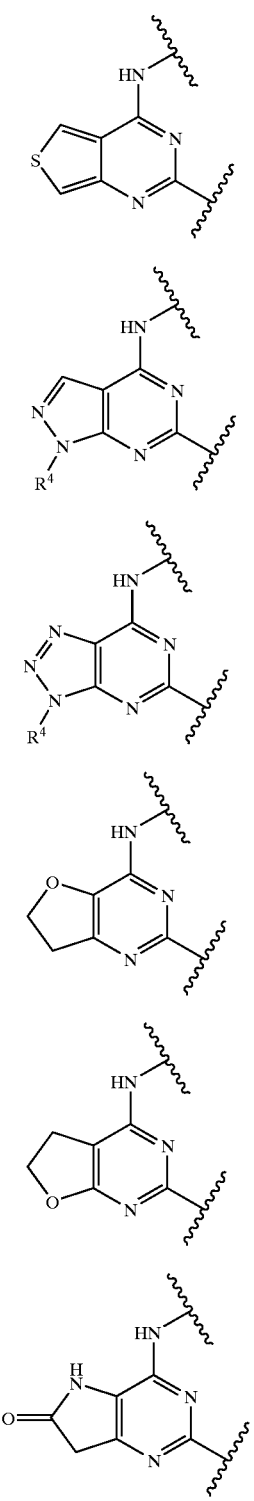

IV-Y

IV-Z

IV-AA

IV-BB

IV-CC

IV-DD

More preferred pyrimidine ring systems of formula IV include IV-E, IV-G, IV-H, IV-J, IV-K, IV-L, IV-M, IV-T, and IV-U.

In the monocyclic pyrimidine ring system of formula IV, preferred $R^x$ groups include hydrogen, amino, nitro, alkyl- or dialkylamino, acetamido, or a $C_{1-4}$ aliphatic group such as methyl, ethyl, cyclopropyl, isopropyl or t-butyl. Preferred $R^y$ groups include T-$R^3$ wherein T is a valence bond or a methylene, and $R^3$ is —R, —N($R^4$)$_2$, or —OR. When $R^3$ is —R or —OR, a preferred R is an optionally substituted group selected from $C_{1-6}$ aliphatic, phenyl, or a 5–6 membered heteroaryl or heterocyclyl ring. Examples of preferred $R^y$ groups include 2-pyridyl, 4-pyridyl, piperidinyl, methyl, ethyl, cyclopropyl, isopropyl, t-butyl, alkyl- or dialkylamino, acetamido, optionally substituted phenyl such as phenyl, methoxyphenyl, trimethoxyphenyl, or halo-substituted phenyl, and methoxymethyl.

In the bicyclic pyrimidine ring system of formula IV, the ring formed when $R^x$ and $R^y$ are taken together may be substituted or unsubstituted. Suitable substituents include —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$, wherein R and $R^4$ are as defined above for compounds of formula IV. Preferred $R^x$/$R^y$ ring substituents include -halo, —R, —OR, —COR, —CO$_2$R, —CON($R^4$)$_2$, —CN, or —N($R^4$)$_2$ wherein R is a substituted or unsubstituted $C_{1-6}$ aliphatic group.

The $R^2$ and $R^{2'}$ groups of formula IV may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula IV compounds having a pyrazole-containing bicyclic ring system:

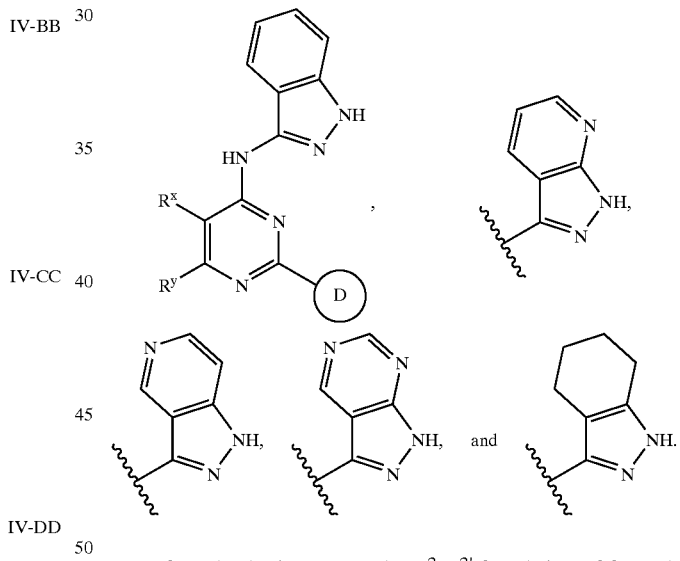

Preferred substituents on the $R^2$/$R^{2'}$ fused ring of formula IV include one or more of the following: -halo, —N($R^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl.

When the pyrazole ring system of formula IV is monocyclic, preferred $R^2$ groups include hydrogen, a substituted or unsubstituted group selected from aryl, heteroaryl, or a C$_{1-6}$ aliphatic group. Examples of such preferred $R^2$ groups include methyl, t-butyl, —CH$_2$OCH$_3$, cyclopropyl, furanyl, thienyl, and phenyl. A preferred $R^{2'}$ group is hydrogen.

Preferred formula IV compounds have one or more, and more preferably all, of the features selected from the group consisting of:

(a) Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ is hydrogen or $C_{1-4}$ aliphatic and $R^y$ is T-$R^3$, or $R^x$ and $R^y$ are taken together with their intervening atoms to form an optionally substituted 5–7 membered unsaturated or partially unsaturated ring having 1–2 ring heteroatoms; and (c) $R^{2'}$ is hydrogen or methyl and $R^2$ is T-W—$R^6$ or R, wherein W is —C($R^6$)$_2$O—, —C($R^6$)$_2$N($R^6$)—, —CO—, —CO$_2$—, —C($R^6$)OC(O)—, —C($R^6$)$_2$N($R^6$)CO—, —C($R^6$)$_2$N($R^6$)C(O)O—, or —CON($R^6$)—, and R is an optionally substituted group selected from $C_{1-6}$ aliphatic or phenyl, or $R^2$ and $R^{2'}$ are taken together with their intervening atoms to form a substituted or unsubstituted benzo, pyrido, pyrimido, or partially unsaturated 6-membered carbocyclo ring.

More preferred compounds of formula IV have one or more, and more preferably all, of the features selected from the group consisting of:

(a) Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ is hydrogen or methyl and $R^y$ is —R, N($R^4$)$_2$, or —OR, or $R^x$ and $R^y$ are taken together with their intervening atoms to form a 5–7 membered unsaturated or partially unsaturated ring having 1–2 ring nitrogens, wherein said ring is optionally substituted with —R, halo, oxo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$; and (c) each $R^5$ is independently selected from halo, oxo, CN, NO$_2$, —N($R^4$)$_2$, —CO$_2$R, —CONH($R^4$), —N($R^4$)COR, —SO$_2$N($R^4$)$_2$, —N($R^4$)SO$_2$R, —SR, —OR, —C(O)R, or a substituted or unsubstituted group selected from 5–6 membered heterocyclyl, $C_{6-10}$ aryl, or $C_{1-6}$ aliphatic.

Even more preferred compounds of formula IV have one or more, and more preferably all, of the features selected from the group consisting of:

(a) $R^x$ and $R^y$ are taken together with their intervening atoms to form a 6-membered unsaturated or partially unsaturated ring having 1–2 ring nitrogens, optionally substituted with halo, CN, oxo, $C_{1-6}$ alkyl, $C_{1-6}$ alkoxy, ($C_{1-6}$ alkyl) carbonyl, ($C_{1-6}$ alkyl)sulfonyl, mono- or dialkylamino, mono- or dialkylaminocarbonyl, mono- or dialkylaminocarbonyloxy, or 5–6 membered heteroaryl;

(b) each $R^5$ is independently selected from -halo, —CN, -oxo, —SR, —OR, —N($R^4$)$_2$, —C(O)R, or a substituted or unsubstituted group selected from 5–6 membered heterocyclyl, $C_{6-10}$ aryl, or $C_{1-6}$ aliphatic; and (c) $R^{2'}$ is hydrogen and $R^2$ is T-W—$R^6$ or R, wherein W is —C($R^6$)$_2$O—, —C($R^6$)$_2$N($R^6$)—, —CO—, —CO$_2$—, —C($R^6$)OC(O)—, —C($R^6$)$_2$N($R^6$)CO—, or —CON($R^6$)—, and R is an optionally substituted group selected from $C_{1-6}$ aliphatic or phenyl, or $R^2$ and $R^{2'}$ are taken together with their intervening atoms to form a benzo, pyrido, or partially unsaturated 6-membered carbocyclo ring optionally substituted with -halo, oxo, —N($R^4$)$_2$, —$C_{1-4}$ alkyl, —$C_{1-4}$ haloalkyl, —NO$_2$, —O($C_{1-4}$ alkyl), —CO$_2$($C_{1-4}$ alkyl), —CN, —SO$_2$($C_{1-4}$ alkyl), —SO$_2$NH$_2$, —OC(O)NH$_2$, —NH$_2$SO$_2$($C_{1-4}$ alkyl), —NHC(O)($C_{1-4}$ alkyl), —C(O)NH$_2$, or —CO($C_{1-4}$ alkyl), wherein the ($C_{1-4}$ alkyl) is a straight, branched, or cyclic alkyl group.

Representative compounds of formula IV are set forth in Table 3 below.

TABLE 3

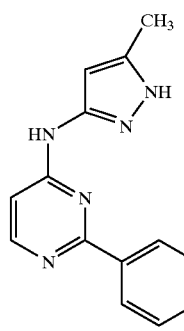

IV-1

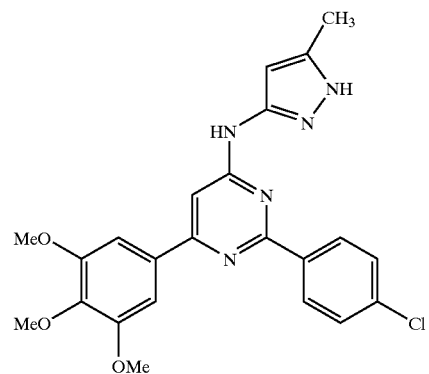

IV-2

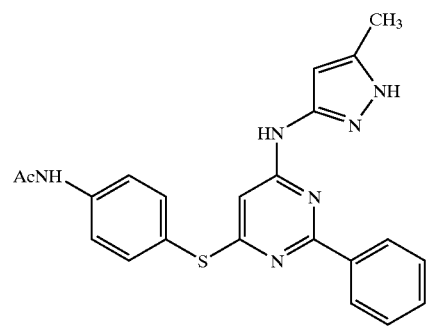

IV-3

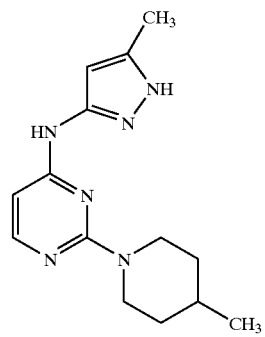

TABLE 3-continued
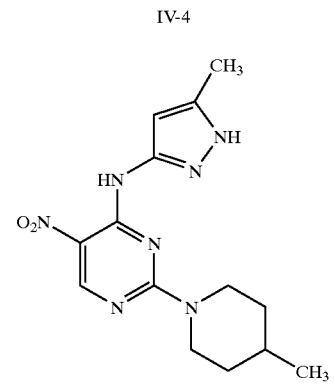
IV-4
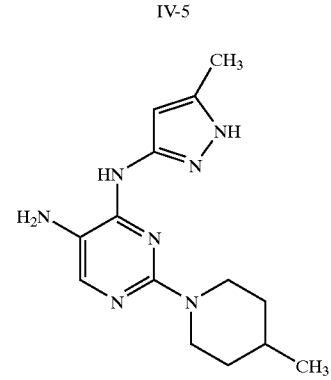
IV-5
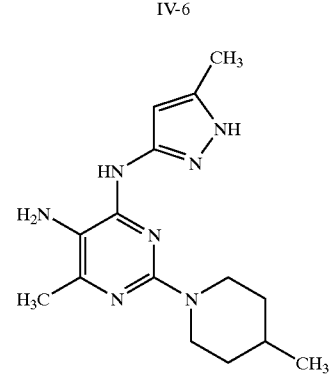
IV-6
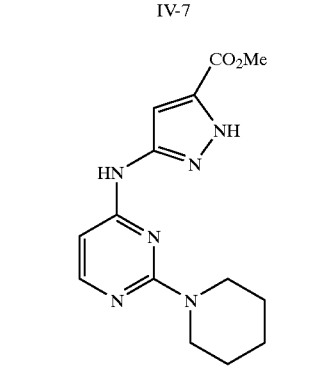
IV-7
TABLE 3-continued
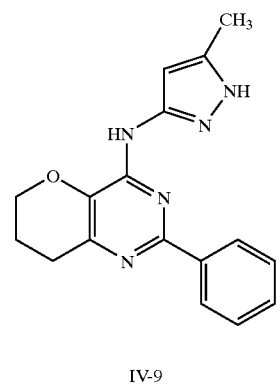
IV-8
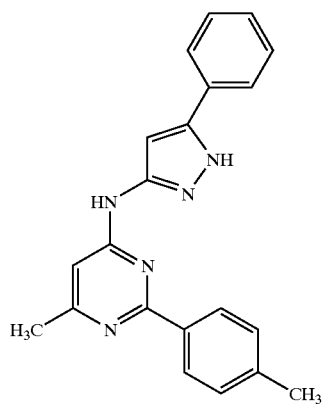
IV-9
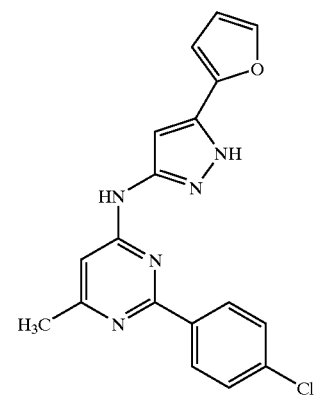
IV-10

TABLE 3-continued
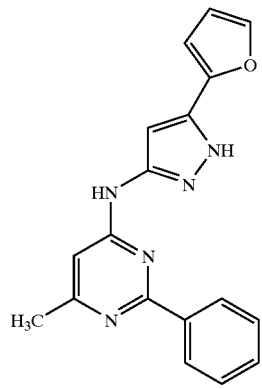
IV-12
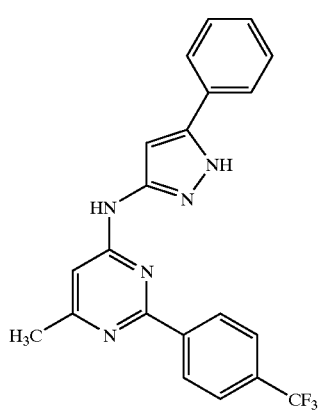
IV-13
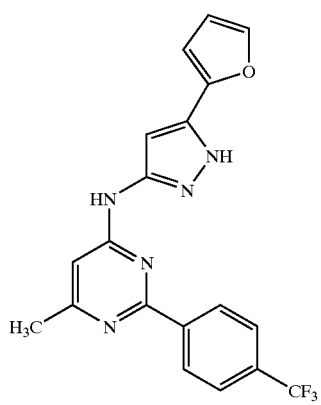
IV-14
TABLE 3-continued
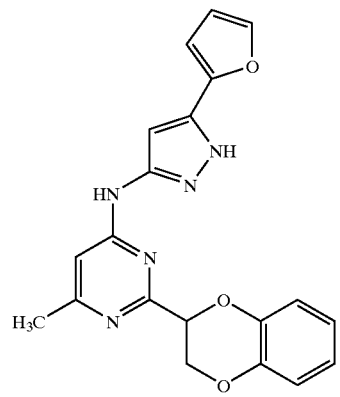
IV-15
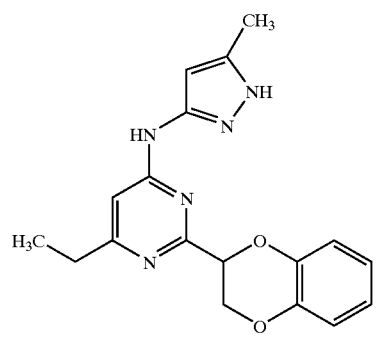
IV-16
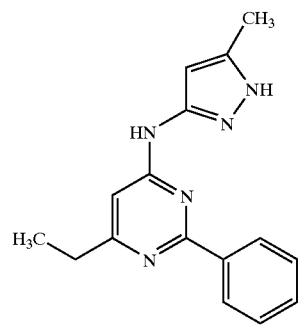
IV-17
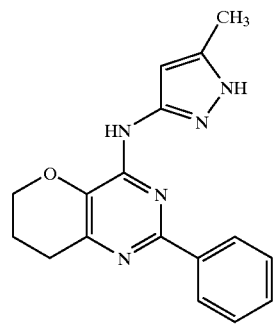
IV-18

TABLE 3-continued
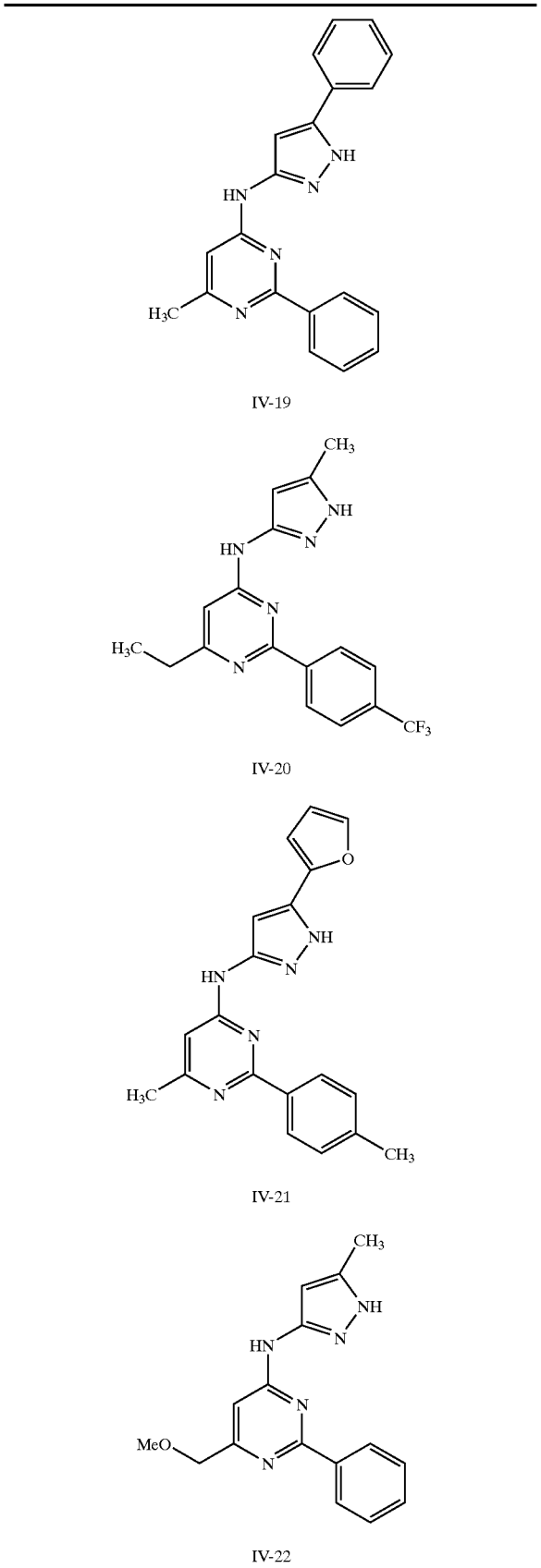
IV-19
IV-20
IV-21
IV-22
TABLE 3-continued
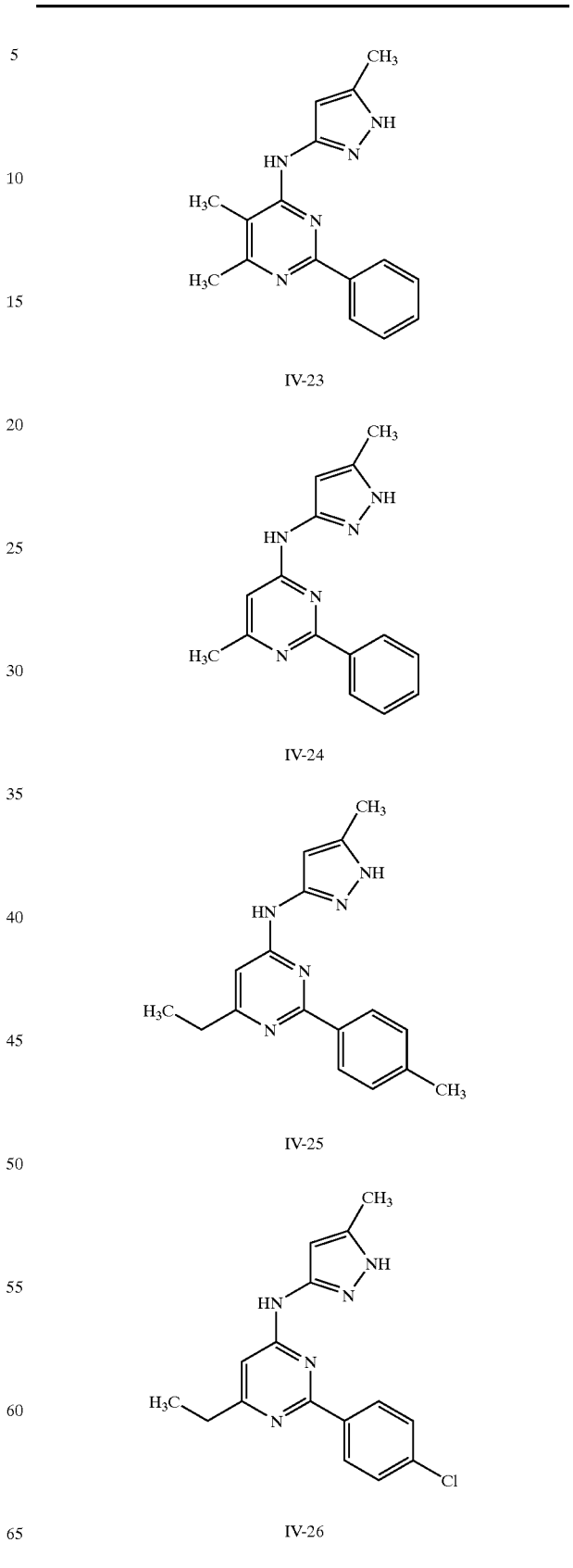
IV-23
IV-24
IV-25
IV-26

TABLE 3-continued

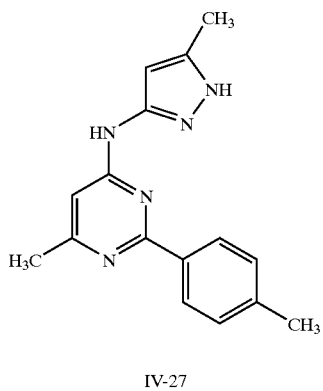

IV-27

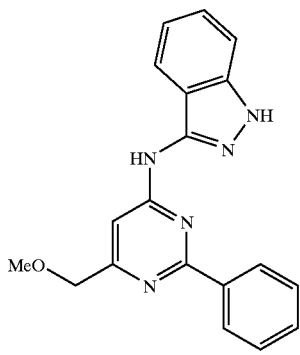

IV-28

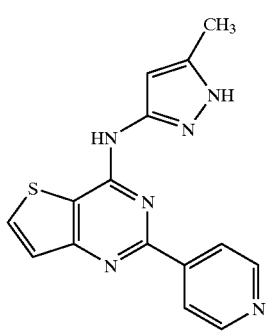

IV-29

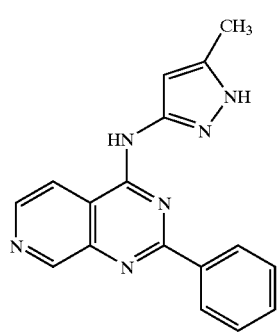

IV-30

TABLE 3-continued

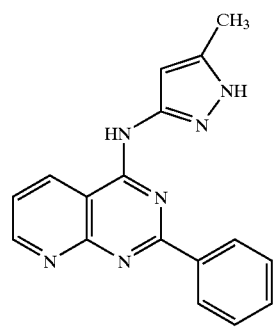

IV-31

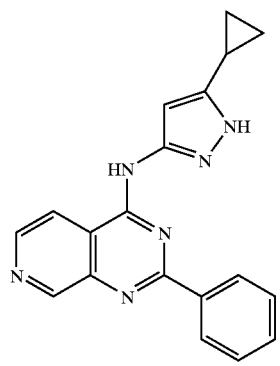

IV-32

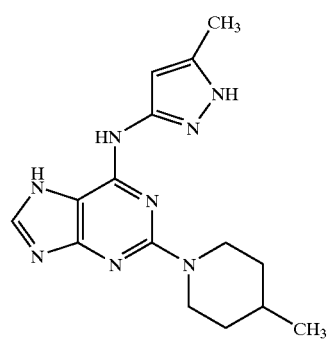

IV-33

In another embodiment, this invention provides a composition comprising a compound of formula IV and a pharmaceutically acceptable carrier.

One aspect of this invention relates to a method of inhibiting GSK-3 activity in a patient, comprising administering to the patient a therapeutically effective amount of a composition comprising a compound of formula IV.

Another aspect relates to a method of treating a disease that is alleviated by treatment with a GSK-3 inhibitor, said method comprising the step of administering to a patient in need of such a treatment a therapeutically effective amount of a composition comprising a compound of formula IV.

Another aspect relates to a method of enhancing glycogen synthesis and/or lowering blood levels of glucose in a patient in need thereof, comprising administering to said patient a therapeutically effective amount of a composition comprising a compound of formula IV. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula IV. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula IV. This method is especially useful for treating schizophrenia.

One aspect of this invention relates to a method of inhibiting Aurora activity in a patient, comprising administering to the patient a therapeutically effective amount of a composition comprising a compound of formula IV.

Another aspect relates to a method of treating a disease that is alleviated by treatment with an Aurora inhibitor, said method comprising the step of administering to a patient in need of such a treatment a therapeutically effective amount of a composition comprising a compound of formula IV. This method is especially useful for treating cancer, such as colon, ovarian, and breast cancer.

One aspect of this invention relates to a method of inhibiting CDK-2 activity in a patient, comprising administering to the patient a therapeutically effective amount of a composition comprising a compound of formula IV.

Another aspect relates to a method of treating a disease that is alleviated by treatment with a CDK-2 inhibitor, said method comprising the step of administering to a patient in need of such a treatment a therapeutically effective amount of a composition comprising a compound of formula IV. This method is especially useful for treating cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

Another method relates to inhibiting GSK-3, Aurora, or CDK-2 activity in a biological sample, which method comprises contacting the biological sample with the GSK-3 or Aurora inhibitor of formula IV, or a pharmaceutical composition thereof, in an amount effective to inhibit GSK-3, Aurora or CDK-2.

Each of the aforementioned methods directed to the inhibition of GSK-3, Aurora or CDK-2, or the treatment of a disease alleviated thereby, is preferably carried out with a preferred compound of formula IV, as described above.

Another embodiment of this invention relates to compounds of formula V:

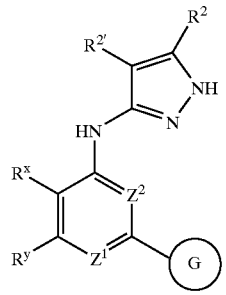

V or a pharmaceutically acceptable derivative or prodrug thereof, wherein:

$Z^1$ is N, $CR^a$, or CH and $Z^2$ is N or CH, provided that one of $Z^1$ and $Z^2$ is nitrogen;

G is Ring C or Ring D;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —$R^8$;

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^1$ is selected from -halo, —CN, —$NO_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

$R^x$ and $R^y$ are independently selected from T-$R^3$, or $R^x$ and $R^y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by $R^x$ and $R^y$ is substituted by oxo or T-$R^3$, and any substitutable nitrogen on said ring formed by $R^x$ and $R^y$ is substituted by $R^4$;

T is a valence bond or a $C_{1-4}$ alkylidene chain;

$R^2$ and $R^{2'}$ are independently selected from —R, -T-W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by $R^2$ and $R^{2'}$ is substituted by halo, oxo, —CN, —$NO_2$, —$R^7$, or —V—$R^6$, and any substitutable nitrogen on said ring formed by $R^2$ and $R^{2'}$ is substituted by $R^4$;

$R^3$ is selected from —R, -halo, —OR, —C(=O)R, —$CO_2$R, —COCOR, —COCH$_2$COR, —$NO_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$ (optionally substituted $C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, COR$^7$, —CO$_2$ (optionally substituted $C_{1-6}$ aliphatic), —CON ($R^7$)$_2$, or —SO$_2$R$^7$, or two $R^4$ on the same nitrogen are taken together to form a 5–8 membered heterocyclyl or heteroaryl ring;

each $R^5$ is independently selected from —R, halo, —OR, —C(=O)R, —CO$_2$R, —COCOR, —$NO_2$, —CN, —S(O)R, —SO$_2$R, —SR, —N($R^4$)$_2$, —CON($R^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, or R$^5$ and an adjacent substituent taken together with their intervening atoms form said ring fused to Ring C;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$_6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each R$^6$ is independently selected from hydrogen, an optionally substituted C$_{1-4}$ aliphatic group, or two R$^6$ groups on the same nitrogen atom are taken together with the nitrogen atom to form a 5–6 membered heterocyclyl or heteroaryl ring;

each R$^7$ is independently selected from hydrogen or an optionally substituted C$_{1-6}$ aliphatic group, or two R$^7$ on the same nitrogen are taken together with the nitrogen to form a 5–8 membered heterocyclyl or heteroaryl ring;

each R$^8$ is independently selected from an optionally substituted C$_{1-4}$ aliphatic group, —OR$^6$, —SR$^6$, —COR$^6$, —SO$_2$R$^6$, —N(R$^6$)$_2$, —N(R$^6$)N(R$^6$)$_2$, —CN, —NO$_2$, —CON(R$^6$)$_2$, or —CO$_2$R$^6$; and R$^a$ is selected from halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, —OC(=O)N(R$^4$)$_2$, or an optionally substituted group selected from C$_{1-6}$ aliphatic, C$_{6-10}$ aryl, a heteroaryl ring having 5–10 ring atoms, or a heterocyclyl ring having 5–10 ring atoms.

Compounds of formula V may be represented by specifying Z$^1$ and Z$^2$ as shown below:

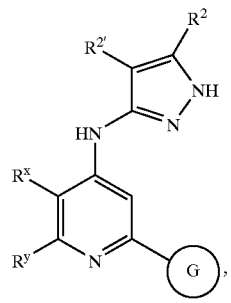

Va

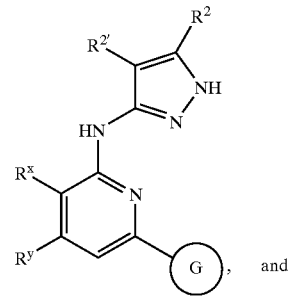

Vb, and

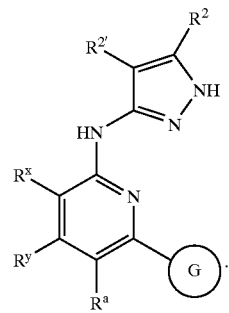

Vc.

When the R$^x$ and R$^y$ groups of formula V are taken together to form a fused ring, preferred R$^x$/R$^y$ rings include a 5-, 6-, 7-, or 8-membered unsaturated or partially unsaturated ring having 0–2 heteroatoms, wherein said R$^x$/R$^y$ ring is optionally substituted. This provides a bicyclic ring system containing a pyridine ring. Examples of preferred bicyclic ring systems of formula V are shown below.

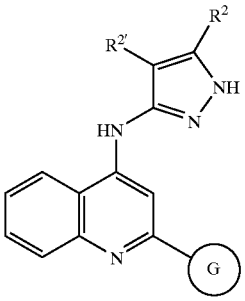

Va-A

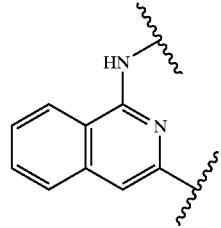

Vb-A

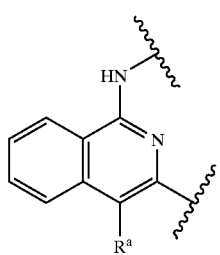
Va-B
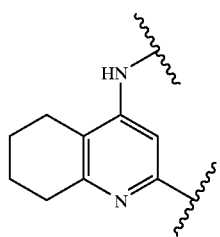
Vb-B
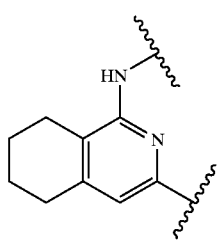
Vc-B
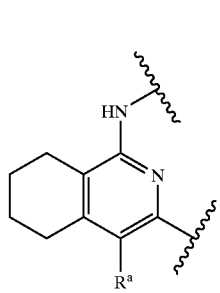
Va-C
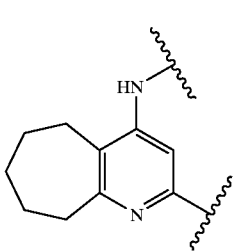
Vb-C
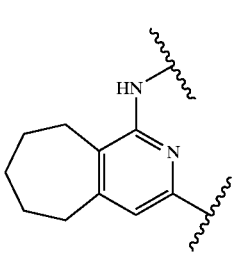
Vc-C
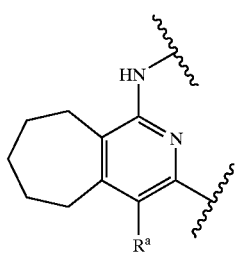
Va-D
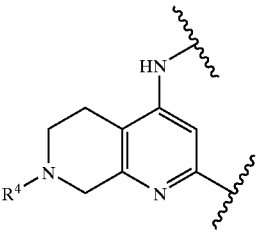
Vb-D
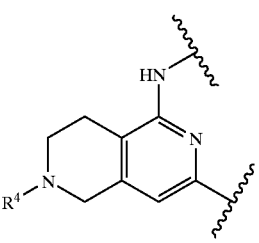
Vc-D
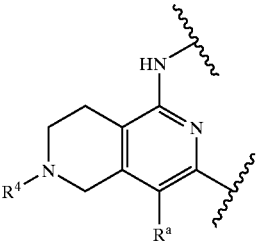
Va-E
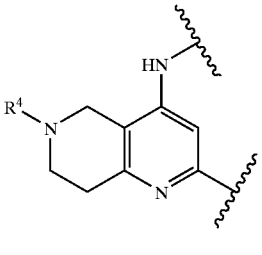
Vb-E Vc-E
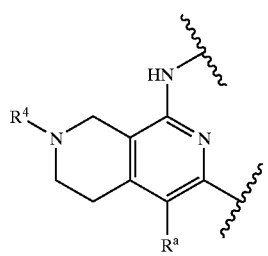
Va-F
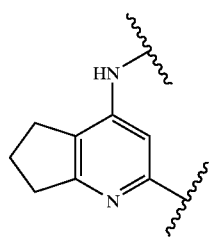
Vb-F
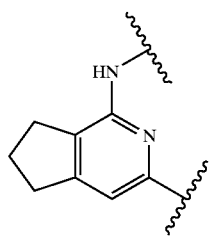
Vc-F
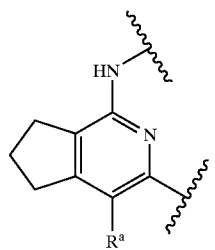
Va-J
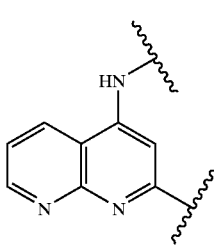
Vb-J
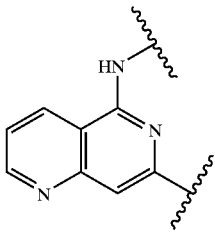
Vc-J
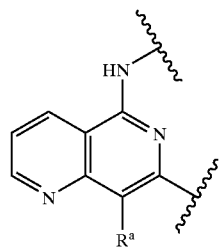
Va-K
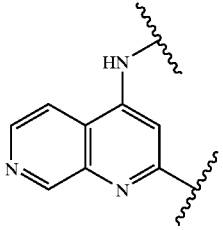
Vb-K
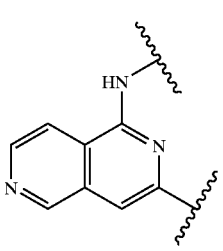
Vc-K
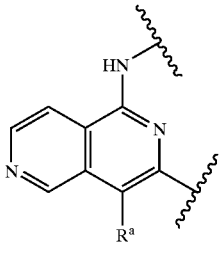
Va-L
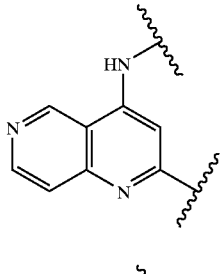
Vb-L
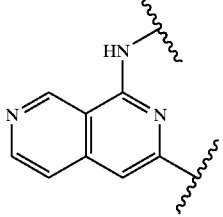

-continued
Vc-L
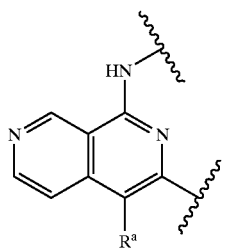
Va-M
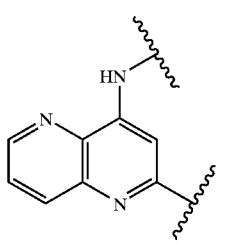
Vb-M
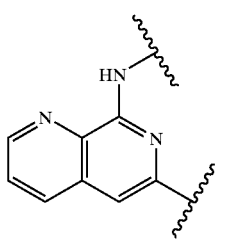
Vc-M
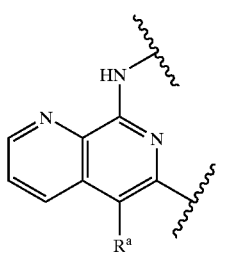
Va-N
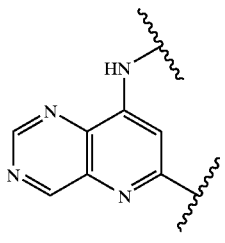
Vb-N
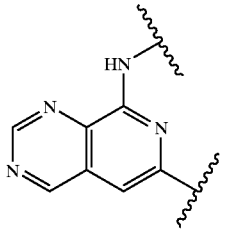
-continued
Vc-N
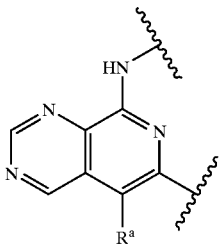
Va-O
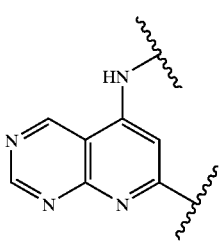
Vb-O
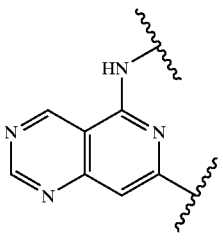
Vc-O
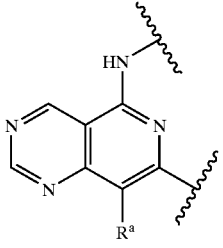
Va-P
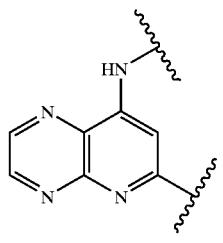
Vb-P
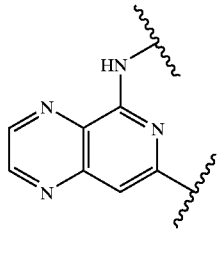

-continued

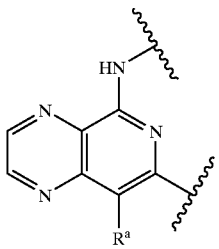

Vc-P

More preferred bicyclic ring systems of formula V include Va-A, Vb-A, Vc-A, Va-B, Vb-B, Vc-B, Va-D, Vb-D, Vc-D, Va-B, Vb-E, Vc-E, Va-J, Vb-J, Vc-J, Va-K, Vb-K, Vc-K, Va-L, Vb-L, Vc-L, Va-M, Vb-M, and Vc-M, most preferably Va-A, Vb-A, Vc-A, Va-B, Vb-B, and Vc-B.

In the monocyclic pyridine ring system of formula V, preferred $R^x$ groups include hydrogen, alkyl- or dialkylamino, acetamido, or a $C_{1-4}$ aliphatic group such as methyl, ethyl, cyclopropyl, isopropyl or t-butyl. Preferred $R^y$ groups include T-$R^3$ wherein T is a valence bond or a methylene, and $R^3$ is —R, —N(R$^4$)$_2$, or —OR. When $R^3$ is —R or —OR, a preferred R is an optionally substituted group selected from $C_{1-6}$ aliphatic, phenyl, or a 5–6 membered heteroaryl or heterocyclyl ring. Examples of preferred $R^y$ include 2-pyridyl, 4-pyridyl, piperidinyl, methyl, ethyl, cyclopropyl, isopropyl, t-butyl, alkyl- or dialkylamino, acetamido, optionally substituted phenyl such as phenyl or halo-substituted phenyl, and methoxymethyl.

In the bicyclic ring system of formula V, the ring formed when $R^x$ and $R^y$ are taken together may be substituted or unsubstituted. Suitable substituents include —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, wherein R and $R^4$ are as defined above. Preferred $R^x/R^y$ ring substituents include -halo, —R, —OR, —COR, —CO$_2$R, —CON(R$^4$)$_2$, —CN, or —N(R$^4$)$_2$ wherein R is an optionally substituted $C_{1-6}$ aliphatic group.

The $R^2$ and $R^{2'}$ groups of formula V may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula V compounds having a pyrazole-containing bicyclic ring system:

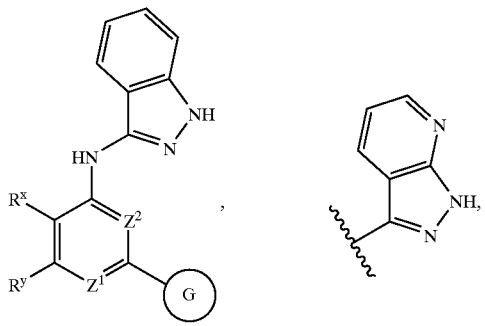

-continued

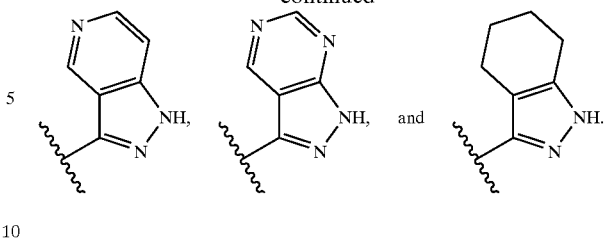

Preferred substituents on the $R^2/R^{2'}$ fused ring of formula V include one or more of the following: -halo, —N(R$^4$)$_2$, —C$_{1-4}$ alkyl, —C$_{1-4}$ haloalkyl, —NO$_2$, —O(C$_{1-4}$ alkyl), —CO2(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO (C$_{1-4}$ alkyl), wherein the (C$_{1-4}$ alkyl) is a straight, branched, or cyclic alkyl group. Preferably, the (C$_{1-4}$ alkyl) group is methyl.

When the pyrazole ring system is monocyclic, preferred $R^2$ groups include hydrogen, C$_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred $R^2$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl). A preferred $R^{2'}$ group is hydrogen.

More preferred ring systems of formula V are the following, which may be substituted as described above, wherein $R^2$ and $R^{2'}$ are taken together with the pyrazole ring to form an optionally substituted indazole ring; and $R^x$ and $R^y$ are each methyl, or $R^x$ and $R^y$ are taken together with the pyridine ring to form an optionally substituted quinoline, isoquinoline, tetrahydroquinoline or tetrahydroisoquinoline ring:

V-Aa

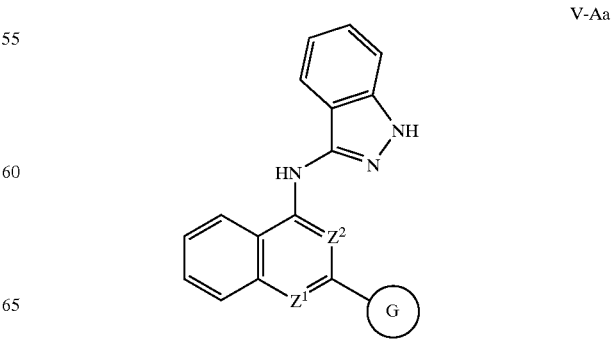

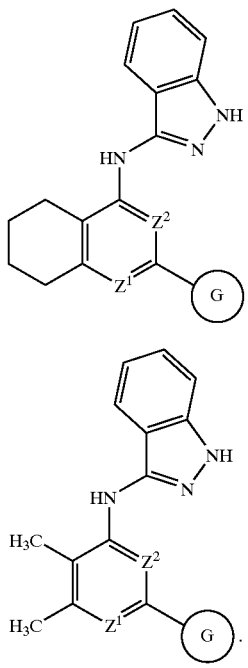

V-Ba

V-Ha

When G is Ring C, preferred formula V Ring C groups are phenyl and pyridinyl. When two adjacent substituents on Ring C are taken together to form a fused ring, Ring C is contained in a bicyclic ring system. Preferred fused rings include a benzo or pyrido ring. Such rings preferably are fused at ortho and meta positions of Ring C. Examples of preferred bicyclic Ring. C systems include naphthyl and isoquinolinyl. Preferred $R^1$ groups include -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —$OC(O)NH_2$, or —$NHSO_2R^6$. When $R^1$ is an optionally substituted $C_{1-6}$ aliphatic group, the most preferred optional substituents are halogen. Examples of preferred $R^1$ groups include —$CF_3$, —Cl, —F, —CN, —$COCH_3$, —$OCH_3$, —OH, —$CH_2CH_3$, —$OCH_2CH_3$, —$CH_3$, —$CF_2CH_3$, cyclohexyl, t-butyl, isopropyl, cyclopropyl, —C≡CH, —C≡C—$CH_3$, —$SO_2CH_3$, —$SO_2NH_2$, —$N(CH_3)_2$, —$CO_2CH_3$, —$CONH_2$, —$NHCOCH_3$, —$OC(O)NH_2$, —$NHSO_2CH_3$, and —$OCF_3$.

On Ring C preferred $R^5$ substituents, when present, include -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$SO_2N(R^4)_2$, and —$N(R^4)SO_2R$. More preferred $R^5$ substituents include —Cl, —F, —CN, —$CF_3$, —$NH_2$, —$NH(C_{1-4}$ aliphatic), —$N(C_{1-4}$ aliphatic$)_2$, —$O(C_{1-4}$ aliphatic), $C_{1-4}$ aliphatic, and —$CO_2$ ($C_{1-4}$ aliphatic). Examples of such preferred $R^5$ substituents include —Cl, —F, —CN, —$CF_3$, —$NH_2$, —NHMe, —$NMe_2$, —OEt, methyl, ethyl, cyclopropyl, isopropyl, t-butyl, and —$CO_2Et$.

When G is Ring D, preferred formula V Ring D monocyclic rings include substituted and unsubstituted phenyl, pyridinyl, piperidinyl, piperazinyl, pyrrolidinyl, thienyl, azepanyl, and morpholinyl rings. When two adjacent substituents on Ring D are taken together to form a fused ring, the Ring D system is bicyclic. Preferred formula V Ring D bicyclic rings include 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, and naphthyl. Examples of more preferred bicyclic Ring D systems include naphthyl and isoquinolinyl.

Preferred substituents on Ring D of formula V include one or more of the following: halo, oxo, CN, —$NO_2$, —$N(R^4)_2$, —$CO_2R$, —$CONH(R^4)$, —$N(R^4)COR$, —$SO_2N(R^4)_2$, —$N(R^4)SO_2R$, —SR, —OR, —C(O)R, or substituted or unsubstituted group selected from 5–6 membered heterocyclyl, $C_{6-10}$ aryl, or $C_{1-6}$ aliphatic. More preferred Ring D substituents include -halo, —CN, -oxo, —SR, —OR, —$N(R^4)_2$, —C(O)R, or a substituted or unsubstituted group selected from 5–6 membered heterocyclyl, $C_{6-10}$ aryl, or $C_{1-6}$ aliphatic. Examples of Ring D substituents include —OH, phenyl, methyl, $CH_2OH$, $CH_2CH_2OH$, pyrrolidinyl, OPh, $CF_3$, C≡CH, Cl, Br, F, I, $NH_2$, $C(O)CH_3$, i-propyl, tert-butyl, SEt, OMe, $N(Me)_2$, methylene dioxy, and ethylene dioxy.

Preferred formula V compounds have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is selected from a naphthyl, quinolinyl or isoquinolinyl ring, and $R^1$ is -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —$OC(O)NH_2$, or —$NHSO_2R^6$; or Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ is hydrogen or $C_{1-4}$ aliphatic and $R^y$ is T-$R^3$, or $R^x$ and $R^y$ are taken together with their intervening atoms to form an optionally substituted 5–7 membered unsaturated or partially unsaturated ring having 0–2 ring nitrogens; and (c) $R^{2'}$ is hydrogen and $R^2$ is hydrogen or a substituted or unsubstituted group selected from aryl, heteroaryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring.

More preferred compounds of formula V have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is a naphthyl ring, and $R^1$ is -halo, a $C_{1-6}$ haloaliphatic group, a $C_{1-6}$ aliphatic group, phenyl, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ is hydrogen or methyl and $R^y$ is —R, $N(R^4)_2$, or —OR, or $R^x$ and $R^y$ are taken together with their intervening atoms to form a benzo ring or a 5–7 membered partially unsaturated carbocyclo ring, said benzo or carbocyclo ring optionally substituted with —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —OC(=O)$N(R^4)_2$;

(c) $R^{2'}$ is hydrogen and $R^2$ is hydrogen or a substituted or unsubstituted group selected from aryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring; and (d) Ring D is substituted by oxo or $R^5$, wherein each $R^5$ is independently selected from -halo, —CN, —NO$_2$, —N(R$^4$)$_2$, optionally substituted $C_{1-6}$ aliphatic group, —OR, —C(O)R, —CO$_2$R, —CONH(R$^4$), —N(R$^4$)COR, —SO$_2$N(R$^4$)$_2$, or —N(R$^4$)SO$_2$R.

Even more preferred compounds of formula V have one or more, and more preferably all, of the features selected from the group consisting of:

(a) Ring C is a phenyl or pyridinyl ring, optionally substituted by —R$^5$, wherein when Ring C and two adjacent substituents thereon form a bicyclic ring system, the bicyclic ring system is a naphthyl ring, and R$^1$ is -halo, a $C_{1-4}$ aliphatic group optionally substituted with halogen, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, isoquinolinyl, quinolinyl, or naphthyl;

(b) $R^x$ is hydrogen or methyl and $R^y$ is methyl, methoxymethyl, ethyl, cyclopropyl, isopropyl, t-butyl, alkyl- or an optionally substituted group selected from 2-pyridyl, 4-pyridyl, piperidinyl, or phenyl, or $R^x$ and $R^y$ are taken together with their intervening atoms to form a benzo ring or a 6-membered partially unsaturated carbocyclo ring optionally substituted with halo, CN, oxo, $C_{1-6}$ alkyl, $C_{1-6}$ alkoxy, ($C_{1-6}$ alkyl)carbonyl, ($C_{1-6}$ alkyl)sulfonyl, mono- or dialkylamino, mono- or dialkylaminocarbonyl, mono- or dialkylaminocarbonyloxy, or 5–6 membered heteroaryl;

(c) $R^2$ and $R^{2'}$ are taken together with their intervening atoms to form a benzo, pyrido, pyrimido or partially unsaturated 6-membered carbocyclo ring optionally substituted with -halo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, or —CO(C$_{1-4}$ alkyl) wherein the (C$_{1-4}$ alkyl) is a straight, branched, or cyclic alkyl group; and (d) Ring D is substituted by oxo or $R^5$, wherein each $R^5$ is independently selected from —Cl, —F, —CN, —CF$_3$, —NH$_2$, —NH(C$_{1-4}$ aliphatic), —N(C$_{1-4}$ aliphatic)$_2$, —O(C$_{1-4}$ aliphatic), C$_{1-4}$ aliphatic, and —CO$_2$(C$_{1-4}$ aliphatic).

Representative compounds of formula V are set forth in Table 4 below.

TABLE 4

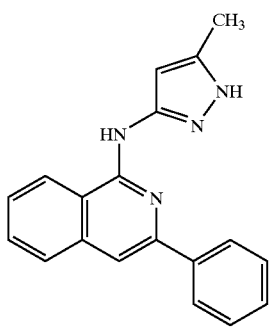

V-1

TABLE 4-continued

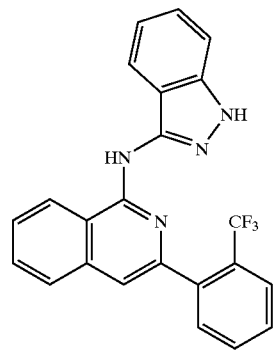

V-2

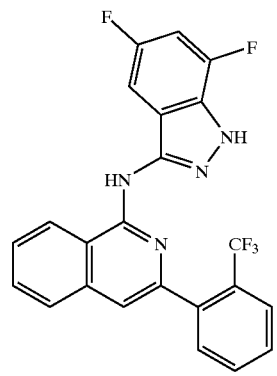

V-3

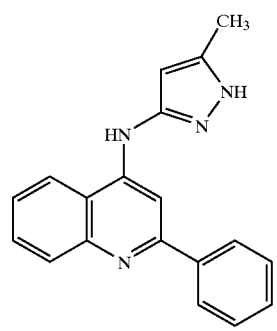

V-4

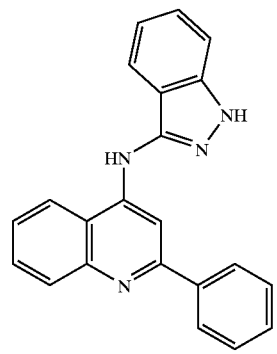

V-5

TABLE 4-continued
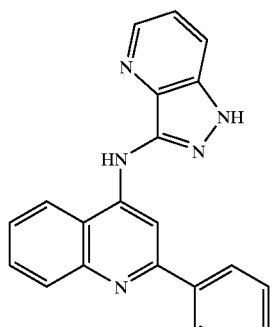
V-6
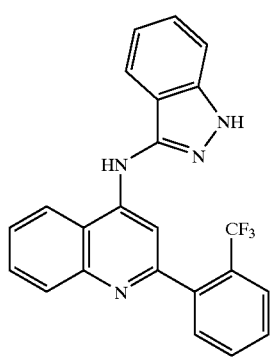
V-7
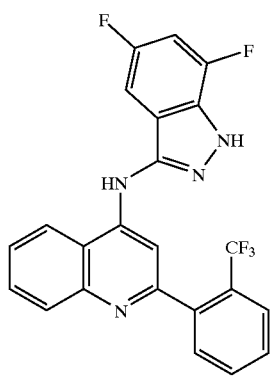
V-8
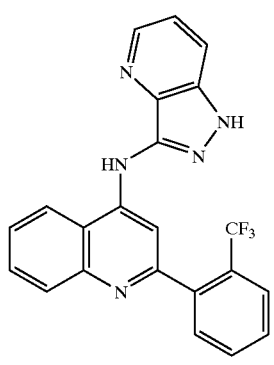
V-9
TABLE 4-continued
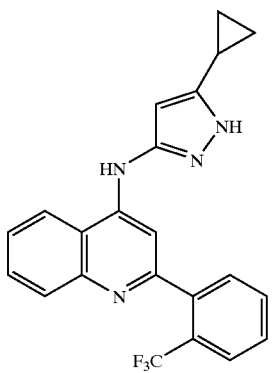
V-10
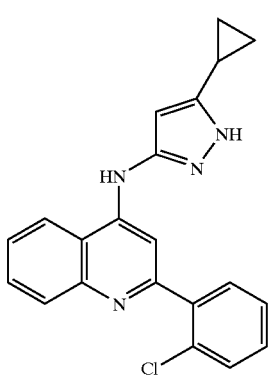
V-11
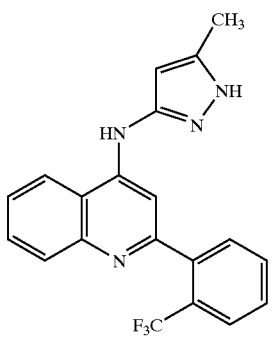
V-12
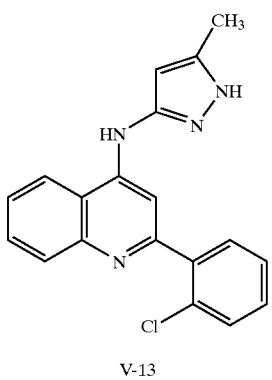
V-13

TABLE 4-continued
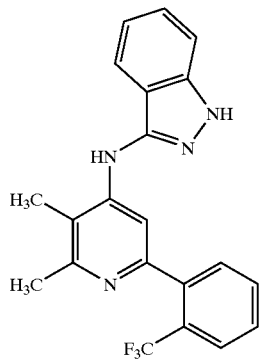
V-14
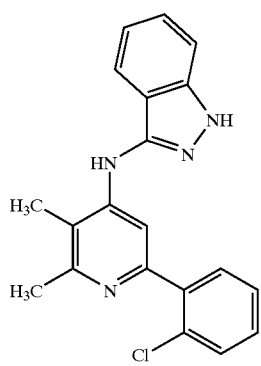
V-15
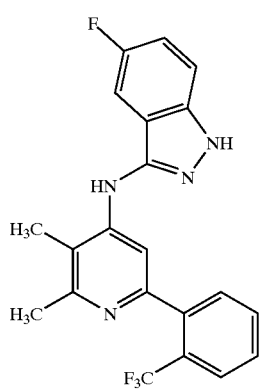
V-16
TABLE 4-continued
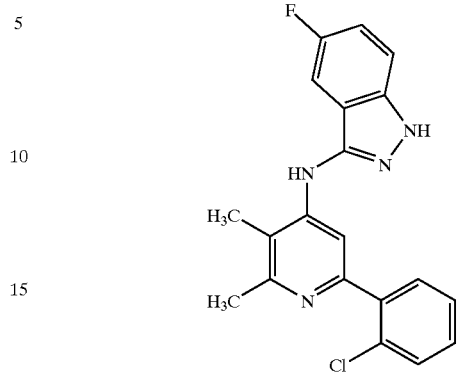
V-17
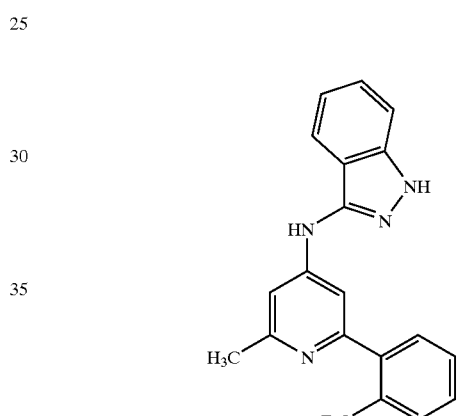
V-18
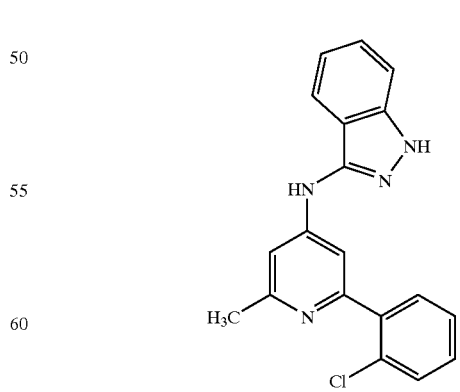
V-19

TABLE 4-continued
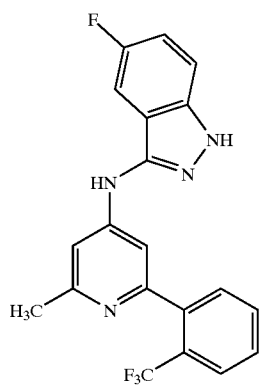
V-20
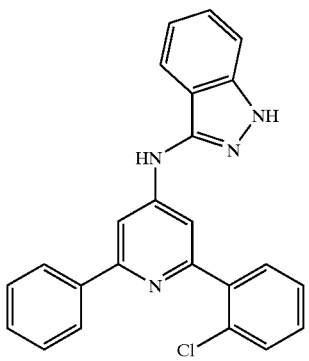
V-23
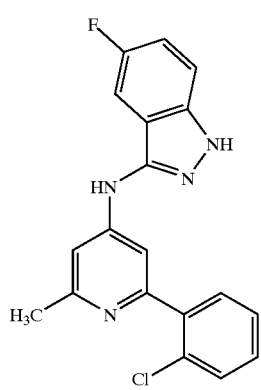
V-21
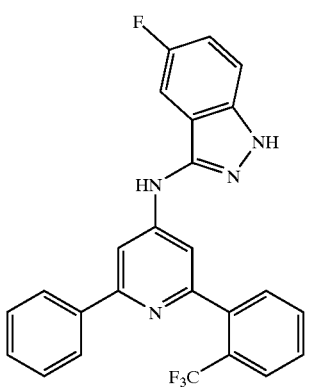
V-24
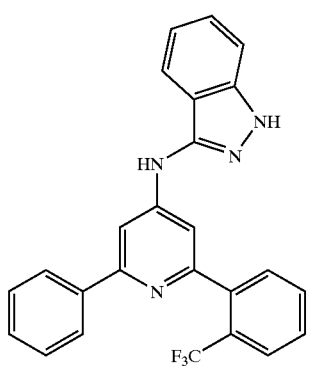
V-22
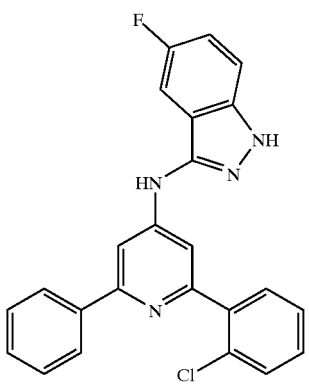
V-25

TABLE 4-continued
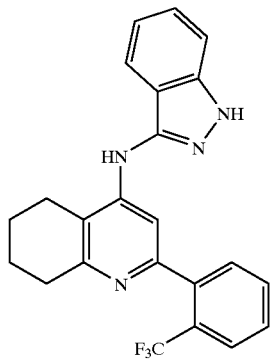
V-26
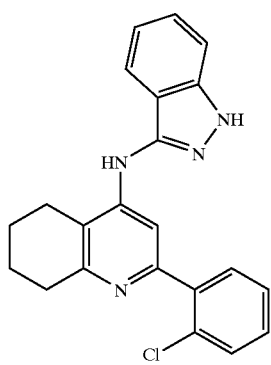
V-27
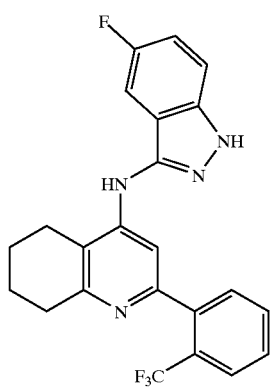
V-28
TABLE 4-continued
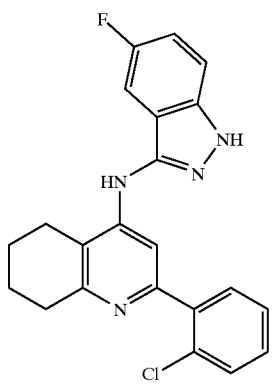
V-29
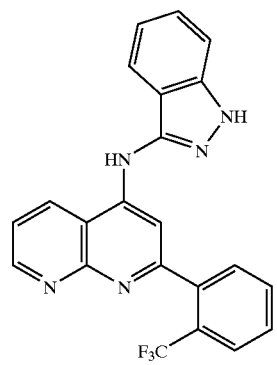
V-30
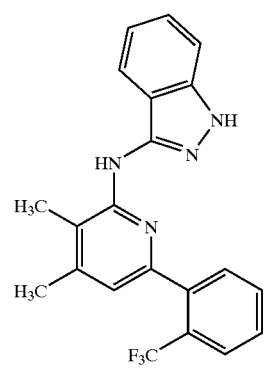
V-31

TABLE 4-continued
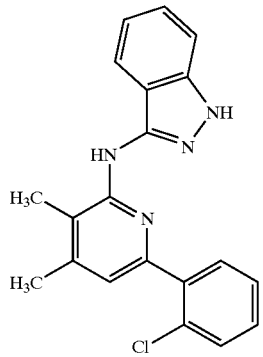
V-32
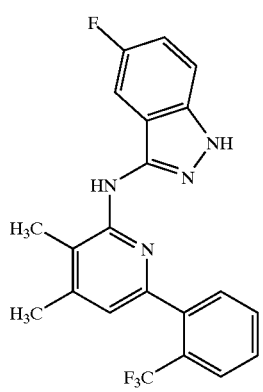
V-33
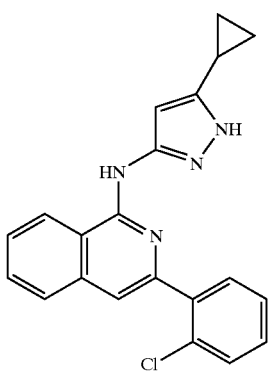
V-34
TABLE 4-continued
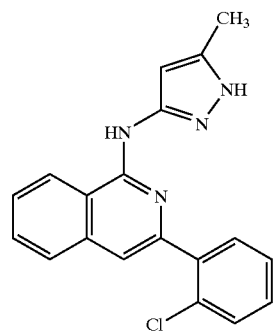
V-35
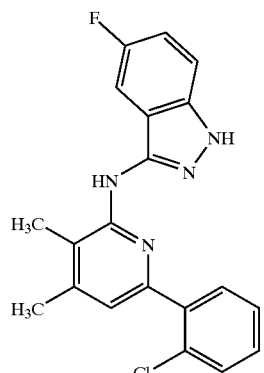
V-36
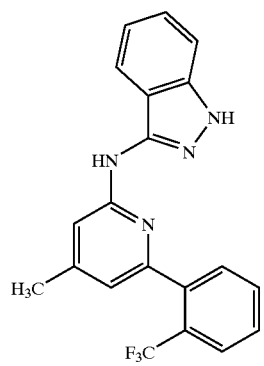
V-37
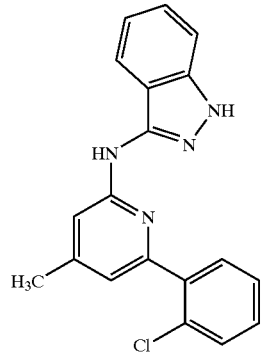
V-38

TABLE 4-continued
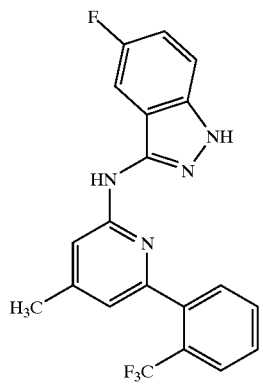
V-39
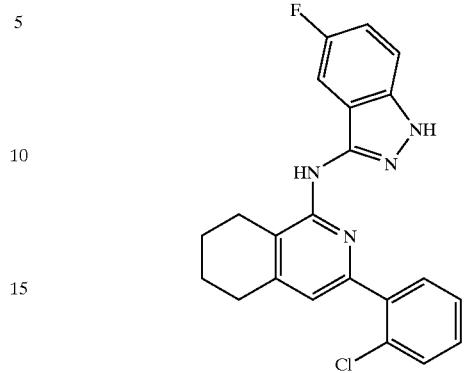
V-42
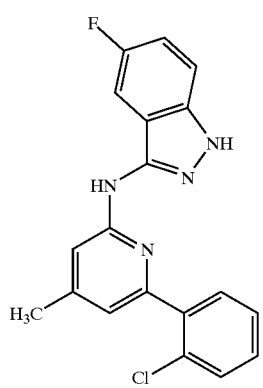
V-40
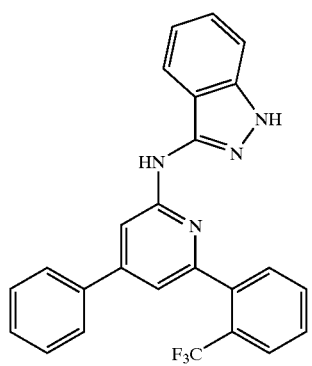
V-43
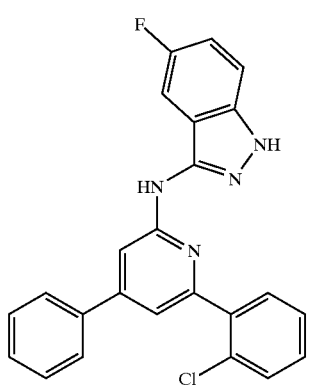
V-41
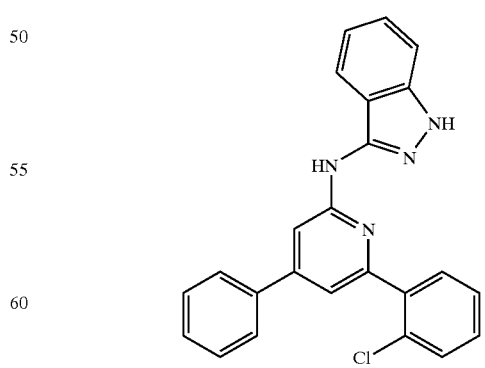
V-44

TABLE 4-continued
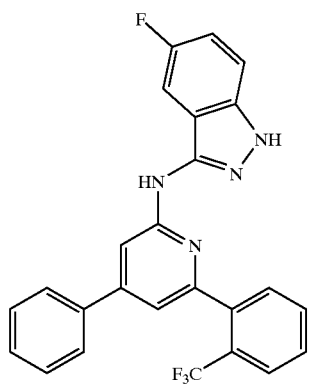
V-45
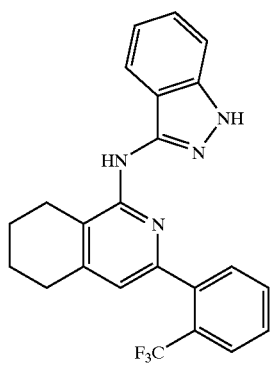
V-46
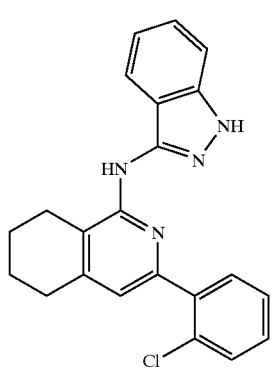
V-47
TABLE 4-continued
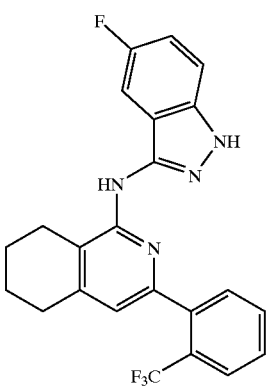
V-48
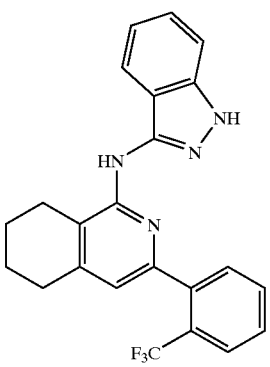
V-49
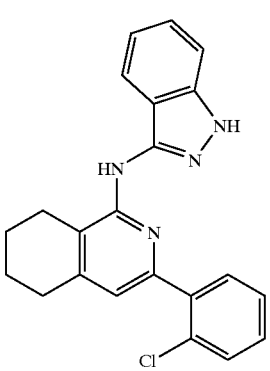
V-50

TABLE 4-continued
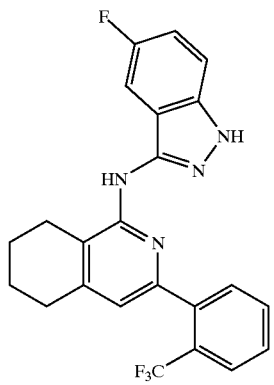
V-51
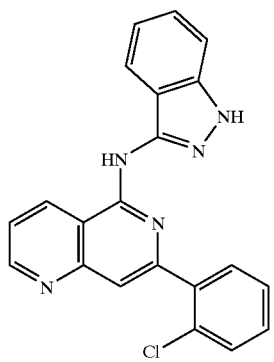
V-52
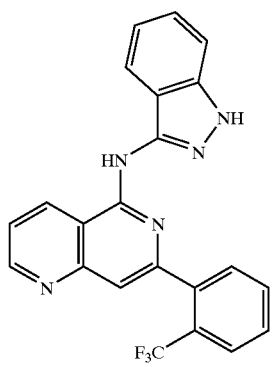
V-53
TABLE 4-continued
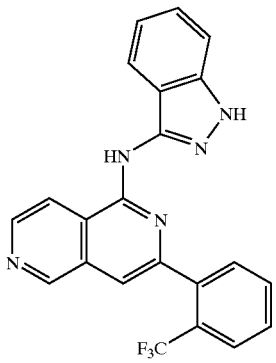
V-54
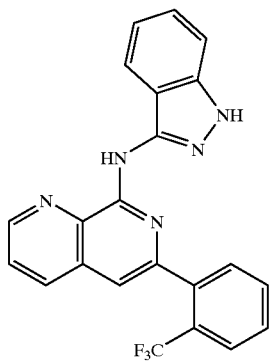
V-55
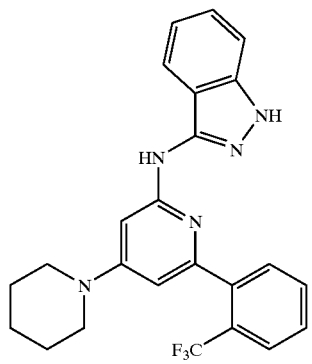
V-56

TABLE 4-continued
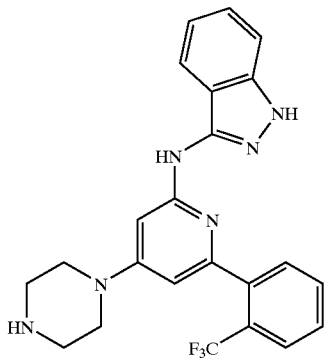
V-57
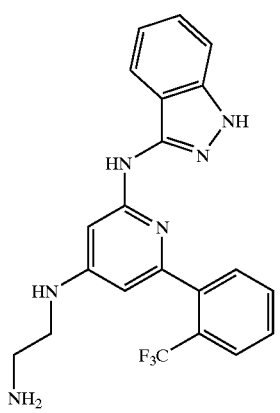
V-58
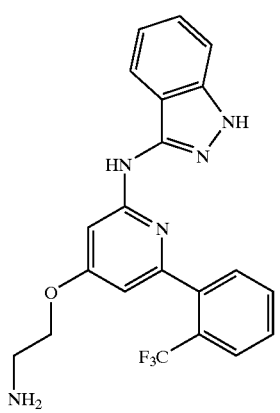
V-59
TABLE 4-continued
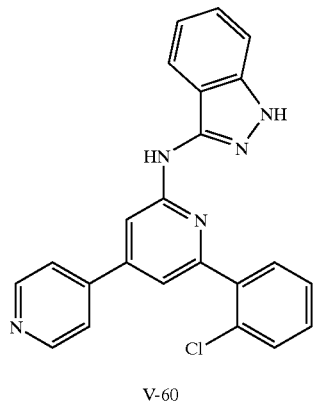
V-60
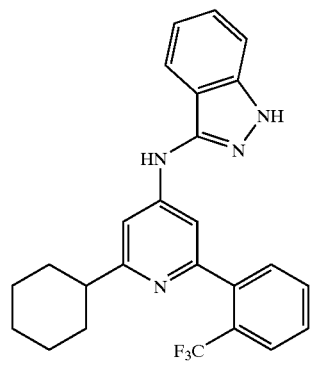
V-61
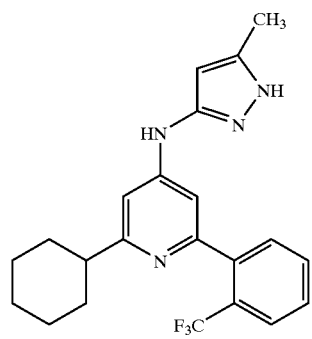
V-62
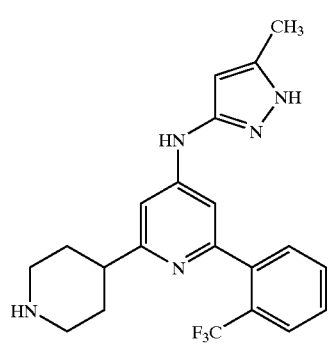
V-63

TABLE 4-continued

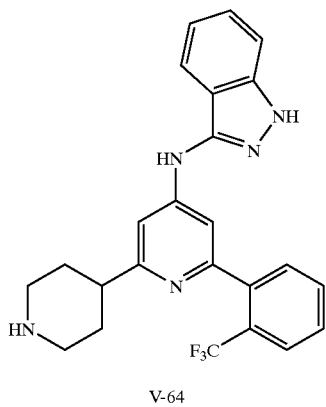

V-64

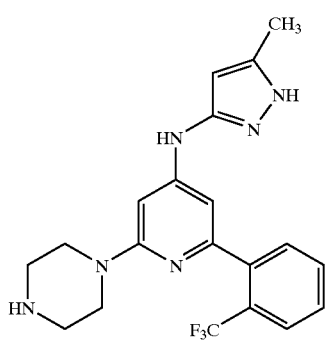

V-65

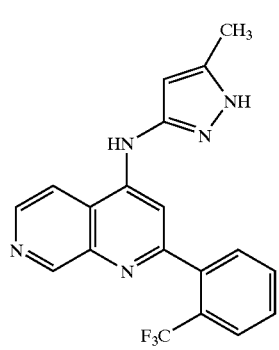

V-66

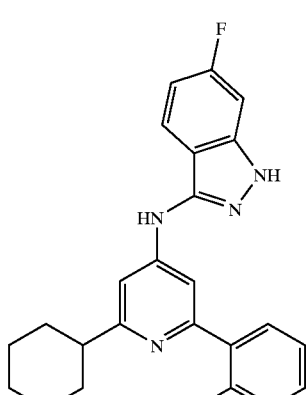

V-67

TABLE 4-continued

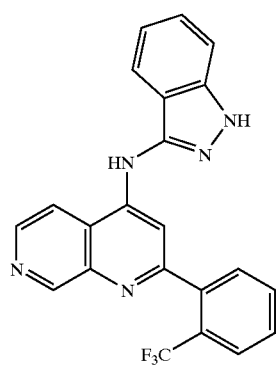

V-68

In another embodiment, this invention provides a composition comprising a compound of formula V and a pharmaceutically acceptable carrier.

One aspect of this invention relates to a method of inhibiting GSK-3 activity in a patient, comprising administering to the patient a therapeutically effective amount of a composition comprising a compound of formula V.

Another aspect relates to a method of treating a disease that is alleviated by treatment with a GSK-3 inhibitor, said method comprising the step of administering to a patient in need of such a treatment a therapeutically effective amount of a composition comprising a compound of formula V.

Another aspect relates to a method of enhancing glycogen synthesis and/or lowering blood levels of glucose in a patient in need thereof, comprising administering to said patient a therapeutically effective amount of a composition comprising a compound of formula V. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula V. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula V. This method is especially useful for treating schizophrenia.

One aspect of this invention relates to a method of inhibiting Aurora activity in a patient, comprising administering to the patient a therapeutically effective amount of a composition comprising a compound of formula V.

Another aspect relates to a method of treating a disease that is alleviated by treatment with an Aurora inhibitor, said method comprising the step of administering to a patient in need of such a treatment a therapeutically effective amount of a composition comprising a compound of formula V. This method is especially useful for treating cancer, such as colon, ovarian, and breast cancer.

One aspect of this invention relates to a method of inhibiting CDK-2 activity in a patient, comprising administering to the patient a therapeutically effective amount of a composition comprising a compound of formula V.

Another aspect relates to a method of treating a disease that is alleviated by treatment with a CDK-2 inhibitor, said method comprising the step of administering to a patient in need of such a treatment a therapeutically effective amount of a composition comprising a compound of formula V. This method is especially useful for treating cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

Another method relates to inhibiting GSK-3, Aurora, or CDK-2 activity in a biological sample, which method comprises contacting the biological sample with the GSK-3 or Aurora inhibitor of formula V, or a pharmaceutical composition thereof, in an amount effective to inhibit GSK-3, Aurora or CDK-2.

Each of the aforementioned methods directed to the inhibition of GSK-3, Aurora or CDK-2, or the treatment of a disease alleviated thereby, is preferably carried out with a preferred compound of formula V, as described above.

Another embodiment of this invention relates to compounds of formula VI:

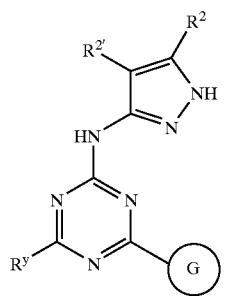

VI or a pharmaceutically acceptable derivative or prodrug thereof, wherein:

G is Ring C or Ring D;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —$R^8$;

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^1$ is selected from -halo, —CN, —$NO_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

$R^y$ is T-$R^{3'}$;

T is a valence bond or a $C_{1-4}$ alkylidene chain;

$R^2$ and $R^{2'}$ are independently selected from —R, -T-W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by $R^2$ and $R^{2'}$ is substituted by halo, oxo, —CN, —$NO_2$, —$R^7$, or —V—$R^6$, and any substitutable nitrogen on said ring formed by $R^2$ and $R^{2'}$ is substituted by $R^4$;

$R^{3'}$ is an optionally substituted group selected from $C_{1-6}$ aliphatic, $C_{3-10}$ carbocyclyl, $C_{6-10}$ aryl, a heteroaryl ring having 5–10 ring atoms, or a heterocyclyl ring having 5–10 ring atoms;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$ (optionally substituted $C_{1-6}$ aliphatic), —CON($R^7$)$_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2R$, —COCOR, —$NO_2$, —CN, —S(O)R, —$SO_2R$, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$, or $R^5$ and an adjacent substituent taken together with their intervening atoms form said ring fused to Ring C;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —CO—, —$CO_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, —C($R^6$)$_2$N($R^6$)CON($R^6$)—, or —CON($R^6$)—;

each $R^6$ is independently selected from hydrogen, an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring; and each $R^8$ is independently selected from an optionally substituted $C_{1-4}$ aliphatic group, —$OR^6$, —$SR^6$, —$COR^6$, —$SO_2R^6$, —N($R^6$)$_2$, —N($R^6$)N($R^6$)$_2$, —CN, —$NO_2$, —CON($R^6$)$_2$, or —$CO_2R^6$.

Preferred $R^y$ groups of formula VI include T-$R^{3'}$ wherein T is a valence bond or a methylene, and $R^{3'}$ is an optionally substituted group selected from $C_{1-6}$ aliphatic, $C_{3-10}$ carbocyclyl, $C_{6-10}$ aryl, a heteroaryl ring having 5–10 ring atoms, or a heterocyclyl ring having 5–10 ring atoms. A preferred $R^{3'}$ group is an optionally substituted group selected from $C_{3-6}$ carbocyclyl, phenyl, or a 5–6 membered heteroaryl or heterocyclyl ring. Examples of preferred $R^y$ include 2-pyridyl, 4-pyridyl, piperidinyl, morpholinyl, cyclopropyl, cyclohexyl, and optionally substituted phenyl such as phenyl or halo-substituted phenyl.

The $R^2$ and $R^{2'}$ groups of formula VI may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula VI compounds having a pyrazole-containing bicyclic ring system:

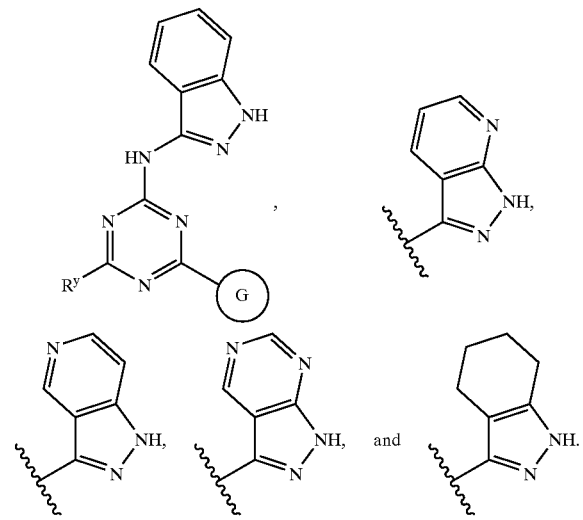

Preferred substituents on the $R^2/R^{2'}$ fused ring include one or more of the following: -halo, —$N(R^4)_2$, —$C_{1-4}$ alkyl, —$C_{1-4}$ haloalkyl, —$NO_2$, —$O(C_{1-4}$ alkyl), —$CO_2(C_{1-4}$ alkyl), —CN, —$SO_2(C_{1-4}$ alkyl), —$SO_2NH_2$, —OC(O)$NH_2$, —$NH_2SO_2(C_{1-4}$ alkyl), —NHC(O) ($C_{1-4}$ alkyl), —C(O)$NH_2$, and —CO($C_{1-4}$ alkyl), wherein the ($C_{1-4}$ alkyl) is a straight, branched, or cyclic alkyl group. Preferably, the ($C_{1-4}$ alkyl) group is methyl.

When the pyrazole ring system is monocyclic, preferred $R^2$ groups of formula VI include hydrogen, $C_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred $R^2$ substituents include methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, CONH(cyclohexyl), $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, CO(3-methoxymethylpyrrolidin-1-yl), CONH(3-tolyl), CONH(4-tolyl), $CONHCH_3$, CO(morpholin-1-yl), CO(4-methylpiperazin-1-yl), $CONHCH_2CH_2OH$, $CONH_2$, and CO(piperidin-1-yl). A preferred $R^{2'}$ group is hydrogen.

When G is Ring C, preferred formula VI Ring C groups are phenyl and pyridinyl. When two adjacent substituents on Ring C are taken together to form a fused ring, Ring C is contained in a bicyclic ring system. Preferred fused rings include a benzo or pyrido ring. Such rings preferably are fused at ortho and meta positions of Ring C. Examples of preferred bicyclic Ring C systems include naphthyl and isoquinolinyl. Preferred $R^1$ groups include -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —OC(O)$NH_2$, or —$NHSO_2R^6$. When $R^1$ is an optionally substituted $C_{1-6}$ aliphatic group, the most preferred optional substituents are halogen. Examples of preferred $R^1$ groups include —$CF_3$, —Cl, —F, —CN, —$COCH_3$, —$OCH_3$, —OH, —$CH_2CH_3$, —$OCH_2CH_3$, —$CH_3$, —$CF_2CH_3$, cyclohexyl, t-butyl, isopropyl, cyclopropyl, —C≡CH, —C≡C—$CH_3$, —$SO_2CH_3$, —$SO_2NH_2$, —$N(CH_3)_2$, —$CO_2CH_3$, —$CONH_2$, —$NHCOCH_3$, —OC(O)$NH_2$, —$NHSO_2CH_3$, and —$OCF_3$.

On Ring C preferred $R^5$ substituents, when present, include -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$SO_2N(R^4)_2$, and —$N(R^4)SO_2R$. More preferred $R^5$ substituents include —Cl, —F, —CN, —$CF_3$, —$NH_2$, —NH($C_{1-4}$ aliphatic), —N($C_{1-4}$ aliphatic)$_2$, —O($C_{1-4}$ aliphatic), $C_{1-4}$ aliphatic, and —$CO_2$ ($C_{1-4}$ aliphatic). Examples of such preferred $R^5$ substituents include —Cl, —F, —CN, —$CF_3$, —$NH_2$, —NHMe, —$NMe_2$, —OEt, methyl, ethyl, cyclopropyl, isopropyl, t-butyl, and —$CO_2Et$.

When G is Ring D, preferred formula VI Ring D monocyclic rings include substituted and unsubstituted phenyl, pyridinyl, piperidinyl, piperazinyl, pyrrolidinyl, thienyl, azepanyl, and morpholinyl rings. When two adjacent substituents on Ring D are taken together to form a fused ring, the Ring D system is bicyclic. Preferred formula VI Ring D bicyclic rings include 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, and naphthyl. Examples of more preferred bicyclic Ring D systems include naphthyl and isoquinolinyl.

Preferred substituents on formula VI Ring D include one or more of the following: halo, oxo, CN, —$NO_2$, —$N(R^4)_2$, —$CO_2R$, —$CONH(R^4)$, —$N(R^4)COR$, —$SO_2N(R^4)_2$, —$N(R^4)SO_2R$, —SR, —OR, —C(O)R, or substituted or unsubstituted group selected from 5–6 membered heterocyclyl, $C_{6-10}$ aryl, or $C_{1-6}$ aliphatic. More preferred Ring D substituents include -halo, —CN, -oxo, —SR, —OR, —$N(R^4)_2$, —C(O)R, or a substituted or unsubstituted group selected from 5–6 membered heterocyclyl, $C_{6-10}$ aryl, or $C_{1-6}$ aliphatic. Examples of Ring D substituents include —OH, phenyl, methyl, $CH_2OH$, $CH_2CH_2OH$, pyrrolidinyl, OPh, $CF_3$, C≡CH, Cl, Br, F, I, $NH_2$, C(O)$CH_3$, i-propyl, tert-butyl, SEt, OMe, $N(Me)_2$, methylene dioxy, and ethylene dioxy.

Preferred formula VI compounds have one or more, and more preferably all, of the features selected from the group consisting of:

(a) Ring C is selected from a phenyl or pyridinyl ring, optionally substituted by —$R^5$, wherein when Ring C and two adjacent substituents thereon form a bicyclic ring system, the bicyclic ring system is selected from a naphthyl, quinolinyl or isoquinolinyl ring, and $R^1$ is -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —OC(O)$NH_2$, or —$NHSO_2R^6$; or Ring D is an optionally substituted ring selected from a phenyl, pyridinyl, piperidinyl, piperazinyl, pyrrolidinyl, thienyl, azepanyl, morpholinyl, 1,2,3,4- tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^y$ is T-$R^{3'}$, wherein T is a valence bond or a methylene; and (c) $R^{2'}$ is hydrogen and $R^2$ is hydrogen or a substituted or unsubstituted group selected from aryl, heteroaryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring.

More preferred compounds of formula VI have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is a naphthyl ring, and $R^1$ is -halo, a $C_{1-6}$ haloaliphatic group, a $C_{1-6}$ aliphatic group, phenyl, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^y$ is T-$R^{3'}$, wherein T is a valence bond or a methylene and $R^{3'}$ is an optionally substituted group selected from $C_{1-6}$ aliphatic, $C_{3-6}$ carbocyclyl, $C_{6-10}$ aryl, a heteroaryl ring having 5–10 ring atoms, or a heterocyclyl ring having 5–10 ring atoms;

(c) $R^{2'}$ is hydrogen and $R^2$ is hydrogen or a substituted or unsubstituted group selected from aryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring; and (d) Ring D is substituted by oxo or $R^5$, wherein each $R^5$ is independently selected from -halo, —CN, —$NO_2$, —$N(R^4)_2$, optionally substituted $C_{1-6}$ aliphatic group, —OR, —C(O)R, —$CO_2R$, —CONH($R^4$), —$N(R^4)$COR, —$SO_2N(R^4)_2$, or —$N(R^4)SO_2R$.

Even more preferred compounds of formula VI have one or more, and more preferably all, of the features selected from the group consisting of:

(a) $R^y$ is T-$R^{3'}$, wherein T is a valence bond or a methylene and $R^{3'}$ is an optionally substituted group selected from $C_{1-4}$ aliphatic, $C_{3-6}$ carbocyclyl, phenyl, or a 5–6 membered heteroaryl or heterocyclyl ring;

(b) Ring C is a phenyl or pyridinyl ring, optionally substituted by —$R^5$, wherein when Ring C and two adjacent substituents thereon form a bicyclic ring system, the bicyclic ring system is a naphthyl ring, and $R^1$ is -halo, a $C_{1-4}$ aliphatic group optionally substituted with halogen, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, isoquinolinyl, quinolinyl, or naphthyl;

(c) $R^2$ and $R^{2'}$ are taken together with their intervening atoms to form a benzo, pyrido, pyrimido or partially unsaturated 6-membered carbocyclo ring optionally substituted with -halo, —$N(R^4)_2$, —$C_{1-4}$ alkyl, —$C_{1-4}$ haloalkyl, —$NO_2$, —O($C_{1-4}$ alkyl), —$CO_2$($C_{1-4}$ alkyl), —CN, —$SO_2$ ($C_{1-4}$ alkyl), —$SO_2NH_2$, —OC(O)$NH_2$, —$NH_2SO_2$($C_{1-4}$ alkyl), —NHC(O) ($C_{1-4}$ alkyl), —C(O)$NH_2$, or —CO($C_{1-4}$ alkyl), wherein the ($C_{1-4}$ alkyl) is a straight, branched, or cyclic alkyl group; and (d) Ring D is substituted by oxo or $R^5$, wherein each $R^5$ is independently selected from —Cl, —F, —CN, —$CF_3$, —$NH_2$, —NH($C_{1-4}$ aliphatic), —N($C_{1-4}$ aliphatic)$_2$, —O($C_{1-4}$ aliphatic), $C_{1-4}$ aliphatic, and —$CO_2$($C_{1-4}$ aliphatic).

Another embodiment of this invention relates to compounds of formula VIa:

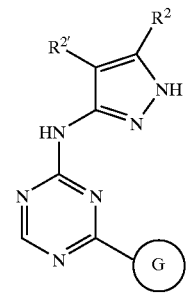

VIa or a pharmaceutically acceptable derivative or prodrug thereof, wherein:

G is Ring C or Ring D;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —$R^8$;

Ring D is a 5–7 membered monocyclic ring or 8–10 membered bicyclic ring selected from aryl heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^1$ is selected from -halo, —CN, —$NO_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

T is a valence bond or a $C_{1-4}$ alkylidene chain;

$R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by $R^2$ and $R^{2'}$ is substituted by halo, oxo, —CN, —$NO_2$, —$R^7$, or —V—$R^6$, and any substitutable nitrogen on said ring formed by $R^2$ and $R^{2'}$ is substituted by $R^4$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —$CO_2$ (optionally substituted $C_{1-6}$ aliphatic), —CON ($R^7$)$_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, or $R^5$ and an adjacent substituent taken together with their intervening atoms form said ring fused to Ring C;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each $R^6$ is independently selected from hydrogen, an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring; and each $R^8$ is independently selected from an optionally substituted $C_{1-4}$ aliphatic group, —OR$^6$, —SR$^6$, —COR$^6$, —SO$_2$R$^6$, —N(R$^6$)$_2$, —N(R$^6$)N(R$^6$)$_2$, —CN, —NO$_2$, —CON(R$^6$)$_2$, or —CO$_2$R$^6$.

Preferred rings formed by the $R^2$ and $R^{2'}$ groups of formula VIa include benzo, pyrido, pyrimido, and a partially unsaturated 6-membered carbocyclo ring. These are exemplified in the following formula VIa compounds having a pyrazole-containing bicyclic ring system:

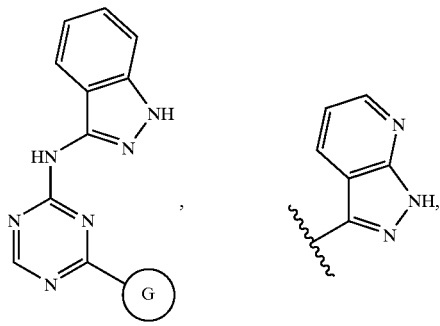

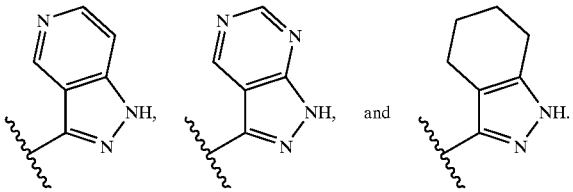

-continued

Preferred substituents on the $R^2/R^{2'}$ fused ring include one or more of the following: -halo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl.

When G is Ring C, preferred formula VIa Ring C groups are phenyl and pyridinyl. When two adjacent substituents on Ring C are taken together to form a fused ring, Ring C is contained in a bicyclic ring system. Preferred fused rings include a benzo or pyrido ring. Such rings preferably are fused at ortho and meta positions of Ring C. Examples of preferred bicyclic Ring C systems include naphthyl and isoquinolinyl. Preferred $R^1$ groups include -halo, an optionally substituted $C_{1-6}$ aliphatic group, phenyl, —COR$^6$, —OR$^6$, —CN, —SO$_2$R$^6$, —SO$_2$NH$_2$, —N(R$^6$)$_2$, —CO$_2$R$^6$, —CONH$_2$, —NHCOR$^6$, —OC(O)NH$_2$, or —NHSO$_2$R$^6$. When $R^1$ is an optionally substituted $C_{1-6}$ aliphatic group, the most preferred optional substituents are halogen. Examples of preferred $R^1$ groups include —CF$_3$, —Cl, —F, —CN, —COCH$_3$, —OCH$_3$, —OH, —CH$_2$CH$_3$, —OCH$_2$CH$_3$, —CH$_3$, —CF$_2$CH$_3$, cyclohexyl, t-butyl, isopropyl, cyclopropyl, —C≡CH, —C≡C—CH$_3$, —SO$_2$CH$_3$, —SO$_2$NH$_2$, —N(CH$_3$)$_2$, —CO$_2$CH$_3$, —CONH$_2$, —NHCOCH$_3$, —OC(O)NH$_2$, —NHSO$_2$CH$_3$, and —OCF$_3$.

On Ring C preferred $R^5$ substituents, when present, include -halo, —CN, —NO$_2$, —N(R$^4$)$_2$, optionally substituted $C_{1-6}$ aliphatic group, —OR, —C(O)R, —CO$_2$R, —CONH(R$^4$), —N(R$^4$)COR, —SO$_2$N(R$^4$)$_2$, and —N(R$^4$)SO$_2$R. More preferred $R^5$ substituents include —Cl, —F, —CN, —CF$_3$, —NH$_2$, —NH(C$_{1-4}$ aliphatic), —N(C$_{1-4}$ aliphatic)$_2$, —O(C$_{1-4}$ aliphatic), C$_{1-4}$ aliphatic, and —CO$_2$ (C$_{1-4}$ aliphatic). Examples of such preferred $R^5$ substituents include —Cl, —F, —CN, —CF$_3$, —NH$_2$, —NHMe, —NMe$_2$, —OEt, methyl, ethyl, cyclopropyl, isopropyl, t-butyl, and —CO$_2$Et.

When G is Ring D, preferred formula VIa Ring D monocyclic rings include substituted and unsubstituted phenyl, pyridinyl, piperidinyl, piperazinyl, pyrrolidinyl, thienyl, azepanyl, and morpholinyl rings. When two adjacent substituents on Ring D are taken together to form a fused ring, the Ring D system is bicyclic. Preferred formula VIa Ring D bicyclic rings include 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, and naphthyl. Examples of more preferred bicyclic Ring D systems include naphthyl and isoquinolinyl.

Preferred substituents on the formula VIa Ring D include one or more of the following: halo, oxo, CN, —NO$_2$, —N(R$^4$)$_2$, —CO$_2$R, —CONH(R$^4$), —N(R$^4$)COR, —SO$_2$N(R$^4$)$_2$, —N(R$^4$)SO$_2$R, —SR, —OR, —C(O)R, or substituted or unsubstituted group selected from 5–6 membered heterocyclyl, $C_{6-10}$ aryl, or $C_{1-6}$ aliphatic. More preferred Ring D substituents include -halo, —CN, -oxo, —SR, —OR, —N(R⁴)₂, —C(O)R, or a substituted or unsubstituted group selected from 5–6 membered heterocyclyl, $C_{6-10}$ aryl, or $C_{1-6}$ aliphatic. Examples of Ring D substituents include —OH, phenyl, methyl, CH₂OH, CH₂CH₂OH, pyrrolidinyl, OPh, CF₃, C≡CH, Cl, Br, F, I, NH₂, C(O)CH₃, i-propyl, tert-butyl, SEt, OMe, N(Me)₂, methylene dioxy, and ethylene dioxy.

Preferred formula VIa compounds have one or more, and more preferably all, of the features selected from the group consisting of:

(a) Ring C is a phenyl or pyridinyl ring, optionally substituted by —R⁵, wherein when Ring C and two adjacent substituents thereon form a bicyclic ring system, the bicyclic ring system is selected from a naphthyl, quinolinyl or isoquinolinyl ring, and R¹ is -halo, an optionally substituted $C_{1-6}$ aliphatic group, phenyl, —COR⁶, —OR⁶, —CN, —SO₂R⁶, —SO₂NH₂, —N(R⁶)₂, —CO₂R⁶, —CONH₂, —NHCOR⁶, —OC(O)NH₂, or —NHSO₂R⁶; or Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring; and (b) R² and R²' are taken together with their intervening atoms to form a substituted or unsubstituted benzo, pyrido, pyrimido or partially unsaturated 6-membered carbocyclo ring.

More preferred compounds of formula VIa have one or more, and more preferably all, of the features selected from the group consisting of:

(a) Ring C is a phenyl or pyridinyl ring, optionally substituted by —R⁵, wherein when Ring C and two adjacent substituents thereon form a bicyclic ring system, the bicyclic ring system is a naphthyl ring, and R¹ is -halo, a $C_{1-6}$ haloaliphatic group, a $C_{1-6}$ aliphatic group, phenyl, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) R² and R²' are taken together with their intervening atoms to form a benzo, pyrido, pyrimido or partially unsaturated 6-membered carbocyclo ring optionally substituted with -halo, —N(R⁴)₂, —C₁₋₄ alkyl, —C₁₋₄ haloalkyl, —NO₂, —O(C₁₋₄ alkyl), —CO₂(C₁₋₄ alkyl), —CN, —SO₂(C₁₋₄ alkyl), —SO₂NH₂, —OC(O)NH₂, —NH₂SO₂(C₁₋₄ alkyl), —NHC(O)(C₁₋₄ alkyl), —C(O)NH₂, and —CO(C₁₋₄ alkyl), wherein the (C₁₋₄ alkyl) is a straight, branched, or cyclic alkyl group; and (c) Ring D is substituted by oxo or R⁵, wherein each R⁵ is independently selected from -halo, —CN, —NO₂, —N(R⁴)₂, optionally substituted $C_{1-6}$ aliphatic group, —OR, —C(O)R, —CO₂R, —CONH(R⁴), —N(R⁴)COR, —SO₂N(R⁴)₂, or —N(R⁴)SO₂R.

Even more preferred compounds of formula VIa have one or more, and more preferably all, of the features selected from the group consisting of:

(a) Ring C is a phenyl or pyridinyl ring, optionally substituted by —R⁵, wherein when Ring C and two adjacent substituents thereon form a bicyclic ring system, the bicyclic ring system is a naphthyl ring, and R¹ is -halo, a $C_{1-4}$ aliphatic group optionally substituted with halogen, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, isoquinolinyl, quinolinyl, or naphthyl;

(b) R² and R²' are taken together with their intervening atoms to form a benzo, pyrido, or partially unsaturated 6-membered carbocyclo ring optionally substituted with -halo, —N(R⁴)₂, —C₁₋₄ alkyl, —C₁₋₄ haloalkyl, —NO₂, —O(C₁₋₄ alkyl), —CO₂(C₁₋₄ alkyl), —CN, —SO₂(C₁₋₄ alkyl), —SO₂NH₂, —OC(O)NH₂, —NH₂SO₂(C₁₋₄ alkyl), —NHC(O)(C₁₋₄ alkyl), —C(O)NH₂, or —CO(C₁₋₄ alkyl), wherein the (C₁₋₄ alkyl) is a straight, branched, or cyclic alkyl group; and (d) Ring D is substituted by oxo or R⁵, wherein each R⁵ is independently selected from —Cl, —F, —CN, —CF₃, —NH₂, —NH(C₁₋₄ aliphatic), —N(C₁₋₄ aliphatic)₂, —O(C₁₋₄ aliphatic), C₁₋₄ aliphatic, and —CO₂(C₁₋₄ aliphatic).

Representative compounds of formula VI and IVa are set forth in Table 5 below.

TABLE 5

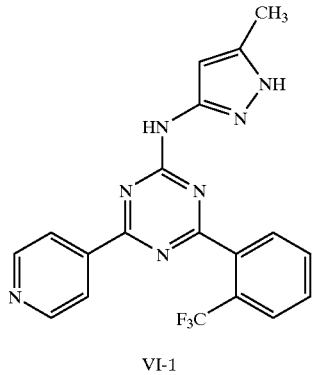

VI-1

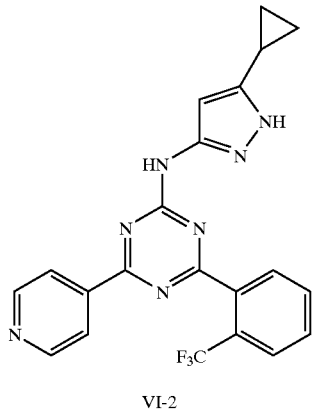

VI-2

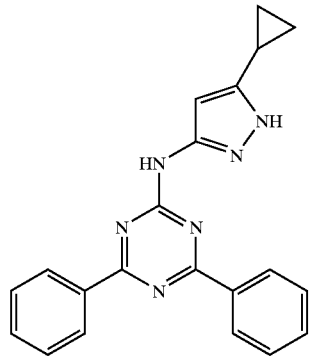

VI-3

TABLE 5-continued
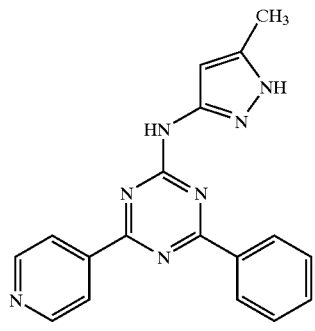
VI-4
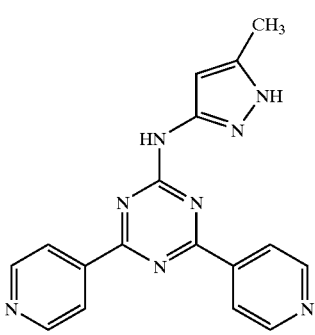
VI-5
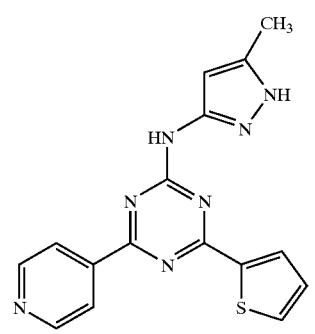
VI-6
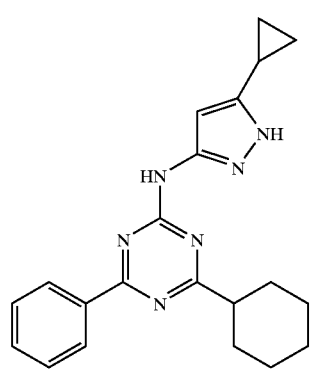
VI-7
TABLE 5-continued
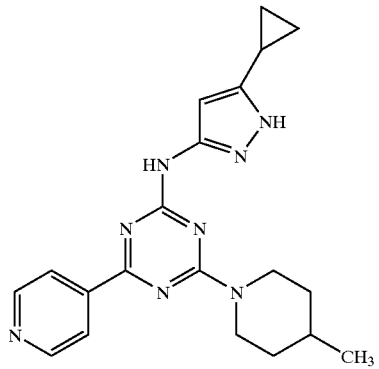
VI-8
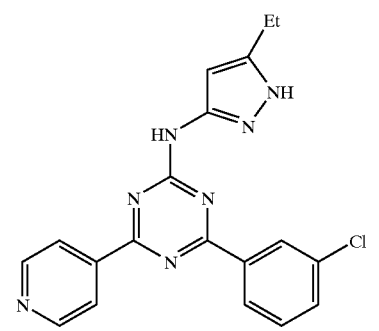
VI-9
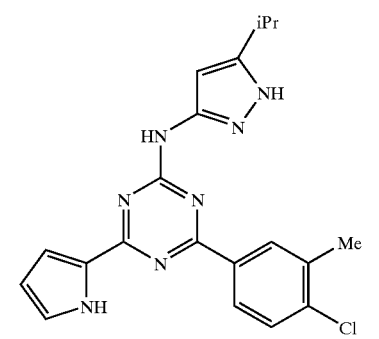
VI-10
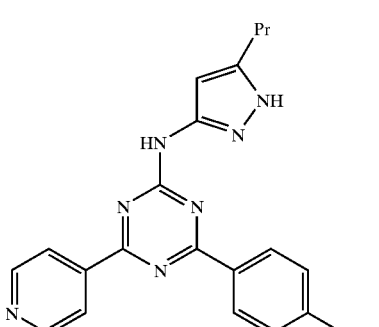
VI-11

TABLE 5-continued
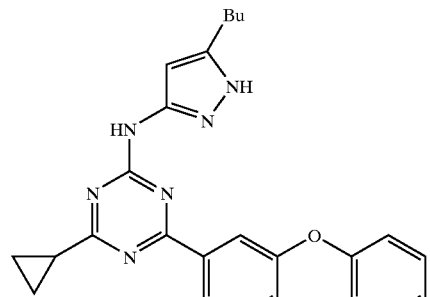
VI-12
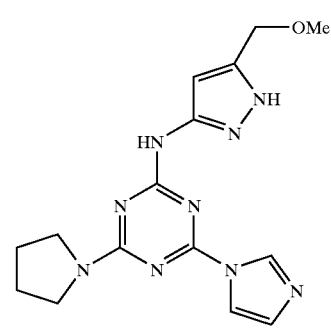
VI-13
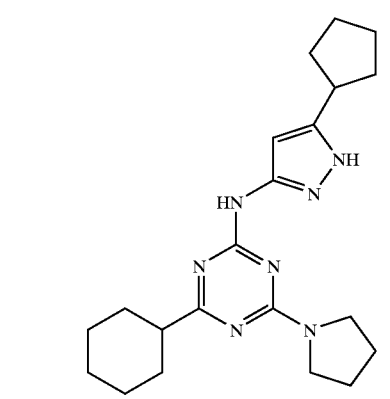
VI-14
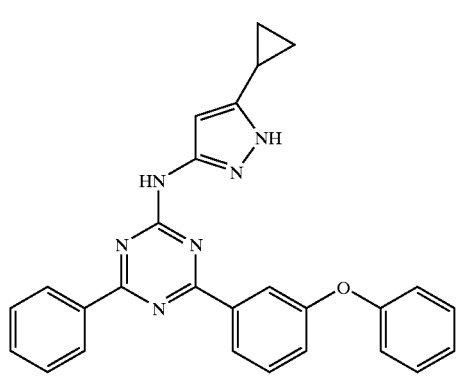
VI-15
TABLE 5-continued
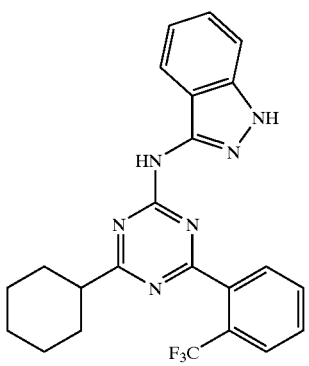
VI-16
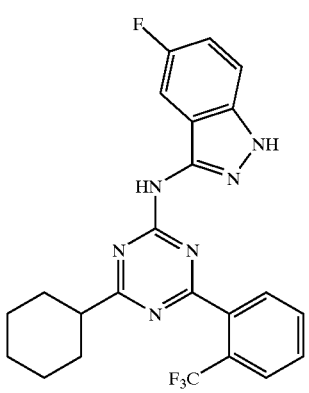
VI-17
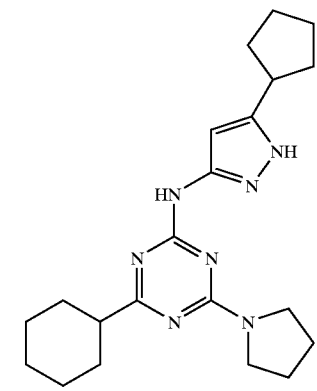
VI-18

TABLE 5-continued
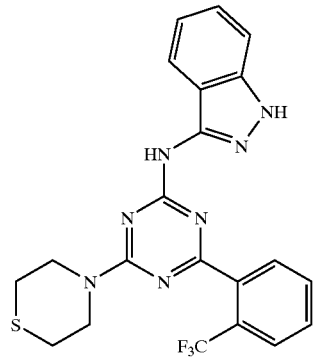
VI-19
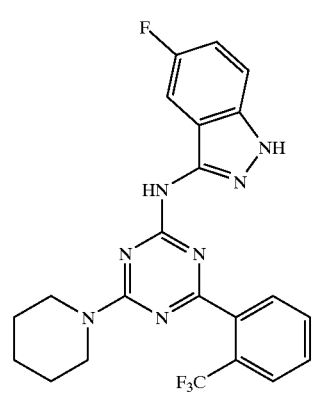
VI-20
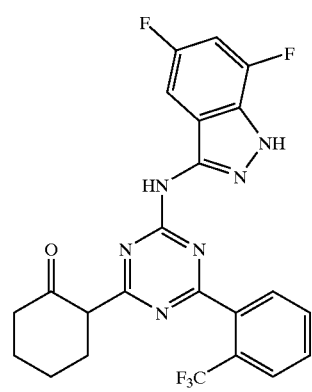
VI-21
TABLE 5-continued
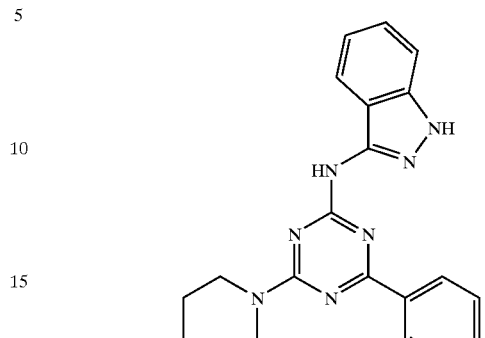
VI-22
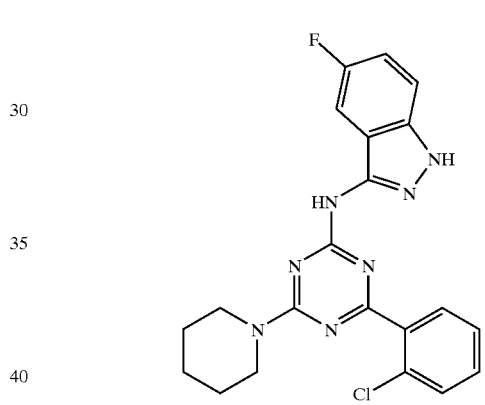
VI-23
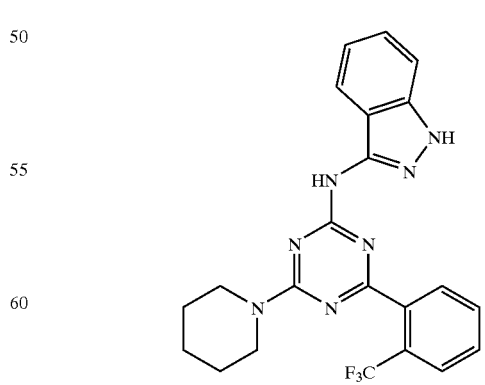
VI-24

TABLE 5-continued
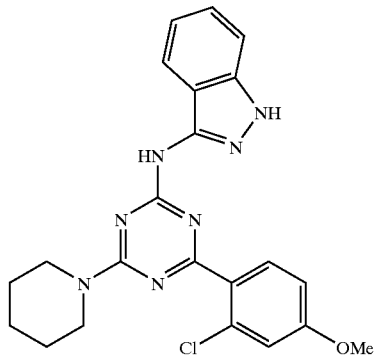
VI-25
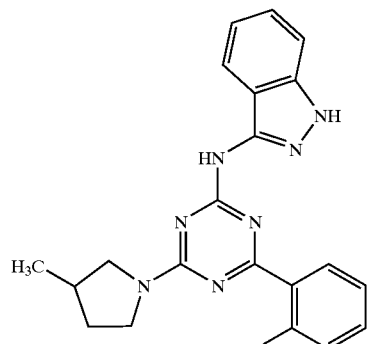
VI-28
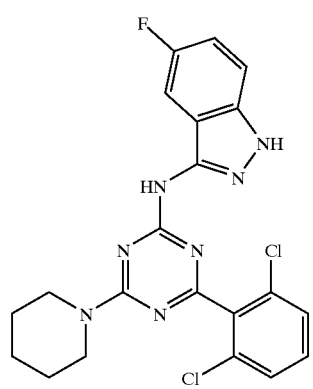
VI-26
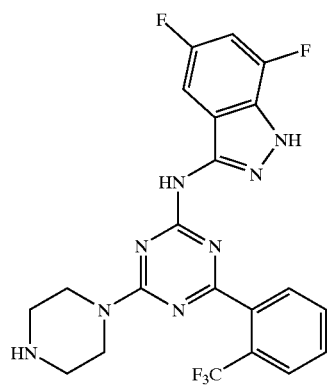
VI-29
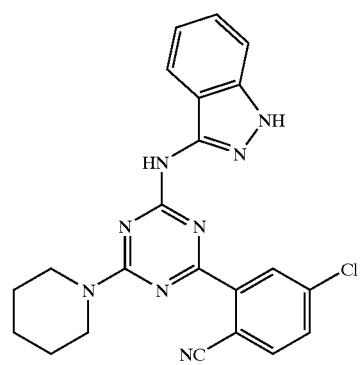
VI-27
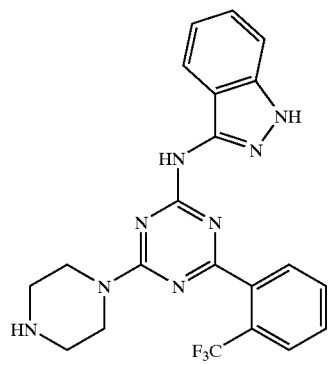
VI-30

TABLE 5-continued
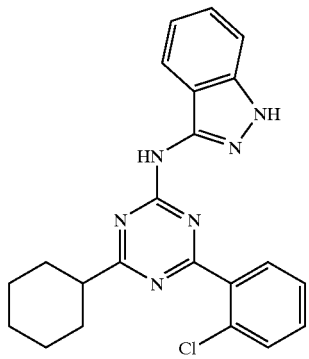
VI-31
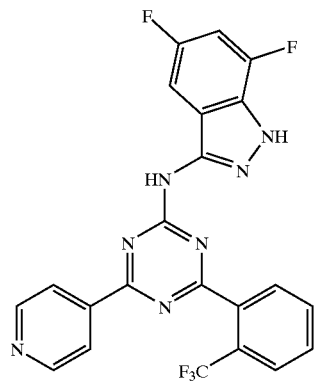
VI-34
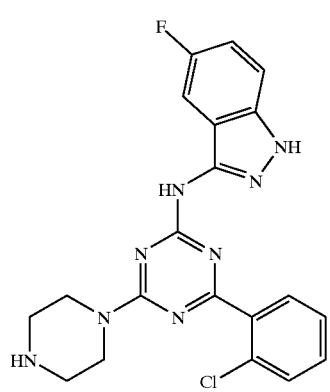
VI-32
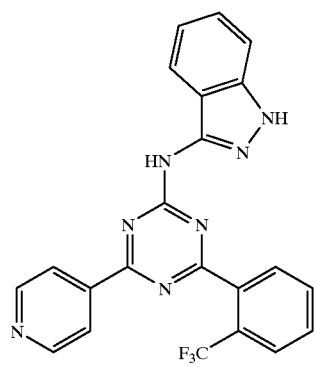
VI-35
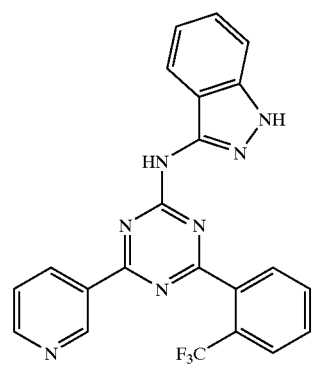
VI-33
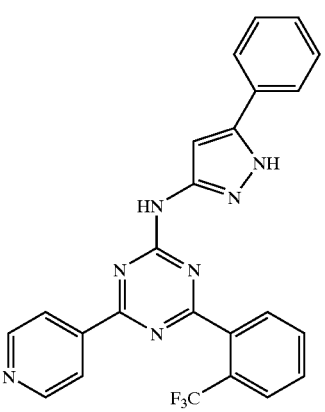
VI-36

TABLE 5-continued
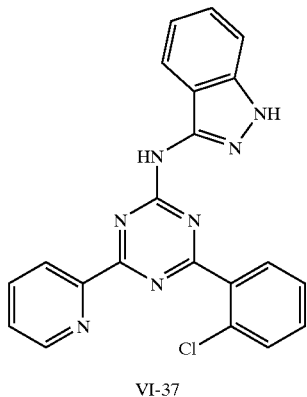
VI-37
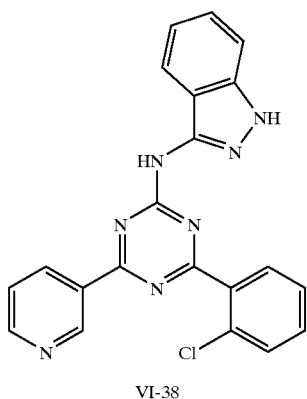
VI-38
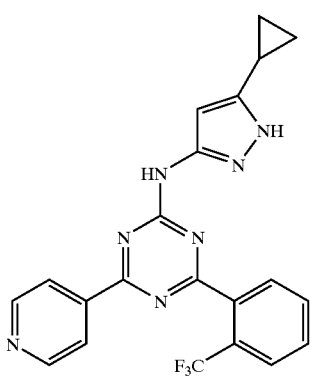
VI-39
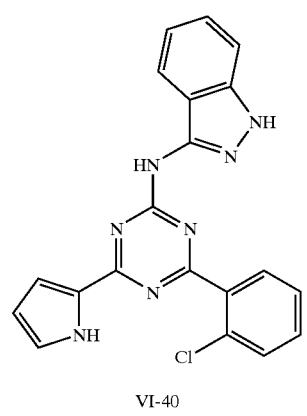
VI-40
TABLE 5-continued
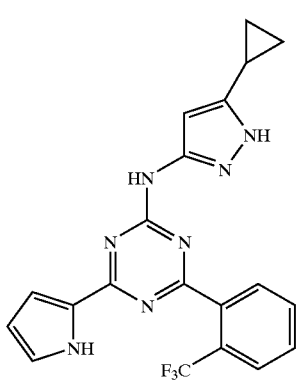
VI-41
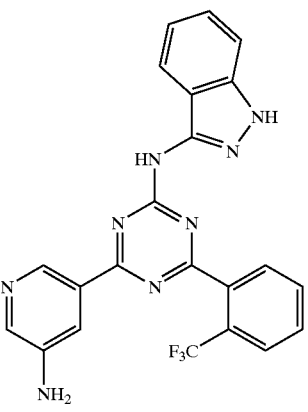
VI-42
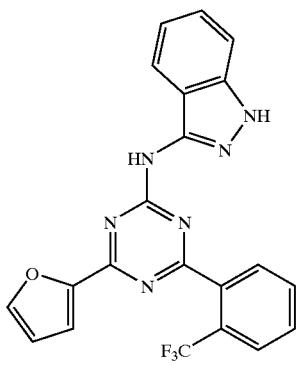
VI-43

TABLE 5-continued
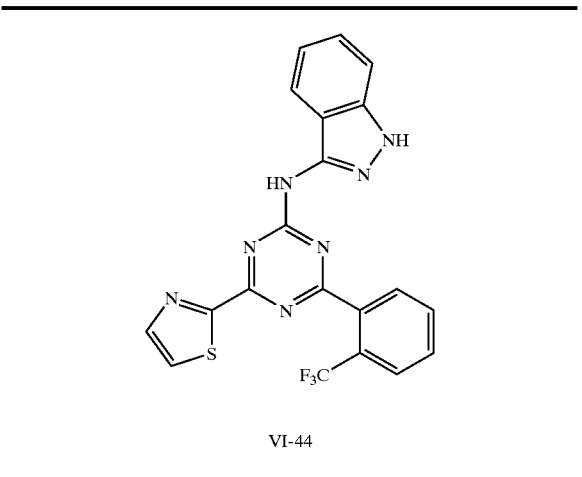
VI-44
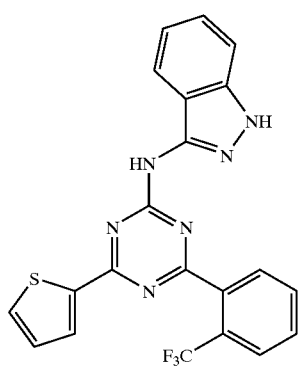
VI-45
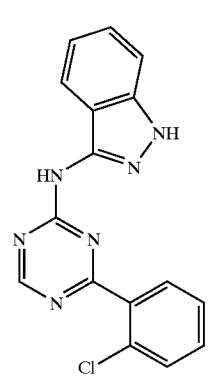
VIa-1
TABLE 5-continued
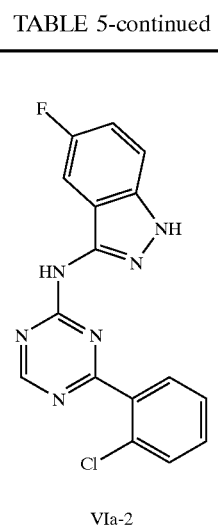
VIa-2
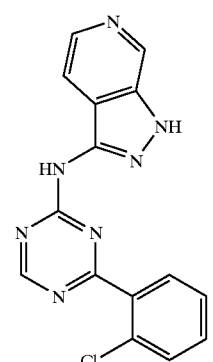
VIa-3
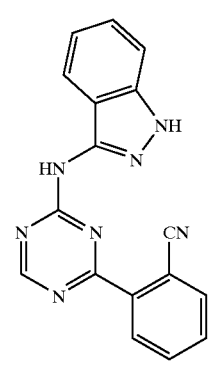
VIa-4

TABLE 5-continued
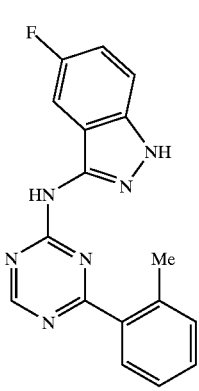
VIa-5
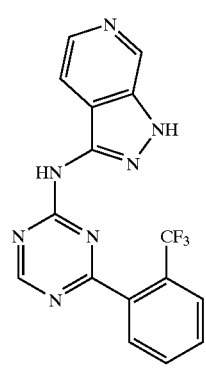
VIa-6
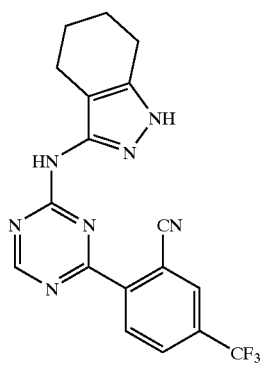
VIa-7
TABLE 5-continued
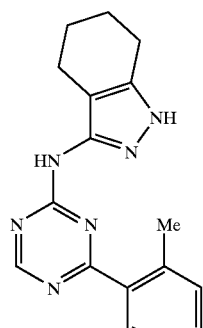
VIa-8
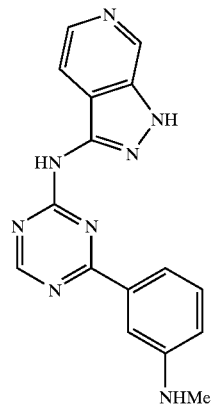
VIa-9
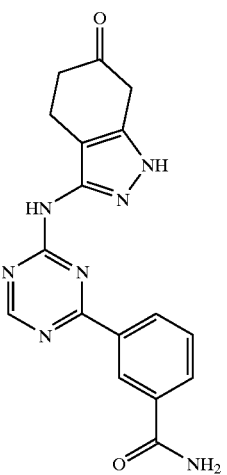
VIa-10

TABLE 5-continued

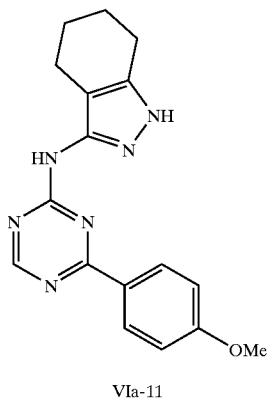

VIa-11

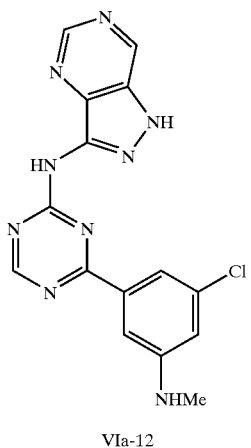

VIa-12

In another embodiment, this invention provides a composition comprising a compound of formula VI or VIa and a pharmaceutically acceptable carrier.

One aspect of this invention relates to a method of inhibiting GSK-3 activity in a patient, comprising administering to the patient a therapeutically effective amount of a composition comprising a compound of formula VI or VIa.

Another aspect relates to a method of treating a disease that is alleviated by treatment with a GSK-3 inhibitor, said method comprising the step of administering to a patient in need of such a treatment a therapeutically effective amount of a composition comprising a compound of formula VI or VIa.

Another aspect relates to a method of enhancing glycogen synthesis and/or lowering blood levels of glucose in a patient in need thereof, comprising administering to said patient a therapeutically effective amount of a composition comprising a compound of formula VI or VIa. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula VI or VIa. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula VI or VIa. This method is especially useful for treating schizophrenia.

One aspect of this invention relates to a method of inhibiting Aurora activity in a patient, comprising administering to the patient a therapeutically effective amount of a composition comprising a compound of formula VI or VIa.

Another aspect relates to a method of treating a disease that is alleviated by treatment with an Aurora inhibitor, said method comprising the step of administering to a patient in need of such a treatment a therapeutically effective amount of a composition comprising a compound of formula VI or VIa. This method is especially useful for treating cancer, such as colon, ovarian, and breast cancer.

One aspect of this invention relates to a method of inhibiting CDK-2 activity in a patient, comprising administering to the patient a therapeutically effective amount of a composition comprising a compound of formula VI or VIa.

Another aspect relates to a method of treating a disease that is alleviated by treatment with a CDK-2 inhibitor, said method comprising the step of administering to a patient in need of such a treatment a therapeutically effective amount of a composition comprising a compound of formula VI or VIa. This method is especially useful for treating cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

Another method relates to inhibiting GSK-3, Aurora, or CDK-2 activity in a biological sample, which method comprises contacting the biological sample with the GSK-3 or Aurora inhibitor of formula VI or VIa, or a pharmaceutical composition thereof, in an amount effective to inhibit GSK-3, Aurora or CDK-2.

Each of the aforementioned methods directed to the inhibition of GSK-3, Aurora or CDK-2, or the treatment of a disease alleviated thereby, is preferably carried out with a preferred compound of formula VI or VIa, as described above.

Another embodiment of this invention relates to compounds of formula VII:

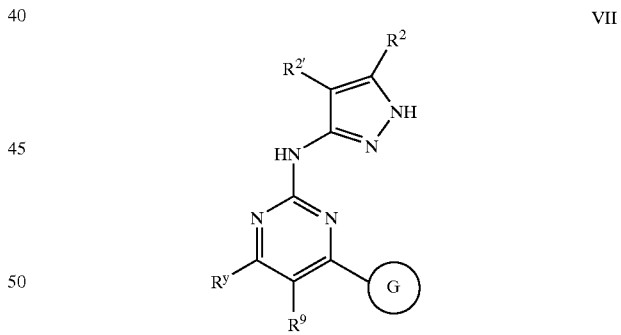

VII or a pharmaceutically acceptable derivative or prodrug thereof, wherein:

G is Ring C or Ring D;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —$R^8$;

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^1$ is selected from -halo, —CN, —$NO_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

$R^y$ is hydrogen or T-$R^{3"}$;

T is a valence bond, hydrogen, or a $C_{1-4}$ alkylidene chain;

$R^2$ and $R^{2'}$ are independently selected from —R, -T-W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by $R^2$ and $R^{2'}$ is substituted by halo, oxo, —CN, —$NO_2$, —$R^7$, or —V—$R^6$, and any substitutable nitrogen on said ring formed by $R^2$ and $R^{2'}$ is substituted by $R^4$;

$R^{3"}$ is selected from an optionally substituted group selected from $C_{3-10}$ carbocyclyl, $C_{6-10}$ aryl, a heteroaryl ring having 5–10 ring atoms, or a heterocyclyl ring having 5–10 ring atoms;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$ (optionally substituted $C_{1-6}$ aliphatic), —CON($R^7$)$_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2R$, —COCOR, —$NO_2$, —CN, —S(O)R, —$SO_2R$, —SR, —N($R^4$)$_2$, —CON($R^4$)$_2$, —$SO_2N(R^4)_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2N(R^4)_2$, —N($R^4$)$SO_2R$, or —OC(=O)N($R^4$)$_2$, or $R^5$ and an adjacent substituent taken together with their intervening atoms form said ring fused to Ring C;

V is —O—, —S—, —SO—, —$SO_2$—, —N($R^6$)$SO_2$—, —$SO_2N(R^6)$—, —N($R^6$)—, —CO—, —$CO_2$—, —N($R^6$)CO—, —N($R^6$)C(O)O—, —N($R^6$)CON($R^6$)—, —N($R^6$)$SO_2N(R^6)$—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2SO_2$—, —C($R^6$)$_2SO_2N(R^6)$—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$ N($R^6$)N($R^6$)—, —C($R^6$)$_2$N($R^6$)$SO_2N(R^6)$—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$ $SO_2$—, —C($R^6$)$_2SO_2N(R^6)$—, —C($R^6$)$_2$N($R^6$)—, —CO—, —$CO_2$—, —C($R^6$)OC(O)—, —C($R^6$) OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2N(R^6)$—, —C($R^6$)$_2$N($R^6$)CON($R^6$)—, or —CON($R^6$)—;

each $R^6$ is independently selected from hydrogen, an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

each $R^8$ is independently selected from an optionally substituted $C_{1-4}$ aliphatic group, —$OR^6$, —$SR^6$, —$COR^6$, —$SO_2R^6$, —N($R^6$)$_2$, —N($R^6$)N($R^6$)$_2$, —CN, —$NO_2$, —CON($R^6$)$_2$, or —$CO_2R^6$; and $R^9$ is selected from —R, halo, —OR, —C(=O)R, —$CO_2R$, —COCOR, —$NO_2$, —CN, —S(O)R, —$SO_2R$, —SR, —N($R^4$)$_2$, —CON($R^4$)$_2$, —$SO_2N(R^4)_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2N(R^4)_2$, —N($R^4$)$SO_2R$, or —OC(=O)N($R^4$)$_2$.

Preferred $R^y$ groups of formula VII include T-$R^{3"}$ wherein T is a valence bond or a methylene. Preferred $R^{3"}$ groups include an optionally substituted group selected from $C_{3-6}$ carbocyclyl, phenyl, or a 5–6 membered heteroaryl or heterocyclyl ring. Examples of preferred $R^y$ include 2-pyridyl, 4-pyridyl, piperidinyl, cyclopropyl, and an optionally substituted phenyl such as phenyl or halo-substituted phenyl.

The $R^2$ and $R^{2'}$ groups of formula VII may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula VII compounds having a pyrazole-containing bicyclic ring system:

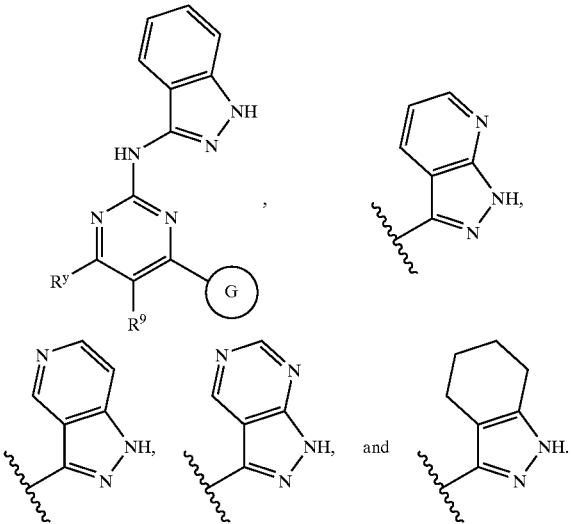

Preferred substituents on the $R^2/R^{2'}$ fused ring include one or more of the following: -halo, —N($R^4$)$_2$, —$C_{1-4}$ alkyl, —$C_{1-4}$ haloalkyl, —$NO_2$, —O($C_{1-4}$ alkyl), —$CO_2(C_{1-4}$ alkyl), —CN, —$SO_2(C_{1-4}$ alkyl), —$SO_2NH_2$, —OC(O)$NH_2$, —$NH_2SO_2(C_{1-4}$ alkyl), —NHC(O) ($C_{1-4}$ alkyl), —C(O)$NH_2$, and —CO($C_{1-4}$ alkyl), wherein the ($C_{1-4}$ alkyl) is a straight, branched, or cyclic alkyl group. Preferably, the ($C_{1-4}$ alkyl) group is methyl.

When the pyrazole ring system of formula VII is monocyclic, preferred $R^2$ groups include hydrogen, $C_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred $R^2$ substituents include methyl, cyclopropyl, ethyl, isopropyl, propyl, t-butyl, cyclopentyl, phenyl, $CO_2H$, $CO_2CH_3$, $CH_2OH$, $CH_2OCH_3$, $CH_2CH_2CH_2OH$, $CH_2CH_2CH_2OCH_3$, $CH_2CH_2CH_2OCH_2Ph$, $CH_2CH_2CH_2NH_2$, $CH_2CH_2CH_2NHCOOC(CH_3)_3$, $CONHCH(CH_3)_2$, $CONHCH_2CH=CH_2$, $CONHCH_2CH_2OCH_3$, $CONHCH_2Ph$, $CONH(cyclohexyl)$, $CON(Et)_2$, $CON(CH_3)CH_2Ph$, $CONH(n-C_3H_7)$, $CON(Et)CH_2CH_2CH_3$, $CONHCH_2CH(CH_3)_2$, $CON(n-C_3H_7)_2$, $CO(3-methoxymethylpyrrolidin-1-yl)$, $CONH(3-tolyl)$, $CONH(4-tolyl)$, $CONHCH_3$, $CO(morpholin-1-yl)$, $CO(4-methylpiperazin-1-yl)$, $CONHCH_2CH_2OH$, $CONH_2$, and $CO(piperidin-1-yl)$. A preferred $R^{2'}$ group is hydrogen.

When G is Ring C, preferred formula VII Ring C groups are phenyl and pyridinyl. When two adjacent substituents on Ring C are taken together to form a fused ring, Ring C is contained in a bicyclic ring system. Preferred fused rings include a benzo or pyrido ring. Such rings preferably are fused at ortho and meta positions of Ring C. Examples of preferred bicyclic Ring C systems include naphthyl and isoquinolinyl. Preferred $R^1$ groups include -halo, an optionally substituted $C_{1-6}$ aliphatic group, phenyl, $—COR^6$, $—OR^6$, $—CN$, $—SO_2R^6$, $—SO_2NH_2$, $—N(R^6)_2$, $—CO_2R^6$, $—CONH_2$, $—NHCOR^6$, $—OC(O)NH_2$, or $—NHSO_2R^6$. When $R^1$ is an optionally substituted $C_{1-6}$ aliphatic group, the most preferred optional substituents are halogen. Examples of preferred $R^1$ groups include $—CF_3$, $—Cl$, $—F$, $—CN$, $—COCH_3$, $—OCH_3$, $—OH$, $—CH_2CH_3$, $—OCH_2CH_3$, $—CH_3$, $—CF_2CH_3$, cyclohexyl, t-butyl, isopropyl, cyclopropyl, $—C≡CH$, $—C≡C—CH_3$, $—SO_2CH_3$, $—SO_2NH_2$, $—N(CH_3)_2$, $—CO_2CH_3$, $—CONH_2$, $—NHCOCH_3$, $—OC(O)NH_2$, $—NHSO_2CH_3$, and $—OCF_3$.

On Ring C preferred $R^5$ substituents, when present, include -halo, $—CN$, $—NO_2$, $—N(R^4)_2$, optionally substituted $C_{1-6}$ aliphatic group, $—OR$, $—C(O)R$, $—CO_2R$, $—CONH(R^4)$, $—N(R^4)COR$, $—SO_2N(R^4)_2$, and $—N(R^4)SO_2R$. More preferred $R^5$ substituents include $—Cl$, $—F$, $—CN$, $—CF_3$, $—NH_2$, $—NH(C_{1-4}$ aliphatic), $—N(C_{1-4}$ aliphatic)$_2$, $—O(C_{1-4}$ aliphatic), $C_{1-4}$ aliphatic, and $—CO_2(C_{1-4}$ aliphatic). Examples of such preferred $R^5$ substituents include $—Cl$, $—F$, $—CN$, $—CF_3$, $—NH_2$, $—NHMe$, $—NMe_2$, $—OEt$, methyl, ethyl, cyclopropyl, isopropyl, t-butyl, and $—CO_2Et$.

When G is Ring D, preferred formula VII Ring D monocyclic rings include substituted and unsubstituted phenyl, pyridinyl, piperidinyl, piperazinyl, pyrrolidinyl, thienyl, azepanyl, and morpholinyl rings. When two adjacent substituents on Ring D are taken together to form a fused ring, the Ring D system is bicyclic. Preferred formula VII Ring D bicyclic rings include 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, and naphthyl. Examples of more preferred bicyclic Ring D systems include naphthyl and isoquinolinyl.

Preferred substituents on Ring D include one or more of the following: halo, oxo, CN, $—NO_2$, $—N(R^4)_2$, $—CO_2R$, $—CONH(R^4)$, $—N(R^4)COR$, $—SO_2N(R^4)_2$, $—N(R^4)SO_2R$, $—SR$, $—OR$, $—C(O)R$, or substituted or unsubstituted group selected from 5–6 membered heterocyclyl, $C_{6-10}$ aryl, or $C_{1-6}$ aliphatic. More preferred Ring D substituents include -halo, $—CN$, -oxo, $—SR$, $—OR$, $—N(R^4)_2$, $—C(O)R$, or a substituted or unsubstituted group selected from 5–6 membered heterocyclyl, $C_{6-10}$ aryl, or $C_{1-6}$ aliphatic. Examples of Ring D substituents include $—OH$, phenyl, methyl, $CH_2OH$, $CH_2CH_2OH$, pyrrolidinyl, OPh, $CF_3$, $C≡CH$, Cl, Br, F, I, $NH_2$, $C(O)CH_3$, i-propyl, tert-butyl, SEt, OMe, $N(Me)_2$, methylene dioxy, and ethylene dioxy.

Preferred formula VII compounds have one or more, and more preferably all, of the features selected from the group consisting of:

(a) Ring C is a phenyl or pyridinyl ring, optionally substituted by $—R^5$, wherein when Ring C and two adjacent substituents thereon form a bicyclic ring system, the bicyclic ring system is selected from a naphthyl, quinolinyl or isoquinolinyl ring, and $R^1$ is -halo, an optionally substituted $C_{1-6}$ aliphatic group, phenyl, $—COR^6$, $—OR^6$, $—CN$, $—SO_2R^6$, $—SO_2NH_2$, $—N(R^6)_2$, $—CO_2R^6$, $—CONH_2$, $—NHCOR^6$, $—OC(O)NH_2$, or $—NHSO_2R^6$; or Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^y$ is $T-R^{3''}$, wherein T is a valence bond or a methylene; and (c) $R^{2'}$ is hydrogen and $R^2$ is hydrogen or a substituted or unsubstituted group selected from aryl, heteroaryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring.

More preferred compounds of formula VII have one or more, and more preferably all, of the features selected from the group consisting of:

(a) Ring C is a phenyl or pyridinyl ring, optionally substituted by $—R^5$, wherein when Ring C and two adjacent substituents thereon form a bicyclic ring system, the bicyclic ring system is a naphthyl ring, and $R^1$ is -halo, a $C_{1-6}$ haloaliphatic group, a $C_{1-6}$ aliphatic group, phenyl, or $—CN$; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^y$ is $T-R^{3''}$, wherein T is a valence bond or a methylene and $R^{3''}$ is an optionally substituted group selected from $C_{3-6}$ carbocyclyl, phenyl, or a 5–6 membered heteroaryl or heterocyclyl ring;

(c) $R^{2'}$ is hydrogen and $R^2$ is hydrogen or a substituted or unsubstituted group selected from aryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring; and (d) Ring D is substituted by oxo or $R^5$, wherein each $R^5$ is independently selected from -halo, $—CN$, $—NO_2$, $—N(R^4)_2$, optionally substituted $C_{1-6}$ aliphatic group, $—OR$, $—C(O)R$, $—CO_2R$, $—CONH(R^4)$, $—N(R^4)COR$, $—SO_2N(R^4)_2$, or $—N(R^4)SO_2R$.

Even more preferred compounds of formula VII have one or more, and more preferably all, of the features selected from the group consisting of:

(a) $R^y$ is $T-R^{3''}$, wherein T is a valence bond or a methylene and $R^3$ is an optionally substituted group selected from phenyl, or a 5–6 membered heteroaryl or heterocyclyl ring;

(b) Ring C is a phenyl or pyridinyl ring, optionally substituted by $—R^5$, wherein when Ring C and two adjacent substituents thereon form a bicyclic ring system, the bicyclic ring system is a naphthyl ring, and $R^1$ is -halo, a $C_{1-4}$ aliphatic group optionally substituted with halogen, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, isoquinolinyl, quinolinyl, or naphthyl;

(c) $R^2$ and $R^{2'}$ are taken together with their intervening atoms to form a benzo, pyrido, pyrimido or partially unsaturated 6-membered carbocyclo ring optionally substituted with -halo, $-N(R^4)_2$, $-C_{1-4}$ alkyl, $-C_{1-4}$ haloalkyl, $-NO_2$, $-O(C_{1-4}$ alkyl), $-CO_2(C_{1-4}$ alkyl), $-CN$, $-SO_2(C_{1-4}$ alkyl), $-SO_2NH_2$, $-OC(O)NH_2$, $-NH_2SO_2(C_{1-4}$ alkyl), $-NHC(O)$ $(C_{1-4}$ alkyl), $-C(O)NH_2$, or $-CO(C_{1-4}$ alkyl), wherein the ($C_{1-4}$ alkyl) is a straight, branched, or cyclic alkyl group; and (d) Ring D is substituted by oxo or $R^5$, wherein each $R^5$ is independently selected from —Cl, —F, —CN, —CF$_3$, —NH$_2$, —NH(C$_{1-4}$ aliphatic), —N(C$_{1-4}$ aliphatic)$_2$, —O(C$_{1-4}$ aliphatic), C$_{1-4}$ aliphatic, and —CO$_2$(C$_{1-4}$ aliphatic).

Representative compounds of formula VII are set forth in Table 6 below.

TABLE 6

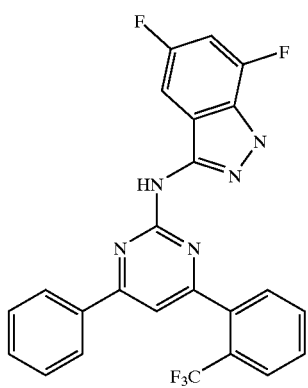

VII-1

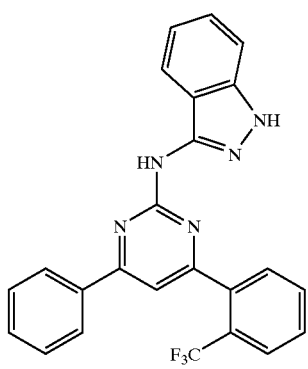

VII-2

TABLE 6-continued

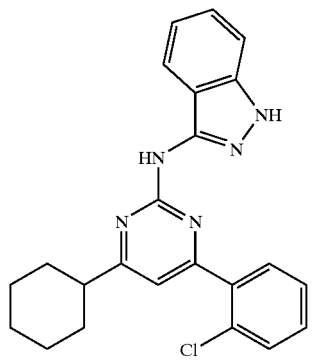

VII-3

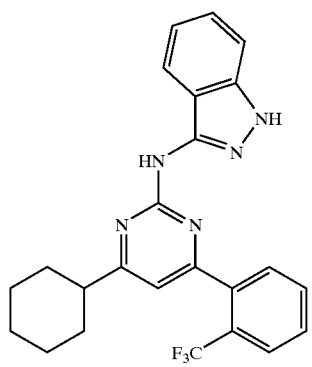

VII-4

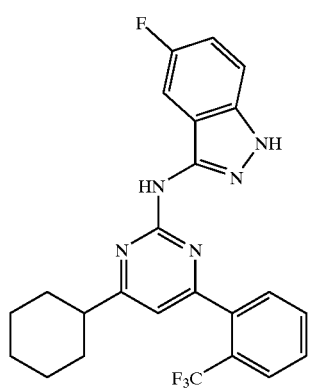

VII-5

TABLE 6-continued
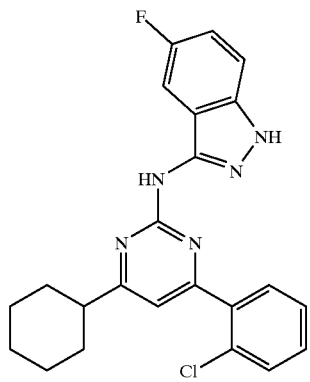
VII-6
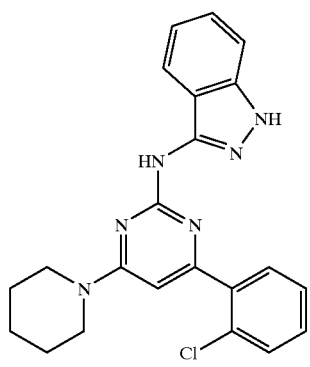
VII-7
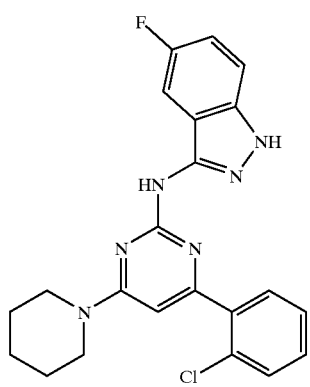
VII-8
TABLE 6-continued
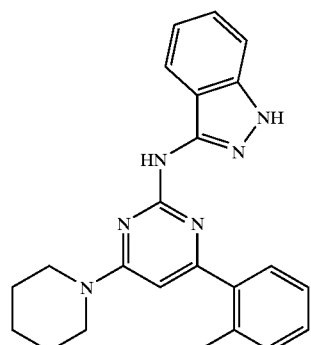
VII-9
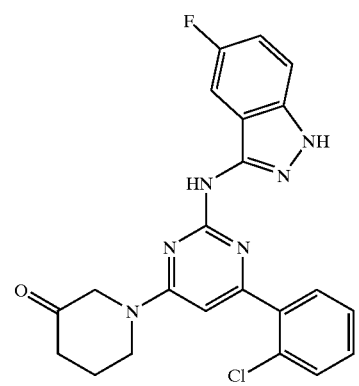
VII-10
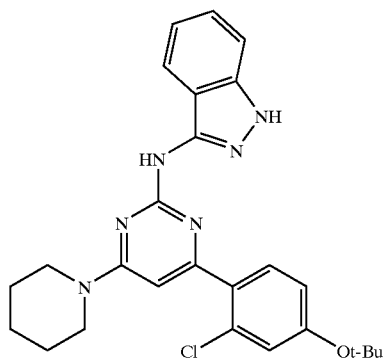
VII-11

TABLE 6-continued
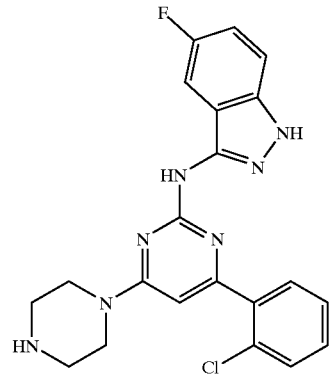
VII-12
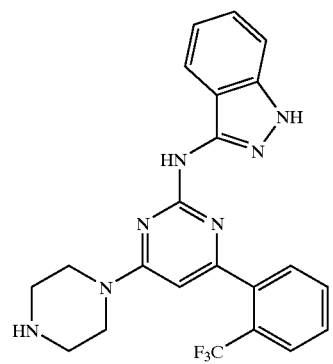
VII-13
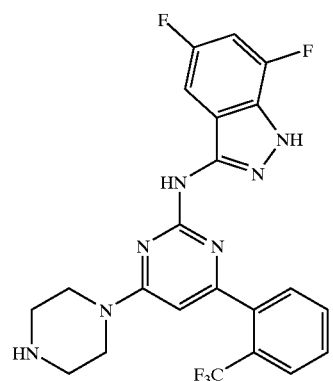
VII-14
TABLE 6-continued
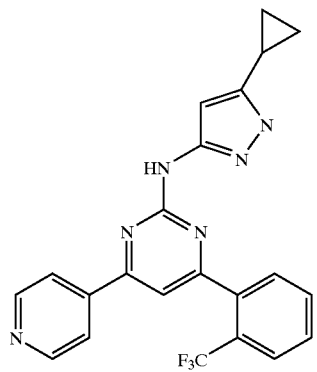
VII-15
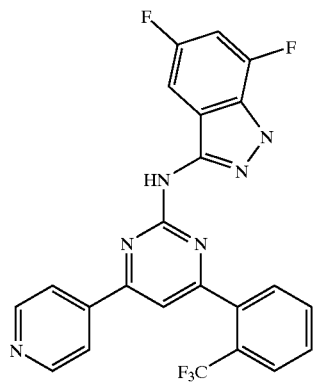
VII-16
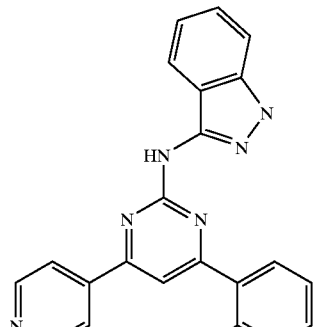
VII-17
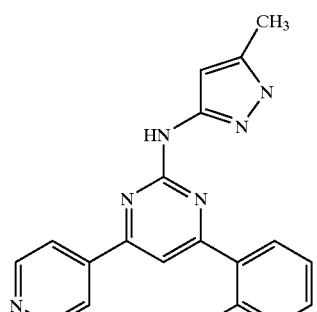
VII-18

TABLE 6-continued
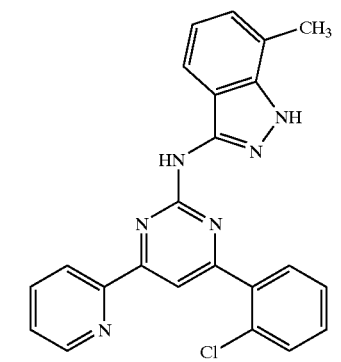
VII-19
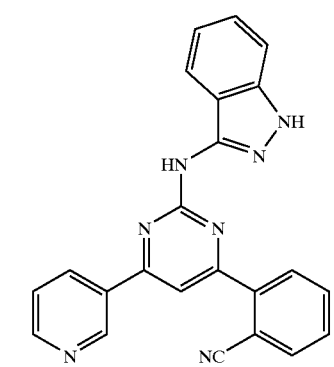
VII-20
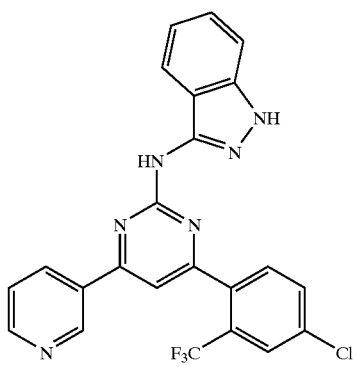
VII-21
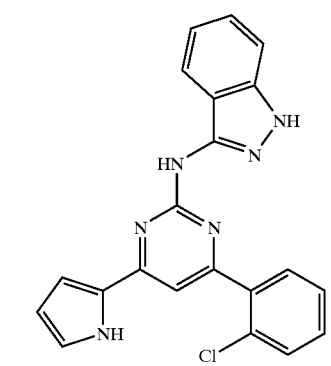
VII-22
TABLE 6-continued
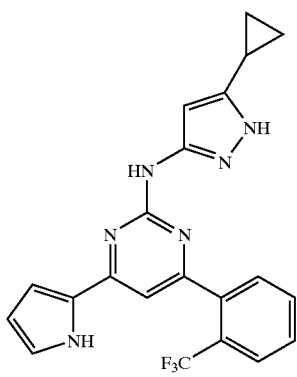
VII-23
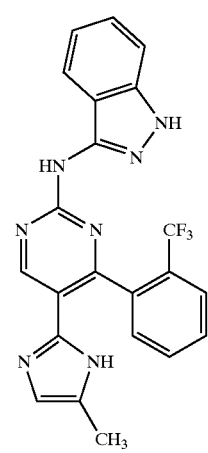
VII-24
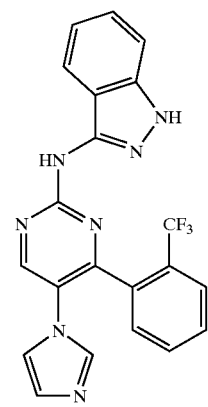
VII-25

TABLE 6-continued
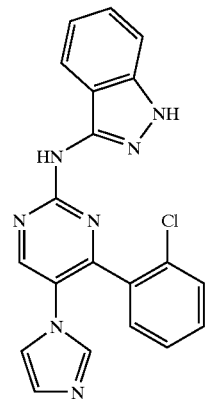
VII-26
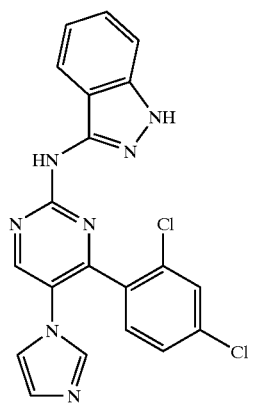
VII-27
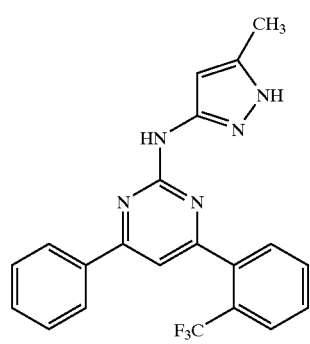
VII-28
TABLE 6-continued
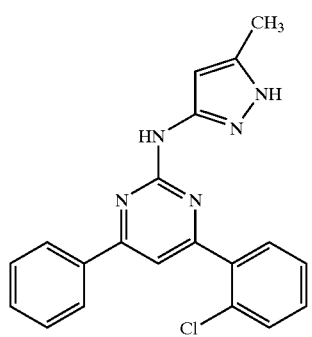
VII-29
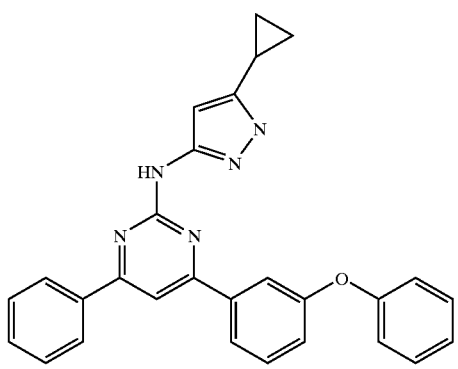
VII-30
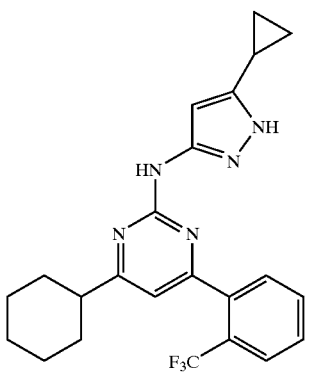
VII-31

TABLE 6-continued

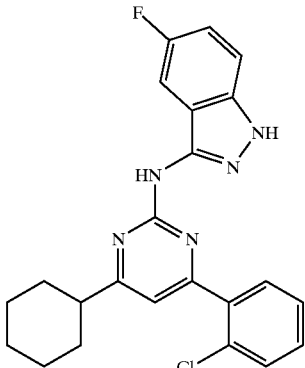

VII-32

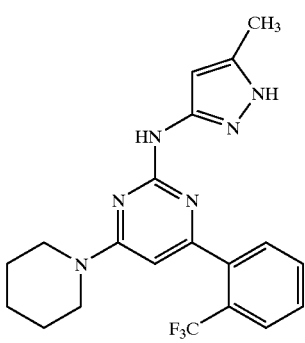

VII-33

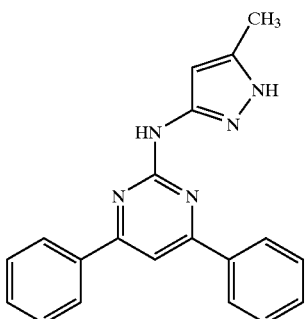

VII-34

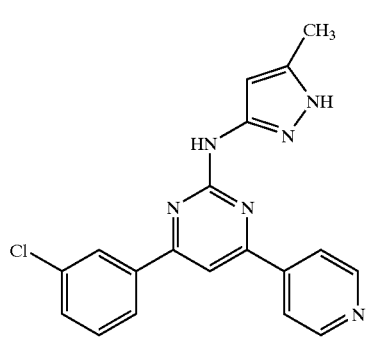

VII-35

TABLE 6-continued

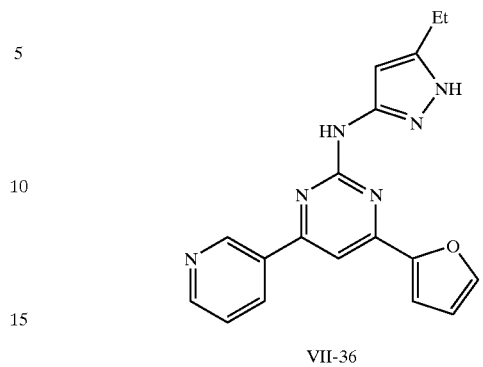

VII-36

In another embodiment, this invention provides a composition comprising a compound of formula VII and a pharmaceutically acceptable carrier.

One aspect of this invention relates to a method of inhibiting GSK-3 activity in a patient, comprising administering to the patient a therapeutically effective amount of a composition comprising a compound of formula VII.

Another aspect relates to a method of treating a disease that is alleviated by treatment with a GSK-3 inhibitor, said method comprising the step of administering to a patient in need of such a treatment a therapeutically effective amount of a composition comprising a compound of formula VII.

Another aspect relates to a method of enhancing glycogen synthesis and/or lowering blood levels of glucose in a patient in need thereof, comprising administering to said patient a therapeutically effective amount of a composition comprising a compound of formula VII. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula VII. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula VII. This method is especially useful for treating schizophrenia.

One aspect of this invention relates to a method of inhibiting Aurora activity in a patient, comprising administering to the patient a therapeutically effective amount of a composition comprising a compound of formula VII.

Another aspect relates to a method of treating a disease that is alleviated by treatment with an Aurora inhibitor, said method comprising the step of administering to a patient in need of such a treatment a therapeutically effective amount of a composition comprising a compound of formula VII. This method is especially useful for treating cancer, such as colon, ovarian, and breast cancer.

One aspect of this invention relates to a method of inhibiting CDK-2 activity in a patient, comprising administering to the patient a therapeutically effective amount of a composition comprising a compound of formula VII.

Another aspect relates to a method of treating a disease that is alleviated by treatment with a CDK-2 inhibitor, said method comprising the step of administering to a patient in need of such a treatment a therapeutically effective amount of a composition comprising a compound of formula VII. This method is especially useful for treating cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

Another method relates to inhibiting GSK-3, Aurora, or CDK-2 activity in a biological sample, which method comprises contacting the biological sample with the GSK-3 or Aurora inhibitor of formula VII, or a pharmaceutical composition thereof, in an amount effective to inhibit GSK-3, Aurora or CDK-2.

Each of the aforementioned methods directed to the inhibition of GSK-3, Aurora or CDK-2, or the treatment of a disease alleviated thereby, is preferably carried out with a preferred compound of formula VII, as described above.

Another embodiment of this invention relates to compounds of formula VIII:

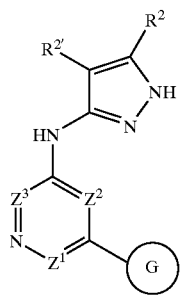

VIII or a pharmaceutically acceptable derivative or prodrug thereof, wherein:

$Z^1$ is N or $CR^9$, $Z^2$ is N or CH, and $Z^3$ is N or $CR^x$, provided that one of $Z^1$ and $Z^3$ is nitrogen;

G is Ring C or Ring D;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —$R^8$;

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by halo, oxo, or —$R^5$, and at any substitutable ring nitrogen by —$R^4$, provided that when Ring D is a six-membered aryl or heteroaryl ring, —$R^5$ is hydrogen at each ortho carbon position of Ring D;

$R^1$ is selected from -halo, —CN, —$NO_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

$R^x$ is T-$R^3$;

T is a valence bond or a $C_{1-4}$ alkylidene chain;

$R^2$ and $R^{2'}$ are independently selected from —R, -T-W—$R^6$, or $R^2$ and $R^{2'}$ are taken together with their intervening atoms to form a fused, 5–8 membered, unsaturated or partially unsaturated, ring having 0–3 ring heteroatoms selected from nitrogen, oxygen, or sulfur, wherein each substitutable carbon on said fused ring formed by $R^2$ and $R^{2'}$ is substituted by halo, oxo, —CN, —$NO_2$, —$R^7$, or —V—$R^6$, and any substitutable nitrogen on said ring formed by $R^2$ and $R^{2'}$ is substituted by $R^4$;

$R^3$ is selected from —R, -halo, —OR, —C(=O)R, —$CO_2R$, —COCOR, —$COCH_2COR$, —$NO_2$, —CN, —S(O)R, —$S(O)_2R$, —SR, —$N(R^4)_2$, —$CON(R^7)_2$, —$SO_2N(R^7)_2$, —OC(=O)R, —$N(R^7)COR$, —$N(R^7)CO_2$ (optionally substituted $C_{1-6}$ aliphatic), —$N(R^4)N(R^4)_2$, —C=$NN(R^4)_2$, —C=N—OR, —$N(R^7)CON(R^7)_2$, —$N(R^7)SO_2N(R^7)_2$, —$N(R^4)SO_2R$, or —OC(=O)N$(R^7)_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$ (optionally substituted $C_{1-6}$ aliphatic), —CON$(R^7)_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —OC(=O)N$(R^4)_2$, or $R^5$ and an adjacent substituent taken together with their intervening atoms form said ring fused to Ring C;

V is —O—, —S—, —SO—, —$SO_2$—, —$N(R^6)SO_2$—, —$SO_2N(R^6)$—, —$N(R^6)$—, —CO—, —$CO_2$—, —$N(R^6)$ CO—, —$N(R^6)C(O)O$—, —$N(R^6)CON(R^6)$—, —$N(R^6)SO_2N(R^6)$—, —$N(R^6)N(R^6)$—, —$C(O)N(R^6)$—, —OC(O)N$(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)$=NN$(R^6)$—, —$C(R^6)$=N—O—, —$C(R^6)_2N(R^6)N(R^6)$—, —$C(R^6)_2N(R^6)SO_2N(R^6)$—, or —$C(R^6)_2N(R^6)CON(R^6)$—;

W is —$C(R^6)_2O$—, —$C(R^6)_2S$—, —$C(R^6)_2SO$—, —$C(R^6)_2 SO_2$—, —$C(R^6)_2SO_2N(R^6)$—, —$C(R^6)_2N(R^6)$—, —CO—, —$CO_2$—, —$C(R^6)OC(O)$—, —$C(R^6)OC(O)N(R^6)$—, —$C(R^6)_2N(R^6)CO$—, —$C(R^6)_2N(R^6)C(O)O$—, —$C(R^6)$=NN$(R^6)$—, —$C(R^6)$=N—O—, —$C(R^6)_2N(R^6)N(R^6)$—, —$C(R^6)_2N(R^6)SO_2N(R^6)$—, —$C(R^6)_2N(R^6)CON(R^6)$—, or —CON$(R^6)$—;

each $R^6$ is independently selected from hydrogen, an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

each $R^8$ is independently selected from an optionally substituted $C_{1-4}$ aliphatic group, —$OR^6$, —$SR^6$, —$COR^6$, —$SO_2R^6$, —$N(R^6)_2$, —$N(R^6)N(R^6)_2$, —CN, —$NO_2$, —$CON(R^6)_2$, or —$CO_2R^6$; and $R^9$ is selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$.

Accordingly, the present invention relates to compounds of formula VIIIa, VIIIb, VIIIc and VIIId as shown below:

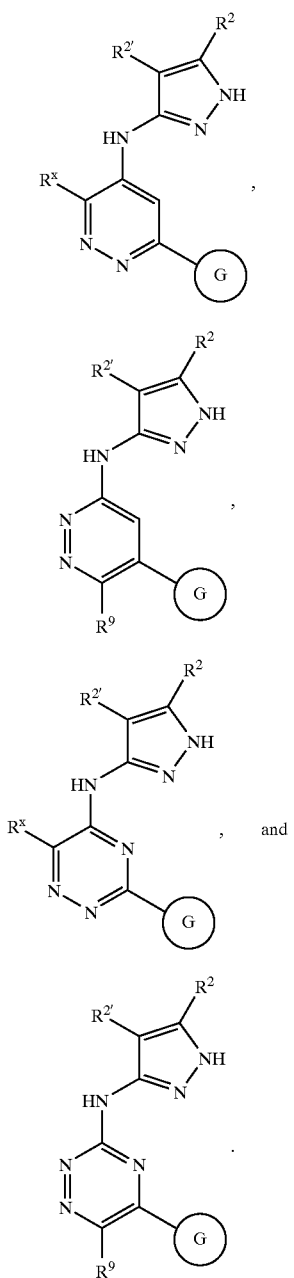

VIIIa

VIIIb

, and

VIIIc

VIIId

Preferred R$^x$ groups of formula VIII include T-R$^3$ wherein T is a valence bond or a methylene and R$^3$ is CN, —R, or —OR. When R$^3$ is —R, preferred R$^3$ groups include an optionally substituted group selected from C$_{1-6}$ aliphatic, phenyl, or a 5–6 membered heteroaryl or heterocyclyl ring. When R$^3$ is —OR, preferred R groups include an optionally substituted group C$_{1-6}$ aliphatic group such as alkyl- or dialkylaminoalkyl and aminoalkyl. Examples of preferred R$^x$ include acetamido, CN, piperidinyl, piperazinyl, phenyl, pyridinyl, imidazol-1-yl, imidazol-2-yl, cyclohexyl, cyclopropyl, methyl, ethyl, isopropyl, t-butyl, NH$_2$CH$_2$CH$_2$NH, and NH$_2$CH$_2$CH$_2$O.

Preferred R$^9$ groups of formula VIII, when present, include R, OR, and N(R$^4$)$_2$. Examples of preferred R$^9$ include methyl, ethyl, NH$_2$, NH$_2$CH$_2$CH$_2$NH, N(CH$_3$)$_2$CH$_2$CH$_2$NH, N(CH$_3$)$_2$CH$_2$CH$_2$O, (piperidin-1-yl)CH$_2$CH$_2$O, and NH$_2$CH$_2$CH$_2$O.

The R$^2$ and R$^{2'}$ groups of formula VIII may be taken together to form a fused ring, thus providing a bicyclic ring system containing a pyrazole ring. Preferred fused rings include benzo, pyrido, pyrimido, and a partially unsaturated 6-membered carbocyclo ring. These are exemplified in the following formula VIII compounds having a pyrazole-containing bicyclic ring system:

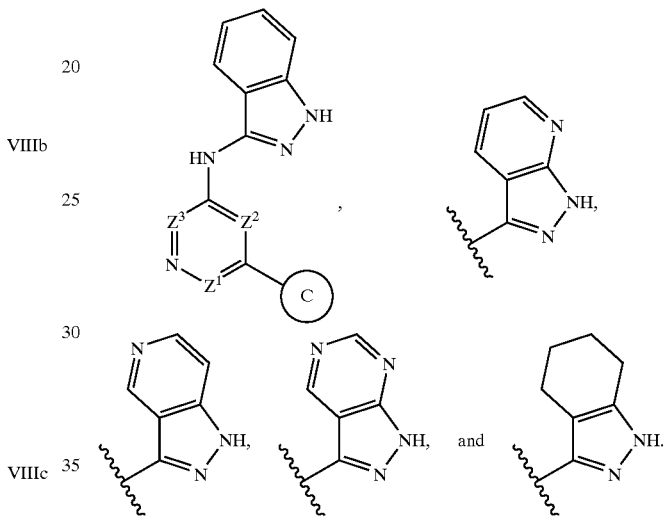

Preferred substituents on the formula VIII R$^2$/R$^{2'}$ fused ring include one or more of the following: -halo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, and —CO(C$_{1-4}$ alkyl), wherein the (C$_{1-4}$ alkyl) is a straight, branched, or cyclic alkyl group. Preferably, the (C$_{1-4}$ alkyl) group is methyl.

When the pyrazole ring system of formula VIII is monocyclic, preferred R$^2$ groups include hydrogen, C$_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred R$^2$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl). A preferred R$^{2'}$ group is hydrogen.

When G is Ring C, preferred formula VIII Ring C groups are phenyl and pyridinyl. When two adjacent substituents on Ring C are taken together to form a fused ring, Ring C is contained in a bicyclic ring system. Preferred fused rings include a benzo or pyrido ring. Such rings preferably are fused at ortho and meta positions of Ring C. Examples of preferred bicyclic Ring C systems include naphthyl and isoquinolinyl. Preferred $R^1$ groups include -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —$OC(O)NH_2$, or —$NHSO_2R^6$. When $R^1$ is an optionally substituted $C_{1-6}$ aliphatic group, the most preferred optional substituents are halogen. Examples of preferred $R^1$ groups include —$CF_3$, —Cl, —F, —CN, —$COCH_3$, —$OCH_3$, —OH, —$CH_2CH_3$, —$OCH_2CH_3$, —$CH_3$, —$CF_2CH_3$, cyclohexyl, t-butyl, isopropyl, cyclopropyl, —C≡CH, —C≡C—$CH_3$, —$SO_2CH_3$, —$SO_2NH_2$, —$N(CH_3)_2$, —$CO_2CH_3$, —$CONH_2$, —$NHCOCH_3$, —$OC(O)NH_2$, —$NHSO_2CH_3$, and —$OCF_3$.

On Ring C preferred $R^5$ substituents, when present, include -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$SO_2N(R^4)_2$, and —$N(R^4)SO_2R$. More preferred $R^5$ substituents include —Cl, —F, —CN, —$CF_3$, —$NH_2$, —$NH(C_{1-4}$ aliphatic), —$N(C_{1-4}$ aliphatic)$_2$, —$O(C_{1-4}$ aliphatic), $C_{1-4}$ aliphatic, and —$CO_2$ ($C_{1-4}$ aliphatic). Examples of such preferred $R^5$ substituents include —Cl, —F, —CN, —$CF_3$, —$NH_2$, —NHMe, —$NMe_2$, —OEt, methyl, ethyl, cyclopropyl, isopropyl, t-butyl, and —$CO_2Et$.

When G is Ring D, preferred formula VIII Ring D monocyclic rings include substituted and unsubstituted phenyl, pyridinyl, piperidinyl, piperazinyl, pyrrolidinyl, thienyl, azepanyl, and morpholinyl rings. When two adjacent substituents on Ring D are taken together to form a fused ring, the Ring D system is bicyclic. Preferred formula VIII Ring D bicyclic rings include 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, and naphthyl. Examples of more preferred bicyclic Ring D systems include naphthyl and isoquinolinyl.

Preferred $R^5$ substituents on Ring D of formula VIII include halo, oxo, CN, —$NO_2$, —$N(R^4)_2$, —$CO_2R$, —$CONH(R^4)$, —$N(R^4)COR$, —$SO_2N(R^4)_2$, —$N(R^4)SO_2R$, —SR, —OR, —C(O)R, or substituted or unsubstituted group selected from 5–6 membered heterocyclyl, $C_{6-10}$ aryl, or $C_{1-6}$ aliphatic. More preferred $R^5$ substituents include -halo, —CN, -oxo, —SR, —OR, —$N(R^4)_2$, —C(O)R, or a substituted or unsubstituted group selected from 5–6 membered heterocyclyl, $C_{6-10}$ aryl, or $C_{1-6}$ aliphatic. Examples of Ring D substituents include —OH, phenyl, methyl, $CH_2OH$, $CH_2CH_2OH$, pyrrolidinyl, OPh, $CF_3$, C≡CH, Cl, Br, F, I, $NH_2$, $C(O)CH_3$, i-propyl, tert-butyl, SEt, OMe, $N(Me)_2$, methylene dioxy, and ethylene dioxy.

Preferred formula VIII compounds have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is selected from a naphthyl, quinolinyl or isoquinolinyl ring, and $R^1$ is -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6_1$, —$CONH_2$, —$NHCOR^6$, —$OC(O)NH_2$, or —$NHSO_2R^6$; or Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ is T-$R^3$ wherein T is a valence bond or a methylene; and (c) $R^{2'}$ is hydrogen and $R^2$ is hydrogen or a substituted or unsubstituted group selected from aryl, heteroaryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring.

More preferred compounds of formula VIII have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is a naphthyl ring, and $R^1$ is -halo, a $C_{1-6}$ haloaliphatic group, a $C_{1-6}$ aliphatic group, phenyl, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ is T-$R^3$ wherein T is a valence bond or a methylene and $R^3$ is CN, —R or —OR;

(c) $R^{2'}$ is hydrogen and $R^2$ is hydrogen or a substituted or unsubstituted group selected from aryl, or a $C_{1-6}$ aliphatic group, or $R^2$ and $R^{2'}$ are taken together with their intervening atoms to form a substituted or unsubstituted benzo, pyrido, pyrimido or partially unsaturated 6-membered carbocyclo ring; and (d) each $R^5$ is independently selected from -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$SO_2N(R^4)_2$, or —$N(R^4)SO_2R$.

Even more preferred compounds of formula VIII have one or more, and more preferably all, of the features selected from the group consisting of:

(a) $R^x$ is T-$R^3$ wherein T is a valence bond or a methylene and $R^3$ is —R or —OR wherein R is an optionally substituted group selected from $C_{1-6}$ aliphatic, phenyl, or a 5–6 membered heteroaryl or heterocyclyl ring;

(b) Ring C is a phenyl or pyridinyl ring, optionally substituted by —$R^5$, wherein when Ring C and two adjacent substituents thereon form a bicyclic ring system, the bicyclic ring system is a naphthyl ring, and $R^1$ is -halo, a $C_{1-4}$ aliphatic group optionally substituted with halogen, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, isoquinolinyl, quinolinyl, or naphthyl;

(c) $R^2$ and $R^{2'}$ are taken together with their intervening atoms to form a benzo, pyrido, pyrimido or partially unsaturated 6-membered carbocyclo ring optionally substituted with -halo, —$N(R^4)_2$, —$C_{1-4}$ alkyl, —$C_{1-4}$ haloalkyl, —$NO_2$, —$O(C_{1-4}$ alkyl), —$CO_2(C_{1-4}$ alkyl), —CN, —$SO_2$ ($C_{1-4}$ alkyl), —$SO_2NH_2$, —$OC(O)NH_2$, —$NH_2SO_2(C_{1-4}$ alkyl), —$NHC(O)(C_{1-4}$ alkyl), —$C(O)NH_2$, or —$CO(C_{1-4}$ alkyl), wherein the ($C_{1-4}$ alkyl) is a straight, branched, or cyclic alkyl group;

(d) each $R^5$ is independently selected from —Cl, —F, —CN, —$CF_3$, —$NH_2$, —$NH(C_{1-4}$ aliphatic), —$N(C_{1-4}$ aliphatic)$_2$, —$O(C_{1-4}$ aliphatic), $C_{1-4}$ aliphatic, and —$CO_2$ ($C_{1-4}$ aliphatic); and (e) $R^9$ is R, OR, or $N(R^4)_2$.

Representative compounds of formula VIII are set forth in Table 7 below.
TABLE 7
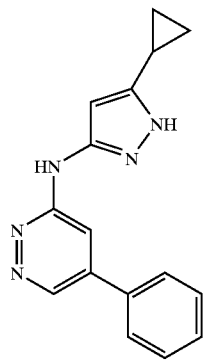
VIII-1
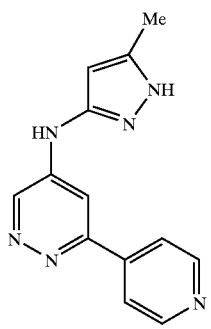
VIII-2
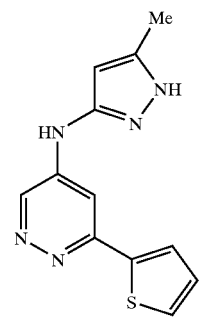
VIII-3
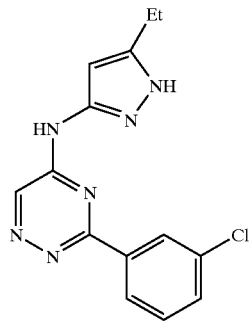
VIII-4
TABLE 7-continued
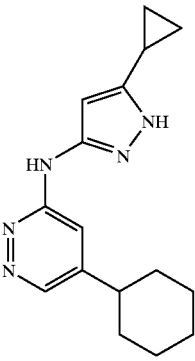
VIII-5
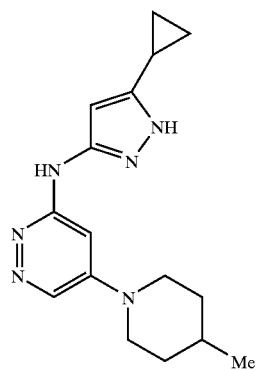
VIII-6
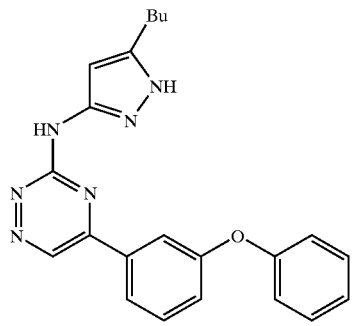
VIII-7
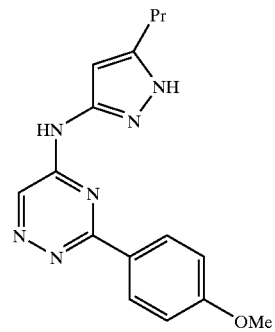
VIII-8

TABLE 7-continued
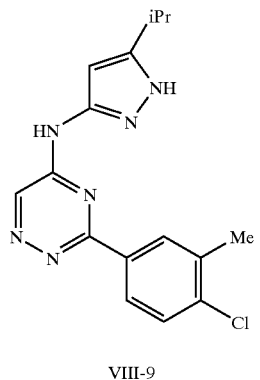
VIII-9
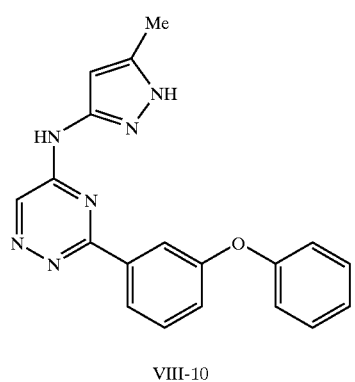
VIII-10
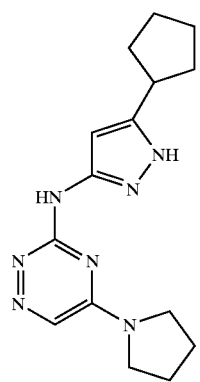
VIII-11
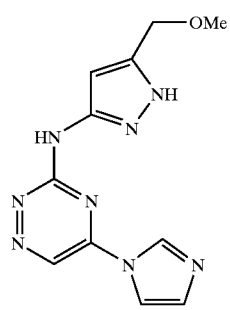
VIII-12
TABLE 7-continued
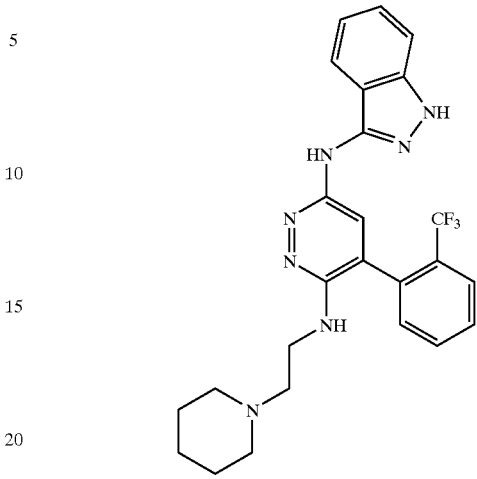
VIII-13
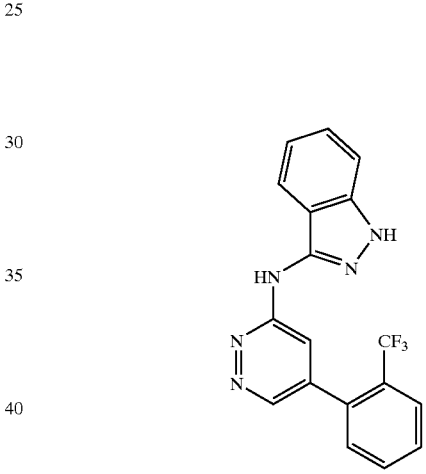
VIII-14
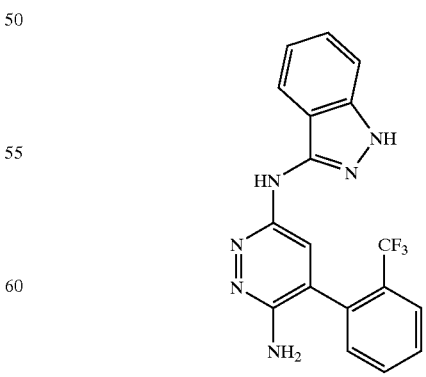
VIII-15

TABLE 7-continued
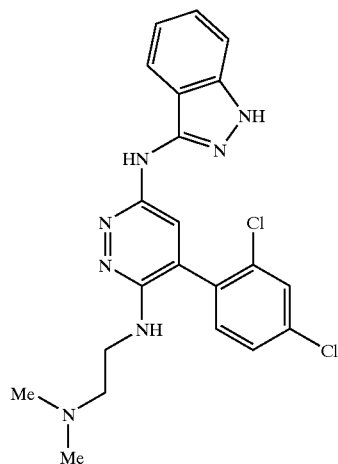
VIII-16
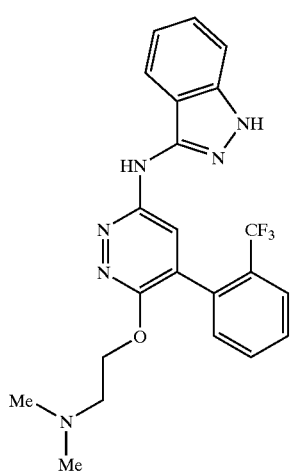
VIII-17
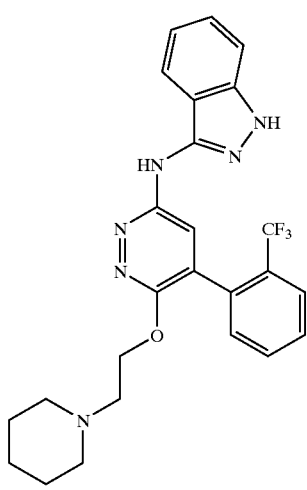
VIII-18
TABLE 7-continued
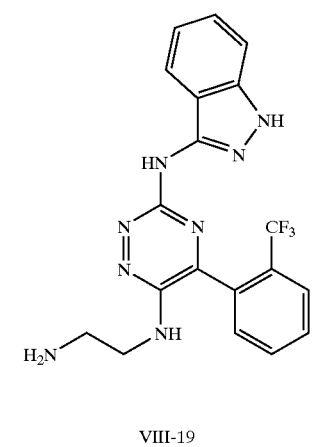
VIII-19
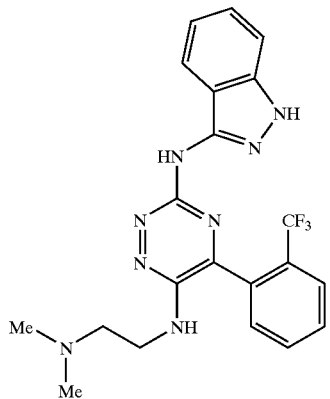
VIII-20
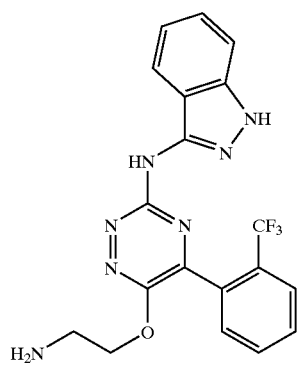
VIII-21

TABLE 7-continued
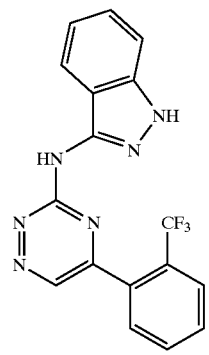
VIII-22
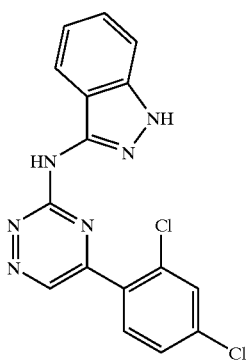
VIII-23
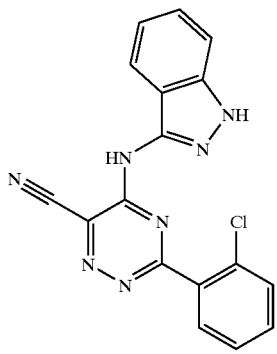
VIII-24
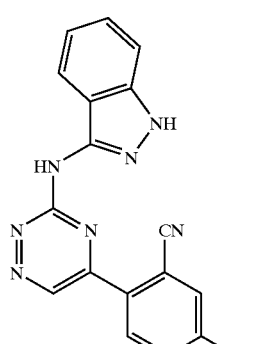
VIII-25
TABLE 7-continued
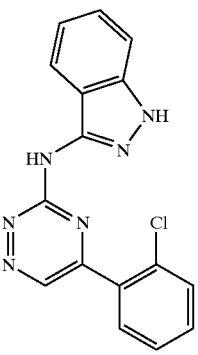
VIII-26
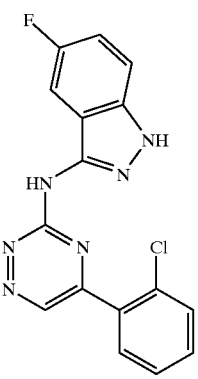
VIII-27
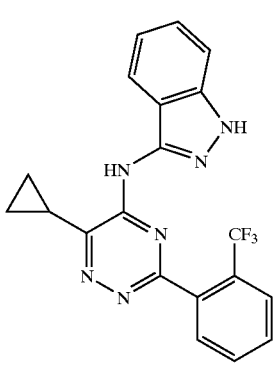
VIII-28
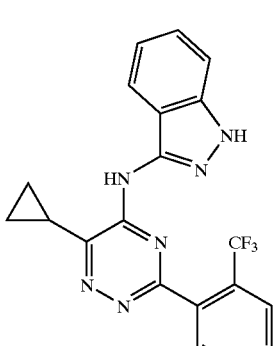
VIII-29

TABLE 7-continued
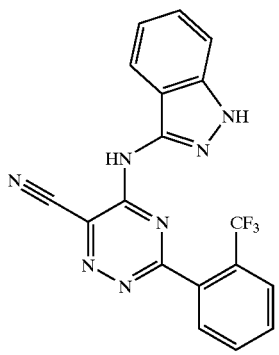
VIII-30
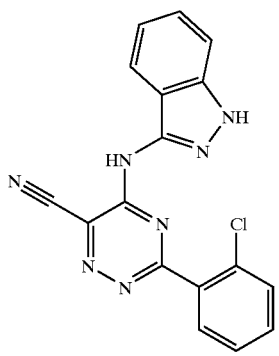
VIII-31
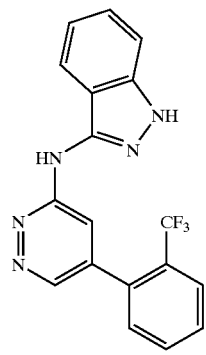
VIII-32
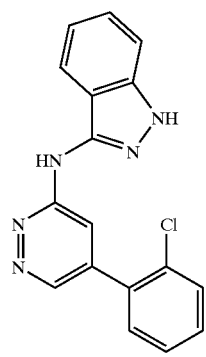
VIII-33
TABLE 7-continued
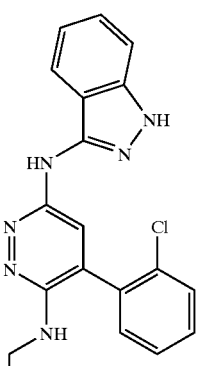
VIII-34
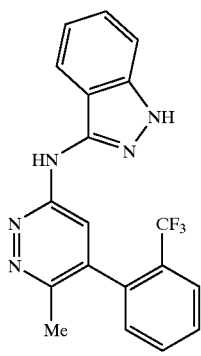
VIII-35
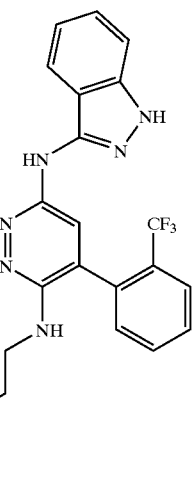
VIII-36

TABLE 7-continued
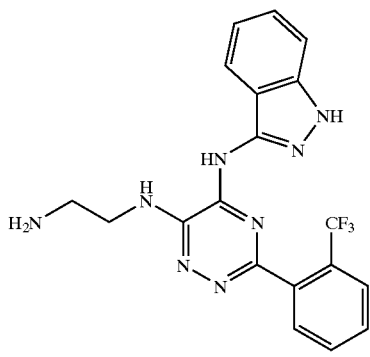
VIII-37
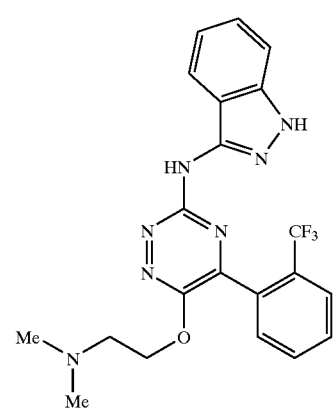
VIII-38
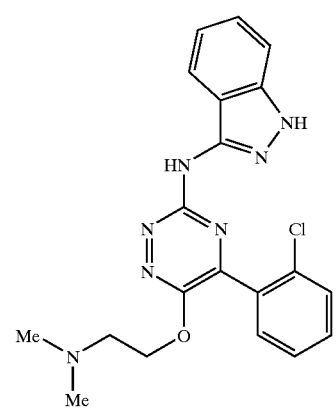
VIII-39
TABLE 7-continued
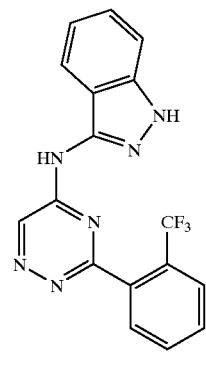
VIII-40
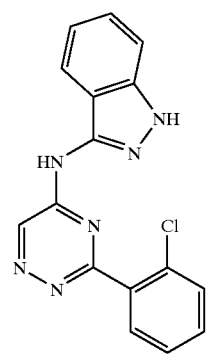
VIII-41
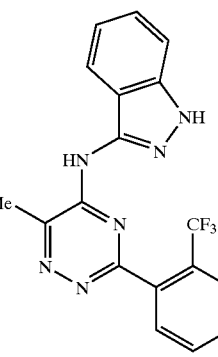
VIII-42
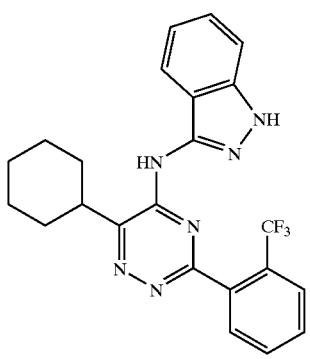
VIII-43

TABLE 7-continued
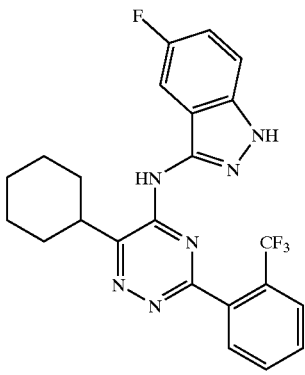
VIII-44
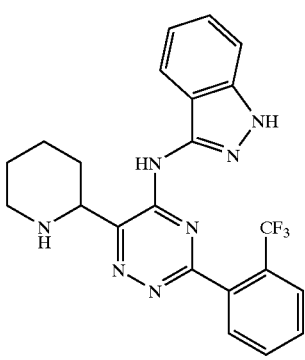
VIII-45
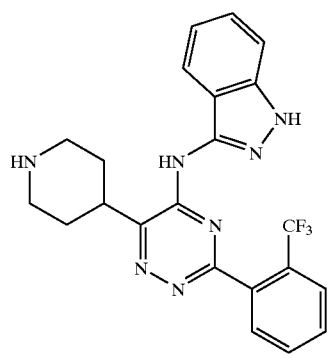
VIII-46
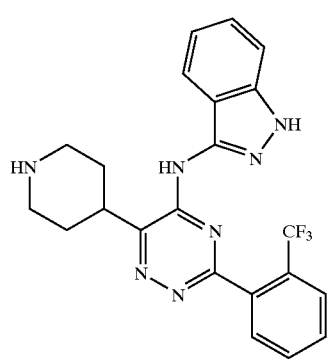
VIII-47
TABLE 7-continued
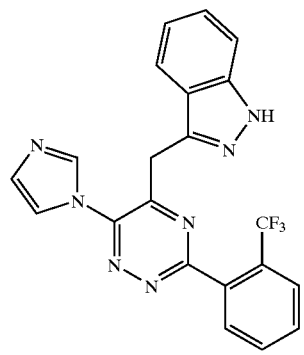
VIII-48
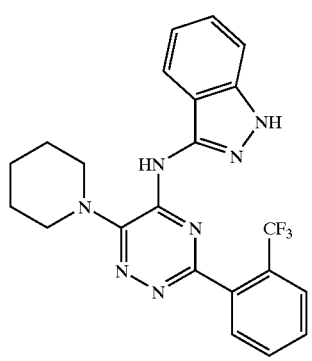
VIII-49
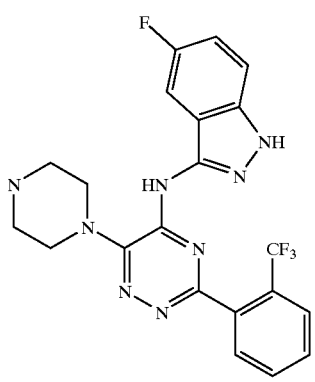
VIII-50
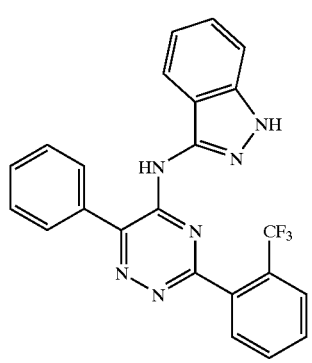
VIII-51

TABLE 7-continued

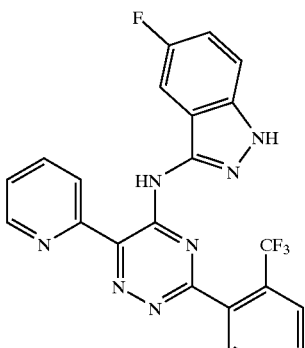

VIII-52

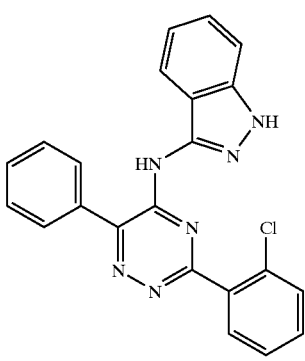

VIII-53

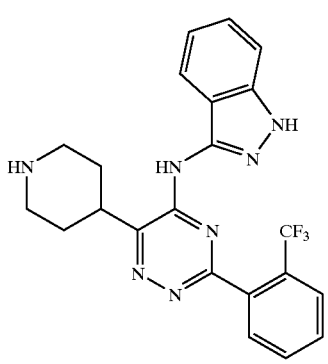

VIII-54

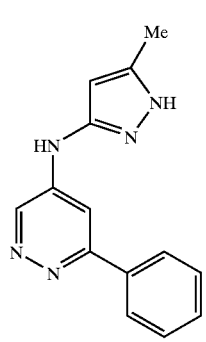

VIII-55

TABLE 7-continued

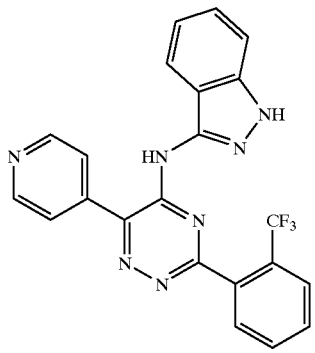

VIII-56

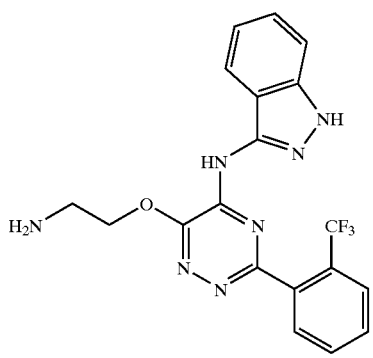

VIII-57

In another embodiment, this invention provides a composition comprising a compound of formula VIII and a pharmaceutically acceptable carrier.

One aspect of this invention relates to a method of inhibiting GSK-3 activity in a patient, comprising administering to the patient a therapeutically effective amount of a composition comprising a compound of formula VIII.

Another aspect relates to a method of treating a disease that is alleviated by treatment with a GSK-3 inhibitor, said method comprising the step of administering to a patient in need of such a treatment a therapeutically effective amount of a composition comprising a compound of formula VIII.

Another aspect relates to a method of enhancing glycogen synthesis and/or lowering blood levels of glucose in a patient in need thereof, comprising administering to said patient a therapeutically effective amount of a composition comprising a compound of formula VIII. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula VIII. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula VIII. This method is especially useful for treating schizophrenia.

One aspect of this invention relates to a method of inhibiting Aurora activity in a patient, comprising administering to the patient a therapeutically effective amount of a composition comprising a compound of formula VIII.

Another aspect relates to a method of treating a disease that is alleviated by treatment with an Aurora inhibitor, said method comprising the step of administering to a patient in need of such a treatment a therapeutically effective amount of a composition comprising a compound of formula VIII. This method is especially useful for treating cancer, such as colon, ovarian, and breast cancer.

One aspect of this invention relates to a method of inhibiting CDK-2 activity in a patient, comprising administering to the patient a therapeutically effective amount of a composition comprising a compound of formula VIII.

Another aspect relates to a method of treating a disease that is alleviated by treatment with a CDK-2 inhibitor, said method comprising the step of administering to a patient in need of such a treatment a therapeutically effective amount of a composition comprising a compound of formula VIII. This method is especially useful for treating cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis.

Another method relates to inhibiting GSK-3, Aurora, or CDK-2 activity in a biological sample, which method comprises contacting the biological sample with the GSK-3 or Aurora inhibitor of formula VIII, or a pharmaceutical composition thereof, in an amount effective to inhibit GSK-3, Aurora or CDK-2.

Each of the aforementioned methods directed to the inhibition of GSK-3, Aurora or CDK-2, or the treatment of a disease alleviated thereby, is preferably carried out with a preferred compound of formula VIII, as described above.

The above formula I compounds contain a pyrazole ring bearing the $R^2$ and $R^{2'}$ substituents. In their search for further inhibitors of the protein kinases GSK and Aurora, applicants sought to replace the pyrazole moiety of formula I with other heteroaromatic rings. One of the more effective pyrazole ring replacements was found to be a triazole ring. Inhibitors having this triazole ring are otherwise structurally similar to the formula I compounds and are represented by the general formula IX:

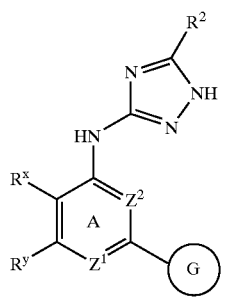

IX or a pharmaceutically acceptable derivative or prodrug thereof, wherein:

$Z^1$ is nitrogen or $CR^9$ and $Z^2$ is nitrogen or CH, provided that at least one of $Z^1$ and $Z^2$ is nitrogen;

G is Ring C or Ring D;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms-selected from oxygen, sulfur or nitrogen, said fused ring being optionally substituted by halo, oxo, or —$R^8$;

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^1$ is selected from -halo, —CN, —$NO_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

$R^x$ and $R^y$ are independently selected from T-$R^3$, or $R^x$ and $R^y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by $R^x$ and $R^y$ is substituted by oxo or T-$R^3$, and any substitutable nitrogen on said ring formed by $R^x$ and $R^y$ is substituted by $R^4$;

T is a valence bond or a $C_{1-4}$ alkylidene chain;

$R^2$ is —R or -T-W—$R^6$;

$R^3$ is selected from —R, -halo, —OR, —C(=O)R, —$CO_2$R, —COCOR, —$COCH_2$COR, —$NO_2$, —CN, —S(O)R, —S(O)$_2$R, —SR, —N($R^4$)$_2$, —CON($R^7$)$_2$, —$SO_2$N($R^7$)$_2$, —OC(=O)R, —N($R^7$)COR, —N($R^7$)$CO_2$ (optionally substituted $C_{1-6}$ aliphatic), —N($R^4$)N($R^4$)$_2$, —C=NN($R^4$)$_2$, —C=N—OR, —N($R^7$)CON($R^7$)$_2$, —N($R^7$)$SO_2$N($R^7$)$_2$, —N($R^4$)$SO_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$ (optionally substituted $C_{1-6}$ aliphatic), —CON($R^7$)$_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$, or $R^5$ and an adjacent substituent taken together with their intervening atoms form said ring fused to Ring C;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$), —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2SO_2$—, —C($R^6$)$_2SO_2$N($R^6$)—, —C($R^6$)$_2$N($R^6$)—, —C($R^6$)$_2$N($R^6$)C(O)—, —C($R^6$)$_2$N($R^6$)C(O)

O—, —C(R$^6$)=NN(R$^6$)—, —C(R$^6$)=N—O—, —C(R$^6$)$_2$(R$^6$)N(R$^6$)—, —C(R$^6$)$_2$N(R$^6$)SO$_2$N(R$^6$)—, or —C(R$^6$)$_2$N(R$^6$)CON(R)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each R$^6$ is independently selected from hydrogen, an optionally substituted C$_{1-4}$ aliphatic group, or, two R$^6$ groups on the same nitrogen atom are taken together with the nitrogen atom to form a 5–6 membered heterocyclyl or heteroaryl ring;

each R$^7$ is independently selected from hydrogen or an optionally substituted C$_{1-6}$ aliphatic group, or two R$^7$ on the same nitrogen are taken together with the nitrogen to form a 5–8 membered heterocyclyl or heteroaryl ring;

each R$^8$ is independently selected from an optionally substituted C$_{1-4}$ aliphatic group, —OR$^6$, —SR$^6$, —COR$^6$, —SO$_2$R$^6$, —N(R$^6$)$_2$, —N(R$^6$)N(R$^6$)$_2$, —CN, —NO$_2$, —CON(R$^6$)$_2$, or —CO$_2$R$^6$; and R$^9$ is selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$.

Compounds of formula IX may exist in alternative tautomeric forms, as in tautomers 1–3 shown below. Unless otherwise indicated, the representation of any of these tautomers is meant to include the other two.

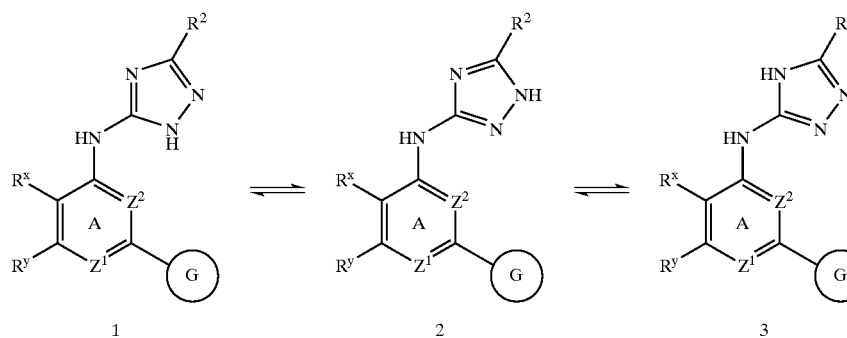

The R$^x$ and R$^y$ groups of formula IX may be taken together to form a fused ring, providing a bicyclic ring system containing Ring A. Preferred R$^x$/R$^y$ rings include a 5-, 6-, 7-, or 8-membered unsaturated or partially unsaturated ring having 0–2 heteroatoms, wherein said R$^x$/R$^y$ ring is optionally substituted. Examples of Ring A systems are shown below by compounds IX-A through IX-DD, wherein Z$^1$ is nitrogen or C(R$^9$) and Z$^2$ is nitrogen or C(H).

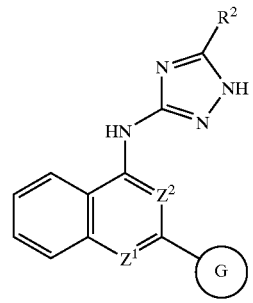

IX-A

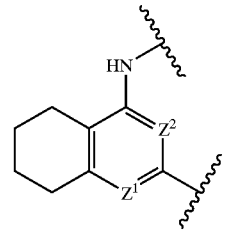

IX-B

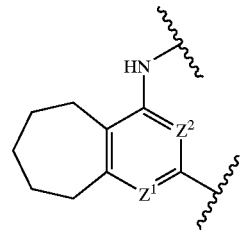

IX-C

-continued

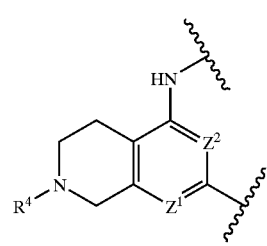

IX-D

IX-E
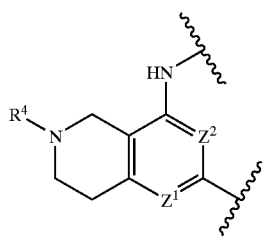
IX-F
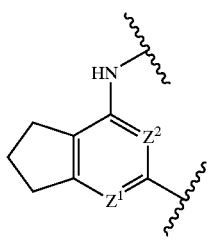
IX-G
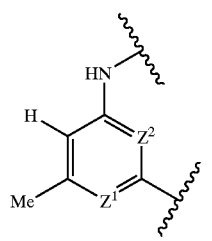
IX-H
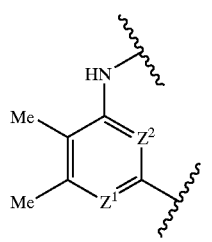
IX-I
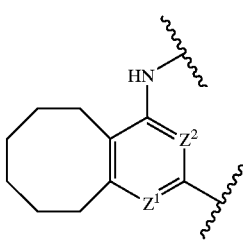
IX-J
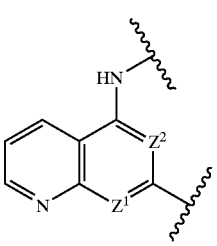
IX-K
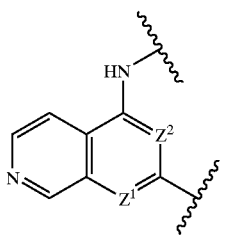
IX-L
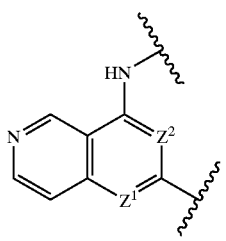
IX-M
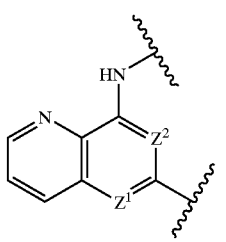
IX-N
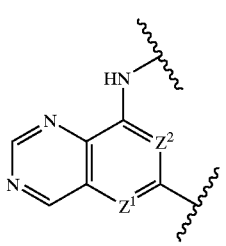
IX-O
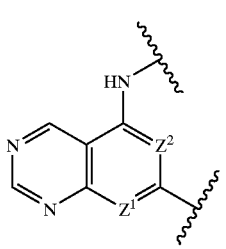
IX-P
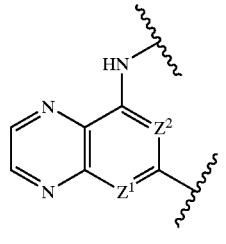

IX-Q 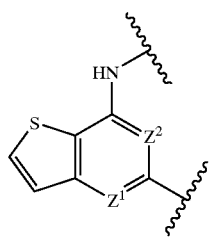
IX-R 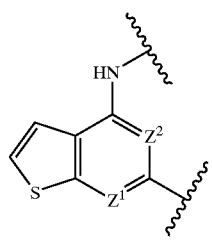
IX-S 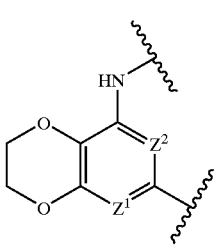
IX-T 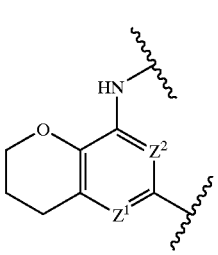
IX-U 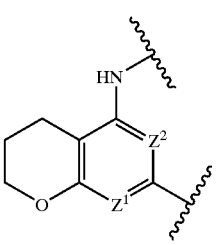
IX-V 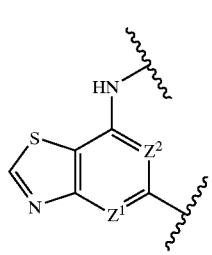
IX-W 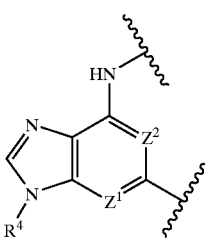
IX-X 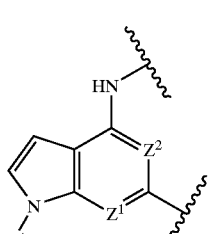
IX-Y 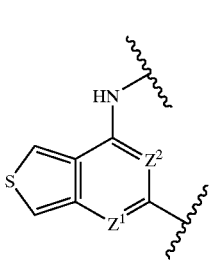
IX-Z 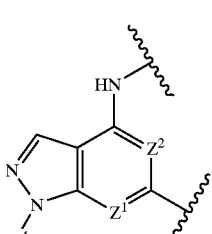
IX-AA 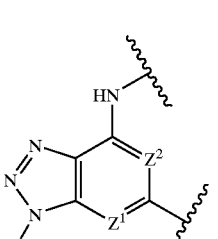
IX-BB 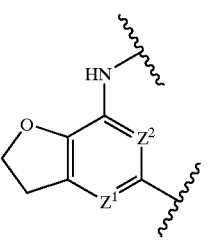

IX-CC

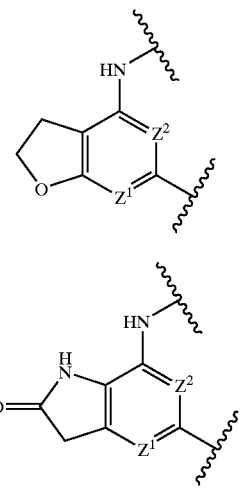

IX-DD

Preferred bicyclic Ring A systems of formula IX include IX-A, IX-B, IX—C, IX-D, IX-E, IX-F, IX-G, IX-H, IX-I, IX-J, IX-K, IX-L, and IX-M, more preferably IX-A, IX-B, IX—C, IX-F, and IX-H, and most preferably IX-A, IX-B, and IX-H.

In the monocyclic Ring A system of formula IX, preferred $R^x$ groups include hydrogen, alkyl- or dialkylamino, acetamido, or a $C_{1-4}$ aliphatic group such as methyl, ethyl, cyclopropyl, isopropyl or t-butyl. Preferred $R^y$ groups, when present, include T-$R^3$ wherein T is a valence bond or a methylene, and $R^3$ is —R, —N($R^4$)$_2$, or —OR. Examples of preferred $R^y$ include 2-pyridyl, 4-pyridyl, piperidinyl, methyl, ethyl, cyclopropyl, isopropyl, t-butyl, alkyl- or dialkylamino, acetamido, optionally substituted phenyl such as phenyl or halo-substituted phenyl, and methoxymethyl.

In the bicyclic Ring A system of formula IX, the ring formed by $R^x$ and $R^y$ taken together may be substituted or unsubstituted. Suitable substituents include —R, halo, —OR, —C(=O)R, —CO$_2$R, —COCOR, —NO$_2$, —CN, —S(O)R, —SO$_2$R, —SR, —N($R^4$)$_2$, —CON($R^4$)$_2$, —SO$_2$N($R^4$)$_2$, —OC(=O)R, —N($R^4$)COR, —N($R^4$)CO$_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)SO$_2$N($R^4$)$_2$, —N($R^4$)SO$_2$R, or —OC(=O)N($R^4$)$_2$, wherein R and $R^4$ are as defined above. Preferred $R^x$/$R^y$ ring substituents include -halo, —R, —OR, —COR, —CO$_2$R, —CON($R^4$)$_2$, —CN, or —N($R^4$)$_2$ wherein R is an optionally substituted $C_{1-6}$ aliphatic group.

Preferred $R^2$ groups of formula IX include hydrogen, $C_{1-4}$ aliphatic, alkoxycarbonyl, (un)substituted phenyl, hydroxyalkyl, alkoxyalkyl, aminocarbonyl, mono- or dialkylaminocarbonyl, aminoalkyl, alkylaminoalkyl, dialkylaminoalkyl, phenylaminocarbonyl, and (N-heterocyclyl)carbonyl. Examples of such preferred $R^2$ substituents include methyl, cyclopropyl, ethyl, isopropyl, propyl, t-butyl, cyclopentyl, phenyl, CO$_2$H, CO$_2$CH$_3$, CH$_2$OH, CH$_2$OCH$_3$, CH$_2$CH$_2$CH$_2$OH, CH$_2$CH$_2$CH$_2$OCH$_3$, CH$_2$CH$_2$CH$_2$OCH$_2$Ph, CH$_2$CH$_2$CH$_2$NH$_2$, CH$_2$CH$_2$CH$_2$NHCOOC(CH$_3$)$_3$, CONHCH(CH$_3$)$_2$, CONHCH$_2$CH=CH$_2$, CONHCH$_2$CH$_2$OCH$_3$, CONHCH$_2$Ph, CONH(cyclohexyl), CON(Et)$_2$, CON(CH$_3$)CH$_2$Ph, CONH(n-C$_3$H$_7$), CON(Et)CH$_2$CH$_2$CH$_3$, CONHCH$_2$CH(CH$_3$)$_2$, CON(n-C$_3$H$_7$)$_2$, CO(3-methoxymethylpyrrolidin-1-yl), CONH(3-tolyl), CONH(4-tolyl), CONHCH$_3$, CO(morpholin-1-yl), CO(4-methylpiperazin-1-yl), CONHCH$_2$CH$_2$OH, CONH$_2$, and CO(piperidin-1-yl). A more preferred $R^2$ group for formula IX compounds is hydrogen.

An embodiment that is particularly useful for treating GSK3-mediated diseases relates to compounds of formula X wherein ring A is a pyrimidine ring:

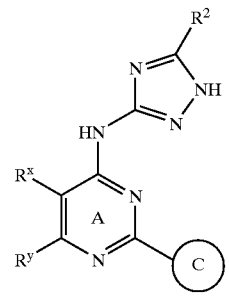

X or a pharmaceutically acceptable derivative or prodrug thereof, wherein;

Ring C is selected from a phenyl, pyridinyl, pyrimidinyl, pyridazinyl, pyrazinyl, or 1,2,4-triazinyl ring, wherein said Ring C has one or two ortho substituents independently selected from —$R^1$, any substitutable non-ortho carbon position on Ring C is independently substituted by —$R^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo, oxo, or —$R^8$;

$R^1$ is selected from -halo, —CN, —NO$_2$, T-V—$R^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —$R^8$, said $C_{1-6}$ aliphatic group optionally substituted with halo, cyano, nitro, or oxygen, or $R^1$ and an adjacent substituent taken together with their intervening atoms form said ring fused to Ring C;

$R^x$ and $R^y$ are independently selected from T-$R^3$, or $R^x$ and $R^y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by $R^x$ and $R^y$ is substituted by oxo or T-$R^3$, and any substitutable nitrogen on said ring formed by $R^x$ and $R^y$ is substituted by $R^4$;

T is a valence bond or a $C_{1-4}$ alkylidene chain;

$R^2$ is —R or -T-W—$R^6$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$ (optionally substituted $C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —CO$_2$ (optionally substituted $C_{1-6}$ aliphatic), —CON($R^7$)$_2$, or —SO$_2$R$^7$, or two $R^4$ on the same nitrogen are taken together to form a 5–8 membered heterocyclyl or heteroaryl ring;

each R⁵ is independently selected from —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂ (optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂, or R⁵ and an adjacent substituent taken together with their intervening atoms form said ring fused to Ring C;

V is —O—, —S—, —SO—, —SO₂—, —N(R⁶)SO₂—, —SO₂N(R⁶)—, —N(R⁶)—, —CO—, —CO₂—, —N(R⁶)CO—, —N(R⁶)C(O)O—, —N(R⁶)CON(R⁶)—, —N(R⁶)SO₂N(R⁶)—, —N(R⁶)N(R⁶)—, —C(O)N(R⁶)—, —OC(O)N(R⁶)—, —C(R⁶)₂O—, —C(R⁶)₂S—, —C(R⁶)₂SO—, —C(R⁶)₂SO₂—, —C(R⁶)₂SO₂N(R⁶)—, —C(R⁶)₂N(R⁶)—, —C(R⁶)₂N(R⁶)C(O)—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, or —C(R⁶)₂N(R⁶)CON(R⁶)—;

W is —C(R⁶)₂O—, —C(R⁶)₂S—, —C(R⁶)₂SO—, —C(R⁶)₂ SO₂—, —C(R⁶)₂SO₂N(R⁶)—, —C(R⁶)₂N(R⁶)—, —CO—, —CO₂—, —C(R⁶)OC(O)—, —C(R⁶)OC(O)N(R⁶)—, —C(R⁶)₂N(R⁶)CO—, —C(R⁶)₂N(R⁶)C(O)O—, —C(R⁶)=NN(R⁶)—, —C(R⁶)=N—O—, —C(R⁶)₂N(R⁶)N(R⁶)—, —C(R⁶)₂N(R⁶)SO₂N(R⁶)—, —C(R⁶)₂N(R⁶)CON(R⁶)—, or —CON(R⁶)—;

each R⁶ is independently selected from hydrogen, an optionally substituted C₁₋₄ aliphatic group, or two R⁶ groups on the same nitrogen atom are taken together with the nitrogen atom to form a 5–6 membered heterocyclyl or heteroaryl ring;

each R⁷ is independently selected from hydrogen or an optionally substituted C₁₋₆ aliphatic group, or two R⁷ on the same nitrogen are taken together with the nitrogen to form a 5–8 membered heterocyclyl or heteroaryl ring; and each R⁸ is independently selected from an optionally substituted C₁₋₄ aliphatic group, —OR⁶, —SR⁶, —COR⁶, —SO₂R⁶, —N(R⁶)₂, —N(R⁶)N(R⁶)₂, —CN, —NO₂, —CON(R⁶)₂, or —CO₂R⁶.

Compounds of formula X are structurally similar to compounds of formula II except for the replacement of the pyrazole ring moiety by the triazole ring moiety. Preferred R², Rˣ, Rʸ and Ring C groups of formula X are as described above for the formula II compounds. Preferred formula X compounds have one or more, and more preferably all, of the features selected from the group consisting of:

(a) Ring C is a phenyl or pyridinyl ring, optionally substituted by —R⁵, wherein when Ring C and two adjacent substituents thereon form a bicyclic ring system, the bicyclic ring system is selected from a naphthyl, quinolinyl or isoquinolinyl ring;

(b) Rˣ is hydrogen or C₁₋₄ aliphatic and Rʸ is T-R³, or Rˣ and Rʸ are taken together with their intervening atoms to form an optionally substituted 5–7 membered unsaturated or partially unsaturated ring having 0–2 ring nitrogens;

(c) R¹ is -halo, an optionally substituted C₁₋₆ aliphatic group, phenyl, —COR⁶, —OR⁶, —CN, —SO₂R⁶, —SO₂NH₂, —N(R⁶)₂, —CO₂R⁶, —CONH₂, —NHCOR⁶, —OC(O)NH₂, or —NHSO₂R⁶; and (d) R² is hydrogen or a substituted or unsubstituted group selected from aryl, heteroaryl, or a C₁₋₆ aliphatic group.

More preferred compounds of formula X have one or more, and more preferably all, of the features selected from the group consisting of:

(a) Ring C is a phenyl or pyridinyl ring, optionally substituted by —R⁵, wherein when Ring C and two adjacent substituents thereon form a bicyclic ring system, the bicyclic ring system is a naphthyl ring;

(b) Rˣ is hydrogen or methyl and Rʸ is —R, N(R⁴)₂, or —OR, or Rˣ and Rʸ are taken together with their intervening atoms to form a benzo ring or a 5–7 membered carbocyclo ring, wherein said ring formed by Rˣ and Rʸ is optionally substituted with —R, halo, —OR, —C(=O)R, —CO₂R, —COCOR, —NO₂, —CN, —S(O)R, —SO₂R, —SR, —N(R⁴)₂, —CON(R⁴)₂, —SO₂N(R⁴)₂, —OC(=O)R, —N(R⁴)COR, —N(R⁴)CO₂ (optionally substituted C₁₋₆ aliphatic), —N(R⁴)N(R⁴)₂, —C=NN(R⁴)₂, —C=N—OR, —N(R⁴)CON(R⁴)₂, —N(R⁴)SO₂N(R⁴)₂, —N(R⁴)SO₂R, or —OC(=O)N(R⁴)₂;

(c) R¹ is -halo, a C₁₋₆ haloaliphatic group, a C₁₋₆ aliphatic group, phenyl, or —CN;

(d) R² is hydrogen or a substituted or unsubstituted group selected from aryl or a C₁₋₆ aliphatic group; and (e) each R⁵ is independently selected from -halo, —CN, —NO₂, —N(R⁴)₂, optionally substituted C₁₋₆ aliphatic group, —OR, —C(O)R, —CO₂R, —CONH(R⁴), —N(R⁴)COR, —SO₂N(R⁴)₂, or —N(R⁴)SO₂R.

Even more preferred compounds of formula X have one or more, and more preferably all, of the features selected from the group consisting of:

(a) Ring C is a phenyl or pyridinyl ring, optionally substituted by —R⁵, wherein when Ring C and two adjacent substituents thereon form a bicyclic ring system, the bicyclic ring system is a naphthyl ring;

(b) Rˣ is hydrogen or methyl and Rʸ is methyl, methoxymethyl, ethyl, cyclopropyl, isopropyl, t-butyl, alkyl- or an optionally substituted group selected from 2-pyridyl, 4-pyridyl, piperidinyl, or phenyl, or Rˣ and Rʸ are taken together with their intervening atoms to form an optionally substituted benzo ring or a 6-membered carbocyclo ring;

(c) R¹ is -halo, a C₁₋₄ aliphatic group optionally substituted with halogen, or —CN;

(d) R² is hydrogen or a C₁₋₆ aliphatic group; and (e) each R⁵ is independently selected from —Cl, —F, —CN, —CF₃, —NH₂, —NH(C₁₋₄ aliphatic), —N(C₁₋₄ aliphatic)₂, —O(C₁₋₄ aliphatic), C₁₋₄ aliphatic, and —CO₂(C₁₋₄ aliphatic).

Another embodiment of this invention relates to compounds of formula XI:

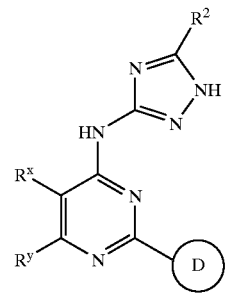

XI or a pharmaceutically acceptable derivative or prodrug thereof, wherein:

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —R⁵, and at any substitutable ring nitrogen by —R⁴, provided that when Ring D is a six-membered aryl or heteroaryl ring, —$R^5$ is hydrogen at each ortho carbon position of Ring D;

$R^x$ and $R^y$ are taken together with their intervening atoms to form a fused benzo ring or 5–8 membered carbocyclo ring, wherein any substitutable carbon on said fused ring formed by $R^x$ and $R^y$ is substituted by oxo or T-$R^3$;

T is a valence bond or a $C_{1-4}$ alkylidene chain;

$R^2$ is —R or -T-W—$R^6$;

$R^3$ is selected from —R, -halo, =O, —OR, —C(=O)R, —$CO_2$R, —COCOR, —$COCH_2$COR, —$NO_2$, —CN, —S(O)R, —$S(O)_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —COR$^7$, —$CO_2$ (optionally substituted $C_{1-6}$ aliphatic), —CON($R^7$)$_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$;

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O)O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —CO—, —$CO_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C(R)$_2$N($R^6$)N($R^6$)—, —C($R^6$)$_2$N($R^6$)$SO_2$N($R^6$)—, —C($R^6$)$_2$N($R^6$)CON($R^6$)—, or —CON($R^6$)—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring; and each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring.

Compounds of formula XI are structurally similar to compounds of formula III except for the replacement of the pyrazole ring moiety by the triazole ring moiety. Preferred $R^2$, $R^x$, $R^y$, and Ring D groups of formula XI are as described above for the formula III compounds. Preferred formula XI compounds have one or more, and more preferably all, of the features selected from the group consisting of:

(a) Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ and $R^y$ are taken together with their intervening atoms to form an optionally substituted benzo ring or 5–7 membered carbocyclo ring; and (c) $R^2$ is hydrogen or a substituted or unsubstituted group selected from aryl, heteroaryl, or a $C_{1-6}$ aliphatic group.

More preferred compounds of formula XI have one or more, and more preferably all, of the features selected from the group consisting of:

(a) Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ and $R^y$ are taken together with their intervening atoms to form a benzo ring or 5–7 membered carbocyclo ring, wherein said ring formed by $R^x$ and $R^y$ is optionally substituted with —R, oxo, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)$SO_2$R, or —OC(=O)N($R^4$)$_2$;

(c) $R^2$ is hydrogen or a substituted or unsubstituted group selected from aryl or a $C_{1-6}$ aliphatic group; and (d) each $R^5$ is independently selected from halo, oxo, CN, $NO_2$, —N($R^4$)$_2$, —$CO_2$R, —CONH($R^4$), —N($R^4$)COR, —$SO_2$N($R^4$)$_2$, —N($R^4$)$SO_2$R, —SR, —OR, —C(O)R, or a substituted or unsubstituted group selected from 5–6 membered heterocyclyl, $C_{6-10}$ aryl, or $C_{1-6}$ aliphatic.

Even more preferred compounds of formula XI have one or more, and more preferably all, of the features selected from the group consisting of:

(a) $R^x$ and $R^y$ are taken together with their intervening atoms to form a benzo ring or 6-membered carbocyclo ring, wherein said ring formed by $R^x$ and $R^y$ is optionally substituted with halo, CN, oxo, $C_{1-6}$ alkyl, $C_{1-6}$ alkoxy, ($C_{1-6}$ alkyl)carbonyl, ($C_{1-6}$ alkyl)sulfonyl, mono- or dialkylamino, mono- or dialkylaminocarbonyl, mono- or dialkylaminocarbonyloxy, or 5–6 membered heteroaryl;

(b) each $R^5$ is independently selected from -halo, —CN, -oxo, —SR, —OR, —N($R^4$)$_2$, —C(O)R, or a substituted or unsubstituted group selected from 5–6 membered heterocyclyl, $C_{6-10}$ aryl, or $C_{1-6}$ aliphatic; and (c) $R^2$ is hydrogen or a $C_{1-6}$ aliphatic group.

Another embodiment of this invention relates to compounds of formula XII:

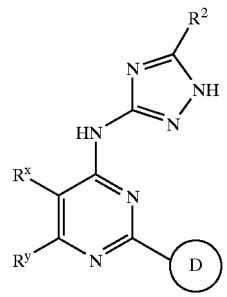

XII or a pharmaceutically acceptable derivative or prodrug thereof, wherein:

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —R$^5$, and at any substitutable ring nitrogen by —R$^4$, provided that when Ring D is a six-membered aryl or heteroaryl ring, —R$^5$ is hydrogen at each ortho carbon position of Ring D;

R$^x$ and R$^y$ are independently selected from T-R$^3$, or R$^x$ and R$^y$ are taken together with their intervening atoms to form a fused, unsaturated or partially unsaturated, 5–8 membered ring having 1–3 ring heteroatoms selected from oxygen, sulfur, or nitrogen, wherein any substitutable carbon on said fused ring is optionally and independently substituted by T-R$^3$, and any substitutable nitrogen on said ring is substituted by R$^4$;

T is a valence bond or a $C_{1-4}$ alkylidene chain;

R$^2$ is —R or -T-W—R$^6$;

R$^3$ is selected from —R, -halo, =O, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each R$^4$ is independently selected from —R$^7$, —COR$^7$, —CO$_2$ (optionally substituted $C_{1-6}$ aliphatic), —CON(R$^7$)$_2$, or —SO$_2$R$^7$, or two R$^4$ on the same nitrogen are taken together to form a 5–8 membered heterocyclyl or heteroaryl ring;

each R$^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each R$^6$ is independently selected from hydrogen or an optionally substituted $C_{1-4}$ aliphatic group, or two R$^6$ groups on the same nitrogen atom are taken together with the nitrogen atom to form a 5–6 membered heterocyclyl or heteroaryl ring; and each R$^7$ is independently selected from hydrogen or an optionally substituted $C_{1-6}$ aliphatic group, or two R$^7$ on the same nitrogen are taken together with the nitrogen to form a 5–8 membered heterocyclyl ring or heteroaryl.

Compounds of formula XII are structurally similar to compounds of formula IV except for the replacement of the pyrazole ring moiety by the triazole ring moiety. Preferred R$^2$, R$^x$, R$^y$, and Ring D groups of formula XII are as described above for the formula IV compounds. Preferred formula XII compounds have one or more, and more preferably all, of the features selected from the group consisting of:

(a) Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) R$^x$ is hydrogen or $C_{1-4}$ aliphatic and R$^y$ is T-R$^3$, or R$^x$ and R$^y$ are taken together with their intervening atoms to form an optionally substituted 5–7 membered unsaturated or partially unsaturated ring having 1–2 ring heteroatoms; and (c) R$^2$ is hydrogen or a substituted or unsubstituted group selected from aryl, heteroaryl, or a $C_{1-6}$ aliphatic group.

More preferred compounds of formula XII have one or more, and more preferably all, of the features selected from the group consisting of:

(a) Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) R$^x$ is hydrogen or methyl and R$^y$ is —R, N(R$^4$)$_2$, or —OR, or R$^x$ and R$^y$ are taken together with their intervening atoms to form a 5–7 membered unsaturated or partially unsaturated ring having 1–2 ring nitrogens, wherein said ring is optionally substituted with —R, halo, oxo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

(c) R$^2$ is hydrogen or a substituted or unsubstituted group selected from aryl or a $C_{1-6}$ aliphatic group; and (d) each R$^5$ is independently selected from halo, oxo, CN, NO$_2$, —N(R$^4$)$_2$, —CO$_2$R, —CONH(R$^4$), —N(R$^4$)COR, —SO$_2$N(R$^4$)$_2$, —N(R$^4$)SO$_2$R, —SR, —OR, —C(O)R, or a substituted or unsubstituted group selected from 5–6 membered heterocyclyl, $C_{6-10}$ aryl, or $C_{1-6}$ aliphatic.

Even more preferred compounds of formula XII have one or more, and more preferably all, of the features selected from the group consisting of:

(a) $R^x$ and $R^y$ are taken together with their intervening atoms to form a 6-membered unsaturated or partially unsaturated ring having 1–2 ring nitrogens, optionally substituted with halo, CN, oxo, $C_{1-6}$ alkyl, $C_{1-6}$ alkoxy, ($C_{1-6}$ alkyl) carbonyl, ($C_{1-6}$ alkyl)sulfonyl, mono- or dialkylamino, mono- or dialkylaminocarbonyl, mono- or dialkylaminocarbonyloxy, or 5–6 membered heteroaryl;

(b) each $R^5$ is independently selected from -halo, —CN, -oxo, —SR, —OR, —N(R$^4$)$_2$, —C(O)R, or a substituted or unsubstituted group selected from 5–6 membered heterocyclyl, $C_{6-10}$ aryl, or $C_{1-6}$ aliphatic; and (c) $R^2$ is hydrogen or a $C_{1-6}$ aliphatic group.

Another embodiment of this invention relates to compounds of formula XIII:

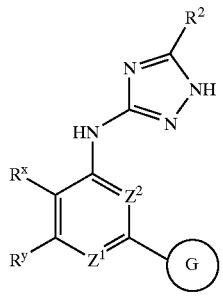

XIII or a pharmaceutically acceptable derivative or prodrug thereof, wherein:

$Z^1$ is nitrogen, $CR^a$, or CH, and $Z^2$ is nitrogen or CH; provided that one of $Z^1$ and $Z^2$ is nitrogen;

G is Ring C or Ring D;

Ring C is selected from a phenyl, pyridinyl, pyrimidinyl, pyridazinyl, pyrazinyl, or 1,2,4-triazinyl ring, wherein said Ring C has one or two ortho substituents independently selected from —R$^1$, any substitutable non-ortho carbon position on Ring C is independently substituted by —R$^5$, and two adjacent substituents on Ring C are optionally taken together with their intervening atoms to form a fused, unsaturated or partially unsaturated, 5–6 membered ring having 0–3 heteroatoms selected from oxygen, sulfur or nitrogen, said fused ring being optionally substituted by halo; oxo, or —R$^8$;

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is substituted at any substitutable ring carbon by oxo or —R$^5$, and at any substitutable ring nitrogen by —R$^4$, provided that when Ring D is a six-membered aryl or heteroaryl ring, —R$^5$ is hydrogen at each ortho carbon position of Ring D;

$R^1$ is selected from -halo, —CN, —NO$_2$, T-V—R$^6$, phenyl, 5–6 membered heteroaryl ring, 5–6 membered heterocyclyl ring, or $C_{1-6}$ aliphatic group, said phenyl, heteroaryl, and heterocyclyl rings each optionally substituted by up to three groups independently selected from halo, oxo, or —R$^8$, said $C_{1-6}$ aliphatic group optionally substituted with halo, cyano, nitro, or oxygen, or $R^1$ and an adjacent substituent taken together with their intervening atoms form said ring fused to Ring C;

$R^x$ and $R^y$ are independently selected from T-R$^3$, or $R^x$ and $R^y$ are taken together with their intervening atoms to form a fused, unsaturated or partially unsaturated, 5–8 membered ring having 0–3 ring heteroatoms selected from oxygen, sulfur, or nitrogen, wherein any substitutable carbon on said fused ring formed by $R^x$ and $R^y$ is substituted by oxo or T-R$^3$, and any substitutable nitrogen on said ring formed by $R^x$ and $R^y$ is substituted by $R^4$;

T is a valence bond or a $C_{1-4}$ alkylidene chain;

$R^2$ is —R or -T-W—R$^6$;

$R^3$ is selected from —R, -halo, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$(optionally substituted $C_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —R$^7$, —COR$^7$, —CO$_2$ (optionally substituted $C_{1-6}$ aliphatic), —CON(R$^7$)$_2$, or —SO$_2$R$^7$, or two $R^4$ on the same nitrogen are taken together to form a 5–8 membered heterocyclyl or heteroaryl ring;

each $R^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$, or $R^5$ and an adjacent substituent taken together with their intervening atoms form said ring fused to Ring C;

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)C(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each $R^6$ is independently selected from hydrogen, an optionally substituted $C_{1-4}$ aliphatic group, or two $R^6$ groups on the same nitrogen atom are taken together with the nitrogen atom to form a 5–6 membered heterocyclyl or heteroaryl ring;

each $R^7$ is independently selected from hydrogen or an optionally substituted $C_{1-6}$ aliphatic group, or two $R^7$ on the same nitrogen are taken together with the nitrogen to form a 5–8 membered heterocyclyl or heteroaryl ring;

each $R^8$ is independently selected from an optionally substituted $C_{1-4}$ aliphatic group, —OR$^6$, —SR$^6$, —COR$^6$, —SO$_2$R$^6$, —N(R$^6$)$_2$, —N(R$^6$)N(R$^6$)$_2$, —CN, —NO$_2$, —CON (R$^6$)$_2$, or —CO$_2$R$^6$; and $R^a$ is selected from halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)

$SO_2R$, $-OC(=O)N(R^4)_2$, or an optionally substituted group selected from $C_{1-6}$ aliphatic, $C_{6-10}$ aryl, a heteroaryl ring having 5–10 ring atoms, or a heterocyclyl ring having 5–10 ring atoms.

Compounds of formula XIII may be represented by specifying $Z^1$ and $Z^2$ as shown below:

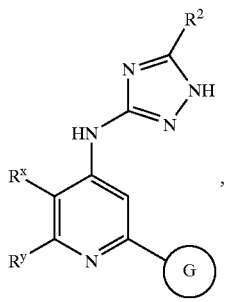

XIIIa

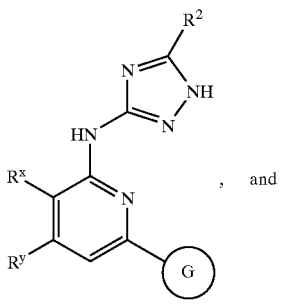

XIIIb

, and

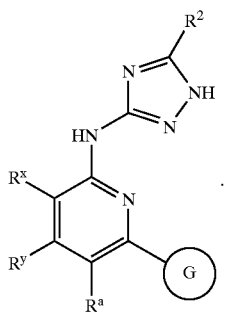

XIIIc

Compounds of formula XIII are structurally similar to compounds of formula V except for the replacement of the pyrazole ring moiety by the triazole ring moiety. Preferred $R^2$, $R^x$, $R^y$, $R^a$, and Ring G groups of formula XIII are as described above for the formula V compounds. Preferred formula XIII compounds have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is selected from a naphthyl, quinolinyl or isoquinolinyl ring, and $R^1$ is -halo, an optionally substituted $C_{1-6}$ aliphatic group, phenyl, —$COR^6$, —$OR^6$, —CN, —$SO_2R^6$, —$SO_2NH_2$, —$N(R^6)_2$, —$CO_2R^6$, —$CONH_2$, —$NHCOR^6$, —$OC(O)NH_2$, or —$NHSO_2R^6$; or Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ is hydrogen or $C_{1-4}$ aliphatic and $R^y$ is T-$R^3$, or $R^x$ and $R^y$ are taken together with their intervening atoms to form an optionally substituted 5–7 membered unsaturated or partially unsaturated ring having 0–2 ring nitrogens; and (c) $R^2$ is hydrogen or a substituted or unsubstituted group selected from aryl, heteroaryl, or a $C_{1-6}$ aliphatic group.

More preferred compounds of formula XIII have one or more, and more preferably all, of the features selected from the group consisting of:

(a) Ring C is a phenyl or pyridinyl ring, optionally substituted by —$R^5$, wherein when Ring C and two adjacent substituents thereon form a bicyclic ring system, the bicyclic ring system is a naphthyl ring, and $R^1$ is -halo, a $C_{1-6}$ haloaliphatic group, a $C_{1-6}$ aliphatic group, phenyl, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ is hydrogen or methyl and $R^y$ is —R, $N(R^4)_2$, or —OR, or $R^x$ and $R^y$ are taken together with their intervening atoms to form a benzo ring or a 5–7 membered carbocyclo ring, wherein said ring formed by $R^x$ and $R^y$ is optionally substituted with —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —$OC(=O)R$, —$N(R^4)COR$, —$N(R^4)CO_2$(optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —N $(R^4)SO_2R$, or —$OC(=O)N(R^4)_2$;

(c) $R^2$ is hydrogen or a substituted or unsubstituted group selected from aryl, or a $C_{1-6}$ aliphatic group; and (d) each $R^5$ is independently selected from -halo, —CN, —$NO_2$, —$N(R^4)_2$, optionally substituted $C_{1-6}$ aliphatic group, —OR, —C(O)R, —$CO_2R$, —$CONH(R^4)$, —$N(R^4)COR$, —$SO_2N(R^4)_2$, or —$N(R^4)SO_2R$, and, when Ring G is Ring D, Ring D is substituted by oxo or $R^5$.

Even more preferred compounds of formula XIII have one or more, and more preferably all, of the features selected from the group consisting of:

(a) $R^x$ is hydrogen or methyl and $R^y$ is methyl, methoxymethyl, ethyl, cyclopropyl, isopropyl, t-butyl, alkyl- or an optionally substituted group selected from 2-pyridyl, 4-pyridyl, piperidinyl, or phenyl, or $R^x$ and $R^y$ are taken together with their intervening atoms to form a benzo ring or a 6-membered carbocyclo ring wherein said ring formed by $R^x$ and $R^y$ is optionally substituted with halo, CN, oxo, $C_{1-6}$ alkyl, $C_{1-6}$ alkoxy, ($C_{1-6}$ alkyl)carbonyl, ($C_{1-6}$ alkyl)sulfonyl, mono- or dialkylamino, mono- or dialkylaminocarbonyl, mono- or dialkylaminocarbonyloxy, or 5–6 membered heteroaryl;

(b) Ring C is a phenyl or pyridinyl ring, optionally substituted by —$R^5$, wherein when Ring C and two adjacent substituents thereon form a bicyclic ring system, the bicyclic ring system is a naphthyl ring, and $R^1$ is -halo, a $C_{1-4}$ aliphatic group optionally substituted with halogen, or —CN; or Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, isoquinolinyl, quinolinyl, or naphthyl;

(c) $R^2$ is hydrogen or a $C_{1-6}$ aliphatic group; and (d) each $R^5$ is independently selected from —Cl, —F, —CN, —$CF_3$, —$NH_2$, —$NH(C_{1-4}$ aliphatic), —$N(C_{1-4}$ aliphatic)$_2$, —$O(C_{1-4}$ aliphatic), $C_{1-4}$ aliphatic, and —$CO_2$ ($C_{1-4}$ aliphatic), and when Ring G is Ring D, Ring D is substituted by oxo or $R^5$.

Representative compounds of formula IX are shown below in Table 8.
TABLE 8
IX-1
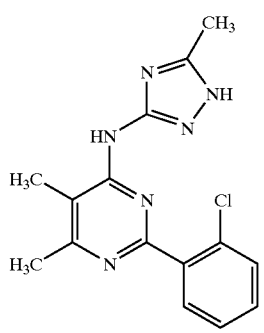
IX-2
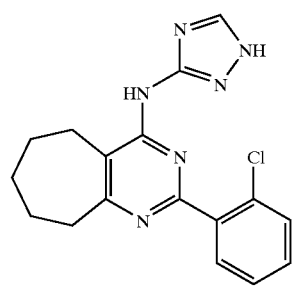
IX-3
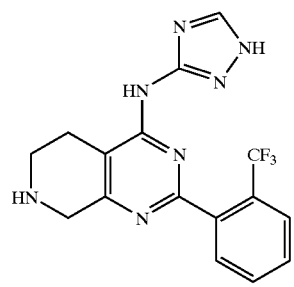
IX-4
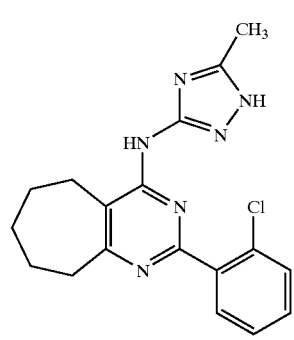
TABLE 8-continued
IX-5
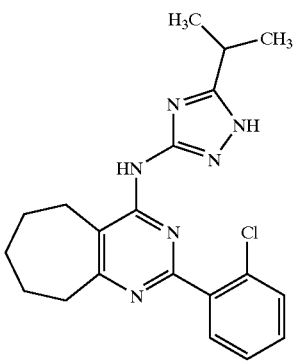
IX-6
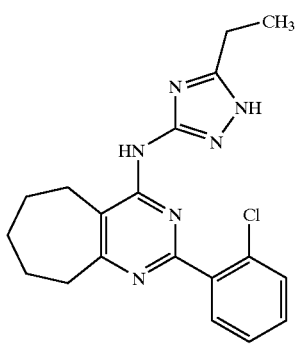
IX-7
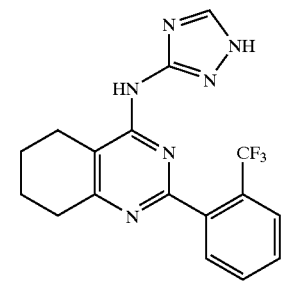
IX-8
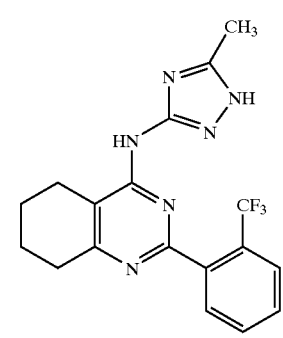

TABLE 8-continued
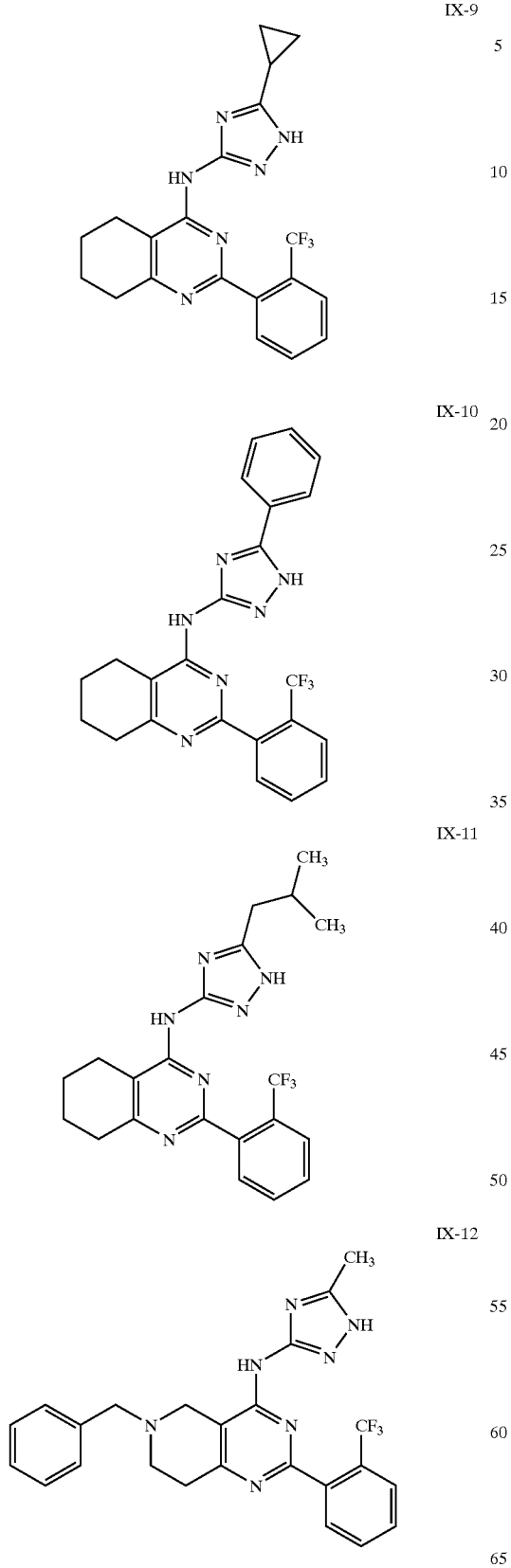
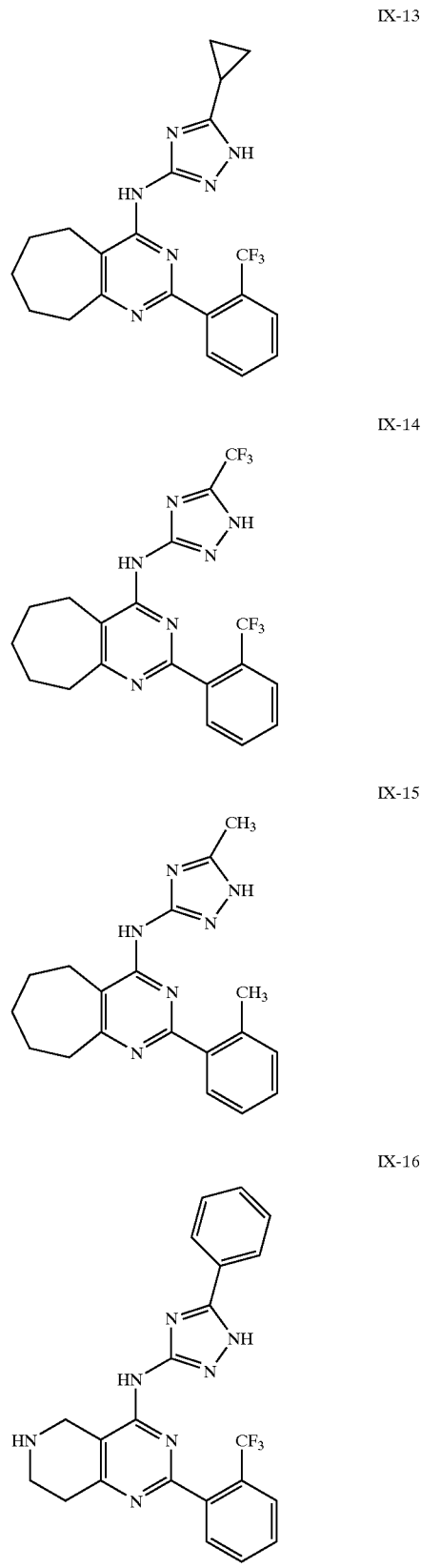

TABLE 8-continued
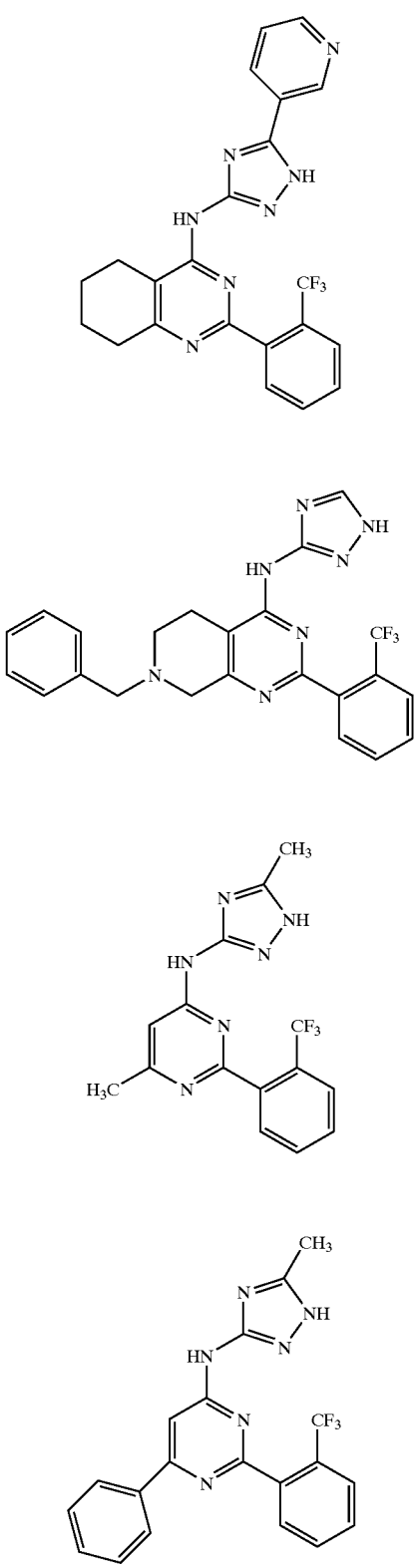
IX-17
IX-18
IX-19
IX-20
TABLE 8-continued
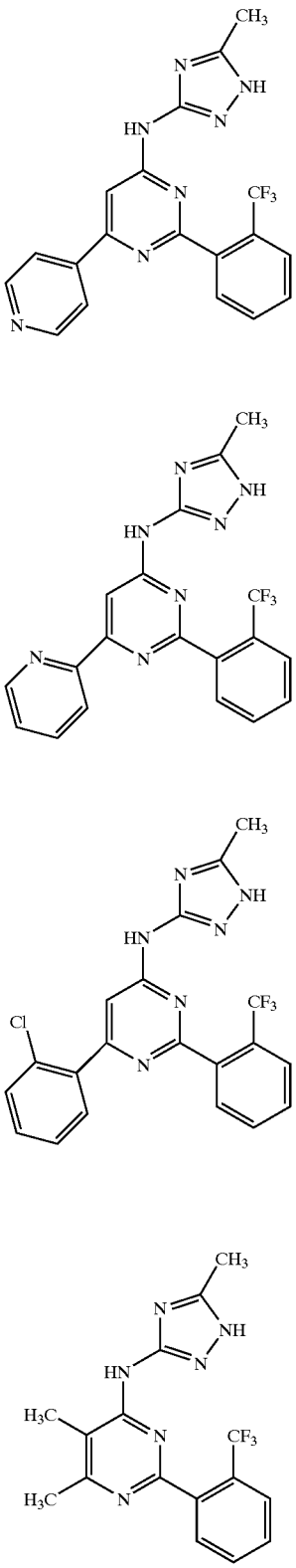
IX-21
IX-22
IX-23
IX-24

TABLE 8-continued

TABLE 8-continued
IX-33
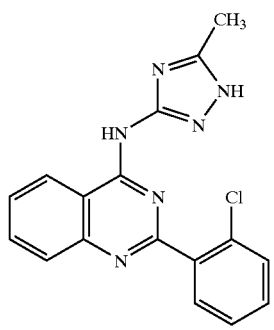
IX-34
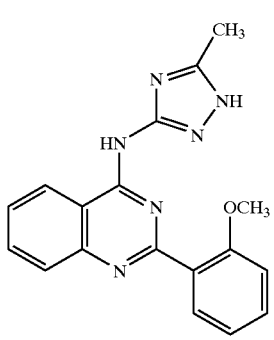
IX-35
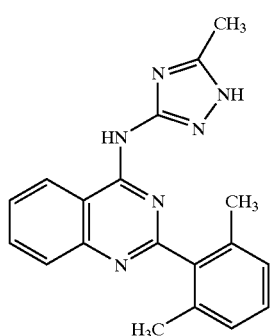
IX-36
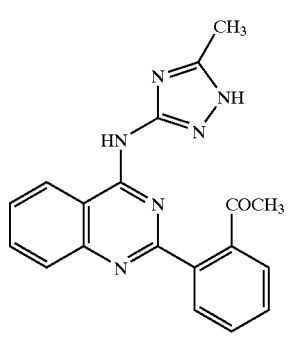
TABLE 8-continued
IX-37
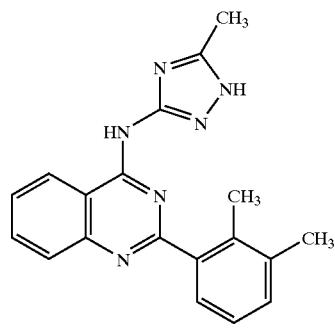
IX-38
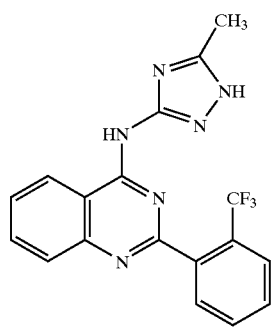
IX-39
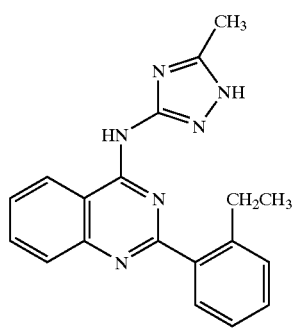
IX-40
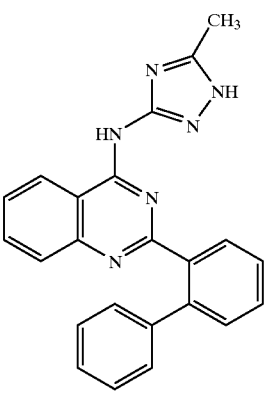

TABLE 8-continued
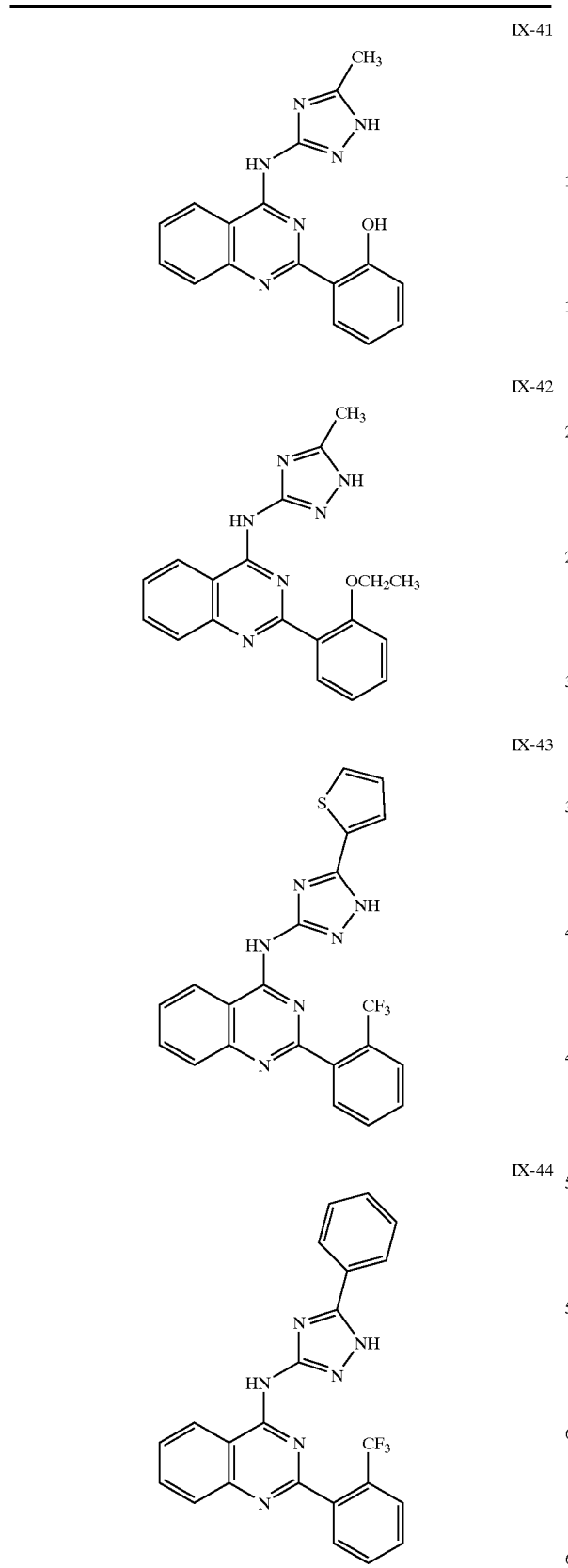
IX-41
IX-42
IX-43
IX-44
TABLE 8-continued
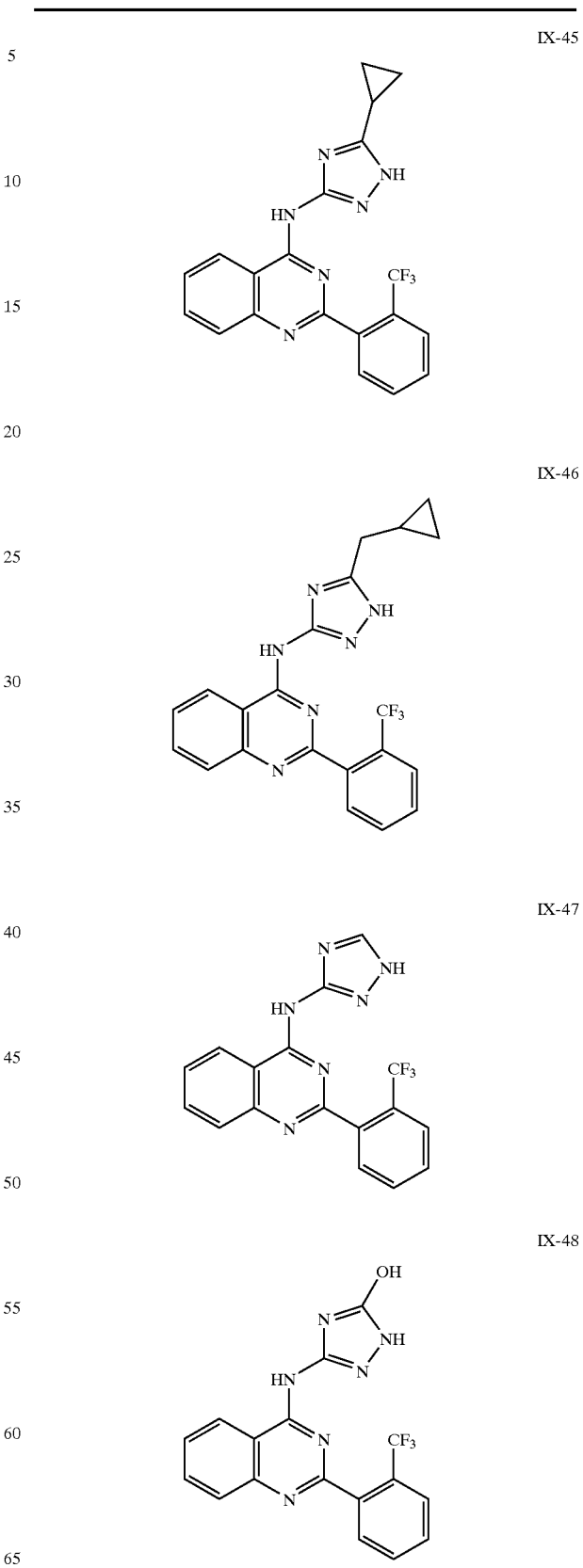
IX-45
IX-46
IX-47
IX-48

TABLE 8-continued
IX-49
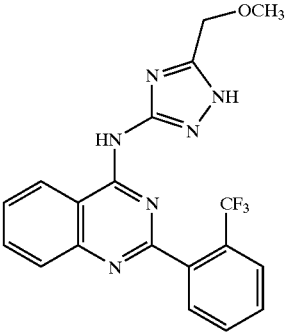
IX-50
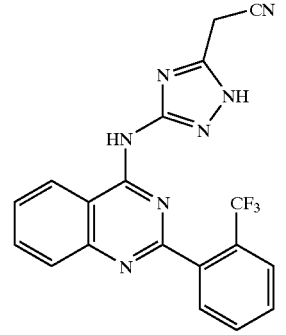
IX-51
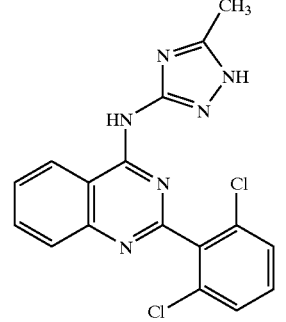
IX-52
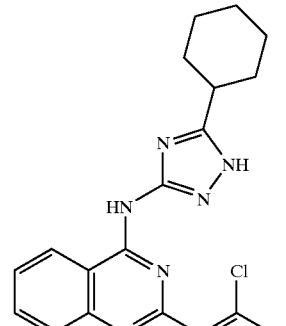
TABLE 8-continued
IX-53
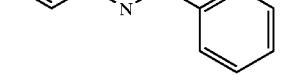
IX-54
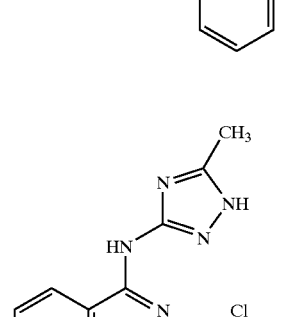
IX-55
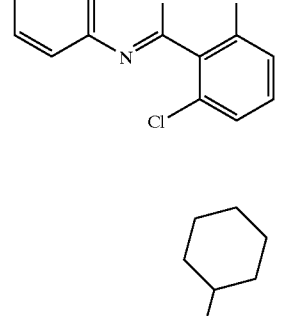
IX-56
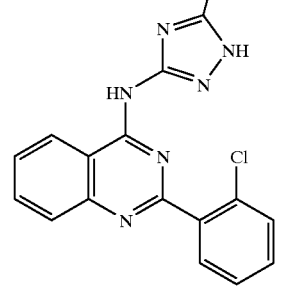

TABLE 8-continued
IX-57
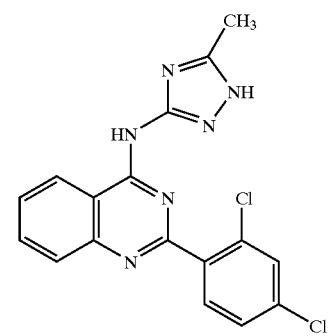
IX-58
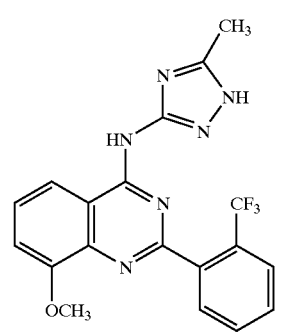
IX-59
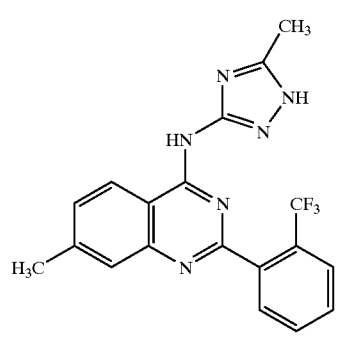
IX-60
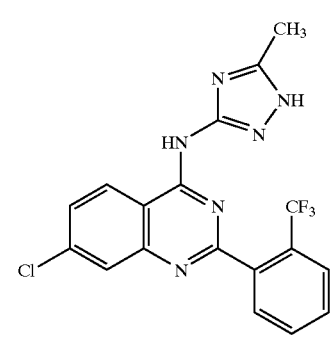
TABLE 8-continued
IX-61
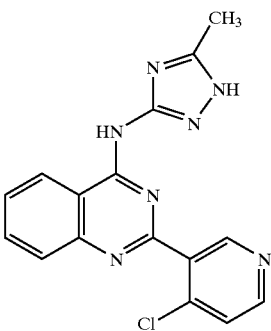
IX-62
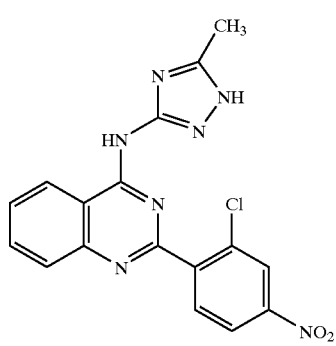
IX-63
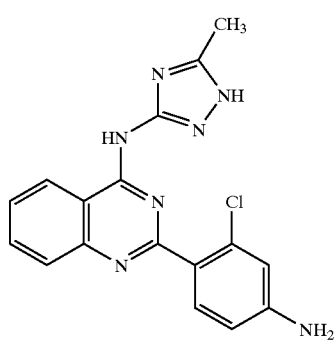
IX-64
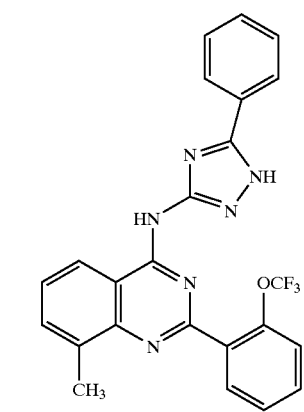

TABLE 8-continued

IX-65
IX-66
IX-67
IX-68
IX-69
IX-70
IX-71
IX-72

TABLE 8-continued
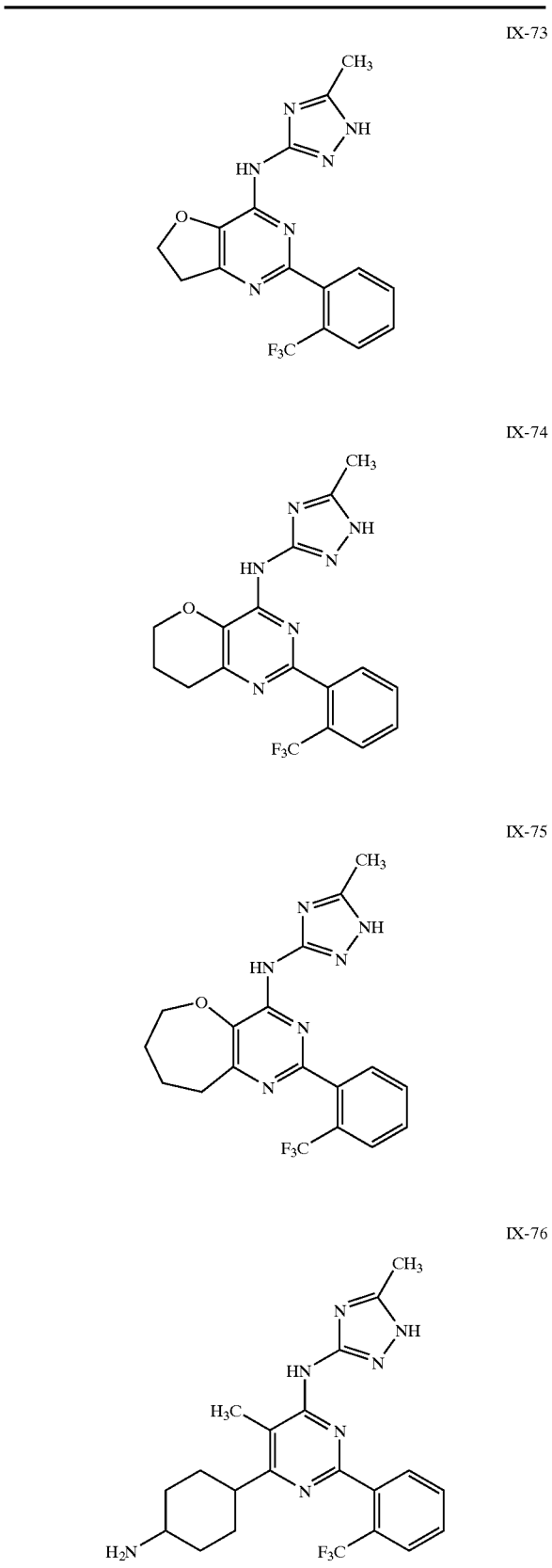
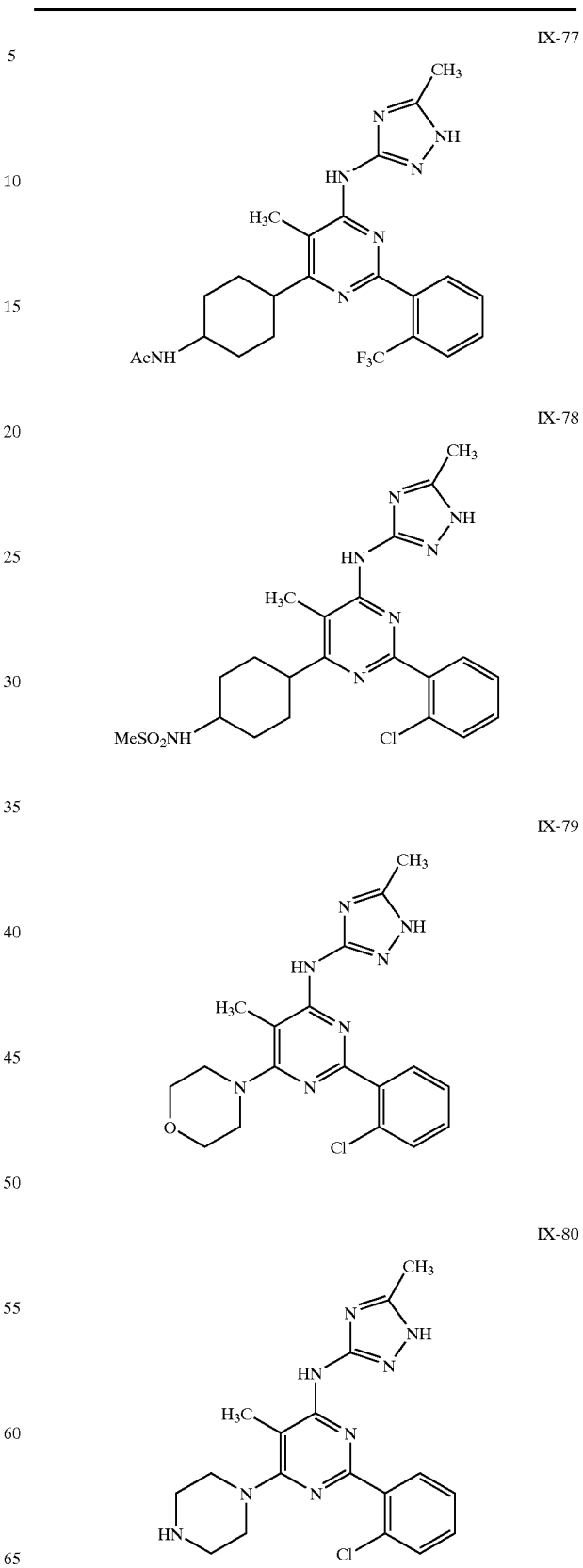

TABLE 8-continued
IX-81
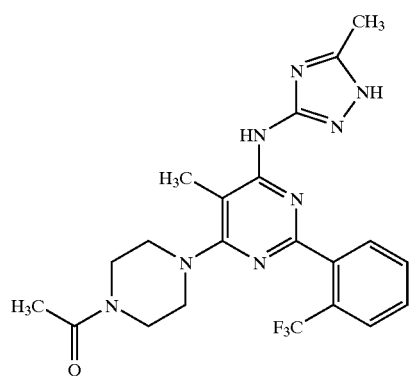
IX-82
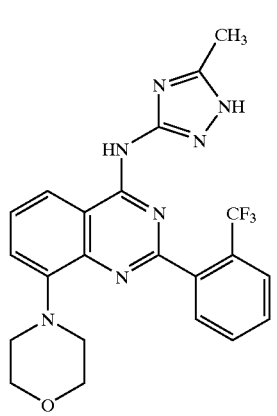
IX-83
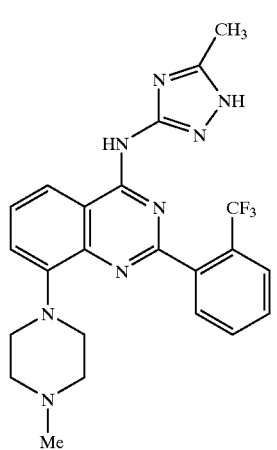
IX-84
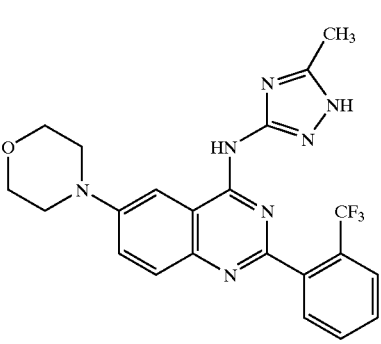
TABLE 8-continued
IX-85
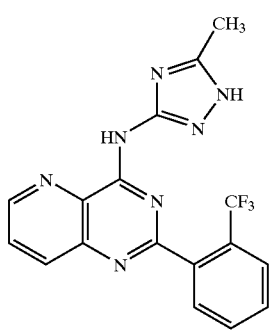
IX-86
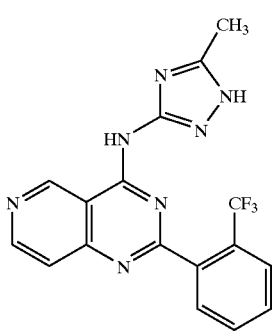
IX-87
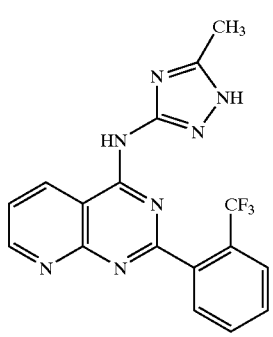
IX-88
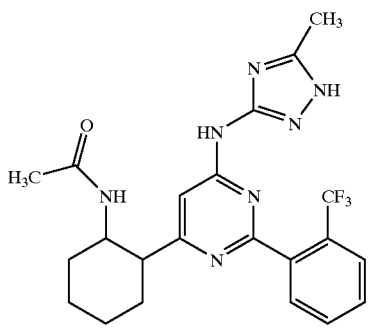

TABLE 8-continued
IX-89
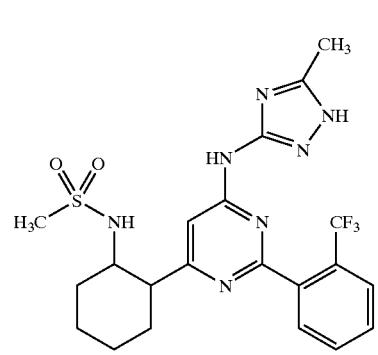
IX-90
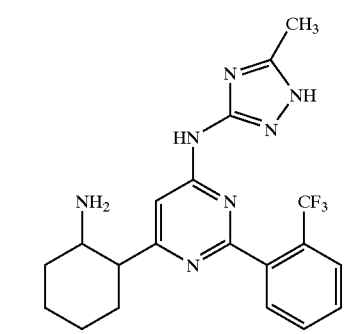
IX-91
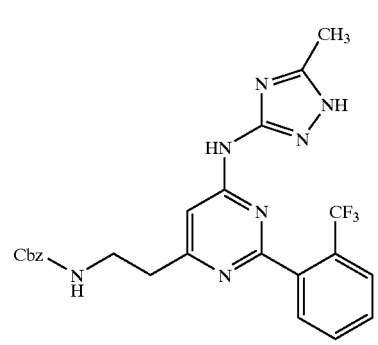
IX-92
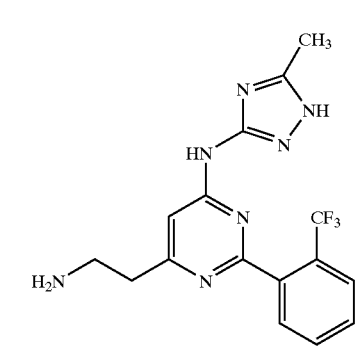
TABLE 8-continued
IX-93
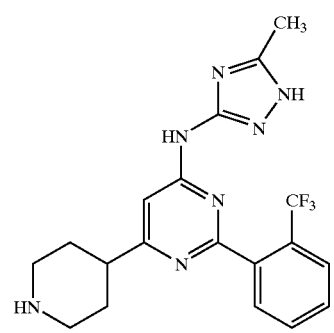
IX-94
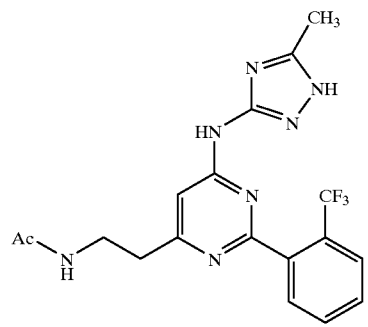
IX-95
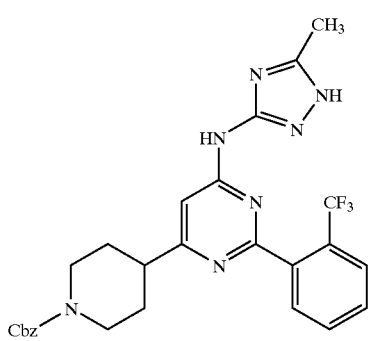
IX-96
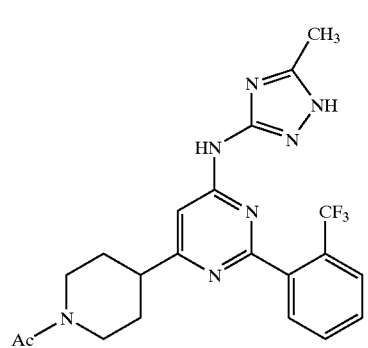

TABLE 8-continued
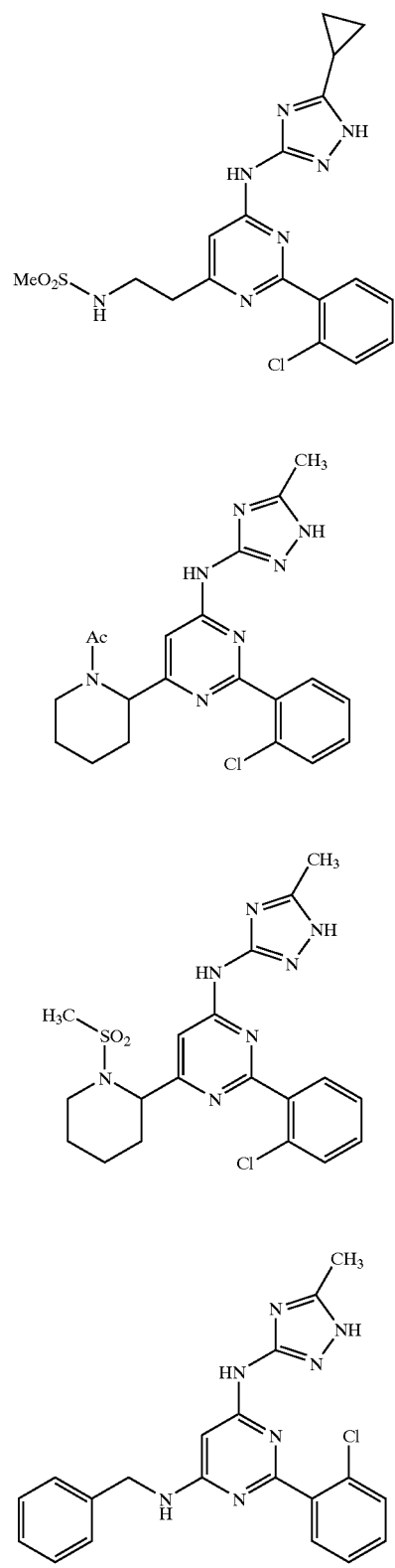
IX-97
IX-98
IX-99
IX-100
TABLE 8-continued
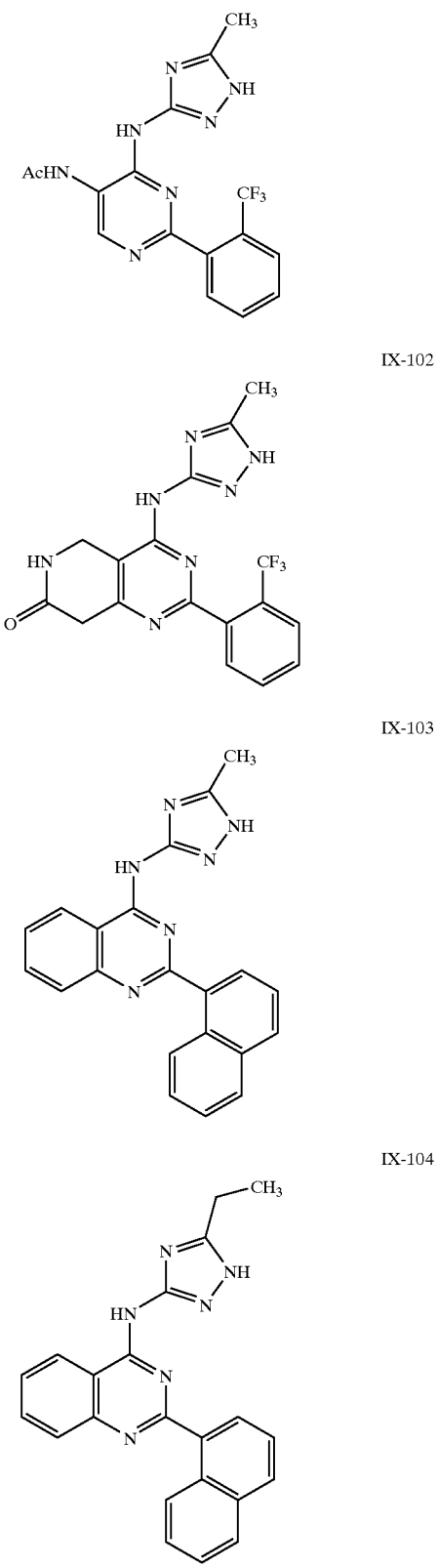
IX-101
IX-102
IX-103
IX-104

TABLE 8-continued
IX-105
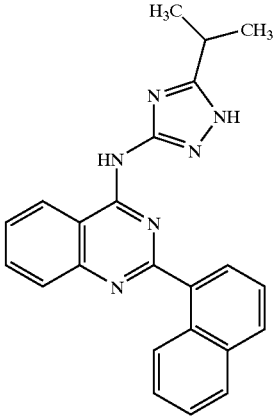
IX-106
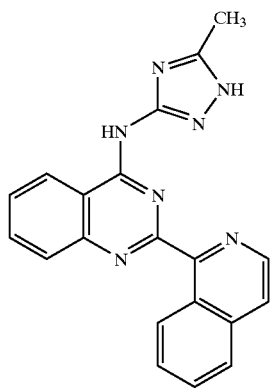
IX-107
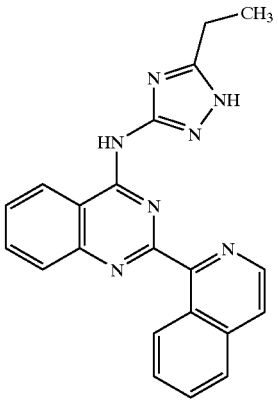
TABLE 8-continued
IX-108
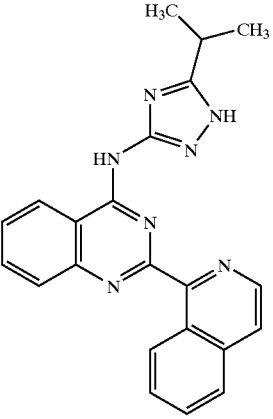
IX-109
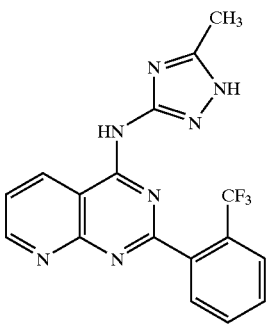
IX-110
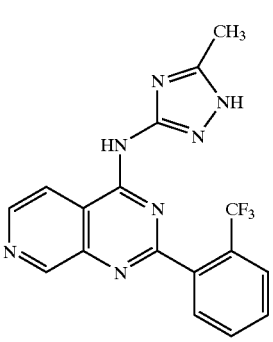
IX-111
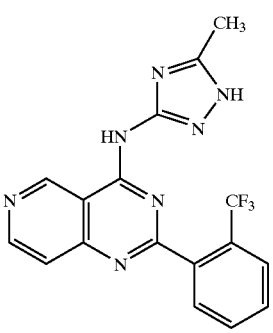

TABLE 8-continued
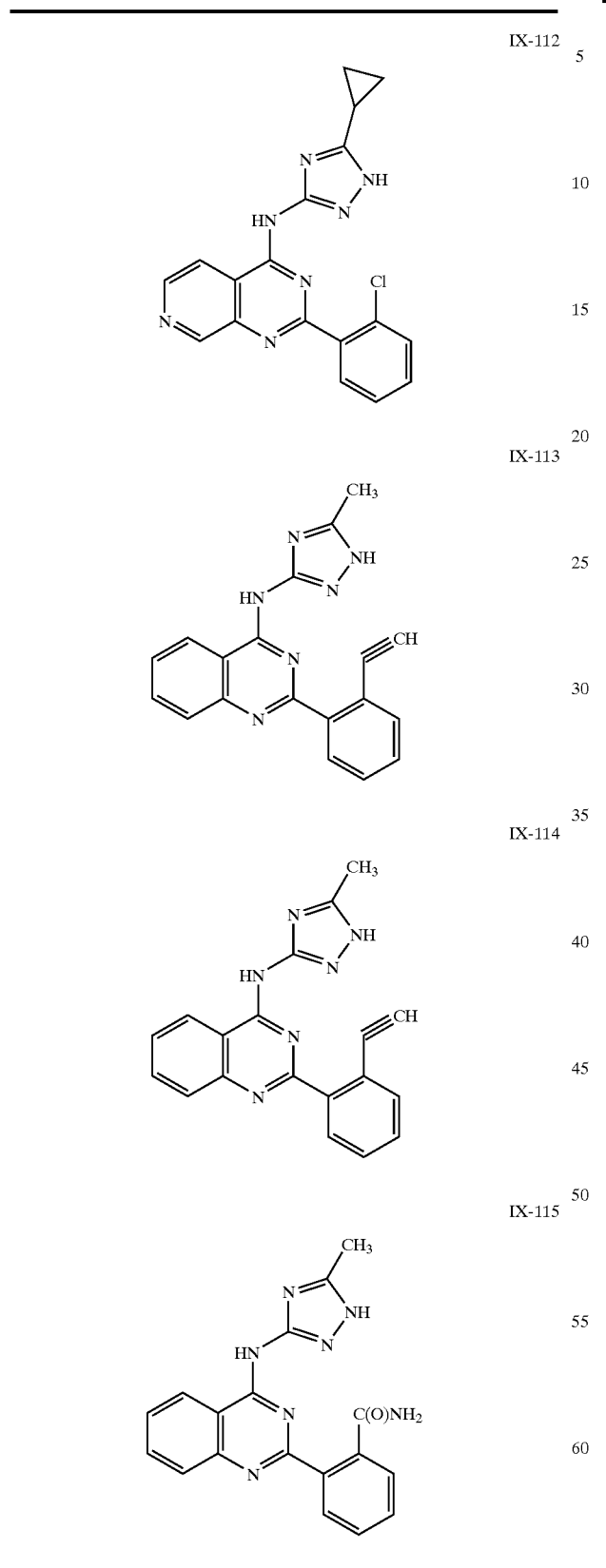
IX-112
IX-113
IX-114
IX-115
TABLE 8-continued
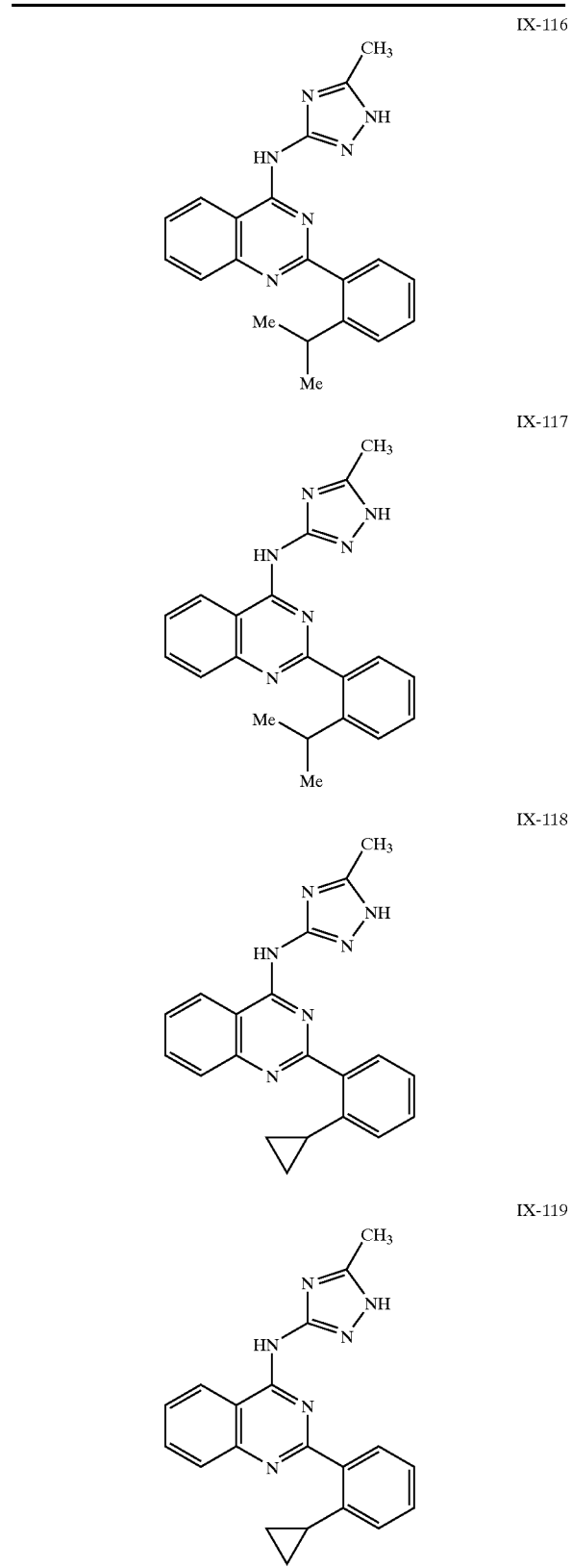
IX-116
IX-117
IX-118
IX-119

TABLE 8-continued
IX-120
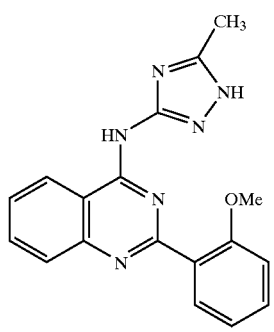
IX-121
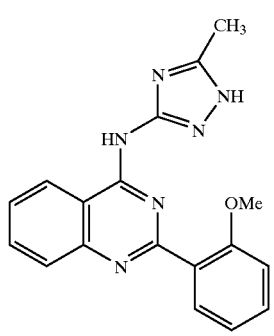
IX-122
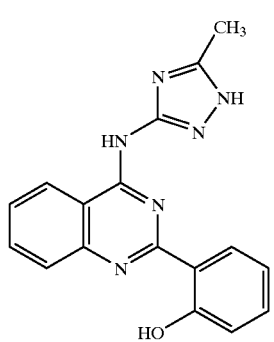
IX-123
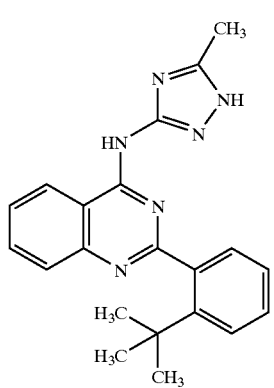
TABLE 8-continued
IX-124
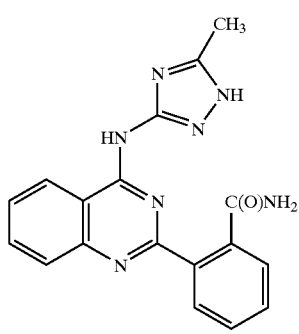
IX-125
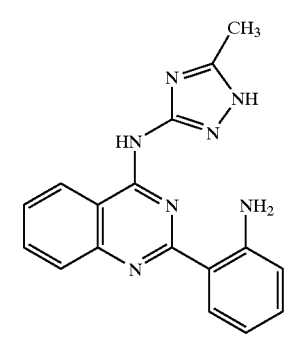
IX-126
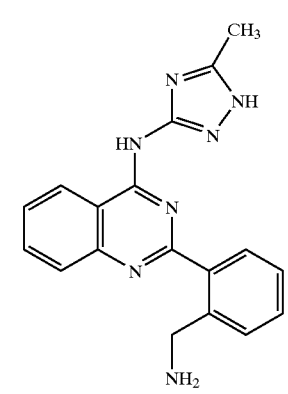
IX-127
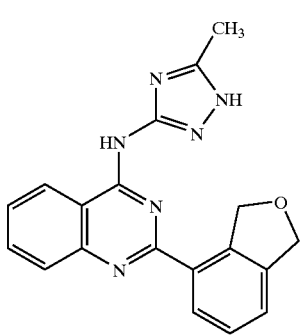

TABLE 8-continued
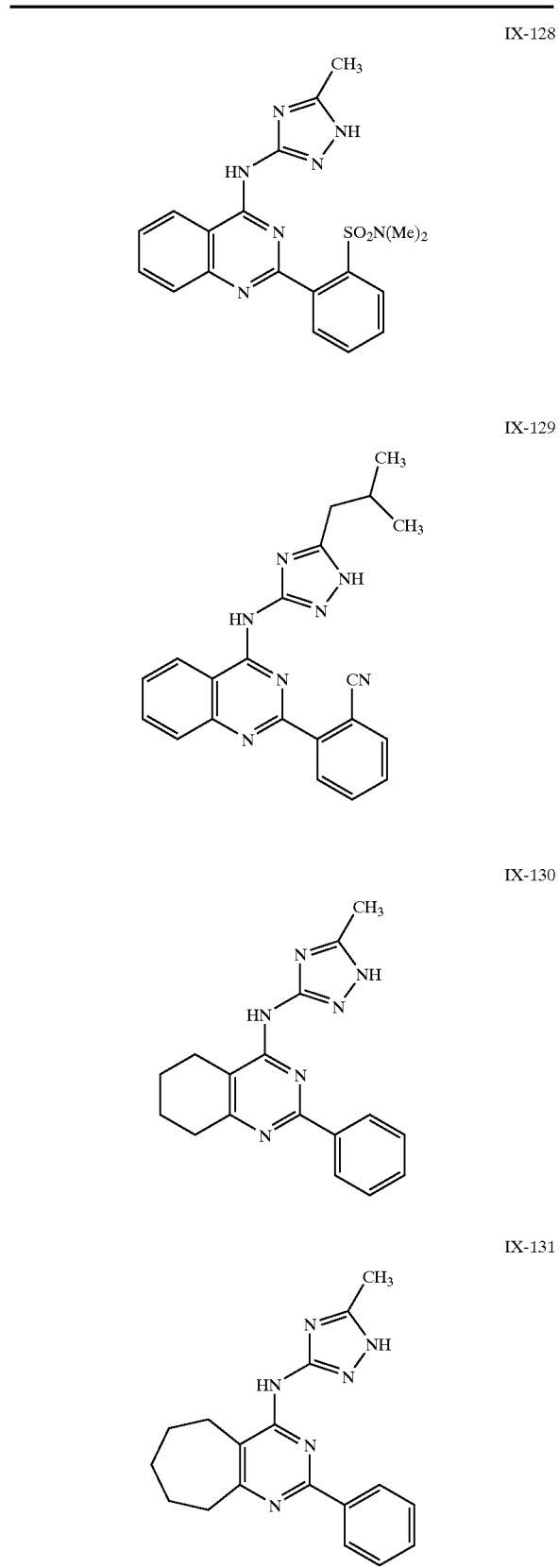
IX-128
IX-129
IX-130
IX-131
TABLE 8-continued
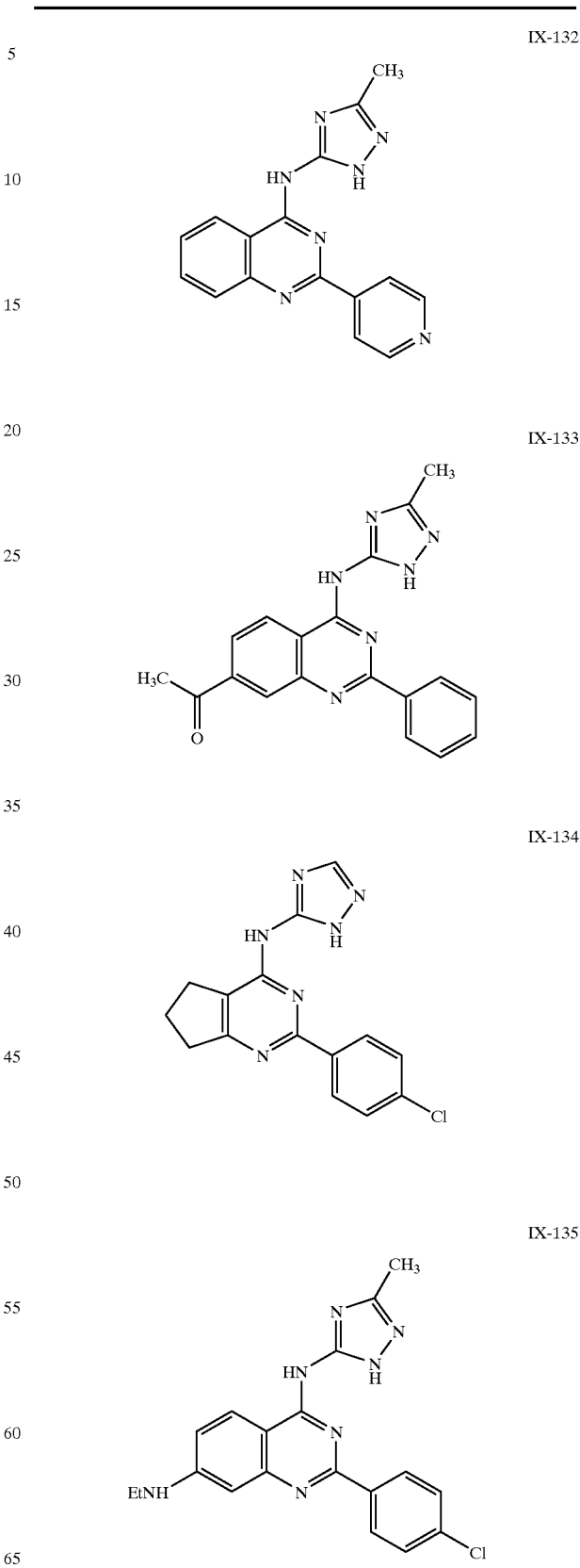
IX-132
IX-133
IX-134
IX-135

TABLE 8-continued
IX-136
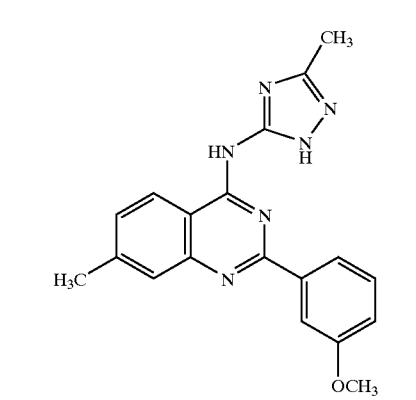
IX-137
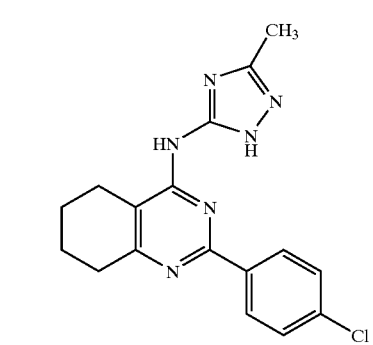
IX-138
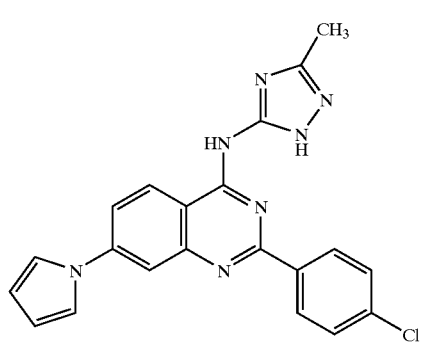
IX-139
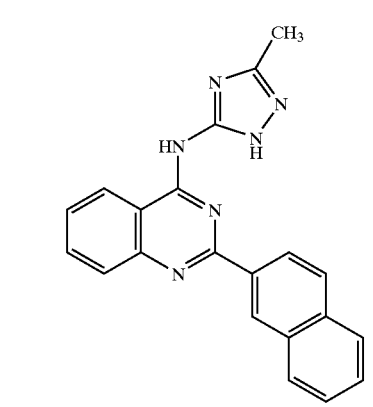
TABLE 8-continued
IX-140
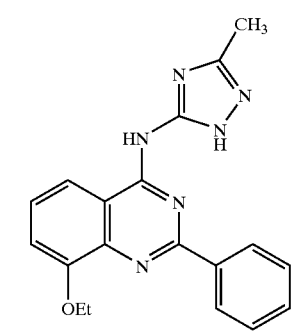
IX-141
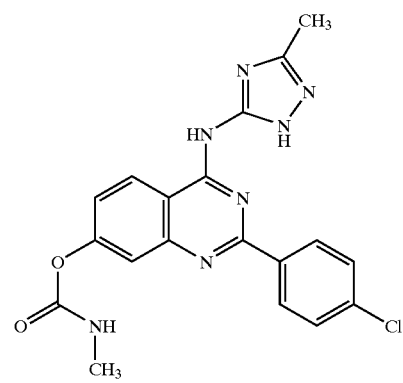
IX-142
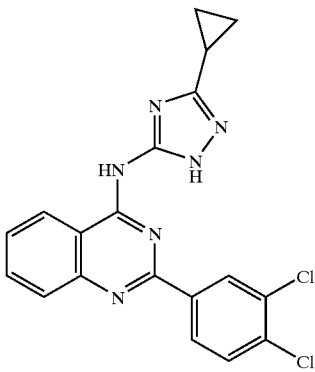
IX-143
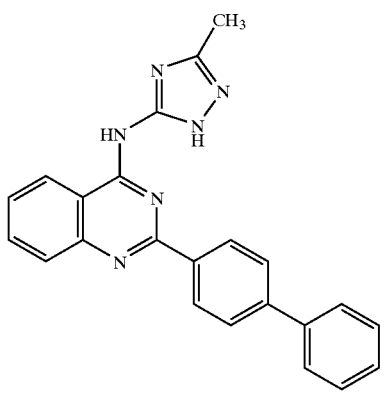

TABLE 8-continued
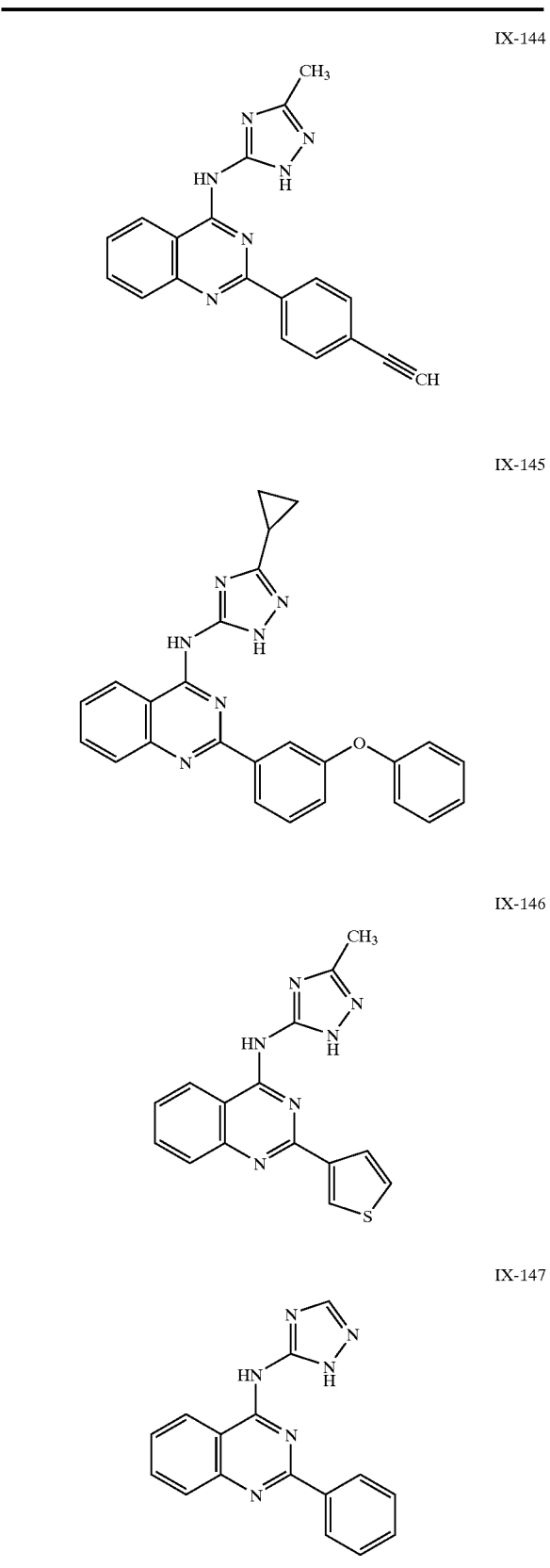
IX-144
IX-145
IX-146
IX-147
TABLE 8-continued
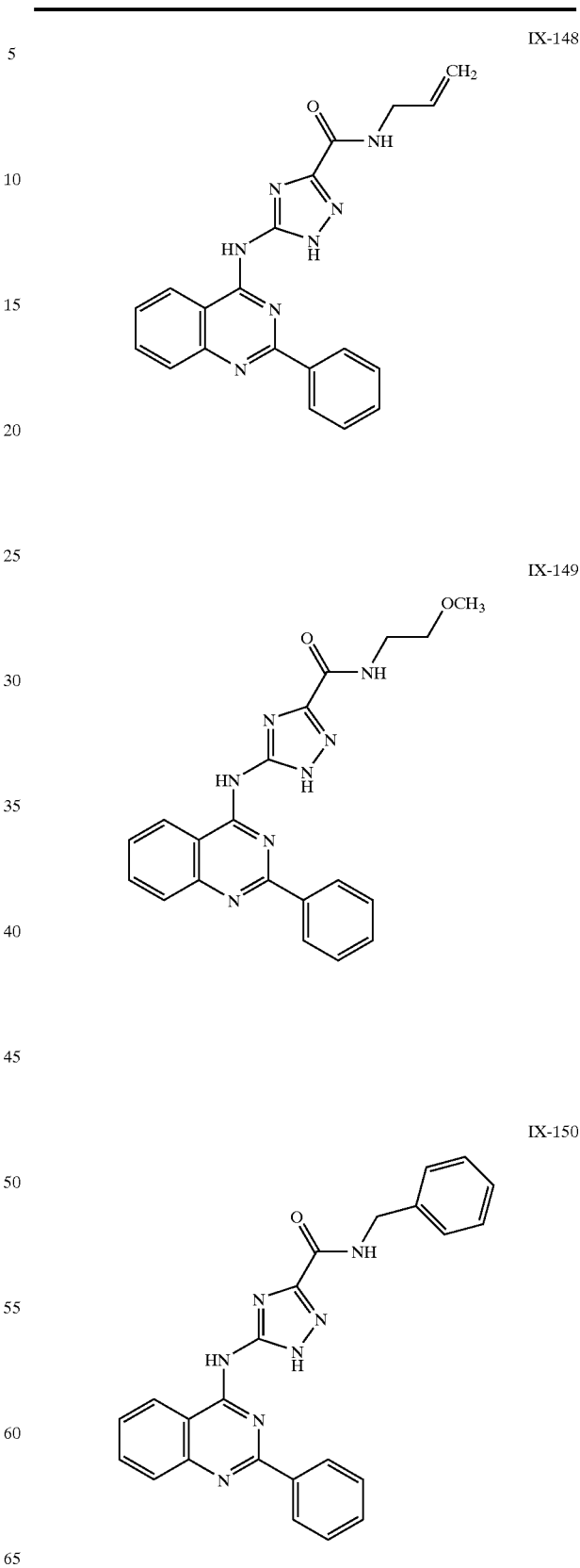
IX-148
IX-149
IX-150

TABLE 8-continued
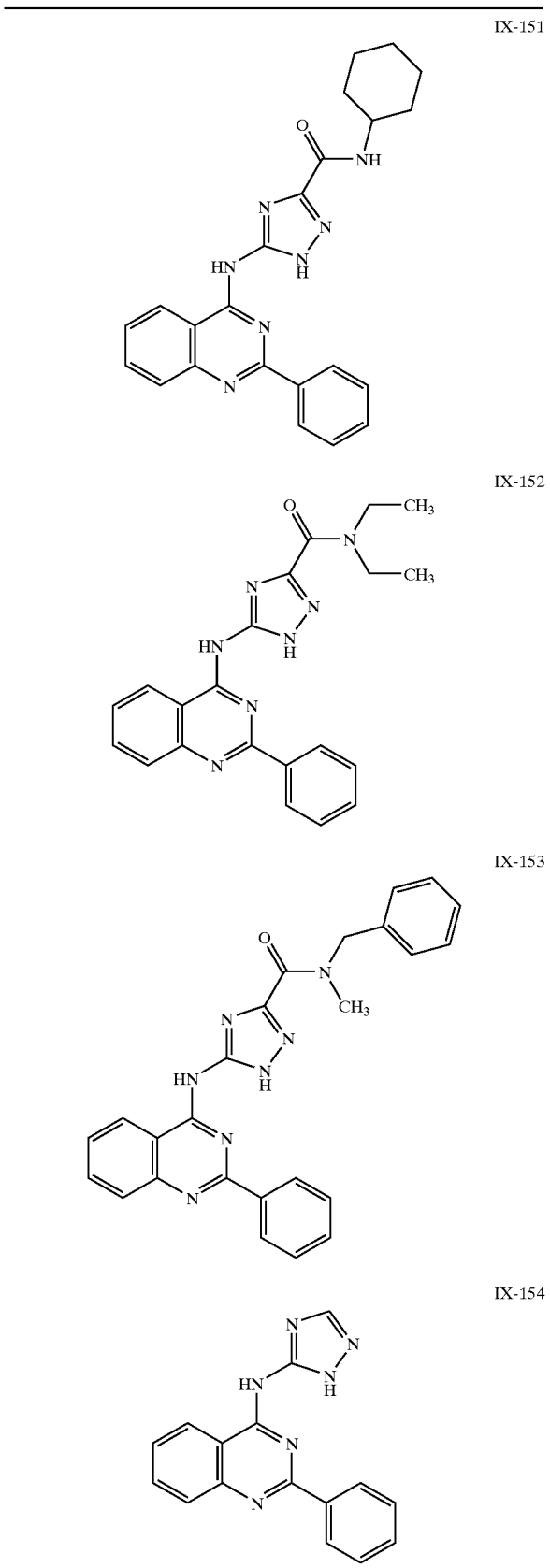
IX-151
IX-152
IX-153
IX-154
TABLE 8-continued
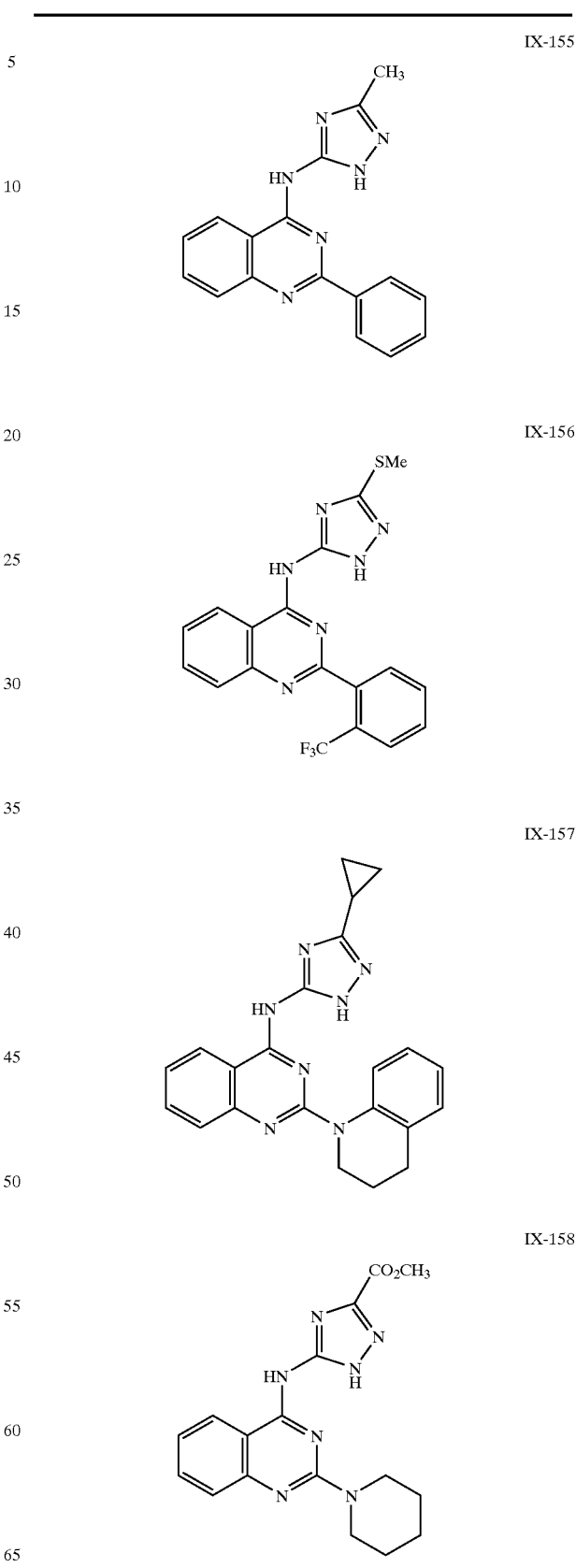
IX-155
IX-156
IX-157
IX-158

TABLE 8-continued
IX-159
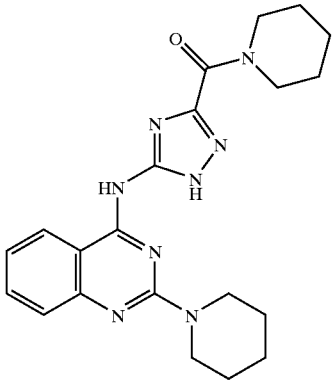
IX-160
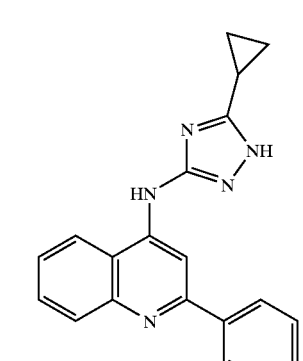
IX-161
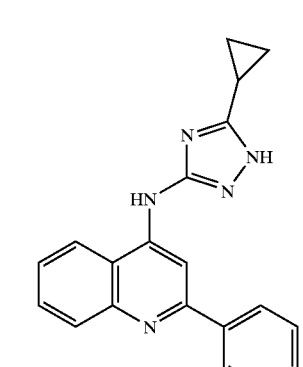
IX-162
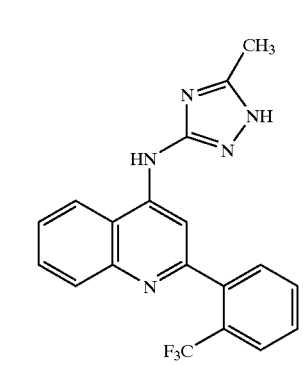
TABLE 8-continued
IX-163
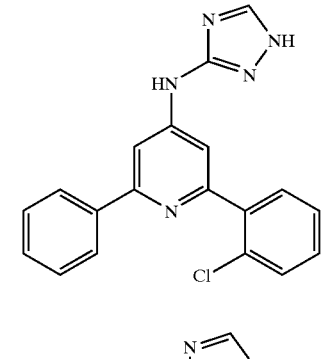
IX-164
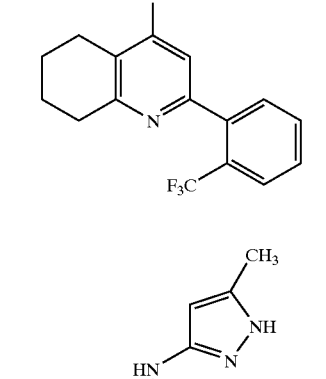
IX-165
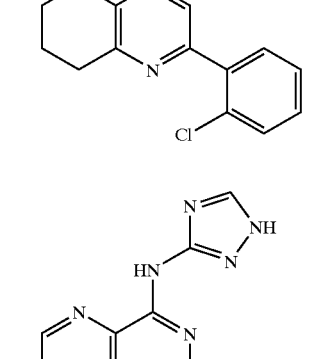
IX-166
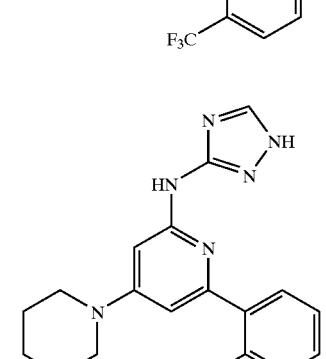
IX-167
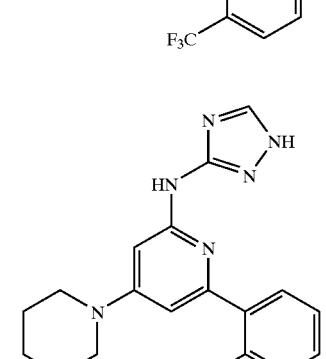

TABLE 8-continued
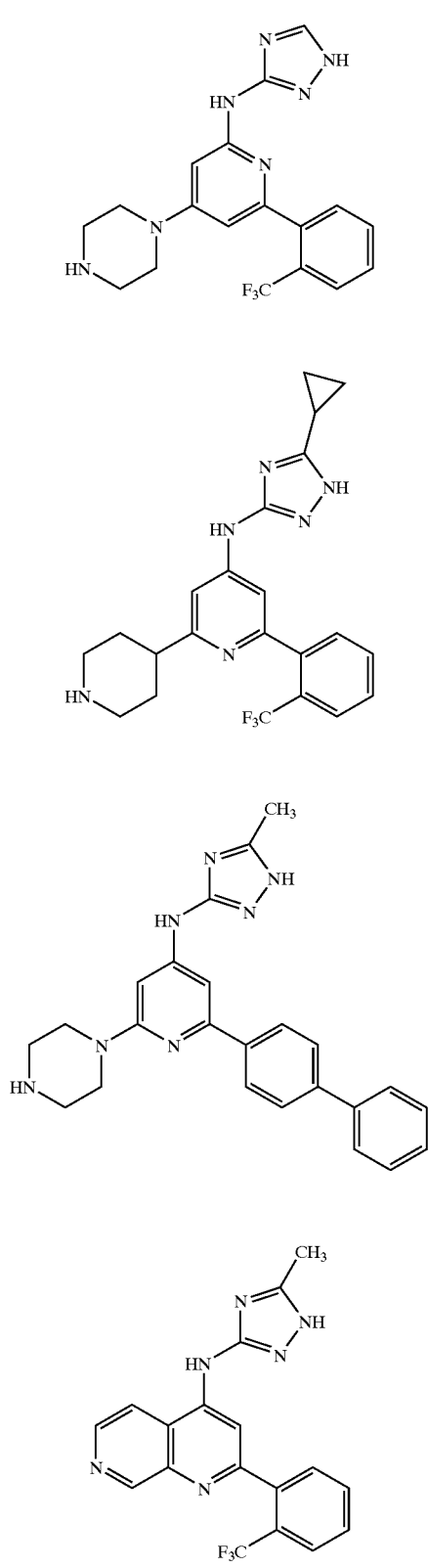
IX-168
IX-169
IX-170
IX-171
TABLE 8-continued
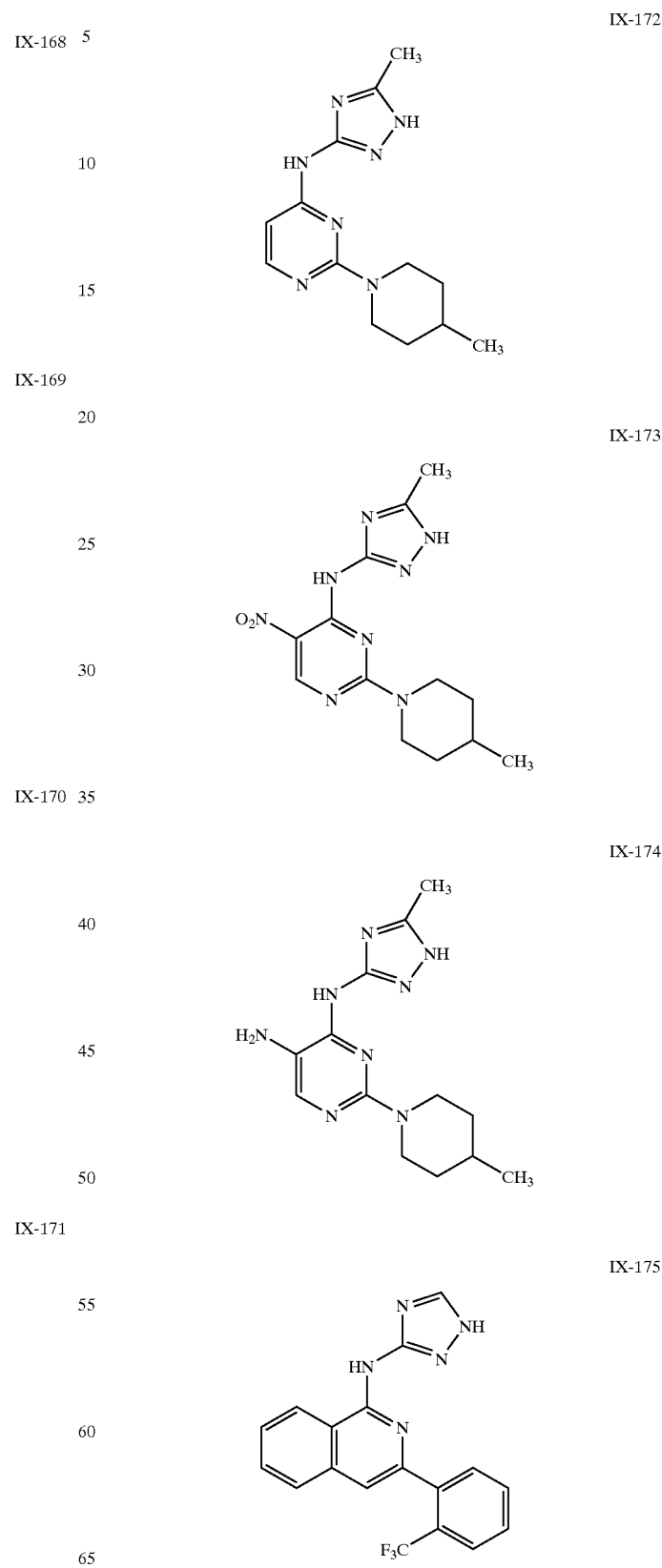
IX-172
IX-173
IX-174
IX-175

TABLE 8-continued

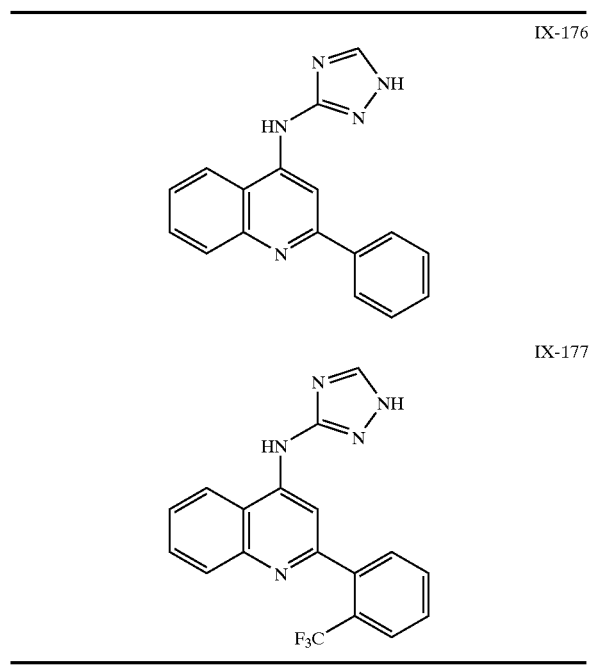

IX-176

IX-177

In another embodiment, this invention provides a composition comprising a compound of formula IX and a pharmaceutically acceptable carrier.

One aspect of this invention relates to a method of inhibiting GSK-3 activity in a patient, comprising administering to the patient a therapeutically effective amount of a composition comprising a compound of formula IX.

Another aspect relates to a method of treating a disease that is alleviated by treatment with a GSK-3 inhibitor, said method comprising the step of administering to a patient in need of such a treatment a therapeutically effective amount of a composition comprising a compound of formula IX.

Another aspect relates to a method of enhancing glycogen synthesis and/or lowering blood levels of glucose in a patient in need thereof, comprising administering to said patient a therapeutically effective amount of a composition comprising a compound of formula IX. This method is especially useful for diabetic patients.

Another aspect relates to a method of inhibiting the production of hyperphosphorylated Tau protein in a patient in need thereof, comprising administering to said patient a therapeutically effective amount of a composition comprising a compound of formula IX. This method is especially useful in halting or slowing the progression of Alzheimer's disease.

Another aspect relates to a method of inhibiting the phosphorylation of β-catenin in a patient in need thereof, comprising administering to said patient a therapeutically effective amount of a composition comprising a compound of formula IX. This method is especially useful for treating schizophrenia.

One aspect of this invention relates to a method of inhibiting Aurora activity in a patient, comprising administering to the patient a therapeutically effective amount of a composition comprising a compound of formula IX.

Another aspect relates to a method of treating a disease that is alleviated by treatment with an Aurora inhibitor, said method comprising the step of administering to a patient in need of such a treatment a therapeutically effective amount of a composition comprising a compound of formula IX.

This method is especially useful for treating cancer, such as colon, ovarian, and breast cancer.

Another method relates to inhibiting GSK-3 or Aurora activity in a biological sample, which method comprises contacting the biological sample with the GSK-3 or Aurora inhibitor of formula IX, or a pharmaceutical composition thereof, in an amount effective to inhibit GSK-3 or Aurora.

Each of the aforementioned compositions and methods directed to the inhibition of GSK-3 or Aurora, or the treatment of a disease alleviated thereby, is preferably carried out with a preferred compound of formula IX, as described above.

The compounds of this invention may be prepared as illustrated by the Synthetic Methods below, by the Synthetic Examples described herein and by general methods known to those skilled in the art.

General Synthetic Methods

The general synthetic methods below provide a series of general reaction routes that were used to prepare compounds of this invention. Methods A–F below are particularly useful for preparing formula II compounds. In most cases, Ring C is drawn as a phenyl ring bearing an ortho $R^1$ substituent. However, it will be apparent to one skilled in the art that compounds having other Ring C groups may be obtained in a similar manner. Methods analogous to methods A–F are also useful for preparing other compounds of this invention. Methods F–I below are particulary useful for preparing compounds of formula III or IV.

Method A

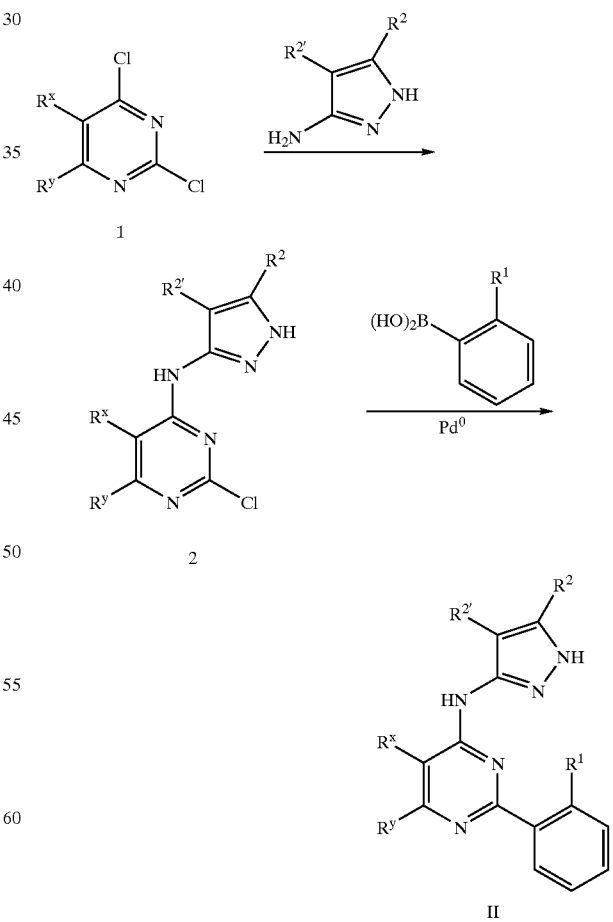

Method A is a general route for the preparation of compounds wherein ring C is an aryl or heteroaryl ring. Preparation of the starting dichloropyrimidine 1 may be achieved in a manner similar to that described in *Chem. Pharm. Bull.,* 30, 9, 1982, 3121–3124. The chlorine in position 4 of intermediate 1 may be replaced by an aminopyrazole or aminoindazole to provide intermediate 2 in a manner similar to that described in *J. Med. Chem.,* 38, 3547–3557 (1995). Ring C is then introduced using a boronic ester under palladium catalysis (see *Tetrahedron,* 48, 37, 1992, 8117–8126). This method is illustrated by the following procedure.

A suspension of 1H-quinazoline-2,4-dione (10.0 g, 61.7 mmol) in POCl$_3$ (60 mL, 644 mmol) and N,N-dimethylaniline (8 mL, 63.1 mmol) is heated under reflux for 2 h. Excess POCl$_3$ is evaporated under vacuum, the residue is poured into ice, and the precipitate is collected by filtration. The crude solid 2,4-dichloroquinazoline product may be used without further purification.

To a solution of 2,4-dichloro-quinazoline (3.3 g, 16.6 mmol) in anhydrous ethanol (150 mL) is added 5-methyl-1H-pyrazol-3-yl amine (3.2 g, 32.9 mmol). The mixture is stirred at room temperature for 4 h, and the resulting precipitate is collected by filtration, washed with ethanol, and dried under vacuum to afford (2-chloro-quinazolin-4-yl)-(5-methyl-1H-pyrazol-3-yl)-amine.

To a solution of (2-chloro-quinazolin-4-yl)-(5-methyl-1H-pyrazol-3-yl)-amine (50 mg, 0.19 mmol) in DMF (1.0 mL) is added the desired arylboronic acid (0.38 mmol), 2M Na2CO3 (0.96 mmol), and tri-t-butylphosphine (0.19 mmol). Under nitrogen, PdCl$_2$(dppf) (0.011 mmol) is added in one portion. The reaction mixture is then heated at 80° C. for 5 to 10 hours, cooled to room temperature, and poured into water (2 mL). The resulting precipitate is collected by filtration, washed with water, and purified by HPLC.

Method B

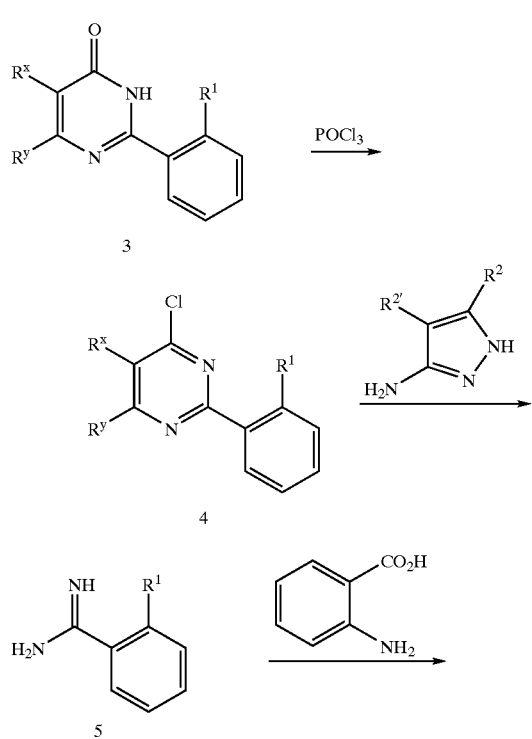

Methods B through F describe routes where the pyrazole ring system is introduced after Ring C and the pyrimidine ring portion are first constructed. A versatile intermediate is the 4-chloropyrimidine 4, which is readily obtained from pyrimidinone 3 as shown in Method B(i). This reaction sequence is generally applicable for a variety of Ring C groups including aliphatic, aryl, heteroaryl, or heterocyclyl. See *J. Med. Chem.,* 38, 3547–3557 (1995).

For quinazoline ring systems (where $R^x$ and $R^y$ are taken together to form a benzo ring), the useful intermediate 6 may be obtained by condensing an anthranilic acid or its derivative with a benzamidine as shown in Method B(ii) or by condensing a benzoylchloride with an anthranilamide as shown in Method B(iii). Many substituted anthranilic acid, anthranilamide, benzamidine and benzoylchloride starting materials may be obtained by known methods. See *Aust. J. Chem.,* 38, 467–474 and *J. Med. Chem.,* 38, 3547–3557 (1995). Method B(iii) is illustrated by the following procedure.

To a solution of anthranilamide (33 mmol) in THF and CH$_2$Cl$_2$ (1:1, 70 mL) is added the desired benzoylchloride (33 mmol), and triethylamine (99 mmol) at room temperature. The mixture is stirred for about 14 hours. The resulting precipitate is collected by filtration, washed with CH$_2$Cl$_2$ and water, and dried under vacuum. The crude 2-benzoylaminobenzamide may be used directly for the next step without further purification.

To a solution of the above crude product (13 mmol) in ethanol (50 mL) is added NaOEt (26 mmol) at room temperature. The mixture is heated under reflux for 48 to 96 h. The solvent is evaporated and the residue is neutralized using concentrated HCl to pH 7. The product is then collected by filtration and dried under vacuum to provide 2-phenyl-3H-quinazolin-4-one that may be used without further purification.

To a suspension of the above product (12 mmol) in POCl$_3$ (120 mmol) is added tri-n-propylamine (24 mmol). The mixture is heated under reflux for 1 h. After removal of the excess POCl$_3$ by evaporation, the residue is dissolved in ethyl acetate, and washed with 1N NaOH (twice) and water (twice). The organic layer is dried over MgSO$_4$, the solvent

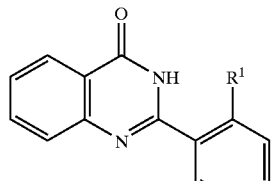

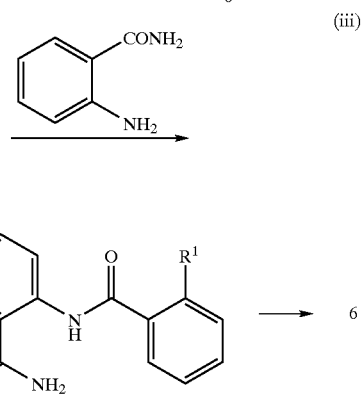

is evaporated under vacuum, and the crude product is purified by flash chromatography (eluting with 10% of ethyl acetate in hexanes) to give 4-chloro-2-aryl quinazoline.

To a solution of 4-chloro-2-aryl quinazoline (0.16 mmol) in DMF (or THF, ethanol) (1 mL) is added the desired aminopyrazole or aminoindazole (0.32 mmol). The mixture is heated in DMF (or THF under reflux) at 100 to 110° C. for 16 h (or in ethanol at 130–160° C. for 16 hours) and then poured into water (2 mL). The precipitate is collected by filtration and purified by HPLC.

Method C

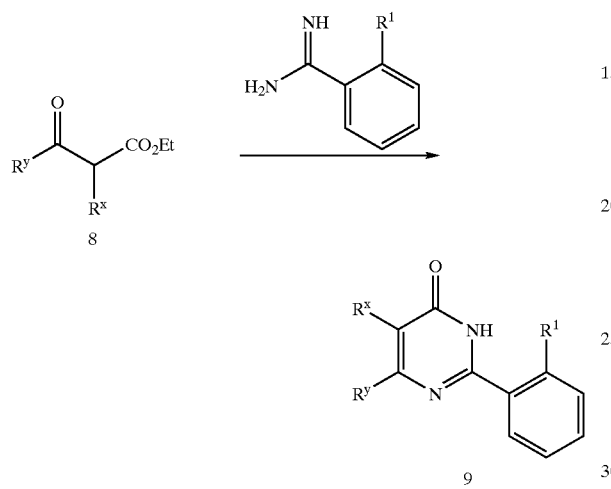

Method D(i)

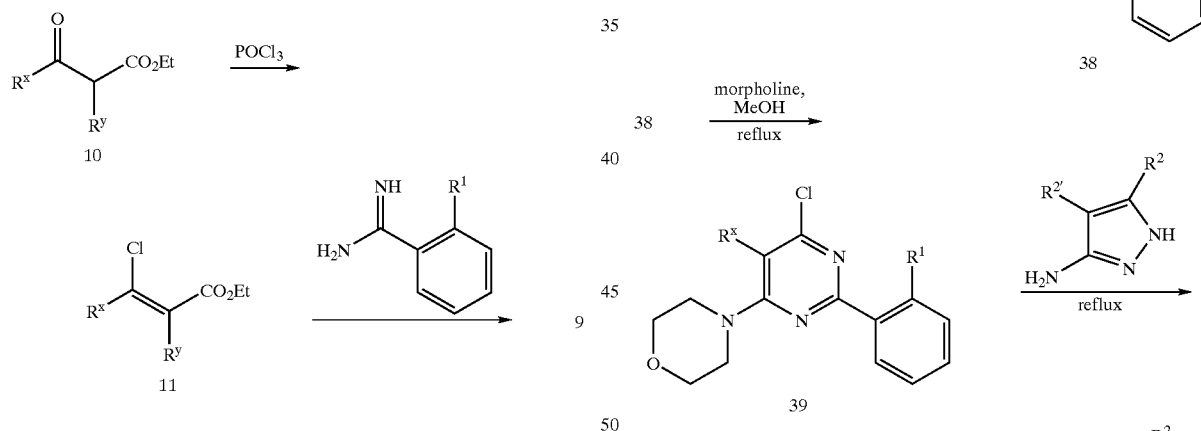

Methods C and D(i) above employ β-ketoesters 8 and 10, respectively, as pyrimidinone precursors. The substitution pattern of the $R^x$ and $R^y$ groups on the pyrimidinone ring will be reversed if a chlorocrotonate 11 (Synth. Comm., (1986), 997–1002), instead of the corresponding β-ketoester 10, is condensed with the desired benzamidine. These methods are illustrated by the following general procedure.

To a solution of a β-ketoester (5.2 mmol) and amidinium chloride (5.7 mmol) in ethanol (5 mL) is added sodium ethoxide (7.8 mmol). The mixture is heated under reflux for 7–14 hours. After evaporation the resulting residue is dissolved in water, acidified with concentrated HCl to pH 6, and then filtered to obtain a solid product 2-aryl-3H-pyrimidin-4-one (yield 75–87%), which may be purified by flash column chromatography if needed. To this pyrimidinone (3.7 mmol) is added POCl$_3$ (4 mL) and n-Pr$_3$N (1.4 mL). The mixture is heated under reflux for 1 hour. After evaporation of the excess POCl$_3$, the residue is dissolved in ethyl acetate, washed with 1N NaOH solution (three times) and NaHCO$_3$ (once), and dried over MgSO$_4$. The solvent is removed under vacuum and the residue is purified by flash column chromatography eluting with 10% of ethyl acetate in hexanes to give 2-aryl-4-chloro-pyrimidine as a pale yellow syrup. This crude product may be treated with a 3-aminopyrazole or 3-aminoindazole as described above.

Method D(ii)

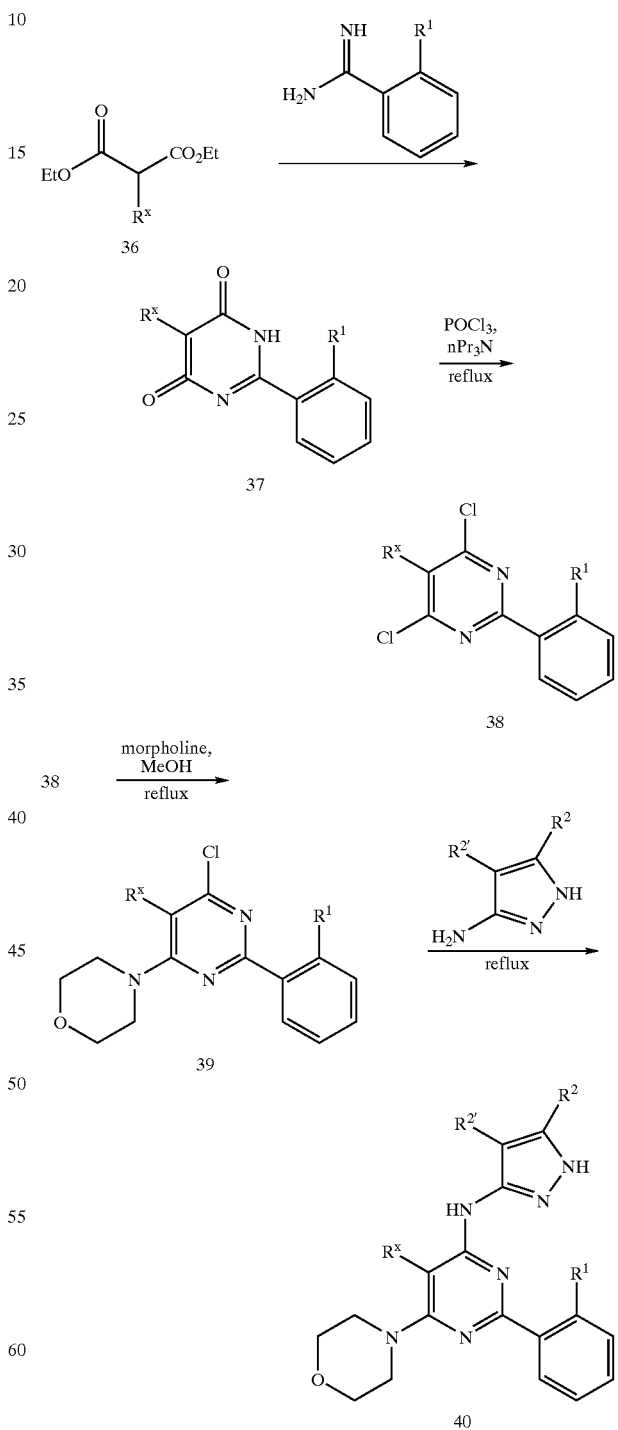

Method D(ii) above shows a general route for the preparation of the present compounds, such as compound 40, wherein $R^y$ is $N(R^4)_2$. See *Il Farmaco*, 52(1) 61–65 (1997).

Displacement of the 6-chloro group is exemplified here using morpholine. This method is illustrated by the following procedure.

To a solution of 2-methylmalonic acid diethyl ester (5 mmol) and sodium ethoxide (15 mmol) is added the appropriate amidine salt (5 mmol) in ethanol (10 mL) and the reaction heated at reflux for 2–24 hours. The residue is dissolved in water and acidified with 2N HCl. The resulting precipitate is filtered off and further purified by flash chromatography (yield 5–35%) to afford the pyrimidinedione 37. To 37 (1.6 mmol) is added POCl₃ (32 mmol) and tri-n-propylamine (6.4 mmol) and the reaction refluxed is for 1 h. After evaporation of excess POCl₃, the residue is dissolved in ethyl acetate, basified with 1N NaOH, separated and the aqueous phase twice more extracted with ethyl acetate. The combined organics are dried (sodium sulfate) and evaporated. Purification by flash chromatography provides the dichloropyrimidine (38) as a yellow oil in 23% yield.

A solution of 38 (0.33 mmol) in methanol (5 mL) is treated with an amine, exemplified here using morpholine (0.64 mmol) and refluxed 1 hour. After evaporation of solvent, the residue is purified by flash chromatography to provide the mono-chloropyrimidine 39 as a colorless oil in 75% yield.

The mono-chloropyrimidine, 39, (0.19 mmol) may be treated with a 3-aminopyrazole or 3-aminoindazole compound in a manner substantially similar those described above in Methods A and B.

Method E

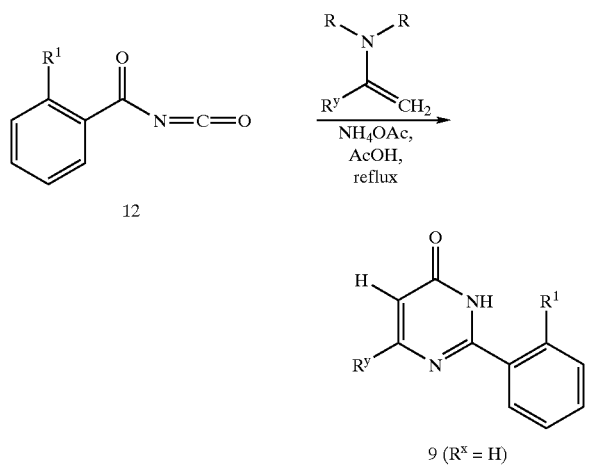

As shown by Method E, an acyl isocyanate 12 may be condensed with an enamine to provide pyrimidinone 9 (J. Org. Chem (1993), 58, 414–418; J. Med. Chem., (1992), 35, 1515–1520; J.Org.Chem., 91967, 32, 313–214). This method is illustrated by the following general procedure.

The enamine is prepared according to W. White, et al, J. Org Chem. (1967), 32, 213–214. The acyl isocyanate is prepared according to G Bradley, et al, J Med. Chem. (1992), 35, 1515–1520. The coupling reaction then follows the procedure of S Kawamura, et al, J. Org. Chem, (1993), 58, 414–418. To the enamine (10 mmol) in tetrahydrofuran (30 mL) at 0° C. under nitrogen is added dropwise over 5 min a solution of acyl isocyanate (10 mmol) in tetrahydrofuran (5 mL). After stirring for 0.5 h, acetic acid (30 mL) is added, followed by ammonium acetate (50 mmol). The mixture is refluxed for 2 h with continuous removal of tetrahydrofuran. The reaction is cooled to room temperature and is poured into water (100 mL). The precipitate is filtered, washed with water and ether and dried to provide the 2-aryl-3H-pyrimidin-4-one.

Method F

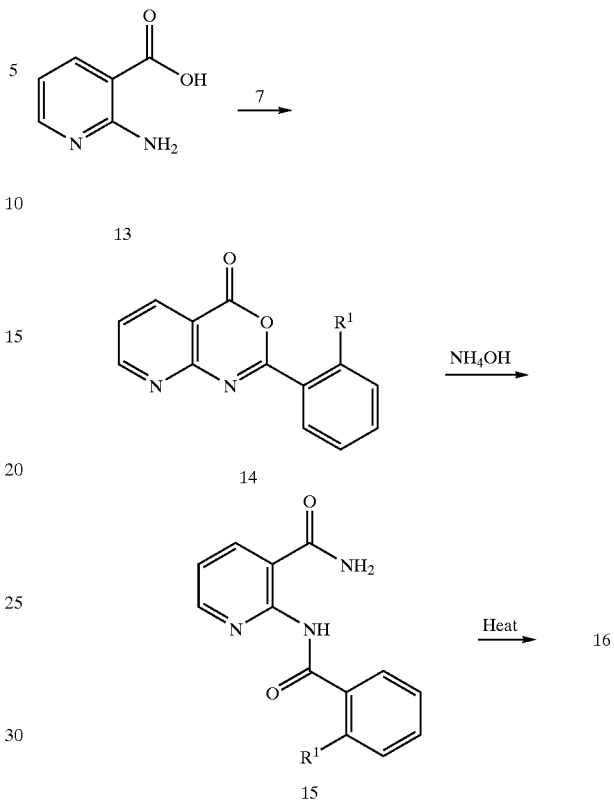

Method F shows a general route for the preparation of the present compounds wherein $R^x$ and $R^y$ are taken together to form a 5–8 membered partially unsaturated saturated or unsaturated ring having 1–3 heteroatoms. The condensation of a 2-amino-carboxylic acid, such as 2-amino-nicotinic acid 13, and an acid chloride 7 provides an oxazinone 14. Treatment of 14 with ammonium hydroxide will furnish the benzamide 15 which may be cyclized to a 2-(substituted)-pyrido[2,3-d][1,3]pyrimidin-4-one 16. This method is illustrated by the following procedure.

2-(Trifluoromethyl)benzoyl chloride (4.2 ml, 29.2 mmol) is added dropwise to a solution of 2-aminonicotinic acid (2.04 g, 14.76 mmol) in 20 ml of pyridine. The reaction mixture is heated at 158 C for 30 min then cooled to room temperature. The reaction is poured into 200 ml of water and an oil forms which solidifies upon stirring. The solid is collected by vacuum filtration and washed with water and diethyl ether. The product is dried to give 2-(2-trifluoromethyl-phenyl)-pyrido[2,3-d][1,3]oxazin-4-one (2.56 g, 60% yield) which may be used in the next step without further purification.

2-(2-Trifluoromethyl-phenyl)-pyrido[2,3-d][1,3]oxazin-4-one (2.51 g) is stirred in 30% ammonium hydroxide (25 ml) at room temperature overnight. The resulting precipitate is filtered and rinsed with water and diethyl ether. The precipitate is dried under vacuum at 50 C overnight to give 2-(2-trifluoromethyl-benzoylamino)-nicotinamide (850 mg, 33% yield)

2-(2-Trifluoromethyl-benzoylamino)-nicotinamide (800 mg, 2.6 mmol) is dissolved in 10 ml of ethanol. Potassium ethoxide. (435 mg, 5.2 mmol) is added to the solution which is heated to reflux for 16 h. The reaction mixture is evaporated in vacuo to afford a gummy residue that is dissolved in water and acidified with 10% sodium hydrogen sulfate to pH 7. The resulting precipitate is filtered and dried under vacuum at 50 C to give 2-(2-trifluoromethyl-phenyl)-3H-pyrido[2,3-d]pyrimidin-4-one.

Method G

Method G is analogous to Method B(i) above. This method is illustrated by the following general procedure.

2-(3,4-Dichloro-phenyl)-3H-quinazolin-4-one (1 g, 3.43 mmol) is suspended in phosphorus oxychloride (4 mL) and the reaction mixture was stirred at 110° C. for 3 hours. The solvents are then evaporated and the residue is treated carefully with an ice cold aqueous saturated solution of $NaHCO_3$. The solid is collected by filtration and washed with ether to give 4-chloro-2-(3,5-dichloro-phenyl)-quinazoline as a white solid (993 mg, 93%).

To 4-chloro-2-(3,5-dichloro-phenyl)-quinazoline (400 mg, 1.29 mmol) in THF (30 mL) is added 3-amino-5-methyl pyrazole (396 mg, 2.58 mmol) and the reaction mixture is heated at 65° C. overnight. The solvents are then evaporated and the residue triturated with ethyl acetate, filtered and washed with a minimum amount of ethanol to give [2-(3,4-dichlorophenyl)-quinazolin-4-yl]-(5-methyl-2H-pyrazol-3-yl)-amine as a white solid (311 mg 65%): mp 274° C.; $^1$H NMR (DMSO) δ 2.34 (3H, s), 6.69 (1H, s), 7.60 (1H, m), 7.84 (1H, d), 7.96 (2H, d), 8.39 (1H, dd), 8.60 (1H, d), 8.65 (1H, d), 10.51 (1H, s), 12.30 (1H, s); IR (solid) 1619, 1600, 1559, 1528, 1476, 1449, 1376, 1352, 797, 764, 738; MS 370.5 $(M+H)^+$.

The THF solvent used in the previous step may be replaced by other organic solvents such as ethanol, N,N-dimethylformamide, or dioxane.

Method H

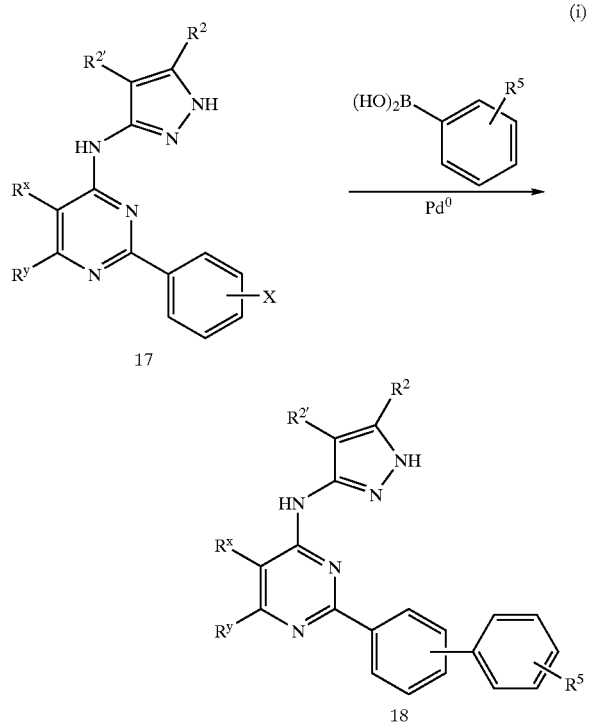

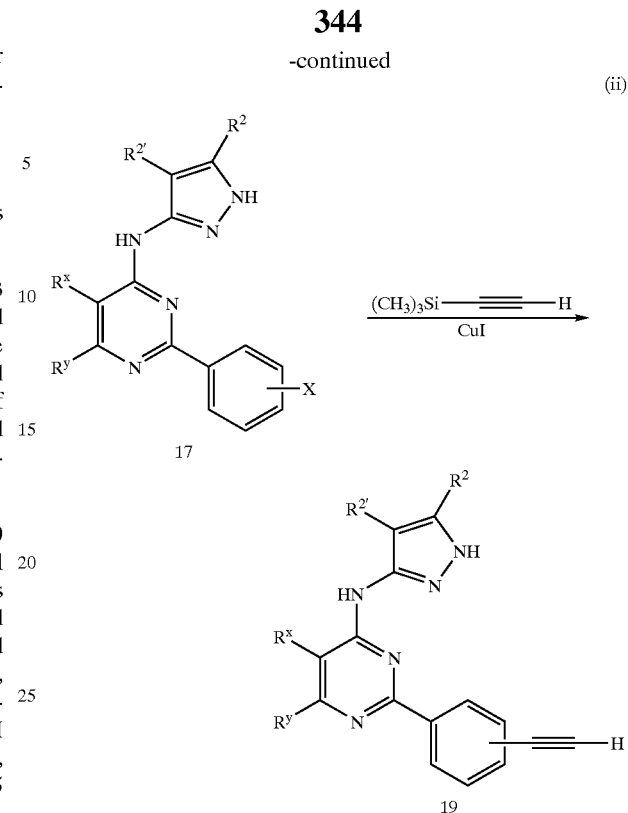

Method H shows routes in which a Ring D aryl group bearing a halogen (X is Br or I) may be converted to-other formula III compounds. Method H(i) shows a phenylboronic acid coupling to Ring D to provide compound 18 and Method H(ii) shows an acetylene coupling to provide compound 19. Substituent X in compound 17 may be bromine or iodine. These methods are illustrated by the following procedures.

Method H(i). To a mixture of [2-(4-bromo-phenyl)-quinazolin-4-yl]-(5-methyl-2H-pyrazol-3-yl)-amine (196 mg, 0.51 mmol) and phenylboronic acid (75 mg, 0.62 mmol) in THF/water (1/1, 4 mL) is added $Na_2CO_3$ (219 mg, 2.06 mmol), triphenylphosphine (9 mg, 1/15 mol %) and palladium acetate (1 mg, 1/135 mol %). The mixture is heated at 80° C. overnight, the solvents are evaporated and the residue is purified by flash chromatography (gradient of $CH_2Cl_2$/MeOH) to give (2-biphenyl-4-yl-quinazolin-4-yl)-(5-methyl-2H-pyrazol-3-yl)-amine as a yellow solid (99 mg, 51%): $^1$H NMR (DMSO) δ 2.37 (3H, s), 6.82 (1H, s), 7.39–7.57 (4H, m), 7.73–7.87 (6H, m), 8.57 (2H, d), 8.67 (1H, d), 10.42 (1H, s), 12.27 (1H, s); MS 378.2 $(M+H)^+$ Method H(ii). To a mixture of [2-(4-bromo-phenyl)-quinazolin-4-yl]-(5-methyl-2H-pyrazol-3-yl)-amine (114 mg, 0.3 mmol), and trimethylsilylacetylene (147 mg, 1.5 mmol)in DMF (2 mL) is added CuI (1.1 mg, 1/50 mol %), $Pd(PPh_3)_2Cl_2$ (4.2 mg, 1/50 mol %) and triethylamine (121 mg, 0.36 mmol). The mixture is heated at 120° C. overnight and the solvent is evaporated. The residue is triturated in ethyl acetate and the precipitate is collected by filtration.

To the above precipitate suspended in THF (3 mL) is added tetrabutylammonium fluoride (1M in THF, 1.1 eq). The reaction mixture is stirred at room temperature for two hours and the solvent is evaporated. The residue is purified by flash chromatography (gradient of $CH_2Cl_2$/MeOH) to give [2-(4-ethynylphenyl)-quinazolin-4-yl]-(5-methyl-2H-pyrazol-3-yl)-amine as a white solid (68 mg, 70%): $^1$H NMR (DMSO) δ 2.34 (3H, s), 4.36 (1H, s), 6.74 (1H, s), 7.55 (1H, m), 7.65 (2H, d), 7.84 (2H, m), 8.47 (2H, d), 8.65 (1H, d), 10.43 (1H, s), 12.24 (1H, S); MS 326.1 (M+H)$^+$ Method I

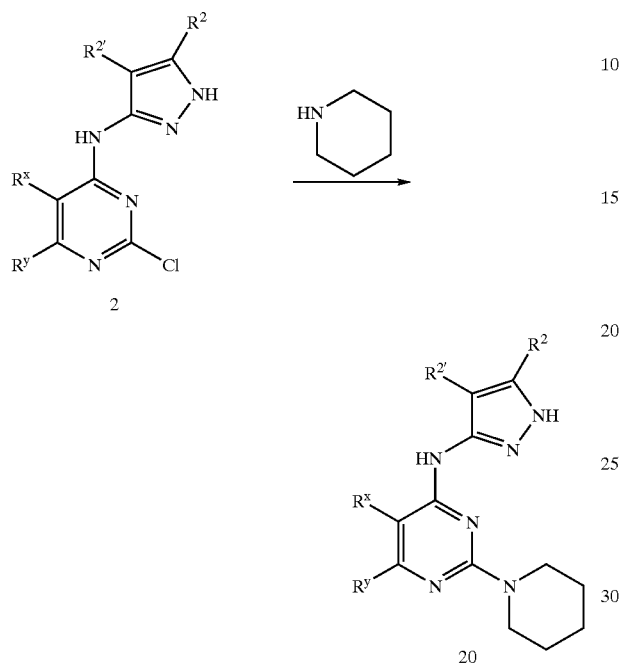

Method I above shows a general route for the preparation of the present compounds wherein ring D is a heteroaryl or heterocyclyl ring directly attached to the pyrimidine 2-position via a-nitrogen atom. Displacement of the 2-chloro group, exemplified here using piperidine, may be carried out in a manner similar to that described in *J. Med. Chem.*, 38, 2763–2773 (1995) and *J. Chem. Soc.*, 1766–1771 (1948). This method is illustrated by the following procedure.

To a solution of (2-chloro-quinazolin-4-yl)-(1H-indazol-3-yl)-amine (1 equivalent, 0.1–0.2 mmol) in N,N-dimethylacetamide (1 ml) is added the desired amine (3 equivalents). The resulting mixture is maintained at 100° C. for 6 h and then purified by reverse-phase HPLC.

Method J

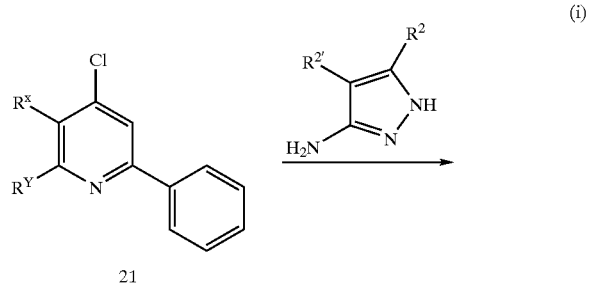

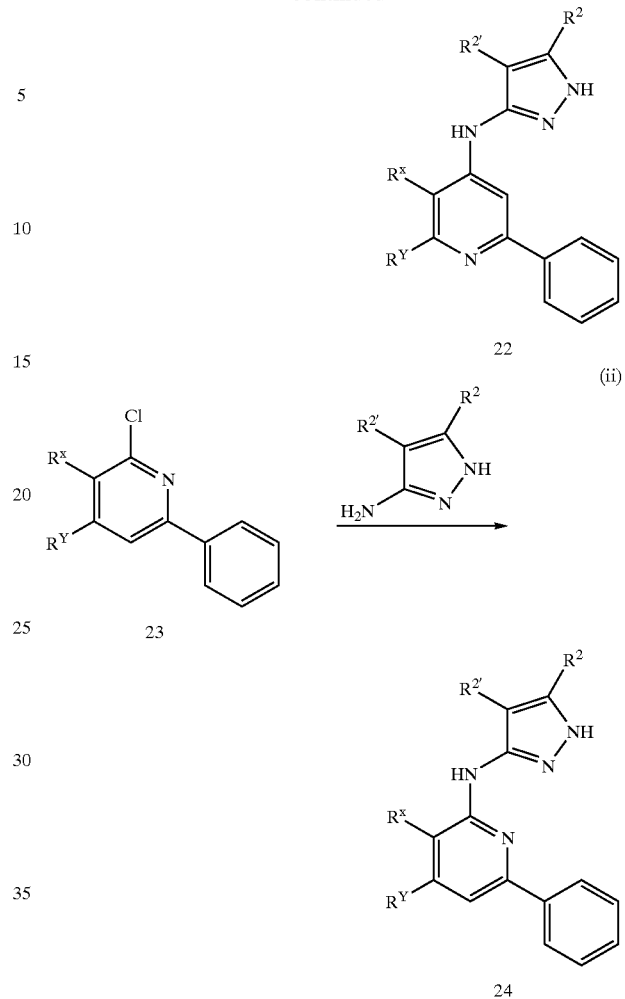

Method J above shows the preparation of compounds of formula V via the displacement of a chloro group from an appropriately substituted pyridyl ring. Method J(i) is a route for preparing compounds of formula Va (see *Indian J. Chem. Sect.*B, 35, 8, 1996, 871–873). Method J(ii) is a route for preparing compounds of formula Vb (see *Bioorg. Med. Chem.*, 6, 12, 1998, 2449–2458). For convenience, the chloropyridines 21 and 23 are shown with a phenyl substituent corresponding to Ring D of formula V. It would be apparent to one skilled in the art that Method J is also useful for preparing compounds of formula V wherein Ring D is heteroaryl, heterocyclyl, carbocyclyl or other aryl rings. Method J is illustrated by the following procedures.

Method J(i). (5-Methyl-2H-pyrazol-3-yl)-(2-phenyl-quinolin-4-yl)-amine. To 4-chloro-2-phenylquinoline (J. Het. Chem., 20, 1983, 121–128)(0.53 g, 2.21 mmol) in diphenylether (5 mL) was added 3-amino-5-methylpyrazole (0.43 g, 4.42 mmol) and the mixture was heated at 200° C. overnight with stirring. To the cooled mixture was added petroleum ether (20 mL) and the resulting crude precipitate was filtered and further washed with petroleum ether. The crude solid was purified by flash chromatography (SiO$_2$, gradient DCM-MeOH) to give the title compound as a white solid: mp 242–244° C.; $^1$H NMR (DMSO) δ 2.27(3H, s), 6.02(1H, s), 7.47(2H, d), 7.53–7.40(2H, br m), 7.67(1H, m), 7.92(1H, m), 8.09(2H, d), 8.48(2H, m), 9.20(1H, s), 12.17 (1H, br s); IR (solid) 1584, 1559, 1554, 1483, 1447, 1430, 1389; MS 301.2 (M+H)$^+$

347

Method J(ii). (5-Methyl-2H-pyrazol-3-yl)-(3-phenyl-isoquinolin-1-yl)-amine. To 1-chloro-3-phenylisoquinoline (J. Het. Chem., 20, 1983, 121–128)(0.33 g, 1.37 mmol) in dry DMF (5 mL) was added 3-amino-5-methylpyrazole (0.27 g, 2.74 mmol) and potassium carbonate (0.57 g, 4.13 mmol)and the mixture was heated under reflux for 6 hours. The mixture was cooled and the bulk of DMF was evaporated. The residue was extracted twice with ethyl acetate and the combined organic layers were washed with brine, dried (MgSO$_4$), filtered and concentrated. The crude was purified by flash chromatography (SiO$_2$, gradient DCM-MeOH) to give the title compound as a colourless oil; $^1$H NMR (MeOD) δ 2.23 (3H, s), 5.61 (1H, s), 7.41 (1H, m), 7.52(2H, m), 7.62(1H, m), 7.81(1H, m), 8.07(1H, d), 8.19(2H, m), 8.29(1H, s), 8.54 (1H, d); MS 301.2 (M+H)$^+$ Method K

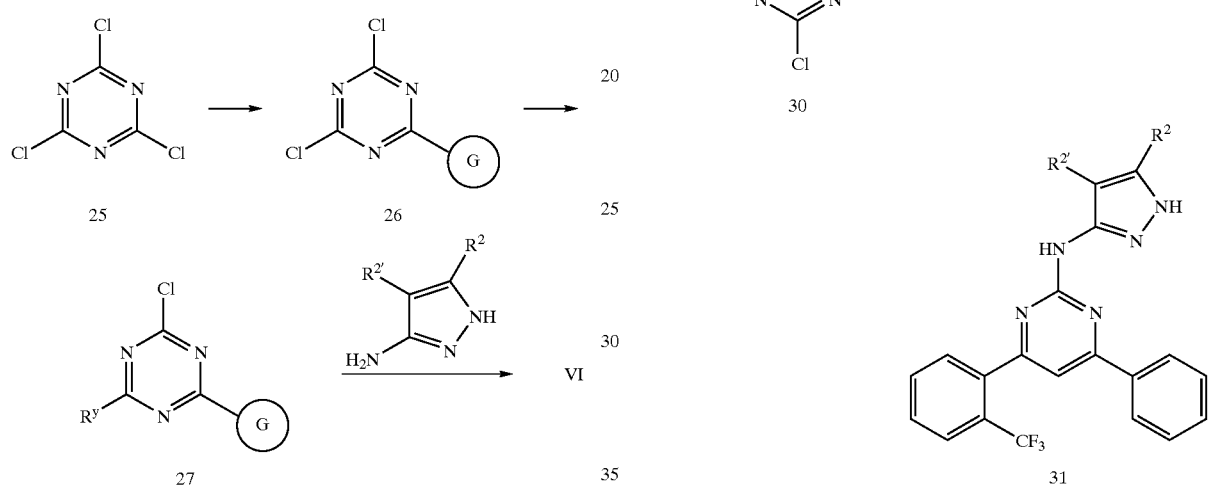

348

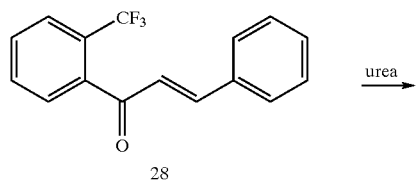

Method K shows a route for the preparation of compounds of formula VI. A versatile starting material is 2,4,6-trichloro-[1,3,5]triazine 25 in which the chlorine substituents may be sequentially displaced. The displacement of one of the chlorines by an aryl Grignard reagent or an aryl boronic acid is described in PCT patent application WO 01/25220 and Helv. Chim. Acta, 33, 1365 (1950). The displacement of one of the chlorines by a heteroaryl ring is described in WO 01/25220; J. Het. Chem., 11, 417 (1974); and Tetrahedron 31, 1879 (1975). These reactions provide a 2,4-dichloro-(6-substituted)[1,3,5]triazine 26 that is a useful intermediate for the preparation of compounds of formula VI. Alternatively, intermediate 26 may be obtained by constructing the triazine ring by known methods. See U.S. Pat. No. 2,832,779; and U.S. Pat. No. 2,691,020 together with J. Am. Chem. Soc. 60, 1656 (1938). In turn, one of the chlorines of 26 may be displaced as described above to provide 2-chloro-(4,6-disubstituted)[1,3,5]triazine 27. The treatment of 27 with an appropriate aminopyrazole provides the desired compound of formula VI.

Method L

Method L shows a route for preparing compounds of formula VII. For illustration purposes the trifluoromethyl-chalcone 28 is used as a starting material; however, it would be apparent to one skilled in the art that other rings may be used in place of the trifluoromethylphenyl and phenyl rings of compound 28. Substituted chalcones may be prepared by known methods, for example as described in the Indian J. Chemistry, 32B, 449 (1993). Condensation of a chalcone with urea provides the pyrimidinone 29, which may be treated with POCl$_3$ to give the chloropyrimidine 30. See J. Chem. Eng. Data, 30(4) 512 (1985) and Egypt. J. Chem., 37(3), 283 (1994). In an alternative approach to compound 30, one of the aryl rings attached to the pyrimidine is introduced by displacement of of the 4-chloro group of 2,4-dichloro-(6-aryl)-pyrimidine by an aryl boronic acid using a palladium catalyst such as (Ph$_3$P)$_4$Pd in the presence of a base such as sodium carbonate as described in Bioorg. Med. Lett., 9(7), 1057 (1999). Displacement of the chlorine of compound 30 by an appropriate aminopyrazole provides compounds of this invention, such as 31. The last step of this method is illustrated by the following procedure.

[4-(4-Methylpiperidin-1-yl)-pyrimidin-2-yl]-(5-methyl-2H-pyrazol-3-yl)-amine. To a solution of 2-chloro-4-(4-methylpiperidin-1-yl)-pyrimidine (prepared using a procedure similar to the one reported in Eur. J. Med. Chem., 26(7) 729(1991))(222 mg, 1.05 mmol) in BuOH (5 mL) was added 3-amino-5-methyl-2H-pyrazole (305 mg, 3.15 mmol) and the reaction mixture was then heated under reflux overnight. The solvent was evaporated and the residue dissolved in a mixture ethanol/water (1/3, 4 mL). Potassium carbonate (57 mg, 0.41 mmol) was added and the mixture was stirred at room temperature for 2 hours. The resulting suspension was filtered, washed with water twice and rinsed with ether twice to give the title compound as a white solid (143 mg, 50%): mp 193–195° C.; $^1$H NMR (DMSO) δ 0.91 (3H, d), 1.04 (2H, m), 1.67 (3H, m), 2.16 (3H, s), 2.83 (2H, t), 4.31 (2H, m), 6.19 (2H, m), 7.87 (1H, d), 8.80 (1H, br s), 11.71 (1H, s); IR (solid) 1627, 1579, 1541, 1498, 1417, 1388, 1322, 1246; MS 273.3(M+H)$^+$.

Method M

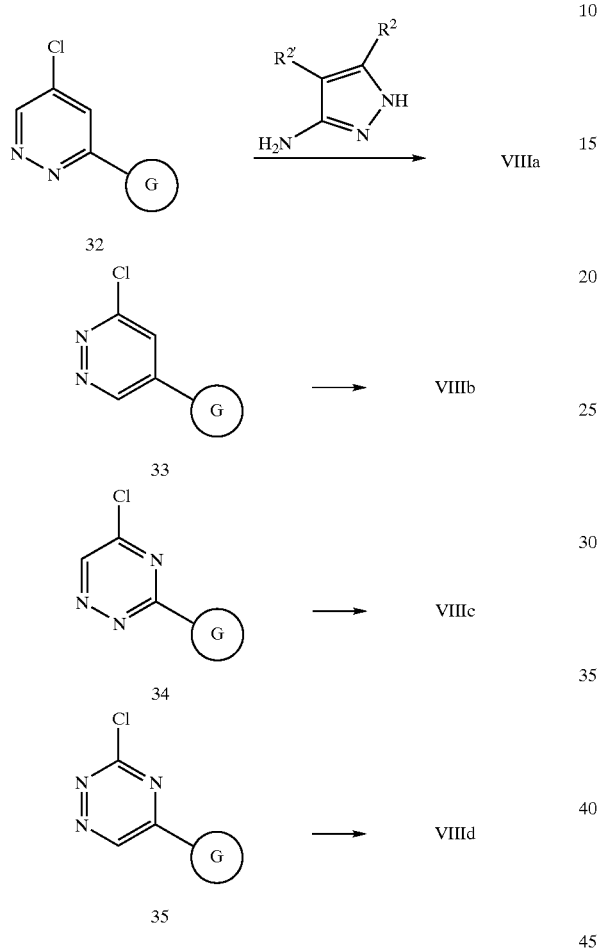

Method M provides routes for obtaining compounds of formula VIII. A general procedure for displacing the chlorine of a 4-chloro-6-substituted-pyridazine, 32, with an appropriately substituted pyrazole to provide VIIIa is described in *J. Het. Chem.*, 20, 1473 (1983). Analogous reactions may be carried out as follows: (a) with 3-chloro-5-substituted-pyridazine, 33, to provide VIIIb is described in *J. Med. Chem.*, 41(3), 311 (1998); (b) with 5-chloro-3-substituted-[1,2,4]triazine, 34, to provide VIIIc is described in *Heterocycles*, 26(12), 3259 (1987); and (c) with 3-chloro-5-substituted-[1,2,4]triazine, 35, to provide VIIId is described in *Pol. J. Chem.*, 57, 7, (1983); *Indian J. Chem. Sect. B*, 26, 496 (1987); and *Agric. Biol. Chem.*, 54(12), 3367 (1990). An alternative procedure to compounds of formula VIIIc is described in *Indian J. Chem. Sect. B*, 29(5), 435 (1990).

Compounds of formula IX are prepared by methods substantially similar to those described above for the pyrazole-containing compounds of formula I. Methods A–J may be used to prepare the triazole-containing compounds of formula IX by replacing the amino-pyrazole compound with an amino-triazole compound. Such methods are specifically exemplified by Synthetic Examples 415–422 set forth below. The amino-triazole intermediate may be obtained by methods described in *J. Org. Chem*. USSR, 27, 952–957 (1991).

Certain synthetic intermediates that are useful for preparing the protein kinase inhibitors of this invention are new. Accordingly, another aspect of this invention relates to a 3-aminoindazole compound of formula A:

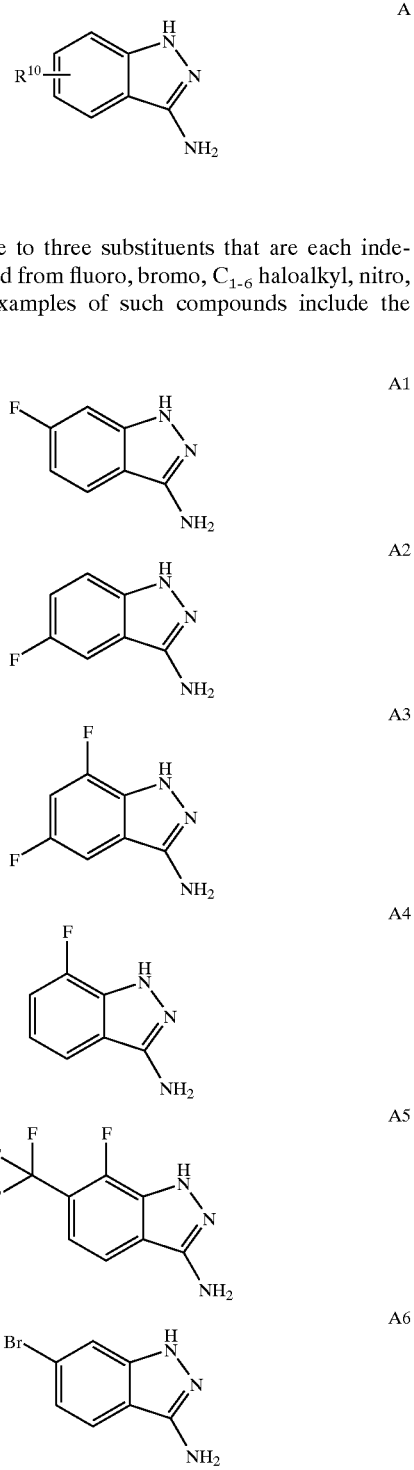

where $R^{10}$ is one to three substituents that are each independently selected from fluoro, bromo, $C_{1-6}$ haloalkyl, nitro, or 1-pyrrolyl. Examples of such compounds include the following:

-continued

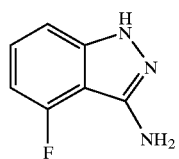
A7

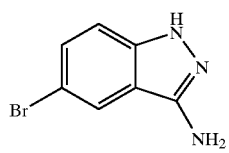
A8

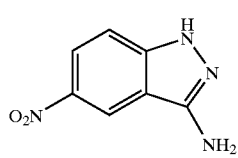
A9

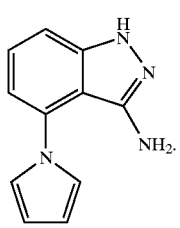
A10

Another aspect of this invention relates to a 4-chloropyrimidine compound of formula B:

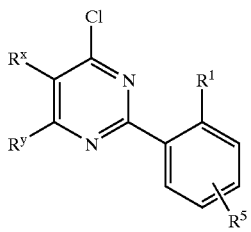
B wherein $R^x$ and $R^y$ are as defined above; $R^1$ is selected from Cl, F, $CF_3$, CN, or $NO_2$; and is one to three substituents that are each independently selected from H, Cl, F, $CF_3$, $NO_2$, or CN; provided that $R^1$ and $R^5$ are not simultaneously Cl. Examples of compounds of formula B are shown below:

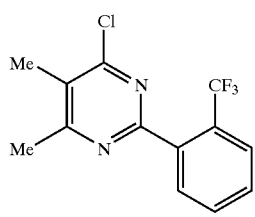
B1

-continued

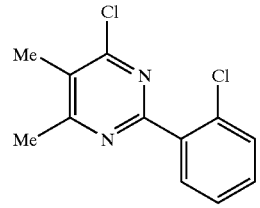
B2

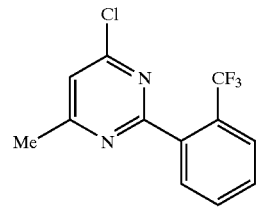
B3

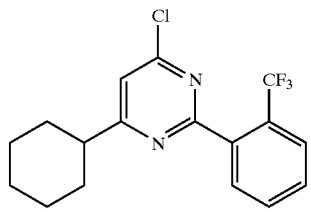
B4

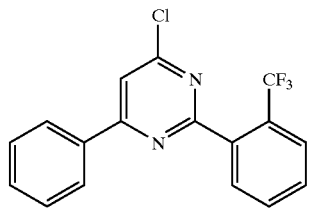
B5

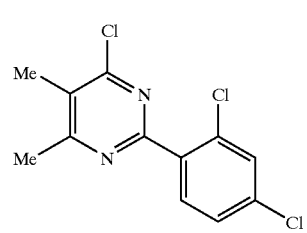
B6

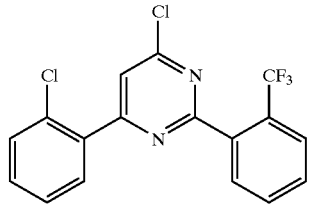
B7

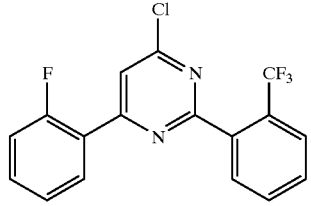
B8

B9
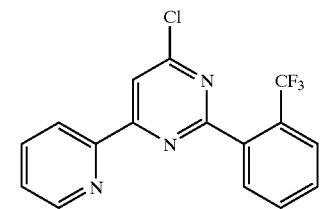
B10
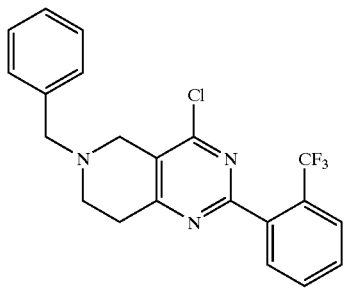
B11
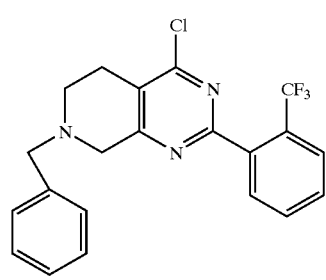
B12
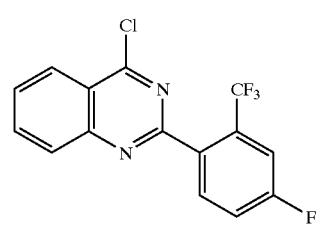
B13
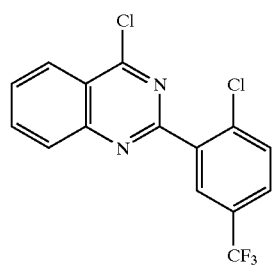
B14
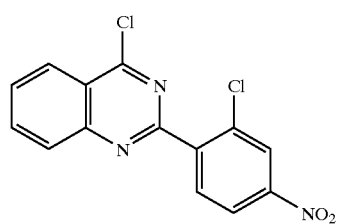
B15
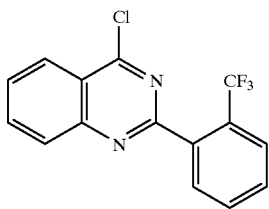
B16
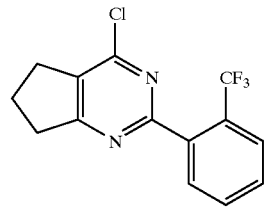
B17
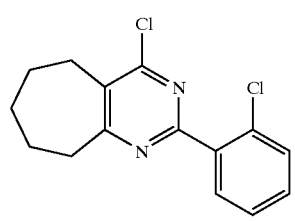
B18
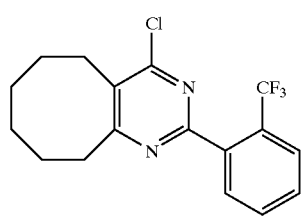
B19
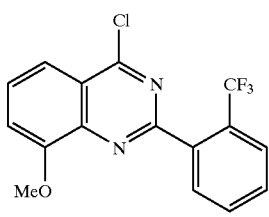
B20
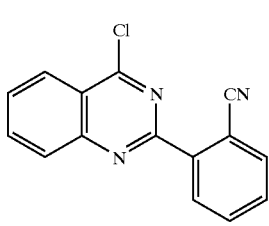

Another aspect of this invention relates to compounds of formula C:
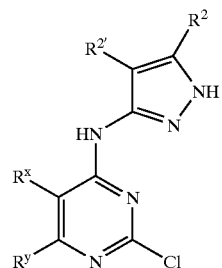
C
wherein $R^x$, $R^y$, $R^2$, and $R^{2'}$ are as defined above. Examples of compounds of formula C are shown below:
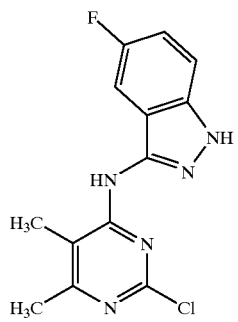
C1
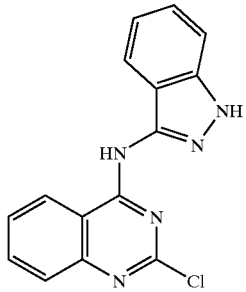
C2
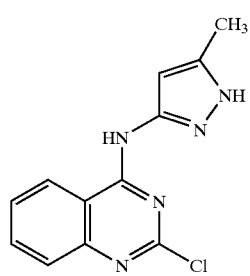
C3
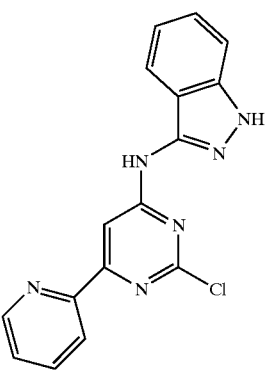
C4
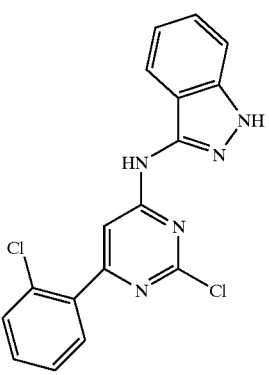
C5
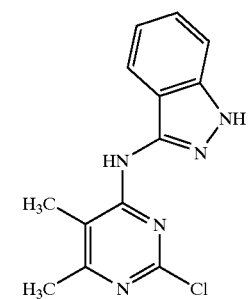
C6
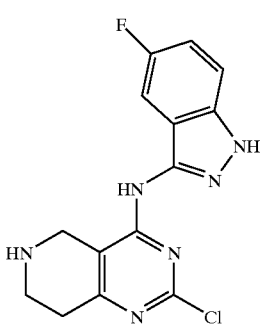
C7

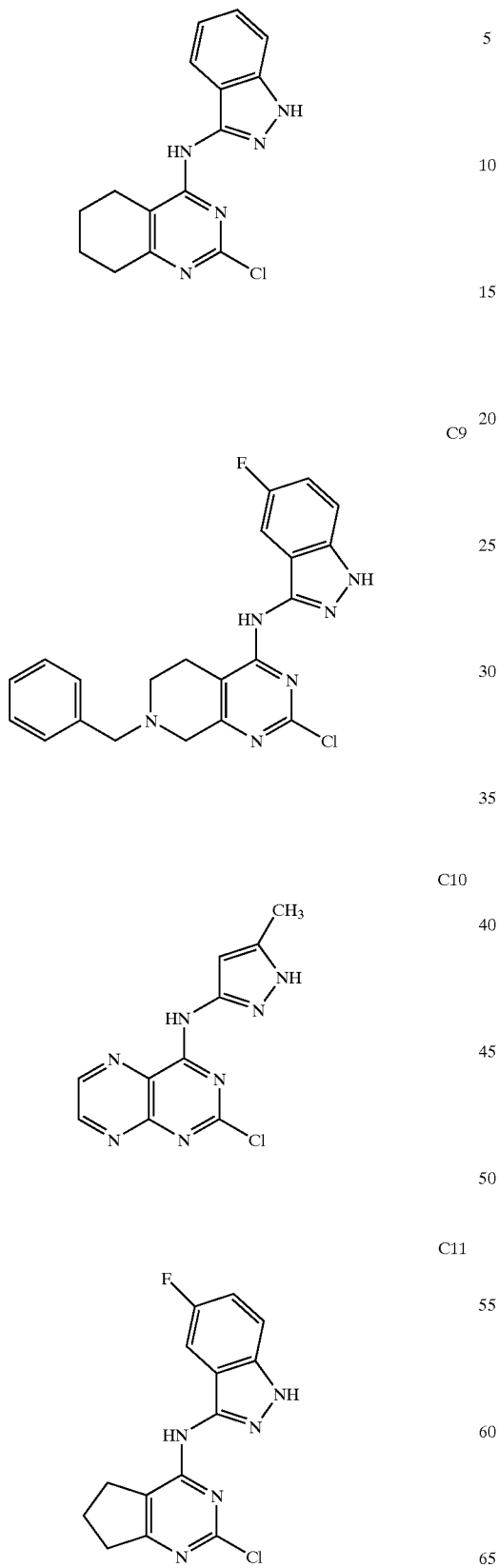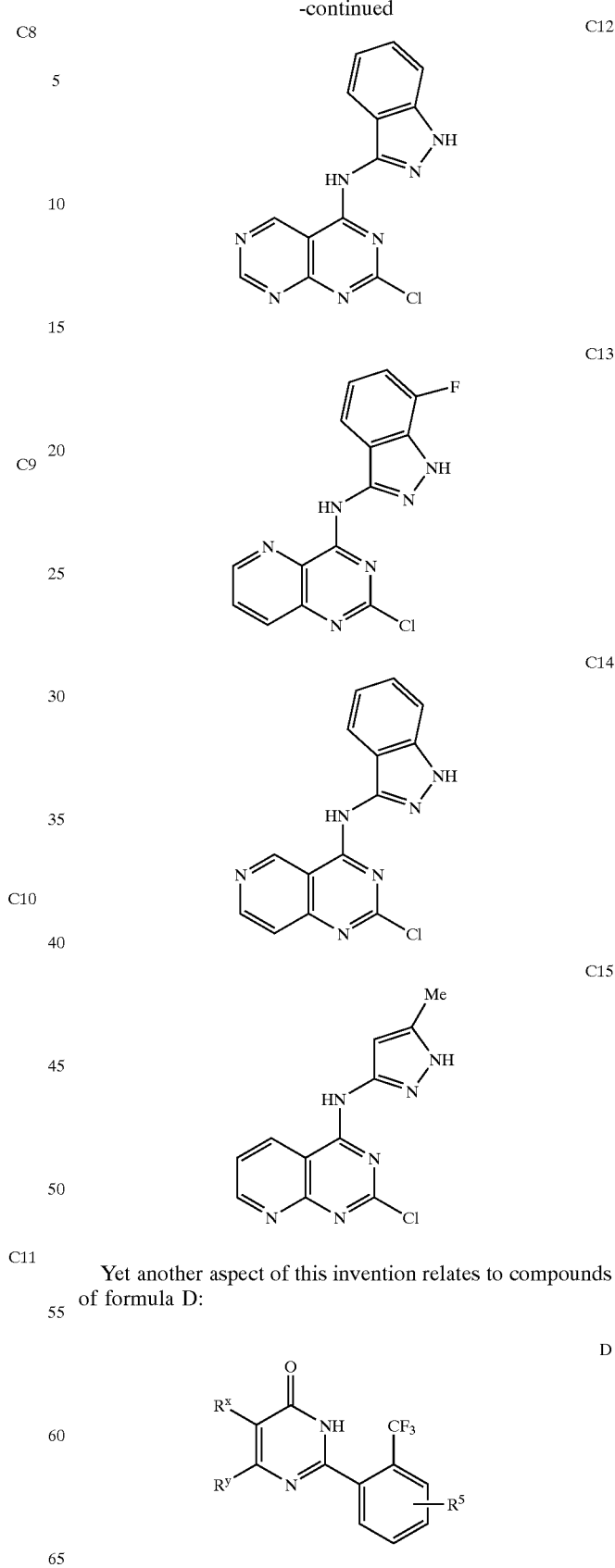
Yet another aspect of this invention relates to compounds of formula D:

where $R^5$, $R^x$ and $R^y$ are as defined above. Examples of formula D compounds and other useful pyrimidinone intermediates are shown below:
D1
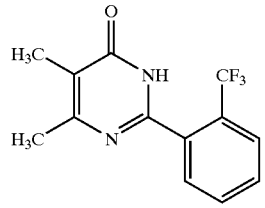
D2
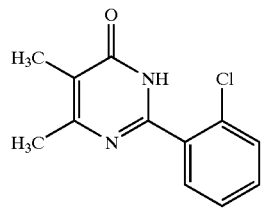
D3
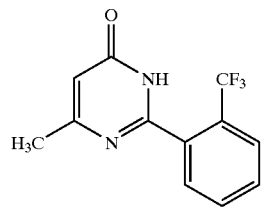
D4
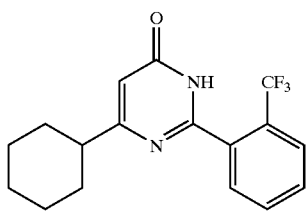
D5
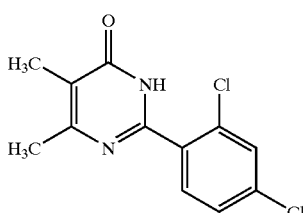
D6
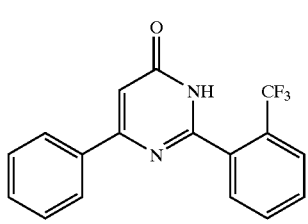
D7
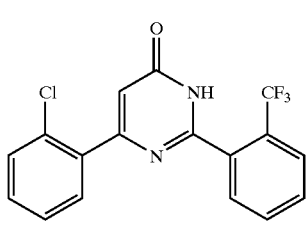
D8
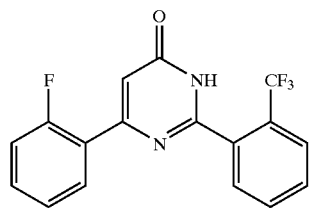
D9
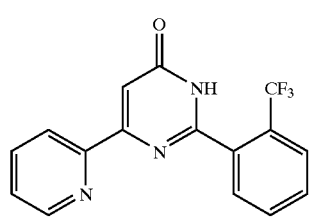
D10
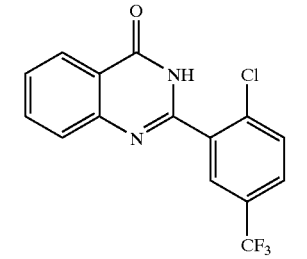
D11
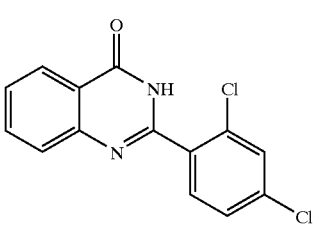
D12
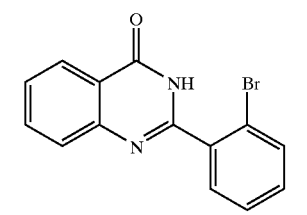
D13
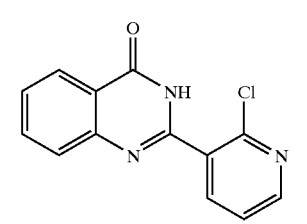
D14
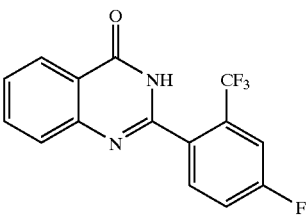

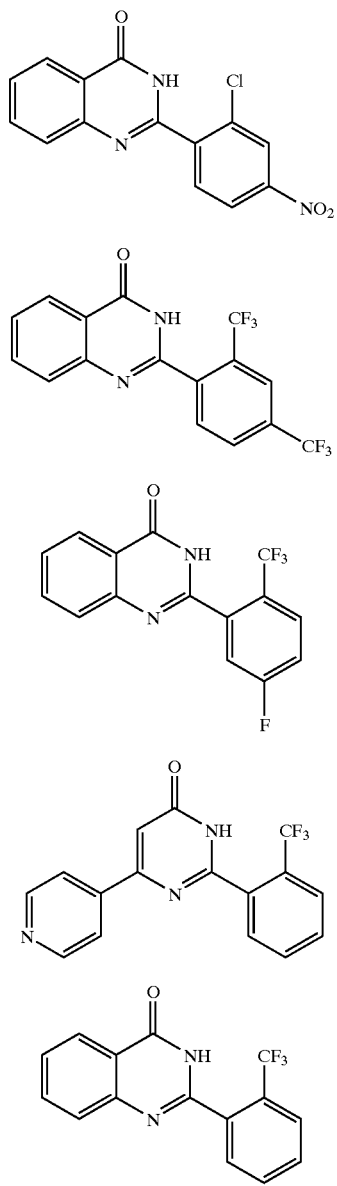

In order that the invention described herein may be more fully understood, the following examples are set forth. It should be understood that these examples are for illustrative purposes only and are not to be construed as limiting this invention in any manner.

SYNTHETIC EXAMPLES

The following HPLC methods were used in the analysis of the compounds as specified in the Synthetic Examples set forth below. As used herein, the term "$R_t$" refers to the retention time observed for the compound using the HPLC method specified.

HPLC-Method A:
Column: C18, 3 um, 2.1×50 mm, "Lighting" by Jones Chromatography.
Gradient: 100% water (containing 1% acetonitrile, 0.1% TFA) to 100% acetonitrile (containing 0.1% TFA) over 4.0 min, hold at 100% acetonitrile for 1.4 min and return to initial conditions. Total run time 7.0 min. Flow rate: 0.8 mL/min.

HPLC-Method B:
Column: $C_{18,\,5}$ um, 4.6×150 mm "Dynamax" by Rainin
Gradient: 100% water (containing 1% acetonitrile, 0.1% TFA) to 100% acetonitrile (containing 0.1% TFA) over 20 min, hold at 100% acetonitrile for 7.0 min and return to initial conditions. Total run time 31.5 min. Flow rate: 1.0 mL/min.

HPLC-Method C:
Column: Cyano, 5 um, 4.6×150 mm "Microsorb" by Varian.
Gradient: 99% water (0.1% TFA), 1% acetonitrile (containing 0.1% TFA) to 50% water (0.1% TFA), 50% acetonitrile (containing 0.1% TFA) over 20 min, hold for 8.0 min and return to initial conditions. Total run time 30 min. Flow rate: 1.0 mL/min.

HPLC-Method D:
Column: Waters (YMC) ODS-AQ 2.0×50 mm, S5, 120A.
Gradient: 90% water (0.2% Formic acid), 10% acetonitrile (containing 0.1% Formic acid) to 10% water (0.1% formic acid), 90% acetonitrile (containing 0.1% formic acid) over 5.0 min, hold for 0.8 min and return to initial conditions. Total run time 7.0 min.
Flow rate: 1.0 mL/min.

HPLC-Method E:
Column: 50×2.0 mm Hypersil C18 BDS; 5 μm
Gradient: elution 100% water (0.1% TFA), to 5% water (0.1% TFA), 95% acetonitrile (containing 0.1% TFA) over 2.1 min, returning to initial conditions after 2.3 min.
Flow rate: 1 mL/min.

Example 1

[2-(2-Clorophenyl)-5,6-dimethylpyrimidin-4-yl]-(5-Methyl-2H-pyrazol-3-yl)-amine (II-1)

$^1$HNMR (500 MHz, DMSO-d6) δ 10.4 (s, br, 1H), 7.74 (m, 2H), 7.68 (m, 1H), 7.60 (m, 1H), 6.39 (s, 1H), 2.52 (s, 3H), 2.30 (s, 3H), 2.22 (s, 3H); MS 314.1 (M+H).

Example 2

[2-(2-Chloro-phenyl)-6,7,8,9-tetrahydro-5H-cycloheptapyrimidin-4-yl]-(1H-indazol-3-yl)-amine (II-2)

Prepared in 30% yield. $^1$HNMR (500 MHz, DMSO-d6) δ 1.72 (m, 4H), 1.91 (m, 2H), 3.02 (m, 4H), 7.05 (t, 1H), 7.33 (t, 1H), 7.39 (m, 1H), 7.47 (d, 1H), 7.55 (m, 3H), 7.59 (d, 1H), 10.4 (m, 1H), 13.11 (br. s, 1H); EI-MS 390.2 (M+H); HPLC-Method A, $R_t$ 2.99 min.

Example 3

(5-Fluoro-1H-indazol-3-yl)-[2-(2-trifluoromethyl-phenyl)-5,6,7,8-tetrahydro-pyrido[3,4-d]pyrimidin-4-yl]-amine (II-3)

Compound II-18 (90 mg, 0.17 mmol) was treated with an equal weight of Pd/C (10%) in 4.4% formic acid in MeOH at room temperature for 14 h. The mixture was filtered through celite, the filtrate was evaporated, and crude product was purified by HPLC to provide 18 mg (24%) of the desired product as pale yellow solid. $^1$HNMR (500 MHz, DMSO-d6) δ12.9 (s, 1H), 9.51 (s, 1H), 9.26 (s, 2H), 7.72 (d, 1H), 7.63 (t, 1H), 7.58 (t, 1H), 7.49 (m, 2H), 7.21 (td, 1H), 7.15 (dd, 1H), 4.24 (s, 2H), 3.56 (m, 2H), 2.95 (m, 2H) ppm. MS (ES+): m/e=429.22 (M+H); HPLC-Method A, $R_t$ 2.88 min.

Example 4

[2-(2-Chloro-phenyl)-6,7,8,9-tetrahydro-5H-cycloheptapyrimidin-4-yl]-(7-fluoro-1H-indazol-3-yl)-amine (II-4)

Prepared in 52% yield to afford a white solid. $^1$HNMR (500 MHz, DMSO-d6) δ 1.72 (m, 4H), 1.92 (m, 2H), 3.00 (m, 4H), 7.02 (td, 1H), 7.20 (dd, 1H), 7.40 (m, 1H), 7.42 (d, 1H), 7.52 (m, 3H), 10.5 (m, 1H), 13.50 (br. s, 1H); EI-MS 408.2 (M+H); HPLC-Method A, $R_t$ 3.00 min.

Example 5

[2-(2-Chloro-phenyl)-6,7,8,9-tetrahydro-5H-cycloheptapyrimidin-4-yl]-(5-fluoro-1H-indazol-3-yl)-amine (II-5)

Prepared in 51% yield. $^1$HNMR (500 MHz, DMSO-d6) δ 1.71 (m, 4H), 1.91 (m, 2H), 3.01 (m, 4H), 7.24 (td, 1H), 7.41 (m, 2H), 7.54 (m, 4H), 10.5 (m, 1H), 13.1 (br. s, 1H); EI-MS 408.2 (M+H); HPLC-Method A, $R_t$ 3.05 min.

Example 6

[2-(2-Chloro-phenyl)-6,7,8,9-tetrahydro-5H-cycloheptapyrimidin-4-yl]-(5,7-difluoro-1H-indazol-3-yl)-amine (II-6)

Prepared according to Method C in 72% yield. $^1$HNMR (500 MHz, DMSO-d6) δ 1.72 (m, 4H), 1.91 (m, 2H), 3.01 (m, 4H), 7.31 (m, 2H), 7.41 (m, 1H), 7.54 (m, 3H), 10.5 (m, 1H), 13.6 (br. s, 1H); EI-MS 426.2 (M+H); HPLC-Method A, $R_t$ 3.21 min.

Example 7

(7-Fluoro-1H-indazol-3-yl)-[2-(2-trifluoromethyl-phenyl)-5,6,7,8-tetrahydroquinazolin-4-yl]-amine (II-7)

Prepared in 62% yield. $^1$HNMR (500 MHz, DMSO-d6) δ13.5 (s, br, 1H), 10.1 br, 1H), 7.75 (m, 4H), 7.33 (d, 1H), 7.17 (dd, 1H), 7.00 (td, 1H), 2.80 (m, 2H), 2.71 (m, 2H), 1.89 (br, 4H) ppm; LC-MS (ES+) 428.44 (M+H), (ES−) 426.43 (M−H); HPLC-Method A, $R_t$ 3.02 min.

Example 8

(5-Fluoro-1H-indazol-3-yl)-[2-(2-trifluoromethyl-phenyl)-5,6,7,8-tetrahydroquinazolin-4-yl]-amine (II-8)

Prepared in 53% yield. $^1$HNMR (500 MHz, DMSO-d6) δ13.1 (s, 1H), 10.2 (s, br, 1H), 7.75 (m, 4H), 7.50 (dd, 1H), 7.27 (dd, 1H), 7.21 (td, 1H), 2.80 (m, 2H), 2.72 (m, 2H), 1.88 (m, 4H) ppm; MS (ES+) 428.43 (M+H), (ES−) 426.43 (M−H); HPLC-Method A, $R_t$ 3.01 min.

Example 9

(5,7-Difluoro-1H-indazol-3-yl)-[2-(2-trifluoromethyl-phenyl)-5,6,7,8-tetrahydroquinazolin-4-yl]-amine (II-9)

Prepared in 37% yield. $^1$HNMR (500 MHz, DMSO-d6) δ13.7 (s, 1H), 10.2 (s, br, 1H), 7.80 (d, 1H), 7.76 (t, 1H), 7.69 (m, 2H), 7.31 (t, 1H), 7.18 (d, 1H), 2.81 (t, br, 2H), 2.72 (t, br, 2H), 1.90 (m, 4H) ppm; MS (ES+) 446.42 (M+H), (ES−) 444.37 (M−H); HPLC-Method A, $R_t$ 3.09 min.

Example 10

(5-Trifluoromethyl-1H-indazol-3-yl)-[2-(2-trifluoromethyl-phenyl)-5,6,7,8-tetrahydroquinazolin-4-yl]-amine (II-10)

Prepared by Method C in ethanol in 35% yield. $^1$HNMR (500 MHz, DMSO-d6) δ13.2 (s, 1H), 10.1 (s, br, 1H), 8.01 (s, 1H), 7.76 (d, 1H), -7.66 (m, 4H), 7.57 (d, 1H), 2.79 (m, 2H), 2.73 (m, 2H), 1.89 (m, 4H) ppm. MS (ES+) 478.45 (M+H), (ES−) 476.42 (M−H); HPLC-Method A, $R_t$ 3.21 min.

Example 11

(5,7-difluoro-1H-indazol-3-yl)-[2-(2-trifluoromethyl-phenyl)-6,7,8,9-tetrahydro-5H-cycloheptapyrimidin-4-yl]-amine (II-11)

Prepared in 60% yield. White solid. $^1$HNMR (500 MHz, DMSO-d6) δ 1.72 (m, 4H), 1.91 (m, 2H), 3.01 (m, 4H), 7.15 (dd, 1H), 7.30 (td, 1H), 7.66 (m, 2H), 7.72 (t, 1H), 7.78 (d, 1H), 10.2 (m, 1H), 13.5 (br. s, 1H); EI-MS 460.2 (M+H); HPLC-Method A, $R_t$ 3.13 min.

Example 12

(6-Benzyl-2-(2-trifluoromethyl-phenyl)-5,6,7,8-tetrahydro-pyrido[4,3-d]pyrimidin-4-yl)-(5-fluoro-1H-indazol-3-yl)-amine (II-12)

Prepared in 49% yield. $^1$HNMR (500 MHz, DMSO-d6) δ12.8 (s, 1H), 9.11 (s, 1H), 7.68 (d, 1H), 7.58 (t, 1H), 7.53 (t, 1H), 7.44 (m, 4H), 7.37 (t, 2H), 7.29 (t, 1H), 7.19 (m, 2H), 3.78 (s, 2H), 3.61 (s, 2H), 2.81 (s, br, 4H) ppm; LC-MS (ES+) 519.24 (M+H); HPLC-Method A, $R_t$ 3.11 min.

Example 13

(1H-Indazol-3-yl)-[2-(2-trifluoromethyl-phenyl)-6,7,8,9-tetrahydro-5H-cycloheptapyrimidin-4-yl]-amine (II-13)

Prepared in 40% yield. $^1$HNMR (500 MHz, DMSO-d6) δ 1.70 (m, 4H), 1.90 (m, 2H), 3.00 (m, 4H), 7.01 (t, 1H), 7.30 (td, 1H), 7.44 (d, 1H), 7.49 (d, 1H), 7.68 (m, 3H), 7.77 (d, 1H), 10.01 (m, 1H), 12.83 (s, 1H); EI-MS 424.2 (M+H); HPLC-Method A, $R_t$ 3.17 min.

Example 14

(7-Fluoro-1H-indazol-3-yl)-[2-(2-trifluoromethyl-phenyl)-6,7,8,9-tetrahydro-5H-cycloheptapyrimidin-4-yl]-amine (II-14)

Prepared in 78% yield. $^1$HNMR (500 MHz, DMSO-d6) δ 1.71 (m, 4H), 1.91 (m, 2H), 3.00 (m, 4H), 6.98 (td, 1H), 7.16 (dd, 1H), 7.31 (d, 1H), 7.68 (m, 3H), 7.77 (d, 1H), 10.25 (m, 1H), 13.40 (br. s, 1H); EI-MS 442.2 (M+H); HPLC-Method A, $R_t$ 3.12 min.

Example 15

(5-Fluoro-1H-indazol-3-yl)-[2-(2-trifluoromethyl-phenyl)-6,7,8,9-tetrahydro-5H-cycloheptapyrimidin-4-yl]-amine (II-15)

Prepared in 63% yield. $^1$HNMR (500 MHz, DMSO-d6) δ 1.71 (m, 4H), 1.91 (m, 2H), 3.00 (m, 4H), 7.20 (td, 1H), 7.25 (dd, 1H), 7.49 (dd, 1H), 7.69 (br. t, 2H), 7.74 (m, 1H), 7.79 (d, 1H), 10.35 (m, 1H), 13.00 (br. s, 1H); EI-MS 442.2 (M+H); HPLC-Method A, $R_t$ 3.21 min.

Example 16

(5-Fluoro-1H-indazol-3-yl)-[2-(2-trifluoromethyl-phenyl)-5,6,7,8-tetrahydro-pyrido[4,3-d]pyrimidin-4-yl]-amine (II-16)

A solution of compound II-12 (45 mg, 0.087 mmol) in methanol (4.4% HCOOH) was treated with an equal weight of Pd/C (10%) at room temperature for 14 h. The mixture was filtered through celite, the filtrate evaporated, and the crude product was purified by preparative HPLC to provide 15 mg (41%) of the desired product as yellow solid. $^1$HNMR (500 MHz, DMSO-d6) δ12.9 (s, 1H), 9.52 (s, 1H), 9.32 (s, 2H, TFA-OH), 7.72 (d, 1H), 7.59 (m, 2H), 7.49 (m, 2H), 7.21 (m, 1H), 7.15 (m, 1H), 4.31 (s, 2H), 3.55 (s, 2H), 3.00 (m, 2H) ppm; LC-MS (ES+) 429.20 (M+H); HPLC-Method A, $R_t$ 2.79 min.

Example 17

(1H-indazol-3-yl)-[2-(2-trifluoromethyl-phenyl)-5,6,7,8-tetrahydroquinazolin-4-yl]-amine (II-17)

Prepared in 58% yield. $^1$HNMR (500 MHz, DMSO-d6) δ13.0 (s, 1H), 10.3 (s, br, 1H), 7.74 (m, 4H), 7.51 (d, 1H), 7.47 (d, 1H), 7.32 (t, 1H), 7.03 (t, 1H), 2.82 (m, 2H), 2.73 (m, 2H), 1.90 (m, 4H) ppm; LC-MS (ES+) 410.21 (M+H); HPLC-Method A, $R_t$ 2.99 min.

Example 18

(7-Benzyl-2-(2-trifluoromethyl-phenyl)-5,6,7,8-tetrahydro-pyrido[4,3-d]pyrimidin-4-yl)-(5-fluoro-1H-indazol-3-yl)-amine (II-18)

Prepared from compound B11 in 92% yield. $^1$HNMR (500 MHz, DMSO-d6) δ12.9 (s, 1H), 10.5 (s, br, 1H), 9.58 (s, 1H, TFA-OH), 7.71 (d, 1H), 7.52 (m, 9H), 7.19 (m, 2H), 4.57 (s, 2H), 4.20 (m, 2H), 3.70 (m, 2H), 3.00 (m, 2H) ppm; LC-MS (ES+) 519.23 (M+H); HPLC-Method A, $R_t$ 3.23 min.

Example 19

(1H-Indazol-3-yl)-[6-methyl-2-(2-trifluoromethyl-phenyl)-pyrimidin-4-yl]-amine (II-19)

Prepared in 42% yield. Melting point 235–237° C.; $^1$HNMR (500 MHz, DMSO) δ 2.44 (3H, s), 7.09 (1H, J=7.5 Hz, t), 7.40 (1H, J=7.1 Hz, t), 7.49 (1H, J=8.3 Hz, d), 7.70 (3H, m), 7.79 (1H, J=7.3 Hz, t), 7.87 (1H, J=8.3 Hz, d), 8.03 (1H, J=7.7 Hz, d), 10.3 (1H, s), 12.6 (1H, s) ppm; HPLC-Method A, $R_t$ 2.958 min; MS (FIA) 370.2 (M+H)$^+$.

Example 20

(1H-Indazol-3-yl)-[6-phenyl-2-(2-trifluoromethyl-phenyl)-pyrimidin-4-yl]-amine (II-20)

Prepared in 32% yield. $^1$HNMR (500 MHz, DMSO) δ 6.94 (1H, J=7.4 Hz, t), 7.24 (1H, J=7.4 Hz, t), 7.33 (1H, J=8.4 Hz, d), 7.42 (3H, m), 7.57 (1H, J=7.3 Hz, t), 7.68 (2H, m), 7.75 (1H, J=7.9 Hz, d), 7.93 (3H, m), 8.18 (1H, br s), 10.45 (1H, br s), 12.5 (1H, br s) ppm; HPLC-Method A, $R_t$ 4.0 min; MS (FIA) 432.2 (M+H)$^+$.

Example 21

(1H-Indazol-3-yl)-[6-(pyridin-4-yl)-2-(2-trifluoromethyl-phenyl)-pyrimidin-4-yl]-amine (II-21)

Prepared in 12% yield. $^1$HNMR (500 MHz, DMSO) δ 7.16 (1H, J=7.4 Hz, t), 7.46 (1H, J=7.6 Hz, t), 7.56 (1H, J=8.3 Hz, d), 7.80 (1H, J=7.2 Hz, t), 7.90 (2H, m), 7.97 (1H, J=7.8 Hz, d), 8.09 (1H, br), 8.22 (2H, J=4.9 Hz, d), 8.45 (1H, br s), 8.93 (2H, J=4.8 Hz, d), 10.9 (1H, s), 12.8 (1H, br s) ppm; HPLC-Method A, $R_t$ 3.307 min; MS (FIA) 433.2 (M+H)$^+$

Example 22

(1H-Indazol-3-yl)-[6-(pyridin-2-yl)-2-(2-trifluoromethyl-phenyl)-pyrimidin-4-yl]-amine (II-22)

Prepared in 42% yield. $^1$HNMR (500 MHz, DMSO) δ 7.07 (1H, J=7.4 Hz, t), 7.36 (1H, J=7.4 Hz, t), 7.46 (1H, J=7.4 Hz, d), 7.53 (1H, J=5.0 Hz, t), 7.70 (1H, J=7.4 Hz, t), 7.79 (1H, J=7.1 Hz, t), 7.83 (1H, J=7.4 Hz, d), 7.88 (1H, J=7.8 Hz, d), 7.97 (1H, J=7.7 Hz, t), 8.02 (1H, J=5.5 Hz, br d), 8.36 (1H, J=7.8 Hz, d), 8.75 (2H, J=4.1 Hz, d), 10.5 (1H, br s), 12.7 (1H, br s) ppm; HPLC-Method A, $R_t$ 3.677 min; MS (FIA) 433.2 (M+H)$^+$.

Example 23

[6-(2-Chlorophenyl)-2-(2-trifluoromethyl-phenyl)-pyrimidin-4-yl]-(1H-indazol-3-yl)-amine (II-23)

Prepared in 44% yield; $^1$HNMR (500 MHz, DMSO) δ 7.08 (1H, J=7.5 Hz, t), 7.37 (1H, J=7.5 Hz, t), 7.45 (1H, J=8.4 Hz, d), 7.51 (2H, m), 7.61 (1H, J=7.4, 1.9 Hz, dd), 7.69 (2H, m), 7.79 (2H, J=4.0 Hz, d), 7.86 (3H, J=7.8 Hz, d), 8.04 (2H, J=6.2 Hz, br d), 10.7 (1H, br s), 12.6 (1H, br s) ppm; HPLC-Method A, $R_t$ 3.552 min; MS (FIA) 466.2 (M+H)$^+$.

Example 24

[5,6-Dimethyl-2-(2-trifluoromethyl-phenyl)-pyrimidin-4-yl]-(1H-indazol-3-yl)-amine (II-24)

Prepared in 35% yield; mp 183–186° C.; $^1$HNMR (500 MHz, DMSO) δ 2.14 (3H, s), 2.27 (3H, s), 6.85 (1H, J=7.5 Hz, t), 7.15 (1H, J=7.6 Hz, t), 7.32 (3H, m), 7.38 (1H, J=7.5 Hz, t), 7.42 (1H, J=7.4 Hz, t), 7.53 (1H, J=7.6 Hz, d), 8.88 (1H, s), 12.5 (1H, s) ppm; HPLC-Method A, $R_t$ 2.889 min.; MS (FIA) 384.2 (M+H)'.

Example 25

[5,6-Dimethyl-2-(2-trifluoromethyl-phenyl)-pyrimidin-4-yl]-(5-fluoro-1H-indazol-3-yl)-amine (II-25)

Prepared in 44% yield. Melting point 160–163° C.; $^1$HNMR (500 MHz, DMSO) δ 2.27 (3H, s), 2.40 (3H, s), 7.16 (2H, m), 7.44 (2H, m), 7.52 (1H, J=7.4 Hz, t), 7.57 (1H, J=7.4 Hz, t), 7.67 (1H, J=7.8 Hz, d), 9.03 (1H, s), 12.75 (1H, s) ppm; HPLC-Method A, $R_t$ 2.790 min; MS (FIA) 402.2 (M+H)$^+$.

Example 26

[2-(2-Chlorophenyl)-5,6-dimethyl-pyrimidin-4-yl]-(1H-indazol-3-yl)-amine (II-26)

Prepared in 30% yield. $^1$HNMR (500 MHz, DMSO) δ 2.14 (3H, s), 2.33 (3H, s), 6.84 (1H, J=7.4 Hz, t), 7.13 (1H, J=7.4 Hz, t), 7.19 (1H, J=6.9 Hz, br t), 7.27 (1H, J=7.4 Hz, d), 7.32 (3H, br m), 7.37 (1H, J=7.1 Hz, d), 10.0 (1H, br), 12.8 (1H, br s) ppm; δ 2.919 min; MS (FIA) 350.1 (M+H)$^+$.

Example 27

[5,6-Dimethyl-2-(2-trifluoromethyl-phenyl)-pyrimidin-4-yl]-(7-fluoro-1H-indazol-3-yl)-amine (II-27)

Prepared in 92% yield. $^1$HNMR (500 MHz, DMSO) δ 2.33 (3H, s), 2.50 (3H, s), 6.97 (1H, m), 7.15 (1H, m), 7.30

(1H, J=8.1 Hz, d), 7.65 (3H, m), 7.76 (1H, J=7.5 Hz, d), 10.0 (1H, s), 13.4 (1H, s) ppm; HPLC-Method A, $R_t$ 3.053 min; MS (FIA) 402.2 (M+H)+.

Example 28

(5,7-Difluoro-1H-indazol-3-yl)-[5,6-Dimethyl-2-(2-trifluoromethyl-phenyl)-pyrimidin-4-yl]-amine (II-28)

Prepared in 50% yield. ¹HNMR (500 MHz, DMSO) δ 2.42 (3H, s), 2.63 (3H, s), 7.22 (1H, J=7.6 Hz, d), 7.38 (1H, J=9.3, 1.7 Hz, dt), 7.71 (1H, m), 7.75 (1H, J=7.0 Hz, d), 7.79 (1H, J=6.7 Hz, d), 7.86 (1H, J=8.0 Hz, d), 10.0 (1H, s), 13.2 (1H, s) ppm; HPLC-Method A, $R_t$ 3.111 min; MS (FIA) 420.2 (M+H)+.

Example 29

[2-(2-Chlorophenyl)-5,6-dimethyl-pyrimidin-4-yl]-(5,7-difluoro-1H-indazol-3-yl)-amine (II-29)

Prepared in 58% yield. ¹HNMR (500 MHz, DMSO) δ 2.47 (3H, s), 2.66 (3H, s), 7.44 (2H, m), 7.53 (1H, m), 7.64 (3H, m), 10.4 (1H, br), 13.8 (1H, br s) ppm; HPLC-Method A, $R_t$ 2.921 min; MS (FIA) 386.1 (M+H)+.

Example 30

[2-(2-Chlorophenyl)-5,6-dimethyl-pyrimidin-4-yl]-(7-fluoro-1H-indazol-3-yl)-amine (II-30)

Prepared in 70% yield. ¹HNMR (500 MHz, DMSO) δ 2.35 (3H, s), 2.51 (3H, s), 7.03 (1H, J=7.8, 4.4 Hz, dt), 7.22 (1H, m), 7.33 (1H, J=7.4 Hz, t), 7.42 (1H, m), 9.19 (1H, s), 13.3 (1H, s) ppm; HPLC-Method A, $R_t$ 2.859 min; MS (FIA) 368.2 (M+H)+.

Example 31

[2-(2-Chlorophenyl)-5,6-dimethyl-pyrimidin-4-yl]-(5-fluoro-1H-indazol-3-yl)-amine (II-31)

Prepared in 86% yield. ¹HNMR (500 MHz, DMSO) δ 2.49 (3H, s), 2.68 (3H, s), 7.38 (1H, J=9.0 Hz, t), 7.54 (2H, m), 7.67 (4H, m), 10.5 (1H, br), 13.2 (1H, br s) ppm; HPLC-Method A, $R_t$ 2.850 min; MS (FIA) 368.1 (M+H)+.

Example 32

[2-(2,4-Dichlorophenyl)-5,6-dimethyl-pyrimidin-4-yl]-(1H-indazol-3-yl)-amine (II-32)

Prepared in 52% yield. ¹HNMR (500 MHz, DMSO) δ 2.46 (3H, s), 2.64 (3H, s), 7.16 (1H, J=7.5 Hz, t), 7.46 (1H, J=7.6 Hz, t), 7.61 (2H, m), 7.68 (2H, J=8.2 Hz, d), 7.82 (1H, m), 10.2 (1H, br), 13.0 (1H, br s) ppm; HPLC-Method A, $R_t$ 2.983 min; MS (FIA) 384.1 (M+H).

Example 33

(5-Methyl-2H-pyrazol-3-yl)-[2-(2-methylphenyl)-quinazolin-4-yl]-amine (II-33)

¹HNMR (DMSO) δ 1.21 (3H, s), 2.25 (3H, s), 6.53 (1H, s), 7.38 (4H, m), 7.62 (1H, d), 7.73 (1H, d), 7.81 (1H, d), 7.89 (1H, t), 8.70 (1H, s), 12.20 (1H, s); MS 316.3 (M+H)+.

Example 34

[2-(2,4-Difluorophenyl)-quinazolin-4-yl]-(5-methyl-2H-pyrazol-3-yl)-amine (II-34)

¹HNMR (500 MHz, DMSO-d6) δ12.4 (br s, 1H), 10.8 (br s, 1H), 8.58 (d, 1H), 7.97 (m, 1H), 8.36 (m, 1H), 7.85 (m, 1H), 7.60 (m, 1H), 6.62 (m, 1H), 2.30 (s, 3H); MS 338.07 (M+H).

Example 35

[2-(2,5-Dimethoxyphenyl)-quinazolin-4-yl]-(5-methyl-2H-pyrazol-3-yl)-amine (II-35)

¹HNMR (500 MHz, DMSO-d6) δ12.5 (br s, 1H), 8.68 (br, 1H), 7.92 (t, J=7.5 Hz, 1H), 7.86 (d, J=8.2 Hz, 1H), 7.65 (t, J=7.5 Hz, 1H), 7.45 (s, 1H), 7.14 (m, 2H), 6.51 (s, 1H), 3.79 (s, 3H), 3.67 (s, 3H), 2.14 (s, 3H); MS 362.2 (M+H).

Example 36

[2-(2-Chlorophenyl)-quinazolin-4-yl]-(5-methyl-2H-pyrazol-3-yl)-amine (II-36)

¹HNMR (500 MHz, DMSO-d6) δ11.8 (br, 1H), 8.80 (d, J=8.3 Hz, 1H), 8.00 (t, J=7.6 Hz, 1H), 7.82 (d, J=8.3 Hz, 1H), 7.78 (m, 2H), 7.67 (d, J=7.8 Hz, 1H), 7.61 (t, J=7.0 Hz, 1H), 7.55 (t, J=7.4 Hz, 1H), 6.56 (s, 1H), 2.18 (s, 3H); MS 336.1 (M+H).

Example 37

[2-(2-Methoxyphenyl)-quinazolin-4-yl]-(5-methyl-2H-pyrazol-3-yl)-amine (II-37)

¹HNMR (500 MHz, DMSO-d6) δ8.78 (s, br, 1H), 8.00 (t, J=7.4 Hz, 1H), 7.90 (m, 2H), 7.74 (t, J=7.5 Hz, 1H), 7.63 (t, J=7.3 Hz, 1H), 7.30 (d, J=8.4 Hz, 1H), 7.18 (t, J=7.5 Hz, 1H), 6.58 (s, br, 1H), 3.90 (s, 3H), 2.21 (s, 3H); MS 332.1 (M+H).

Example 38

[2-(2,6-Dimethylphenyl)-quinazolin-4-yl]-(5-methyl-2H-pyrazol-3-yl)-amine (II-38)

¹HNMR (500 MHz, DMSO-d6) δ12.2 (s, br, 2H), 8.88 (d, J=7.7 Hz, 1H), 8.05 (t, J=7.7 Hz, 1H), 7.80 (m, 2H), 7.37 (t, J=7.6 Hz, 1H), 7.21 (d, J=7.7 Hz, 2H), 6.36 (s, 1H), 2.16 (s, 3H), 2.15 (s, 6H); MS 330.1 (M+H).

Example 39

[2-(2-Acetylphenyl)-quinazolin-4-yl]-(5-methyl-2H-pyrazol-3-yl)-amine (II-39)

¹HNMR (500 MHz, DMSO-d6) δ12.35 (s, br, 1H), 8.93 (d, J=8.4 Hz, 1H), 8.37 (d, J=8.6 Hz, 1H), 8.20 (d, J=7.6 Hz, 1H), 8.11 (t, J=8.0 Hz, 2H), 7.89 (m, 2H), 7.77 (m, 2H), 6.93 (s, 1H), 2.33 (s, 3H), 2.04 (s, 3H) MS 344.1 (M+H).

Example 40

[2-(2,3-Dimethylphenyl)-quinazolin-4-yl]-(5-methyl-2H-pyrazol-3-yl)-amine (II-40)

¹HNMR (500 MHz, DMSO-d6) δ12.6 (s, br, 1H), 12.1 (s, br, 1H), 8.91 (d, J=7.7 Hz, 1H), 8.14 (t, J=7.2 Hz, 1H), 7.95 (d, J=8.4 Hz, 1H), 7.89 (t, J=7.7 Hz, 1H), 7.58 (d, J=7.6 Hz, 1H), 7.53 (d, J=7.0 Hz, 1H), 7.42 (t, J=7.6 Hz, 1H), 6.60 (s, 1H), 2.43 (s, 3H), 2.35 (s, 3H), 2.32 (s, 3H); MS 330.1 (M+H).

Example 41

(5-Methyl-2H-pyrazol-3-yl)-[2-(2-trifluoromethylphenyl)-quinazolin-4-yl]-amine (II-41)

¹HNMR (500 MHz, DMSO-d6) δ12.3 (s, 1H), 10.5 (s, 1H), 8.77 (d, J=8.2 Hz, 1H), 7.92 (m, 2H), 7.85 (m, 3H), 7.56 (t, J=8.1 Hz, 1H), 7.67 (t, J=7.4 Hz, 1H), 6.63 (s, 1H), 2.27 (s, 3H); MS 370.1 (M+H).

Example 42

[2-(2-Ethylphenyl)-quinazolin-4-yl]-(5-Methyl-2H-pyrazol-3-yl)-amine (II-42)

$^1$HNMR (500 MHz, DMSO-d6) δ8.80 (m, 1H), 8.02 (s, br, 1H), 7.82 (d, J=8.4 Hz, 1H), 7.77 (m, 1H), 7.62 (d, J=7.6 Hz, 1H), 7.54 (m, 1H), 7.41 (m, 2H), 6.40 (s, 1H), 2.75 (q, J=7.1 Hz, 2H), 2.17 (s, 3H), 0.99 (t, J=7.5 Hz, 3H); MS 330.1 (M+H).

Example 43

(2-Biphenyl-2-yl-quinazolin-4-yl)-(5-methyl-2H-pyrazol-3-yl)-amine (II-43)

$^1$HNMR (500 MHz, DMSO-d6) δ 8.76 (d, J=7.6 Hz, 1H), 8.04 (m, 1H), 7.75 (m, 6H), 7.30 (m, 5H), 5.34 (s, 1H), 2.14 (s, 3H); MS 378.2 (M+H).

Example 44

[2-(2-Hydroxyphenyl)-quinazolin-4-yl]-(5-Methyl-2H-pyrazol-3-yl)-amine (II-44)

$^1$HNMR (500 MHz, DMSO-d6) δ10.9 (s, br, 1H), 8.62 (d, J=8.2 Hz, 1H), 8.28 (d, J=7.9 Hz, 1H), 7.87 (m, 2H), 7.60 (t, J=7.9 Hz, 1H), 7.37 (t, J=7.8 Hz, 1H), 6.92 (m, 2H), 6.45 (s, 1H), 2.27 (s, 3H); MS 318.1 (M+H).

Example 45

[2-(2-Ethoxyphenyl)-quinazolin-4-yl]-(5-Methyl-2H-pyrazol-3-yl)-amine (II-45)

$^1$HNMR (500 MHz, DMSO-d6) δ12.1 (s, br, 1H), 8.75 (d, J=8.3 Hz, 1H), 7.97 (t, J=7.8 Hz, 1H), 7.82 (d, J=8.3 Hz, 1H), 7.78 (d, J=7.5 Hz, 1H), 7.70 (t, J=7.8 Hz, 1H), 7.56 (t, J=7.8 Hz, 1H), 7.22 (d, J=8.4 Hz, 1H), 7.12 (t, J=7.6 Hz, 1H), 6.55 (s, 1H), 4.11 (q, J=6.9 Hz, 2H), 2.16 (s, 3H), 1.22 (t, J=6.9 Hz, 3H); MS 346.1 (M+H).

Example 46

[5-(Thiophen-2-yl)-2H-pyrazol-3-yl]-[2-(2-trifluoromethylphenyl)-quinazolin-4-yl]-amine (II-46)

$^1$HNMR (500 MHz, DMSO-d6) δ8.04 (d, J=8.3 Hz, 1H), 8.05 (dd, J=7.3, 8.2 Hz, 1H), 7.93 (d, J=6.5 Hz, 1H), 7.81 (m, 5H), 7.34 (d, J=5.0 Hz, 1H), 7.25 (m, 1H), 7.00 (m, 1H), 6.87 (s, 1H); MS 438.1 (M+H).

Example 47

[4-(Thiophen-2-yl)-2H-pyrazol-3-yl]-[2-(2-trifluoromethylphenyl)-quinazolin-4-yl]-amine (II-47)

Prepared according to Method B. $^1$HNMR (500 MHz, DMSO-d6) δ 6.97 (m, 1H), 7.08 (m, 1H), 7.27 (m, 1H), 7.36 (m, 1H), 7.66 (m, 2H), 7.77 (m, 3H), 7.83 (m, 1H), 8.00 (m, 1H), 8.18 (s, 1H), 8.62 (d, J=8.2 Hz, 1H), 10.7 (br. s, 1H); EI-MS 438.1 (M+H); HPLC-Method A, $R_t$ 2.97 min.

Example 48

(4-Phenyl-2H-pyrazol-3-yl)-[2-(2-trifluoromethylphenyl)-quinazolin-4-yl]-amine (II-48)

Prepared according to Method B. $^1$HNMR (500 MHz, DMSO-d6) δ 7.05 (br. s, 1H), 7.14 (t, J=7.8 Hz, 1H), 7.25 (m, 3H), 7.43 (m, 2H), 7.60 (m, 2H), 7.73 (m, 2H), 7.80 (d, 1H), 7.95 (m, 1H), 8.12 (br. s, 1H), 8.60 (m, 1H), 10.6 (br. s, 1H); EI-MS 432.2 (M+H); HPLC-Method A, $R_t$ 3.04 min.

Example 49

(5-tert-Butyl-2H-pyrazol-3-yl)-[2-(2-trifluoromethylphenyl)-quinazolin-4-yl]-amine (II-49)

$^1$HNMR (500 MHz, DMSO-d6) δ 8.76 (d, J=8.3 Hz, 1H), 7.94 (m, 2H), 7.79 (m, 4H), 7.70 (t, J=7.6 Hz, 1H), 6.51 (s, 1H), 1.16 (s, 9H); MS 412.2 (M+H).

Example 50

(5-Phenyl-2H-pyrazol-3-yl)-[2-(2-trifluoromethylphenyl)-quinazolin-4-yl]-amine (II-50)

$^1$HNMR (500 MHz, DMSO-d6) δ 7.09 (s, 1H), 7.36 (td, J=7.8, 1.1 Hz, 1H), 7.46 (t, J=7.8 Hz, 2H), 7.65 (br. d, J=8.1 Hz, 2H), 7.78 (m, 2H), 7.90 (m, 4H), 7.95 (d, J=7.7 Hz, 1H), 8.00 (t, J=7.8 Hz, 1H), 8.81 (d, J=8.6 Hz, 1H), 11.29 (br. s, 1H); EI-MS 432.1 (M+H); HPLC-Method A, $R_t$ 3.24 min.

Example 51

(4,5-Diphnyl-2H-pyrazol-3-yl)-[2-(2-trifluoromethylphenyl)-quinazolin-4-yl]-amine (II-51)

$^1$HNMR (500 MHz, DMSO-d6) δ 7.13 (m, 1H), 7.18 (m, 5H), 7.36 (m, 5H), 7.62 (m, 3H), 7.73 (m, 2H), 7.85 (m, 1H), 8.48 (d, J=8.7 Hz, 1H), 10.02 (s, 1H), 13.19 (s, 1H); EI-MS 508.2 (M+H); HPLC-Method A, $R_t$ 3.39 min.

Example 52

(4-Carbamoyl-2H-pyrazol-3-yl)-[2-(2-trifluoromethylphenyl)-quinazolin-4-yl]-amine (II-52)

Prepared in 40% yield. $^1$HNMR (500 MHz, DMSO-d6): δ 12.85 (s, 1H), 12.77 (s, 1H), 11.80 (s, 1H), 10.80 (s, 1H), 8.35–7.42 (m, 9H); MS 399.13 (M+H) HPLC-Method A, $R_t$ 2.782 min.

Example 53

(2H-Pyrazol-3-yl)-[2-(2-trifluoromethylphenyl)-quinazolin-4-yl]-amine (II-53)

Prepared in 38% yield. $^1$HNMR (500 MHz, DMSO-d6) δ 12.52 (s, 1H), 10.65 (s, 1H), 8.75 (d, 1H), 7.91–7.68 (m, 8H), 6.87 (s, 1H). MS: (M+H) 356.17. HPLC-Method A, $R_t$ 2.798 min.

Example 54

(5-Hydroxy-2H-pyrazol-3-yl)-[2-(2-trifluoromethylphenyl)-quinazolin-4-yl]-amine (II-54)

Prepared in 36% yield; $^1$HNMR (500 MHz, DMSO-d6) δ 10.61 (s, 1H), 8.75 (s, 1H), 8.03–7.75 (m, 9H), 5.97 (s, 1H); MS 372.18 (M+H); HPLC-Method A, $R_t$ 2.766 min.

Example 55

(5-Cyclopropyl-2H-pyrazol-3-yl)-[2-(2-trifluoromethyl-phenyl)-quinazolin-4-yl]-amine (II-55)

Prepared in 30% yield. $^1$HNMR (500 MHz, DMSO-d6) δ12.21 (s, 1H), 10.45 (s, 1H), 8.68 (s, 1H), 7.89–7.45 (m, 8H), 6.48 (s, 1H), 0.89 (m, 2H), 0.62 (s, 2H). MS 396.18 (M+H); HPLC-Method A, $R_t$ 3.069 min.

Example 56

(5-Methoxymethyl-2H-pyrazol-3-yl)-[2-(2-trifluoromethyl-phenyl)-quinazolin-4-yl]-amine (II-56)

Prepared in 33% yield; $^1$HNMR (500 MHz, DMSO-d6) δ 12.51 (s, 1H), 10.48 (s, 1H), 8.60 (s, 1H), 7.81–7.55 (m, 7H), 6.71 (s, 1H), 4.28 (s, 2H), 3.18 (s, 3H). MS 400.19 (M+H): HPLC-Method A, $R_t$ 2.881 min.

Example 57

(1H-indazol-3-yl)-[2-(2-trifluoromethyl-phenyl)-quinazolin-4-yl]-amine (II-57)

Prepared to afford 51 mg (78% yield) as pale yellow solid. $^1$HNMR (500 MHz, DMSO-d6) δ12.7 (s, 1H), 10.4 (s, 1H), 8.55 (d, 1H), 7.81 (t, 1H), 7.71 (d, 1H), 7.61 (d, 1H), 7.58 (t, 1H), 7.46 (m, 4H), 7.36 (d, 1H), 7.22 (t, 1H), 6.91 (t, 1H) ppm; LC-MS (ES+) 406.16 (M+H), (ES−) 404.19 (M−H); HPLC-Method A, $R_t$ 3.00 min.

Example 58

(4-Chloro-1H-indazol-3-yl)-[2-(2-trifluoromethyl-phenyl)-quinazolin-4-yl]-amine (II-58)

Prepared in DMF (70% yield) as pale yellow solid. $^1$HNMR (500 MHz, DMSO-d6) δ13.3 (s, br, 1H), 10.9 (s, br, 1H), 8.60 (d, 1H), 7.97 (t, 1H), 7.81 (d, 1H), 7.75 (t, 1H), 7.67 (d, 1H), 7.63 (dd, 1H), 7.57 (m, 2H), 7.43 (d, 1H), 7.28 (dd, 1H), 7.08 (d, 1H) ppm; LC-MS (ES+) 440.10 (M+H), (ES−) 438.12 (M−H); HPLC-Method A, $R_t$ 3.08 min.

Example 59

(5-Fluoro-1H-indazol-3-yl)-[2-(2-trifluoromethyl-phenyl)-quinazolin-4-yl]-amine (II-59)

Prepared in DMF (34% yield) as pale yellow solid. $^1$HNMR (500 MHz, DMSO-d6) δ13.0 (s, 1H), 10.6 (s, 1H), 8.72 (d, 1H), 7.99 (t, 1H), 7.89 (d, 1H), 7.79 (d, 1H), 7.75 (t, 1H), 7.68 (m, 3H), 7.56 (dd, 1H), 7.39 (d, 1H), 7.28 (t, 1H) ppm; LC-MS (ES+) 424.12 (M+H), (ES−) m/e=422.13 (M−H); HPLC-Method A, $R_t$ 3.05 min.

Example 60

(7-Fluoro-1H-indazol-3-yl)-[2-(2-trifluoromethyl-phenyl)-quinazolin-4-yl]-amine (II-60)

Prepared in DMF (51% yield) as yellow solid. $^1$HNMR (500 MHz, DMSO-d6) δ13.4 (s, 1H), 10.6 (s, 1H), 8.68 (d, 1H), 7.95 (t, 1H), 7.85 (d, 1H), 7.72 (m, 2H), 7.63 (m, 2H), 7.58 (m, 1H), 7.43 (d, 1H), 7.18 (dd, 1H), 7.00 (m, 1H) ppm; LC-MS (ES+) 424.11 (M+H), (ES−) 422.15 (M−H); HPLC-Method A, $R_t$ 3.06 min.

Example 61

(5-Methyl-1H-indazol-3-yl)-[2-(2-trifluoromethyl-phenyl)-quinazolin-4-yl]-amine (II-61)

Prepared in DMF (81% yield) as yellow solid. $^1$HNMR (500 MHz, DMSO-d6) δ13.0 (s, br, 1H), 8.79 (br, 1H), 8.11 (br, 1H), 7.96 (d, 1H), 7.82 (m, 5H), 7.46 (s, 1H), 7.41 (d, 1H), 7.20 (d, 1H), 2.33 (s, 3H) ppm; MS (ES+) 420.15 (M+H), (ES−) 418.17 (M−H); HPLC-Method A, $R_t$ 3.07 min.

Example 62

[2-(2,6-Dichloro-phenyl)-quinazolin-4-yl]-(5-fluoro-1H-indazol-3-yl)-amine (II-62)

Prepared in DMF (37% yield) as yellow solid. $^1$HNMR (500 MHz, DMSO-d6) δ 13.0 (s, 1H), 10.8 (s, 1H), 8.72 (d, 1H), 7.97 (t, 1H), 7.90 (d, 1H), 7.75 (t, 1H), 7.53 (m, 3H), 7.43 (t, 1H), 7.35 (d, 1H), 7.23 (t, 1H) ppm; LCMS (ES+) 424.08 (M+H), (ES−) 422.10 (M−H); HPLC-Method A, $R_t$ 3.06 min.

Example 63

[2-(2-Chloro-phenyl)-quinazolin-4-yl]-(1H-indazol-3-yl)-amine (II-63)

Prepared in 91% yield. $^1$HNMR (500 MHz, DMSO-d6) δ 7.06 (t, 1H), 7.36 (t, 1H), 7.39 (t, 1H), 7.52 (m, 3H), 7.62 (d, 1H), 7.72 (d, 1H), 7.82 (m, 1H), 7.90 (d, 1H), 8.05 (m, 1H), 8.76 (d, 1H), 11.5 (m, 1H), 13.02 (s, 1H); EI-MS 372.1 (M+1); HPLC-Method A, $R_t$ 2.93 min.

Example 64

(5-Trifluoromethyl-1H-indazol-3-yl)-[2-(2-trifluoromethyl-phenyl)-quinazolin-4-yl]-amine (II-64)

Prepared in DMF (57% yield) as yellow solid. $^1$HNMR (500 MHz, DMSO-d6) δ13.4 (s, br, 1H), 11.4 (br, 1H), 8.72 (d, 1H), 8.12 (s, 1H), 7.98 (t, 1H), 7.83 (d, 1H), 7.76 (d, 1H), 7.73 (d, 1H), 7.60 (m, 4H), 7.52 (d, 1H) ppm; LC-MS (ES+) 474.12 (M+H), (ES−) 472.17 (M−H); HPLC-Method A, $R_t$ 3.25 min.

Example 65

(4-Trifluoromethyl-1H-indazol-3-yl)-[2-(2-trifluoromethyl-phenyl)-quinazolin-4-yl]-amine (II-65)

Prepared in DMF (8% yield) as yellow solid. $^1$HNMR (500 MHz, DMSO-d6) δ13.7 (s, br, 1H), 11.2 (br, 1H), 8.70 (d, 1H), 8.05 (s, 1H), 7.85 (m, 3H), 7.65 (m, 4H), 7.51 (m, 2H) ppm; LC-MS (ES+) 474.13 (M+H), (ES−) 472.17 (M−H); HPLC-Method A, $R_t$ 3.15 min.

Example 66

[2-(2,6-Dichloro-phenyl)-quinazolin-4-yl]-(1H-indazol-3-yl)-amine (II-66)

Prepared in DMF (30% yield) as yellow solid. $^1$HNMR (500 MHz, DMSO-d6) δ12.9 (s, 1H), 11.1 (s, 1H), 8.69 (d, 1H), 7.95 (t, 1H), 7.82 (d, 1H), 7.73 (t, 1H), 7.56 (d, 1H), 7.47 (s, 1H), 7.45 (s, 1H), 7.39 (m, 2H), 7.26 (t, 1H), 6.92 (t, 1H) ppm; LC-MS (ES+) 406.11 (M+H), (ES−) 404.12 (M−H); HPLC-Method A, $R_t$ 3.00 min.

Example 67

(1H-indazol-3-yl)-[2-(2-methyl-phenyl)-quinazolin-4-yl]-amine (II-67): Prepared in 55% yield.

$^1$HNMR (500 MHz, DMSO-d6) δ 2.15 (s, 3H), 7.09 (t, 1H), 7.26 (d, 1H), 7.31 (t, 1H), 7.39 (t, 1H), 7.42 (m, 1H), 7.55 (d 1H), 7.64 (d, 1H), 7.74 (d, 1H), 7.89 (m, 1H), 7.96 (d, 1H), 8.10 (m, 1H), 8.81 (d, 1H), 12.0 (m, 1H), 13.18 (s, 1H); EI-MS 352.2 (M+1); HPLC-Method A, $R_t$ 2.93 min.

Example 68

-(7-Trifluoromethyl-1H-indazol-3-yl)-[2-(2-trifluoromethyl-phenyl)-quinazolin-4-yl]-amine (II-68)

Prepared in DMF (75% yield) as yellow solid. $^1$HNMR (500 MHz, DMSO-d6) δ13.5 (s, br, 1H), 11.2 (s, br, 1H), 8.68 (d, 1H), 7.97 (t, 1H), 7.92 (d, 1H), 7.82 (d, 1H), 7.74 (t, 1H), 7.70 (d, 1H), 7.68 (d, 1H), 7.64 (m, 2H), 7.57 (m, 1H), 7.14 (t, 1H) ppm; LC-MS (ES+) 474.11 (M+H), (ES−) 472.14 (M−H); HPLC-Method A, $R_t$ 3.24 min.

Example 69

(6-Trifluoromethyl-1H-indazol-3-yl)-[2-(2-trifluoromethyl-phenyl)-quinazolin-4-yl]-amine (II-69)

Prepared by Method B in DMF (78% yield) as yellow solid.

$^1$HNMR (500 MHz, DMSO-d6) δ 13.4 (s, br, 1H), 11.1 (s, br, 1H), 8.67 (d, 1H), 7.95 (t, 1H), 7.82 (m, 3H), 7.72 (m, 2H), 7.63 (m, 2H), 7.57 (t, 1H), 7.23 (d, 1H) ppm; LC-MS (ES+) 474.12 (M+H), (ES−) 472.15 (M−H); HPLC-Method A, $R_t$ 3.28 min.

Example 70

(5-Nitro-1H-indazol-3-yl)-[2-(2-trifluoromethyl-phenyl)-quinazolin-4-yl]-amine (II-70)

Prepared in DMF (82% yield) as yellow solid. $^1$HNMR (500 MHz, DMSO-d6) δ13.6 (s, br, 1H), 11.4 (s, br, 1H), 8.75 (s, 1H), 8.72 (d, 1H), 8.09 (dd, 1H), 7.98 (t, 1H), 7.83 (d, 1H), 7.75 (t, 1H), 7.70 (m, 2H), 7.61 (m, 3H) ppm; LC-MS (ES+) 451.14 (M+H), (ES−) 449.12 (M−H); HPLC-Method A, $R_t$ 3.02 min.

Example 71

(5,7-Difluoro-1H-indazol-3-yl)-[2-(2-trifluoromethyl-phenyl)-quinazolin-4-yl]-amine (II-71)

Prepared in DMF (60% yield) as yellow solid. $^1$HNMR (500 MHz, DMSO-d6) δ13.7 (s, br, 1H), 11.2 (s, br, 1H), 8.73 (d, 1H), 8.03 (t, 1H), 7.88 (d, 1H), 7.80 (m, 2H), 7.70 (m, 3H), 7.32 (m, 2H) ppm; LC-MS (ES+) 442.14 (M+H), (ES−) 440.14 (M−H); HPLC-Method A, $R_t$ 3.11 min.

Example 72

(4-Pyrrol-1-yl-1H-indazol-3-yl)-[2-(2-trifluoromethyl-phenyl)-quinazolin-4-yl]-amine (II-72)

Prepared in DMF (33% yield) as yellow solid. $^1$HNMR (500 MHz, DMSO-d6) δ13.4 (s, br, 1H), 11.0 (s, br, 1H), 8.53 (d, 1H), 7.98 (t, 1H), 7.75 (m, 4H), 7.62 (m, 2H), 7.52 (d, 1H), 7.43 (t, 1H), 7.05 (d, 1H), 6.80 (s, 2H), 5.61 (s, 2H) ppm; LC-MS (ES+) 471.18 (M+H), (ES−) 469.18 (M−H); HPLC-Method A, $R_t$ 3.12 min.

Example 73

(5-Amino-1H-indazol-3-yl)-[2-(2-trifluoromethyl-phenyl)-quinazolin-4-yl]-amine (II-73)

A solution of compound. II-70 (70 mg, 0.16 mmol) in MeOH (2 mL) was treated with Raney Ni until solution was colorless (about 1.5 g Raney Ni was added). After stirring at room temperature for 40 min, the mixture was filtered through celite, the resulting celite was washed with MeOH (5 times), and the solvent was evaporated in vacuo to provide a crude product that was then purified by HPLC to give the title compound as a yellow solid (10 mg, 15%). m.p. 221–223° C.; $^1$HNMR (500 MHz, DMSO-d6) δ13.2 (s, br, 1H), 10.7 (s, br, 1H), 9.80 (br, 2H), 8.68 (d, 1H), 7.97 (t, 1H), 7.87 (d, 1H), 7.75 (m, 2H), 7.65 (m, 5H), 7.30 (d, 1H) ppm; MS (ES+) 421.16 (M+H), (ES−) 419.17 (M−H); HPLC-Method A, $R_t$ 2.41 min.

Example 74

[2-(2-Chloro-phenyl)-quinazolin-4-yl]-(7-fluoro-1H-indazol-3-yl)-amine (II-74)

Prepared in DMF (35% yield) as yellow solid. $^1$HNMR (500 MHz, DMSO-d6) δ13.7 (s, 1H), 11.7 (s, br, 1H), 8.80 (d, 1H), 8.15 (t, 1H), 7.99 (d, 1H), 7.88 (t, 1H), 7.68 (d, 1H), 7.60 (m, 2H), 7.53 (t, 1H), 7.46 (t, 1H), 7.25 (dd, 1H), 7.04 (m, 1H) ppm; LC-MS (ES+) 390.16 (M+H); HPLC-Method A, $R_t$ 3.00 min.

Example 75

[2-(2-Chloro-phenyl)-quinazolin-4-yl]-(5-fluoro-1H-indazol-3-yl)-amine (II-75)

Prepared in DMF.

$^1$HNMR (500 MHz, DMSO-d6) δ13.2 (s, 1H), 11.7 (s, br, 1H), 8.80 (d, 1H), 8.10 (t, 1H), 7.91 (m, 2H), 7.70 (d, 1H), 7.58 (m, 4H), 7.50 (t, 1H), 7.29 (t, 1H) ppm; LC-MS (ES+) 390.17 (M+H); HPLC-Method A, $R_t$ 3.00 min.

Example 76

[2-(2-Chloro-phenyl)-quinazolin-4-yl]-(5,7-difluoro-1H-indazol-3-yl)-amine (II-76)

Prepared in DMF (55% yield) as yellow solid. $^1$HNMR (500 MHz, DMSO-d6) δ13.8 (s, 1H), 11.5 (s, br, 1H), 8.76 (d, 1H), 8.08 (t, 1H), 7.93 (d, 1H), 7.84 (t, 1H), 7.64 (d, 1H), 7.55 (d, 1H), 7.50 (t, 1H), 7.44 (m, 2H), 7.36 (t, 1H) ppm; LC-MS (ES+) 408.15 (M+H), (ES−) 406.17 (M−H); HPLC-Method A, $R_t$ 3.08 min.

Example 77

[2-(2-Chloro-phenyl)-quinazolin-4-yl]-(5-trifluoromethyl-1H-indazol-3-yl)-amine (II-77)

Prepared in DMF (66% yield) as yellow solid. $^1$HNMR (500 MHz, DMSO-d6) δ13.5 (s, 1H), 11.4 (s, br, 1H), 8.79 (d, 1H), 8.29 (s, 1H), 8.07 (t, 1H), 7.93 (d, 1H), 7.84 (t, 1H), 7.72 (d, 1H), 7.63 (d, 2H), 7.53 (d, 1H), 7.48 (t, 1H), 7.36 (t, 1H) ppm; LC-MS (ES+): m/e=440.16 (M+H); (ES−): m/e=438.18 (M−H); HPLC-Method A, $R_t$ 3.22 min.

Example 78

[2-(2-cyano-phenyl)-quinazolin-4-yl]-(1H-indazol-3-yl)-amine (II-78)

Prepared in 13% yield. $^1$H-NMR (500 MHz, DMSO) δ 12.9 (br, 1H), 10.8 (br, 1H), 8.73 (br s, 1H), 7.97 (m, 4H), 7.74 (m, 1H), 7.5 (m, 4H), 7.42 (m, 1H), 7.08 (m, 1H) ppm; MS (FIA) 363.2 (M+H); HPLC-Method A, $R_t$ 2.971 min.

Example 79

(5-Bromo-1H-indazol-3-yl)-[2-(2-trifluoromethyl-phenyl)-quinazolin-4-yl]-amine (II-79)

Prepared in DMF (64% yield) as yellow solid. $^1$HNMR (500 MHz, DMSO-d6) δ13.4 (s, 1H), 11.6 (s, br, 1H), 8.93 (d, 1H), 8.21 (t, 1H), 8.14 (s, 1H), 8.05 (d, 1H), 7.95 (m, 4H), 7.86 (t, 1H), 7.65 (d, 1H), 7.59 (d, 1H) ppm; MS (ES+) 486.10 (M+H), (ES−) 484.09 (M−H); HPLC-Method A, $R_t$ 3.22 min.

Example 80

(6-Chloro-1H-indazol-3-yl)-[2-(2-trifluoromethyl-phenyl)-quinazolin-4-yl]-amine (II-80)

Prepared in DMF (94% yield) as yellow solid. $^1$HNMR (500 MHz, DMSO-d6) δ13.1 (s, 1H), 11.2 (s, br, 1H), 8.73 (d, 1H), 8.03 (t, 1H), 7.87 (d, 1H), 7.79 (m, 2H), 7.73 (m, 2H), 7.67 (m, 2H), 7.58 (s, 1H), 7.04 (dd, 1H) ppm. LC-MS (ES+) 440.14 (M+H), (ES−) 438.16 (M−H); HPLC-Method A, $R_t$ 3.25 min.

Example 81

(7-Fluoro-6-trifluoromethyl-1H-indazol-3-yl)-[2-(2-trifluoromethyl-phenyl)-quinazolin-4-yl]-amine (II-81)

Prepared in DMF (30% yield) as yellow solid. $^1$HNMR (500 MHz, DMSO-d6) δ13.9 (s, 1H), 11.0 (s, br, 1H), 8.64 (d, 1H), 7.94 (t, 1H), 7.81 (d, 1H), 7.71 (m, 2H), 7.60 (m, 4H), 7.20 (dd, 1H) ppm. LC-MS (ES+) 492.18 (M+H), (ES−) 490.18 (M−H); HPLC-Method A, $R_t$ 3.44 min.

Example 82

(6-Bromo-1H-indazol-3-yl)-[2-(2-trifluoromethyl-phenyl)-quinazolin-4-yl]-amine (II-82)

Prepared in DMF (40% yield) as yellow solid. $^1$HNMR (500 MHz, DMSO-d6) δ13.1 (s, 1H), 11.2 (s, br, 1H), 8.73 (d, 1H), 8.03 (t, 1H), 7.87 (d, 1H), 7.80 (m, 2H), 7.73 (m, 3H), 7.67 (m, 1H), 7.61 (d, 1H), 7.15 (dd, 1H) ppm; MS (ES+) 486.07 (M+H); HPLC-Method A, $R_t$ 3.28 min.

Example 83

[2-(2,4-Bis-trifluoromethyl-phenyl)-quinazolin-4-yl]-(5,7-difluoro-1H-indazol-3-yl)-amine (II-83)

Prepared in DMF in 28% yield. $^1$HNMR (500 MHz, MeOH-d4) δ 8,81 (d, J=8.4 Hz, 1H), 8.35–8.20 (m, 3H), 8.19–7.96 (m, 3H), 7.40–7.34 (m, 1H), 7.29–7.14 (m, 1H); LC-MS (ES+) 510.14 (M+H); HPLC-Method C, $R_t$ 8.29 min.

Example 84

(5,7-Difluoro-1H-indazol-3-yl)-[2-(4-fluoro-2-trifluoromethyl-phenyl)-quinazolin-4-yl]-amine (II-84)

Prepared in 48% yield. $^1$HNMR (500 MHz, MeOH-d4) δ8.74–8.63 (m, 1H), 8.23–8.10 (m, 1H), 7.99–7.90 (m, 2H), 7.89–7.80 (m, 1H), 7.71–7.61 (m, 1H), 7.61–7.50 (m, 1H), 7.24–7.15 (m, 1H), 7.14–7.02 (m, 1H); LC-MS (ES+) 460.14 (M+H); HPLC-Method C, $R_t$ 7.59 min.

Example 85

[2-(2-Bromo-phenyl)-quinazolin-4-yl]-(5,7-difluoro-1H-indazol-3-yl)-amine (II-85)

Prepared in THF (21% yield). $^1$HNMR (500 MHz, MeOH-d4) δ8.81 (d, J=8.4 Hz, 1H), 8.35–8.20 (m, 3H), 8.19–7.96 (m, 3H), 7.40–7.34 (m, 1H), 7.29–7.14 (m, 1H); LC-MS (ES+) 510.14 (M+H); HPLC-Method C, $R_t$ 8.29 min.

Example 86

(5,7-Difluoro-1H-indazol-3-yl)-[2-(5-fluoro-2-trifluoromethyl-phenyl)-quinazolin-4-yl]-amine (II-86)

Prepared in THF (26% yield). $^1$HNMR (500 MHz, MeOH-d4) δ8.62 (d, J=8.4 Hz, 1H), 8.16–8.02 (m, 1H), 7.96–7.73 (m, 3H), 7.59–7.48 (m, 1H), 7.48–7.35 (m, 1H), 7.21–7.09 (m, 1H), 7.09–6.89 (m, 1H); LC-MS (ES+) 460.16 (M+H); HPLC-Method C, $R_t$ 7.28 min.

Example 87

[2-(2,4-Dichloro-phenyl)-quinazolin-4-yl]-(5,7-Difluoro-1H-indazol-3-yl)-amine (II-87)

Prepared in THF (16% yield). $^1$HNMR (500 MHz, MeOH-d4) δ8.81 (d, J=8.4 Hz, 1H), 8.35–8.20 (m, 3H), 8.19–7.96 (m, 3H), 7.40–7.34 (m, 1H), 7.29–7.14 (m, 1H); LC-MS (ES+) 510.14 (M+H); HPLC-Method C, $R_t$ 8.29 min.

Example 88

[2-(2-Chloro-5-trifluoromethyl-phenyl)-quinazolin-4-yl]-(5,7-Difluoro-1H-indazol-3-yl)-amine (II-88)

Prepared in THF (33% yield). $^1$HNMR (500 MHz, DMSO-d6) δ 10.76 (s, 1H), 8.66 (d, J=8.3 Hz, 1H), 8.06–7.84 (m, 3H), 7.81–7.63 (m, 3H), 7.48–7.16 (m, 2H); LC-MS (ES+) 476.16 (M+H); HPLC-Method C, $R_t$ 19.28 min.

Example 89

(4-Fluoro-1H-indazol-3-yl)-[2-(2-trifluoromethyl-phenyl)-quinazolin-4-yl]-amine (II-89)

Prepared in NMP (79% yield) as yellow solid. $^1$HNMR (500 MHz, DMSO-d6) δ13.2 (s, 1H), 10.8 (s, br, 1H), 8.63 (d, 1H), 7.97 (t, 1H), 7.85 (d, 1H), 7.74 (m, 2H), 7.64 (t, 1H), 7.57 (m, 2H), 7.32 (m, 2H), 6.82 (m, 1H) ppm; LC-MS (ES+) 424.17 (M+H); HPLC-Method A, $R_t$ 3.14 min.

Example 90

(1H-Indazol-3-yl)-[8-methoxy-2-(2-trifluoromethyl-phenyl)-quinazolin-4-yl]-amine (II-90)

Prepared using THF as solvent to afford the title compound as a TFA salt (23% yield). HPLC-Method A, $R_t$ 2.97 min (95%); $^1$HNMR (DMSO-d6, 500 MHz) δ 12.9 (1H, bs), 11.0–10.7(1H, bs), 8.25 (1H, m), 7.75–7.50 (8H, s), 7.30 (1H, m), 6.90 (1H, m), 4.0 (3H, s); MS (m/z) 43.62 (M+H).

Example 91

(5-Fluoro-1H-indazol-3-yl)-[8-methoxy-2-(2-trifluoromethyl-phenyl)-quinazolin-4-yl]-amine (II-91)

Prepared using TFA as solvent to afford the title compound as a TFA salt (23% yield). HPLC-Method A, $R_t$ 3.10 min. (99%); $^1$HNMR (DMSO-d6, 500 MHz): 13.0 (1H, bs), 11.0–10.7(1H, bs), 8.25 (1H, m), 7.75–7.50 (7H, m), 7.35 (1H, m), 7.25 (1H, m), 4.0 (3H, s); MS (m/z) 454.2 (M+H).

Example 92

(7-Fluoro-1H-indazol-3-yl)-[8-methoxy-2-(2-trifluoromethyl-phenyl)-quinazolin-4-yl]-amine (II-92)

Prepared using THF as solvent to afford the title compound as a TFA salt (98 mg, 58% yield). HPLC-Method A, $R_t$ 3.20 min (92%); $^1$HNMR (DMSO-d6, 500 MHz) δ 13.45 (1H, bs), 11.0–10.7(1H, bs), 8.25 (1H, m), 7.75–7.60 (5H, m), 7.50 (1H, m), 7.40 (1H, m), 7.15 (1H, m), 6.95 (1H, m) 4.0 (3H, s); MS (m/z) 454.2 (M+H).

Example 93

(5,7-Difluoro-1H-indazol-3-yl)-[8-methoxy-2-(2-trifluoromethyl-phenyl)-quinazolin-4-yl]-amine (II-93)

Prepared using THF as solvent to afford the title compound as a TFA salt (36% yield). HPLC-Method A, $R_t$ 3.27 min. (95%); $^1$HNMR (DMSO-d6, 500 MHz): 13.65 (1H, bs), 11.0–10.7(1H, bs), 8.22 (1H, m), 7.75–7.60 (5H, m), 7.40 (1H, m), 7.35 (1H, m), 7.19 (1H, m), 4.0 (3H, s); MS (m/z) 472.2 (M+H).

Example 94

[2-(2-Chloro-pyridin-3-yl)-quinazolin-4-yl]-(5,7-Difluoro-1H-indazol-3-yl)-amine (II-94)

Prepared in DMF. $^1$HNMR (500 MHz, DMSO-d6) δ 13.62 (br s, 1H, 11.06–10.71 (m, 1H), 8.16–7.70 (m, 4H), 7.60–7.09 (m, 3H); LC-MS (ES+) 409.14 (M+H); HPLC-Method A, $R_t$ 2.89 min.

Example 95

[2-(2-Chloro-4-nitro-phenyl)-quinazolin-4-yl]-(5,7-difluoro-1H-indazol-3-yl)-amine (II-95)

Prepared in THF. $^1$HNMR (500 MHz, DMSO-d6) δ 13.35 (s, 1H), 10.74 (s, 1H), 8.67 (d, J=8.4 Hz, 1H), 8.29 (d, J=2.05 Hz, 1H), 8.18–8.08 (m, 1H), 8.07–7.60 (m, 4H), 7.53–7.10 (m, 2H). LC-MS (ES+) 453.15 (M+H); HPLC-Method D, $R_t$ 3.63 min.

Example 96

[2-(4-Amino-2-chloro-phenyl)-quinazolin-4-yl]-(5,7-Difluoro-1H-indazol-3-yl)-amine (II-96)

A solution of compound II-95 (8 mg, 0.018 mmol) and tin chloride dihydrate (22 mg, 0.1 mmol) in ethanol (2 mL) was heated at 100° C. for 24 h. The reaction was diluted with EtOAc (10 mL), washed with 1N NaOH solution (2×10 mL), brine, and dried over anhydrous sodium sulfate to afford the crude product. Purification was achieved by flash chromatography on silica gel (eluting with 1–3% MeOH in $CH_2Cl_2$.) The title compound was isolated as pale yellow solid (1.2 mg, 16% yield). LC-MS (ES+) 423.12 (M+H), HPLC-Method C, $R_t$ 13.78 min.

Example 97

(4,5,6,7-Tetrahydro-1H-indazol-3-yl)-[2-(2-trifluoromethyl-phenyl)-quinazolin-4-yl]-amine (II-97)

Prepared in 34% yield. $^1$HNMR (500 MHz, DMSO-d6) δ 1.58 (m, 2H), 1.66 (m, 2H), 2.24 (m, 2H), 2.54 (m 2H), 7.63 (m, 3H), 7.71 (t, 1H), 7.75 (d, 1H), 7.78 (d, 1H), 7.85 (t, 1H), 8.53 (d, 1H), 9.99 (s, 1H), 12.09 (s, 1H); EI-MS 410.2 (M+1); HPLC-Method A, $R_t$ 3.05 min.

Example 98

(1H-Pyrazolo[4,3-b]pyridin-3-yl)-[2-(2-trifluoromethyl-phenyl)-quinazolin-4-yl]-amine (II-98)

Prepared in DMF (37% yield) as yellow solid. $^1$HNMR (500 MHz, DMSO-d6) δ13.1 (s, br, 1H), 11.2 (s, br, 1H), 8.73 (d, 1H), 8.54 (dd, 1H), 8.12 (d, 1H), 8.06 (t, 1H), 7.90 (d, 1H), 7.84 (t, 1H), 7.75 (d, 1H), 7.69 (m, 2H), 7.65 (t, 1H), 7.47 (dd, 1H) ppm; LC-MS (ES+) 407.18 (M+H); HPLC-Method A, $R_t$ 2.77 min.

Example 99

(1H-Pyrazolo[3,4-b]pyridin-3-yl)-[2-(2-trifluoromethyl-phenyl)-quinazolin-4-yl]-amine (II-99)

Prepared in DMF (45% yield). $^1$HNMR (500 MHz, DMSO-d6) δ13.5 (s, br, 1H), 11.3 (s, br, 1H), 8.78 (d, 1H), 8.49 (d, 1H), 8.17 (d, 1H), 8.03 (t, 1H), 7.89 (d, 1H), 7.80 (m, 2H), 7.74 (m, 2H), 7.68 (m, 1H), 7.08 (dd, 1H) ppm. MS (ES+) 407.16 (M+H), (ES−) 405.16 (M−H); HPLC-Method A, $R_t$ 2.80 min.

Example 100

(6-Methyl-1H-pyrazolo[3,4-b]pyridin-3-yl)-[2-(2-trifluoromethyl-phenyl)-quinazolin-4-yl]-amine (II-100)

Prepared in DMF (11% yield). $^1$HNMR (500 MHz, DMSO-d6) δ13.2 (s, br, 1H), 10.8 (s, br, 1H), 8.57 (d, 1H), 7.95 (t, 1H), 7.82 (d, 1H), 7.72 (t, 1H), 7.65 (m, 2H), 7.58 (m, 2H), 2.44 (s, 3H, buried by DMSO), 2.20 (s, 3H) ppm. LC-MS (ES+) 435.22 (M+H), (ES−) 433.25 (M−H); HPLC-Method A, $R_t$ 2.94 min.

Example 101

(6-Oxo-5-phenyl-5,6-dihydro-1H-pyrazolo[4,3-c]pyridazin-3-yl)-[2-(2-trifluoromethyl-phenyl)-quinazolin-4-yl]-amine II-101

Prepared in DMF (6% yield). $^1$HNMR (500 MHz, DMSO-d6) δ12.6 (s, 1H), 11.0 (s, br, 1H), 8.60 (d, 1H), 7.95 (t, 1H), 7.88 (d, 1H), 7.80 (d, 1H), 7.68 (m, 4H), 7.40 (s, 3H), 7.22 (s, 2H), 6.61 (s, 1H) ppm. LC-MS (ES+) 500.21 (M+H), (ES−) 498.16 (M−H); HPLC-Method A, $R_t$ 3.00 min.

Example 103

[6-Methyl-2-(2-trifluoromethoxy-phenyl)-pyrimidin-4-yl]-(5-phenyl-2H-pyrazol-3-yl)-amine (II-103)

MS 412.13 (M+H); HPLC-Method E $R_t$ 1.248 min.

Example 104

(5-Furan-2-yl-2H-pyrazol-3-yl)-[6-methyl-2-(2-trifluoromethoxy-phenyl)-pyrimidin-4-yl]-amine (II-104)

MS 402.12 (M+H); HPLC-Method E, $R_t$ 1.188 min.

Example 105

[6-Ethyl-2-(2-trifluoromethoxy-phenyl)-pyrimidin-4-yl]-(5-methyl-2H-pyrazol-3-yl)-amine (II-105)

MS 364.14 (M+H); HPLC-Method E, $R_t$ 1.112 min.

Example 106

[2-(2-Chloro-phenyl)-pyrido[2,3-d]pyrimidin-4-yl]-(5-methyl-2H-pyrazol-3-yl)-amine (II-106)

$^1$HNMR (500 MHz, DMSO) δ12.23 (s, 1H), 10.78 (s, 1H), 7.73–7.47 (m, 7H), 6.72 (s, 1H), 2.21 (s, 3H). MS: (M+H) 337.02. HPLC-Method A, $R_t$ 2.783 min.

Example 107

(5-Fluoro-1H-indazol-3-yl)-[2-(2-trifluoromethyl-phenyl)-6,7-dihydro-5H-cyclopentapyrimidin-4-yl]-amine (II-107)

Prepared in 68% yield. $^1$HNMR (500 MHz, DMSO-d6) δ 2.16 (t, 2H), 2.88 (m, 2H), 2.98 (t, 2H), 7.21 (td, 1H), 7.29 (dd, 1H), 7.50 (dd, 1H), 7.65 (t, 1H), 7.67 (t, 1H), 7.73 (t, 1H), 7.79 (d, 1H), 10.22 (br. s, 1H), 12.99 (br. s, 1H); EI-MS 414.2 (M+H); HPLC-Method A, $R_t$ 2.92 min.

Example 108

(1H-Indazol-3-yl)-[2-(2-trifluoromethyl-phenyl)-pyrido[2,3-d]pyrimidin-4-yl]-amine (II-108)

HPLC-Method A, $R_t$ 2.78 min. (95%); $^1$HNMR (DMSO-d6, 500 MHz): 12.95 (1H, bs), 11.45 δ 11.15(1H, bs), 9.20 (2H, m), 7.85–7.70 (2H, m), 7.70–7.55 (4H, m), 7.50 (1H, m), 7.35 (1H, m), 7.05 (1H, m); MS (m/z) 407.03 (M+H).

Example 109

(5,7-Difluoro-1H-indazol-3-yl)-[2-(2-trifluoromethyl-phenyl)-pyrido[2,3-d]pyrimidin-4-yl]-amine (II-109)

Yellow, di-TFA salt (25% yield). HPLC (Method A) 3.10 min. (95%); $^1$HNMR (DMSO-d6, 500 MHz): 13.8–13.6 (1H, bs), 11.4–11.2(1H, bs), 9.15 (2H, m), 7.85–7.75 (2H, m), 7.75–7.62 (3H, m), 7.32 (2H, m); MS (m/z) 442.98 (M+H).

Example 110

[2-(2-Chloro-phenyl)-pyrido[2,3-d]pyrimidin-4-yl]-(1H-indazol-3-yl)-amine (II-110)

Prepared from 2-aminonicotinic acid and 2-chlorobenzoyl chloride afforded the title compound as a di-TFA salt (28% yield). HPLC-Method A, $R_t$ 2.85 min. (95%); $^1$HNMR (DMSO-d6, 500 MHz): 12.90 (1H, s), 11.10–10.90 (1H, bs), 9.05 (2H, m), 7.75–7.60 (2H, m), 7.51 (1H, m), 7.45–7.25 (5H, m), 6.95 (1H, m); MS (m/z) 372.99(M+H).

Example 111

(5-Fluoro-1H-indazol-3-yl)-[2-(2-trifluoromethyl-phenyl)-5,6,7,8,9,10-hexahydro-cyclooctapyrimidin-4-yl]-amine (II-111)

Prepared in 43% yield. $^1$HNMR (500 MHz, DMSO-d6) δ 1.46 (m, 2H), 1.53 (m, 2H), 1.77 (m, 4H), 2.95 (m, 2H), 3.04 (m, 2H), 7.22 (m, 2H), 7.50 (dd, 1H), 7.72 (m, 3H), 7.80 (d, 1H), 10.5 (m, 1H), 13.05 (br s, 1H); EI-MS 456.2 (M+H); HPLC-Method C, $R_t$ 11.93 min.

Example 112

[2-(2-Chloro-phenyl)-6,7-dihydro-5H-cyclopentapyrimidin-4-yl]-(5-fluoro-1H-indazol-3-yl)-amine (II-112)

Prepared in 67% yield. $^1$HNMR (500 MHz, DMSO-d6) δ2.18 (m, 2H), 2.89 (m, 2H), 3.02 (t, 2H), 7.24 (td, 1H), 7.42 (m, 2H), 7.49 (td, 1H), 7.52 (dd, 1H), 7.54 (d, 1H), 7.57 (dd, 1H), 10.50 (br. s, 1H), 13.06 (br. s, 1H); EI-MS 380.1 (M+1); HPLC-Method C, $R_t$ 9.68 min.

Example 113

(1H-Indazol-3-yl)-[2-(2-trifluoromethyl-phenyl)-6,7-dihydro-5H-cyclopentapyrimidin-4-yl]-amine (II-113)

Prepared in 37% yield. $^1$HNMR (500 MHz, DMSO-d6) δ 2.65 (m, 2H), 2.85 (m, 2H), 2.99 (t, 2H), 7.02 (t, 1H), 7.32 (t, 1H), 7.47 (d, 1H), 7.55 (d, 1H), 7.68 (t, 1H), 7.74 (t, 1H), 7.80 (d, 1H), 10.37 (br. s, 1H), 12.91 (br. s, 1H); EI-MS 396.1 (M+H); HPLC-Method B, $R_t$ 9.88 min.

Example 114

(7-Fluoro-1H-indazol-3-yl)-[2-(2-trifluoromethyl-phenyl)-6,7-dihydro-5H-cyclopentapyrimidin-4-yl]-amine (II-114)

Prepared in 40% yield. $^1$HNMR (500 MHz, DMSO-d6) δ 2.15 (m, 2H), 2.87 (m, 2H), 2.97 (t, 2H), 6.99 (td, 1H), 7.17 (dd, 1H), 7.38 (d, 1H), 7.65 (m, 2H), 7.71 (t, 1H), 7.78 (d, 1H), 10.21 (br. s, 1H), 13.40 (br. s, 1H); EI-MS 414.1 (M+H); HPLC-Method C, $R_t$ 9.99 min.

Example 115

(5,7-Difluoro-1H-indazol-3-yl)-[2-(2-trifluoromethyl-phenyl)-6,7-dihydro-5H-cyclopentapyrimidin-4-yl]-amine (II-115)

Prepared according to Method C in 52% yield. $^1$HNMR (500 MHz, DMSO-d6) δ 2.16 (m, 2H), 2.89 (m, 2H), 2.97 (t, 2H), 7.19 (dd, 1H), 7.29 (td, 1H), 7.63 (t, 1H), 7.66 (d, 1H), 7.71 (t, 1H), 7.78 (d, 1H), 10.16 (br. s, 1H), 13.55 (br. s, 1H); EI-MS 432.1 (M+H); HPLC-Method C, $R_t$ 10.09 min.

Example 116

[2-(2-Chloro-phenyl)-6,7-dihydro-5H-cyclopentapyrimidin-4-yl]-(1H-indazol-3-yl)-amine (II-116)

Prepared in 56% yield. $^1$HNMR (500 MHz, DMSO-d6) δ 2.16 (m, 2H), 2.85 (m, 2H), 3.01 (t, 2H), 7.06 (t, 1H), 7.34 (t, 1H), 7.40 (t, 1H), 7.48 (m, 2H), 7.53 (d, 1H), 7.56 (d, 1H), 7.63 (d, 1H), 10.39 (br. s, 1H), 12.91 (s, 1H); EI-MS 362.1 (M+H); HPLC-Method A, $R_t$ 3.09 min.

Example 117

[2-(2-Chloro-phenyl)-6,7-dihydro-5H-cyclopentapyrimidin-4-yl]-(7-fluoro-1H-indazol-3-yl)-amine (II-117)

Prepared in 63% yield. $^1$HNMR (500 MHz, DMSO-d6) δ 2.15 (m, 2H), 2.87 (m, 2H), 3.00 (t, 2H), 7.01 (td, 1H), 7.19 (dd, 1H), 7.39 (t, 1H), 7.45 (m, 2H), 7.51 (d, 1H), 7.55 (d, 1H), 10.35 (br. s, 1H), 13.45 (br. s, 1H); EI-MS 380.1 (M+H); HPLC-Method A, $R_t$ $R_t$ 3.15 min.

Example 118

[2-(2-Chloro-phenyl)-6,7-dihydro-5H-cyclopentapyrimidin-4-yl]-(5,7-difluoro-1H-indazol-3-yl)-amine (II-118)

Prepared in 60% yield. $^1$HNMR (500 MHz, DMSO-d6) δ 2.18 (m, 2H), 2.91 (m, 2H), 3.01 (t, 2H), 7.32 (t, 1H), 7.33 (td, 1H), 7.41 (t, 1H), 7.48 (t, 1H), 7.53 (d, 1H), 7.55 (dd, 1H), 10.35 (br. s, 1H), 13.45 (br. s, 1H); EI-MS 398.1 (M+H); HPLC-Method A, $R_t$ $R_t$ 3.24 min.

Example 119

(1H-Indazol-3-yl)-[2-(2-trifluoromethyl-phenyl)-5,6,7,8,9,10-hexahydro-cyclooctapyrimidin-4-yl]-amine (II-119)

Prepared in 36% yield. $^1$HNMR (500 MHz, DMSO-d6) δ 1.47 (m, 2H), 1.53 (m, 2H), 1.78 (m, 4H), 2.96 (m, 2H), 3.06

(t, 2H), 7.03 (t, 1H), 7.47 (t, 1H), 7.72 (d, 1H), 7.73 (d, 1H), 7.72 (m, 3H), 7.81 (d, 1H), 10.52 (m, 1H), 12.97 (br. s, 1H); EI-MS 438.2 (M+1); HPLC-Method A, $R_t$ 3.37 min.

Example 120

(7-Fluoro-1H-indazol-3-yl)-[2-(2-trifluoromethyl-phenyl)-5,6,7,8,9,10-hexahydro-cyclooctapyrimidin-4-yl]-amine (II-120)

Prepared in 40% yield. $^1$HNMR (500 MHz, DMSO-d6) δ 1.46 (m, 2H), 1.52 (m, 2H), 1.77 (m, 4H), 2.94 (m, 2H), 3.04 (m, 2H), 7.00 (td, 1H), 7.17 (dd, 1H), 7.30 (d, 1H), 7.70 (m, 3H), 7.79 (d, 1H), 10.5 (m, 1H), 13.49 (br s, 1H); EI-MS 456.1 (M+H); HPLC-Method A, $R_t$ 3.43 min.

Example 121

(5,7-Difluoro-1H-indazol-3-yl)-[2-(2-trifluoromethyl-phenyl)-5,6,7,8,9,10-hexahydro-cyclooctapyrimidin-4-yl]-amine (II-121)

Prepared in 48% yield. $^1$HNMR (500 MHz, DMSO-d6) δ 1.46 (m, 2H), 1.52 (m, 2H), 1.77 (m, 4H), 2.95 (m, 2H), 3.03 (m, 2H), 7.14 (d, 1H), 7.30 (t, 1H), 7.73 (m, 3H), 7.80 (d, 1H), 10.5 (m, 1H), 13.62 (br. s, 1H); EI-MS 475.1 (M+1); HPLC-Method A, $R_t$ 3.52 min.

Example 122

[6-Cyclohexyl-2-(2-trifluoromethyl-phenyl)-pyrimidin-4-yl]-(1H-indazol-3-yl)-amine (II-122)

Prepared in 45% yield. $^1$HNMR (500 MHz, CDCl3) δ 1.30 (2H, m), 1.46 (2H, m), 1.65 (2H, m), 1.76 (2H, m), 1.91 (2H, m), 2.61 (1H, br m), 7.08 (1H, t, J=7.4 Hz), 7.27 (1H, d, J=8.0 Hz), 7.35 (1H, t, J=7.1 Hz), 7.50 (1H, t, J=7.0 Hz), 7.58 (1H, t, J=7.4 Hz), 7.66 (3H, m), 7.72 (1H, d, J=7.8 Hz), 8.0 (1H, br), 9.87 (1H, br) ppm; HPLC-Method D, $R_t$ 3.57 min; LC-MS 438.17 (M+H)$^+$

Example 123

[6-(2-Fluoro-phenyl)-2-(2-trifluoromethyl-phenyl)-pyrimidin-4-yl]-(1H-indazol-3-yl)-amine (II-123)

Prepared in 8% yield. $^1$HNMR (500 MHz, CDCl$_3$) δ 7.18 (3H, m), 7.37 (1H, m), 7.43 (1H, t, J=7.9 Hz), 7.51 (1H, d, J=7.9 Hz), 7.55 (1H, t, J=7.6 Hz), 7.65 (1H, t, J=7.4 Hz), 7.79 (1H, d, J=7.9 Hz), 7.85 (1H, d, J=7.6 Hz), 8.19 (2H, m), 8.70 (1H, d, J=8.5 Hz) ppm; HPLC-Method D, $R_t$ 4.93 min; LC-MS 450.13 (M+H)$^+$

Example 124

(6-Fluoro-1H-indazol-3-yl)-[2-(2-trifluoromethyl-phenyl)-quinazolin-4-yl]-amine (II-124)

Prepared in DMF (87% yield) as yellow solid. $^1$HNMR (500 MHz, DMSO-d6) δ13.0 (s, 1H), 11.1 (s, br, 1H), 8.66 (d, 1H), 7.95 (t, 1H), 7.80 (d, 1H), 7.72 (m, 2H), 7.62 (m, 4H), 7.21 (dd, 1H), 6.84 (td, 1H) ppm. LC-MS (ES+) 424.15 (M+H); HPLC-Method A, $R_t$ 3.05 min.

Example 125

3-[2-(2-Trifluoromethyl-phenyl)-quinazolin-4-ylamino]-1H-indazole-5-carboxylic acid methyl ster (II-125)

To a solution of compound II-79 (100 mg 0.21 mmol) in DMF (2 mL) was added MeOH (1 mL), DIEA (54 uL, 0.31 mmol) and PdCl$_2$(dppf) (4 mg, 0.005 mmol). The flask was flushed with CO three times and then charged with a CO balloon. The reaction mixture was heated at 80° C. for 14 h then poured into water. The resulting precipitate was collected and washed with water. The crude product was then purified first by flash column (silica gel, 50% ethyl acetate in hexanes) then by preparative HPLC to to afford II-125 (32%) as yellow solid. $^1$HNMR (500 MHz, DMSO-d6) δ13.3 (s, 1H), 11.3 (s, br, 1H), 8.70 (d, 1H), 8.36 (s, 1H), 7.97 (t, 1H), 7.82 (m, 2H), 7.71 (m, 3H), 7.58 (m, 2H), 7.51 (d, 1H), 3.75 (s, 3H) ppm; LC-MS (ES+) 464.13 (M+H); HPLC-Method A, $R_t$ 3.12 min.

Example 208

(5-Methyl-2H-pyrazol-3-yl)-[2-(2-naphthyl-1-yl)-quinazolin-4-yl]-amine (II-208)

$^1$HNMR (500 MHz, DMSO-d6) δ8.92 (s, 1H), 8.73 (m, 1H), 8.39 (m, 1H), 8.09 (m, 2H), 7.95 (m, 3H), 7.62 (m, 3H), 6.78 (s, 1H), 2.32 (s, 3H); MS 352.2 (M+H).

Example 209

[2-(2-Chloro-phenyl)-pyrido[2,3-d]pyrimidin-4-yl]-(7-fluoro-1H-indazol-3-yl)-amine (II-214)

Prepared from 4-Chloro-2-(2-chloro-phenyl)-pyrido[2,3-d]pyrimidine (100 mg, 0.36 mmol) and 7-Fluoro-1H-indazol-3-ylamine (108 mg, 0.72 mmol). Purification by preparative HPLC afforded the title compound as a yellow, di-TFA salt (93 mg, 46% yield). HPLC-Method A, $R_t$ 3.04 min; $^1$H NMR (DMSO, 500 MHz): δ 13.67 (1H, s), 11.40–11.25 (1H, bs), 9.35–9.25 (2H, m), 7.95 (1H, m), 7.80–7.47 (5H, m), 7.35(1H, m), 7.15 (1H, m); MS (m/z), MH$^+$ 391.1.

Example 210

[2-(2-Chloro-phenyl)-pyrido[2,3-d]pyrimidin-4-yl]-(5-fluoro-1H-indazol-3-yl)-amine (II-215)

Prepared from 4-Chloro-2-(2-chloro-phenyl)-pyrido[2,3-d]pyrimidine (100 mg, 0.36 mmol) and 5-Fluoro-1H-indazol-3-ylamine (108 mg, 0.72 mmol). Purification by preparative HPLC afforded the title compound as a yellow, di-TFA salt (45 mg, 22% yield). HPLC-Method A, $R_t$ 3.00 min; $^1$H NMR (DMSO, 500 MHz): δ 13.0 (1H, s), 10.90(1H, bs), 9.15–9.05 (2H, m), 7.70 (1H, m), 7.60–7.30 (6H, m), 7.20 (1H, m); MS (m/z), MH$^+$ 391.1.

Example 211

[2-(2-Chloro-phenyl)-pyrido[2,3-d]pyrimidin-4-yl]-(5,7-difluoro-1H-indazol-3-yl)-amine (II-216)

Prepared from 4-Chloro-2-(2-chloro-phenyl)-pyrido[2,3-d]pyrimidine (100 mg, 0.36 mmol) and 7-Difluoro-1H-indazol-3-ylamine (112 mg, 0.66 mmol). Purification by preparative HPLC afforded the title compound as a yellow, di-TFA salt (130 mg, 62% yield). HPLC-Method A, $R_t$ 3.12 min; $^1$H NMR (DMSO, 500 MHz): 13.80–13.60 (1H, bs), 11.30–11.10 (1H, bs), 9.20–9.10 (2H, m), 7.80 (1H, m), 7.60–7.30 (6H, m); MS (m/z), MH$^+$ 409.1.

Example 212

[2-(2-Chloro-phenyl)-pyrido[3,4-d]pyrimidin-4-yl]-(1H-indazol-3-yl)-amine (II-217)

Prepared from 4-Chloro-2-(2-chloro-phenyl)-pyrido[3,4-d]pyrimidine (100 mg, 0.36 mmol) and 1H-indazol-3- ylamine (88 mg, 0.66 mmol). Purification by preparative HPLC afforded the title compound as a yellow, di-TFA salt (72 mg, 33% yield). HPLC-Method A, $R_t$ 3.21 min; $^1$H NMR (DMSO, 500 MHz): δ 12.95 (1H, s), 10.90 (1H, bs), 9.25 (1H, s), 8.75 (1H, m), 8.55 (1H, m), 7.65 (1H, m), 7.55 (1H, m), 7.50–7.30 (5H, m), 7.00(1H, m); MS (m/z), MH$^+$ 373.1.

Example 213

[2-(2-Chloro-phenyl)-pyrido[3,4-d]pyrimidin-4-yl]-(7-fluoro-1H-indazol-3-yl)-amine (II-218)

Prepared from 4-Chloro-2-(2-chloro-phenyl)-pyrido[3,4-d]pyrimidine (100 mg, 0.36 mmol) and 7-Fluoro-1H-indazol-3-ylamine (108 mg, 0.72 mmol). Purification by preparative HPLC afforded the title compound as a yellow, di-TFA salt (48.7 mg, 22% yield). HPLC-Method A, $R_t$ 3.35 min; $^1$H NMR (DMSO, 500 MHz): δ 12.95 (1H, s), 10.90 (1H, bs), 9.25 (1H, s), 8.75 (1H, m), 8.55 (1H, m), 7.70–7.35 (5H, m), 7.25(1H, m), 6.95 (1H, m),; MS (m/z), MH$^+$ 391.08.

Example 214

[2-(2-Chloro-phenyl)-pyrido[3,4-d]pyrimidin-4-yl]-(5-fluoro-1H-indazol-3-yl)-amine (II-219)

Prepared from 4-chloro-2-(2-chloro-5-fluoro-1H-indazol-3-ylamine (108 mg, 0.72 mmol). Purification by preparative HPLC afforded the title compound as a yellow, di-TFA salt (57.2 mg, 26% yield). HPLC-Method A, $R_t$ 3.27 min; $^1$H NMR (DMSO, 500 MHz): δ 13.05 (1H, s), 10.95 (1H, s), 9.25 (1H, s), 8.75 (1H, m), 8.55 (1H, m), 7.60 (1H, m), 7.55 (1H, m), 7.50–7.30 (5H, m), 7.25(1H, m); MS (m/z), MH+ 391.1.

Example 215

[2-(2-Chloro-phenyl)-pyrido[3,4-d]pyrimidin-4-yl]-(5,7-difluoro-1H-indazol-3-yl)-amine (II-220)

Prepared from 4-chloro-2-(2-chloro-7-difluoro-1H-indazol-3-ylamine (112 mg, 0.66 mmol). Purification by preparative HPLC afforded the title compound as a yellow, di-TFA salt (57.2 mg, 26% yield). HPLC-Method A, $R_t$ 3.45 min; $^1$H NMR (DMSO, 500 MHz): δ 13.65 (1H, s), 11.0 (1H, s), 9.25 (1H, s), 8.80 (1H, m), 8.50 (1H, m), 7.60 (1H, m), 7.55 (1H, m), 7.50–7.30 (5H, m); MS (m/z), MH$^+$ 409.1.

Example 216

6-Fluoro-1H-indazol-3-ylamine (A1)

$^1$HNMR (500 MHz, DMSO-d6) δ11.4 (s, 1H), 7.68 (dd, 1H), 6.95 (dd, 1H), 6.75 (td, 1H), 5.45 (s, 2H) ppm; LC-MS (ES+) 152.03 (M+H); HPLC-Method A, $R_t$ 2.00 min.

Example 217

5-Fluoro-1H-indazol-3-ylamine (A2)

$^1$HNMR (500 MHz, DMSO-d6) δ11.3 (s, 1H), 7.43 (d, 1H), 7.22 (m, 1H), 7.08 (m, 1H), 5.29 (s, 2H) ppm; LC-MS (ES+) 152.01 (M+H); HPLC-Method A, $R_t$ 1.93 min.

Example 218

5,7-Difluoro-1H-indazol-3-yl-amine (A3)

$^1$HNMR (500 MHz, CD$_3$OD) δ7.22 (dd, J=2.0, 8.45 Hz, 1H), 7.04–6.87 (m, 1H); LC-MS (ES+) 169.95 (M+H); HPLC-Method C, $R_t$ 2.94 min Example 219

7-Fluoro-1H-indazol-3-ylamine (A4)

$^1$HNMR (500 MHz, DMSO-d6) δ11.8 (s, 1H), 7.42 (d, 1H), 6.97 (m, 1H), 6.78 (m, 1H), 5.40 (s, 2H) ppm; LCMS (ES+) 152.01 (M+H); HPLC-Method A, $R_t$ 2.00 min.

Example 220

7-Fluoro-6-trifluoromethyl-1H-indazol-3-ylamine (A5)

$^1$H-NMR (500 MHz, DMSO) δ 12.5 (s, 1H), 7.75 (d, 1H), 7.25 (m, 1H), 5.85 (m, 1H) ppm; MS (FIA) 220.0 (M+H); HPLC-Method A, $R_t$ 2.899 min.

Example 221

6-Bromo-1H-indazol-3-ylamine (A6)

$^1$H-NMR (500 MHz, DMSO) δ 11.5 (s, 1H), 7.65 (d, 1H), 7.40 (s, 1H), 7.00 (d, 1H), 5.45 (br s, 1H) ppm; MS (FIA) 213.8 (M+H); HPLC-Method A, $R_t$ 2.441 min.

Example 222

4-Fluoro-1H-indazol-3-ylamine (A7)

$^1$H-NMR (500 MHz, DMSO) δ 11.7 (s, 1H), 7.17 (m, 1H), 7.05 (d, 1H), 6.7 (br, 1H), 6.60 (dd, 1H), 5.20 (br s, 2H) ppm; MS (FIA) 152.0 (M+H); Method A, $R_t$ 2.256 min.

Example 223

5-Bromo-1H-indazol-3-ylamine (A8)

$^1$H-NMR (500 MHz, DMSO) δ 11.55 (br s, 1H), 7.95 (s, 1H), 7.30 (d, 1H), 7.20 (d, 1H), 5.45 (br s, 2H) ppm; MS (FIA) 213.8 (M+H); Method A, $R_t$ 2.451 min.

Example 224

5-Nitro-1H-indazol-3-ylamine (A9)

$^1$H-NMR (500 MHz, DMSO-d6) δ 9.00 (s, 1H), 8.20 (d, 1H), 7.45 (d, 1H), 6.15 (br s, 1H) ppm; Method A, $R_t$ 2.184 min Example 225

4-Pyrrol-1-yl-1H-indazol-3-ylamine (A10)

$^1$H-NMR (500 MHz, DMSO) δ 7.20 (s, 2H), 7.00 (s, 2H), 6.75 (m, 1H), 6.25 (s, 2H), 4.30 (d, 1H) ppm; Method A, $R_t$ 2.625 min.

Example 226

4-Chloro-5,6-dimethyl-2-(2-trifluoromethyl-phenyl)-pyrimidine (B1)

Prepared to afford a colorless oil in 75% yield. $^1$H-NMR (500 MHz, CDCl3) δ 7.70 (d, J=7.8 Hz, 1H), 7.64 (d, J=7.6 Hz, 1H), 7.55 (t, J=7.6 Hz, 1H), 7.48 (t, J=7.5 Hz, 1H), 2.54 (s, 3H), 2.36 (s, 3H) ppm; MS (FIA) 287.0 (M+H); HPLC-Method A, $R_t$ 3.891 min.

Example 227

4-Chloro-2-(2-chloro-phenyl)-5,6-dimethyl-pyrimidine (B2)

Prepared to afford a yellow-orange oil in 71% yield. $^1$H-NMR (500 MHz, CDCl3) δ 7.73 (m, 1H), 7.52 (m, 1H), 7.39 (m, 2H), 2.66 (s, 3H), 2.45 (s, 3H) ppm; MS (FIA) 253.0 (M+H); HPLC-Method A, R$_t$ R$_t$ 4.156 min.

Example 228

4-Chloro-6-methyl-2-(2-trifluoromethyl-phenyl)-pyrimidine (B3)

Prepared to afford a pale yellow oil in 68% yield. $^1$H-NMR (500 MHz, CDCl3) δ 7.72 (d, J=7.8 Hz, 1H), 7.65 (d, J=7.9 Hz, 1H), 7.57 (t, J=7.5 Hz, 1H), 7.52 (t, J=7.8 Hz, 1H), 7.16 (s, 1H), 2.54 (s, 3H) ppm; MS (FIA) 273.0 (M+H); HPLC-Method A, R$_t$ 3.746 min.

Example 229

4-Chloro-6-cycloh xyl-2-(2-trifluoromethyl-phenyl)-pyrimidine (B4)

Prepared to afford a yellow oil in 22% yield. $^1$H-NMR (500 MHz, CDCl3) δ 7.70 (m, 2H), 7.57 (t, J=7.5 Hz, 1H), 7.50 (t, J=7.5 Hz, 1H), 7.19 (s, 1H), 2.65 (m, 1H), 1.9 (m, 2H), 1.8 (m, 2H), 1.5 (m, 2H), 1.3 (m, 2H), 1.2 (m, 2H) ppm; MS (FIA) 341.0 (M+H).

Example 230

4-Chloro-6-phenyl-2-(2-trifluoromethyl-phenyl)-pyrimidine (B5)

Prepared to afford a yellow oil in 53% yield. $^1$H-NMR (500 MHz, CDCl3) δ 8.08 (dd, J=7.9, 1.6 Hz, 2H), 7.80 (d, J=7.6 Hz, 1H), 7.77 (d, J=7.8 Hz, 1H), 7.67 (s, 1H), 7.61 (t, J=7.5 Hz, 1H), 7.54 (t, J=7.6 Hz, 1H), 7.47 (m, 3H) ppm; MS (FIA) 335.0 (M+H); HPLC-Method A, R$_t$ 4.393 min.

Example 231

4-Chloro-2-(2,4-dichloro-phenyl)-5,6-dimethyl-pyrimidine (B6)

Prepared to afford a white solid in 91% yield. $^1$H-NMR (500 MHz, CDCl3) δ 7.62 (d, J=8.3 Hz, 1H), 7.43 (d, J=7.0 Hz, 1H), 7.27 (dd, J=8.3, 2.0 Hz, 1H), 2.55 (s, 3H), 2.35 (s, 3H) ppm; MS (FIA) 287, 289 (M+H); HPLC-Method A, R$_t$ 4.140 min.

Example 232

4-Chloro-6-(2-chloro-phenyl)-2-(2-trifluoromethyl-phenyl)-pyrimidine (B7)

Prepared to affod a yellow oil in 52% yield. $^1$H-NMR (500 MHz, CDCl3) δ 7.75 (m, 3H), 7.65 (m, 2H), 7.53 (m, 1H), 7.44 (m, 1H), 7.36 (m, 2H) ppm; MS (FIA) 369.1 (M+H); HPLC-Method A, R$_t$ 4.426 min.

Example 233

4-Chloro-6-(2-fluoro-phenyl)-2-(2-trifluoromethyl-phenyl)-pyrimidine (B8)

Prepared to afford a yellow oil in 95% yield. $^1$H-NMR (500 MHz, CDCl3) δ 8.24 (t, J=7.9 Hz, 1H), 7.84 (s, 1H), 7.78 (d, J=7.7 Hz, 1H), 7.76 (d, J=8.0 Hz, 1H), 7.60 (t, J=7.5 Hz, 1H), 7.53 (t, J=7.6 Hz, 1H), 7.43 (m, 1H), 7.23 (t, J=7.6 Hz, 1H), 7.13 (m, 1H) ppm; MS (FIA) 353.0 (M+H).

Example 234

4-Chloro-6-pyridin-2-yl-2-(2-trifluoromethyl-phenyl)-pyrimidine (B9)

Prepared to afford a pale yellow solid in 50% yield. $^1$H-NMR (500 MHz, CDCl3) δ 8.68 (m, 1H), 8.48 (dd, J=7.9, 0.8 Hz, 1H), 8.38 (d, J=2.3 Hz, 1H), 7.84 (m, 3H), 7.62 (t, J=7.6 Hz, 1H), 7.55 (t, J=7.6 Hz, 1H), 7.38 (m, 1H) ppm; MS (FIA) 336.0 (M+H); HPLC-Method A, R$_t$ 4.575 min.

Example 235

6-Benzyl-4-chloro-2-(2-trifluoromethyl-phenyl)-5,6,7,8-tetrahydro-pyrido[4,3-d]pyrimidine (B10)

$^1$HNMR (500 MHz, CDCl$_3$) δ7.70 (d, 1H), 7.62 (d, 1H), 7.55 (t, 1H), 7.48 (t, 1H), 7.32 (m, 4H), 7.25 (m, 1H), 3.74 (s, 2H), 3.66 (s, 2H), 2.99 (t, 2H), 2.80 (t, 2H) ppm; LCMS (ES+) 404.17 (M+H); HPLC-Method A, R$_t$ 3.18 min.

Example 236

7-Benzyl-4-chloro-2-(2-trifluoromethyl-phenyl)-5,6,7,8-tetrahydro-pyrido[3,4-d]pyrimidine (B11)

$^1$HNMR (500 MHz, CDCl$_3$) δ7.69 (d, 1H), 7.60 (d, 1H), 7.54 (t, 1H), 7.47 (t, 1H), 7.28 (m, 4H), 7.20 (m, 1H), 3.68 (s, 2H), 3.67 (s, 2H), 2.86 (t, 2H), 2.79 (t, 2H) ppm. MS (ES+) 404.18 (M+H); HPLC-Method A, R$_t$ 3.12 min.

Example 237

4-Chloro-2-(4-fluoro-2-trifluoromethyl-phenyl)-quinazoline (B12)

$^1$HNMR (500 MHz, CD$_3$OD) δ 8.43 (d, J=8.1 Hz, 1H), 8.20–8.05 (m, 2H), 8.05–7.82 (m, 2H), 7.71–7.51 (m, 2H). LC-MS (ES+) 327.09 (M+H). HPLC-Method D, R$_t$ 4.56 min.

Example 238

4-Chloro-2-(2-chloro-5-trifluorom thyl-phenyl)-quinazoline (B13)

LC-MS (ES+) 342.97 (M+H). HPLC-Method D, R$_t$ 4.91 min.

Example 239

4-Chloro-2-(2-chloro-4-nitro-phenyl)-quinazoline (B14)

LC-MS (ES+) 319.98 (M+H). HPLC-Method D, R$_t$ 4.45 min.

Example 240

4-Chloro-2-(2-trifluoromethyl-phenyl)-quinazoline (B15)

Prepared in 57% yield. White solid.
$^1$HNMR (500 MHz, DMSO-d6) δ 7.79 (t, 1H), 7.86 (t, 1H), 7.94 (m, 3H), 8.15 (dd, 1H), 8.20 (td, 1H), 8.37 (m, 1H); EI-MS 308.9 (M).

Example 241

4-Chloro-2-(2-trifluoromethyl-phenyl)-6,7-dihydro-5H-cyclopentapyrimidine (B16)

Prepared in 22% yield. $^1$HNMR (500 MHz, DMSO-d6) δ 2.19 (m, H), 3.01 (t, 2H), 3.08 (t, 2H), 7.49 (t, 1H), 7.55 (t, 1H), 7.62 (d, 1H), 7.71 (d, 1H). EI-MS 299.0 (M+H).

Example 242

4-Chloro-2-(2-chloro-phenyl)-6,7,8,9-tetrahydro-5H-cycloheptapyrimidine (B17)

Prepared according to Method C in 82% yield to afford a white solid. $^1$HNMR (500 MHz, CDCl$_3$) δ 1.67 (m 4H), 1.87

(m 2H), 3.02 (m 4H), 7.28 (m, 2H), 7.40 (m, 1H), 7.65 (m, 1H); EI-MS 293.0 (M+1).

Example 243

4-Chloro-2-(2-trifluoromethyl-phenyl)-5,6,7,8,9,10-hexahydro-cyclooctapyrimidine (B18)

Prepared in 38% yield to afford a brown oil. $^1$HNMR (500 MHz, CDCl$_3$) δ 1.35 (m 2H), 1.41 (m 2H), 1.76 (m 4H), 2.96 (m, 4H), 7.48 (t, 1H), 7.56 (t, 1H), 7.66 (d, 1H), 7.70 (d, 1H); EI-MS 341.0 (M+1).

Example 244

4-Chloro-8-methoxy-2-(2-trifluoromethyl-phenyl)-quinazoline (B19)

Prepared from 8-methoxy-2-(2-trifluoromethyl-phenyl)-3H-quinazolin-4-one (1.0 g, 3.12 mmol), triethylamine hydrochloride (472 mg, 3.43 mmol), and POCl$_3$. Purification by flash chromatography afforded a white solid (89% yield). HPLC-Method A, R$_t$ 4.10 min, (98%), MS (m/z) 258.08 (M+H).

Example 245

2-(4-Chloro-quinazolin-2-yl)-benzonitrile (B20)

Prepared to afford a yellow solid in 1.5% yield.
$^1$H-NMR (500 MHz, CDCl3) δ 8.47 (d, 1H), 8.24 (d, 1H), 8.16 (d, 1H), 8.07 (impurity), 7.94 (t, 1H), 7.92 (impurity), 7.86 (d, 1H), 7.68 (m, 2H), 7.65 (impurity), 7.54 (impurity), 7.49 (t, 1H), 4.2 (impurity), 1.05 (impurity) ppm; MS (LC/MS) 266.05 (M+H); HPLC-Method A, R$_t$ 3.88 min.

Example 246

6-Methyl-2-(2-trifluoromethyl-phenyl)-3H-pyrimidin-4-one (D3)

Prepared to afford a yellow solid in 50% yield. $^1$H-NMR (500 MHz, DMSO-d6) δ 12.7 (br s, 1H), 7.9 (m, 1H), 7.8 (m, 2H), 7.7 (m, 1H), 6.3 (s, 1H), 2.21 (s, 3H) ppm; MS (FIA) 255.0. (M+H); HPLC-Method A, R$_t$ 2.578 min.

Example 247

6-Cyclohexyl-2-(2-trifluoromethyl-phenyl)-3H-pyrimidin-4-one (D4)

Prepared to afford an off-white solid in 54% yield. $^1$H-NMR (500 MHz, DMSO-d6) δ 12.9 (br s, 1H), 7.9 (m, 4H), 6.3 (s, 1H), 2.5 (m, 1H), 1.9 (m, 5H), 1.4 (m, 5H) ppm; MS (FIA) 323.1 (M+H); HPLC-Method A, R$_t$ 3.842 min.

Example 248

2-(2-Chloro-5-trifluoromethyl-phenyl)-3H-quinazoli-4-one (D10)

$^1$HNMR (500 MHz, CD$_3$OD) δ 8.32–8.25 (m, 1H), 8.01 (s, 1H), 7.91–7.72 (m, 1H), 7.66–7.55 (m, 1H). LC-MS (ES+) 325.01 (M+H). HPLC-Method D, R$_t$ 3.29 min.

Example 249

2-(4-Fluoro-2-trifluoromethyl-phenyl)-3H-quinazolin-4-one (D14)

$^1$HNMR (500 MHz, CD$_3$OD) δ 8.28 (d, 8.0 Hz, 1H), 7.94–7.84 (m, 1H), 7.84–7.77 (m, 1H), 7.76–7.67 (m, 2H), 7.65–7.53 (m, 2H). LC-MS (ES+) 309.06 (M+H). HPLC-Method D, R$_t$ 2.88 min.

Example 250

2-(4-Nitro-2-chloro-phenyl)-3H-quinazolin-4-one (D15)

LC-MS (ES+) 302.03 (M+H). HPLC-Method D, R$_t$ 2.81 min.

Example 251

2-(5-Fluoro-2-trifluoromethyl-phenyl)-3H-quinazolin-4-one (D17)

$^1$HNMR (500 MHz, CD$_3$OD) δ 8.28 (d, R$_t$ J=8.05 Hz, 1H), 7.96 (dd, J=5.05, 8.55 Hz, 1H), 7.89 (t, J=7.9 Hz, 1H), 7.78–7.69 (m, 1H), 7.66–7.46 (m, 3H). LC-MS (ES+) 309.14 (M+H). HPLC-Method D, R$_t$ 2.90 min.

Example 252

(1H-Indazol-3-yl)-(2-phenyl-quinazolin-4-yl)-amine (III-1)

Prepared by Method A in DMF to afford 70 mg (50% yield) as pale yellow solid. $^1$H NMR (500 MHz, DMSO-d6) δ13.1 (s, br, 1H), 8.48 (d, 1H), 7.91 (d, 2H), 7.76 (br, 2H), 7.45 (m, 2H), 7.36 (d, 1H), 7.20 (m, 4H), 6.86 (t, 1H) ppm. MS. (ES+) 338.07 (M+H); (ES–) 336.11 (M–H); HPLC-Method A, R$_t$ 2.88 min.

Example 253

(5-Methyl-2H-pyrazol-3-yl)-(2-phenyl-5,6,7,8-tetrahydroquinazolin-4-yl)-amine (III-7)

Prepared according to Method A. $^1$H NMR (500 MHz, DMSO-d6) δ12.1 (s, br, 1H), 8.70 (s, br, 1H), 8.37 (d, J=6.7 Hz, 2H), 7.54 (m, 3H), 6.67 (s, 1H), 2.82 (m, 2H), 2.68 (m, 2H), 2.37 (s, 3H), 1.90 (s, br, 4H); MS 306.1 (M+H).

Example 254

(5-Methyl-2H-pyrazol-3-yl)-(2-ph nyl-6,7,8,9-tetrahydro-5H-cycloheptapyrimidin-4-yl)-amine (III-8)

MS 320.48 (M+H); HPLC-Method E, R$_t$ 1.124 min.

Example 255

(5-Methyl-2H-pyrazol-3-yl)-(2-pyridin-4-yl-quinazolin-4-yl)-amine (III-9)

Yellow solid, mp 286–289° C., $^1$H NMR (DMSO) δ 2.35 (3H, s), 6.76 (1H, s), 7.61 (1H, m), 7.89 (2H, m), 8.32 (2H, d), 8.70 (1H, d), 8.78 (2H, d), 10.56 (1H, br s), 12.30 (1H, br s); IR (solid) 1620, 1598, 1571, 1554, 1483, 1413, 1370, 1328; MS 303.2 (M+H)$^+$

Example 256

(7-Chloro-2-pyridin-4-yl-quinazolin-4-yl)-(5-methyl-2H-pyrazol-3-yl)-amine (III-28)

$^1$H NMR (DMSO-d6) δ2.35 (3H, s), 6.75 (1H, s), 7.65 (1H, d), 7.93 (1H, s), 8.30 (2H, d), 8.73 (1H, d), 8.79 (2H, d), 10.69 (1H, s), 12.33 (1H, s); MS m/z 337.2 (M+H)$^+$.

Example 257

(6-Chloro-2-pyridin-4-yl-quinazolin-4-yl)-(5-methyl-2H-pyrazol-3-yl)-amine (III-29)

$^1$H NMR (DMSO-d6) δ 2.31 (3H, s), 6.74 (1H, s), 7.89 (1H, s), 8.30 (2H, d), 8.80 (2H, d), 8.91 (1H, s), 10.63 (1H, s), 12.29 (1H, s); MS 337.2 (M+H)$^+$.

Example 258

(2-Cyclohexyl-quinazolin-4-yl)-(5-methyl-2H-pyrazol-3-yl)-amine (III-30)

$^1$H NMR (DMSO) δ 2.35 (3H, s), 1.70 (3H, m), 1.87 (2H, d), 1.99 (2H, d), 2.95 (1H, t), 6.72 (1H, s), 7.75 (1H, d), 7.88 (1H, s), 7.96 (1H, s), 8.83 (1H, s), 11.95 (1H, s), 12.70 (1H, s); MS 308.4 (M+H)$^+$.

Example 259

(5-Methyl-2H-pyrazol-3-yl)-(2-phenyl-quinazolin-4-yl)-amine (III-31)

mp 246° C.; $^1$H NMR (400 MHz) δ2.35 (3H, s), 6.70 (1H, br s), 7.51–7.57 (4H, m), 7.83–7.84 (2H, d), 8.47–8.50 (2H, d), 8.65 (1H, d), 10.4 (1H, s), 12.2 (1H, bs); IR (solid) 3696, 3680, 2972, 2922, 2865; MS 302.1 (M+H)+.

Example 260

[2-(4-Iodophenyl)-quinazolin-4-yl]-(5-methyl-2H-pyrazol-3-yl)-amine (III-32)

$^1$H NMR (DMSO-d6) δ 2.34 (3H, s), 6.72 (1H, s), 7.56 (1H, d), 7.84 (2H, d), 7.93 (2H, d), 8.23 (2H, d), 8.65 (1H, s), 10.44 (1H, s), 12.24 (1H, s); MS 428.5 (M+H)+.

Example 261

[2-(3,4-Dichlorophenyl)-quinazolin-4-yl]-(5-methyl-2H-pyrazol-3-yl)-amine (III-33)

A suspension of 2-(3,4-dichloro-phenyl)-3H-quinazolin-4-one (1 g, 3.43 mmol) in phosphorus oxychloride (4 mL) was stirred at 110° C. for 3 hours. The solvent was removed by evaporation and the residue is treated carefully with cold aqueous, saturated NaHCO$_3$. The resulting solid was collected by filtration and washed with ether to afford 4-chloro-2-(3,5-dichloro-phenyl)-quinazoline as a white solid (993 mg, 93%). To the above compound (400 mg, 1.29 mmol) in THF (30 mL) was added 3-amino-5-methyl pyrazole (396 mg, 2.58 mmol) and the resulting mixture heated at 65° C. overnight. The solvents were evaporated and the residue triturated with ethyl acetate, filtered, and washed with the minimum amount of ethanol to afford compound III-33 as a white solid (311 mg 65%): mp 274° C.; $^1$H NMR (DMSO) δ 2.34 (3H, s), 6.69 (1H, s), 7.60 (1H, m), 7.84 (1H, d), 7.96 (2H, d), 8.39 (1H, dd), 8.60 (1H, d), 8.65 (1H, d), 10.51 (1H, s), 12.30 (1H, s); IR (solid) 1619, 1600, 1559, 1528, 1476, 1449, 1376, 1352, 797, 764, 738; MS 370.5 (M+H)$^+$.

Example 262

[2-(4-Bromophenyl)-quinazolin-4-yl]-(5-methyl-2H-pyrazol-3-yl)-amine (III-34)

mp 262–265° C.; $^1$H NMR (DMSO) δ 2.34 (3S, s), 6.73 (1H, s), 7.55 (1H, m), 7.74 (2H, d), 7.83 (2H, m), 8.40 (2H, d), 8.65 (1H, d), 10.44 (1H, s), 12.25 (1H, s); IR (solid) 1603, 1579, 1546, 1484, 1408, 1365; MS 380.1/382.1 (M+H)+.

Example 263

[2-(4-Chlorophenyl)-quinazolin-4-yl]-(5-methyl-2H-pyrazol-3-yl)-amine (III-35)

mp >300° C.; $^1$H NMR (DMSO) δ 2.34 (3H, s), 6.74 (1H, s), 7.53–7.62 (3H, m), 7.84 (2H, d), 8.47 (2H, d), 8.65 (1H, d), 10.44 (1H, s), 12.26 (1H, s); IR (solid) 1628, 1608, 1584, 1546, 1489, 1408, 1369, 1169; MS 336.2 (M+H)+.

Example 264

[2-(3,5-Dichlorophenyl)-quinazolin-4-yl]-(5-methyl-2H-pyrazol-3-yl)-amine (III-36)

mp 228° C.; $^1$H NMR (DMSO) δ 2.34 (3H, s), 6.69 (1H, s), 7.96 (1H, d), 8.21 (3H, m), 8.56 (1H, d), 8.60 (2H, d), 10.51 (1H, s), 12.30 (1H, s); IR (solid) 1546, 1331, 802, 763, 729, 658, 652; MS 370.5 (M+H)+.

Example 265

[2-(4-Cyanophenyl)-quinazolin-4-yl]-(5-methyl-2H-pyrazol-3-yl)-amine (III-37)

mp 263° C.; $^1$H NMR (DMSO) δ 2.34 (3H, s), 6.72 (1H, s), 7.61 (1H, d), 7.88 (2H, s), 8.04 (2H, d), 8.63 (2H, d), 8.67 (1H, s), 10.52 (1H, s), 12.27 (1H, s); IR (solid) 1739, 1436, 1366, 1229, 1217; MS 327.2 (M+H)$^+$.

Example 266

[2-(3-Iodophenyl)-quinazolin-4-yl]-(5-methyl-2H-pyrazol-3-yl)-amine (III-38)

mp 234–235° C.; $^1$H NMR (DMSO) δ 2.35 (3H, s), 6.73 (1H, s), 7.35 (1H, m), 7.56 (1H, m), 7.85 (3H, m), 8.47 (1H, m), 8.65 (1H, m), 8.86 (1H, s), 10.49 (1H, s), 12.28 (1H, br s); IR (solid) 1560, 1541, 1469, 1360; MS 428.1 (M+H)+.

Example 267

[2-(4-Ethylsulfanylphenyl)-quinazolin-4-yl]-(5-methyl-2H-pyrazol-3-yl)-amine (III-39)

mp 229–231° C.; $^1$H NMR (DMSO) δ 1.29 (3H, t), 2.35 (3H, s), 3.07 (2H, q), 6.76 (1H, s), 7.43 (2H, d), 7.51 (1H, m), 7.81 (2H, m), 8.41 (2H, d), 8.64 (1H, d), 10.38 (1H, s), 12.24 (1H, br s); IR (solid) 1587, 1574, 1555, 1531, 1484, 1412, 1369; MS 362.1 (M+H)+.

Example 268

(5-Cyclopropyl-2H-pyrazol-3-yl)-(2-phenyl-quinazolin-4-yl)-amine (III-40)

mp 218–219° C.; $^1$H NMR (DMSO-d6) δ 0.70–0.80(2H, m), 0.90–1.00 (2H, m), 6.70 (1H, s), 7.45–7.55 (4H, m), 7.80–7.85 (2H, m), 8.45–8.55 (2H, m), 8.65 (1H, d), 10.40 (1H, s), 12.27 (1H, s); IR (solid) 1624, 1605, 1591, 1572, 1561, 1533, 1479, 1439, 1419, 1361, 1327, 997, 828, 803, 780, 762, 710; MS 328.2 (M+H)$^+$.

Example 269

[2-(4-tert-Butylphenyl)-quinazolin-4-yl]-(5-methyl-2H-pyrazol-3-yl)-amine (III-41)

mp >300° C.; $^1$H NMR (DMSO-d6) δ 1.35 (9H, s), 2.34 (3H, s), 6.79 (1H, s), 7.55 (3H, d), 7.85 (2H, d), 8.39 (2H, d), 8.62 (1H, d), 10.35 (1H, s), 12.22 (1H, s); IR (solid) 1603, 1599, 1577, 1561, 1535, 1481, 1409, 1371, 1359, 998, 841, 825, 766, 757; MS 358.3 (M+H)$^+$.

Example 270

[2-(4-Chlorophenyl)-quinazolin-4-yl]-(5-cyclopropyl-2H-pyrazol-3-yl)-amine (III-42)

$^1$H NMR (DMSO-d6) δ 0.77 (4H, br m), 2.05 (1H, m), 6.59 (1H, s), 7.60 (1H, d), 7.85 (2H, d), 7.91 (2H, d), 8.22 (2H, d), 8.65 (1H, s), 10.51 (1H, s), 12.33 (1H, s); MS 362.1 (M+H)$^+$.

Example 271

(2-Bnzo[1,3]dioxol-5-yl-quinazolin-4-yl)-(5-methyl-2H-pyrazol-3-yl)-amine (III-43)

$^1$H NMR (DMSO) δ 2.33 (3H, s), 6.13 (2H, s), 6.78 (1H,s), 7.11 (1H, d), 7.80 (1H, t), 7.94 (1H, s), 8.09 (3H, m), 8.25 (1H, d), 10.34 (1H, s), 12.21 (1H, s); MS 346.5 (M+H)$^+$.

Example 272

[2-(4-Dimethylaminophenyl)-quinazolin-4-yl]-(5-methyl-2H-pyrazol-3-yl)-amine (III-44)

$^1$H NMR (DMSO-d6) δ 2.02 (6H, s), 2.39 (3H, s), 6.83 (1H, s), 7.71 (1H, d), 7.98 (2H, s), 8.04 (2H, d), 8.33 (2H, d), 8.67 (1H, s), 11.82 (1H, s), 12.72 (1H, s); MS 345.3 (M+H)$^+$.

Example 273

[2-(3-Methoxyphenyl)-quinazolin-4-yl]-(5-methyl-2H-pyrazol-3-yl)-amine (III-45)

mp 226° C.; $^1$H NMR (DMSO) δ 2.34 (3H, s), 3.92 (3H, s), 6.72 (1H, s), 7.21 (1H, d), 7.57 (1H, t), 7.79 (1H, t), 8.02 (3H, m), 8.14 (1H, s), 8.79 (1H, d), 10.39 (1H, s), 12.22 (1H, s); IR (solid) 1599, 1572, 1538, 1478, 1427, 1359, 833, 761, 661; MS 332.2 (M+H)$^+$.

Example 275

(5-Cyclopropyl-2H-pyrazol-3-yl)-[2-(3,4-dichlorophenyl)-quinazolin-4-yl]-amine (III-46)

$^1$H NMR (DMSO-d6) δ 0.86 (2H, d), 1.02 (2H, d), 1.69 (1H, m), 6.56 (1H, s), 7.57 (1H, d), 7.84 (4H, m), 8.40 (1H, d), 8.58 (1H, s), 8.64 (1H, s), 10.53 (1H, s), 12.36 (1H, s); MS 396.0 (M+H)$^+$.

Example 276

(2-Biphenyl-4-yl-quinazolin-4-yl)-(5-methyl-2H-pyrazol-3-yl)-amine (III-47)

To a mixture of [2-(4-bromo-phenyl)-quinazolin-4-yl]-(5-methyl-2H-pyrazol-3-yl)-amine (III-34) (196 mg, 0.51 mmol) and phenylboronic acid (75 mg, 0.62 mmol) in THF:water (1:1, 4 mL) was added Na$_2$CO$_3$ (219 mg, 2.06 mmol), triphenylphosphine (9 mg, 1/15 mol %) and palladium acetate (1 mg, 1:135 mol %). The resulting mixture was heated at 80° C. overnight, the solvents were evaporated and the residue purified by flash chromatography (gradient of dichloromethane:MeOH) to afford III-21 as a yellow solid (99 mg, 51%): $^1$H NMR (DMSO) δ 2.37 (3H, s), 6.82 (1H, s), 7.39–7.57 (4H, m), 7.73–7.87 (6H, m), 8.57 (2H, d), 8.67 (1H, d), 10.42 (1H, s), 12.27 (1H, s); MS 378.2 (M+H)$^+$.

Example 277

[2-(4-Ethynylphenyl)-quinazolin-4-yl]-(5-methyl-2H-pyrazol-3-yl)-amine (III-48)

To a mixture of [2-(4-bromo-phenyl)-quinazolin-4-yl]-(5-methyl-2H-pyrazol-3-yl)-amine (III-34) (114 mg, 0.3 mmol), and trimethylsilylacetylene (147 mg, 1.5 mmol)in DMF (2 mL) was added CuI (1.1 mg, 1:50 mol %), Pd(PPh$_3$)$_2$Cl$_2$ (4.2 mg, 1:50 mol %) and triethylamine (121 mg, 0.36 mmol). The resulting mixture was heated at 120° C. overnight and the solvent evaporated. The residue was triturated in ethyl acetate and the resulting precipitate collected by filtration. The collected solid was suspended in THF (3 mL) and TBAF (1M in THF, 1.1 eq) was added. The reaction mixture was stirred at room temperature for 2 hours and the solvent evaporated. The residue was purified by flash chromatography (silica gel, gradient of DCM:MeOH) to afford III-48 as a white solid (68 mg, 70%): $^1$H NMR (DMSO) δ 2.34 (3H, s), 4.36 (1H, s), 6.74 (1H, s), 7.55 (1H, m), 7.65 (2H, d), 7.84 (2H, m), 8.47 (2H, d), 8.65 (1H, d), 10.43 (1H, s), 12.24 (1H, s); MS 326.1 (M+H)$^+$.

Example 278

[2-(3-Ethynylphenyl)-quinazolin-4-yl]-(5-methyl-2H-pyrazol-3-yl)-amine (III-49)

mp 204–207° C.; $^1$H NMR (DMSO) δ 2.34 (3H, s), 4.28 (1H, s), 6.74 (1H, s), 7.55–7.63 (3H, m), 7.83–7.87 (2H, m), 8.49 (1H, d), 8.57 (1H, s), 8.65 (1H, d), 10.46 (1H, s), 12.27 (1H, s); IR (solid) 1598, 1574, 1541, 1489, 1474, 1422, 1365; MS 326.1 (M+H)+.

Example 279

[2-(3-Methylphenyl)-quinazolin-4-yl]-(5-methyl-2H-pyrazol-3-yl)-amine (III-50)

A suspension of 1H-quinazoline-2,4-dione (10.0 g, 61.7 mmol) in POCl$_3$ (60 mL, 644 mmol) and N,N-dimethylaniline (8 mL, 63.1 mmol) was heated under reflux for 2 h. The excess POCl$_3$ was removed in vacuo, the residue poured into ice, and the resulting precipitate collected by filtration. The crude solid product 2,4-dichloro-quinazoline (6.5 g, 53% yield) was washed with water and dried under vacuum for next step use without further purification. To a solution of the 2,4-dichloro-quinazoline (3.3 g, 16.6 mmol) in anhydrous ethanol (150 mL) was added 5-methyl-1H-pyrazol-3-yl amine (3.2 g, 32.9 mmol) and the resulting mixture was stirred at room temperature for 4 hours. The resulting precipitate was collected by filtration, washed with ethanol, and dried under vacuum to afford 4.0 g (93% yield) of (2-chloro-quinazolin-4-yl)-(5-methyl-1H-pyrazol-3-yl)-amine which was used in the next step without further purification. To a solution of the (2-chloro-quinazolin-4-yl)-(5-methyl-1H-pyrazol-3-yl)-amine (50 mg, 0.19 mmol) in DMF (1.0 mL) was added m-tolyl boronic acid (0.38 mmol), 2M Na$_2$CO$_3$ (0.96 mmol), and tri-t-butylphosphine (0.19 mmol). The flask was flushed with nitrogen and the catalyst PdCl$_2$(dppf) (0.011 mmol) added in one portion. The reaction mixture was then heated at 80° C. for 10 hours, cooled to room temperature, and poured into water (2 mL). The resulting precipitate was collected by filtration, washed with water, and purified by HPLC to afford III-50 as a pale yellow solid (61 mg, 75%): $^1$H NMR (500 MHz, DMSO-d6) δ12.3 (br s, 1H), 10.4 (br s, 1H), 8.75 (d, 1H), 8.30 (s, 1H), 8.25 (d, 1H), 7.78 (s, 2H), 7.55 (m, 1H), 7.45 (m, 1H), 7.35 (m, 1H), 6.80 (s, 1H), 2.47 (s, 3H), 2.30 (s, 3H); MS 316.1 (M+H).

Example 280

[2-(3,5-Difluorophenyl)-quinazolin-4-yl]-(5-methyl-2H-pyrazol-3-yl)-amine (III-51)

$^1$H NMR (500 MHz, DMSO-d6) δ12.3 (br s, 1H), 10.8 (br s, 1H), 8.63 (d, 1H), 7.95 (d, 2H), 7.85 (m, 2H), 7.58 (t, 1H), 7.41 (t, 1H), 6.59 (s, 1H), 2.27 (s, 3H); MS 338.1 (M+H).

Example 281

[2-(3-Chloro-4-fluorophenyl)-quinazolin-4-yl]-(5-methyl-2H-pyrazol-3-yl)-amine (III-52)

$^1$H NMR (500 MHz, DMSO-d6) δ12.4 (br s, 1H), 10.8 (br s, 1H), 8.65 (d, 1H), 8.50 (d, 1H), 8.36 (m, 1H), 7.85 (m, 1H), 7.60 (m, 1H), 6.62 (s, 1H), 2.30 (s, 3H); MS 354.1 (M+H).

Example 282

(5-Methyl-2H-pyrazol-3-yl)-[2-(3-trifluoromethylphenyl)-quinazolin-4-yl]-amine (III-53)

¹H NMR (500 MHz, DMSO-d6) δ12.2 (br, 1H), 10.45(br, 1H), 7.53 (s, 1H), 7.43 (d, J=7.2 Hz, 1H), 7.06 (d, J=8.2 Hz, 1H), 6.65 (d, J=8.3 Hz, 1H), 6.57 (t, J=7.6 Hz, 1H), 6.51 (d, J=7.8 Hz, 1H), 6.43 (t, J=7.8 Hz, 1H), 6.32 (t, J=7.6 Hz, 1H), 5.51 (s, 1H), 2.03 (s, 3H); MS 370.2 (M+H).

Example 283

[2-(3-Cyanophenyl)-quinazolin-4-yl]-(5-methyl-2H-pyrazol-3-yl)-amine (III-54)

¹H NMR (500 MHz, DMSO-d6) δ9.01 (s, 1H), 8.96 (m, 2H), 8.28 (d, J=7.3 Hz, 1H), 8.16 (s, br, 2H), 8.06 (t, J=7.8 Hz, 1H), 7.88 (m, 1H), 6.96 (S, 1H), 2.58 (s, 3H); MS 327.1 (M+H).

Example 284

[2-(3-Isopropylphenyl)-quinazolin-4-yl]-(5-m thyl-2H-pyrazol-3-yl)-amine (III-55)

¹H NMR (500 MHz, DMSO-d6) δ8.89 (d, J=7.5 Hz, 1H), 8.37 (s, 1H), 8.26 (s, 1H), 8.08 (m, 2H), 7.81 (t, br, 1H), 7.67 (m, 2H), 6.88 (s, 1H), 3.12 (m, 1H), 2.40 (s, 3H), 1.38 (d, J=6.9 Hz, 6H); MS 344.2 (M+H).

Example 285

(5-Methyl-2H-pyrazol-3-yl)-(2-pyridin-3-yl-quinazolin-4-yl)-amine (III-56)

¹H NMR (500 MHz, DMSO-d6) δ9.50 (s, 1H), 8.84 (d, J=7.3 Hz, 1H), 8.80 (d, J=4.4 Hz, 1H), 8.66 (d, J=8.2 Hz, 1H), 7.87 (m, 2H), 7.77 (m, 1H), 7.60 (t, J=7.2 Hz, 1H), 6.67 (s, 1H), 2.28 (s, 3H); MS 303.1 (M+H).

Example 286

[2-(3-Acetylphenyl)-quinazolin-4-yl]-(5-methyl-2H-pyrazol-3-yl)-amine (III-57)

¹H NMR (500 MHz, DMSO-d6) δ8.80 (s, 1H), 8.55 (d, J=7.7 Hz, 1H), 8.42 (d, J=7.6 Hz, 1H), 8.00 (d, J=7.0 Hz, 1H), 7.76 (m, 2H), 7.58 (t, J=7.7 Hz, 1H), 7.48 (s, br, 1H), 6.60 (s, 1H), 2.49 (s, 3H), 2.03 (s, 3H); MS 344.1 (M+H).

Example 287

[2-(3,5-Ditrifluoromethylphenyl)-quinazolin-4-yl]-(5-methyl-2H-pyrazol-3-yl)-amine (III-58)

¹H NMR (500 MHz, DMSO-d6) δ10.7 (s, br, 1H), 8.95 (s, 2H), 8.63 (d, J=8.2 Hz, 1H), 8.25 (s, 1H), 7.86 (m, 2H), 7.58 (t, J=6.9 Hz, 1H), 6.62 (s, 1H), 2.26 (s, 3H); MS 438.1 (M+H).

Example 288

[2-(3-Hydroxymethylphenyl)-quinazolin-4-yl]-(5-methyl-2H-pyrazol-3-yl)-amine (III-59)

¹H NMR (500 MHz, DMSO-d6) δ 8.74 (d, J=7.9 Hz, 1H), 8.33 (s, 1H), 8.17 (s, br, 1H), 7.95 (s, br, 1H), 7.89 (s, br, 1H), 7.62 (m, 3H), 6.72 (s, 1H), 5.53 (s, 1H), 4.60 (s, 2H), 2.28 (s, 3H); MS 332.1 (M+H).

Example 289

(5-Methyl-2H-pyrazol-3-yl)-[2-(3-phenoxyphenyl)-quinazolin-4-yl]-amine (III-60)

mp 231–232° C.; ¹H NMR (DMSO-d6) δ 2.21 (3H, s), 6.59 (1H, s), 7.10–7.22 (4H, m), 7.41–7.45 (2H, m), 7.54–7.59 (2H, m), 7.81 (2H, s), 8.09 (1H, s), 8.27 (1H, m), 8.64 (1H, m), 10.40 (1H, s), 12.20 (1H, s); IR (solid); IR (solid) 1589, 1560, 1541, 1536, 1484, 1360, 1227; MS 394.7 (M+H)⁺.

Example 290

(5-Cyclopropyl-2H-pyrazol-3-yl)-[2-(3-phenoxyphenyl)-quinazolin-4-yl]-amine (III-61)

mp 193–195° C.; ¹H NMR (DMSO-d6) δ 0.67 (2H, m), 0.93 (2H, m), 1.87 (1H, m), 6.56 (1H, s), 7.06–7.20 (4H, m), 7.40–7.43 (2H, m), 7.55–7.59 (2H, m), 7.81 (2H, s), 8.11 (1H, s), 8.27 (1H, m), 8.63 (1H, m), 10.43 (1H, s), 12.26 (1H, s); IR (solid); IR (solid) 1589, 1574, 1527, 1483, 1369, 1226; MS 420.7 (M+H)⁺.

Example 291

(5-Methyl-2H-pyrazol-3-yl)-(2-thiophen-3-yl-quinazolin-4-yl)-amine (III-62)

¹H NMR (500 MHz, DMSO-d6) δ11.78 (s, br, 1H), 8.75 (d, J=8.1 Hz, 1H), 8.68 (s, 1H), 7.98 (dd, J 7.9, 7.5 Hz, 1H), 7.89 (m, 2H), 7.81 (m, 1H), 7.68 (t, J=7.5 Hz, 1H), 6.69 (s, 1H), 2.30 (s, 3H); MS 308.1 (M+H).

Example 292

(2-Phenyl-quinazolin-4-yl)-(2H-pyrazol-3-yl)-amine (III-63)

mp 247–249° C.; ¹H NMR (DMSO) δ 6.99 (1H, br s), 7.49–7.58 (5H, m), 7.81 (1H, br s), 7.83 (2H, m), 8.47–8.49 (2H, m), 8.66 (1H, d), 10.54 (1H, s), 12.59 (1H, s); IR (solid) 3145, 2922, 1622, 1597; MS 288.2 (M+H)⁺.

Example 293

(2H-Pyrazol-3-yl)-(2-pyridin-4-yl-quinazolin-4-yl)-amine (III-64)

mp 285–286° C.; ¹H NMR (DMSO) δ 6.99 (1H, br s), 7.65 (1H, m), 7.81–7.94 (3H, m), 8.3–8.35 (2H, m), 8.73 (1H, d), 8.84–8.90 (2H, m), 10.76 (1H, s), 12.6 (1H, s); IR (solid) 3180, 2972, 1600, 1574; MS 289.2 (M+H)⁺.

Example 294

5-Ethyl-2H-pyrazol-3-yl)-(2-phenyl-quinazolin-4-yl)-amine (III-65)

mp 221–222° C.; ¹H NMR (DMSO) δ 1.31 (3H, t), 2.68 (2H, d), 6.80 (1H, s), 7.50–7.60 (4H, m), 8.45–8.55 (2H, m), 8.65–8.75 (1H, m), 10.44 (1H, s), 12.27 (1H, s); IR (solid) 3190, 1622, 1595, 1575, 1533, 1482, 1441, 1420, 1403, 1361, 758, 711; MS 316.2 (M+H)⁺.

Example 295

(2-Phenyl-quinazolin-4-yl)-(5-propyl-2H-pyrazol-3-yl)-amine (III-66)

mp 204–205° C.; ¹H NMR (DMSO-d6) δ 1.02 (3H, t), 1.66–1.75 (2H, m), 2.69 (2H, t), 6.80 (1H, s), 7.45–7.60 (4H, m), 7.80–7.88 (2H, m), 8.45–8.50 (2H, m), 8.65 (1H, d), 10.39 (1H, s), 12.25 (1H, s); IR (solid) 1621, 1560, 1572, 1533, 1479, 1441, 1421, 1363, 1328, 999, 827, 808, 763, 709, 697; MS 330.2 (M+H)⁺.

Example 296

(5-Isopropyl-2H-pyrazol-3-yl)-(2-phenyl-quinazolin-4-yl)-amine (III-67)

mp 218–219° C.; ¹H NMR (DMSO-d6) δ 1.36 (6H, d), 3.05 (1H, m), 6.86 (1H, s), 7.48–7.59 (4H, m), 7.80–7.88

(2H, m), 8.49–8.58 (2H, m), 8.66 (1H, d), 10.47 (1H, s), 12.30 (1H, s); IR (solid) 3173, 2968, 1619, 1593, 1573, 1533, 1478, 1438, 1413, 1398, 1363, 1329, 995, 822, 798, 761, 707, 666, 659; MS 330.2 (M+H)$^+$.

Example 297

(5-tert-Butyl-2H-pyrazol-3-yl)-(2-phenyl-quinazolin-4-yl)-amine (III-68)

mp 136–137° C.; $^1$H NMR (DMSO-d6) δ 1.38 (9H, s), 6.87 (1H, br s), 7.51–7.57 (4H, m), 7.84–7.85 (2H, m), 8.49–8.51 (2H, m), 8.65 (1H, d), 10.43 (1H, s), 12.21 (1H, br s); IR (solid) 3162, 2963, 1621, 1590, 1572; MS 344.2 (M+H)$^+$.

Example 298

(5-tert-Butyl-2H-pyrazol-3-yl)-(2-pyridin-4-yl-quinazolin-4-yl)-amine (III-69)

mp >300° C.; $^1$H NMR (DMSO) δ 1.38 (9H, s), 6.82 (1H, br s), 7.63 (1H, m), 7.86–7.91 (2H, m), 8.32–8.33 (2H, d), 8.69 (1H, d), 8.75–8.76 (2H, d), 10.60 (1H, s), 12.31 (1H, br s); IR (solid) 3683, 3149, 2963, 1621; MS 345.2(M+H)$^+$.

Example 299

(5-Cyclopentyl-2H-pyrazol-3-yl)-(2-phenyl-quinazolin-4-yl)-amine (III-70)

mp 240–241° C.; $^1$H NMR (DMSO-d6) δ 1.68–1.89 (6H, m), 2.03–2.17 (2H, m), 3.14–3.22 (1H, m), 6.80 (1H, s), 7.50–7.60 (4H, m), 7.80–7.89 (2H, m), 8.45–8.52 (2H, m), 8.67 (1H, d), 10.52 (1H, s), 12.26 (1H, s); IR (solid) 2957, 1621, 1591, 1571, 1531, 1476, 1438, 1405, 1370, 1325, 999, 951, 801, 775, 761, 747, 710695, 668, 654; MS 356.2(M+H)+.

Example 300

(5-Phenyl-2H-pyrazol-3-yl)-(2-phenyl-quinazolin-4-yl)-amine (III-71)

mp 207–209° C.; $^1$H NMR (DMSO) δ 7.38–7.40 (1H, m), 7.50–7.58 (6H, m), 7.82–7.88 (4H, m), 8.51 (2H, m), 8.67 (1H, s), 10.58 (1H, s), 13.11 (1H, br s); IR (solid) 3345, 3108, 1627, 1612; MS 364.2 (M+H)$^+$.

Example 301

(5-Carboxy-2H-pyrazol-3-yl)-(2-phenyl-quinazolin-4-yl)-amine (III-72)

(5-Methoxycarbonyl-2H-pyrazol-3-yl)-(2-phenyl-quinazolin-4-yl)-amine (III-73) (345 mg, 1 mmole in THF, 6 mL) was treated with NaOH (1M, 4.0 mL), stirred at 50° C. for 5 hours, cooled to room temperature, and neutralised with 1M HCl. The mixture was concentrated in vacuo to remove THF then diluted with water and the resulting precipitate filtered. The residual solid was dried at 80° C. under vacuum to afford III-72 as an off-white solid (312 mg, 94%): mp 289–291° C. (dec.); $^1$H NMR (DMSO) δ 7.45 (1H, br s), 7.50–7.60 (5H, m), 7.80–7.88 (2H, m), 7.40–7.50 (2H, m), 8.60–8.70 (1H, d), 10.70 (1H, s), 13.00–13.80 (2H, br s); IR (solid) 1699, 1624, 1607, 1570,1539, 1506, 1486, 1398, 1333, 1256, 1177, 1004, 827, 764, 705; MS 332.3 (M+H)$^+$.

Example 302

(5-Methoxycarbonyl-2H-pyrazol-3-yl)-(2-phenyl-quinazolin-4-yl)-amine (III-73)

mp 271–273° C.; $^1$H NMR (DMSO) δ 3.95 (3H, s), 7.50–7.65 (5H, m), 7.80–7.98 (2H, m), 8.40–8.50 (2H, m), 8.65–8.73 (1H, m), 10.80 (1H, s), 13.80 (1H, s); IR (solid) 3359, 1720, 1624, 1597, 1561, 1538, 1500, 1475, 1435, 1410, 1358, 1329, 1283, 1261, 1146, 1125, 1018, 1010, 944, 827, 806, 780, 763, 703, 690, 670; MS 346.3(M+H)$^+$.

Example 303

(5-Hydroxymethyl-2H-pyrazol-3-yl)-(2-phenyl-quinazolin-4-yl)-amine (III-74)

A solution of (5-Methoxycarbonyl-2H-pyrazol-3-yl)-(2-phenyl-quinazolin-4-yl)-amine (III-73) (345 mg, 1 mmol) in anhydrous THF (10 mL) was treated with lithium borohydride (125 mg, 5.75 mmol) at 65° C. for 5 hours. The mixture was cooled to room temperature then combined with 2M HCl and ethyl acetate. Solid sodium hydrogen carbonate was added to achieve pH 8 and the resulting mixture extracted with ethyl acetate. The extracts were dried over magnesium sulphate and concentrated. Purification by flash chromatography (SiO$_2$, methanol-dichloromethane gradient) afforded III-74 (95 mg, 30%) as an off-white solid: mp 238–239° C.; $^1$H NMR (DMSO) δ 4.58 (2H, d, CH2), 5.35 (1H, s, OH), 6.94 (1H, s), 7.50–7.60 (4H, m), 7.85–7.90 (2H, m), 8.48–8.54 (2H, m), 8.69 (1H, 1H), 10.40 (1H, s), 12.48 (1H, s); IR (solid) 1652, 1621, 1603, 1575, 1558, 1539, 1532, 1480, 1373, 1320, 1276, 1175, 1057, 1037, 1007, 951, 865, 843, 793, 780, 7124; MS 318.2(M+H)$^+$.

Example 304

(5-Methoxymethyl-2H-pyrazol-3-yl)-(2-phenyl-quinazolin-4-yl)-amine (III-75)

mp 190–191° C.; $^1$H NMR (DMSO) δ 3.34 (3H, s), 4.45 (2H, s), 7.00 (1H, s), 7.50–7.62 (4H, m), 7.82–7.90 (2H, m), 8.45–8.52 (2H, m), 8.65 (1H, br s), 10.50 (1H, s), 12.30 (1H, s); IR (solid) 3177, 1606, 1589, 1530, 1479, 1441, 1406, 1374, 1363, 1329, 1152, 1099, 999, 954, 834, 813, 766, 707, 691; MS 332.3(M+H)$^+$.

Example 305

[5-(3-Hydroxyprop-1-yl)-2H-pyrazol-3-yl]-(2-phenyl-quinazolin-4-yl)-amine (III-76)

A solution of (5-benzyloxypropyl-2H-pyrazol-3-yl)-(2-phenyl-quinazolin-4-yl)-amine (III-78) (200 mg, 0.46 mmol) in toluene (4 mL) and acetonitrile (8 mL) was stirred with trimethylsilyl iodide (0.64 ml, 4.6 mmol) at 55° C. for 3 hours to afford an amber coloured solution. This mixture was diluted with ethyl acetate and aqueous sodium hydrogen carbonate. The resulting layers were separated, the organic layer was dried over magnesium sulphate and concentrated in vacuo. Purification by flash chromatography (SiO$_2$, methanol-dichloromethane gradient) affords a yellow oil (115 mg). Trituration with dichloromethane affords III-76 as an off-white solid dried at 75° C. under vacuum (83 mg, 52%): mp 164–165° C.; $^1$H NMR (DMSO) δ 1.80–1.90 (2H, m), 2.70–2.80 (2H, m), 3.50–3.60 (2H, m), 4.59 (1H, s), 6.80 (1H, s), 7.50–7.60 (4H, m), 7.82–7.90 (2H, m), 8.48–8.53 (2H, m), 8.63 (1H, s), 10.40 (1H, s), 12.25 (1H, s); IR (solid) 1622, 1587, 1574, 1562, 1528, 1480, 1440, 1421, 1368, 1329, 1173, 1052, 1030, 1006, 952, 833, 762, 734, 706, 690, 671, 665; MS 346.0(M+H)$^+$.

Example 306

[5-(3-Methoxyprop-1-yl)-2H-pyrazol-3-yl]-(2-phenyl-quinazolin-4-yl)-amine (III-77)

mp 169–170° C.; $^1$H NMR (DMSO-d6) δ 1.86–1.97 (2H, m), 2.75 (2H, t), 3.30 (3H, s), 3.45 (2H, t), 6.80 (1H, s), 7.50–7.60 (4H, m), 7.80–7.90 (2H, m), 8.45–8.55 (2H, m), 8.67 (1H, d), 10.30 (1H, s), 12.25 (1H, s); IR (solid) 1620, 1591, 1572, 1532, 1476, 1425, 1408, 1373, 1326, 1117, 1003, 831, 764, 714, 695; MS 360.3(M+H)$^+$.

Example 307

[5-(3-Benzyloxyprop-1-yl)-2H-pyrazol-3-yl]-(2-phenyl-quinazolin-4-yl)-amine (III-78)

mp 177–178° C.;

$^1$H NMR (DMSO) δ 1.92–2.03 (2H, m), 3.76–3.85 (2H, m), 3.52–3.62 (2H, m), 4.51 (2H, s), 6.82 (1H, s), 7.28–7.40 (5H, m), 7.46–7.58 (4H, m), 7.80–7.85 (2H, m), 8.47–8.52 (2H, m), 8.66 (1H, d), 10.45 (1H, s); IR (solid) 1621, 1591, 1562, 1532, 1479, 1454, 1426, 1408, 1374, 1101, 1006, 835, 766, 738, 712, 696; MS 436.3(M+H)$^+$.

Example 308

[5-(3-Aminoprop-1-yl)-2H-pyrazol-3-yl]-(2-phenyl-quinazolin-4-yl)-amine (III-79)

A solution of [5-(3-tert-butoxycarbonylaminoprop-1-yl)-2H-pyrazol-3-yl]-(2-phenyl-quinazolin-4-yl)-amine (III-80) (250 mg, 0.56 mmol), in dichloromethane (3 mL) at 0° C. was treated with TFA (2 mL). The mixture was warmed to room temperature then concentrated in vacuo. The residue was triturated and concentrated from dichloromethane (3×5 mL) and ether, then triturated with dichloromethane to crystallize the TFA salt. The resulting solid was collected by filtration and dissolved in a mixture of ethanol (3 mL) and water (3 mL). Potassium carbonate was added in portions to achieve pH 8 then the mixture allowed to crystallize. The product was collected by filtration and dried at 80° C. under vacuum to afford III-79 as an off-white powder (122 mg, 63%): mp 205–207° C.; $^1$H NMR (DMSO) δ 1.68–1.83 (2H, m), 2.65–2.80(4H, m), 6.80 (1H, s), 7.50–7.60 (4H, m), 7.80–7.90 (2H, m), 8.45–8.53 (2H, m), 8.65 (1H, d), 10.45 (1H, br s); IR (solid) 1621, 1598, 1568, 1533, 1484, 1414, 1364, 1327, 1169, 1030, 951, 830, 776, 764, 705, 677; MS 345.3(M+H)$^+$.

Example 309

[5-(3-tert-Butoxycarbonylaminoprop-1-yl)-2H-pyrazol-3-yl]-(2-phenyl-quinazolin-4-yl)-amine (III-80)

mp 199–200° C.; $^1$H NMR (DMSO) δ 1.37 (9H, s), 1.71–1.82 (2H, m), 2.67 (2H, t), 3.00–3.11 (2H, m), 7.81 (1H, s), 7.99 (1H, s), 7.50–7.60 (4H, m), 7.80–7.85 (2H, m), 8.48–8.52 (2H, m), 8.63 (1H, d), 10.40 (1H, s), 12.26 (1H, m); IR (solid) 2953, 1687, 1622, 1594, 1573, 1535, 1481, 1441, 1419, 1364, 1327, 1281, 1252, 1166, 1070, 1028, 998, 951, 848, 807, 768, 740, 728, 710, 693; MS 445.3 (M+H)$^+$.

Example 310

5-Isopropylcarbamoyl-2H-pyrazol-3-yl)-(2-phenyl-quinazolin-4-yl)-amine (III-81)

$^1$H NMR (500 MHz, DMSO-d6) δ 1.20 (d, J=6.6 Hz, 6H), 4.13 (m, 1H), 7.42 (br. s, 1H), 7.61 (dd, J=7.0, 7.7 Hz, 2H), 7.66 (t, J=7.1 Hz, 1H), 7.71 (m, 1H), 7.99 (m, 2H), 8.39 (m, 1H), 8.42 (d, J=7.1 Hz, 2H), 8.74 (d, J=8.2 Hz, 1H), 11.41 (br. s, 1H); EI-MS 373.2 (M+H); HPLC-Method C, R$_t$ 14.09 min.

Example 311

(5-Allylcarbamoyl-2H-pyrazol-3-yl)-(2-phenyl-quinazolin-4-yl)-amine (III-82)

$^1$H NMR (500 MHz, DMSO-d6) δ 4.02 (m, 2H), 5.15 (m, 1H), 5.23 (m, 1H), 5.94 (m, 1H), 7.45 (br. s, 1H), 7.60 (t, J=6.9 Hz, 2H), 7.64 (m, 1H), 7.72 (m, 1H), 7.98 (m, 2H), 8.43 (m 2H), 8.72 (d, J=8.2 Hz, 1H), 8.84 (br. s, 1H), 11.34 (br. s, 1H); EI-MS 371.2 (M+H); HPLC-Method C, R$_t$ 13.67 min.

Example 312

[5-(2-Methoxyethylcarbamoyl)-2H-pyrazol-3-yl]-(2-ph nyl-quinazolin-4-yl)-amine (III-83)

$^1$H NMR (500 MHz, DMSO-d6) δ 3.32 (s, 3H), 3.48 (m, 4H), 7.36 (br. s, 1H), 7.62 (m, 2H), 7.63 (m, 1H), 7.71 (m, 1H), 7.98 (m, 2H), 8.41 (dd, J=1.4, 7.0, 2H), 8.70 (m, 2H), 11.30 (br. s, 1H); EI-MS 389.2 (M+H); HPLC-Method C, R$_t$ 12.37 min.

Example 313

(5-Benzylcarbamoyl-2H-pyrazol-3-yl)-(2-phenyl-quinazolin-4-yl)-amine (III-84)

$^1$H NMR (500 MHz, DMSO-d6) δ 4.52 (d, J=6.0 Hz, 2H), 7.29 (m, 1H), 7.38 (d, J=4.2 Hz, 4H), 7.58 (t, J=7.5 Hz, 2H), 7.63 (m, 1H), 7.72 (m, 1H), 7.98 (m, 2H), 8.43 (d, J=7.7 Hz, 2H), 8.72 (d, J=7.5 Hz, 1H), 9.23 (br. s, 2H), 11.34 (br. s, 1H); EI-MS 421.2 (M+H); HPLC-Method C, R$_t$ 16.76 min.

Example 314

(5-Cyclohexylcarbamoyl-2H-pyrazol-3-yl)-(2-phenyl-quinazolin-4-yl)-amine (III-85)

$^1$H NMR (500 MHz, DMSO-d6) δ 1.16 (m, 1H), 1.34 (m, 4H), 1.62 (d, J=2.6 Hz, 1H), 1.76 (m, 2H), 1.85 (m, 2H), 3.79 (m, 1H), 7.43 (m, 1H), 7.60 (t, J=7.2 Hz, 2H), 7.65 (t, J=7.1 Hz, 1H), 7.71 (ddd, J=2.2, 5.4, 8.2 Hz, 1H), 7.98 (m, 2H), 8.35 (m, 1H), 8.43 (dd, J=1.4, 7.2 Hz, 2H), 8.72 (d, J=8.2 Hz, 1H), 11.34 (br. s, 1H); EI-MS 413.5 (M+H); HPLC-Method C, R$_t$ 17.18 min.

Example 315

(5-Diethylcarbamoyl-2H-pyrazol-3-yl)-(2-phenyl-quinazolin-4-yl)-amine (III-86)

$^1$H NMR (500 MHz, DMSO-d6) δ 1.18 (br. s, 3H), 1.25 (br. s, 3H), 3.49 (br. s, 2H), 3.69 (b. s, 2H), 7.21 (s, 1H), 7.59 (t, J=6.9 Hz, 2H), 7.62 (m, 1H), 7.70 (m, 1H), 7.96 (m, 2H), 8.39 (d, J=7.1 Hz, 2H), 8.74 (d, J=8.4 Hz, 1H), 11.37 (br. s, 1H); EI-MS 387.2 (M+H); HPLC-Method C, R$_t$ 14.50 min.

Example 316

[5-(B nzyl-methyl-carbamoyl)-2H-pyrazol-3-yl]-(2-phenyl-quinazolin-4-yl)-amine (III-87)

$^1$H NMR (500 MHz, DMSO-d6) δ 3.33 (s, 3H), 4.75 (s, 2H), 7.26 (m, 1H), 7.31 (m, 1H), 7.38 (m, 4H), 7.58 (m, 2H), 7.70 (m, 1H), 7.95 (m, 3H), 8.26 (m, 1H), 8.40 (d, J=7.8 Hz, 2H), 8.75 (m, 1H), 11.2 (br. s, 1H); EI-MS 435.2 (M+H); HPLC-Method C, R$_t$ 16.77 min.

Example 317

(2-Phenyl-quinazolin-4-yl)-(5-propylcarbamoyl-2H-pyrazol-3-yl)-amine (III-88)

$^1$H NMR (500 MHz, DMSO-d6) δ 0.94 (t, J=7.3 Hz, 3H), 1.57 (m, 2H), 3.24 (q, J=6.5 Hz, 2H), 7.39 (br. s, 1H), 7.60 (t, J=7.3 Hz, 2H), 7.64 (m, 1H), 7.71 (br. t, J=6.5 Hz, 1H), 7.98 (m, 2H), 8.42 (d, J=7.2 Hz, 2H), 8.61 (br. s, 1H), 8.72

(d, J=8.5 Hz, 1H), 11.34 (br. s, 1H); EI-MS 373.3 (M+H); HPLC-Method C, R$_t$ 13.51 min.

Example 318

[5-(Ethyl-isopropyl-carbamoyl)-2H-pyrazol-3-yl]-(2-phenyl-quinazolin-4-yl)-amine (III-89)

$^1$H NMR (500 MHz, DMSO-d6) δ 0.92 (t, J=7.4 Hz, 6H), 1.52 (m, 2H), 1.59 (m, 1H), 3.79 (m, 2H), 7.53 (br. s, 1H), 7.57 (t, J=7.5 Hz, 2H), 7.65 (t, J=7.2 Hz, 1H), 7.71 (m, 1H), 7.99 (m, 2H), 8.23 (br. d, J=8.8 Hz, 1H), 8.46 (d, J=7.5 Hz, 2H), 8.74 (d, J=8.4 Hz, 1H), 11.34 (br. s, 1H); EI-MS 401.2 (M+H); HPLC-Method C, R$_t$ 15.51 min.

Example 319

(5-Cyclopropylcarbamoyl-2H-pyrazol-3-yl)-(2-phenyl-quinazolin-4-yl)-amine (III-90)

$^1$H NMR (500 MHz, DMSO-d6) δ 0.60 (m, 2H), 0.74 (m, 2H), 2.86 (m, 1H), 7.34 (br. s, 1H), 7.62 (m, 3H), 7.70 (m, 1H), 7.97 (m, 2H), 8.41 (d, J=7.9 Hz, 2H), 8.63 (br. s, 1H), 8.72 (d, J=7.8 Hz, 1H), 11.35 (br. s, 1H); EI-MS 371.2 (M+H); HPLC-Method C, R$_t$ 12.64 min.

Example 320

(5-Isobutylcarbamoyl-2H-pyrazol-3-yl)-(2-phenyl-quinazolin-4-yl)-amine (III-91)

$^1$H NMR (500 MHz, DMSO-d6) δ 0.94 (d, J=6.7 Hz, 6H), 1.88 (m, 1H), 3.12 (t, J=6.4 Hz, 2H), 7.45 (br. s, 1H), 7.58 (t, J=7.2 Hz, 3H), 7.64 (t, J=7.1 Hz, 1H), 7.71 (m, 1H), 7.98 (m, 2H), 8.44 (dd, J=1.3, 7.9 Hz, 2H), 8.62 (br. s, 1H), 8.72 (d, J=8.3 Hz, 1H), 11.33 (br. s, 1H); EI-MS 387.2 (M+H); HPLC-Method C, R$_t$ 14.70 min.

Example 321

{5-[(3S)-3-Methoxymethyl-pyrrolidine-1-carbonyl]-2H-pyrazol-3-yl}-(2-phenyl-quinazolin-4-yl)-amine (III-93)

$^1$H NMR (500 MHz, DMSO-d6) δ 2.00 (m, 2H), 2.12 (m, 1H), 3.29 (s, 3H), 3.45 (t, J=8.7 Hz, 1H), 3.57 (dd, J=3.2, 9.3 Hz, 1H), 3.86 (m, 1H), 3.92 (m, 1H), 4.36 (m, 2H), 7.45 (br. s, 1H), 7.59 (t, J=7.2 Hz, 2H), 7.63 (m, 1H), 7.69 (m, 1H), 7.97 (m, 2H), 8.40 (d, J=7.5 Hz, 2H), 8.74 (d, J=7.6 Hz, 1H), 11.38 (br. s, 1H); EI-MS 429.2 (M+H); HPLC-Method C, R$_t$ 13.84 min.

Example 322

(2-Phenyl-quinazolin-4-yl)-(5-m-tolylcarbamoyl-2H-pyrazol-3-yl)-amine (III-94)

$^1$H NMR (500 MHz, DMSO-d6) δ 2.33 (s, 3H), 6.97 (d, J=7.5 Hz, 1H), 7.27 (t, J=7.8 Hz, 1H), 7.62 (m, 7H), 7.72 (m, 1H), 7.98 (m, 2H), 8.46 (dd, J=2.0, 7.9 Hz, 2H), 8.71 (m, 1H), 10.29 (s, 1H), 11.31 (br. s, 1H); EI-MS 421.2 (M+H); HPLC-Method C, R$_t$ 17.11 min.

Example 323

(2-Phenyl-quinazolin-4-yl)-(5-p-tolylcarbamoyl-2H-pyrazol-3-yl)-amine (III-95)

$^1$H NMR (500 MHz, DMSO-d6) δ 2.30 (s, 3H), 7.20 (d, J=8.3 Hz, 2H), 7.62 (m, 5H), 7.68 (d, J=8.3 Hz, 2H), 7.72 (m, 1H), 7.98 (m, 2H), 8.46 (dd, J=1.8, 7.0 Hz, 2H), 8.72 (m, 1H), 10.31 (s, 1H), 11.36 (br. s, 1H); EI-MS 421.2 (M+H); HPLC-Method C, R$_t$ 16.95 min.

Example 324

(5-Methylcarbamoyl-2H-pyrazol-3-yl)-(2-phenyl-quinazolin-4-yl)-amine (III-96)

$^1$H NMR (500 MHz, DMSO-d6) δ 2.82 (d, J=4.6 Hz, 3H), 7.31 (br. s, 1H), 7.62 (m, 3H), 7.69 (m, 1H), 7.97 (m, 2H), 8.42 (d, J=7.1 Hz, 2H), 8.59 (br. s, 1H), 8.71 (d, J=8.0 Hz, 1H), 11.30 (br. s, 1H); EI-MS 345.1 (M+H); HPLC-Method C, R$_t$ 11.02 min.

Example 325

[5-(Morpholine-4-carbonyl)-2H-pyrazol-3-yl]-(2-phenyl-quinazolin-4-yl)-amine (III-97)

$^1$H NMR (500 MHz, DMSO-d6) δ 3.33 (m, 4H), 3.83 (m 4H), 7.34 (br. s, 1H), 7.53 (m, 4H), 7.86 (m, 2H), 8.43 (m, 2H), 8.67 (d, J=8.6 Hz, 1H), 10.70 (s, 1H), 13.56 (s, 1H); EI-MS 401.2 (M+H); HPLC-Method A, R$_t$ 2.68 min.

Example 326

[5-(1-Methylpiperazine-4-carbonyl)-2-H-pyrazol-3-yl]-(2-phenyl-quinazolin-4-yl)-amine (III-98)

$^1$H NMR (500 MHz, DMSO-d6) δ 2.25 (s, 3H), 2.43 (m, 4H), 3.87 (m 4H), 7.33 (br. s, 1H), 7.53 (m, 4H), 7.87 (m, 2H), 8.45 (m, 2H), 8.67 (d, J=7.6 Hz, 1H), 10.70 (s, 1H), 13.30 (s, 1H); EI-MS 414.2 (M+H); HPLC-Method A, R$_t$ 2.38 min.

Example 327

[5-(2-Hydroxyethylcarbamoyl-2H-pyrazol-3-yl]-(2-phenyl-quinazolin-4-yl)-amine (III-99)

$^1$H NMR (500 MHz, DMSO-d6) δ 3.36 (m, 2H), 3.52 (m, 2H), 4.79 (m, 1H), 7.50 (m, 5H), 7.83 (m, 2H), 8.50 (m, 4H), 10.52 (br. s, 1H), 13.25 (s, 1H); EI-MS 375.1 (M+H); HPLC-Method A, R$_t$ 2.51 min.

Example 328

(5-Carbamoyl-2H-pyrazol-3-yl)-(2-phenyl-quinazolin-4-yl)-amine (III-100)

To a solution of 5-(2-phenyl-quinazolin-4-ylamino)-1H-pyrazole-3-carboxylic acid 2,5-dioxo-pyrrolidin-1-yl ester (270 mg, 0.63 mmol) in DMF (20 ml) was added a solution of ammonia in 1,4-dioxane (0.5 M, 10 ml). The resulting mixture was stirred at room temperature for 24 h. After concentration of the solvents, the residue was added to water (20 ml). The resulting precipitate was collected to afford III-100 (168 mg, 80%) as a yellow solid. $^1$H NMR (500 MHz, DMSO-d6) δ 7.77–7.51 (m, 6H), 7.86 (br s, 2H), 8.11 (m, 1H), 8.50 (m, 2H), 8.63 (m, 1H), 10.52 (s, 1H), 11.25 (s, 1H); EI-MS 331.1 (M+H); HPLC-Method A, R$_t$ 2.52 min.

Example 329

(4-Bromo-2-H-pyrazol-3-yl)-(2-phenyl-quinazolin-4-yl)-amine (III–101)

Prepared according to Method A to afford a yellow solid, mp 189° C.; $^1$H NMR (DMSO-d6) δ 7.44–7.46 (3H, m), 7.58 (1H, m), 7.87 (2H, d), 8.15 (1H, s), 8.31–8.34 (2H, m), 8.49 (1H, d), 10.08 (1H, s), 13.13 (1H, s); IR (solid) 3286, 2969, 1738, 1632; MS 366.2/368.2(M+H)$^+$.

Example 330

(4-Bromo-5-methyl-2H-pyrazol-3-yl)-(2-phenyl-quinazolin-4-yl)-amine (III-102)

mp 183–185° C.; $^1$H NMR (DMSO) δ 2.33 (3H, br s), 7.44–7.46 (3H, m), 7.57 (1H, m), 7.84–7.87 (2H, m), 8.31–8.34 (2H, m), 8.48 (1H, d), 10.05 (1H, s), 12.91 (1H, br s); IR (solid) 3362, 3065, 2831, 1619, 1578; MS 380.2/382.2(M+H)$^+$.

Example 331

(4-Cyano-2H-pyrazol-3-yl)-(2-phenyl-quinazolin-4-yl)-amine (III-103)

mp >250° C.; $^1$H NMR (DMSO) δ 7.47–7.49 (3H, m), 7.64 (1H, m), 7.91 (2H, m), 8.40–8.43 (2H, m), 8.53 (1H, d), 8.71 (1H, d), 10.61 (1H, s), 13.60 (1H, s); IR (solid) 3277, 3069, 2855, 2231, 1625; MS 313.2(M+H)$^+$.

Example 332

(5-Methyl-2H-pyrazol-3-yl)-(2-morpholin-4-yl-quinazolin-4-yl)-amine (III-104)

mp 223–224° C.; $^1$H NMR (DMSO) δ 2.26(3H, s), 3.65(4H, m), 3.75(4H, m), 6.44(1H, s), 7.12(1H, d), 7.33 (1H, d), 7.56(1H, t), 8.37(1H, d), 10.01(1H, s), 12.13(1H, br s); IR (solid) 1621, 1578, 1537, 1475, 1434, 1385; MS 311.0 (M+H)$^+$.

Example 333

(5-Methyl-2H-pyrazol-3-yl)-(2-piperazin-1-yl-quinazolin-4-yl)-amine (III-105)

mp 179–181° C.; $^1$H NMR (DMSO) δ 2.26(3H, s), 2.74 (4H, br s), 3.71(4H, br s), 6.43(1H, s), 7.08(1H, t), 7.30(1H, d), 7.53(1H, t), 8.34(1H, d), 9.50(1H, s), 12.08(1H, br s); IR (solid) 2853, 1619, 1603, 1566, 1549, 1539; MS 310.0 (M+H)$^+$

Example 334

[2-(4-Methylpiperidin-1-yl)-quinazolin-4-yl]-(5-methyl-2H-pyrazol-3-yl)-amine (III-106)

mp 148–150° C.;

$^1$H NMR (DMSO) δ 1.06(3H, d), 1.03(2H, m), 1.51–1.70 (3H, m), 2.26(3H, s), 2.86(2H, m), 4.73(2H, d), 6.44(1H, s), 7.06(1H, d), 7.29(1H, d), 7.52(1H, t), 8.32(1H, d), 9.92(1H, s), 12.09(1H, br s); IR (solid) 2917, 2840, 1629, 1593, 1562, 1546, 1486; MS 323.0 (M+H)$^+$.

Example 335

[2-(4-Methylpiperazin-1-yl)-quinazolin-4-yl]-(5-methyl-2H-pyrazol-3-yl)-amine (III-107)

mp 105–107° C.;

$^1$H NMR (DMSO) δ 2.21(3H, s), 2.26(3H, s), 2.34(4H, m), 3.75(4H, m), 6.45(1H, s), 7.09(1H, t), 7.31(1H, d), 7.54(1H, t), 8.34(1H, d), 9.96(1H, s), 12.12(1H, br s); IR (solid) 2934, 2844, 2804, 1620, 1593, 1572, 1536, 1476; MS 324.0 (M+H)$^+$.

Example 336

(5-Methyl-2H-pyrazol-3-yl)-(2-piperidin-1-yl-quinazolin-4-yl)-amine (III-108)

mp 294° C.; $^1$H NMR (DMSO) δ 1.45–1.58 (4H, m), 1.63 (2H, m), 2.26 (3H, s), 3.79 (4H, m), 6.45 (1H, br s), 7.06 (1H, t), 7.29 (1H, d), 7.52 (1H, t), 8.33 (1H, d), 9.92 (1H, s), 12.11 (1H, br s); IR (solid) 2929, 2847, 1632, 1591, 1500, 1482, 1437, 1382; MS 309.3 (M+H)$^+$.

Example 337

(2-Azepan-1-yl)-quinazolin-4-yl]-(5-methyl-2H-pyrazol-3-yl)-amine (III-109)

mp 269° C.; $^1$H NMR (DMSO) δ 1.50 (4H, br s), 1.76 (4H, br s), 2.25 (3H, s), 3.78 (4H, t), 6.55 (1H, br s), 7.03 (1H, t), 7.28 (1H, d), 7.50 (1H, t), 8.33 (1H, d), 9.92 (1H, s), 12.09 (1H, br s); IR (solid) 3427, 2963, 2927, 2909, 2872, 2850, 1623, 1595, 1586, 1568, 1504, 1486, 1468, 1386, 1427; MS 323.3 (M+H)$^+$.

Example 338

[2-(4-(2-Hydroxyethylpiperidin-1-yl)-quinazolin-4-yl]-(5-methyl-2H-pyrazol-3-yl)-amine (III-110)

mp 175° C.; $^1$H NMR (DMSO) δ 1.08 (2H, m), 1.38 (2H, m), 1.57–1.83 (3H, m), 2.26 (3H, s), 2.85 (2H, t), 3.47 (2H, m), 4.38 (1H, t), 4.75 (2H, d), 6.45 (1H, br s), 7.06 (1H, t), 7.29 (1H, d), 7.52 (1H, t), 8.32 (1H, d), 9.93 (1H, s), 12.12 (1H, br s); IR (solid) 3365, 3073, 2972, 2868, 1622, 1604, 1586, 1568, 1486, 1463, 1440, 1394; MS.353.2 (M+H)$^+$.

Example 339

(5-Cyclopropyl-2H-pyrazol-3-yl)-[2-(4-methylpiperidin-1-yl)-quinazolin-4-yl]-amine (III-111)

To a solution of (5-cyclopropyl-1H-pyrazol-3-yl)-(2-chloro-quinazolin-4-yl)-amine (118 mg, 0.41 mmol) in tert-butanol (3.0 mL) was added 4-methylpiperidine (0.49 mL, 4.1 mmol) and the reaction mixture heated at reflux overnight. The reaction mixture was concentrated in vacuo and the residue dissolved in a mixture EtOH:water (1:3, 4 mL). Potassium carbonate (57 mg, 0.41 mmol) was added and the mixture stirred at room temperature for 2 hours. The resulting suspension was filtered, washed with water (×2), and rinsed with Et$_2$O (×2) to afford III-111 as a white solid (123 mg, 85%): mp 190° C.; $^1$H NMR (DMSO) δ 0.66 (2H, s), 0.93 (5H, br s), 1.07 (2H, d), 1.66 (3H, s), 1.91 (1H, s), 2.85 (2H, t), 4.72 (2H, d), 6.33 (1H, s), 7.06 (1H, t), 7.29 (1H, d), 7.52 (1H, t), 8.31 (1H, d), 9.95 (1H, s), 12.18 (1H, br s); IR (solid) 2925, 2852, 1622, 1590, 1581, 1558, 1494, 1481, 1453, 1435, 1394; MS 349.2 (M+H)$^+$.

Example 340

[2-(1,4-Dioxa-8-aza-spiro[4,5]dec-8-yl)-quinazolin-4-yl]-(5-methyl-2H-pyrazol-3-yl)-amine (III-112)

mp 191° C.; $^1$H NMR (DMSO) δ 1.65 (4H, s), 2.26 (3H, 9), 3.90 (4H, s), 3.93 (4H, s), 6.43 (1H, br s), 7.09 (1H, t), 7.32 (1H, d), 7.54 (1H, t), 8.35 (1H, d), 9.99 (1H, br s), 12.13 (1H, br s); IR (solid) 3069, 2964, 2927, 2868, 1618, 1581, 1568, 1540, 1495, 1481, 1435, 1390; MS 367.3 (M+H)$^+$.

Example 341

[2-(4-Cyclopentylamino-piperidin-1-yl)-quinazolin-4-yl]-(5-methyl-2H-pyrazol-3-yl)-amine (III-113)

mp 191° C.; $^1$H NMR (DMSO) δ 1.33 (2H, d), 1.65 (4H, s), 1.87 (2H, d), 2.20 (1H, s), 2.26 (3H, s), 2.49 (2H, s), 3.00 (2H, t), 3.36 (2H, s), 4.61 (2H, d), 6.45 (1H, br s), 7.07 (1H, s), 7.31 (1H, d), 7.52 (1H, s), 8.33 (1H, d), 9.94 (1H, br s), 12.12 (1H, br s); IR (solid) 3371, 2943, 1622, 1600, 1581, 1545, 1509, 1463, 1440, 1390; MS 378.2 (M+H)+.

Example 342

[2-(4-Hydroxypiperidin-1-yl)-quinazolin-4-yl]-(5-methyl-2H-pyrazol-3-yl)-amine (III-114)

mp 123° C.;
$^1$H NMR (DMSO) δ 1.34 (2H, d), 1.80 (2H, d), 2.26 (3H, s ), 3.24 (2H, t), 3.72 (1H, br s), 4.39 (2H, d), 4.70 (1H, d), 6.44 (1H, br s), 7.07 (1H, t), 7.30 (1H, d), 7.53 (1H, t), 8.33 (1H, d), 9.94 (1H, br s), 12.11 (1H, br s); IR (solid) 3265, 3151, 2927, 2863, 1622, 1600, 1572, 1540, 1504, 1476, 1440, 1390, 1349, 1066, 1098; MS 325.3 (M+H)+.

Example 343

(5-Cyclopropyl-2H-pyrazol-3-yl)-[2-(4-hydroxy-4-phenylpiperidin-1-yl)-quinazolin-4-yl]-amine (III-115)

mp 131° C.; $^1$H NMR (DMSO) δ 0.64 (2H, q), 0.93 (2H, q), 1.68 (2H, d), 1.83–1.97 (3H, m), 3.20–3.45 (2H, m), 4.69 (2H, d), 5.11 (1H, s), 6.37 (1H, br s), 7.08 (1H, t), 7.20 (1H, t), 7.31 (3H, t), 7.49 (2H, d), 7.53 (1H, t), 8.33 (1H, d), 9.98 (1H, br s), 12.18 (1H, br s); IR (solid) 3362, 2952, 2934, 2911, 2870, 2825, 1618, 1584, 1570, 1559, 1536, 1481, 1459, 1431, 1372, 1336, 1213, 994; MS 427.6 (M+H)+.

Example 344

(5-Cyclopropyl-2H-pyrazol-3-yl)-[2-(1,3-dihydro-isoindol-2-yl)-quinazolin-4-yl]-amine (III-116)

Prepared according to Method E-I to afford an off-white solid, mp 237° C.; $^1$H NMR (DMSO-d6) δ 0.79 (2H, s), 1.00 (2H, d), 1.99 (1H, m), 4.92 (4H, d), 6.72 (1H, br s), 7.13 (1H, t), 7.33 (2H, s), 7.30–7.48 (3H, m), 7.58 (1H, t), 8.40 (1H, d), 10.12 (1H, s), 12.17 (1H, s); IR (solid) 3449, 3318, 2850, 1623, 1595, 1577, 1541, 1509, 1482, 1432, 1391, 1359, 1141, 1027, 877, 814; MS 369.4 (M+H)+.

Example 345

(2-Azepan-1-yl)-quinazolin-4-yl]-(5-cyclopropyl-2H-pyrazol-3-yl)-amine (III-117)

mp 199–200° C.; $^1$H NMR (DMSO-d6) δ 0.60–0.70 (2H, m), 0.90–1.00 (2H, m), 1.45–1.57 (4H, m), 1.70–1.85 (4H, m), 1.88–1.97 (1H, m), 3.75–3.87 (4H, m), 6.42 (1H, s), 7.02 (1H, t), 7.27 (1H, d), 7.49 (1H, t), 8.29 (1H, d), 9.91 (1H, s), 12.19 (1H, br s); IR (solid) 2929, 1624, 1595, 1581, 1563, 1542, 1498, 1482, 1440, 1426, 1397, 1356, 1305, 1000, 825, 754; MS 349.2 (M+H)+.

Example 346

(5-Cyclopropyl-2H-pyrazol-3-yl)-[2-(3,4-dihydro-1H-isoquinolin-2-yl)-quinazolin-4-yl]-amine (III-118)

mp 182–184° C.; $^1$H NMR (DMSO) δ 0.75 (2H, d), 1.02 (2H, d), 1.96 (1H, m), 2.89 (2H, m), 4.05 (2H, m), 4.94 (2H, s), 6.46 (1H, s), 7.10 (1H, t), 7.21 (4H, d), 7.37 (1H, d), 7.55 (1H, d), 8.36 (1H, d), 10.05 (1H, s), 12.23 (1H, br s); IR (solid) 1621, 1581, 1560, 1537, 1479, 1456, 1426, 1396, 1374, 1341, 1222; MS 383.3 (M+H)+.

Example 347

(5-Cyclopropyl-2H-pyrazol-3-yl)-[2-(2,3-dihydro-indol-1-yl)-quinazolin-4-yl]-amine (III-119)

mp 150–153° C.; $^1$H NMR (DMSO) δ 0.74 (2H, d), 0.98 (2H, d), 1.96 (1H, m), 3.15 (2H, t), 4.25 (2H, t), 6.45 (1H, br s), 6.88 (1H, t), 7.09 (1H, t), 7.20 (2H, m), 7.53 (1H, d), 7.65 (1H, t), 8.43 (2H, br s), 10.09 (1H, s), 12.28 (1H, br s); IR (solid) 1621, 1588, 1577, 1564, 1537, 1487, 1455, 1425, 1386, 1259; MS 369.3 (M+H)+.

Example 348

(5-Cyclopropyl-2H-pyrazol-3-yl)-[2-(4-hydroxymethylpiperidin-1-yl)-quinazolin-4-yl]-amine (III-120)

mp 142° C.; $^1$H NMR (DMSO) δ 0.67 (2H, d), 0.96 (2H, d), 1.10 (2H, q), 1.55–1.70 (3H, m), 1.91 (1H, m), 2.85 (2H, t), 3.28 (2H, s), 4.48 (1H, s), 4.76 (2H, d), 6.34 (1H, s), 7.06 (1H, t), 7.30 (1H, d), 7.52 (1H, t), 8.31 (1H, d), 9.96 (1H, s), 12.19 (1H, s); IR (solid) 3363, 3000, 2927, 2854, 1618, 1604, 1573, 1536, 1509, 1477, 1436, 1395, 1354, 1314, 1241, 1186, 1091, 995, 941, 823; MS 365.8 (M+H)+.

Example 349

(5-Cyclopropyl-2H-pyrazol-3-yl)-[2-(3,4-dihydro-2H-quinolin-1-yl)-quinazolin-4-yl]-amine (III-121)

mp 137–145° C.; $^1$H NMR (DMSO-d6) δ 0.55 (2H, d), 0.88 (2H, d), 1.78 (1H, m), 1.92 (2H, t), 2.75 (2H, t), 4.04 (2H, t), 6.20 (1H, br s), 6.97 (1H, t), 7.14 (1H, m), 7.19 (1H, t), 7.42 (1H, d), 7.61 (1H, t), 7.67 (1H, d), 8.43 (1H, d), 10.04 (1H, s), 12.21 (1H, br s); IR (solid) 1622, 1572, 1539, 1493, 1454, 1420, 1373, 1249; MS 383.3 (M+H)+.

Example 350

(5-Methoxycarbonyl-2H-pyrazol-3-yl)-[2-(piperidine-1-yl)-quinazolin-4-yl]-amine (III-122)

$^1$H NMR (500 MHz, CDCl$_3$) δ1.7–1.8(6H, m), δ 3.8 (4H, m), δ 3.9 (3H, s), δ 5.5 (1H, s), δ 7.15 (1H, t), δ 7.4 (1H, d), δ 7.6 (1H, t), δ 8.0 (1H, d). HPLC-Method B, (starting with 95% H$_2$O) R$_t$ 7.4 min; MS (ES+) 353.24 (M+H).

Example 351

[5-(Piperidine-1-carbonyl)-2H-pyrazol-3-yl]-[2-(piperidine-1-yl)-quinazolin-4-yl]-amine (III-123)

HPLC-Method B, (starting with 95% H$_2$O:0.1% TFA) R$_t$ 8.0 min; MS (ES+) 406.30, (ES−) 404.30.

Example 352

(5-Hydroxymethyl-2H-pyrazol-3-yl)-[2-(piperidin-1-yl)-quinazolin-4-yl]-amine (III-124)

To a solution of III-122 (10.0 mg, 0.028 mmol) in THF (6 mL) at ambient temperature was slowly added a 1M solution of LiAlH$_4$ in THF (0.05 mL, 0.05 mmol). After 15 minutes the solution was quenched with water and 1N HCl. The product was extracted from the aqueous layer with EtOAc. The organic layer was dried over MgSO$_4$, filtered, and concentrated in vacuo. The residue was purified by preparatory HPLC to afford III-124 (4.0 mg, 44%). HPLC-Method B, (starting with 95% H$_2$O:0.1% TFA) R$_t$ 6.1 min; MS (ES+) 325.13 (M+H), (ES−) 323.13 (M−H).

Example 353

(5-Carbamoyl-2H-pyrazol-3-yl)-[2-(piperidin-1 -yl)-quinazolin-4-yl]-amine (III-125)

A solution of III-122 (1.5 g, 4.3 mmol) in 2.0 M NH$_3$/MeOH (100 mL) was heated at 110° C. for 2 days. The dark brown reaction mixture was concentrated in vacuo to afford a viscous oil which was purified by column chromatography to yield 0.7 g (50%) of III-125. $^1$H NMR (500 MHz, CD3OD-d$_3$) δ1.6 (4H, m), δ1.7 (2H, m), δ 3.3 (1H, s), δ 3.8 (4H, m), δ 5.5 (1H, s), δ 7.15 (1H, t), δ 7.45 (1H, d), δ 7.55 (1H, t), δ 8.0 (1H, d); HPLC-Method B, (starting with 95% H$_2$O:0.1% TFA) R$_t$ 5.9 min; MS (ES+) 338.13, (ES−) 336.15.

Example 354

(5-Carbamoyl-2H-pyrazol-3-yl)-[2-(4-methylpiperidin-1-yl)-quinazolin-4-yl]-amine (III-126)

HPLC-Method B, (starting with 95% H$_2$O:0.1% TFA) R$_t$ 6.4 min; MS (ES+) 352.19, (ES−) 350.20.

Example 355

(5,7-Difluoro-1H-indazol-3-yl)-(2-phenyl-5,6,7,8-tetrahydroquinazolin-4-yl)-amine (III-127)

$^1$H NMR (500 MHz, DMSO-d6) δ13.7 (s, 1H), 10.3 (s, br, 1H), 7.90 (d, 2H), 7.52 (t, 1H), 7.45 (m, 3H), 7.26 (d, 1H), 2.99 (m, 2H), 2.75 (m, 2H), 1.95 (br, 4H) ppm; MS (ES+) 378.24 (M+H); (ES−) 376.23 (M−H); HPLC-Method A, R$_t$ 3.04 min.

Example 356

(2-Phenyl-5,6,7,8-tetrahydroquinazolin-4-yl)-(5-trifluoromethyl-1H-indazol-3-yl)-amine (III-128)

$^1$H NMR (500 MHz, DMSO-d6) δ13.4 (s, 1H), 10.2 (s, br, 1H), 8.13 (s, 1H), 7.86 (d, 2H), 7.78 (d, 1H), 7.69 (d, 1H), 7.50 (t, 1H), 7.35 (dd, 2H), 2.89 (m, 2H), 2.72 (m, 2H), 1.90 (s, br, 4H) ppm; MS (ES+) 410.24 (M+H); (ES−) 408.23 (M−H); HPLC-Method A, R$_t$ 3.19 min.

Example 357

(7-Fluoro-1H-indazol-3-yl)-(2-phenyl-quinazolin-4-yl)-amine (III-129)

$^1$H NMR (500 MHz, DMSO-d6) δ13.6 (s, 1H), 11.1 (s, br, 1H), 8.65 (d, 1H), 8.03 (d, 2H), 7.95 (s, 2H), 7.67 (m, 1H), 7.45 (m, 2H), 7.33 (t, 2H), 7.22 (dd, 1H), 6.99 (td, 1H) ppm. MS (ES+): m/e=356.20 (M+H); HPLC-Method A R$_t$ 3.00 min.

Example 358

(5-Fluoro-1H-indazol-3-yl)-(2-phenyl-quinazolin-4-yl)-amine (III-130)

$^1$H NMR (500 MHz, DMSO-d6) δ13.2 (s, 1H), 11.3 (s, br, 1H), 8.67 (d, 1H), 8.04 (d, 2H), 7.96 (s, 2H), 7.70 (m, 1H), 7.58 (dd, 1H), 7.43 (m, 4H), 7.28 (td, 1H) ppm. MS (ES+) 356.20 (M+H); HPLC-Method A, R$_t$ 3.00 min.

Example 359

(5,7-Difluoro-1H-indazol-3-yl)-(2-phenyl-quinazolin-4-yl)-amine (III-131)

$^1$H NMR (500 MHz, DMSO-d6) δ13.7 (s, 1H), 8.65 (d, 1H), 8.04 (d, 2H), 7.95 (s, 2H), 7.68 (m, 1H), 7.45 (m, 1H), 7.35 (m, 4H) ppm. MS (ES+): m/e=374.17 (M+H); HPLC-Method A, R$_t$ 3.07 min.

Example 360

(1H-Indazol-3-yl)-[2-(3-trifluoromethyl-phenyl)-quinazolin-4-yl]-amine (III-132)

$^1$H NMR (500 MHz, DMSO-d6) δ 7.06 (t, 1H), 7.42 (t, 1H), 7.59 (d, 1H), 7.63 (t, 1H), 7.66 (d, 1H), 7.71 (m, 1H), 7.80 (d, 1H), 7.98 (m, 2H), 8.33 (s, 1H), 8.46 (d, 1H), 8.71 (d, 1H), 11.04 (br. s, 1H), 12.97 (s, 1H); EI-MS 406.1 (M+1); HPLC-Method A, R$_t$ 3.15 min.

Example 361

(2-Phenyl-quinazolin-4-yl)-(1H-pyrazolo[4,3-b]pyridin-3-yl)-amine (III-133)

$^1$H NMR (500 MHz, DMSO-d6) δ13.3 (s, br, 1H), 11.4 (s, br, 1H), 8.78 (d, 1H), 8.58 (dd, 1H), 8.24 (d, 1H), 8.10 (m, 2H), 7.95 (d, 2H), 7.86 (t, 1H), 7.56 (m, 2H), 7.44 (t, 2H) ppm. MS (ES+) 339.11 (M+H); HPLC-Method A, R$_t$ 2.63 min.

Example 362

[5-(3-Methoxy-phenyl)-6-oxo-5,6-dihydro-1H-pyrazolo[4,3-c]pyridazin-3-yl]-(2-phenyl-quinazolin-4-yl)-amine (III-134)

$^1$H NMR (500 MHz, MeOH-d4) δ8.65 (d, 1H), 8.17 (m, 3H), 8.10 (d, 1H), 7.90 (t, 1H), 7.75 (t, 1H), 7.58 (m, 2H), 7.25 (t, 1H), 6.95 (m, 2H), 6.85 (d, 1H), 6.80 (s, 1H), 3.64 (s, 3H) ppm. MS (ES+): m/e=462.2(M+H).

Example 363

(6-Oxo-5-phenyl-5,6-dihydro-1H-pyrazolo[4,3-c]pyridazin-3-yl)-(2-phenyl-quinazolin-4-yl)-amine (III-135)

$^1$H NMR (500 MHz, MeOH-d4) δ8.61 (d, 1H), 8.13 (m, 3H), 8.05 (d, 1H), 7.85 (t, 1H), 7.70 (t, 1H), 7.58 (m, 2H), 7.32 (m, 5H), 6.79 (s, 1H) ppm. MS (ES+): m/e=432.2(M+H).

Example 364

[5-(4-Methoxy-phenyl)-6-oxo-5,6-dihydro-1H-pyrazolo[4,3-c]pyridazin-3-yl]-(2-phenyl-quinazolin-4-yl)-amine (III-136)

MS (ES+) 462.2(M+H).

Example 365

[5-(2,4-Dichloro-phenyl)-6-oxo-5,6-dihydro-1H-pyrazolo[4,3-c]pyridazin-3-yl]-(2-phenyl-quinazolin-4-yl)-amine (III-137)

$^1$H NMR (500 MHz, MeOH-d4) δ8.63 (d, 1H), 8.17 (m, 4H), 7.89(t, 1H), 7.73 (t, 1H), 7.61 (t, 2H), 7.57 (d, 1H), 7.32 (m, 1H), 7.21 (d, 1H), 6.84 (s, 1H) ppm. MS (ES+): m/e=500.1(M+H).

Example 366

[6-Oxo-5-(3-trifluoromethyl-phenyl)-5,6-dihydro-1H-pyrazolo[4,3-c]pyridazin-3-yl]-(2-phenyl-quinazolin-4-yl)-amine (III-138)

$^1$H NMR (500 MHz, MeOH-d4) δ8.55 (d, 1H), 8.19 (d, 2H), 7.92 (m, 2H), 7.65 (m, 3H), 7.45 (t, 2H), 7.25 (t, 1H), 7.13 (t, 1H), 7.05 (t, 1H), 6.75 (s, 1H) ppm. MS (ES+): m/e=500.2 (M+H).

Example 367

[6-Oxo-5-(4-Phenoxy-phenyl)-5,6-dihydro-1H-pyrazolo[4,3-c]pyridazin-3-yl]-(2-phenyl-quinazolin-4-yl)-amine (III-139)

MS (ES+) 524.3(M+H).

Example 368

[5-(4-Chloro-phenyl)-6-oxo-5,6-dihydro-1H-pyrazolo[4,3-c]pyridazin-3-yl]-(2-phenyl-quinazolin-4-yl)-amine (III-140)

MS (ES+) 466.2(M+H).

Example 369

(2-imidazol-1-yl-quinazolin-4-yl)-(1H-indazol-3-yl)-amine (III-141)

$^1$H NMR (500 MHz, DMSO-d6) δ 7.10 (t, 1H), 7.44 (t, 1H), 7.50 (br. s, 1H), 7.60 (d, 1H), 7.72 (m, 2H), 7.77 (m, 1H), 7.88 (d, 1H), 7.98 (t, 1H), 8.73 (d, 1H), 8.96 (s, 1H), 11.23 (s, 1H), 13.06 (s, 1H); EI-MS 328.1 (M+1); HPLC-Method A, $R_t$ 2.93 min.

Example 370

(1H-Indazol-3-yl)-[2-(2-methyl-imidazol-1-yl-quinazolin-4-yl]-amine (III-142)

$^1$H NMR (500 MHz, DMSO-d6) δ 2.48 (s, 3H), 7.10 (t, 1H), 7.43 (t, 1H), 7.57 (d, 1H), 7.60 (d, 1H), 7.67 (d, 1H), 7.76 (td, 1H), 7.86 (d, 1H), 7.91 (d, 1H), 8.01 (td, 1H), 8.72 (d, 1H), 11.15 (s, 1H), 13.10 (s, 1H); EI-MS 342.1 (M+1); HPLC-Method A, $R_t$ 3.06 min.

Example 371

(1H-Indazol-3-yl)-(2-piperidin-1-yl-quinazolin-4-yl)-amine (III-143)

$^1$H NMR (500 MHz, DMSO-d6) δ 1.48 (m, 6H), 3.60 (m, 4H), 7.11 (t, 1H), 7.52 (t, 1H), 7.55 (d, 1H), 7.64 (d, 1H), 7.69 (d, 1H), 7.75 (d, 1H), 7.90 (t, 1H), 8.58 (d, 1H), 11.82 (br. s, 1H), 13.25 (s, 1H); EI-MS 345.1 (M+1); HPLC-Method A, $R_t$ 3.03 min.

Example 372

(1H-Indazol-3-yl)-[2-(octahydro-quinolin-1-yl)-quinazolin-4-yl]-amine (III-144)

$^1$H NMR (500 MHz, DMSO-d6) δ 0.6–1.9 (m, 13H), 3.15 (m, 1H), 3.25 (m, 1H), 4.0 (m, 1H), 7.10 (t, 0.5H), 7.12 (t, 0.5H), 7.55 (m, 2H), 7.66 (d, 0.5 H), 7.69 (d, 0.5H), 7.77 (d, 1H), 7.91 (t, 1H), 8.55 (d, 0.5 H), 8.59 (d, 0.5 H), 11.46 (s, 0.5 H), 11.54 (s, 0.5H), 11.78 (s, 0.5H), 11.84 (s, 0.5H), 13.10 (s, 0.5H), 13.12 (s, 0.5H); EI-MS 399.3 (M+1); HPLC-Method A, $R_t$ 3.37 min.

Example 373

(1H-Indazol-3-yl)-[2-(2,6-dimethyl-morpholin-4-yl)-quinazolin-4-yl]-amine (III-145)

$^1$H NMR (500 MHz, DMSO-d6) δ 1.0 (m, 6H), 4.0 (m, 6H), 7.12 (t, 1H), 7.41 (td, 1H), 7.56 (t, 1H), 7.58 (d, 1H), 7.68 (dd, 1H), 7.77 (t, 1H), 7.93 (t, 1H), 8.60 (d, 1H), 11.69 (s, 1H), 13.16 (s, 1H); EI-MS 375.3 (M+1); HPLC-Method A, $R_t$ 2.93 min.

Example 374

(5-Methyl-2H-pyrazol-3-yl)-(2-phenyl-pyrimidin-4-yl)-amine (IV-1)

mp 245–246° C.; $^1$H NMR (DMSO) δ 2.26 (3H, s), 6.32 (1H, br s), 7.07 (1H, br s), 7.48–7.54 (3H, m), 8.33–8.39 (3H, m), 9.87 (1H, s), 12.03 (1H, s); IR (solid) 1628, 1589, 1579, 1522, 1479, 1441, 1393, 1336; MS 252.2 (M+H)$^+$.

Example 375

[6-(4-Acetamidophenylsulfanyl)-2-phenyl-pyrimidin-4-yl]-(5-methyl-2H-pyrazol-3-yl)-amine (IV-3)

A suspension of Fenclorim (4,6-dichloro-2-phenylpyrimidine)(0.1 g, 0.44 mmol), 3-amino-5-methylpyrazole (0.045 g, 0.47 mmol), N,N-diisopropylethylamine (0.08 ml, 0.47 mmol) and sodium iodide (0.067 g, 0.44 mmol) in n-butanol (5 ml) were heated at 117° C. for 18 hours. The solvent was removed in vacuo and the crude product purified by flash chromatography (silica gel, 3:2 Petrol:EtOAc) to afford 0.037 g (29% yield) of (6-Chloro-2-phenyl-pyrimidin-4-yl)-(5-methyl-2H-pyrazol-3-yl)-amine as a off-white solid. A suspension of the above pyrimidine (0.037 g, 0.13 mmol) and thioacetamidothiophenol (0.108 g, 0.64 mmol) in tert-butanol was heated at 85° C. under nitrogen for 2 days. The reaction mixture was cooled to room temperature and the solvent removed in vacuo. The concentrate was dissolved in EtOAc, and washed with NaHCO$_3$ (sat, aq.). The organic layer is concentrated in vacuo, and the crude product by preperative HPLC. The residual disulfide that still remained in the mixture after HPLC may be removed by precipitation from EtOAc and filtration. The mother liquor was concentrated to afford IV-3 (7 mg, 13% yield) as an off-white solid: mp 235–236° C.; $^1$H NMR (DMSO) δ 2.10 (3H, s), 2.21 (3H, s), 6.33 (1H, br s), 7.50 (3H, m), 7.7–7.59 (2H, m), 7.76–7.78 (2H, m), 8.25 (2H, m), 9.72, 10.26 and 11.93 (3 H, 3×br s); IR (solid) 1669, 1585, 1551, 1492, 1392, 1372, 1312, 1289, 1259, 1174, 1102, 1.089, 1027, 1015, 984; MS 417.3 (M+H)$^+$.

Example 376

[2-(4-Methylpiperidin-1-yl)-pyrimidin-4-yl]-(5-methyl-2H-pyrazol-3-yl)-amine (IV-4)

mp 215–216° C.; $^1$H NMR (CD$_3$OD) δ 0.96 (3H, d), 1.16 (2H, m), 1.66 (3H, m), 2.27 (3H, s), 2.86 (2H, t), 4.58 (2H, m), 4.78 (2H, exch.protons), 6.13 (2H, m), 7.83 (1H, d); IR (solid) 1593, 1550, 1489, 1436, 1331, 1246, 1231; MS 273.1 (M+H)$^+$.

Example 377

[2-(4-Methylpiperidin-1-yl)-5-nitropyrimidin-4-yl]-(5-methyl-2H-pyrazol-3-yl)-amine (IV-5)

mp 185–187° C.; $^1$H NMR (DMSO) δ 0.93 (3H, d), 1.06–1.18 (2H, m), 1.68–1.80 (3H, m), 2.26 (3H, s), 3.01–3.12 (2H, m), 4.63 (1H, d), 4.80 (1H, d), 6.39 (1H, s), 9.00 (1H, s), 10.41 (1H, s), 12.36 (1H, s); IR (solid) 1589, 1517, 1479, 1446, 1346, 1317, 1246, 1222, 1055; MS 318.2 (M+H)$^+$.

Example 378

[5-Amino-2-(4-Methylpiperidin-1-yl)-pyrimidin-4-yl]-(5-methyl-2H-pyrazol-3-yl)-amine (IV-6)

To a solution of IV-5 (48 mg, 0.151 mmol) in ethanol (2.0 mL) was added tin dichloride dihydrate (171 mg, 0.756 mmol) and the resulting mixture heated at reflux for 3 hours. The reaction was cooled to room temperature and poured onto a mixture of 1M NaOH:dichloromethane:propanol (18:8:4 mL) and stirred for 15 minutes. The layers were separated and the aqueous layer extracted twice with dichloromethane. The combined organic layers were concentrated in vacuo and the residue purified by flash chromatography (silica gel, gradient dichloromethane:MeOH) to afford IV-6 as a grey solid (27 mg, 63%): $^1$H NMR (DMSO) δ 0.88–1.04 (5H, m), 1.55–1.62 (3H, m), 2.21 (3H, s), 2.70 (2H, m), 3.36 (2H, m), 4.40 (2H, m), 6.37 (1H, s), 7.49 (1H, s), 8.40 (1H, s), 11.92 (1H, br s); MS 288.2 (M+H)$^+$.

Example 379

[5-Amino-6-methyl-2-(4-methylpiperidin-1-yl)-pyrimidin-4-yl]-(5-methyl-2H-pyrazol-3-yl)-amine (IV-7)

mp 172–175° C.; $^1$H NMR (DMSO) δ 0.90 (3H, d), 1.03 (2H, m), 1.52–1.62 (3H, m). 2.13 (3H, s), 2.20 (3H, s), 2.69 (2H, m), 3.92 (2H, br s), 4.44 (2H, d), 6.35 (1H, s), 8.41 (1H, s), 11.85 (1H, br s); IR (solid) 1612, 1589, 1489, 1446, 1317; MS 302.5 (M+H)$^+$.

Example 380

[6-Methyl-2-(4-methyl-phenyl)-pyrimidin-4-yl]-(5-phenyl-2H-pyrazol-3-yl)-amine (IV-10)

MS 342.34 (M+H); HPLC-Method E, R$_t$ 1.334 min.

Example 381

[2-(4-Chloro-phenyl)-6-methyl-pyrimidin-4-yl]-(5-furan-2-yl-2H-pyrazol-3-yl)-amine (IV-11)

MS 352.11 (M+H); HPLC Method E, R$_t$ 1.194 min.

Example 382

5-Furan-2-yl-2H-pyrazol-3-yl)-(6-methyl-2-phenyl-pyrimidin-4-yl)-amine (IV-12)

MS 318.21 (M+H); HPLC-Method E, 1.192 min.

Example 383

[6-Methyl-2-(4-trifluoromethyl-phenyl)-pyrimidin-4-yl]-(5-phenyl-2-yl-2H-pyrazol-3-yl)-amine (IV-13)

MS 396.24 (M+H); HPLC-Method E, R$_t$ 1.419 min.

Example 384

(5-Furan-2-yl-2H-pyrazol-3-yl)-[6-methyl-2-(4-trifluoromethyl-phenyl)-pyrimidin-4-yl]-amine (IV-14)

MS 386.08 (M+H); HPLC-Method E 1.347 min.

Example 385

[2-(2,3-Dihydro-benzo[1,4]dioxin-2-yl)-6-methyl-pyrimidin-4-yl]-(5-furan-2-yl-2H-pyrazol-3-yl)-amine (IV-15)

MS 376.18 (M+H); HPLC-Method E, R$_t$ 1.181 min.

Example 386

[2-(2,3-Dihydro-bezo[1,4]dioxin-2-yl)-6-ethyl-pyrimidin-4-yl]-(5-methyl-2H-pyrazol-3-yl)-amine (IV-16)

MS 338.17 (M+H); HPLC-Method E, R$_t$ 1.082 min.

Example 387

(6-Ethyl-2-phenyl-pyrimidin-4-yl)-(5-methyl-2H-pyrazol-3-yl)-amine (IV-17)

MS 280.18 (M+H); HPLC-Method E, R$_t$ 1.024 min.

Example 388

(6-Methyl-2-phenyl-pyrimidin-4-yl)-(5-phenyl-2H-pyrazol-3-yl)-amine (IV-19)

MS 328.51 (M+H); HPLC-Method E, R$_t$ 1.192 min.

Example 389

[6-Ethyl-2-(4-trifluoromethyl-ph nyl)-pyrimidin-4-yl]-(5-methyl-2H-pyrazol-3-yl)-amine (IV-20)

MS 348.5 (M+H); HPLC-Method E, R$_t$ 1.224 min.

Example 390

(5-Furan-2-yl-2H-pyrazol-3-yl)-[6-methyl-2-(4-methyl-phenyl)-pyrimidin-4-yl]-amine (IV-21)

MS 332.23 (M+H); HPLC-Method E, R$_t$ 1.139 min.

Example 391

(6-Methoxymethyl-2-phenyl-pyrimidin-4-yl)-(5-methyl-2H-pyrazol-3-yl)-amine (IV-22)

MS 296.31 (M+H); HPLC-Method E, R$_t$ 0.971 min.

Example 392

(5,6-Dimethyl-2-phenyl-pyrimidin-4-yl)-(5-methyl-2H-pyrazol-3-yl)-amine (IV-23)

MS 280.2 (M+H); HPLC-Method E, R$_t$ 0.927 min.

Example 393

(6-Methyl-2-phenyl-pyrimidin-4-yl)-(5-methyl-2H-pyrazol-3-yl)-amine (IV-24)

MS 266.18 (M+H); HPLC-Method E, R$_t$ 0.925 min.

Example 394

[6-Ethyl-2-(4-methyl-phenyl)-pyrimidin-4-yl]-(5-methyl-2H-pyrazol-3-yl)-amine (IV-25)

MS 294.46 (M+H); HPLC-Method E, R$_t$ 1.174 min.

Example 395

[2-(4-Chloro-phenyl)-6-ethyl-pyrimidin-4-yl]-(5-methyl-2H-pyrazol-3-yl)-amine (IV-26)

MS 314.42 (M+H); HPLC-Method E R$_t$ 1.213 min.

Example 396

(5-Methyl-1H-pyrazol-3-yl)-(6-methyl-2-p-tolyl-pyrimidin-4-yl)-amine (IV-27)

MS 280.45 (M+H); HPLC-Method E, R$_t$ 1.135 min.

Example 397

(1H-Indazol-3-yl)-(6-methoxymethyl-2-phenyl-pyrimidin-4-yl)-amine (IV-28)

$^1$H NMR (500 MHz, DMSO) δ 3.57 (3H, s), 4.65 (2H, s), 7.23 (1H, J=7.5 Hz, t), 7.52 (1H, J=7.6 Hz, t), 7.63 (4H, m), 7.75 (1H, br), 8.13 (1H, J=5.5 Hz, br d), 8.44 (1H, J=5.7 Hz, br d), 10.6 (1H, br), 12.8 (1H, br s) ppm; HPLC-Method A, $R_t$ 2.944 min; MS (FIA) 332.1 $(M+H)^+$.

Example 398

(5-Methyl-2H-pyrazol-3-yl)-(2-pyridin-4-yl-thieno[3,2-d]pyrimidin-4-yl)-amine (IV-29)

$^1$H NMR (DMSO) δ 2.34 (3H, s), 6.66 (1H, s), 7.53 (1H, d), 7.84 (1H, d), 8.32 (2H, d), 8.70 (2H, d); MS 309.6 $(M+H)^+$.

Example 399

(5-Methyl-2H-pyrazol-3-yl)-(2-phenyl-pyrido[3,4-d]pyrimidin-4-yl)-amine (IV-30)

mp 225° C.; $^1$H NMR (DMSO) δ 2.35 (3H, s), 6.81 (1H, s), 7.50–7.63 (3H, m), 8.45–8.52 (2H, m), 8.54 (1H, d), 8.62 (1H, d), 9.20 (1H, s), 10.79 (1H, s), 12.38 (1H, br s); IR (solid) 2958, 2917, 2852, 1593, 1565, 1524, 1467, 1450; MS 303.2 $(M+H)^+$.

Example 400

(5-Methyl-2H-pyrazol-3-yl)-(2-phenyl-pyrido[2,3-d]pyrimidin-4-yl)-amine (IV-31)

To a solution of 4-chloro-2-phenyl-pyrido[2,3-d]pyrimidine (J. Pharm. Belg., 29, 1974, 145–148) (109 mg, 0.45 mmol) in THF (15 mL) was added 3-amino-5-methyl pyrazole (48 mg, 0.5 mmol) and the resulting mixture heated at 65° C. overnight. The mixture was cooled to room temperature and the resulting suspension was filtered and washed with Et$_2$O. The solid was dissolved in a mixture EtOH:water and the pH adjusted to pH 7. The aqueous was extracted twice with ethyl acetate and the combined organic layers were dried (MgSO$_4$), filtered, and concentrated in vacuo. The residue was purified by flash chromatography (SiO$_2$, DCM-MeOH gradient) to afford IV-31 as an off-white solid (69 mg, 50%): mp 234° C.; $^1$H NMR (DMSO) δ 2.14 (3H, s), 5.99 (1H, s), 7.20–7.40 (3H, m), 7.40–7.50 (3H, m), 8.60 (1H, d), 8.79 (1H, d), 12.82 (1H, br s); IR (solid) 2957, 2921, 2857, 1644, 1560, 1459, 1427; MS 303.2 $(M+H)^+$.

Example 401

(5-Cyclopropyl-2H-pyrazol-3-yl)-(2-phenyl-pyrido[3,4-d]pyrimidin-4-yl)-amine (IV-32)

off-white solid, mp 232–233° C.; $^1$H NMR (DMSO) δ 0.70–0.85 (2H, m), 0.90–1.05 (2H, m), 1.05–2.07 (1H, m), 6.75 (1H, s), 7.50–7.75 (3H, m), 8.40–8.70 (4H, m), 9.20 (1H, s), 10.80 (1H, s), 12.41 (1H); IR (solid) 3178, 1601, 1573, 1532, 1484, 1452, 1409, 1367, 1328, 802, 781, 667; MS 329.2 $(M+H)^+$.

Example 402

[2-(4-Methylpiperidin-1-yl)-purin-4-yl]-(5-methyl-2H-pyrazol-3-yl)-amine (IV-33)

To a suspension of 2,4-dichloro-purine (2.0 g, 10.6 mmol) in anhydrous ethanol (10 mL) was added 5-methyl-1H-pyrazol-3-yl amine (2.05 g, 21.2 mmol). The resulting mixture was stirred at room temperature for 48 h. The resulting precipitate was collected by filtration, washed with ethanol, and dried under vacuum to afford 1.524 g (58% yield) of (2-chloro-purin-4-yl)-(5-methyl-1H-pyrazol-3-yl)-amine which was used in the next step without further purification. To a solution of (2-chloro-purin-4-yl)-(5-methyl-1H-pyrazol-3-yl)-amine (200 mg, 0.80 mmol) was added 4-methylpiperidine (4 mL, 8.01 mmol) and the reaction mixture heated at reflux overnight. The solvent was evaporated and the residue dissolved in a mixture EtOH:water (1:3, 4 mL). Potassium carbonate (57 mg, 0.41 mmol) was added and the mixture was stirred at room temperature for 2 hours. The resulting suspension was filtered, washed with water (×2) and rinsed with Et$_2$O (×2) to afford IV-33 as a white solid (225 mg, 90%): mp >300° C.;

$^1$H NMR (DMSO) δ 0.91 (3H, d), 1.10 (2H, m), 1.65 (3H, m), 2.24 (3H, s), 2.84 (2H, m), 4.60 (2H, m), 6.40 (1H, s), 7.87 (1H, m), 9.37–9.59 (1H, m), 12.03–12.39 (2H, m); IR (solid) 1651, 1612, 1574, 1484, 1446, 1327, 1317, 1255, 1203; MS 313.3 $(M+H)^+$.

Example 403

(5-Cyclopropyl-2H-pyrazol-3-yl)-[2-(4-methylpiperidin-1-yl)-pyrrolo[3,2-d]pyrimidin-4-yl]-amine (IV-34)

white solid; $^1$H NMR (DMSO) δ 0.65 (2H, m), 0.91–0.96 (5H, m), 1.08 (2H, m), 1.58–1.64 (3H, m), 1.89 (1H, m), 2.77 (2H, t), 4.57 (2H, d), 6.09 (1H, s), 6.38 (1H, s), 7.33 (1H, s), 9.42 (1H, s), 10.65 (1H, s), 12.02 (1H, br s); MS 338.3 $(M+H)^+$.

Example 404

[6-Benzyl-2-phenyl-5,6,7,8-tetrahydro-pyrido[4,3-d]pyrimidin-4-yl]-(5-fluoro-1H-indazol-3-yl)-amine (IV-35)

$^1$H NMR (500 MHz, DMSO-d6) δ 13.0 (s, 1H), 10.4 (s, br, 1H), 9.73 (s, 1H, TFA-OH), 8.00 (d, 2H), 7.64 (m, 2H), 7.59 (dd, 1H), 7.52 (m, 3H), 7.41 (t, 1H), 7.31 (m, 3H), 7.14 (dd, 1H), 4.58 (s, 2H), 4.35 (br, 2H), 3.74 (m, 2H), 3.17 (s, 2H) ppm. MS (ES+): m/e=451.30 (M+H); HPLC-Method A, $T_{ret}$ 2.96 min.

Example 405

(5-Fluoro-1H-indazol-3-yl)-(2-phenyl-5,6,7,8-tetrahydro-pyrido[4,3-d]pyrimidin-4-yl)-amine (IV-36)

Prepared from IV-35 (0.13 mmol) by treatment with an equal weight of Pd/C (10%) in 4.4% HCOOH in MeOH at room temperature for 12 h. The mixture was filtered through celite, the filtrate was evaporated, and crude product was purified by HPLC to afford IV-36 as yellow solid in 35% yield. $^1$H NMR (500 MHz, DMSO-d6) δ12.9 (s, 1H), 9.06 (s, 1H), 7.99 (d, 2H), 7.57 (dd, 1H), 7.34 (m, 1H), 7.28 (m, 3H), 7.22 (d, 1H), 3.83 (s, 2H), 3.05 (m, 2H), 2.72 (m, 2H) ppm. MS (ES+): m/e=361.20 (M+H); HPLC-Method A, $T_{ret}$ 2.68 min.

Example 406

(5-Methyl-2H-pyrazol-3-yl)-(3-phenyl-isoquinolin-1-yl)-amine (V-1)

To a solution of 1-chloro-3-phenylisoquinoline (J. Het. Chem., 20, 1983, 121–128)(0.33 g, 1.37 mmol) in DMF (anhydrous, 5 mL) was added 3-amino-5-methylpyrazole (0.27 g, 2.74 mmol) and potassium carbonate (0.57 g, 4.13 mmol) and the resulting mixture was heated at reflux for 6 hours. The reaction mixture was then cooled and solvent removed in vacuo. The residue was extracted twice with ethyl acetate and the combined organic layers washed with brine, dried (MgSO$_4$), filtered and concentrated in vacuo. The crude product was purified by flash chromatography (SiO$_2$, gradient DCM-MeOH) to afford V-1 as a colourless oil; $^1$H NMR (MeOD) δ 2.23 (3H, s), 5.61 (1H, s), 7.41 (1H, m), 7.52(2H, m), 7.62(1H, m), 7.81(1H, m), 8.07(1H, d), 8.19(2H, m), 8.29(1H, s), 8.54 (1H, d); MS 301.2 (M+H)$^+$.

Example 407

(1H-Indazol-3-yl)-[3-(2-trifluoromethyl-phenyl)-isoquinoline-1-yl]-amine (V-2)

A solution of 1-chloro-3-(2-trifluoromethyl-phenyl)-isoquinoline (100 mg, 0.326 mmol) and 1H-indazol-3-ylamine (86 mg, 0.651 mmol) in ethanol (3 mL) was heated at 160 C. and the solvent evaporated with a stream of nitrogen. The remaining oil was then heated at 160 C. for 18 hours under nitrogen. The resulting melt was dissolved in 5% methanol:dichloromethane (50 mL), washed with saturated aqueous sodium bicarbonate (1×25 mL) then dried over magnesium sulfate. Purification by silica gel chromatography (25% to 50% hexane:ethyl acetate) afforded V-2 as a yellow solid (35 mg, 27%). $^1$H NMR (500 MHz, d$_6$-DMSO) δ 9.78 (br s, 1H), 8.62 (d, 1H), 7.9–7.85 (m, 1H), 7.78–7.72 (m, 1H), 7.70–7.68 (m, 1H), 7.65–7.62 (m, 1H), 7.60–7.55 (m, 1H), 7.52–7.45 (m, 3H), 7.41–7.38 (m, 1H), 7.28–7.25 (m, 1H), 7.18 (s, 1H), 6.95–6.92 (m, 1H), 5.76 (s, 1H); LC-MS (ES+) m/e=405.18 (M+H); HPLC-Method D R$_t$ 2.74 min.

Example 408

(5,7-Difluoro-1H-indazol-3-yl)-[3-(2-trifluoromethyl-phenyl)-isoquinolin-1-yl]-amine (V-3)

Prepared from 5,7-difluoro-1H-indazol-3-ylamineto afford compound V-3 as a yellow solid (90 mg, 63%). $^1$H NMR (500 MHz, d$_6$-DMSO) δ 13.25 (s, 1H), 9.92 (br s, 1H), 8.61 (d, 1H), 7.9 (d, 1H), 7.81–7.49 (m, 6H), 7.26–7.2 (m, 2H), 7.12–7.10 (m, 1H); LC-MS (ES+) m/e=441.16 (M+H); HPLC-Method D, R$_t$ 3.58 min.

Example 409

(5-Methyl-2H-pyrazol-3-yl)-(2-phenyl-quinolin-4-yl)-amine (V-4)

To a mixture of 4-chloro-2-phenylquinoline (J. Het. Chem., 20, 1983, 121–128)(0.53 g, 2.21 mmol) in diphenylether (5 mL) was added 3-amino-5-methylpyrazole (0.43 g, 4.42 mmol) and the resulting mixture heated at 200° C. overnight with stirring. The reaction mixture was cooled to ambient temperature then petroleum ether (20 mL) was added and the resulting precipitate was isolated by filtration. The crude solid was purified by flash chromatography (SiO$_2$, gradient DCM-MeOH) to afford V-4 as a white solid: mp 242–244° C.; $^1$H NMR (DMSO) δ 2.27(3H, s), 6.02(1H, s), 7.47(2H, d), 7.53–7.40(2H, br m), 7.67(1H, m) 7.92(1H, m), 8.09(2H, d), 8.48(2H, m), 9.20(1H, s), 12.17(1H, br s); IR (solid) 1584, 1559, 1554, 1483, 1447, 1430, 1389; MS 301.2 (M+H)$^+$.

Example 410

(1H-Indazol-3-yl)-(2-phenyl-quinolin-4-yl)-amine (V-5)

$^1$H NMR (500 MHz, d$_6$-DMSO) δ 12.78 (s, 1H), 9.50 (s, 1H), 8.65 (d, 1H), 8.15 (s, 1H), 8.04–7.98 (m, 3H), 7.94 (s, 1H), 7.78–7.75 (m, 1H), 7.60–7.40 (m, 6H), 7.15–7.10 (m, 1H). LC-MS (ES+) m/e=337.11 (M+H); HPLC-Method D, R$_t$ 2.10 min.

Example 411

(2-Phenyl-quinolin-4-yl)-(1H-pyrazolo[4,3-b]pyridin-3-yl)-amine (V-6)

$^1$H NMR (500 MHz, DMSO-d6) δ13.6 (s, 1H), 11.4 (s, 1H), 8.94 (d, 1H), 8.61 (dd, 1H), 8.23 (d, 1H), 8.16 (dd, 1H), 8.12 (t, 1H), 7.89 (t, 1H), 7.86 (d, 1H), 7.65 (m, 4H), 7.54 (s, 1H), 7.52 (dd, 1H) ppm. MS (ES+): m/e=338.11 (M+H); HPLC-Method A, HPLC-Method D, R$_t$ 2.91 min.

Example 412

(1H-Indazol-3-yl)-[2-(2-trifluoromethyl-phenyl)-quinolin-4-yl]-amine (V-7)

$^1$H NMR (500 MHz, d$_6$-DMSO) δ 12.68 (s, 1H), 9.51 (s, 1H), 8.7 (d, 1H), 7.95–7.89 (m, 2H), 7.83–7.70 (m, 3H), 7.68–7.62 (m, 2H), 7.60 (s, 1H), 7.55–7.52 (m, 1H), 7.49–7.45 (m, 1H), 7.40–7.37 (m, 1H), 7.12–7.09 (m, 1H); LC-MS (ES+) m/e=405.15 (M+H); HPLC-Method D R$_t$ 2.25 min.

Example 413

(5,7-Difluoro-1H-indazol-3-yl)-[2-(2-trifluoromethyl-phenyl)-quinolin-4-yl]-amine (V-8)

$^1$H NMR (500 MHz, d$_6$-DMSO) δ 13.31 (s, 1H), 9.49 (s, 1H), 8.70–8.67 (m, 1H), 7.96–7.92 (m, 1H), 7.85–7.66 (m, 7H), 7.63–7.60 (m, 1H), 7.42–7.40 (m, 1H). LC-MS (ES+) m/e=441.18 (M+H); HPLC-Method D R$_t$ 2.39 min.

Example 414

[2-(2-trifluoromethyl-phenyl)-quinolin-4-yl]-(1H-pyrazolo[4,3-b]pyridin-3-yl)-amine (V-9)

$^1$H NMR (500 MHz, DMSO-d6) δ13.6 (s, 1H), 11.6 (s, br, 1H), 8.98 (d, 1H), 8.57 (dd, 1H), 8.12 (m, 3H), 7.97 (m, 2H), 7.86 (m, 3H), 7.49 (dd, 1H), 7.23 (s, 1H) ppm. MS (ES+): m/e=406.20 (M+H); HPLC-Method A R$_t$ 2.91 min.

Example 415

(2-Phenyl-quinazolin-4-yl)-(2H-[1,2,4]triazol-3-yl)-amine (IX-154)

off-white solid, mp 266–267° C.; $^1$H NMR (DMSO) δ 7.50–7.70 (4H, m), 7.85–8.00 (2H, m), 8.15–8.25 (2H, m), 8.37–8.45 (2H, m), 8.58 (1H, d), 13.90 (1H, br s); IR (solid) 3344, 3059, 1630, 1609, 1570, 1557, 1543, 1501, 1495, 1445, 1411, 1355, 1326, 1267, 1182, 1053, 1038, 760, 676, 667, 654; MS 289.2 (M+H)$^+$.

Example 416

(5-Methyl-2H-[1,2,4]triazol-3-yl)-(2-phenyl-quinazolin-4-yl)-amine (IX-155)

$^1$H NMR (500 MHz, DMSO-d6) δ8.59 (s, 1H), 8.42 (d, J=6.7 Hz, 2H), 7.79 (m, 4H), 8.03 (m, 2H), 7.74 (m, 4H), 2.51 (s, 3H) ppm. MS (ES+): m/e=303.08 (M+H); HPLC-Method A, R$_t$ 2.64 min.

Example 417

(2H-[1,2,4]-Triazol-3-yl)-[2-(2-trifluoromethylphenyl)-guinazolin-4-yl]-amine (IX-47)

Pale yellow solid (52% yield). $^1$H NMR (500 MHz, DMSO-d6) δ8.54 (s, 1H), 8.15 (s, br, 1H), 7.91 (t, 1H), 7.85

(m, 2H), 7.76 (m, 3H), 7.66 (t, 1H) ppm. MS (ES+): m/e=357.13 (M+H); (ES–): m/e=355.15 (M–H); HPLC-Method A, $R_t$ 2.81 min.

Example 418

(5-Methyl-2H-[1,2,4]triazol-3-yl)-[2-(2-trifluoromethylphenyl)-quinazolin-4-yl]-amine (IX-38)

Pale yellow solid (54% yield). $^1$H NMR (500 MHz, DMSO-d6) δ8.44 (s, br, 1H), 7.92 (m, 3H), 7.84 (m, 1H), 7.77 (m, 2H), 7.68 (t, 1H), 2.28 (s, 3H) ppm. MS (ES+): m/e=371.14 (M+H); (ES–): m/e=369.18 (M–H); HPLC-Method A, $R_t$ 2.89 min.

Example 419

(5-Methylsulfanyl-2H-[1,2,4]triazol-3-yl)-[2-(2-trifluorom thylphenyl)-quinazolin-4-yl]-amine (IX-156)

Pale yellow solid (65% yield). $^1$H NMR (500 MHz, DMSO-d6) δ8.56 (br, 1H), 7.90 (t, 1H), 7.84 (m, 2H), 7.78 (m, 2H), 7.67 (m, 2H), 2.51 (s, 3H, buried by DMSO) ppm. MS (ES+): m/e=403.12 (M+H); (ES–): m/e=401.16 (M–H); HPLC-Method A, $R_t$ 3.20 min.

Example 420

(1H-[1,2,4]Triazol-3-yl)-[3-(2-trifluoromethyl-phenyl)-isoquinolin-1-yl]-amine (IX-175)

A solution of 1-chloro-3-(2-trifluoromethyl-phenyl)-isoquinoline (0.326 mmol) and 1H-[1,2,4]triazol-3-ylamine (0.651 mmol) in ethanol (3 mL) was heated at 160° C. and the solvent evaporated with a stream of nitrogen. The remaining oil was then heated at 160° C. for 18 hours under nitrogen. The resulting melt was dissolved in 5% methanol/dichloromethane (50 mL), washed with saturated aqueous sodium bicarbonate (1×25 mL) then dried over magnesium sulfate. Purification by silica gel chromatography afforded IX-175 as a colorless oil (4% yield). $^1$H NMR (500 MHz, CDCl$_3$) δ 9.18 (d, 1H), 8.82 (s, 1H), 7.90 (d, 1H), 7.85–7.75 (m, 3H), 7.71–7.62 (m, 3H), 7.60–7.55 (m, 2H), 4.42–4.35 (m, 1H). LC-MS (ES+) 356.16 (M+H); HPLC-Method D, $R_t$ 3.55 min.

Example 421

(2-Phenyl-quinolin-4-yl)-(1H-[1,2,4]triazol-3-yl)-amine (IX-176)

Pale yellow solid (30% yield). $^1$H NMR (500 MHz, d$_6$-DMSO) δ 13.82 (s, 1H), 9.91 (s, 1H), 8.80 (s, 1H), 8.70–8.65 (m, 1H), 8.55 (s, 1H), 8.15–8.12 (m, 2H), 8.03–7.98 (m, 1H), 7.75–7.72 (m, 1H), 7.57–7.49 (m, 3H). LC-MS (ES+) m/e=288.11 (M+H); HPLC-Method D, $R_t$ 1.55 min.

Example 422

(1H-[1,2,4]triazol-3-yl)-[2-(2-trifluoromethyl-phenyl)-quinolin-4-yl]-amine (IX-177)

Pale yellow solid (46% yield). $^1$H NMR (500 MHz, d$_6$-DMSO) δ 13.70 (s, 1H), 9.98 (s, 1H), 8.70 (d, 1H), 8.49 (s, 1H), 8.30 (s, 1H), 7.94–7.88 (m, 2H), 7.80–7.68 (m, 3H), 7.64–7.56 (m, 2H). LC-MS (ES+) m/e=356.18 (M+H); HPLC-Method D, $R_t$ 1.68 min.

Example 423

(1-H-Indazol-3-yl)-[5-methyl-6-morpholin-4-yl-2-(2-trifluoromethyl-phenyl)-pyrimidin-4-yl]-amine (II-251)

Colorless film; 2% yield; $^1$H-NMR (500 MHz, CD$_3$OD) δ 7.84 (m, 2H), 7.71 (m, 3H), 7.41 (t, 2H), 7.14 (m, 1H), 3.74 (m, 4H), 3.69 (m, 4H), 1.24 (s, 3H) ppm; HPLC-Method A $R_t$ 3.26 min; MS (FIA) 455.1 (M+H).

BIOLOGICAL TESTING

The activity of the compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

Biological Testing Example 1

$K_i$ Determination for the Inhibition of GSK-3

Compounds were screened for their ability to inhibit GSK-3β (AA 1–420) activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (HSSPHQS (PO$_3$H$_2$)EDEEE, American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM) Rates of reaction were obtained using a Molecular Devices Spectramax plate reader (Sunnyvale, Calif.) over 10 min at 30° C. The $K_i$ values were determined from the rate data as a function of inhibitor concentration.

The following compounds were shown to have $K_i$ values less than 0.1 μM for GSK-3: compounds II-1, II-105, II-33, II-34, II-36, II-39, II-38, II-39, II-40, II-41, II-42, II-46, II-57, II-59, II-60, II-61, II-62, II-63, II-64, II-66, II-67, II-69, II-70, II-53, II-71, II-99, II-73, II-74, II-75, II-76, II-77, II-7, II-8, II-9, II-10, II-24, II-19, II-78, II-54, II-79, II-80, II-81, II-82, II-83, II-84, II-56, II-86, II-20, II-25, II-26, II-85, II-21, II-27, II-28, II-87, II-88, II-29, II-11, II-12, II-30, II-31, II-13, II-14, II-15, II-16, II-17, II-18, II-79, II-23, II-2, II-90, II-91, II-92, II-93, II-3, II-4, II-5, II-6, II-94, II-95, II-96, II-107, II-108, II-109, II-110, II-124, II-125, II-111, II-112, II-113, II-114, II-115, II-116, II-117, II-118, II-119, II-120, II-121, II-208, III-8, III-7, III-9, III-37, III-38, III-39, III-40, III-42, III-45, III-46, III-47, III-48, III-49, III-51, III-52, III-53, III-54, III-55, III-56, III-57, III-58, III-59, III-60, III-61, III-62, III-63, III-30, III-65, III-66, III-67, III-70, III-73, III-31, III-75, III-76, III-77, III-33, III-34, III-106, III-108, III-109, III-111, III-35, III-116, III-117, III-118, III-119, III-120, III-121, III-127, III-128, III-141, III-130, III-131, IV-15, IV-16, IV-17, IV-20, IV-25, IV-26, IV-30, IV-34, V-3, and IX-47.

The following compounds were shown to have $K_i$ values between 0.1 and 1.0 μM for GSK-3: compounds II-103, II-104, II-35, II-44, II-45, II-49, II-50, II-97, II-101, II-22, II-32, III-41, III-43, III-44, III-28, III-50, III-29, III-64, III-71, III-74, III-78, III-82, III-88, III-90, III-102, III-105, III-107, III-110, III-112, III-114, III-115, III-122, III-124, III-124, IV-1, III-1, III-138, III-140, III-142, III-129, III-132, III-134, III-135, III-136, IV-1, IV-10, IV-11, IV-12, IV-13, IV-14, IV-19, IV-21, IV-22, IV-23, IV-24, IV-3, IV-4, IV-6, IV-7, IV-8, IV-29, IV-31, IV-32, IV-33, IV-36, V-2, V-7, IX-38, IX-154, and IX-177.

The following compounds were shown to have $K_i$ values between 1.0 and 20 μM for GSK-3: compounds II-43, II-65, II-48, II-47, II-51, II-68, II-52, II-72, II-100, II-98, II-89, III-68, III-81, III-83, III-91, III-94, III-95, III-96, III-97, III-98, III-99, III-100, III-101, III-103, III-123, III-137, III-139, III-143, III-145, III-146, V-4, V-8, IX-156, and IX-176.

Biological Testing Example 2

$K_i$ Determination for the Inhibition of Aurora-2

Compounds were screened in the following manner for their ability to inhibit Aurora-2 using a standard coupled enzyme assay (Fox et al (1998) Protein Sci 7, 2249).

To an assay stock buffer solution containing 0.1 M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 40 mM ATP, and 800 μM peptide (LRRASLG, American Peptide, Sunnyvale, Calif.) was added a DMSO solution of a compound of the present invention to a final concentration of 30 μM. The resulting mixture was incubated at 30° C. for 10 min. The reaction was initiated by the addition of 10 μL of Aurora-2 stock solution to give a final concentration of 70 nM in the assay. The rates of reaction were obtained by monitoring absorbance at 340 nm over a 5 minute read time at 30° C. using a BioRad Ultramark plate reader (Hercules, Calif.). The $K_i$ values were determined from the rate data as a function of inhibitor concentration.

The following compounds were shown to have $K_i$ values less than 0.1 μM for Aurora-2: compounds II-33, II-34, II-36, II-37, II-40, II-41, II-55, III-7, III-9, III-37, III-38, III-39, III-40, III-41, III-42, III-44, III-45, III-46, III-47, III-48, III-49, III-50, III-51, III-52, III-53, III-54, III-55, III-56, III-57, III-59, III-60, III-61, III-63, III-30, III-65, III-66, III-67, III-70, III-31, III-76, III-77, III-78, III-80, III-32, III-33, III-34, III-106, III-108, III-109, III-110, III-111, III-112, III-114, III-35, III-115, III-116, III-117, III-118, III-119, III-120, III-121, IV-7, IV-30, IV-32, and IV-34.

The following compounds were shown to have $K_i$ values between 0.1 and 1.0 μM for Aurora-2: compounds II-1, II-105, II-35, II-38, II-39, II-42, II-64, II-70, II-53, II-99, II-77, II-79, II-86, II-20, II-93, II-94, III-28, III-58, III-64, III-71, III-73, III-74, III-75, III-102, III-105, III-107, III-113, III-124, III-1, III-130, IV-1, IV-3, IV-4, IV-6, IV-29, IV-33, and V-4.

The following compounds were shown to have $K_i$ values between 1.0 and 20 μM for Aurora-2: compounds II-103, II-104, II-57, II-59, II-61, II-63, II-67, II-69, II-75, II-76, II-10, II-19, II-78, II-54, II-80, II-82, II-21, II-90, II-91, II-96, II-107, III-68, III-79, III-82, III-101, III-103, III-127, III-141, III-129, III-132, IV-31, V-2, IX-47, IX-154, and IX-177.

Biological Testing Example 3

CDK-2 Inhibition Assay

Compounds were screened in the following manner for their ability to inhibit CDK-2 using a standard coupled enzyme assay (Fox et al (1998) Protein Sci 7, 2249).

To an assay stock buffer solution containing 0.1M HEPES 7.5, 10 mM $MgCl_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 μM peptide (MAHHHRSPRKRAKKK, American Peptide, Sunnyvale, Calif.) was added a DMSO solution of a compound of the present invention to a final concentration of 30 μM. The resulting mixture was incubated at 30° C. for 10 min.

The reaction was initiated by the addition of 10 μL of CDK-2/Cyclin A stock solution to give a final concentration of 25 nM in the assay. The rates of reaction were obtained by monitoring absorbance at 340 nm over a 5-minute read time at 30° C. using a BioRad Ultramark plate reader (Hercules, Calif.). The $K_i$ values were determined from the rate data as a function of inhibitor concentration.

Biological Testing Example 4

ERK Inhibition Assay

Compounds were assayed for the inhibition of ERK2 by a spectrophotometric coupled-enzyme assay (Fox et al (1998) Protein Sci 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $IC_{50}$ was evaluated from the rate data as a function of inhibitor concentration.

The following compounds were shown to have a $K_i$ value of <1 μM for ERK-2: III-109, III-111, III-115, III-117, III-118, III-120, and IV-4.

The following compounds were shown to have a $K_i$ value of between 1 μM and 12 μM for ERK-2: III-63, III-40, and III-108.

Biological Testing Example 5

AKT Inhibition Assay

Compounds were screened for their ability to inhibit AKT using a standard coupled enzyme assay (Fox et al., Protein Sci., (1998) 7, 2249). Assays were carried out in a mixture of 100 mM HEPES 7.5, 10 mM MgCl2, 25 mM NaCl, 1 mM DTT and 1.5% DMSO. Final substrate concentrations in the assay were 170 μM ATP (Sigma Chemicals) and 200 μM peptide (RPRAATF, American Peptide, Sunnyvale, Calif.). Assays were carried out at 30° C. and 45 nM AKT. Final concentrations of the components of the coupled enzyme system were 2.5 mM phosphoenolpyruvate, 300 μM NADH, 30 μg/ML pyruvate kinase and 10 μg/ml lactate dehydrogenase.

An assay stock buffer solution was prepared containing all of-the reagents listed above, with the exception of AKT, DTT, and the test compound of interest. 56 μl of the stock solution was placed in a 384 well plate followed by addition of 1 μl of 2 mM DMSO stock containing the test compound (final compound concentration 30 μM). The plate was pre-incubated for about 10 minutes at 30° C. and the reaction initiated by addition of 10 μl of enzyme (final concentration 45 nM) and 1 mM DTT. Rates of reaction were obtained using a BioRad Ultramark plate reader (Hercules, Calif.) over a 5 minute read time at 30° C. Compounds showing greater than 50% inhibition versus standard wells containing the assay mixture and DMSO without test compound were titrated to determine $IC_{50}$ values.

Biological Testing Example 6

SRC Inhibition Assay

The compounds were evaluated as inhibitors of human Src kinase using either a radioactivity-based assay or spectrophotometric assay.

SRC Inhibition Assay A: Radioactivity-based Assay

The compounds were assayed as inhibitors of full length recombinant human Src kinase (from Upstate Biotechnology, cat. no. 14–117) expressed and purified from baculo viral cells. Src kinase activity was monitored by following the incorporation of $^{33}P$ from ATP into the tyrosine of a random poly Glu-Tyr polymer substrate of composition, Glu:Tyr=4:1 (Sigma, cat. no. P-0275). The following were the final concentrations of the assay components: 0.05 M HEPES, pH 7.6, 10 mM $MgCl_2$, 2 mM DTT, 0.25 mg/ml BSA, 10 μM ATP (1–2 μCi $^{33}P$-ATP per reaction), 5 mg/ml poly Glu-Tyr, and 1–2 units of recombinant human Src kinase. In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with $^{33}P$-ATP. After 20 min of reaction, the reactions were quenched with 150 μl of 10% trichloroacetic acid (TCA) containing 20 mM $Na_3PO_4$. The quenched samples were then transferred to a 96-well filter plate (Whatman, UNI-Filter GF/F Glass Fiber Filter, cat no. 7700-3310) installed on a filter plate vacuum manifold. Filter plates were washed four times with 10% TCA containing 20 mM $Na_3PO_4$ and then 4 times with methanol. 200 μl of scintillation fluid was then added to each well. The plates were sealed and the amount of radioactivity associated with the filters was quantified on a TopCount scintillation counter. The radioactivity incorporated was plotted as a function of the inhibitor concentration. The data was fitted to a competitive inhibition kinetics model to get the $K_i$ for the compound.

SRC Inhibition Assay B: Spectrophotometric Assay

The ADP produced from ATP by the human recombinant Src kinase-catalyzed phosphorylation of poly Glu-Tyr substrate was quanitified using a coupled enzyme assay (Fox et al (1998) Protein. Sci 7, 2249). In this assay one molecule of NADH is oxidised to NAD for every molecule of ADP produced in the kinase reaction. The disappearance of NADH can be conveniently followed at 340 nm.

The following were the final concentrations of the assay components: 0.025 M HEPES, pH 7.6, 10 mM MgCl2, 2 mM DTT, 0.25 mg/ml poly Glu-Tyr, and 25 nM of recombinant human Src kinase. Final concentrations of the components of the coupled enzyme system were 2.5 mM phosphoenolpyruvate, 200 μM NADH, 30 μg/ml pyruvate kinase and 10 μg/ml lactate dehydrogenase.

In a typical assay, all the reaction components with the exception of ATP were pre-mixed and aliquoted into assay plate wells. Inhibitors dissolved in DMSO were added to the wells to give a final DMSO concentration of 2.5%. The assay plate was incubated at 30° C. for 10 min before initiating the reaction with 100 μM ATP. The absorbance change at 340 nm with time, the rate of the reaction, was monitored on a molecular devices plate reader. The data of rate as a function of the inhibitor concentration was fitted to compettive inhibition kinetics model to get the $K_i$ for the compound.

The following compounds were shown to have a $K_i$ value of <100 nM on SRC: III-31, III-32, III-33, III-34, III-35, III-47, III-65, III-66, III-37, III-38, III-39, III-40, III-42, III-44, III-48, III-49, III-70, III-45, III-78, III-76, and IV-32.

The following compounds were shown to have a $K_i$ value of between 100 nM and 1 μM for SRC: III-63, III-71, III-75, III-73, III-72, III-74, III-80, III-50, IV-30.

The following compounds were shown to have a $K_i$ value of between 1 μM and 6 μM for SRC: III-79, IV-1, and IV-31.

While we have hereinbefore presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:

1. A compound of formula IV:

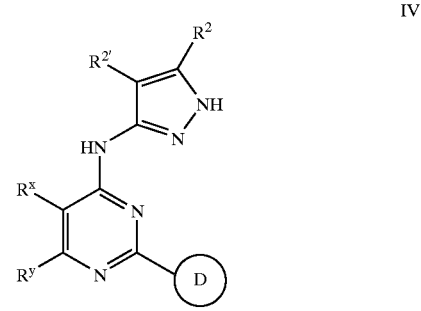

IV or a pharmaceutically acceptable salt thereof, wherein:

Ring D is a 5–7 membered monocyclic ring or 8–10 membered bicyclic ring selected from aryl, heteroaryl, heterocyclyl or carbocyclyl, said heteroaryl or heterocyclyl ring having 1–4 ring heteroatoms selected from nitrogen, oxygen or sulfur, wherein Ring D is independently substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D;

$R^x$ and $R^y$ are taken together with their intervening atoms to form a fused, unsaturated or partially unsaturated, 5–8 membered ring having 1–3 ring heteroatoms selected from oxygen, sulfur, or nitrogen, wherein any substitutable carbon on said fused ring is optionally and independently substituted by T-$R^3$, and any substitutable nitrogen on said ring is substituted by $R^4$;

T is a valence bond or a $C_{1-4}$ alkylidene chain;

$R^2$ and $R^{2'}$ are independently selected from —R, -T-W—$R^6$;

$R^3$ is selected from —R, -halo, =O, —OR, —C(=O)R, —$CO_2$R, —COCOR, —$COCH_2$COR, —$NO_2$, —CN, —S(O)R, —$S(O)_2$R, —SR, —$N(R^4)_2$, —$CON(R^4)_2$, —$SO_2N(R^4)_2$, —OC(=O)R, —$N(R^4)$COR, —$N(R^4)$$CO_2$(optionally substituted $C_{1-6}$ aliphatic), —$N(R^4)$N$(R^4)_2$, —C=$NN(R^4)_2$, —C=N—OR, —$N(R^4)$CON$(R^4)_2$, —$N(R^4)SO_2N(R^4)_2$, —$N(R^4)SO_2$R, or —OC(=O)$N(R^4)_2$;

each R is independently selected from hydrogen or an optionally substituted group selected from $C_{1-6}$ aliphatic, $C_{6-10}$ aryl, a heteroaryl ring having 5–10 ring atoms, or a heterocyclyl ring having 5–10 ring atoms;

each $R^4$ is independently selected from —$R^7$, —$COR^7$, —$CO_2$(optionally substituted $C_{1-6}$ aliphatic), —CON$(R^7)_2$, or —$SO_2R^7$, or two $R^4$ on the same nitrogen are taken together to form a 5–8 membered heterocyclyl or heteroaryl ring;

each $R^5$ is independently selected from —R, halo, —OR, —C(=O)R, —$CO_2$R, —COCOR, —$NO_2$, —CN, —S(O)R, —$SO_2$R, —SR, —$N(R^4)_2$, —$CON(R^4)_2$, —$SO_2N(R^4)_2$, —OC(=O)R, —$N(R^4)$COR, —$N(R^4)$$CO_2$(optionally substituted $C_{1-6}$ aliphatic), —$N(R^4)$N$(R^4)_2$, —C=$NN(R^4)_2$, —C=N—OR, —$N(R^4)$CON$(R^4)_2$, —$N(R^4)SO_2N(R^4)_2$, —$N(R^4)SO_2$R, or —OC(=O)$N(R^4)_2$;

V is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)$C(O)O—, —$N(R^6)$CON$(R^6)$—, —$N(R^6)SO_2N(R^6)$—, —$N(R^6)N(R^6)$—, —C(O)$N(R^6)$—, —OC(O)$N(R^6)$—, —$C(R^6)_2$O—, —$C(R^6)_2$S—, —$C(R^6)_2$SO—, —$C(R^6)_2SO_2$—, —$C(R^6)_2SO_2N(R^6)$—, —$C(R^6)_2N(R^6)$—, —$C(R^6)_2$N$(R^6)$C(O)—, —$C(R^6)_2N(R^6)$C(O)O—, —$(R^6)$=NN$(R^6)$—, C$(R^6)$=N—O—, —$C(R^6)_2N(R^6)N(R^6)$—, —$C(R^6)_2N(R^6)SO_2N(R^6)$—, or —$C(R^6)_2N(R^6)$CON$(R^6)$—,

W is —$C(R^6)_2$O—, —$C(R^6)_2$S—, —$C(R^6)_2$SO—, —$C(R^6)_2SO_2$—, —$C(R^6)_2SO_2N(R^6)$—, —$C(R^6)_2$N$(R^6)$—, —CO—, —$CO_2$—, —$C(R^6)$OC(O)—, —$C(R^6)$OC(O)$N(R^6)$—, —$C(R^6)_2N(R^6)$CO—, —$C(R^6)_2N(R^6)$C(O)O—, —$C(R^6)$=NN$(R^6)$—, —$C(R^6)$=N—O—, —$C(R^6)_2N(R^6)N(R^6)$—, —$C(R^6)_2N(R^6)SO_2N(R^6)$—, —$C(R^6)_2N(R^6)$CON$(R^6)$—, or —CON$(R^6)$—;

each $R^6$ is independently selected from hydrogen or an optionally substituted $C_{1-4}$ aliphatic group, or two $R^6$ groups on the same nitrogen atom are taken together with the nitrogen atom to form a 5–6 membered heterocyclyl or heteroaryl ring; and each $R^7$ independently selected from hydrogen or an optionally substituted $C_{1-6}$ aliphatic group, or two $R^7$ on the same nitrogen are taken together with the nitrogen to form a 5–8 membered heterocyclyl ring or heteroaryl.

2. The compound according to claim 1, wherein said compound has one or more features selected from the group consisting of:

(a) Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ and $R^y$ are taken together with their intervening atoms to form an optionally substituted 5–7 membered unsaturated or partially unsaturated ring having 1–2 ring heteroatoms; and (c) $R^{2'}$ is hydrogen or methyl and $R^2$ is T-W—$R^6$ or R, wherein W is —$C(R^6)_2$O—, —$C(R^6)_2N(R^6)$—, —CO—, —$CO_2$—, —$C(R^6)$OC(O)—, —$C(R^6)_2N(R^6)$CO—, —$C(R^6)_2N(R^6)$C(O)O—, or —CON$(R^6)$—, and R is an optionally substituted group selected from $C_{1-6}$ aliphatic or phenyl.

3. The compound according to claim 2, wherein:

(a) Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ and $R^y$ are taken together with their intervening atoms to form an optionally substituted 5–7 membered unsaturated or partially unsaturated ring having 1–2 ring heteroatoms; and (c) $R^{2'}$ is hydrogen or methyl and $R^2$ is T-W—$R^6$ or R, wherein W is —$C(R^6)_2$O—, —$C(R^6)_2N(R^6)$—, —CO—, —$CO_2$—, —$C(R^6)$OC(O)—, —$C(R^6)_2N(R^6)$CO—, —$C(R^6)_2N(R^6)$C(O)O—, or —CON$(R^6)$—, and R is an optionally substituted group selected from $C_{1-6}$ aliphatic or phenyl.

4. The compound according to claim 2, wherein said compound has one or more features selected from the group consisting of:

(a) Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ and $R^y$ are taken together with their intervening atoms to form a 5–7 membered unsaturated or partially unsaturated ring having 1–2 ring nitrogens, wherein said ring is optionally substituted with —R, halo, oxo, —OR, —C(=O)R, —$CO_2$R, —COCOR, —$NO_2$, —CN, —S(O)R, —$SO_2$R, —SR, —$N(R^4)_2$, —CON$(R^4)_2$, —$SO_2N(R^4)_2$, —OC(=O)R, —$N(R^4)$COR, —$N(R^4)CO_2$(optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2$R, or —OC(=O)$N(R^4)_2$; and (c) each $R^5$ is independently selected from halo, oxo, CN, $NO_2$, —$N(R^4)_2$, —$CO_2$R, —CONH$(R^4)$, —$N(R^4)$COR, —$SO_2N(R^4)_2$, —$N(R^4)SO_2$R, —SR, —OR, —C(O)R, or a substituted or unsubstituted group selected from 5–6 membered heterocyclyl, $C_{6-10}$ aryl, or $C_{1-6}$ aliphatic.

5. The compound according to claim 4, wherein:

(a) Ring D is an optionally substituted ring selected from phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl;

(b) $R^x$ and $R^y$ are taken together with their intervening atoms to form a 5–7 membered unsaturated or partially unsaturated ring having 1–2 ring nitrogens, wherein said ring is optionally substituted with —R, halo, oxo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$(optionally substituted C$_{1-6}$ is aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$; and (c) each R$^5$ is independently selected from halo, oxo, CN, NO$_2$, —N(R$^4$)$_2$, —CO$_2$R, —CONH(R$^4$), —N(R$^4$)COR, —SO$_2$N(R$^4$)$_2$, —N(R$^4$)SO$_2$R, —SR, —OR, —C(O)R, or a substituted or unsubstituted group selected from 5–6 membered heterocyclyl, C$_{6-10}$ aryl, or C$_{1-6}$ aliphatic.

6. The compound according to claim 4, wherein said compound has one or more features selected from the group consisting of:

(a) R$^x$ and R$^y$ are taken together with their intervening atoms to form a 6-membered unsaturated or partially unsaturated ring having 1–2 ring nitrogens, optionally substituted with halo, CN, oxo, C$_{1-6}$ alkyl, C$_{1-6}$ alkoxy, (C$_{1-6}$ alkyl)carbonyl, (C$_{1-6}$ alkyl)sulfonyl, mono- or dialkylamino, mono- or dialkylaminocarbonyl, mono- or dialkylaminocarbonyloxy, or 5–6 membered heteroaryl;

(b) each R$^5$ is independently selected from -halo, —CN, -oxo, —SR, —OR, —N(R$^4$)$_2$, —C(O)R, or a substituted or unsubstituted group selected from 5–6 membered heterocyclyl, C$_{6-10}$ aryl, and C$_{1-6}$ aliphatic; and (c) R$^2$ and R$^{2'}$ are taken together with their intervening atoms to form a substituted or unsubstituted benzo, pyrido, or partially unsaturated 6-membered carbocyclo ring optionally substituted with -halo, oxo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, or —CO(C$_{1-4}$ alkyl), wherein the (C$_{1-4}$ alkyl) is a straight, branched, or cyclic alkyl group.

7. The compound according to claim 6, wherein:

(a) R$^x$ and R$^y$ are taken together with their intervening atoms to form a 6-membered unsaturated or partially unsaturated ring having 1–2 ring nitrogens, optionally substituted with halo, CN, oxo, C$_{1-6}$ alkyl, C$_{1-6}$ alkoxy, (C$_{1-6}$ alkyl)carbonyl, (C$_{1-6}$ alkyl)sulfonyl, mono- or dialkylamino, mono- or dialkylaminocarbonyl, mono- or dialkylaminocarbonyloxy, or 5–6 membered heteroaryl;

(b) each R$^5$ independently selected from -halo, —CN, -oxo, —SR, —OR, —N(R$^4$)$_2$, —C(O)R, or a substituted or unsubstituted group selected from 5–6 membered heterocyclyl, C$_{6-10}$ aryl, and C$_{1-6}$ aliphatic; and (c) R$^2$ and R$^{2'}$ are taken together with their intervening atoms to form a substituted or unsubstituted benzo, pyrido, or partially unsaturated 6-membered carbocyclo ring optionally substituted with -halo, oxo, —N(R$^4$)$_2$, —C$_{1-4}$ alkyl, —C$_{1-4}$ haloalkyl, —NO$_2$, —O(C$_{1-4}$ alkyl), —CO$_2$(C$_{1-4}$ alkyl), —CN, —SO$_2$(C$_{1-4}$ alkyl), —SO$_2$NH$_2$, —OC(O)NH$_2$, —NH$_2$SO$_2$(C$_{1-4}$ alkyl), —NHC(O)(C$_{1-4}$ alkyl), —C(O)NH$_2$, or —CO(C$_{1-4}$ alkyl), wherein the (C$_{1-4}$ alkyl) is a straight, branched, or cyclic alkyl group.

8. The compound according to claim 7, wherein said compound is selected from the following Table 3 compounds:

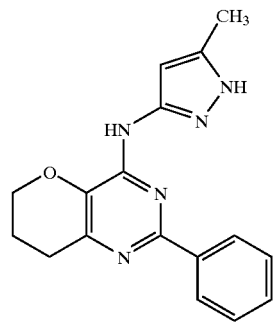

IV-18

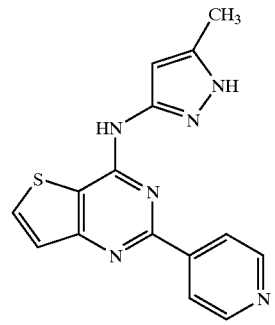

IV-29

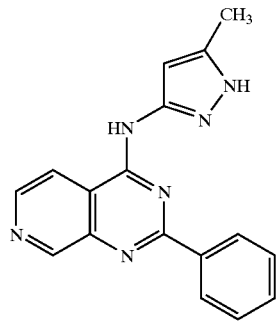

IV-30

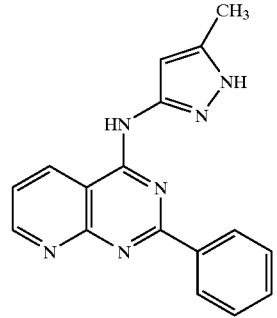

IV-31

-continued

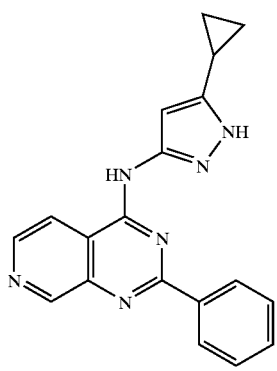
IV-32

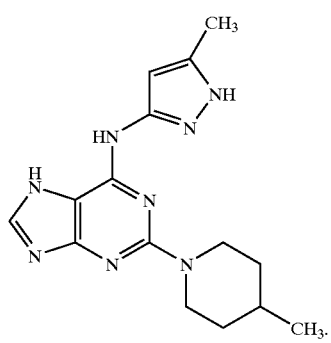
IV-33

9. A composition comprising an effective amount of a compound according to any of claims 1–8 and a pharmaceutically acceptable carrier.

10. The composition according to claim 9 further comprising a second therapeutic agent selected from an agent for treating diabetes, a chemotherapeutic agent or anti-proliferative agent, an anti-inflammatory agent, an immunomodulatory or immunosuppressive agent, a neurotrophic factor, an agent for treating cardiovascular disease, and agent for treating liver disease, an anti-viral agent, or an agent for treating a blood disorder.

11. A method of inhibiting GSK-3 or Aurora activity in a biological sample comprising contacting said biological sample with the compound according to claim 1.

12. A method of enhancing glycogen synthesis in a patient in need thereof, which method comprises the step of administering to a patient a therapeutically effective amount of the composition according to claim 9.

13. A method of lowering blood levels of glucose in a patient in need thereof, which method comprises the step of administering to a patient a therapeutically effective amount of the composition according to claim 9.

14. A method of treating a disease in a patient, wherein said disease is colon, breast, or ovarian cancer said method comprising the step of administering to said patient a composition according to claim 9.

15. A method of treating diabetes in a patient in need thereof, comprising the step of administering to said patient a therapeutically effective amount of the composition according to claim 9.

16. A method of treating schizophrenia in a patient in need thereof, comprising the step of administering to said patient a therapeutically effective amount of the composition according to claim 9.

* * * * *